United States Patent
Gillis et al.

(10) Patent No.: US 11,541,055 B2
(45) Date of Patent: Jan. 3, 2023

(54) INHIBITORS OF HUMAN IMMUNODEFICIENCY VIRUS REPLICATION

(71) Applicant: ViiV Healthcare UK (No. 5) LIMITED, Brentford (GB)

(72) Inventors: Eric P. Gillis, Branford, CT (US); Kyle E. Parcella, Branford, CT (US); Manoj Patel, Branford, CT (US)

(73) Assignee: ViiV Healthcare UK (No.5) Limited, Brentford (GB)

( * ) Notice: Subject to any disclaimer, the term of this patent is extended or adjusted under 35 U.S.C. 154(b) by 0 days.

(21) Appl. No.: 16/762,209

(22) PCT Filed: Oct. 22, 2019

(86) PCT No.: PCT/IB2019/059020
§ 371 (c)(1),
(2) Date: May 7, 2020

(87) PCT Pub. No.: WO2020/084492
PCT Pub. Date: Apr. 30, 2020

(65) Prior Publication Data
US 2020/0360384 A1 Nov. 19, 2020

Related U.S. Application Data

(60) Provisional application No. 62/749,818, filed on Oct. 24, 2018.

(51) Int. Cl.
| | |
|---|---|
| *A61K 31/517* | (2006.01) |
| *A61K 31/496* | (2006.01) |
| *A61K 31/4985* | (2006.01) |
| *A61K 31/5365* | (2006.01) |
| *A61K 9/00* | (2006.01) |
| *C07D 403/14* | (2006.01) |
| *A61K 31/7068* | (2006.01) |

(52) U.S. Cl.
CPC .......... *A61K 31/517* (2013.01); *A61K 9/0019* (2013.01); *A61K 9/0053* (2013.01); *A61K 31/496* (2013.01); *A61K 31/4985* (2013.01); *A61K 31/5365* (2013.01); *A61K 31/7068* (2013.01); *C07D 403/14* (2013.01)

(58) Field of Classification Search
CPC ................ A61K 31/517; A61K 9/0053; A61K 31/4985; A61K 31/5365; A61K 31/7068; A61K 31/496; A61K 9/0019; C07D 403/14
USPC ......................................................... 514/49
See application file for complete search history.

(56) References Cited

U.S. PATENT DOCUMENTS

| | | |
|---|---|---|
| 2021/0214345 A1 | 7/2021 | Belema et al. |
| 2021/0323961 A1 | 10/2021 | Iwuagwu et al. |
| 2021/0323967 A1 | 10/2021 | Gillis et al. |
| 2021/0379071 A1 | 12/2021 | Bowsher et al. |
| 2021/0393633 A1 | 12/2021 | Gillis et al. |
| 2021/0395248 A1 | 12/2021 | Bowsher et al. |
| 2021/0395262 A1 | 12/2021 | Gillis et al. |
| 2021/0403465 A1 | 12/2021 | Gillis et al. |

FOREIGN PATENT DOCUMENTS

| | | |
|---|---|---|
| WO | WO 2016/033243 A1 | 3/2016 |
| WO | WO 2019/198024 | * 10/2019 |
| WO | WO 2019/198024 A1 | 10/2019 |
| WO | WO 2020/053811 A1 | 3/2020 |
| WO | WO 2020/157692 A1 | 8/2020 |
| WO | WO 2020/176366 | 9/2020 |
| WO | WO 2020/209900 A1 | 10/2020 |
| WO | WO 20201222108 A1 | 11/2020 |
| WO | WO 2021/176367 A1 | 3/2021 |
| WO | WO 2020/070054 A1 | 4/2021 |
| WO | WO 2021/064570 A1 | 4/2021 |
| WO | WO 2021/064571 A1 | 4/2021 |
| WO | WO 2021/064677 A1 | 4/2021 |

* cited by examiner

*Primary Examiner* — Yih-Horng Shiao
(74) *Attorney, Agent, or Firm* — Nora L. Stein

(57) ABSTRACT

Compounds of Formula I, including pharmaceutically acceptable salts thereof, and compositions and methods for treating human immunodeficiency virus (HIV) infection are set forth:

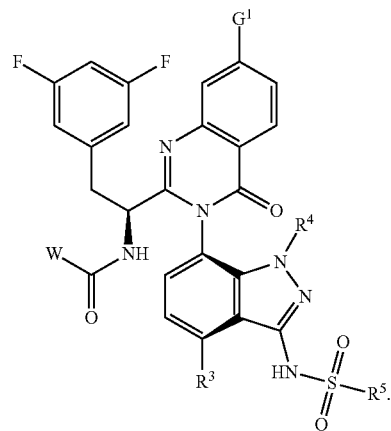

Formula I

28 Claims, No Drawings

INHIBITORS OF HUMAN IMMUNODEFICIENCY VIRUS REPLICATION

This application is a § 371 of International Application No. PCT/IB2019/059020, filed 22 Oct. 2019, which claims the benefit of U.S. Provisional Application No. 62/749,818, filed 24 Oct. 2018.

FIELD OF THE INVENTION

The invention relates to compounds, compositions, and methods for the treatment of human immunodeficiency virus (HIV) infection. More particularly, the invention provides novel Capsid inhibitors, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The vast majority of this number live in low- and middle-income countries. In the same year, 1.1 million people died of AIDS-related illnesses.

Current therapy for HIV-infected individuals consists of a combination of approved anti-retroviral agents. Close to four dozen drugs are currently approved for HIV infection, either as single agents, fixed dose combinations or single tablet regimens; the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INSTIs), or entry inhibitors (one, maraviroc, targets the host CCR5 protein, while the other, enfuvirtide, is a peptide that targets the gp41 region of the viral gp160 protein). In addition, a pharmacokinetic enhancer (cobicistat or ritonavir) can be used in combinations with antiretroviral agents (ARVs) that require boosting.

Despite the armamentarium of agents and drug combinations, there remains a medical need for new anti-retroviral agents. High viral heterogeneity, drug-associated toxicity, tolerability problems, and poor adherence can all lead to treatment failure and may result in the selection of viruses with mutations that confer resistance to one or more antiretroviral agents or even multiple drugs from an entire class (Beyrer, C., Pozniak A. HIV drug resistance—an emerging threat to epidemic control. N. Engl. J. Med. 2017, 377, 1605-1607; Gupta, R. K., Gregson J., et al. HIV-1 drug resistance before initiation or re-initiation of first-line antiretroviral therapy in low-income and middle-income countries: a systematic review and meta-regression analysis. Lancet Infect. Dis. 2017, 18, 346-355; Zazzi, M., Hu, H., Prosperi, M. The global burden of HIV-1 drug resistance in the past 20 years. PeerJ. 2018, DOI 10.7717/peerj.4848). As a result, new drugs are needed that are easier to take, have high genetic barriers to the development of resistance and have improved safety over current agents. In this panoply of choices, novel mechanisms of action (MOAs) that can be used as part of the preferred antiretroviral therapy (ART) can still have a major role to play since they should be effective against viruses resistant to current agents.

Certain potentially therapeutic compounds have now been described in the art and set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and PCT Patent applications with the following numbers: WO 2012065062, WO 2013006738, WO 2013006792, WO 2014110296, WO 2014110297, WO 2014110298, WO 2014134566, WO 2015130964, WO2015130966, WO 2016033243, WO2018035359, WO2018203235, WO 2019161017, and WO 2019161280.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, bioavailability or reduced frequency of dosing. Also needed are new formulations and methods of treatment which utilize these compounds.

SUMMARY OF THE INVENTION

Briefly, in one aspect, the present invention discloses a compound of Formula I, or a pharmaceutically acceptable salt thereof:

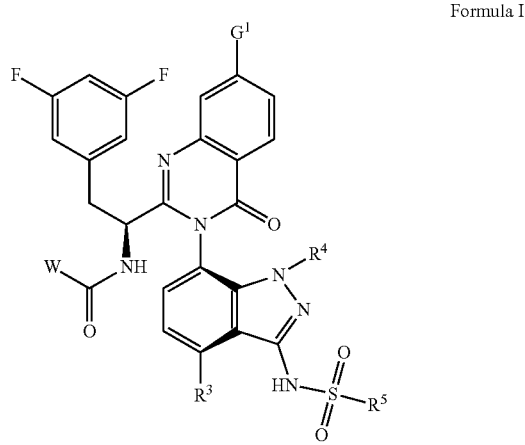

Formula I wherein:
G1 is phenyl substituted once with —N(CH3)S(O2)CH3, —S(O2)C(CH3)3, —CHF2, —CF3, —OCHF2, —OCF3, or —C(CH3)2OH, with the proviso that when G1 is —CHF2 or CF3, G1 is not in the para position or G1 is one of the following:

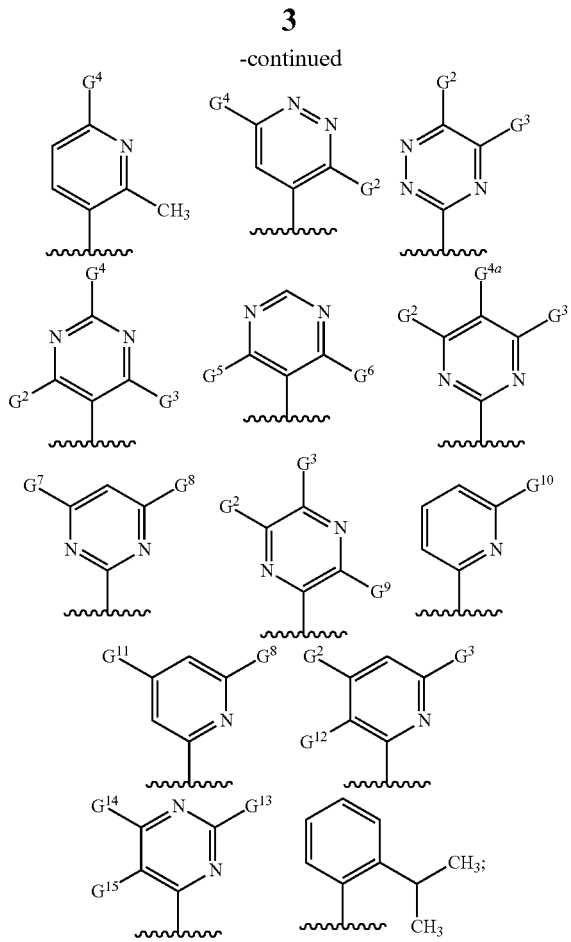

G² and G³ are independently selected from is H or —CH₃;
G⁴ is H, —CH₃, or —OCH₃;
G⁴a is —CH₃, or —OCH₃;
G⁵ is —CH₃, or CH₂CH₃;
G⁶ is H, —CH₃, or CH₂CH₃;
G⁷ is ethyl, isopropyl, tert-butyl, —CHF₂, or —CF₃;
G⁸ is H, methyl, ethyl, —CHF₂, —CF₃, —OCH₃, or —OCH₂CH₃;
G⁹ is ethyl, isopropyl, cyclopropyl, —CH₂OH, —OCH₃;
G¹⁰ is ethyl, isopropyl, cyclopropyl, tert-butyl, —CHF₂, or —CF₃;
G¹¹ is methyl, —OCH₃, —CHF₂, —CF₃, —S(O₂)CH₃;
G¹² is F, —CH₃, —CHF₂, —CF₃, —OCH₃, —S(O₂)CH₃;
G¹³ is $C_1$-$C_4$alkyl, $C_1$-$C_6$cycloalkyl, —CH₂O($C_1$-$C_3$alkyl);
G¹⁴ is H, $C_1$-$C_4$alkyl, —CHF₂, —CF₃, —O($C_1$-$C_3$alkyl);
G¹⁵ is H, F, —CH₃, or OCH₃;
R³ is H, F, C₁, —CH₃, or —OCH₃;
R⁴ is H or $C_1$-$C_3$alkyl wherein $C_1$-$C_3$alkyl is optionally substituted with 1-3 fluorines;
R⁵ is $C_1$-$C_6$ alkyl or $C_3$-$C_6$ cycloalkyl;
W is selected from:

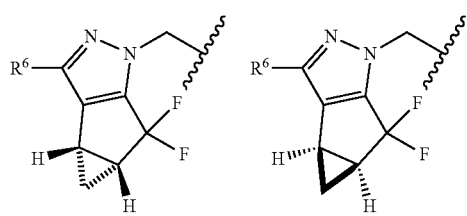

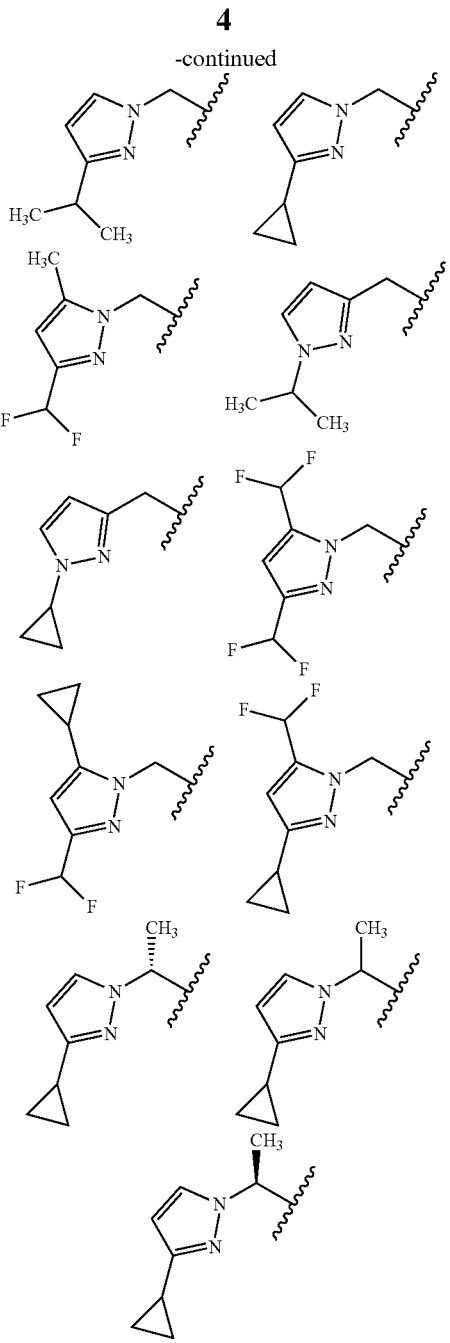

where R⁶ is methyl optionally substituted with 1 to 3 fluorines.

In another aspect, the present invention discloses a composition comprising a compound of Formula I or a pharmaceutically acceptable salt thereof.

In another aspect, the present invention discloses a method of treating HIV infection comprising administering a composition comprising a compound of Formula I or a pharmaceutically acceptable salt thereof to a patient.

In another aspect, the present invention discloses a compound of Formula I or pharmaceutically acceptable salt thereof for use in therapy.

In another aspect, the present invention discloses a compound of Formula I or pharmaceutically acceptable salt thereof for use in treating HIV infection.

In another aspect, the present invention discloses the use of a compound of Formula I or pharmaceutically acceptable salt thereof in the manufacture of a medicament for the treatment of HIV infection.

DETAILED DESCRIPTION OF THE INVENTION

In one embodiment, the present invention discloses a compound of Formula II or a pharmaceutically acceptable salt thereof,

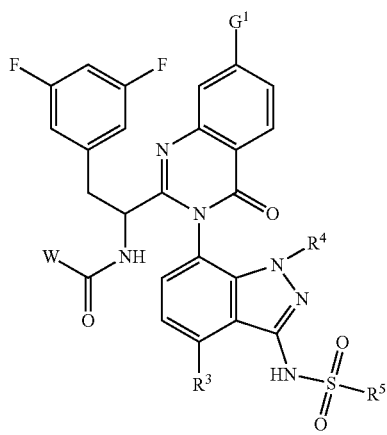

Formula II wherein all variables have the same meanings as defined for Formula I.

In one embodiment, the present invention discloses a compound of Formula I or Formula II, or a salt thereof, wherein W is

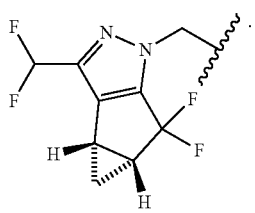

In another embodiment, the present invention discloses a compound of Formula I or Formula II, or a salt thereof, wherein W is

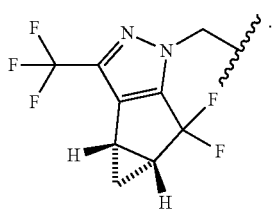

In another embodiment, the present invention discloses a compound of Formula I or Formula II, or a salt thereof, wherein W is one of the following:

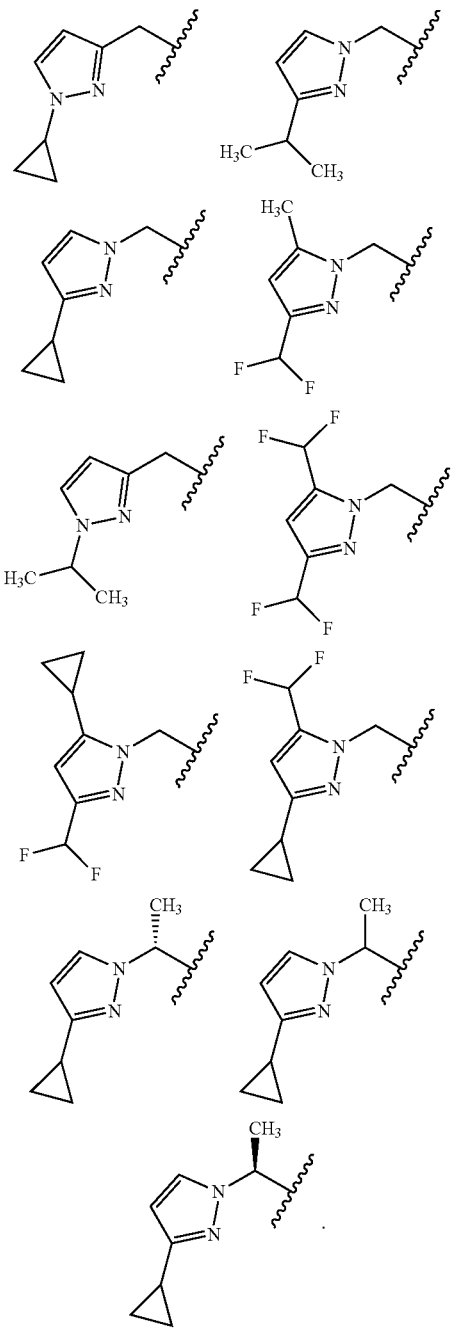

In one embodiment, the present invention discloses a compound of Formula I or Formula II, or a salt thereof, wherein $R^3$ is Cl; $R^4$ is —$CH_3$, —$CH_2CHF_2$, —$CH_2CF_3$; and $R^5$ is methyl or cyclopropyl. In another embodiment, the present invention discloses a compound of Formula I or Formula II, or a salt thereof, wherein $R^3$ is —$CH_3$; $R^4$ is —$CH_3$, —$CH_2CHF_2$, —$CH_2CF_3$; and $R^5$ is methyl or cyclopropyl. In another embodiment, the present invention discloses a compound of Formula I or Formula II, or a salt thereof, wherein $R^3$ is Cl; $R^4$ is —$CH_3$, and $R^5$ is methyl.

In one embodiment, the present invention discloses a compound of Formula I or Formula II, or a salt thereof, wherein $G^1$ is one of the following:

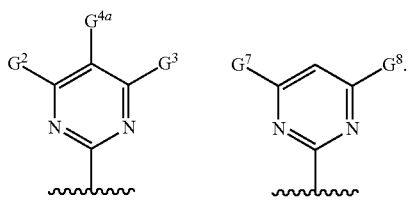 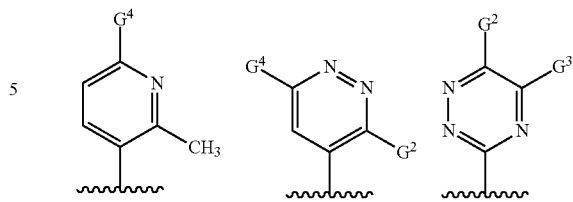

In another embodiment, the present invention discloses a compound of Formula I or Formula II, or a salt thereof, wherein $G^1$ is one of the following:

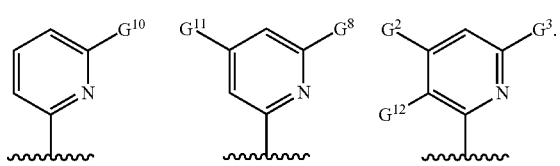

In another embodiment, the present invention discloses a compound of Formula I or Formula II, or a salt thereof, wherein $G^1$ is the following:

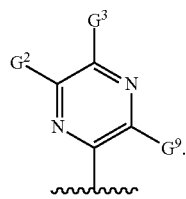

In another embodiment, the present invention discloses a compound of Formula I or Formula II, or a salt thereof, wherein $G^1$ is one of the following:

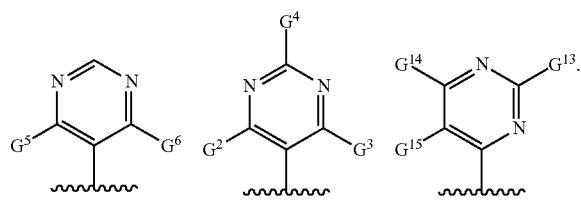

In another embodiment, the present invention discloses a compound of Formula I or Formula II, wherein $G^1$ is one of the following:

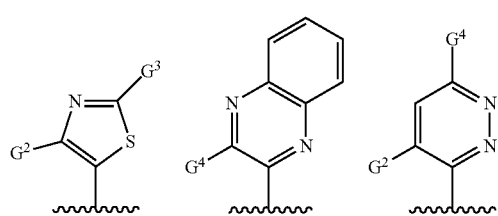

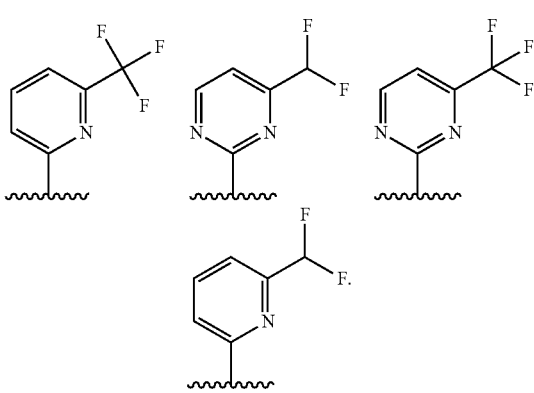

In another embodiment, the present invention discloses a compound of Formula I or Formula II, or a salt thereof, wherein $G^1$ is one of the following:

In another embodiment, the present invention discloses a compound of Formula I or Formula II, or a salt thereof, wherein $G^1$ is one of the following:

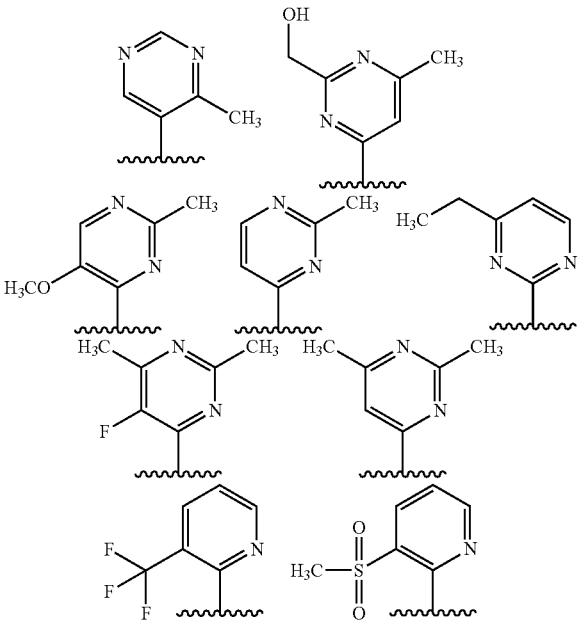

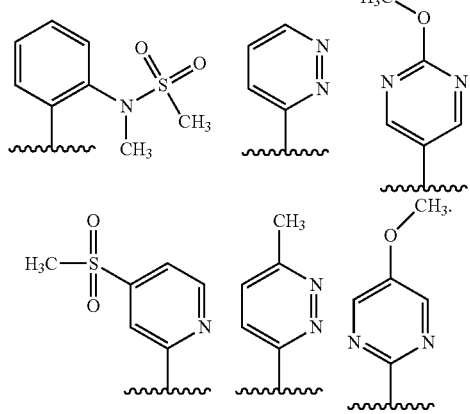
In another embodiment, the present invention discloses a compound of Formula I or Formula II, or a salt thereof, wherein $G^1$ is one of the following:
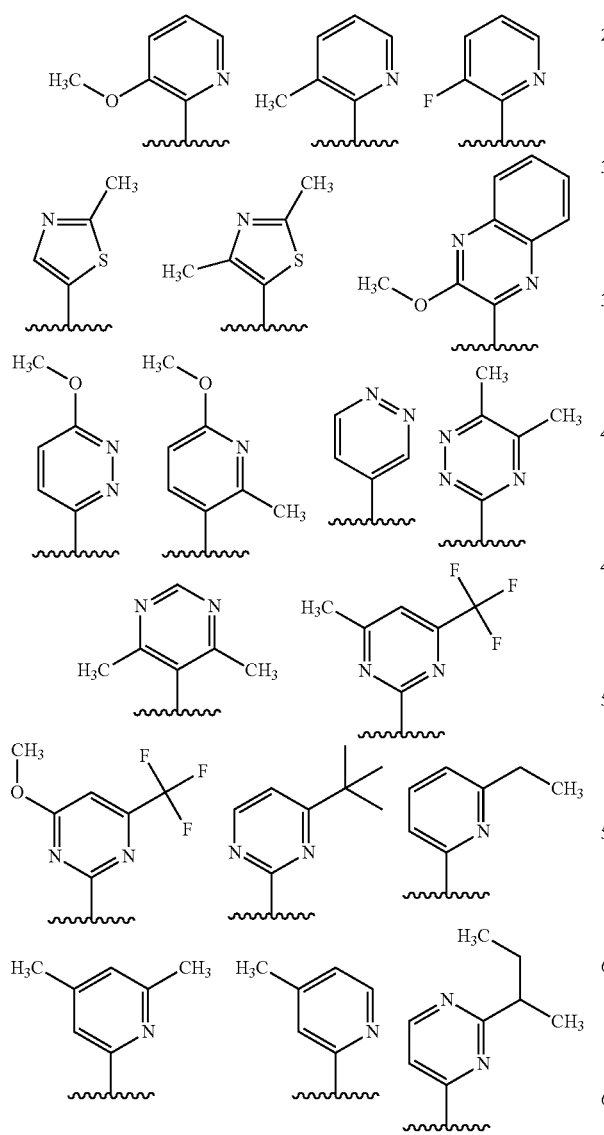
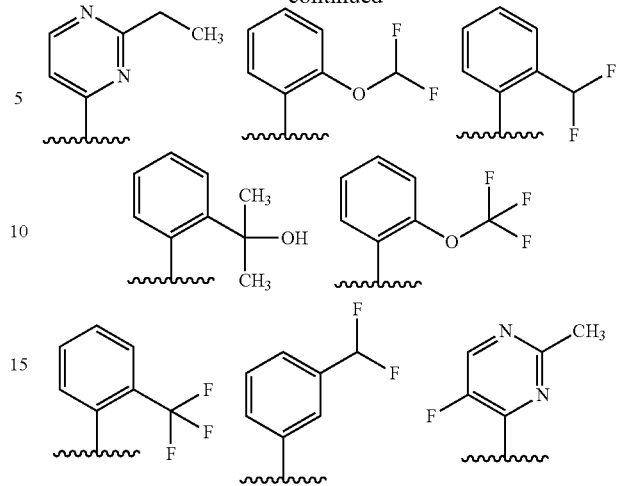
In another embodiment, the present invention discloses a compound of Formula I or Formula II, or a salt thereof, wherein $G^1$ is one of the following:

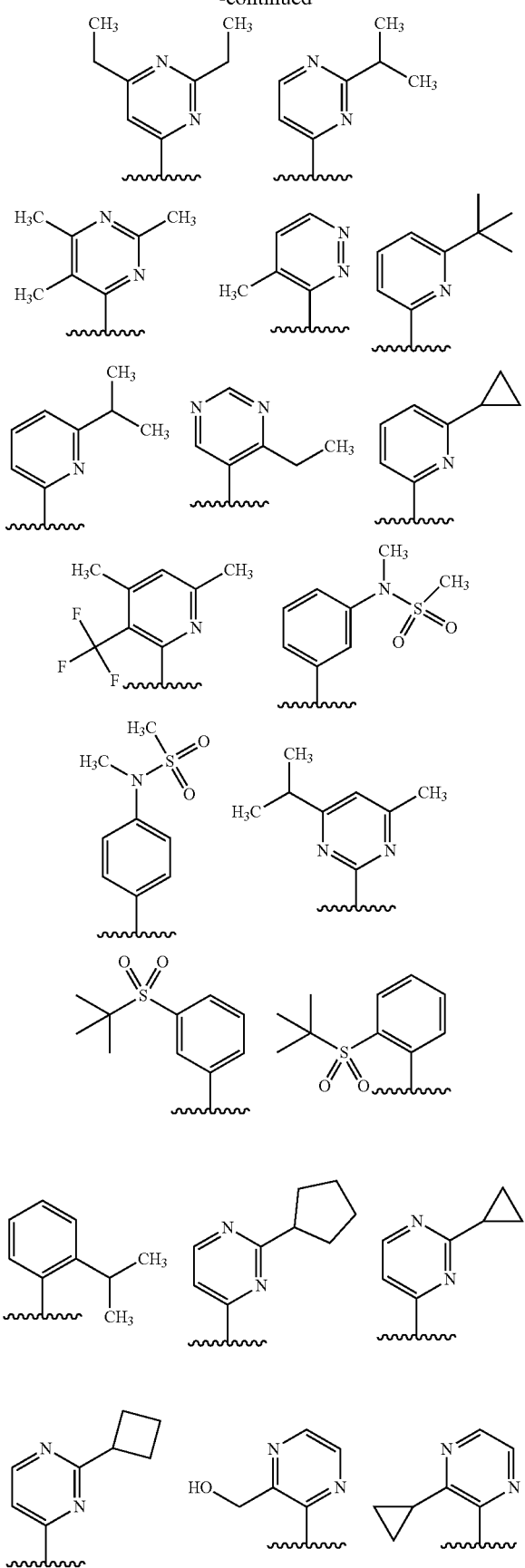
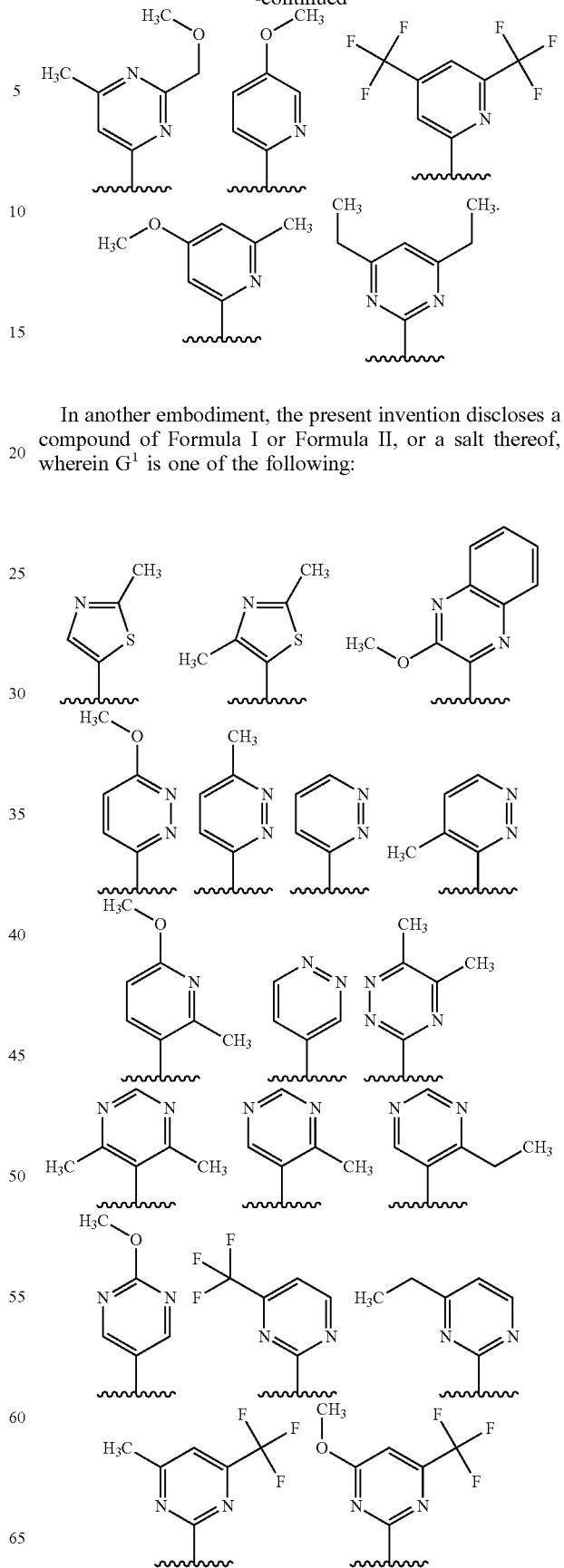
In another embodiment, the present invention discloses a compound of Formula I or Formula II, or a salt thereof, wherein $G^1$ is one of the following:

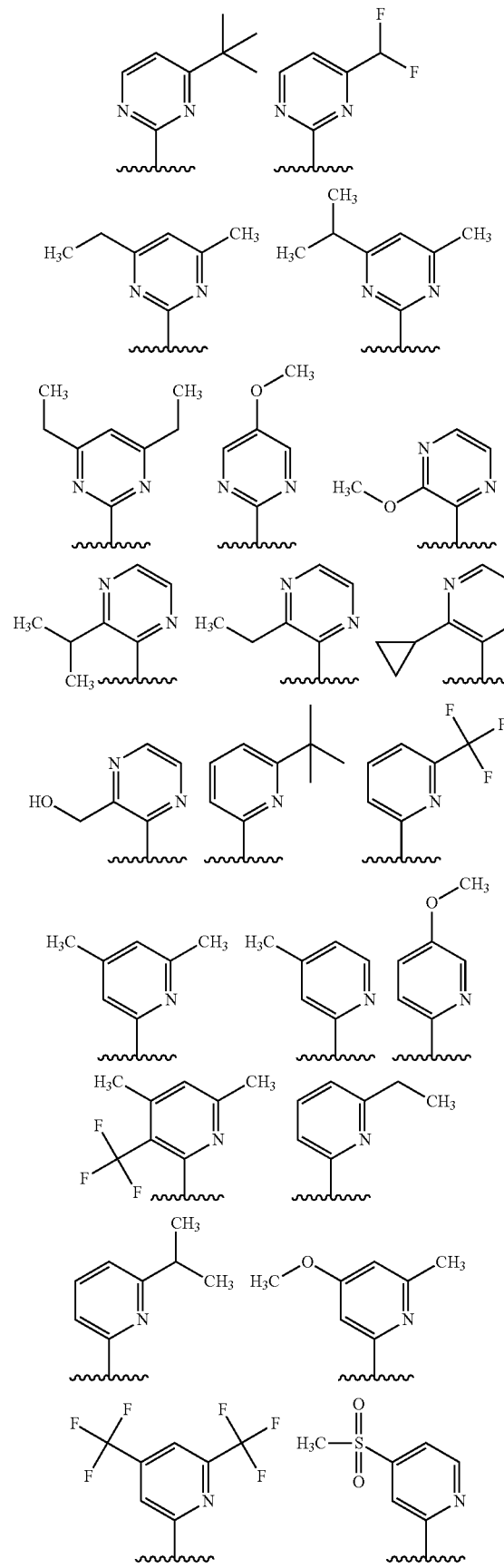
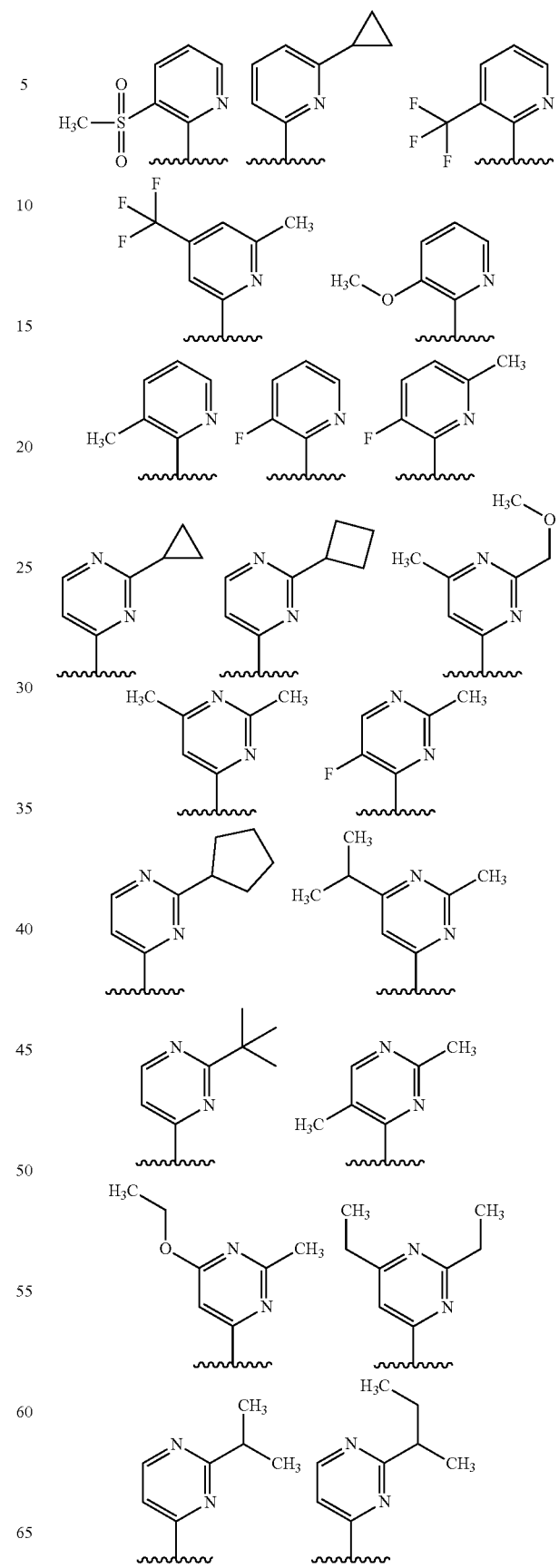

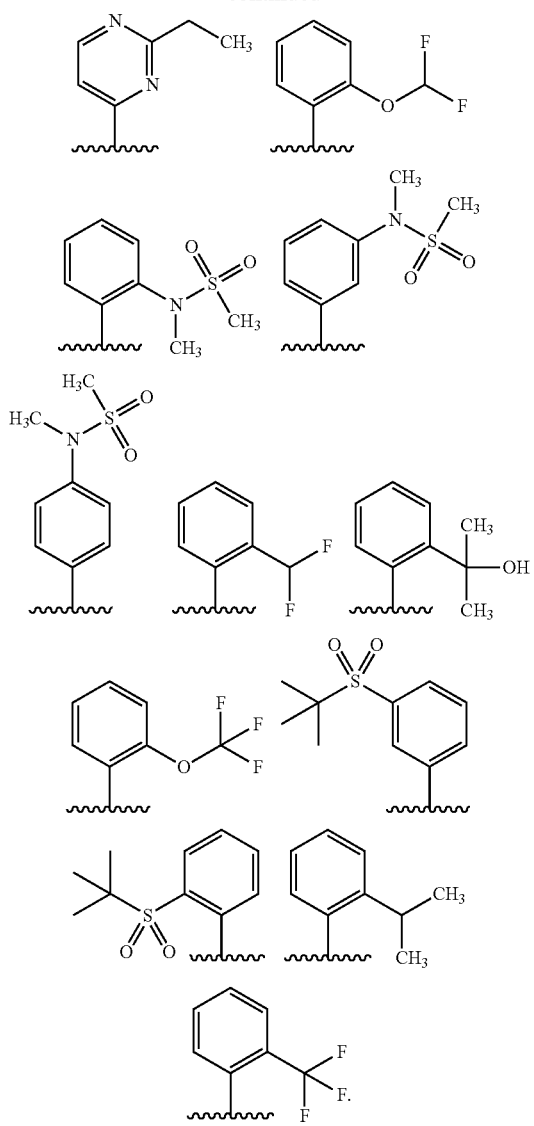

In another embodiment, the present invention discloses a compound of Formula I or Formula II, or a salt thereof, wherein $G^1$ contains a fluorine atom.

In another embodiment, the present invention discloses a compound of Formula I or Formula II, or a salt thereof, wherein $G^1$ is

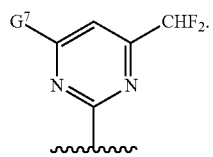

In another embodiment, the present invention discloses a compound of Formula I or Formula II, or a salt thereof, wherein $G^1$ is:

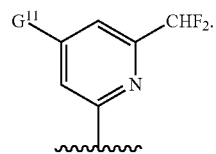

In another embodiment, the present invention discloses a compound of Formula I or Formula II, or a salt thereof, wherein $G^1$ is:

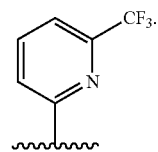

In another embodiment, the present invention discloses a compound of Formula I or Formula II, or a salt thereof, $G^1$ is:

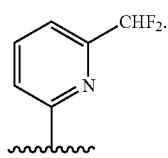

In another embodiment, the present invention discloses a compound of Formula I or Formula II, or a salt thereof, wherein $G^1$ is:

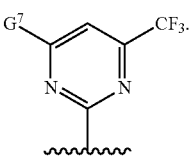

In another embodiment, the present invention discloses a compound of Formula I or Formula II, or a salt thereof, wherein $G^1$ is:

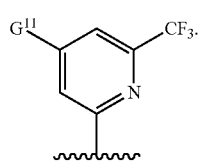

In another embodiment, the present invention discloses a compound of Formula I or Formula II, or a salt thereof, wherein $G^1$ is:

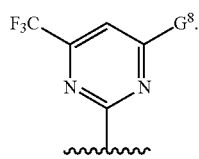

In another embodiment, the present invention discloses a compound of Formula I or Formula II, or a salt thereof, wherein $G^1$ is:

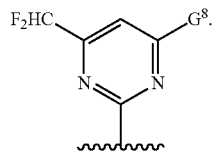

In another embodiment, the present invention discloses a compound of Formula I, or a salt thereof, selected from the group consisting of:

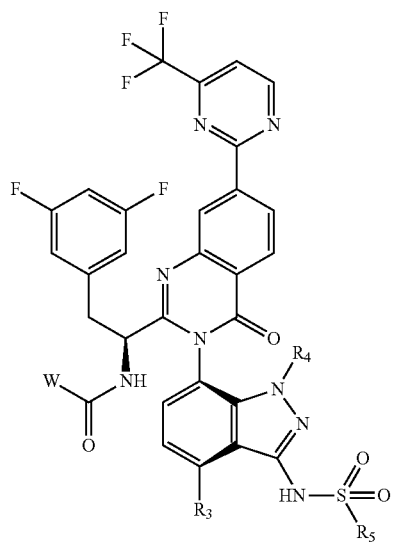

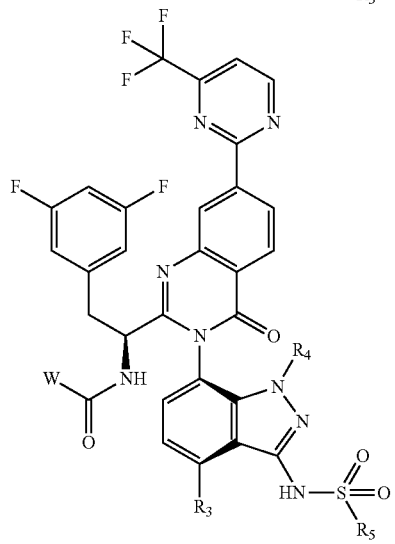

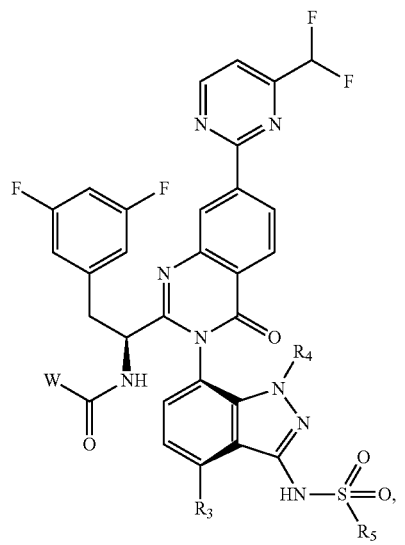

pharmaceutically acceptable salts thereof.

In another embodiment, the present invention discloses a compound or salt selected from the group consisting of:

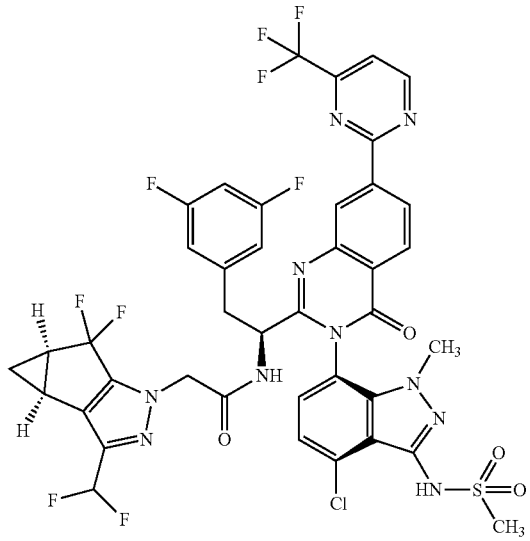

19
-continued
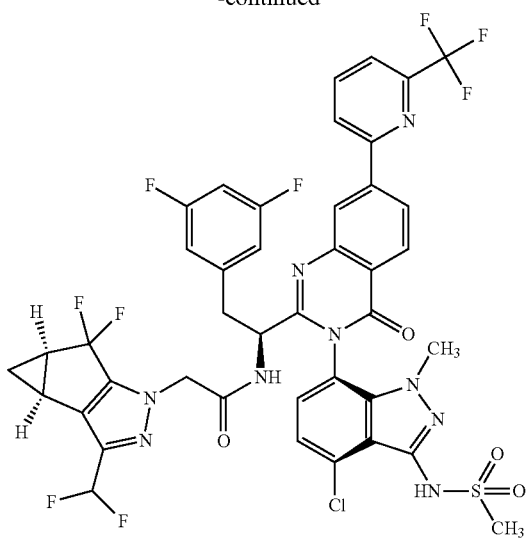
and pharmaceutically acceptable salts thereof.
In another embodiment, the present invention discloses a compound or salt selected from the group consisting of:
20
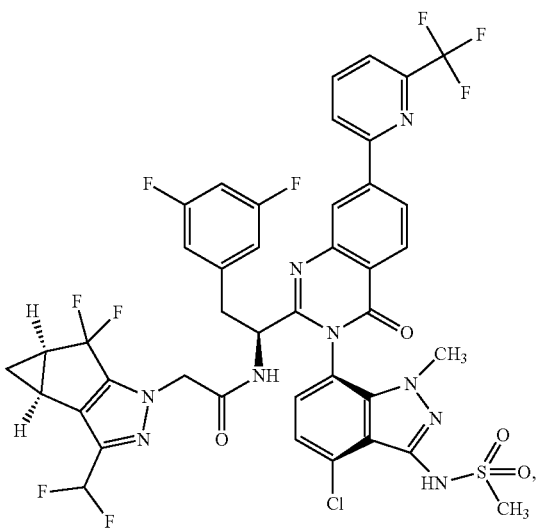
and pharmaceutically acceptable salts thereof.
In another embodiment, the present invention discloses a compound or salt selected from the group consisting of:

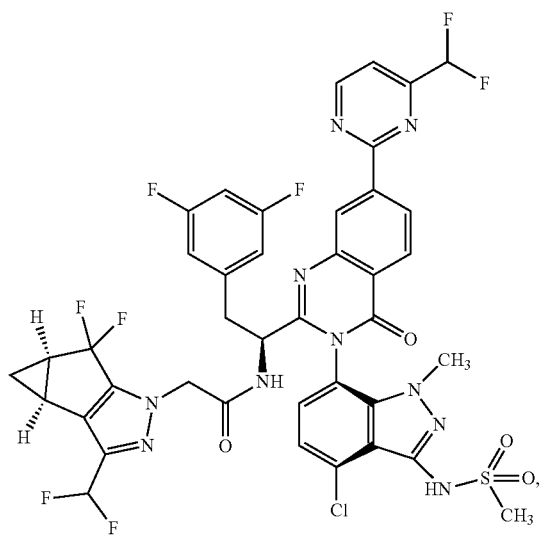
and
pharmaceutically acceptable salts thereof.
In another embodiment, the present invention discloses a compound or salt selected from the group consisting of:
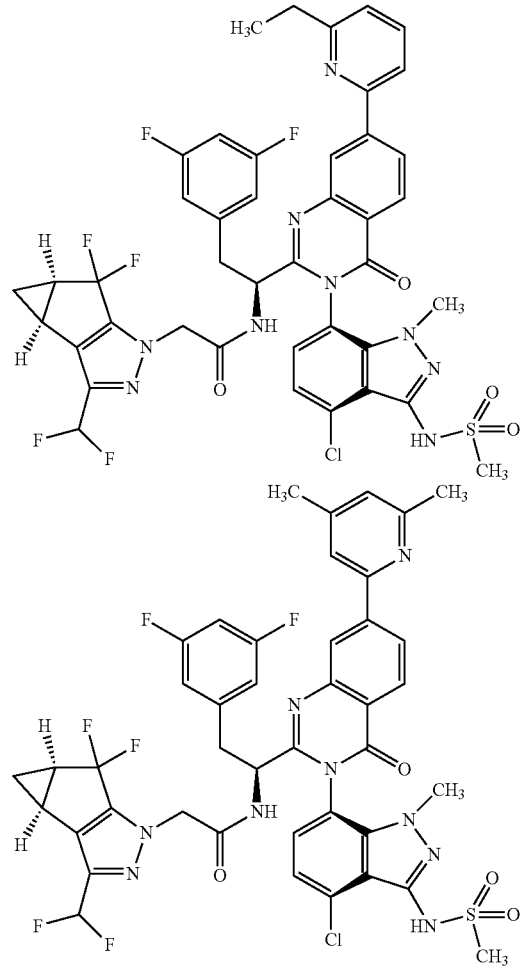
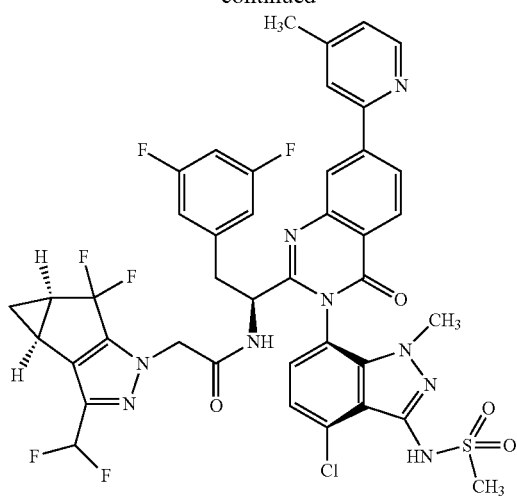
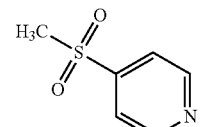
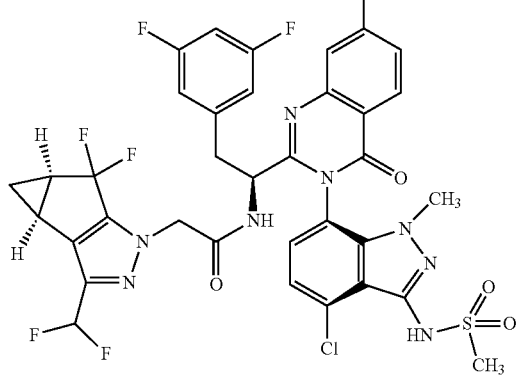
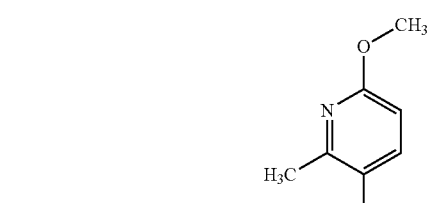
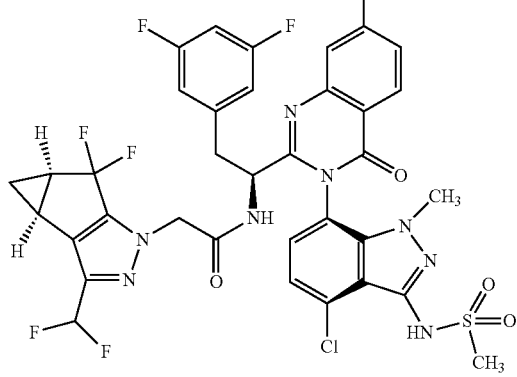

23
-continued
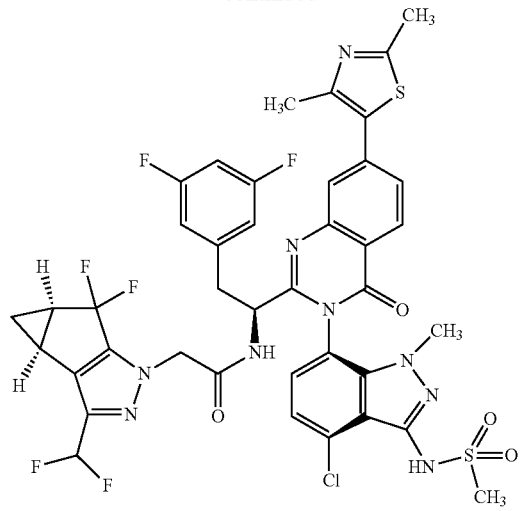
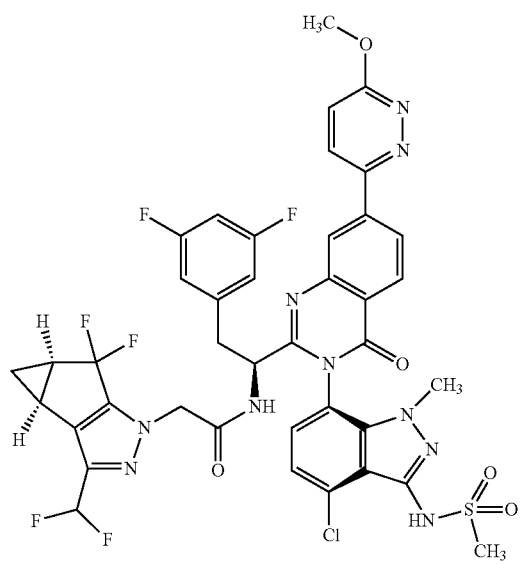
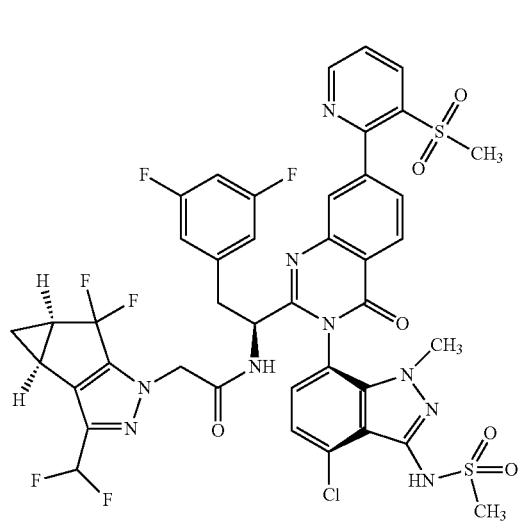
24
-continued
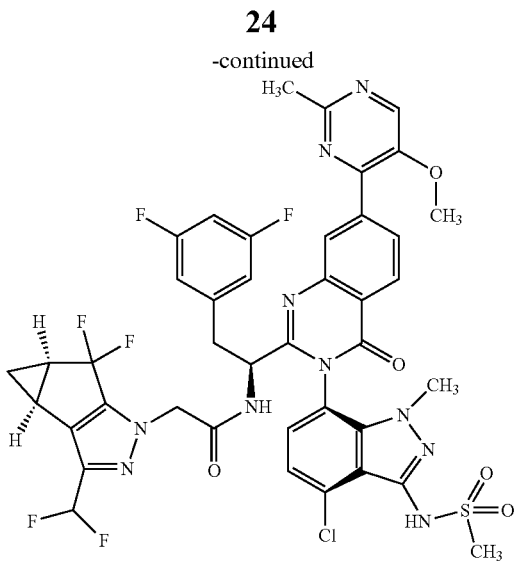
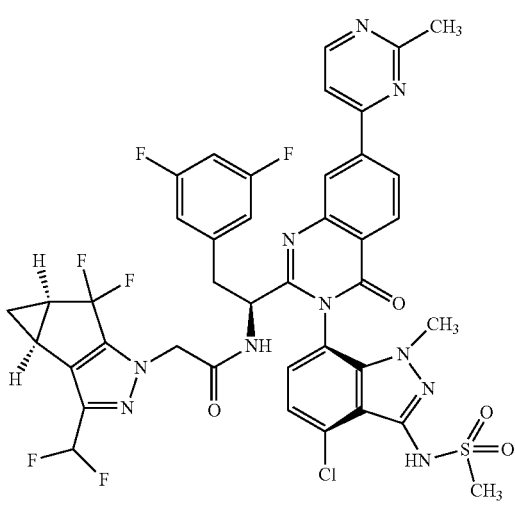
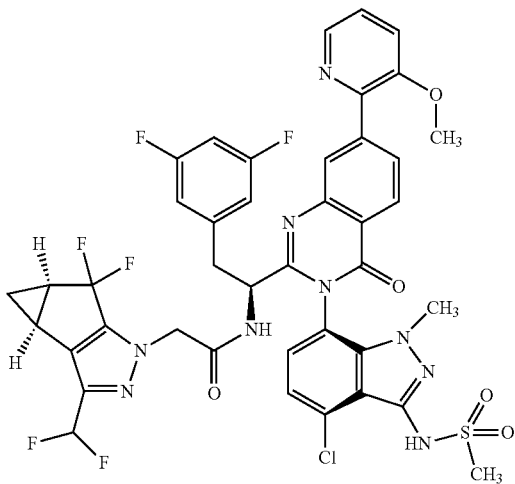

25
-continued
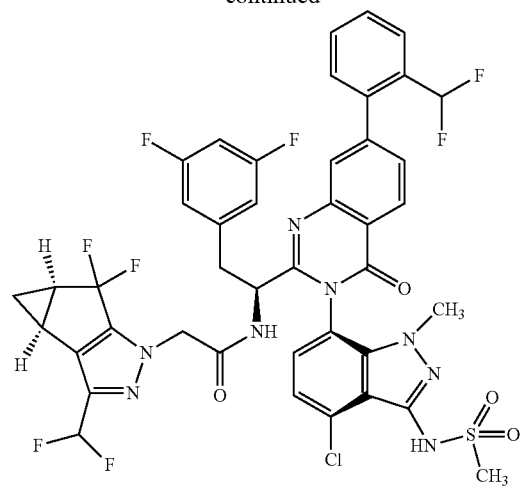
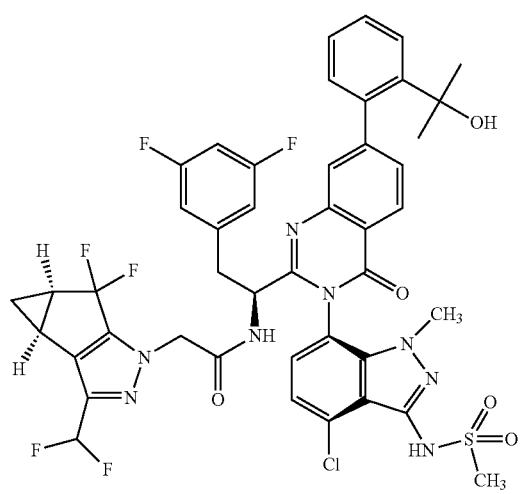
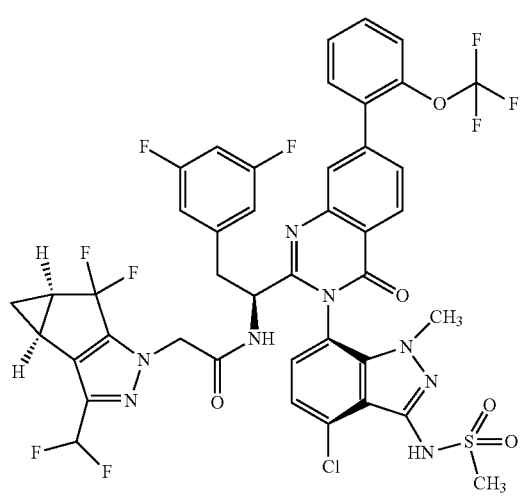
26
-continued
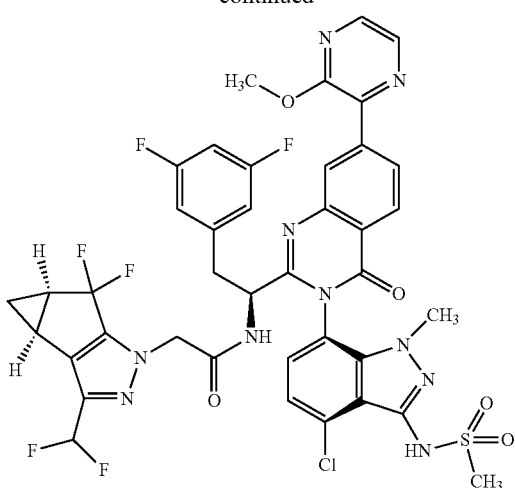
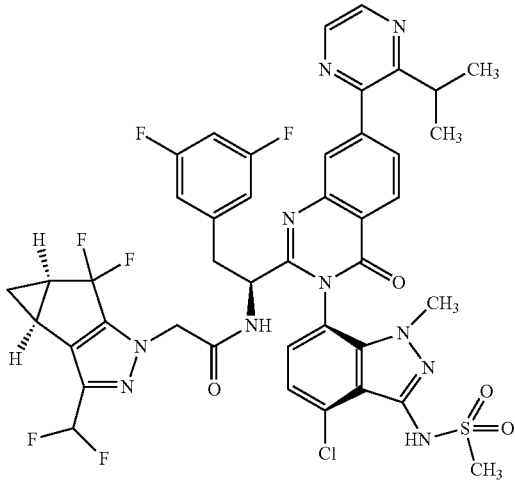
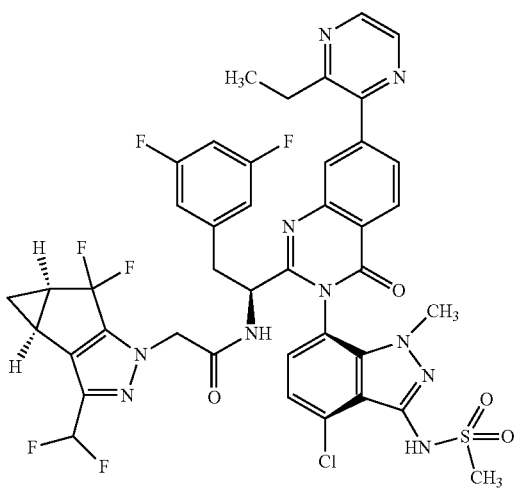

27
-continued
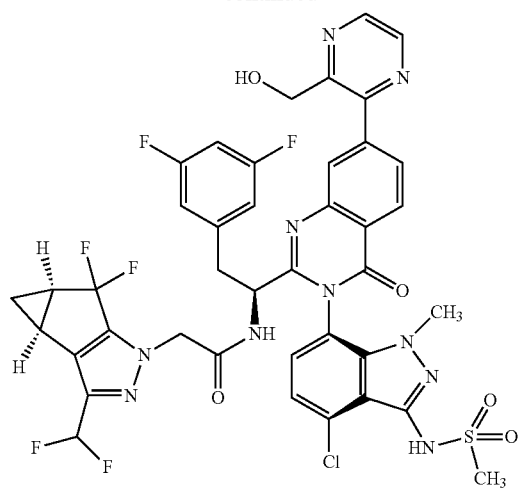
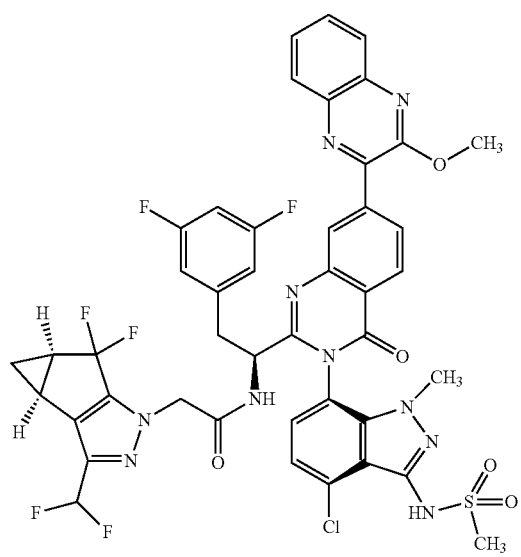
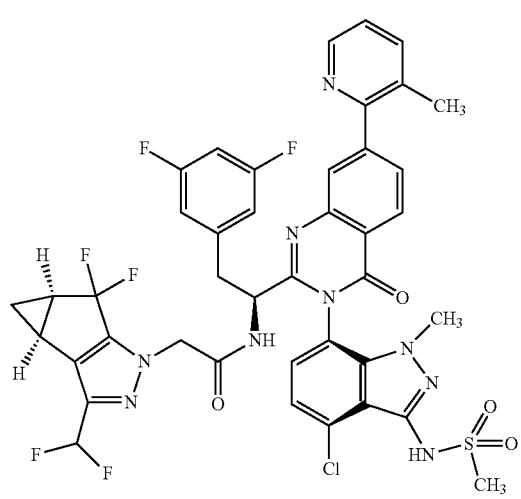
28
-continued
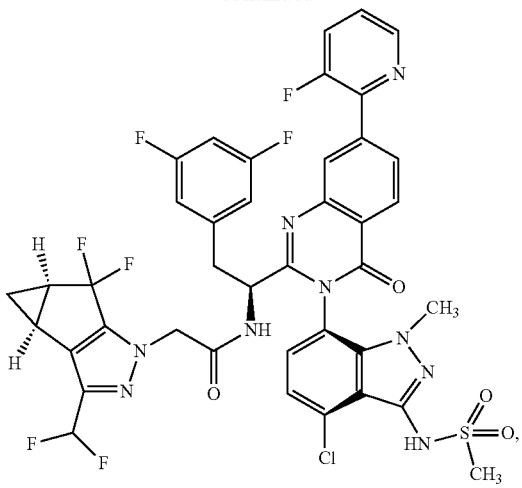
and pharmaceutically acceptable salts thereof.
In another embodiment, the present invention discloses a compound or salt selected from the group consisting of:
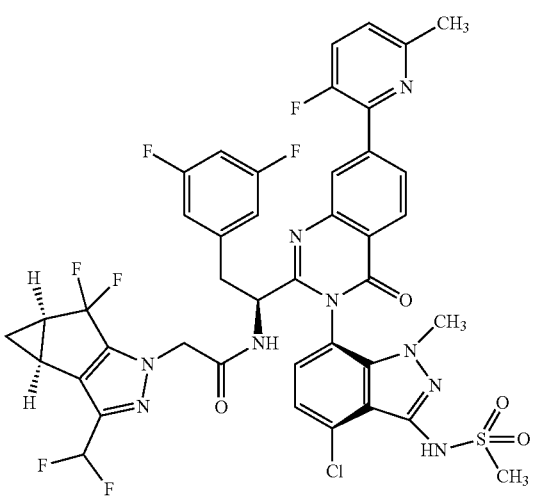
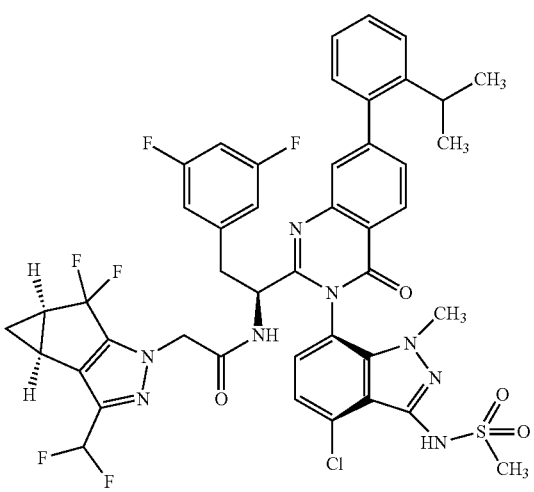

29
-continued
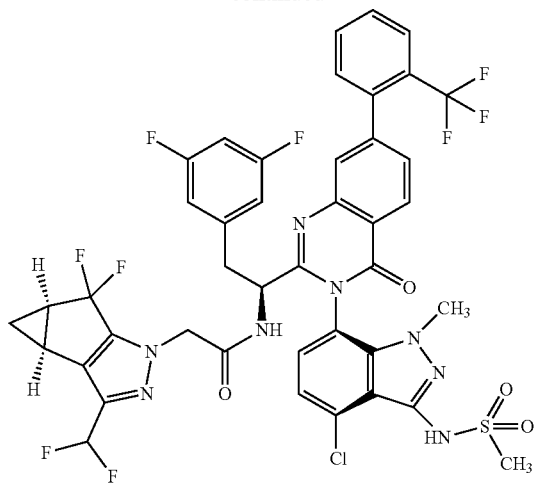
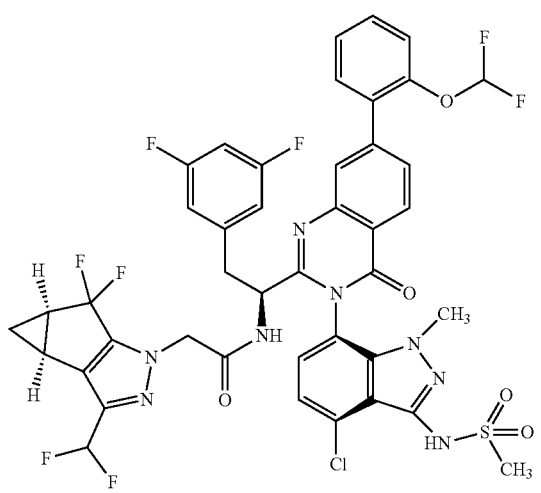
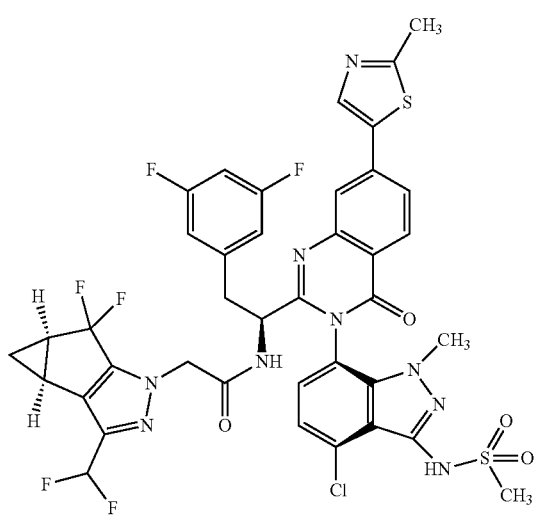
30
-continued
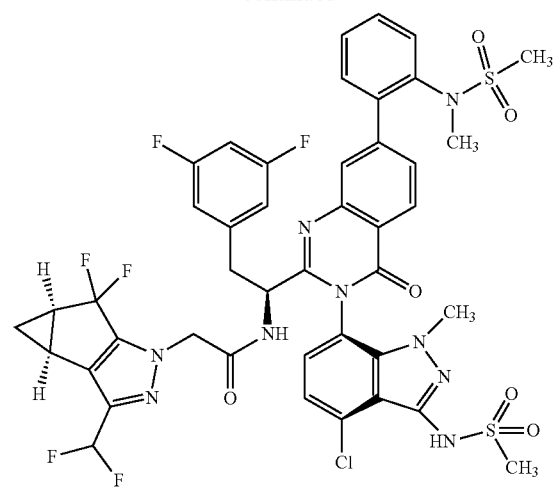
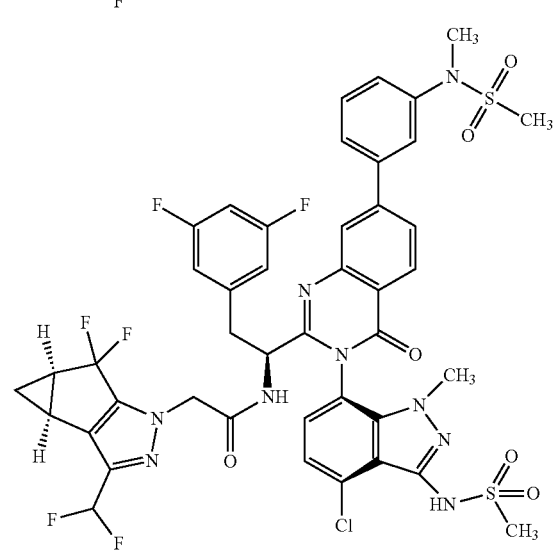
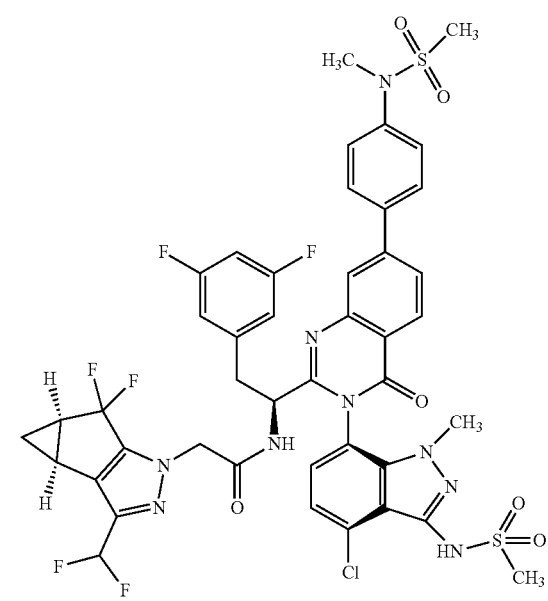

31
-continued
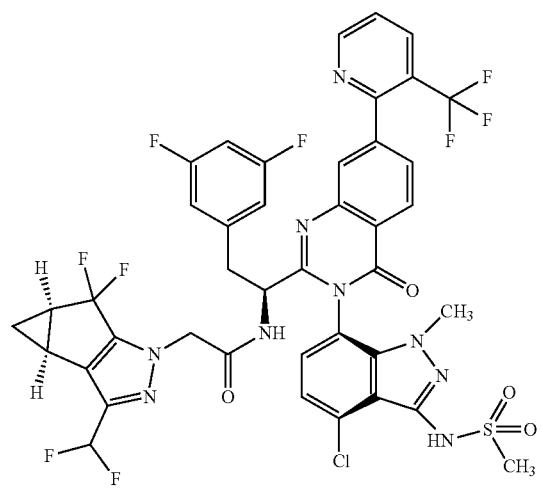
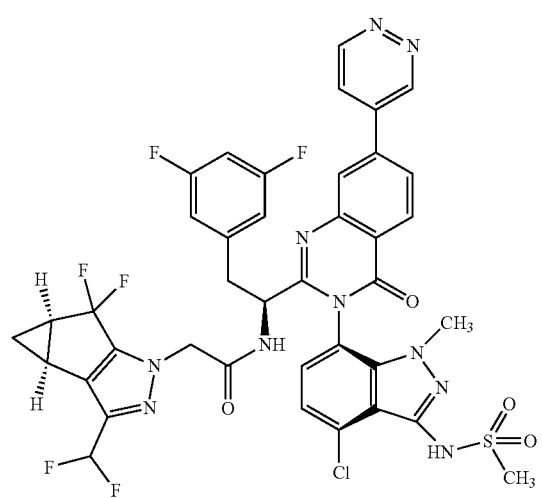
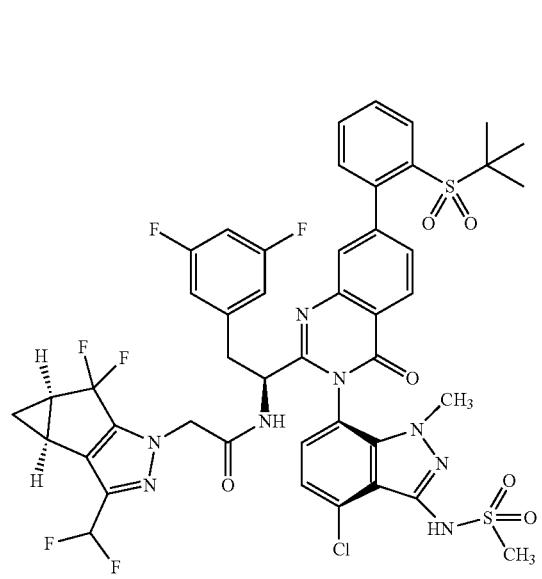
32
-continued
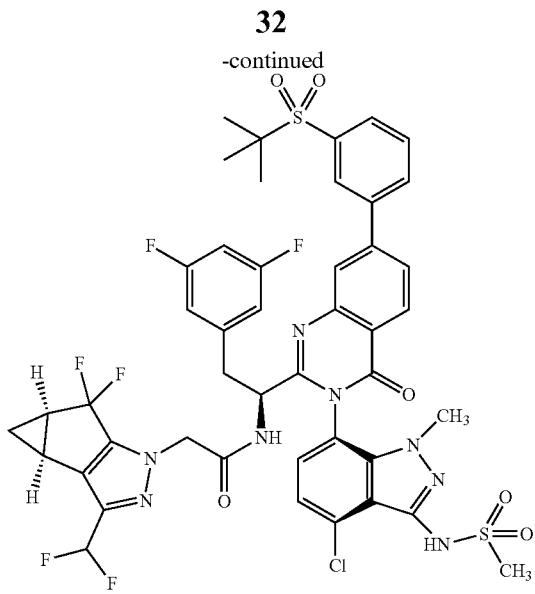
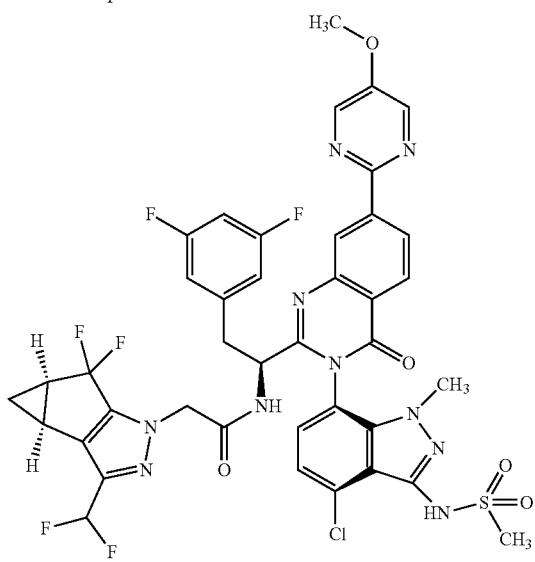
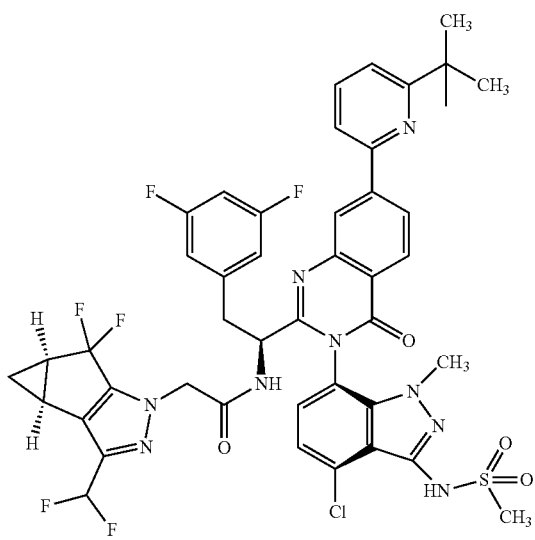

-continued
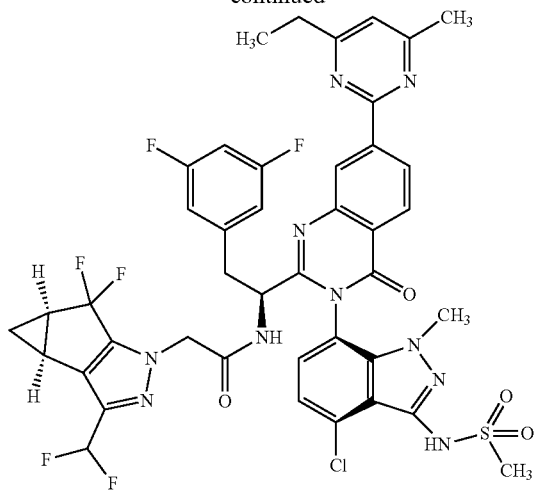
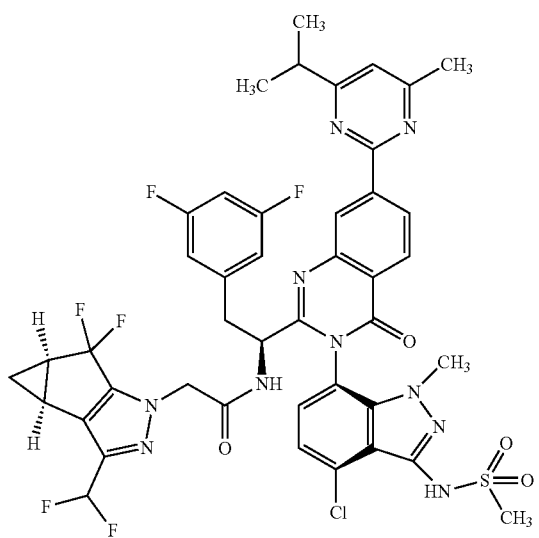
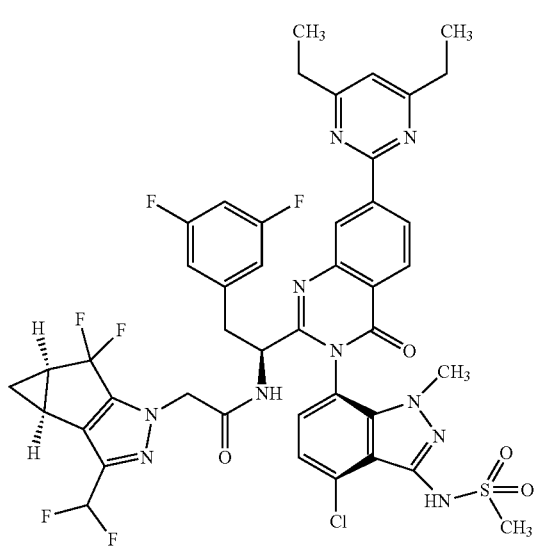
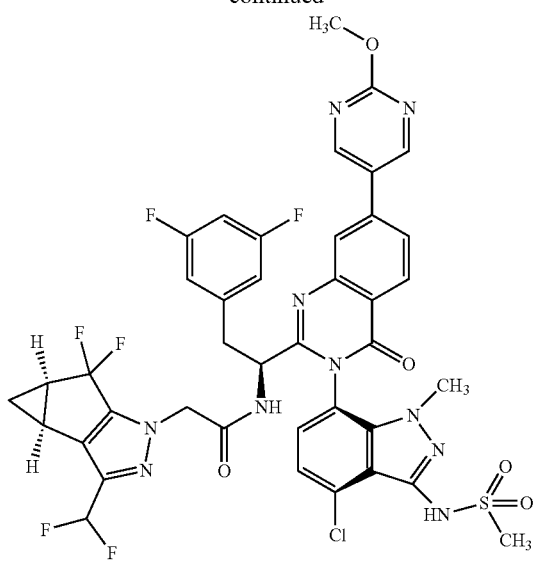
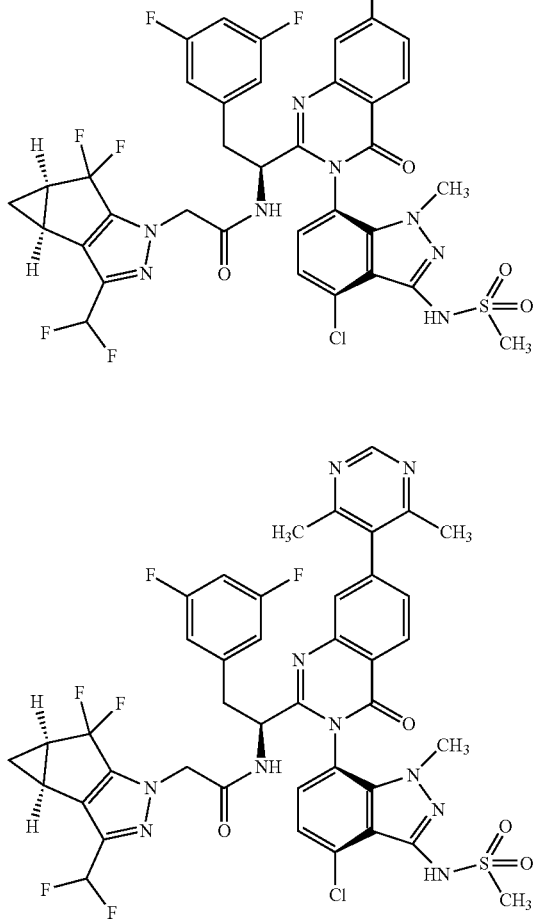

35
-continued
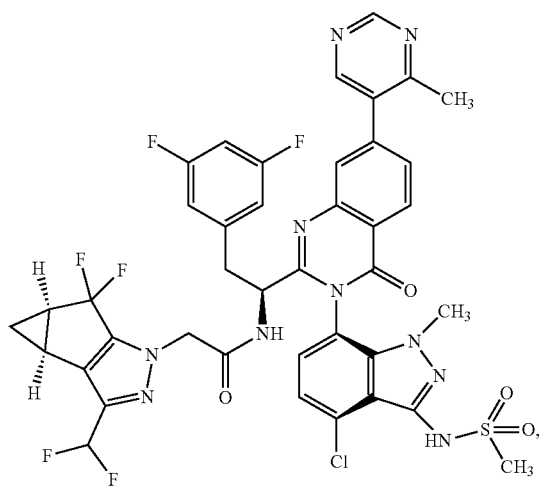
and pharmaceutically acceptable salts thereof.
In another embodiment, the present invention discloses a compound or salt selected from the group consisting of:
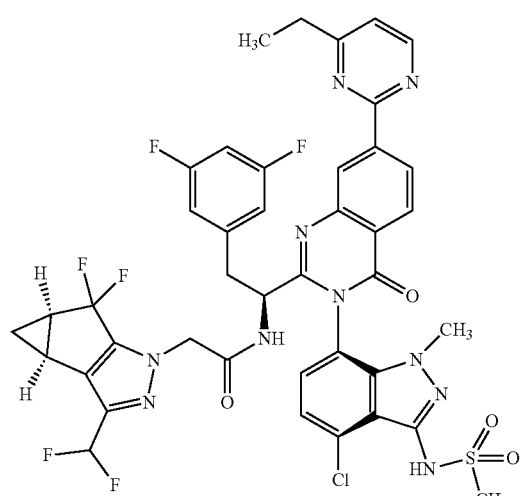
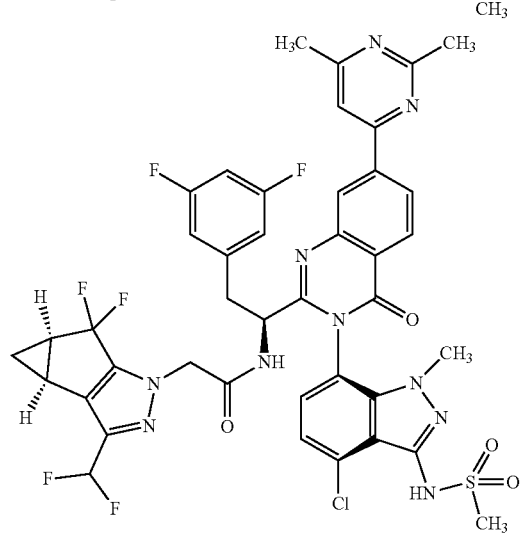
36
-continued
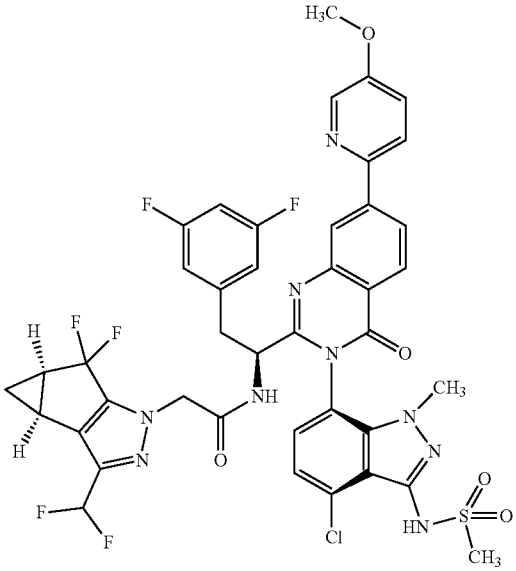
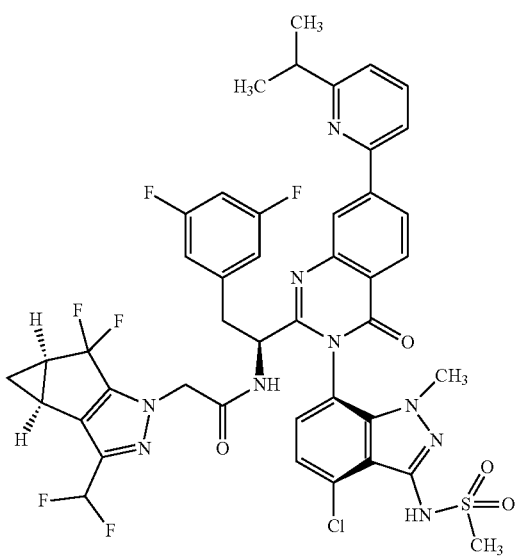
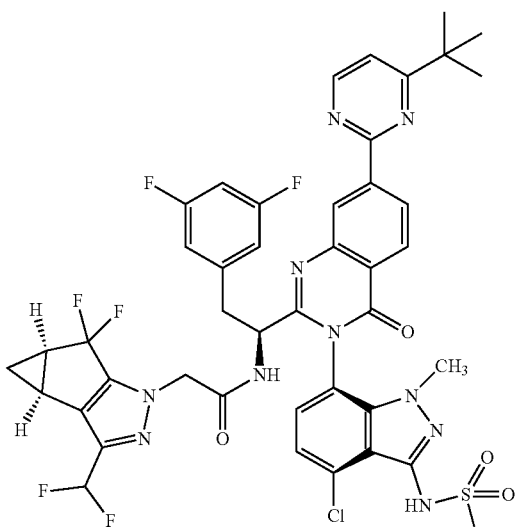

37
-continued
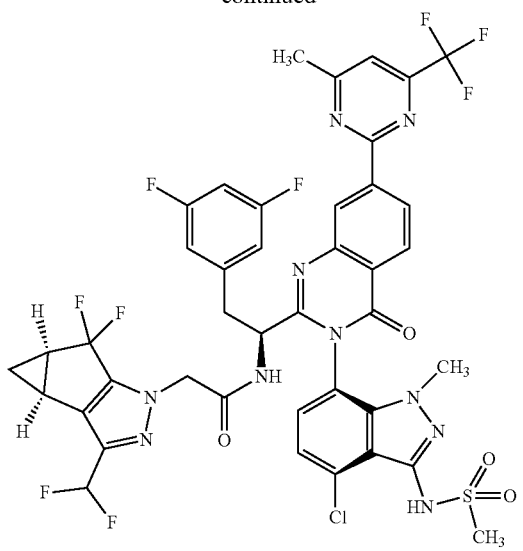
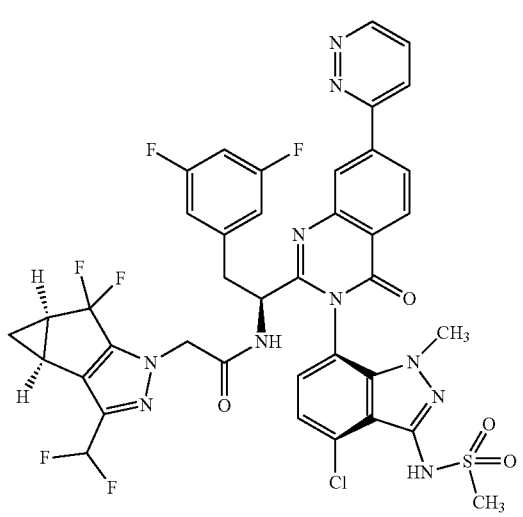
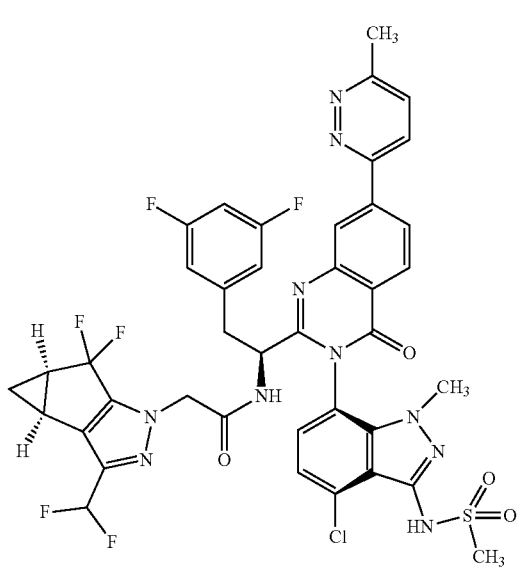
38
-continued
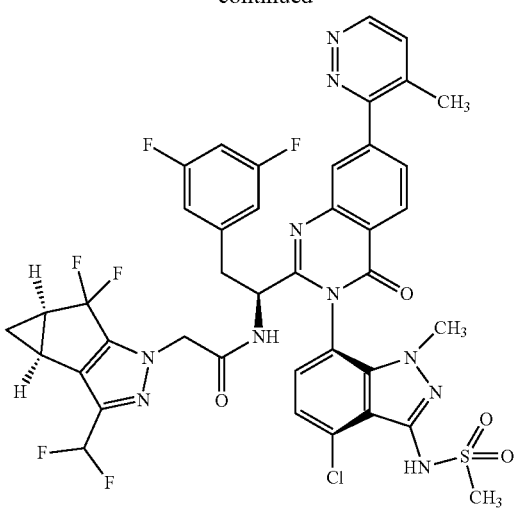
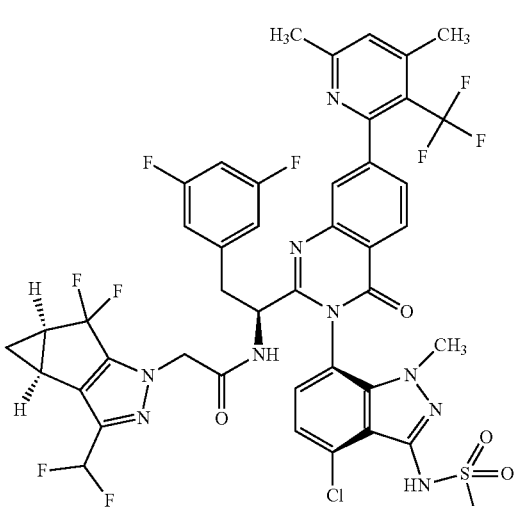
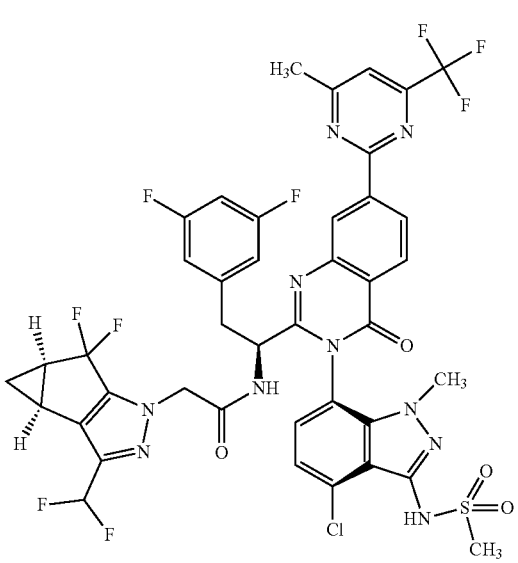

-continued
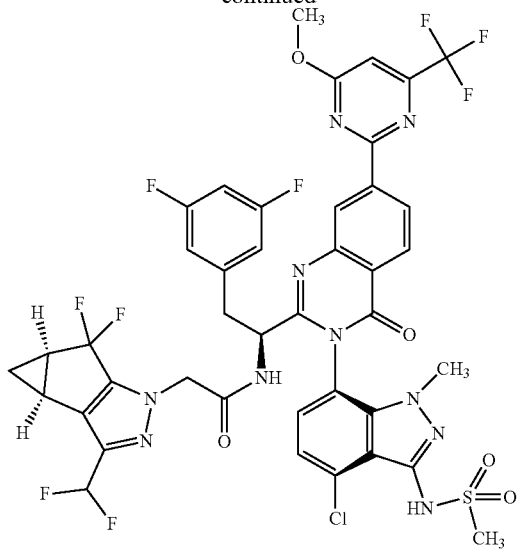
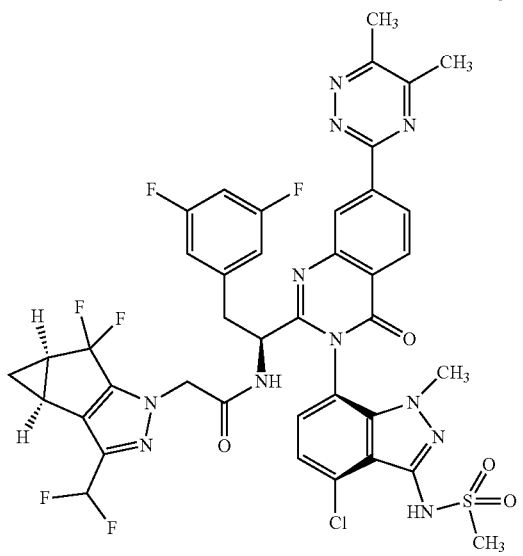
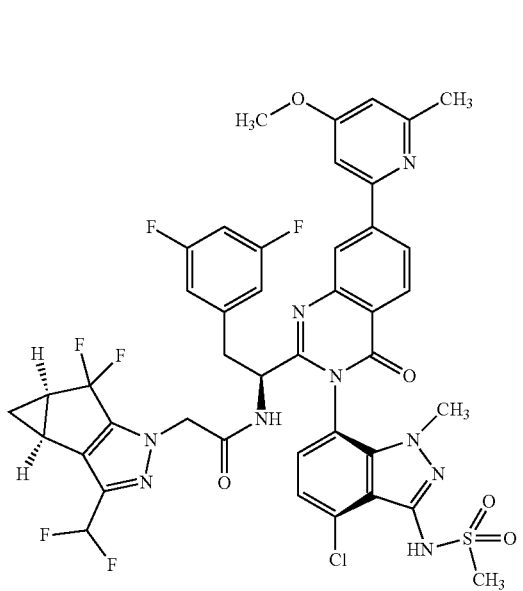
-continued
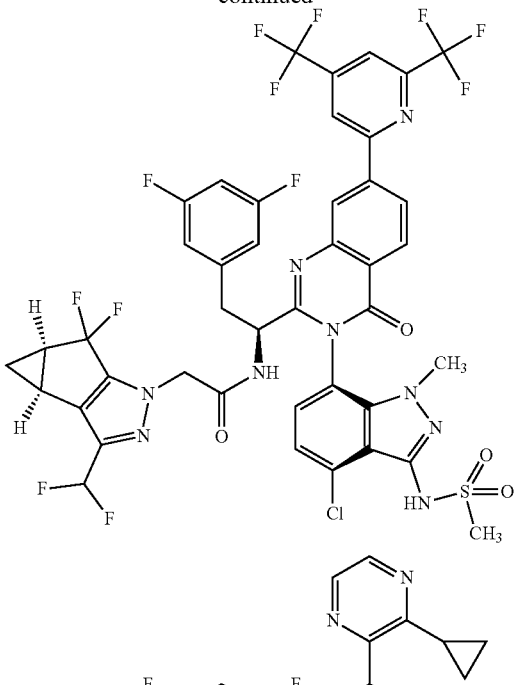
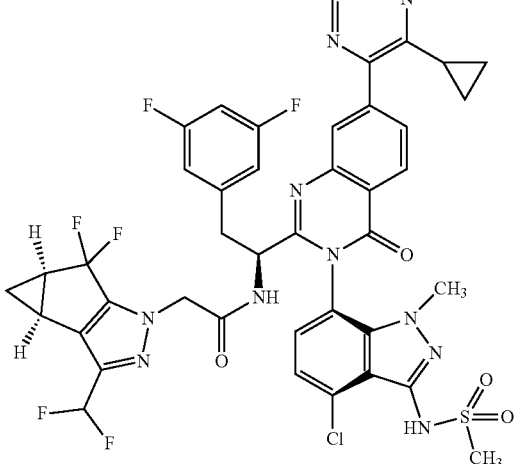
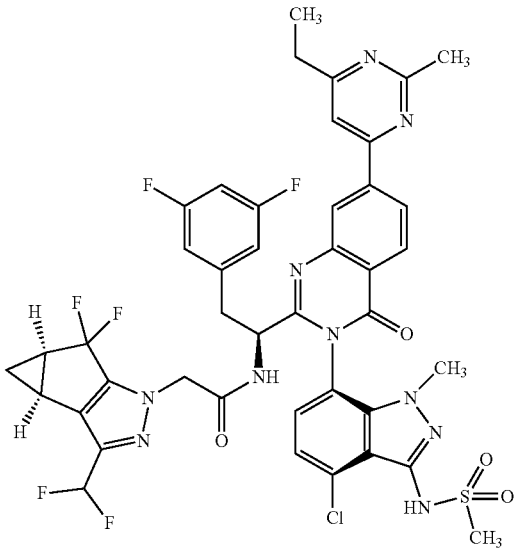

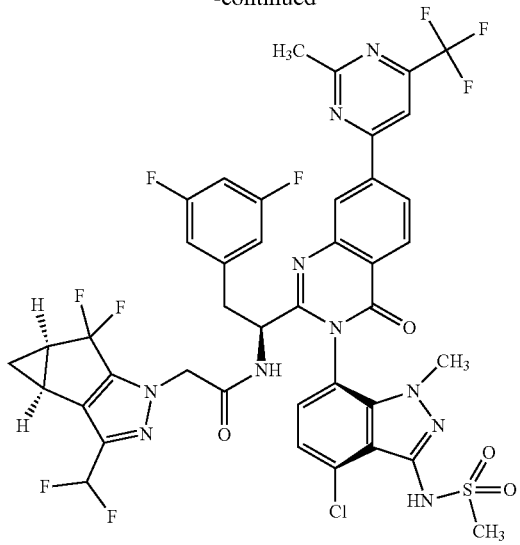
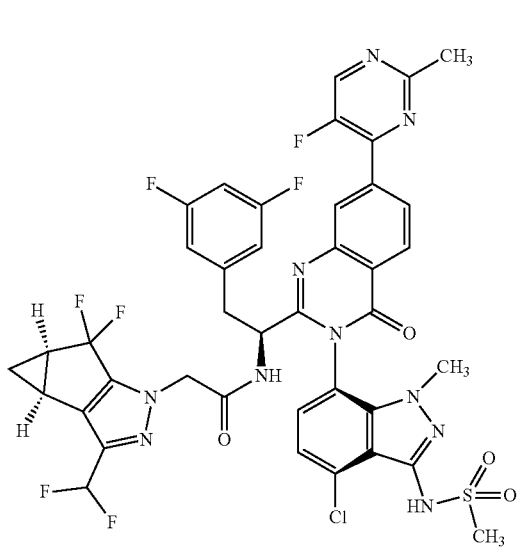
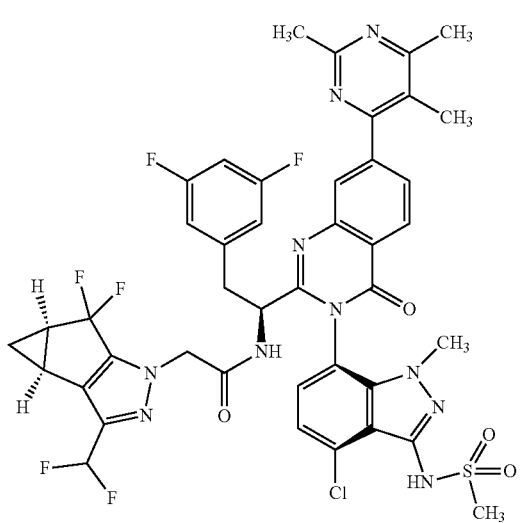
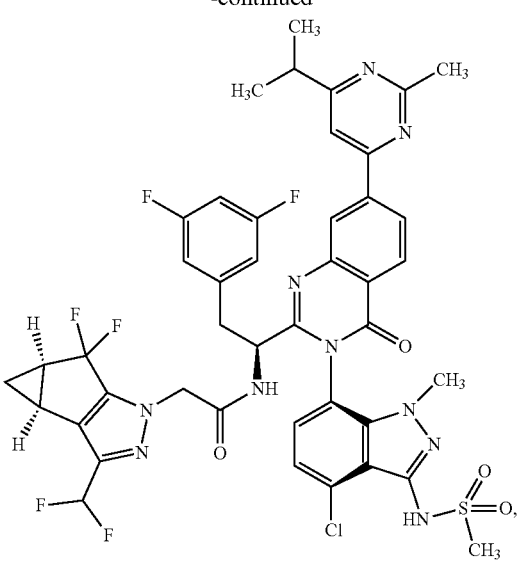
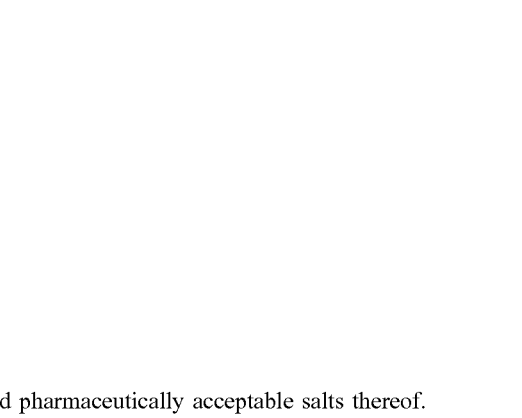
and pharmaceutically acceptable salts thereof.
In another embodiment, the present invention discloses a compound or salt selected from the group consisting of:
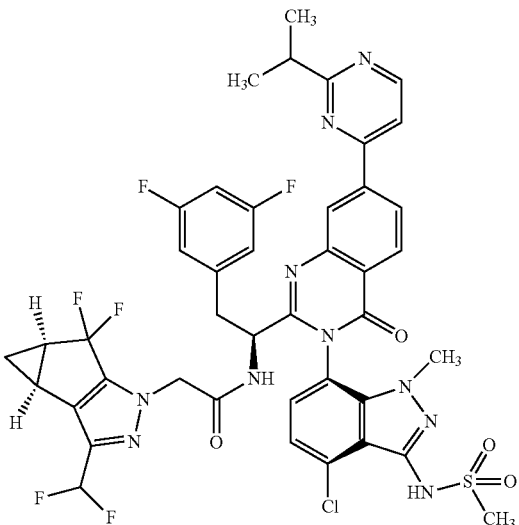

43
-continued
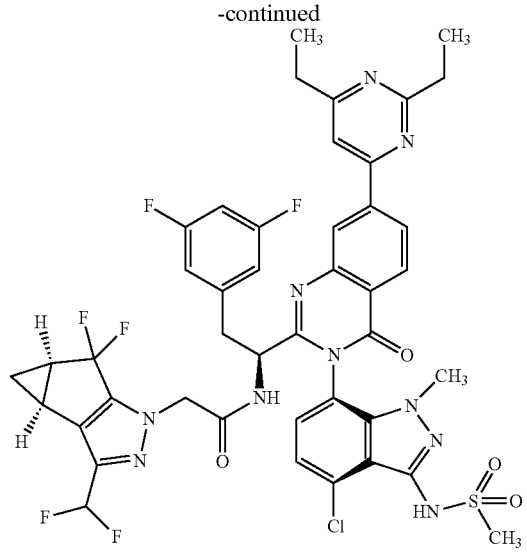
44
-continued
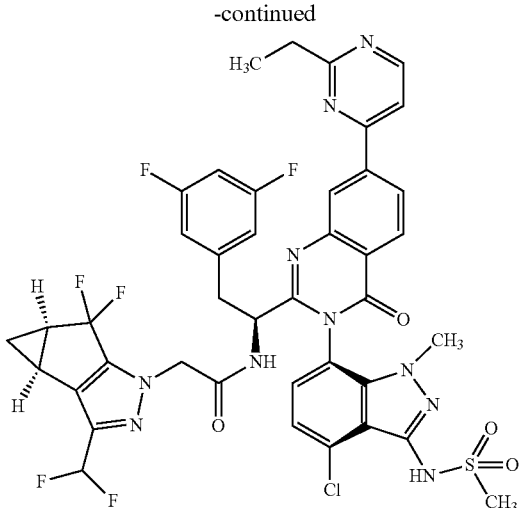
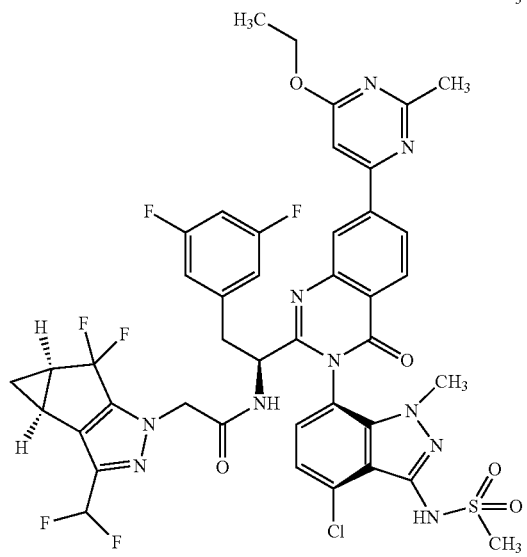
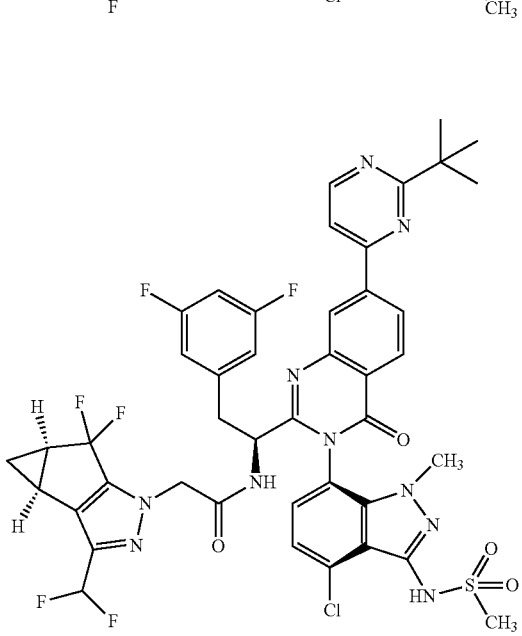

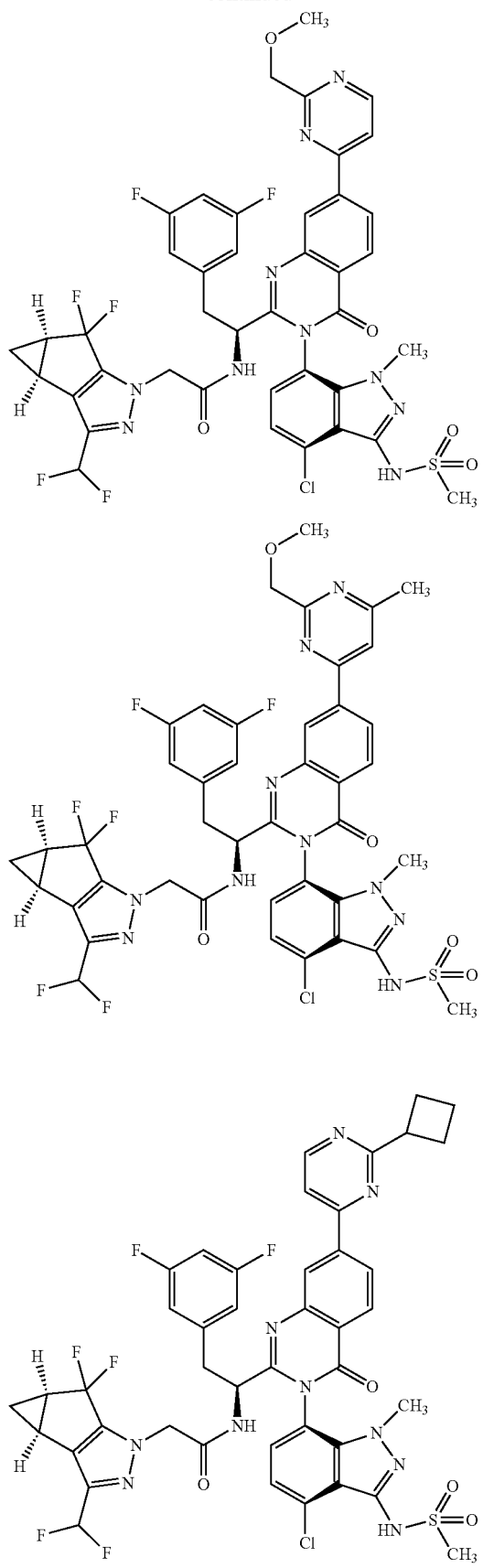
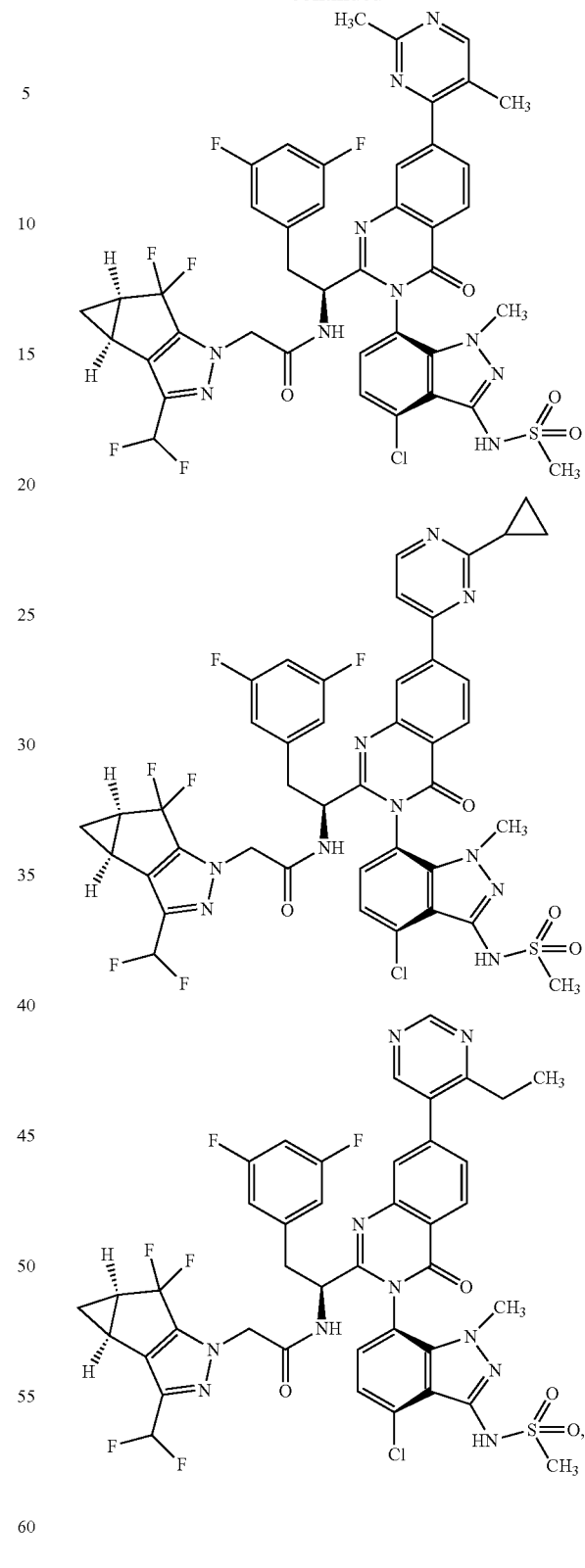
and pharmaceutically acceptable salts thereof.
In another embodiment, the present invention discloses a compound or salt selected from the group consisting of:

47
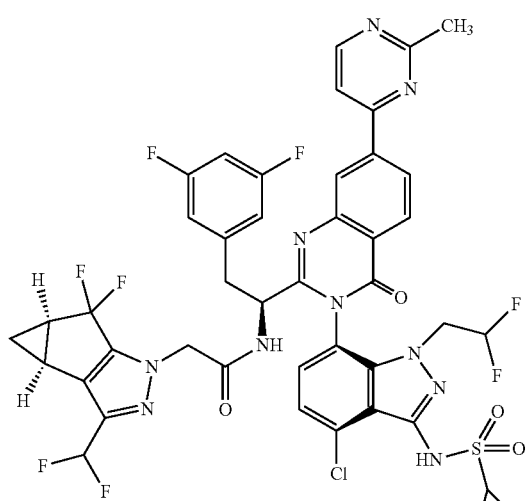
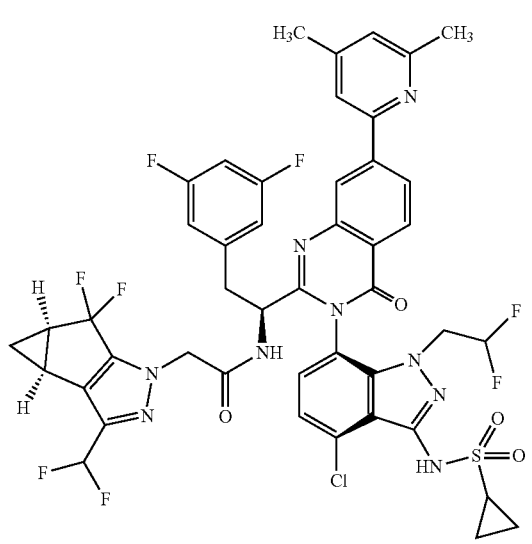
48
-continued
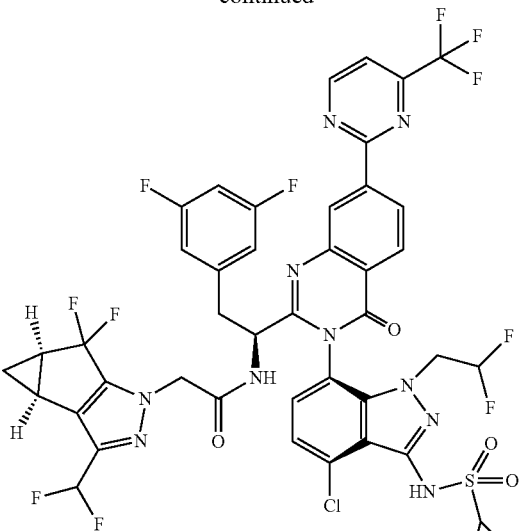
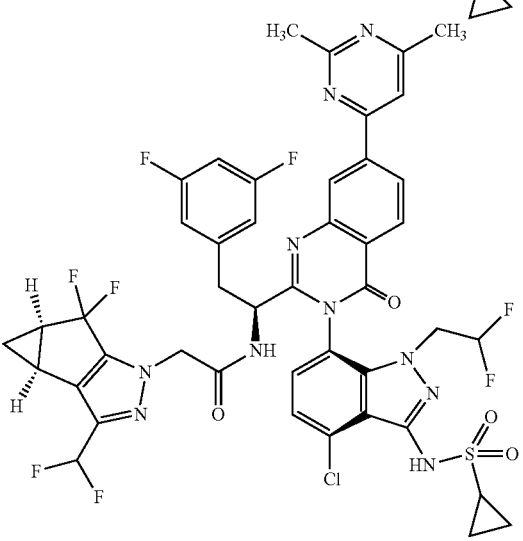
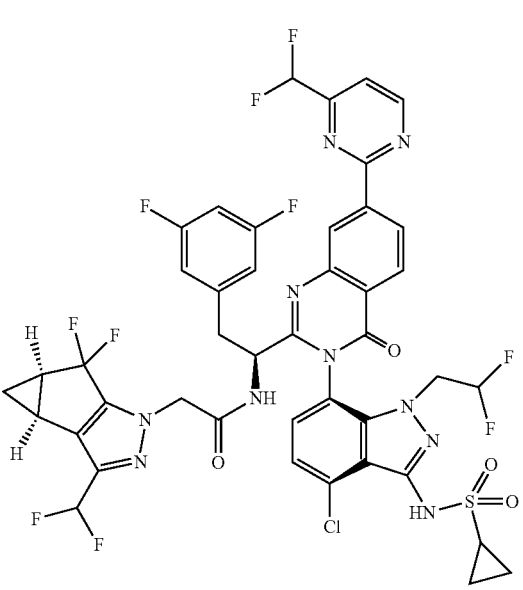

49
-continued
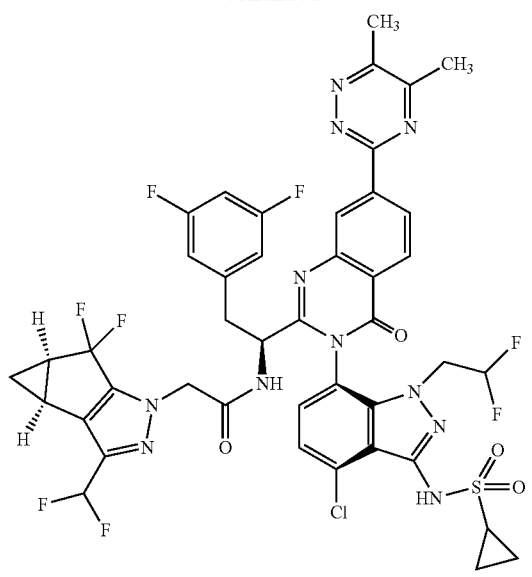
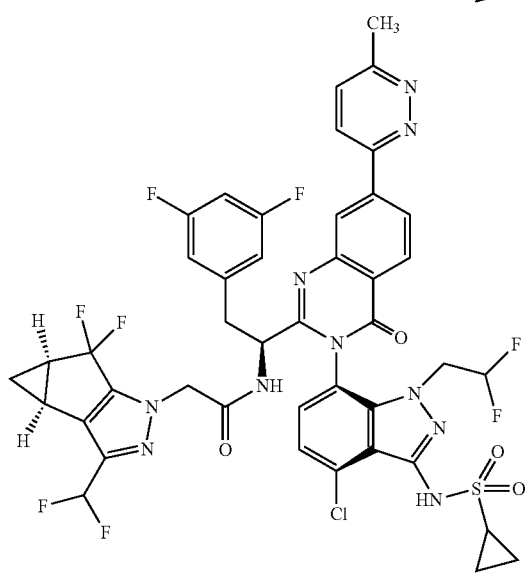
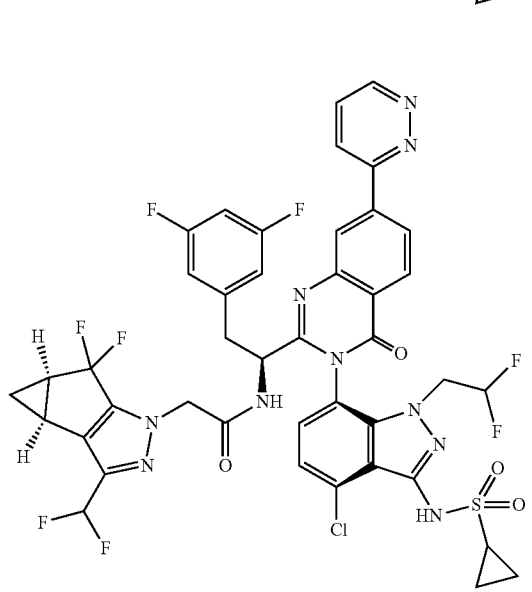
50
-continued
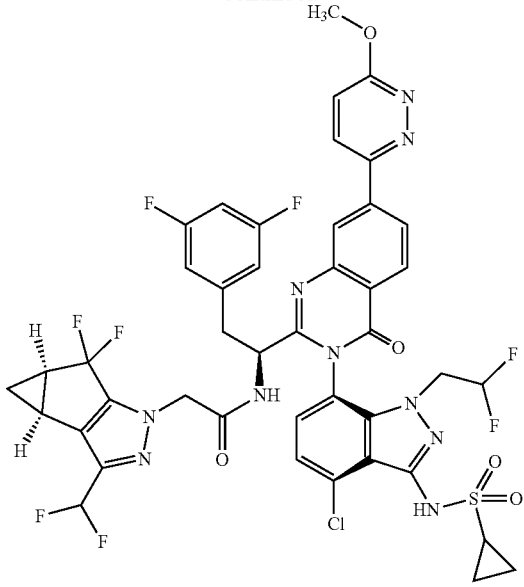
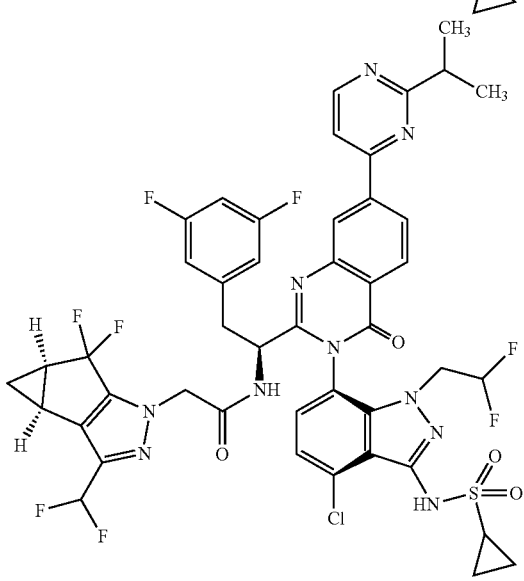
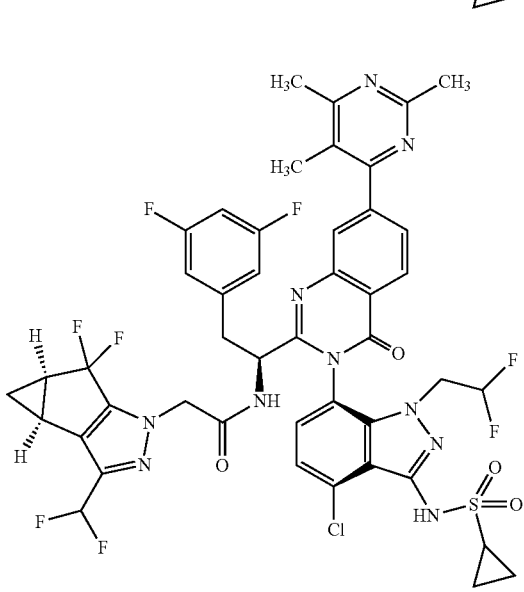

51
-continued
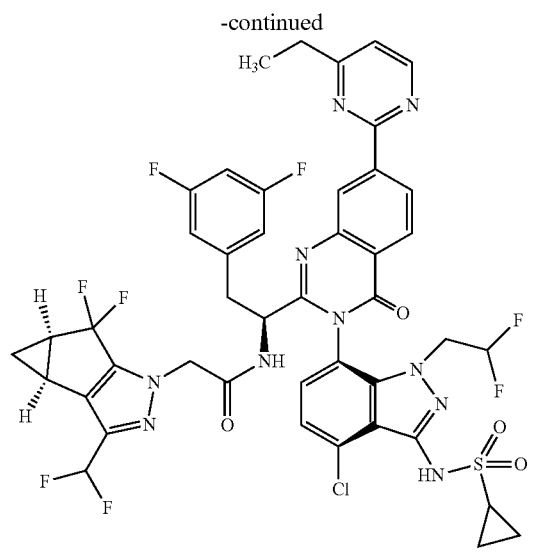
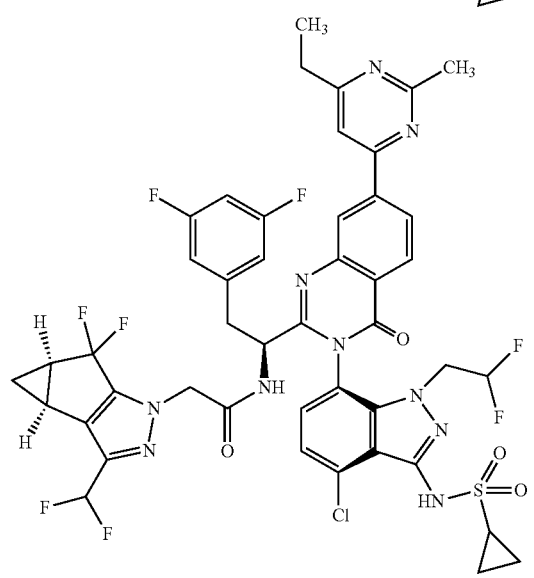
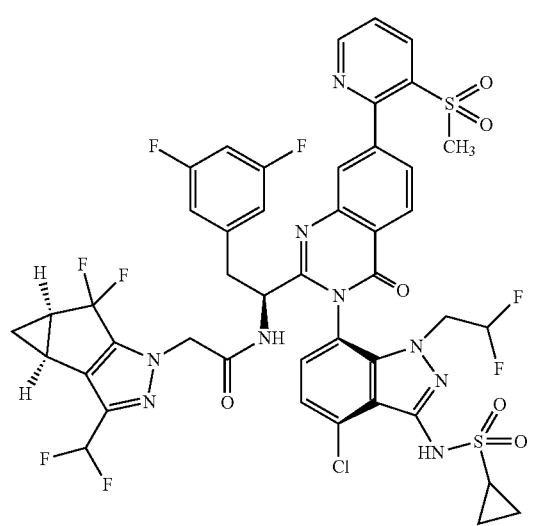
52
-continued
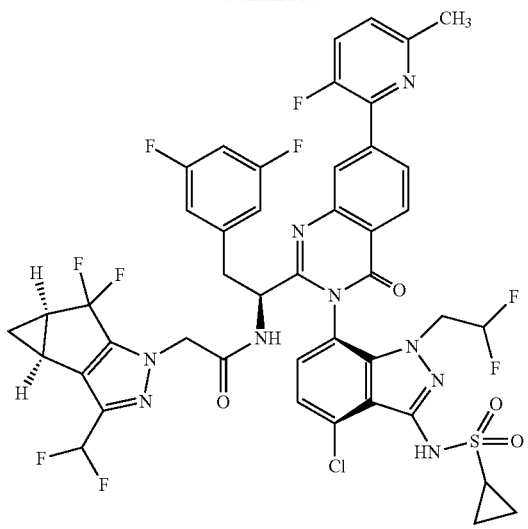
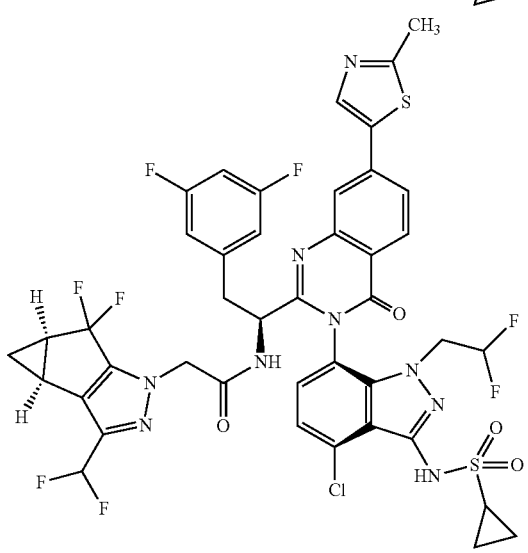
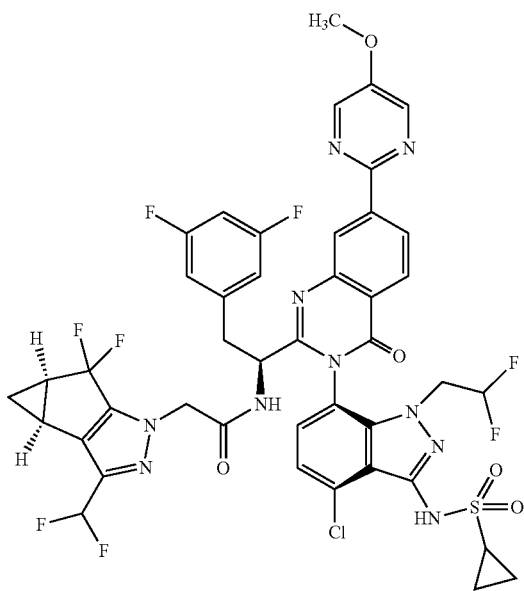

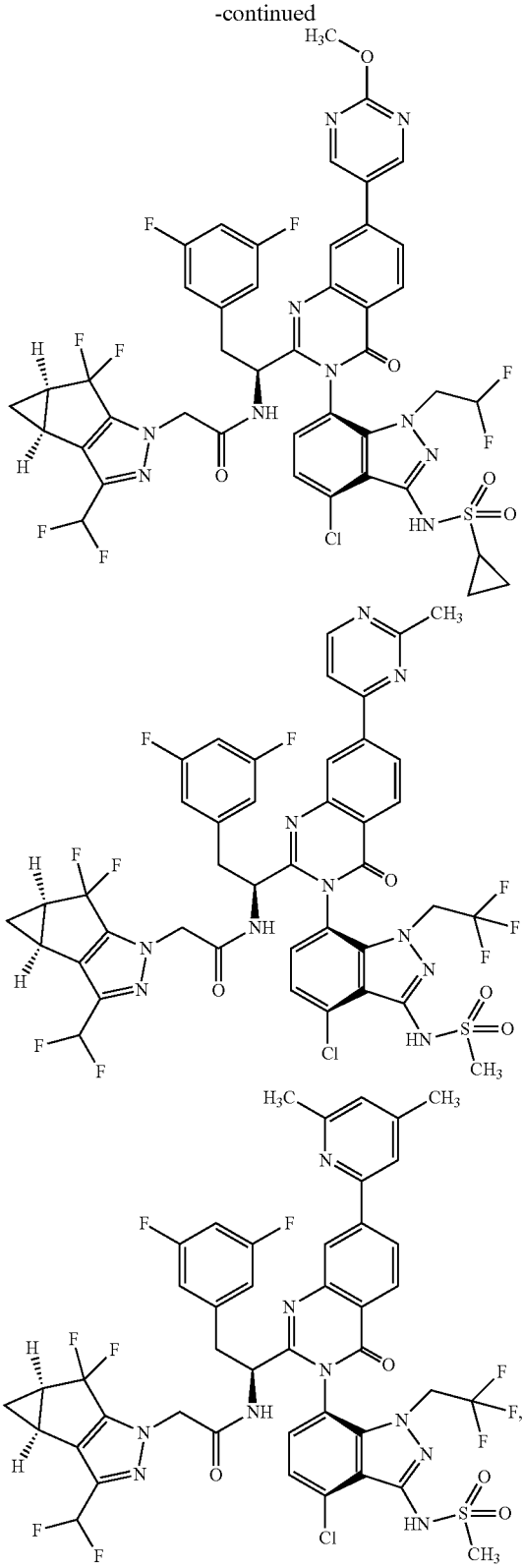
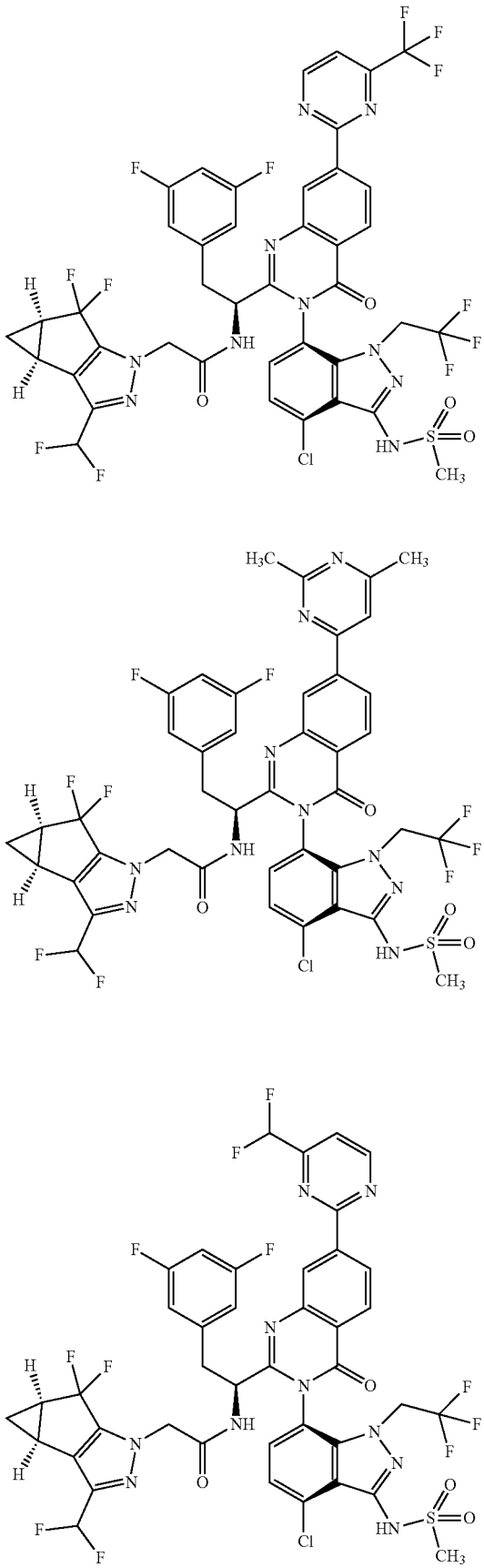
and pharmaceutically acceptable salts thereof.
In another embodiment, the present invention discloses a compound or salt selected from the group consisting of:

55
-continued
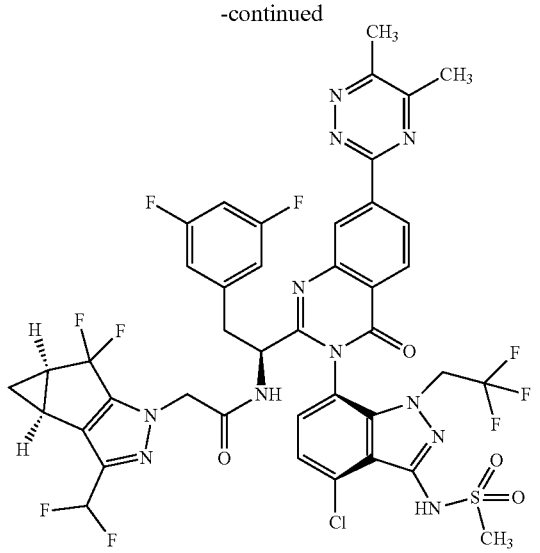
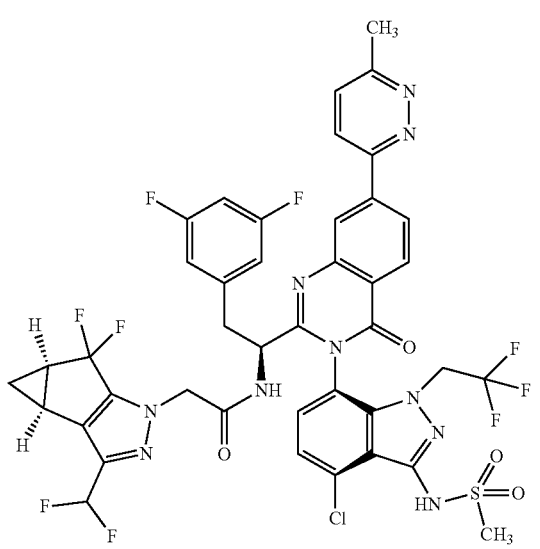
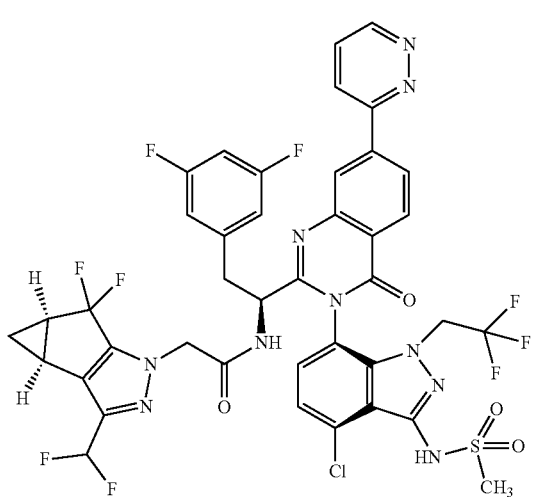
56
-continued
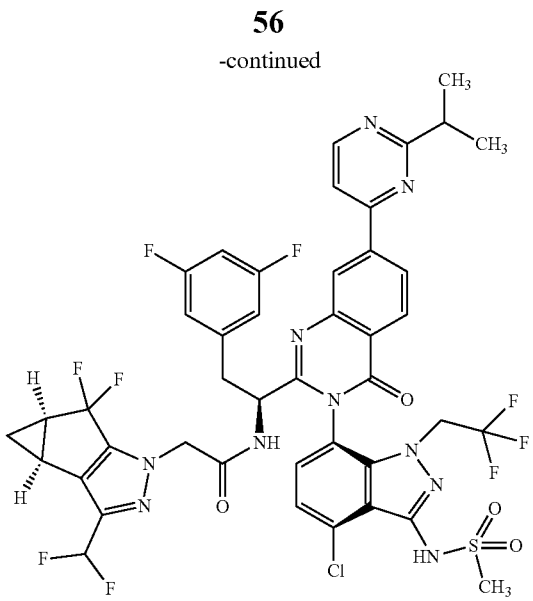
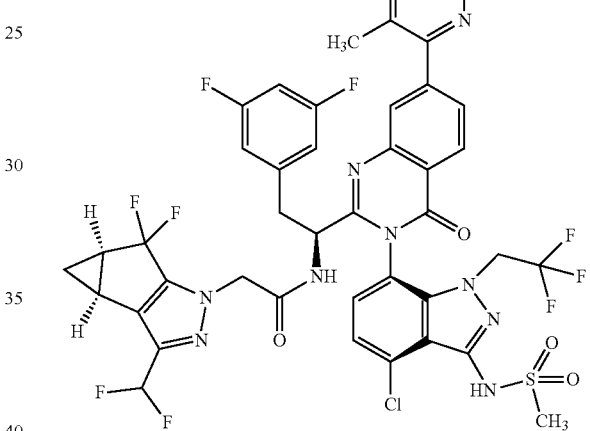
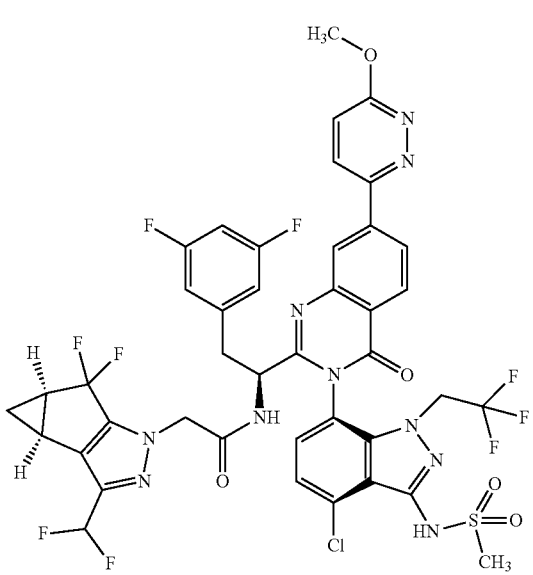

57
-continued
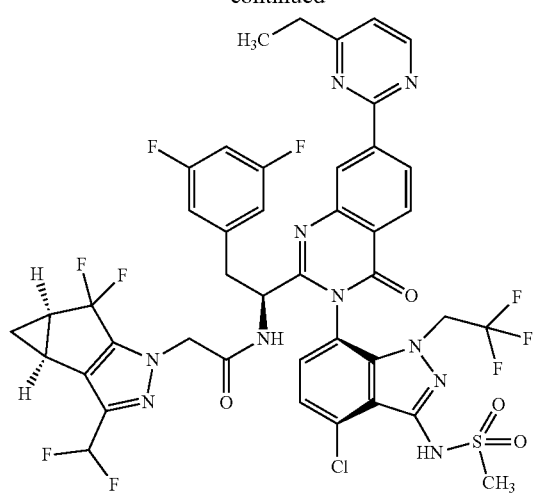
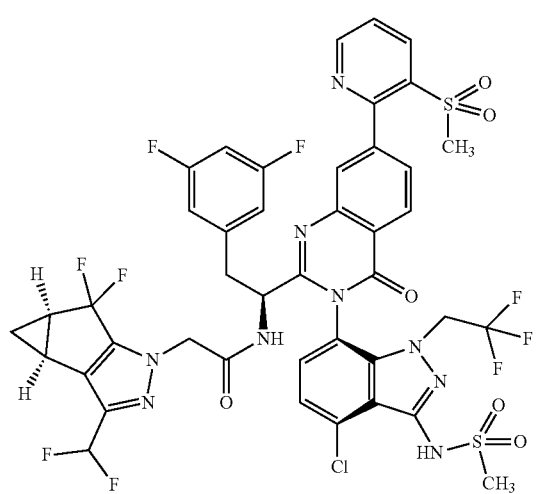
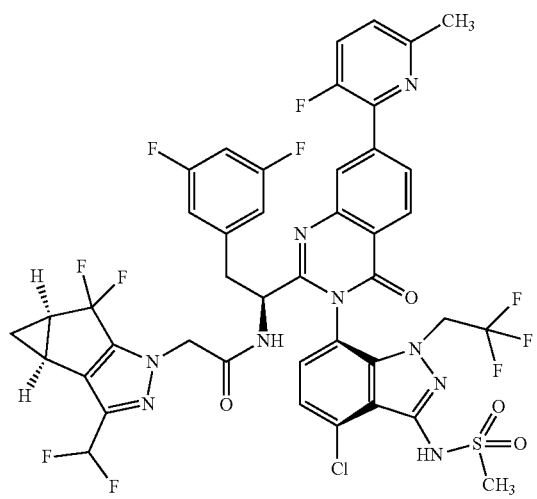
58
-continued
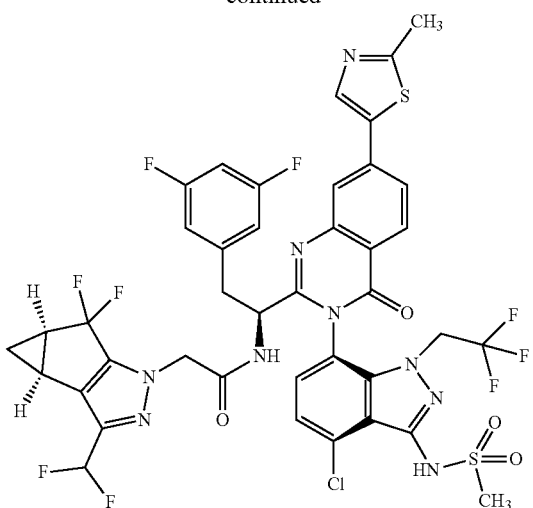
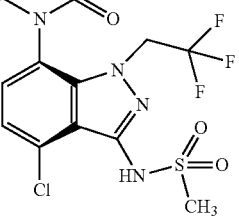
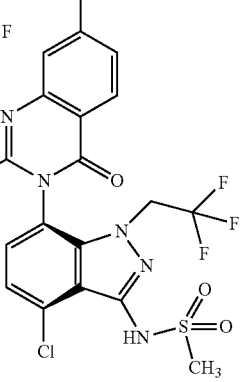

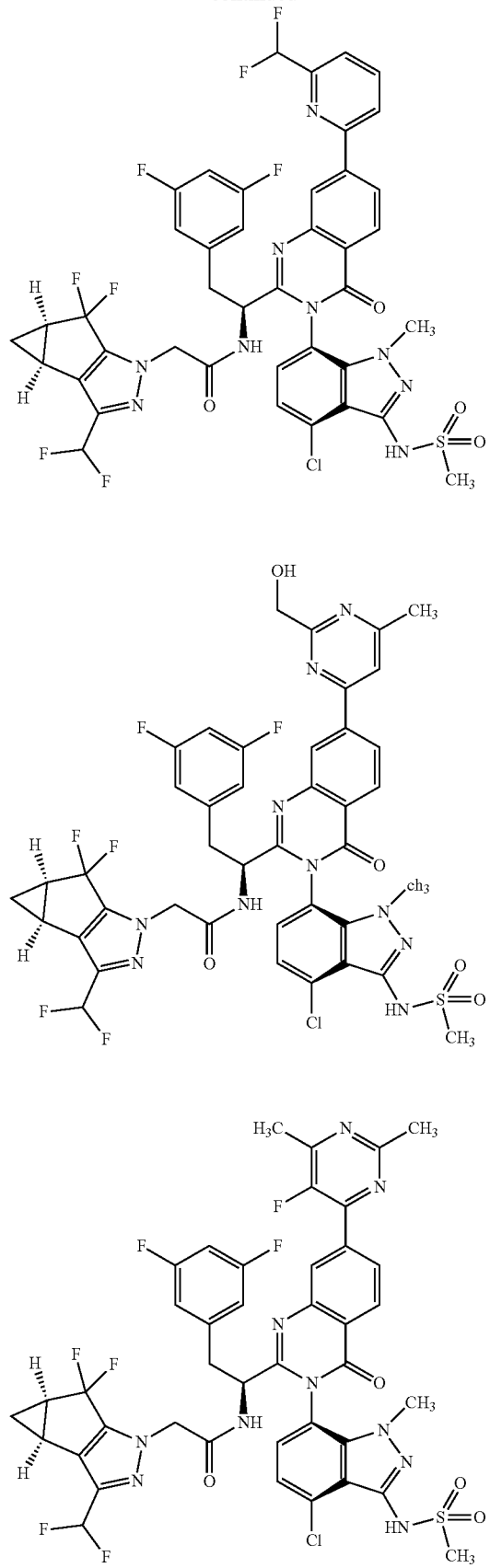
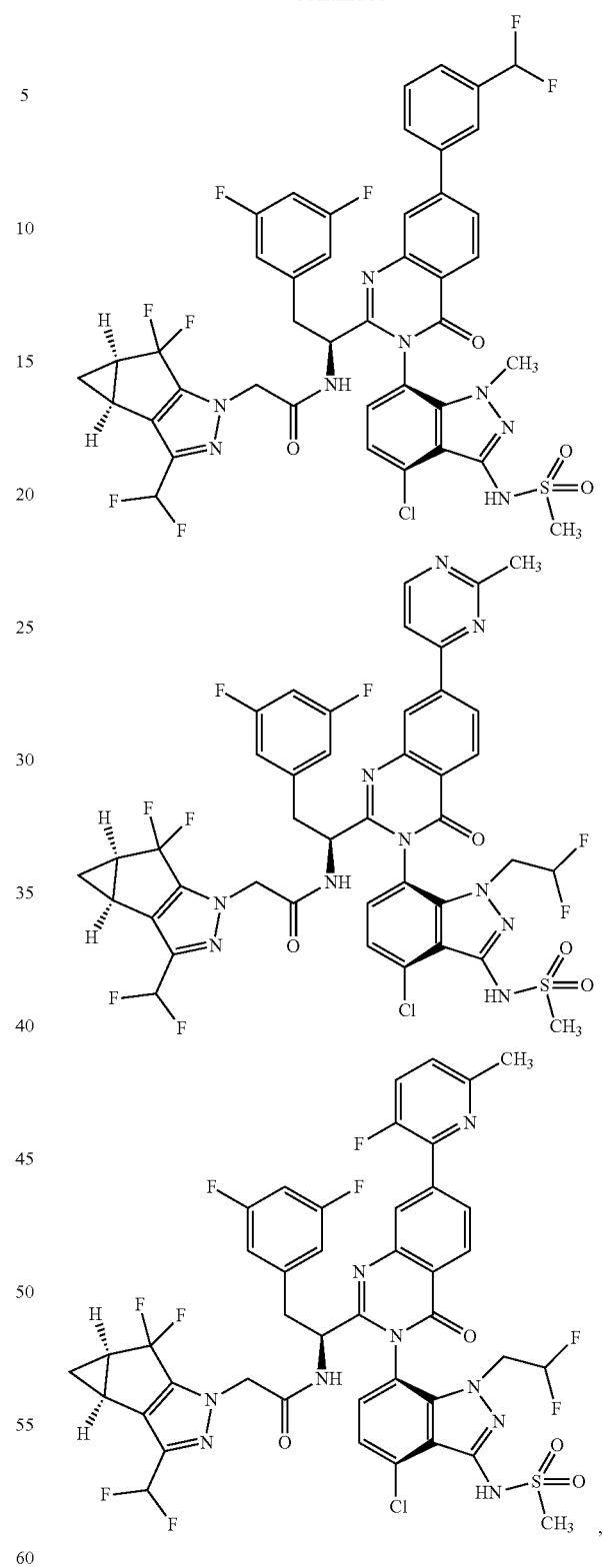
and pharmaceutically acceptable salts thereof.
In another embodiment, the present invention discloses a compound or salt selected from the group consisting of:

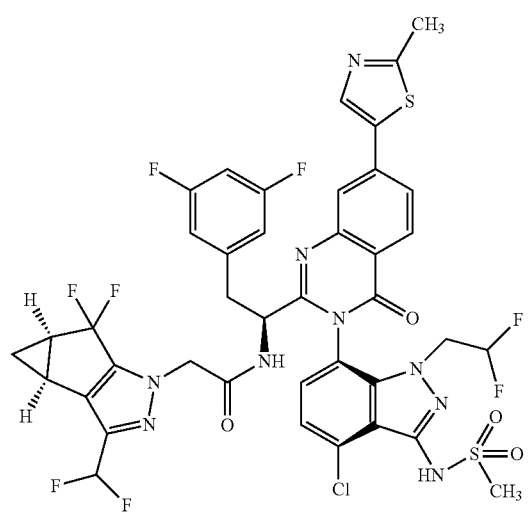
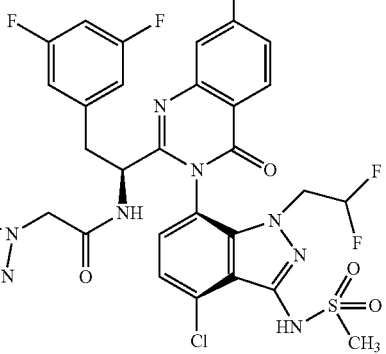
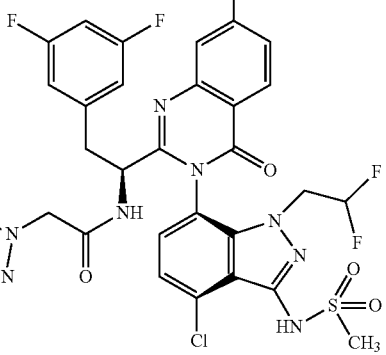
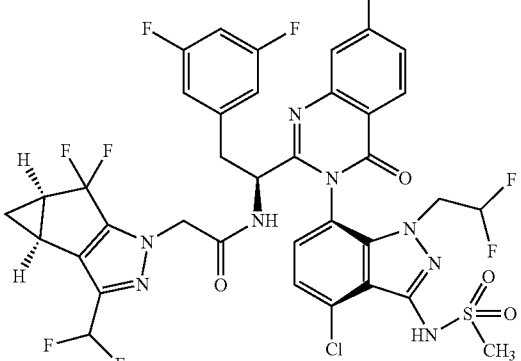

-continued
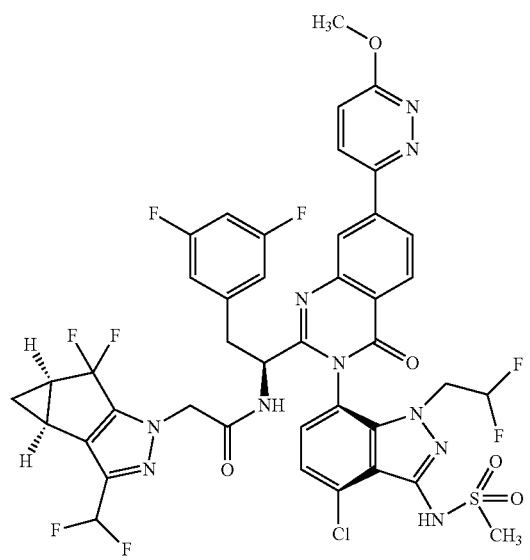
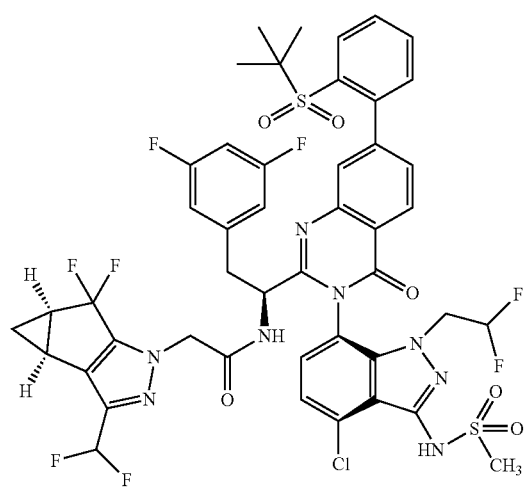
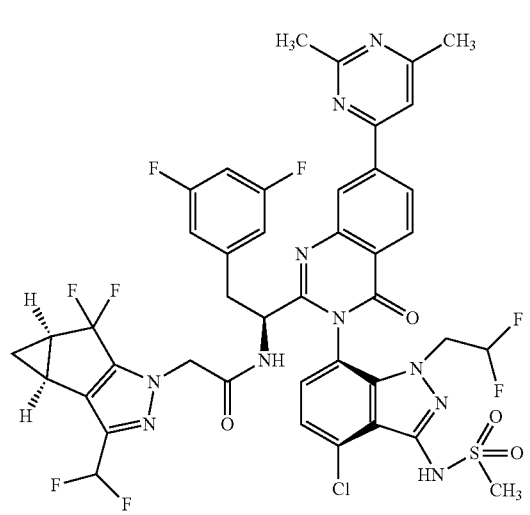
-continued
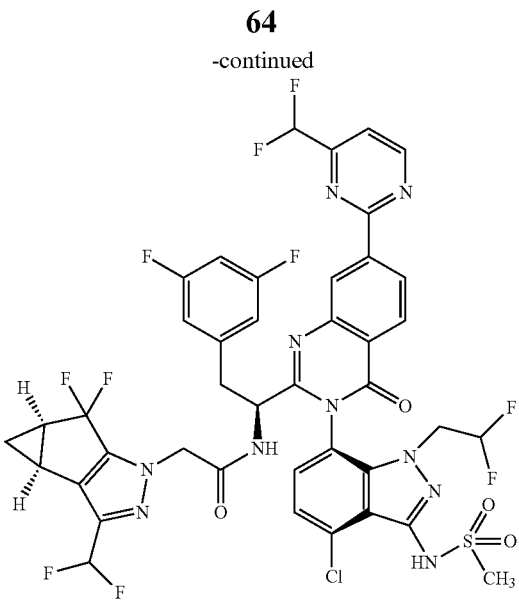
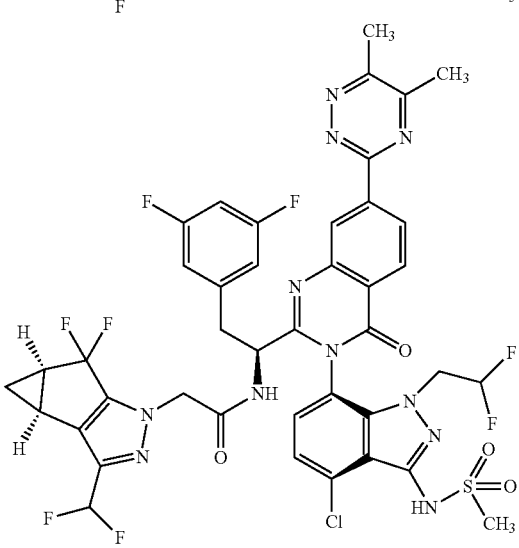
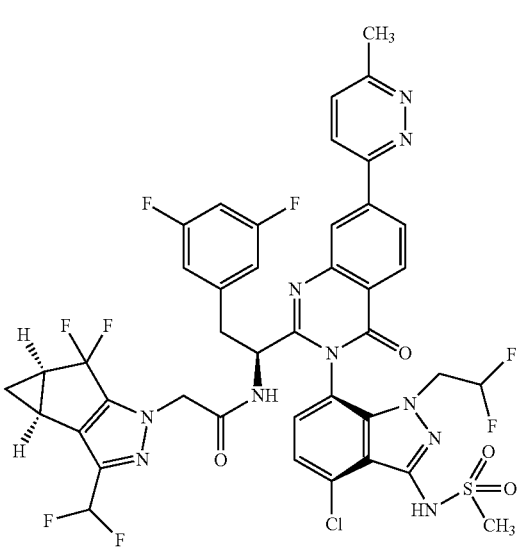

65
-continued
66
-continued
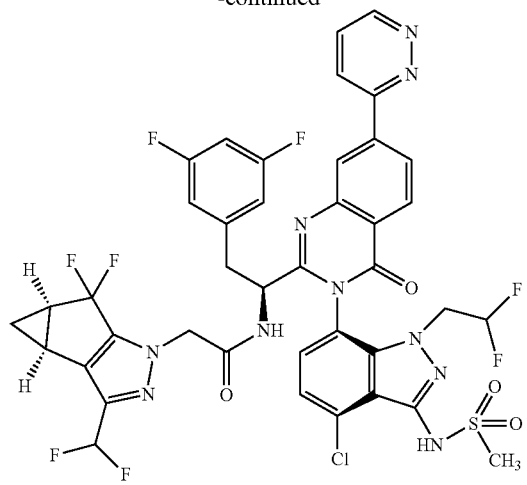
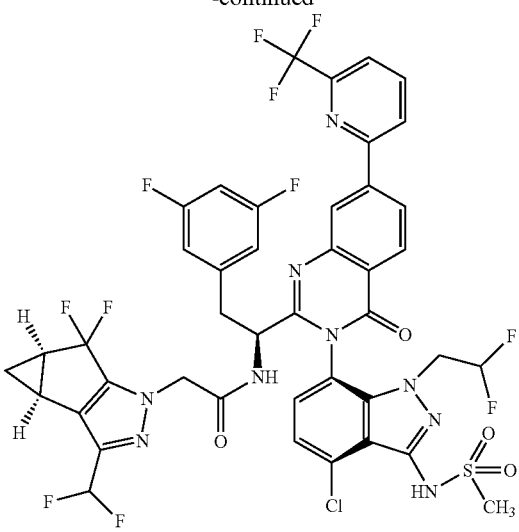

67
-continued
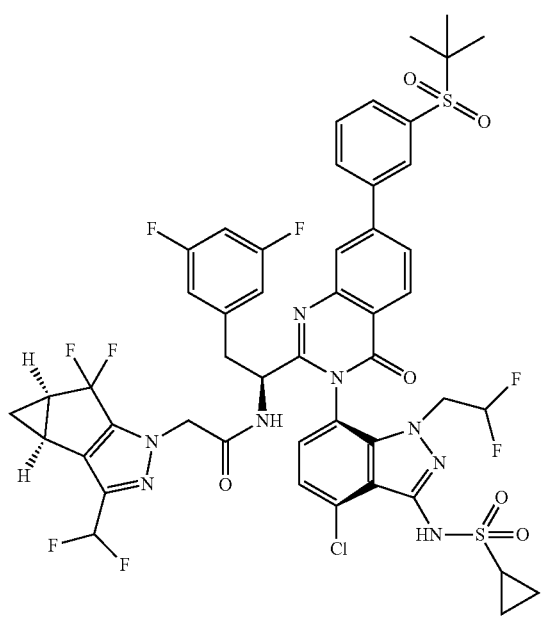
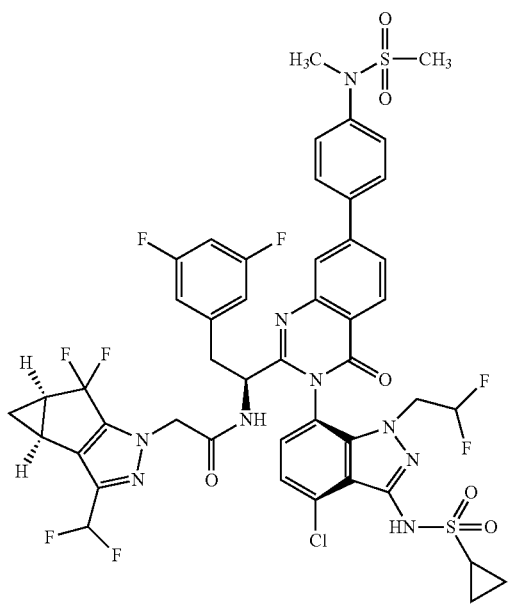
68
-continued
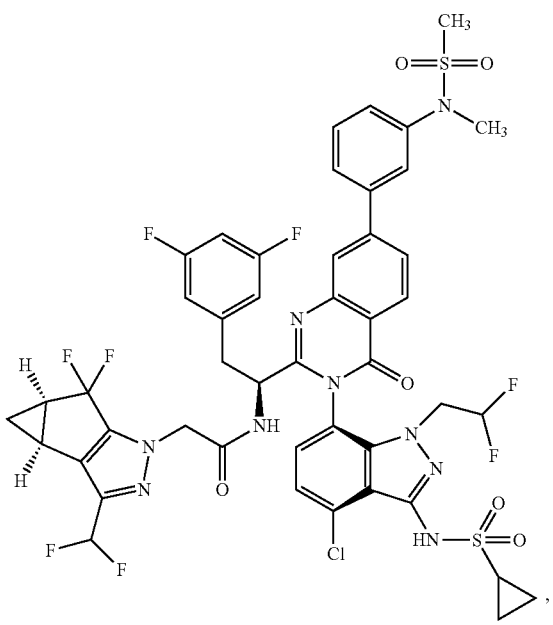
and pharmaceutically acceptable salts thereof.
In another embodiment, the present invention discloses a compound or salt selected from the group consisting of:
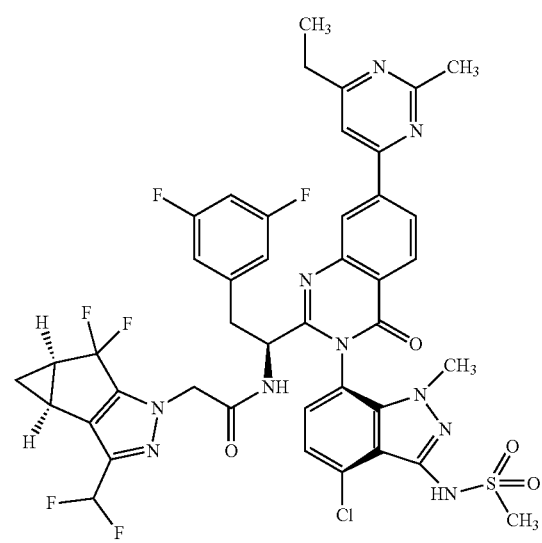

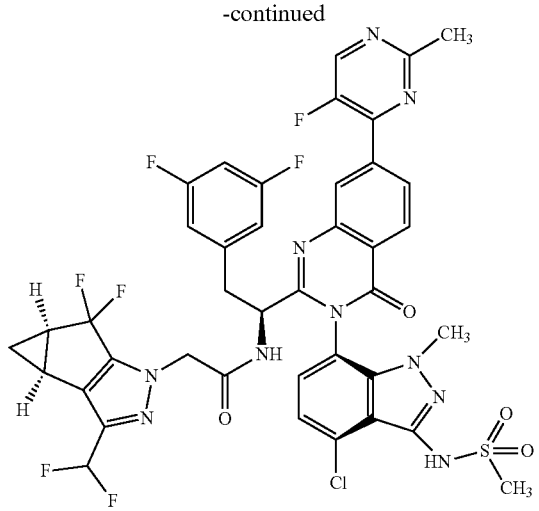
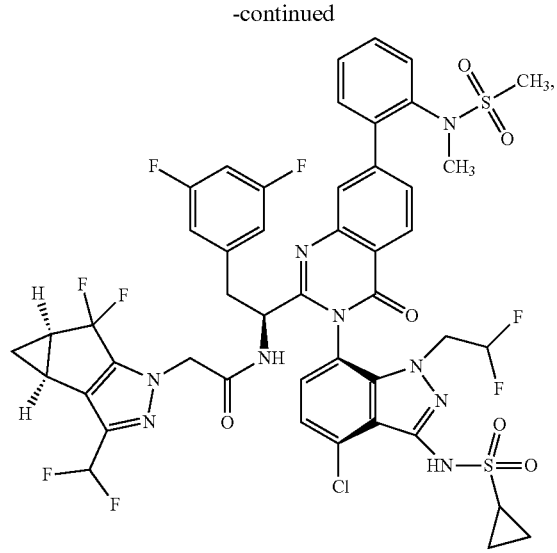
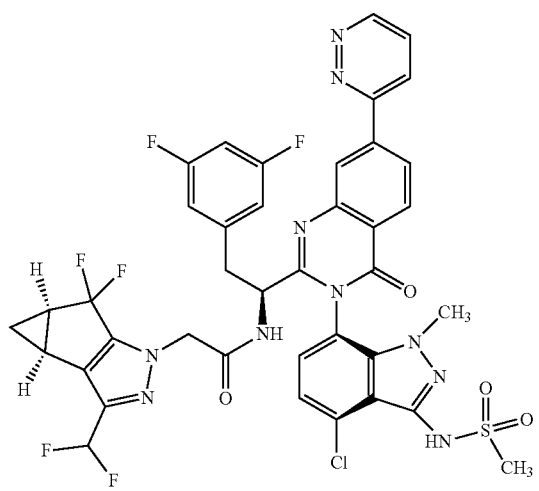
and pharmaceutically acceptable salts thereof.
In another embodiment, the present invention discloses a compound of Formula II, or a salt thereof, selected from the group consisting of:
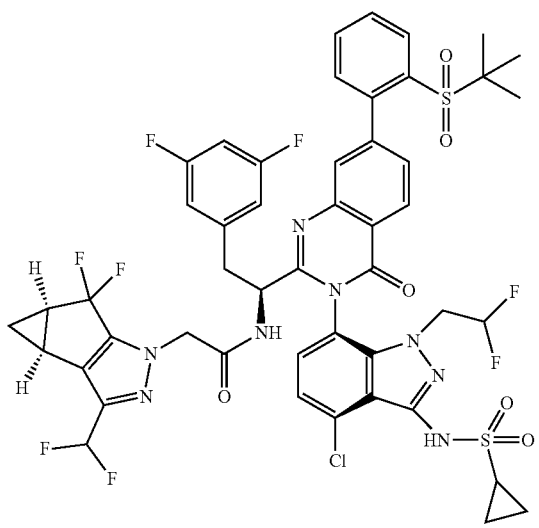

71
-continued
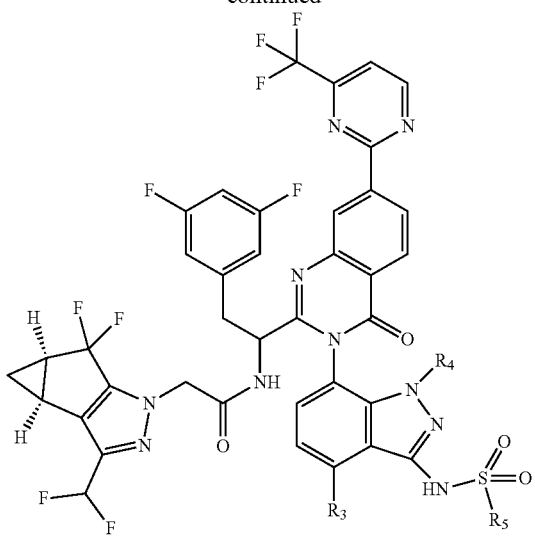
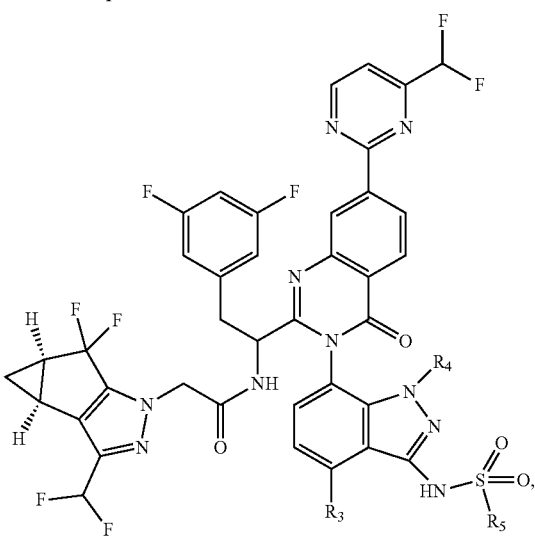
and pharmaceutically acceptable salts thereof.
In another embodiment, the present invention discloses a compound or salt selected from the group of:
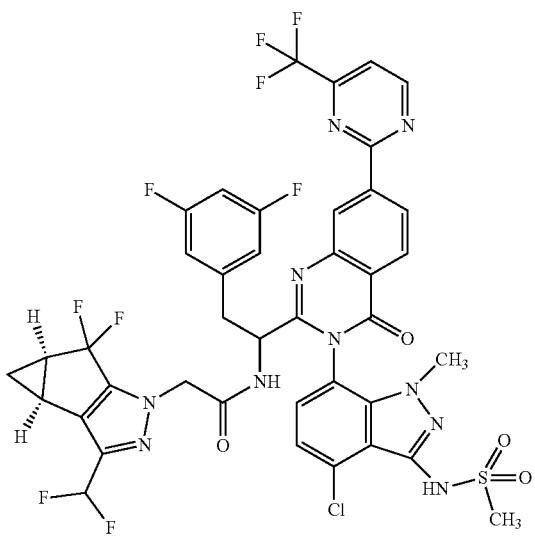
72
-continued
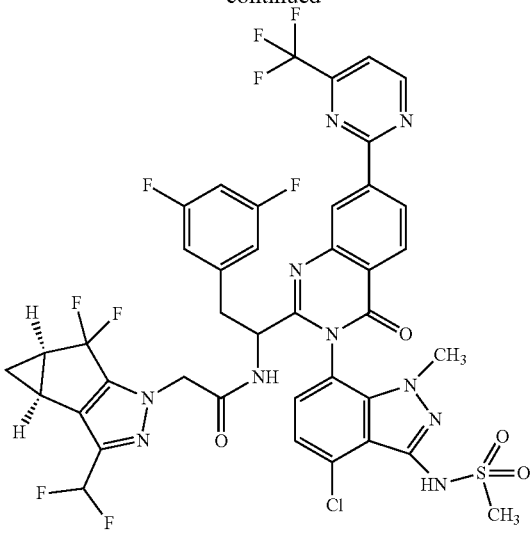
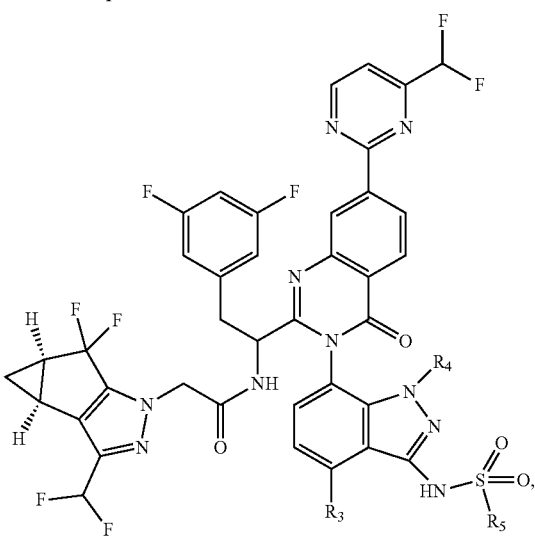
and pharmaceutically acceptable salts thereof.
In another embodiment, the present invention discloses a compound of Formula II, or a salt thereof, selected from the group consisting of:

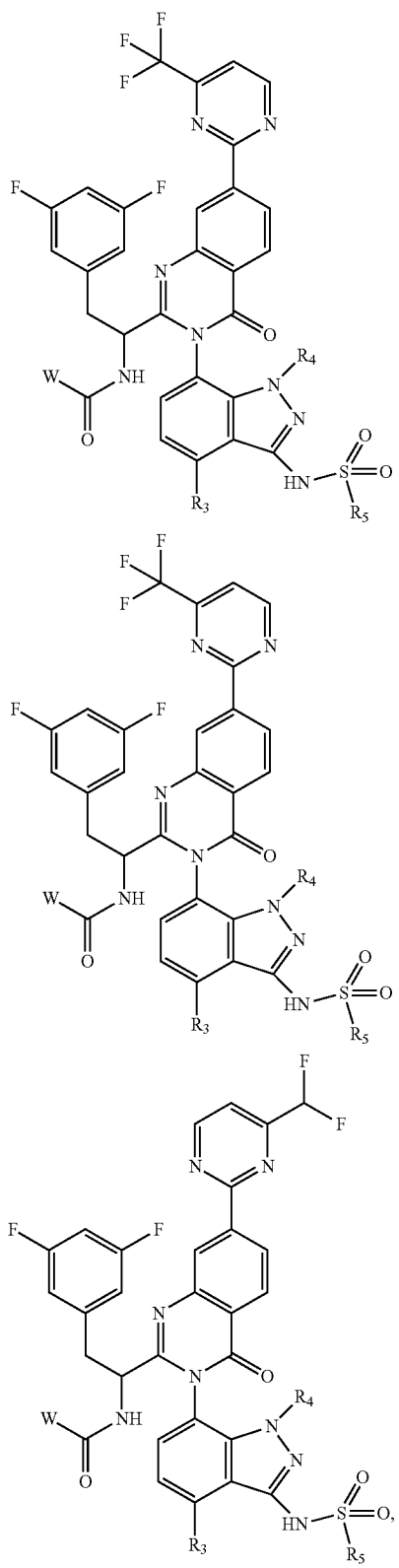

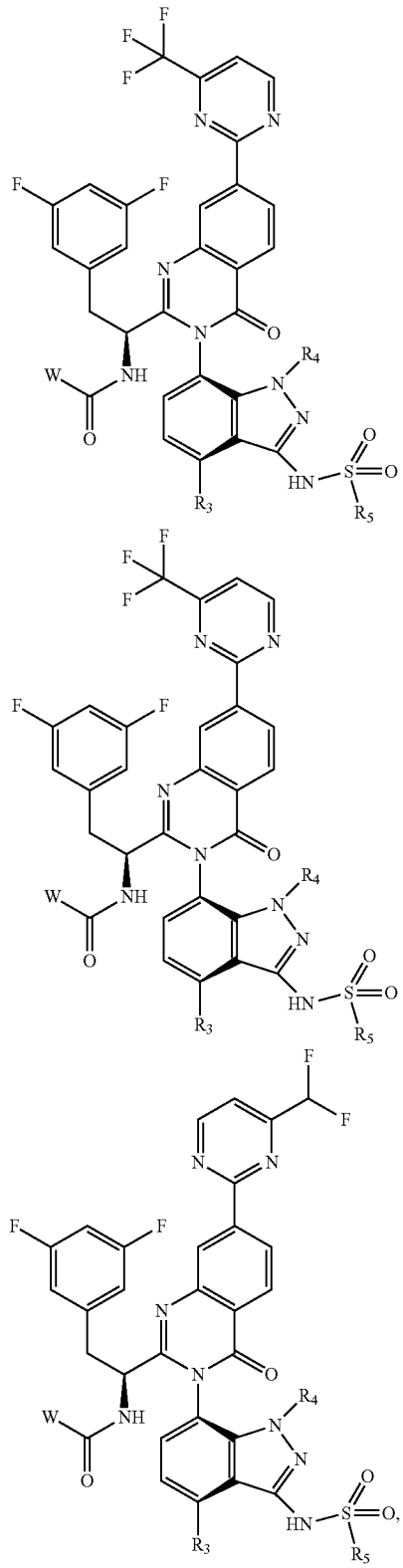

and pharmaceutically acceptable salts thereof.

In another embodiment, the present invention discloses a compound of Formula I, or a salt thereof, selected from the group consisting of:

and pharmaceutically acceptable salts thereof.

The salts of compounds of Formula I and Formula II are pharmaceutically acceptable. Such salts may be acid addition salts or base addition salts. For a review of suitable pharmaceutically acceptable salts see Berge et al, J. Pharm, Sci., 66, 1-19, 1977. In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates, oxalates and choline salts) may be used in the manufacture of compounds of Formula I and Formula II and their pharmaceutically acceptable salts and are included within the scope of the invention. All possible stoichiometric and non-stoichiometric forms of the salts of compounds of Formula I and Formula II are included within the scope of the invention. Acid and base addition salts may be prepared by the skilled chemist, by treating a compound of Formula I and Formula II with the appropriate acid or base in a suitable solvent, followed by crystallisation and filtration.

Some of the compounds of the invention exist in stereoisomeric forms. The invention includes all stereoisomeric forms of the compounds including enantiomers and diastereromers including atropisomers. The term homochiral is used as a descriptor, per accepted convention, to describe a structure which is a single stereoisomer. Absolute stereochemistry was not assigned in all cases. Thus, the compound is drawn at the chiral center as unspecified but labelled as homochiral and in the procedures it is identified by its properties such as for example first eluting off a normal or chiral column per the conventions of chemists. It should be noted that the provided experimental procedures teach how to make the exact compound even if not drawn with absolute configuration. Methods of making and separating stereoisomers are known in the art. The invention includes all tautomeric forms of the compounds. The invention includes atropisomers and rotational isomers.

For the compounds of Formula I and Formula II, the scope of any instance of a variable substituent can be used independently with the scope of any other instance of a variable substituent. As such, the invention includes combinations of the different embodiments. In some Examples, atropisomers can be observed and these are understood to convert at slow or fast rates or even not at all depending on the conditions for handling the compound. These are referred to as mixtures of atropisomers where they interconvert at ambient temperatures or as atropisomer 1 and atropisomer 2 where they were isolated. Since the compounds are identified by their properties rather than exact structural assignment from a crystal structure, it is understood in the art that where not specified, atropisomers are covered and inferred to be covered by the chemical structure.

In the method of this invention, preferred routes of administration are oral and by injection to deliver subcutaneously. Therefore, preferred pharmaceutical compositions include composition suitable for oral administration (for example tablets) and formulations suitable for injection including intramuscular injection.

The compounds and salts of this invention are believed to have as their biological target the HIV Capsid and thus their mechanism of action is to modify in one or more ways the function of the HIV capsid.

The compounds of the present invention and their salts, solvates, or other pharmaceutically acceptable derivatives thereof, may be employed alone or in combination with other therapeutic agents. The compounds and salts of the present invention and any other pharmaceutically active agent(s) may be administered together or separately and, when administered separately, administration may occur simultaneously or sequentially, in any order. The amounts of the compounds and salts of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of the compound(s) of Formulas I or II, or salts thereof and the other pharmaceutically active agent (s) and the relative timings of administration will be selected in order to achieve the desired combined therapeutic effect.

As such, the compounds and salts of the present invention may be used in combination with one or more agents useful in the prevention or treatment of HIV.

In another aspect, the present invention discloses a compound of Formula I or Formula II, or pharmaceutically acceptable salt thereof, for use in treating HIV infection wherein said method further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

In another aspect, the present invention discloses a compound of Formula I or Formula II, or pharmaceutically acceptable salt thereof, for use in treating HIV infection wherein said method further comprises administration of at least one other agent selected from the group consisting of Dolutegravir, lamivudine, Fostemsavir, Cabotegravir, maraviroc, rilpiverine, Reyataz, Tenofovir, Afenamide, EfDA, Doravirine, and Preziata.

In another aspect, the present invention discloses a compound of Formula I or Formula II, or pharmaceutically acceptable salt thereof, for use in treating HIV infection wherein said method further comprises administration of at least one other agent selected from the group consisting of Dolutegravir, lamivudine, Fostemsavir, and Cabotegravir.

EXAMPLES

General Synthesis Methods:
General Procedure D:
To a vial equipped with a stir bar and placed under argon atmosphere was added Pd(OAc)$_2$ (0.1 equiv), dicyclohexyl (2',6'-dimethoxy-[1,1'-biphenyl]-2-yl)phosphane (0.2 equiv), tribasic potassium phosphate (3 equiv), N—((S)-1-((3P)-3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 25-50 mg), and the appropriate aryl/heteroaryl halide (3 equiv). The vial was sealed with a septum cap. To the vial was added THF:water (4:1) to afford a reaction volume 0.05M in boronic ester. The reaction mixture was degassed with argon, then the reaction mixture was stirred at either ambient temperature or 45° C. for 16 to 48 h. Upon cooling to ambient temperature, the reaction mixture was concentrated in vacuo and the resulting residue was subjected to HPLC purification to afford the indicated product.

HPLC Purification:

HPLC purification was performed using one of the conditions indicated below, optionally followed by a second HPLC purification using a different condition indicated below. Based on analytical HPLC data obtained on the crude reaction mixture, the purification condition was optimized for each target compound by modifying the initial Solvent A:Solvent B ratio, the gradient time, the final Solvent A:Solvent B ratio, and the hold time at the final Solvent A:Solvent B concentration.

HPLC Condition A: Column: Zorbax Eclipse Plus C18, 21.2×100 mm, 5 m particles; Solvent A=0.1% Formic Acid in 100% Water. Solvent B=Acetonitrile. Flow Rate=40 mL/min. Wavelength=215 and 254 nm. ESI+ Range: 150 to 1500 dalton.

HPLC Condition B: Column: Sunfire prep C18 OBD, 30×100 mm, 5 m particles; Solvent A: water:MeCN 95:5 w/0.1% TFA, Solvent B: MeCN:water 95:5 w/0.1% TFA. Flow Rate=42 mL/min. Wavelength=220 and 254 nm.

HPLC Condition C: Column: Waters Xterra C18, 19×100 mm, 10 m particles; Solvent A=0.1% NH$_4$OH in 100% Water. Solvent B=Acetonitrile. Flow Rate=40 mL/min. Wavelength=215 and 254 nm. ESI+ Range: 150 to 1500 dalton.

General LCMS analysis methods:

LCMS Method C:

Column: Acquity UPLC BEH C18, 2.1×30 mm, 1.7 m particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

LCMS Method F:

Column: Acquity BEH C18, 2.1×30 mm, 1.7 m particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm.

Preparation of
3-bromo-6-chloro-2-fluorobenzaldehyde

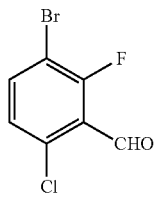 [SMILES: O=Cc1c(Cl)ccc(Br)c1F]

To a stirred solution of 1-bromo-4-chloro-2-fluorobenzene (200 g, 0.955 mol, 1.0 equiv.) in anhydrous THF (2.0 L) was added a solution of LDA in THF (2.0 M, 620 mL, 1.24 mol, 1.3 equiv.) at −50° C. The reaction mixture was allowed to warm to −20° C. and was stirred for 1 h. The mixture was cooled to −50° C. and slowly to the mixture was added DMF (184.8 mL, 2.48 mol, 2.6 equiv.) maintaining a temperature of −50° C. The mixture was allowed to warm to 0° C. and was stirred for 30-45 min at the same temperature (0° C.). The mixture was quenched via the slow addition of ice-cold water (2.0 L). The reaction mixture was diluted with ethyl acetate (2.0 L) and stirred for 15 min at room temperature. The organic layer was separated and reserved; the aqueous layer was extracted with ethyl acetate (2×1.0 L). The combined organic layers were washed with water (2×1.0 L); 1.0 N HCl (1.0 L) and then 15% NaCl solution (2.0 L). The organic solution was dried over Na$_2$SO$_4$; filtered; and then concentrated in vacuo. The resultant crude solid was used directly in the next step without further purification. Yield for the crude product: 210.0 g (93%).

Preparation of
3-bromo-6-chloro-2-fluorobenzonitrile

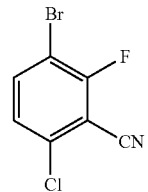 [SMILES: N#Cc1c(Cl)ccc(Br)c1F]

To a stirred solution of 3-bromo-6-chloro-2-fluorobenzaldehyde (210.0 g, 0.89 mol, 1.0 equiv.) in water (2.1 L) at room temperature was added hydroxylamine-O-sulfonic acid (175.15 g, 1.55 mol, 1.75 equiv.). The reaction mixture was heated to 50° C. and stirred for 18 h). The mixture was cooled to room temperature and stirred for 1-1.5 h. The solids were isolated via filtration and were then washed with water. The wet solid was dried under vacuum at 50° C. for 12-15 h to afford 3-bromo-6-chloro-2-fluorobenzaldehyde, 190.0 g (91%).

Preparation of
7-bromo-4-chloro-1H-indazol-3-amine

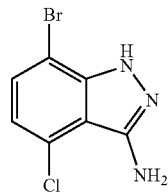 [SMILES: Nc1n[nH]c2c(Br)ccc(Cl)c12]

To a 3 L three neck round bottom flask fitted with a water-cooled condenser, a thermometer and a mechanical stirrer was added 3-bromo-6-chloro-2-fluorobenzonitrile (100 g, 427 mmol) and ethanol (500 mL). To the solution was added hydrazine hydrate (104 ml, 2133 mmol) at room temperature. The solution was heated to 80° C. and was maintained at that temperature for 1 h upon which the mixture became a homogeneous solution and LCMS analysis indicated the reaction was complete. The solution was allowed to cool to 45° C. and then water (1 L) was added slowly to produce a white ppt. as a thick slurry. Following the addition the mixture was stirred for 30 minutes. The solids were isolated via filtration. The solids were washed with water (1 L) and then dried under vacuum at 45° C. to afford 7-bromo-4-chloro-1H-indazol-3-amine as a pale orange solid, 103 g (98%). $^1$H NMR (400 MHz, DMSO-d6): δ 12.21 (bs, 1H), 7.41 (d, J=7.8 Hz, 1H), 6.84 (d, J=7.8 Hz, 1H), 5.34 (bs, 2H) ppm.

Preparation of 7-bromo-4-chloro-1-methyl-H-indazol-3-amine

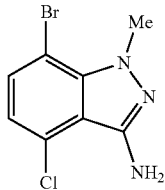 [SMILES: Cn1nc(N)c2c(Cl)ccc(Br)c21]

To a solution of 3-bromo-6-chloro-2-fluorobenzonitrile (360.0 g, 1.55 mol, 1.0 equiv.) in ethanol (1.08 L) was added methylhydrazine sulphate (1.11 kg, 7.73 mol, 5.0 equiv.) followed by the addition of triethylamine (1.3 L, 9.3 mol, 6.0 equiv.) at 25-35° C. The reaction mixture was heated to 110° C. and maintained at that temperature for 15 h. The mixture was cooled to room temperature and to the mixture was added water (3.0 L). The mixture was stirred at room temperature for 1 h. The solids were isolated via filtration and were washed with water. The wet solid was dried under vacuum at 50° C. for 12-15 hours. The material was subjected to silica gel column chromatography (hexanes:EtOAc 90:10→60:40) to afford 7-bromo-4-chloro-1-methyl-1H-indazol-3-amine as a pale-yellow solid, 185.0 g (46%).

Preparation of 7-bromo-4-chloro-1-(2,2-difluoro-ethyl)-1H-indazol-3-amine

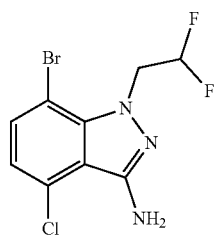 [SMILES: Nc1nn(CC(F)F)c2c(Br)ccc(Cl)c12]

To a stirred solution of 7-bromo-4-chloro-1H-indazol-3-amine (128.0 g, 0.52 mol, 1.0 equiv.) in dry THF (1.92 L) at 0° C. was added $^t$BuOK (76 g, 0.67 mol, 1.3 equiv.) in portions. The reaction mixture was stirred for 10 min at 0° C.; then to the solution was slowly added 2,2-difluoroethyl trifluoro-methanesulfonate (122.5 g, 0.57 mol, 1.1 equiv.) at 0° C. The mixture was slowly warmed to room temperature and then was stirred for 2 h. The mixture was diluted with ice-cold water (3.0 L) and MTBE (2×1.5 L). The organic layer was separated, washed with water (2×1.2 L), dried over Na$_2$SO$_4$, filtered, and then concentrated in vacuo. The resulting crude material was subjected to silica gel chromatography (hexanes:EtOAc 95:5490:10). Product-containing fractions contaminated with the undesired regioisomer were concentrated and then triturated with DCM (5 mL/g) to afford the pure desired product which was then combined with fractions of the pure material. This process afforded 7-bromo-4-chloro-1-(2,2-difluoroethyl)-1H-indazol-3-amine as a light-yellow solid, 110 g (68%). $^1$H NMR (DMSO-d$_6$, 500 MHz) δ 7.55 (d, 1H, J=7.9 Hz), 6.96 (d, 1H, J=7.9 Hz), 6.1-6.5 (m, 1H), 5.62 (s, 2H), 4.94 (dt, 2H, J=3.8, 14.1 Hz).

Preparation of 7-bromo-4-chloro-1-(2,2,2-trifluoro-ethyl)-H-indazol-3-amine

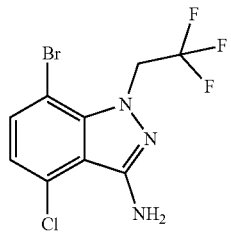 [SMILES: Nc1nn(CC(F)(F)F)c2c(Br)ccc(Cl)c12]

To a stirred solution of 7-bromo-4-chloro-1H-indazol-3-amine (70 g, 284 mmol, 1.0 equiv.) in dry DMF (700 mL) at room temperature was added in portions Cs$_2$CO$_3$ (184 g, 568 mmol, 2 equiv.). The reaction mixture was stirred for 10 min at room temperature. To the reaction mixture was added slowly at room temperature 2,2,2-trifluoroethyl trifluoromethanesulfonate (72.5 g, 312 mmol, 1.10 equiv.). After completion of the reaction (monitored by TLC), the mixture was diluted with ice cold water (700 mL) upon which a precipitate was formed. The mixture was allowed to warm to room temperature and then was stirred for 30 minutes at room temperature. The solids were isolated via filtration and then were washed with water (500 mL). The wet product was dissolved in DMF (350 mL) and then was diluted with water (350 mL) at room temperature. The mass was stirred for 30 min., then the solids were collected via filtration and were washed with water (200 mL) followed by hexanes (700 mL). The wet solids were dried under vacuum at 50-55° C. for 18-20 h to afford 7-bromo-4-chloro-1-(2,2,2-trifluoroethyl)-1H-indazol-3-amine (4) as a light-yellow solid, 64.0 g (69%).

Preparation of N-(7-bromo-4-chloro-1-methyl-H-indazol-3-yl)methanesulfonamide

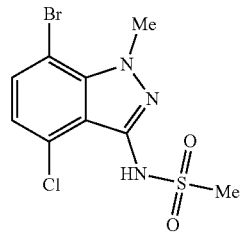 [SMILES: Cn1nc(NS(C)(=O)=O)c2c(Cl)ccc(Br)c21]

To a solution of 7-bromo-4-chloro-1-methyl-1H-indazol-3-amine (90 g, 0.34 mol, 1.0 equiv.) in CH$_2$Cl$_2$ (900 mL) was added diisopropylethylamine ("DIPEA", 180.4 mL, 1.04 mol, 3.0 equiv.) and 4-dimethylaminopyridine ("DMAP", 2.07 g, 0.017 mol, 0.05 equiv.). The mixture was stirred for 5 min, then was cooled to 0° C. and methanesulfonyl chloride (67.7 mL, 0.87 mol, 2.5 equiv.) was added resulting in a noted exotherm. The reaction mixture was warmed to room temperature and stirred at that temperature 3 h upon which a precipitate formed. The mixture was diluted with dichloromethane (1.0 L) and then was washed with water (2.0 L) followed by aq. HCl (1.0M, 1.0 L), and then brine (1.5 L). The organic solution was dried over Na$_2$SO$_4$; filtered, and then concentrated in vacuo. The crude residue was dissolved in EtOH (1.8 L). To the solution was added aq. NaOH (20%, 650 mL) at room temperature upon which a slight exotherm was noted. The resulting mixture was stirred for 2 h upon which the mixture became a homogeneous solution. The solution was diluted with water (2.0 L) and the pH was adjusted to pH 2-3 using aq. HCl (1.0M, app. 3.0 L). The precipitate that was formed was collected by filtration. The solids were washed with water and then dried in vacuo to afford N-(7-bromo-4-chloro-1-methyl-1H-indazol-3-yl)methanesulfonamide as an off-white solid, 96 g (82%). $^1$H NMR (500 MHz, CDCl$_3$) δ 7.48 (d, J=7.9 Hz, 1H), 7.24 (br s, 1H), 6.95 (d, J=7.9 Hz, 1H), 4.38 (s, 3H), 3.42 (s, 3H). LC/MS (M+H)$^+$=337.80.

Preparation of N-(7-bromo-4-chloro-1-(2,2-difluoroethyl)-H-indazol-3-yl)methanesulfonamide

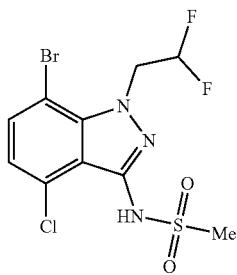 [SMILES: CS(=O)(=O)Nc1nn(CC(F)F)c2c(Br)ccc(Cl)c12]

To a stirred solution of 7-bromo-4-chloro-1-(2,2-difluoroethyl)-1H-indazol-3-amine (40.0 g, 0.12 mol, 1.0 equiv.) in dry DCM (400 mL) was added DIPEA (67 mL, 0.38 mol, 3.0 equiv.) and DMAP (0.78 g, 0.0064 mol, 0.05 equiv.). The solution was stirred for 5 min, then the reaction mixture was cooled to 0° C. and to the mixture was slowly added methanesulfonyl chloride (31.0 mL, 0.38 mol, 3.0 equiv.). The reaction mixture was allowed to warm to room temperature and was then stirred for 2 h. After completion of the reaction (monitored by TLC), the mixture was diluted with DCM (2×2.5 L) and water (2.0 L). The organic layer was separated and was washed with water (2×1.5 L); brine (1.5 L); dried over Na$_2$SO$_4$; filtered; and was concentrated in vacuo. The residue was dissolved in ethanol (320 mL) and to the solution was aq. NaOH (20% w/w, 320 mL). The reaction mixture was stirred at room temperature for 2 h. After completion of the reaction (monitored by TLC), the mixture was diluted with water (1.0 L) and acidified to pH 2-3 using aq. HCl (1.0 M). The resulting solids were collected via filtration. The solids were triturated with hexanes:EtOAc (95:5, 10 V) and again isolated via filtration. The wet solids were dried under vacuum at 50° C. to afford N-(7-bromo-4-chloro-1-(2,2-difluoroethyl)-1H-indazol-3-yl)methane sulfonamide (5) as a light-yellow solid, 45.7 g (91%). $^1$H NMR (400 MHz, CDCl$_3$): δ 7.52 (d, J=8.0 Hz, 1H), 7.41 (bs, 1H), 7.00 (d, J=8.0 Hz, 1H), 6.16 (tt, J$_1$=4.3 Hz, J$_2$=8.6 Hz, J$_3$=55.4 Hz, 1H), 5.15 (td, J$_1$=4.3 Hz, J$_2$=12.7 Hz, 2H), 3.41 (s, 3H).

Preparation of N-(7-bromo-4-chloro-1-(2,2-difluoroethyl)-H-indazol-3-yl)cyclopropanesulfonamide

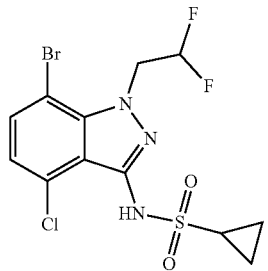 [SMILES: O=S(=O)(Nc1nn(CC(F)F)c2c(Br)ccc(Cl)c12)C1CC1]

To a stirred solution of 7-bromo-4-chloro-1-(2,2-difluoroethyl)-1H-indazol-3-amine (10 g, 0.032 mol, 1.0 equiv.) in dry pyridine (100 mL) was added cyclopropylsulfonyl chloride (18.1 g, 0.128 mol, 4.0 equiv.). The reaction mixture was stirred at room temperature for 48 h. The mixture was diluted with water (400 mL) and extracted with MTBE (2×100 mL). The combined organic layers were washed with water (3×300 mL), brine (300 mL), dried over Na$_2$SO$_4$, filtered and concentrated in vacuo. The resulting crude material was triturated with hexanes (15 V) to obtain N-(7-Bromo-4-chloro-1-(2,2-difluoroethyl)-1H-indazol-3-yl)cyclopropanesulfonamide as a light-red solid, 11.1 g (82%).

Preparation of N-(7-bromo-4-chloro-1-(2,2,2-trifluoroethyl)-H-indazol-3-yl)methanesulfonamide

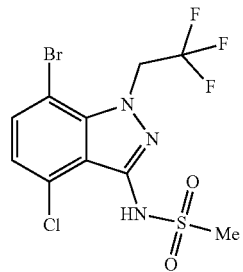 [SMILES: CS(=O)(=O)Nc1nn(CC(F)(F)F)c2c(Br)ccc(Cl)c12]

To a stirred solution of 7-bromo-4-chloro-1-(2,2,2-trifluoroethyl)-1H-indazol-3-amine (60 g, 182.64 mmol, 1.0 equiv.) in dry DCM (600 mL, 10 V) was added DIPEA (94.8 ml, 547.92 mmol, 3.0 equiv.) and DMAP (1.11 g, 9.13 mmol, 0.05 equiv.). After being stirring for 15 min the solution was cooled to 0° C. To the solution was slowly added methanesulfonyl chloride (52.3 g, 456.6 mmol, 3.0 equiv.). The reaction mixture was then allowed to warm to room temperature and was stirred at room temperature for 2 h. The progress of the reaction (bis-mesylation) was monitored by TLC. After the reaction was determined to be complete the mixture was diluted with DCM (200 mL) and water (200 mL). The organic layer was isolated and washed with water (500 mL), brine (300 mL), dried over Na$_2$SO$_4$, filtered and concentrated in vacuo. The resulting residue was dissolved in ethanol (600 mL) and to the solution was aq. NaOH (20% w/w, 600 mL). The reaction mixture was stirred for 2 h at room temperature. After completion of the reaction (mono demesylation, monitored by TLC) the solution was diluted with water (300 mL) and acidified to pH 2-3 using aq. HCl (1.0 M). The resulting solids were isolated via filtration and were then washed with water. The solids were dried under vacuum at 50-55° C. The solid material was further purified by trituration using hexanes:EtOAc (95:5, 15V) to afford N-(7-Bromo-4-chloro-1-(2,2,2-trifluoroethyl)-1H-indazol-3-yl)methanesulfonamide as a light-yellow solid, 55.1 g (75%).

Preparation of N-(7-bromo-4-chloro-1-methyl-H-indazol-3-yl)-N-(4-methoxybenzyl)methanesulfonamide

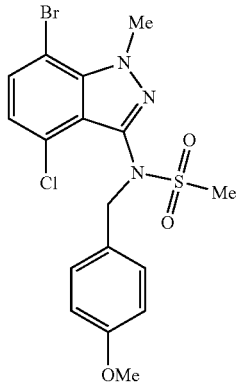 [SMILES: COc1ccc(CN(c2nn(C)c3c(Br)ccc(Cl)c23)S(C)(=O)=O)cc1]

To a mixture of N-(7-bromo-4-chloro-1-methyl-1H-indazol-3-yl)methanesulfonamide (49 g, 0.144 mol, 1.0 equiv.) in DMF (980 mL) was added 1-(chloromethyl)-4-methoxybenzene (23.54 mL, 0.17 mol, 1.2 equiv.). To the mixture was added cesium carbonate (61.3 g, 0.18 mol, 1.3 equiv.). The mixture was heated to 80° C. and maintained at that temperature for 2 h. After completion of the reaction (monitored by TLC) the mixture was poured into water (2.0 L). The mixture was extracted with EtOAc (2×1.5 L). The combined organic layers were washed with brine (1.0 L); dried over $Na_2SO_4$; filtered and then concentrated in vacuo. The residue was crystallised from hexanes:EtOAc (9:1, 120 mL) to afford the desired product N-(7-Bromo-4-chloro-1-methyl-1H-indazol-3-yl)-N-(4-methoxybenzyl) methane sulfonamide as a white solid. Yield: 62 g (94%). $^1$H NMR (500 MHz, $CDCl_3$) δ 7.44 (d, J=7.9 Hz, 1H), 7.31 (d, J=8.5 Hz, 2H), 6.99 (d, J=7.9 Hz, 1H), 6.84 (d, J=8.5 Hz, 2H), 4.99 (br s, 1H), 4.76 (br s, 1H), 4.40 (s, 3H), 3.80 (s, 3H), 3.01 (s, 3H).

Preparation of N-(7-bromo-4-chloro-1-(2,2-difluoroethyl)-1H-indazol-3-yl)-N-(4-methoxybenzyl)methanesulfonamide

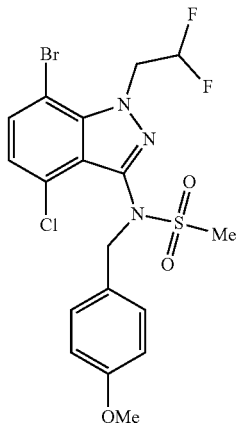 [SMILES: COc1ccc(CN(c2nn(CC(F)F)c3c(Br)ccc(Cl)c23)S(C)(=O)=O)cc1]

To a stirred solution of N-(7-bromo-4-chloro-1-(2,2-difluoroethyl)-1H-indazol-3-yl)methanesulfonamide (45.7 g, 0.117 mol, 1.0 equiv.) and 1-(chloromethyl)-4-methoxybenzene (22.1 g, 0.141 mol, 1.2 equiv.) in DMF (460 mL, 10 V) was added cesium carbonate (49.8 g, 0.152 mol, 1.3 equiv.). The reaction mixture was heated to 80° C. and stirred for 2 h at the same temperature. After completion of the reaction (monitored by TLC), the mixture was cooled to room temperature and then poured into water (2.0 L). The mixture was extracted with EtOAc (2×1.5 L). The combined organic layers were washed with brine (1.0 L), dried over $Na_2SO_4$, filtered and concentrated in vacuo. The resulting crude material was subjected to silica gel column purification (eluting with hexanes:EtOAc 85:15→75:25) to afford N-(7-bromo-4-chloro-1-(2,2-difluoroethyl)-1H-indazol-3-yl)-N-(4-methoxy benzyl)methanesulfonamide as a light-yellow solid, 56 g (93%).

Preparation of N-(7-bromo-4-chloro-1-(2,2-difluoroethyl)-H-indazol-3-yl)-N-(4-methoxybenzyl)cyclopropanesulfonamide

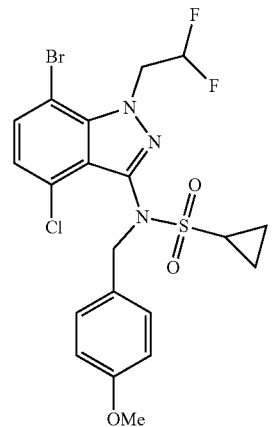 [SMILES: COc1ccc(CN(c2nn(CC(F)F)c3c(Br)ccc(Cl)c23)S(=O)(=O)C2CC2)cc1]

To a stirred mixture of N-(7-bromo-4-chloro-1-(2,2-difluoroethyl)-1H-indazol-3-yl)cyclo-propanesulfonamide (15 g, 0.036 mol, 1.0 equiv.) and 1-(chloromethyl)-4-methoxybenzene (6.79 g, 0.043 mol, 1.2 equiv.) in DMF (150 mL) was added cesium carbonate (15.32 g, 0.047 mol, 1.3 equiv.). The reaction mixture was heated to 80° C. and stirred at that temperature for 2 h. After completion of the reaction (monitored by TLC), the mixture was poured into water (300 mL) and the product was extracted with MTBE (2×200 mL). The combined organic layers were washed with brine (300 mL), dried over $Na_2SO_4$, filtered and concentrated in vacuo. The resulting crude material was subjected to silica gel column purification (hexanes:EtOAc 80:20→75:25) to afford N-(7-Bromo-4-chloro-1-(2,2-difluoroethyl)-1H-indazol-3-yl)-N-(4-methoxybenzyl)methanesulfonamide as a gummy liquid, 16.5 g (86%).

Preparation of N-(7-bromo-4-chloro-1-(2,2,2-trifluoroethyl)-H-indazol-3-yl)-N-(4-methoxybenzyl)methanesulfonamide

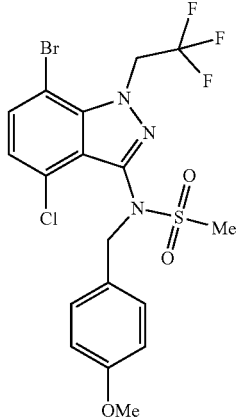 [SMILES: COc1ccc(CN(c2nn(CC(F)(F)F)c3c(Br)ccc(Cl)c23)S(C)(=O)=O)cc1]

To a stirred solution of N-(7-Bromo-4-chloro-1-(2,2,2-trifluoroethyl)-1H-indazol-3-yl)methanesulfonamide (6.0 g, 14.77 mmol, 1.0 equiv.) in dry DMF (60 mL, 10 V) at room temperature was added in portions Cs$_2$CO$_3$ (6.25 g, 19.20 mmol, 1.3 equiv.). The mixture was stirred for 10 min at room temperature, then to the mixture was slowly added 1-(chloromethyl)-4-methoxybenzene (2.77 g, 17.724 mmol, 1.2 equiv.). The reaction mixture was heated to 80° C. and maintained at that temperature for 2 h. After completion of the reaction (monitored by TLC), the mixture was cooled to room temperature and then was diluted with ice cold water (60 mL) and ethyl acetate (60 mL). The organic layer was isolated; washed with water (40 mL); dried over Na$_2$SO$_4$; filtered and concentrated in vacuo. The resulting crude material was triturated using hexanes:EtOAc (97:3, 15V) to afford N-(7-bromo-4-chloro-1-(2,2,2-trifluoroethyl)-1H-indazol-3-yl)-N-(4-methoxybenzyl)methanesulfonamide as a light-yellow solid, 7.0 g (90%).

Preparation of N-(7-amino-4-chloro-1-methyl-H-indazol-3-yl)-N-(4-methoxybenzyl)methanesulfonamide

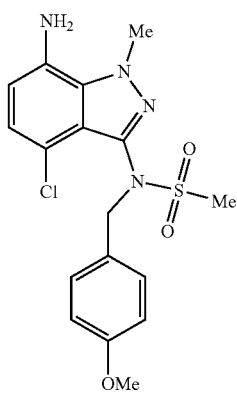 [SMILES: COc1ccc(CN(c2nn(C)c3c(N)ccc(Cl)c23)S(C)(=O)=O)cc1]

To a stirred solution of N-(7-Bromo-4-chloro-1-methyl-1H-indazol-3-yl)-N-(4-methoxybenzyl) methanesulfonamide (55 g, 0.12 mol, 1.0 equiv.) in NMP (900 mL) at room temperature was added copper (I) iodide (4.57 g, 0.024 mol, 0.2 equiv.), sodium ascorbate (47.4 g, 0.24 mol, 2 equiv.) and (1R, 2R)—N$_1$,N$_2$-dimethylcyclohexane-1,2-diamine (8.52 g, 0.06 mol, 0.5 equiv.) were added at room temperature. Then a solution of sodium azide (23.3 g, 0.36 mol, 3.0 equiv.) in water (182 mL). The mixture was heated to 100° C. and maintained at that temperature for 12 h. The reaction mixture was cooled to room temperature and diluted with ethyl acetate (1.5 L), then filtered through a pad of Celite. The filter pad was extracted with EtOAc (500 mL). The combined filtrate was diluted with water (2.0 L) and the organic layer was isolated and reserved. The aqueous phase was extracted with EtOAc (2×1.0 L). The combined organic layers were washed with water (1.0 L); brine (1.0 L); dried over Na$_2$SO$_4$; filtered; and concentrated in vacuo. The crude material was purified by silica column chromatography (hexanes: EtOAc 100:0→80:20) to afford the title compound, N-(7-Amino-4-chloro-1-methyl-1H-indazol-3-yl)-N-(4-methoxybenzyl) methanesulfonamide, as an off-white solid, 27.0 g (57%). $^1$H NMR (400 MHz, CDCl$_3$) δ 7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS (M+H)$^+$=395.00.

Preparation of N-(7-amino-4-chloro-1-(2,2-difluoroethyl)-H-indazol-3-yl)-N-(4-methoxybenzyl)methanesulfonamide

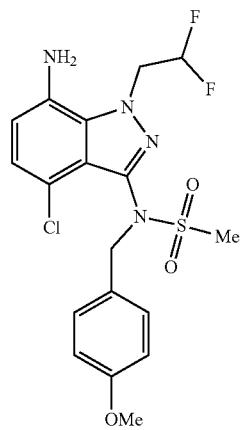 [SMILES: COc1ccc(CN(c2nn(CC(F)F)c3c(N)ccc(Cl)c23)S(C)(=O)=O)cc1]

To a stirred solution of N-(7-bromo-4-chloro-1-(2,2-difluoroethyl)-1H-indazol-3-yl)-N-(4-methoxybenzyl)methanesulfonamide (62 g, 0.12 mol, 1.0 equiv.) in NMP (745 mL) at room temperature was added copper (I) iodide (4.64 g, 0.024 mol, 0.2 equiv.), sodium ascorbate (48.3 g, 0.24 mol, 2 equiv.) and (1R, 2R)—N$_1$,N$_2$-dimethylcyclohexane-1,2-diamine (8.7 g, 0.06 mol, 0.5 equiv.). To the mixture was added a solution of sodium azide (23.8 g, 0.36 mol, 3.0 equiv.) in water (204 mL). The mixture was heated to 100° C. and maintained at that temperature for 15 h. The mixture was cooled to room temperature and was then diluted with ethyl acetate (1.5 L). The mixture was filtered through a pad of Celite and the filter pad was extracted with EtOAc (500 mL). The combined filtrate was diluted with water (2.0 L), organic layer was separated and aqueous layer extracted with EtOAc (2×1.0 L). The combined organic layers were washed with water (1.2 L), brine (1.0 L), dried over Na$_2$SO$_4$, filtered and then concentrated in vacuo. The resulting residue was subjected to silica gel column chromatography (hexanes:EtOAc 100:04→75:25) to afford the title compound, N-(7-amino-4-chloro-1-(2,2-difluoroethyl)-1H-indazol-3-yl)-N-(4-methoxybenzyl)methanesulfonamide, as an off-white solid, 23.0 g, (44%).

Preparation of N-(7-amino-4-chloro-1-(2,2-difluoroethyl)-H-indazol-3-yl)-N-(4-methoxybenzyl)cyclopropanesulfonamide

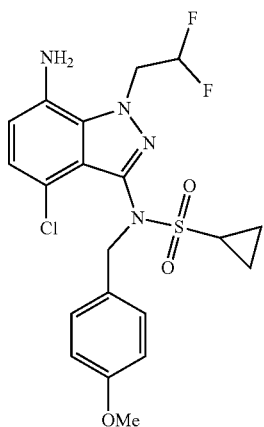 [SMILES: COc1ccc(CN(c2nn(CC(F)F)c3c(N)ccc(Cl)c23)S(=O)(=O)C2CC2)cc1]

To a stirred solution of N-(7-bromo-4-chloro-1-(2,2-difluoroethyl)-1H-indazol-3-yl)-N-(4-methoxybenzyl)cyclopropanesulfonamide (32 g, 0.059 mol, 1.0 equiv.) in NMP (512 mL) at room temperature was added copper (I) iodide (2.27 g, 0.012 mol, 0.2 equiv.), sodium ascorbate (23.7 g, 0.12 mol, 2 equiv.) and (1R, 2R)—$N_1,N_2$-dimethylcyclohexane-1,2-diamine (4.25 g, 0.03 mol, 0.5 equiv.). To the mixture was added a solution of sodium azide (11.6 g, 0.18 mol, 3.0 equiv.) in water (112 mL). The reaction was heated to 100° C. and stirred for 18 h the same temperature. The mixture was cooled to room temperature and diluted with ethyl acetate (1.2 L). The mixture was filtered through a pad of Celite, extracting with EtOAc (300 mL). The combined filtrate was poured into water (1.5 L) and the organic layer was isolated and reserved. The aqueous layer was extracted with EtOAc (2×0.8 L). The combined organic layers were washed with water (0.8 L), brine (0.8 L), dried over $Na_2SO_4$, filtered and then concentrated in vacuo. The crude residue was subjected to silica gel column chromatography (hexanes: EtOAc 100:0→80:20) to afford the title compound, N-(7-amino-4-chloro-1-(2,2-difluoroethyl)-1H-indazol-3-yl)-N-(4-methoxybenzyl)cyclopropanesulfonamide as an off-white solid, 14.2 g (50%).

Preparation of N-(7-amino-4-chloro-1-(2,2,2-trifluoroethyl)-H-indazol-3-yl)-N-(4-methoxybenzyl)methanesulfonamide

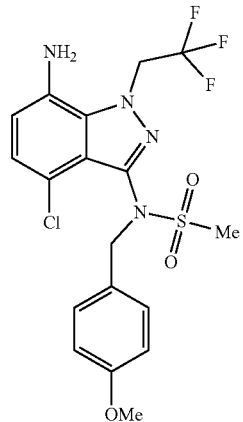 [SMILES: COc1ccc(CN(c2nn(CC(F)(F)F)c3c(N)ccc(Cl)c23)S(C)(=O)=O)cc1]

To a stirred solution of N-(7-bromo-4-chloro-1-(2,2,2-trifluoroethyl)-1H-indazol-3-yl)-N-(4-methoxybenzyl)methanesulfonamide (3 g, 5.69 mmol, 1.0 equiv.) in NMP (45 mL) was added at room temperature copper (I) iodide (0.22 g, 1.13 mmol, 0.2 equiv.), sodium ascorbate (2.25 g, 11.38 mmol, 2 equiv.) and (1R, 2R)—$N_1,N_2$-dimethylcyclohexane-1,2-diamine (0.4 g, 2.84 mmol, 0.5 equiv.). To the mixture was added a solution of sodium azide (1.1 g, 17.07 mmol) in water (15 mL). The mixture was heated to 100° C. and maintained at that temperature for 13 h. The reaction mixture was cooled to room temperature and was then diluted with ethyl acetate (50 mL). The mixture was filtered through a pad of Celite bed extracting with EtOAc (30 mL). The combined filtrate was poured into water (50 mL) and the organic layer was isolated and reserved. The aqueous phase was extracted with EtOAc (2×30 mL). The combined organics were washed with water (50 mL), brine (40 mL), dried over $Na_2SO_4$, filtered and concentrated in vacuo. The resulting residue was subjected to silica gel column chromatography (hexanes: EtOAc 100:0→75:25) to afford the title compound, N-(7-amino-4-chloro-1-(2,2,2-trifluoroethyl)-1H-indazol-3-yl)-N-(4-methoxybenzyl)methanesulfonamide as an off-white solid, 1.6 g (61%).

Preparation of bicyclo[3.1.0]hexan-3-ol

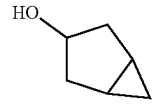

To a stirred solution of cyclopent-3-enol (130 g, 1545 mmol) in DCM (1200 mL) under $N_2$ atmosphere at 0-5° C. was added dropwise a solution of diethyl zinc in hexane (1.0 M, 3091 mL, 3091 mmol) over a period of 3 h. To the solution at 0° C. was added dropwise a solution of diiodomethane (249 mL, 3091 mmol) in DCM (300 mL) over a period of 1 h. The reaction mixture was allowed to warm to 27° C. upon which formation of a white precipitation was observed. The mixture stirred for 16 h. Progress of the reaction was monitored by TLC ($SiO_2$, 20% EtOAc/ pet, Rf=0.3, UV-inactive, PMA-active). The reaction mixture was quenched via the careful addition of aq. saturated NH₄Cl solution (1.5 L). The mixture was filtered through pad of Celite. The aqueous layer was extracted with DCM (2×1 L). The combined organic layers were dried over anhydrous Na₂SO₄, filtered and then concentrated under reduced pressure to afford crude bicyclo[3.1.0]hexan-3-ol as red liquid, 180 g. ¹H NMR (400 MHz, CDCl₃) δ=4.41-4.35 (m, 1H), 2.18-2.05 (m, 2H), 1.73 (d, J=13.9 Hz, 2H), 1.35-1.25 (m, 2H), 1.21-1.14 (m, 1H), 0.57-0.43 (m, 2H). GCMS: m/z=98.1).

Preparation of bicyclo[3.1.0]hexan-3-one

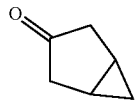

To a stirred solution of bicyclo[3.1.0]hexan-3-ol (210 g, 2054 mmol) in DCM (5000 mL) under N₂ atmosphere at 0° C. was added portion-wise Dess-Martin periodinane (954 g, 225 mmol). The mixture was allowed to warm to 27° C. and was then stirred for 16 h. Progress of the reaction was monitored by TLC (SiO₂, 20% Acetone/Hex, Rf=0.3, UV in-active, PMA-active). The reaction mixture was filtered through pad of Celite and the filtrate was washed with aq. NaOH (1N, 8×1 L). The combined aqueous phases were extracted with DCM (5×1 L). The combined organic layers were dried over anhydrous Na₂SO₄, filtered, and then concentrated under reduced pressure (bath temperature: 20° C.) to afford crude bicyclo[3.1.0]hexan-3-one as brown liquid. The liquid was further purified by downward distillation at 70° C. to afford bicyclo[3.1.0]hexan-3-one as a pale-yellow viscous liquid, 125 g (62%). ¹H NMR (400 MHz, CDCl₃) δ=2.61-2.54 (m, 2H), 2.17-2.12 (m, 2H), 1.54-1.46 (m, 2H), 0.92-0.86 (m, 1H), −0.01-−0.08 (m, 1H); GCMS: M/Z=96.1.

Preparation of 2-(2,2-difluoroacetyl)bicyclo[3.1.0]hexan-3-one

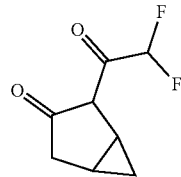 [SMILES: O=C1CC2CC2C1C(=O)C(F)F]

To a stirred solution of bicyclo[3.1.0]hexan-3-one (125 g, 1274 mmol) in THF (1500 mL) under N₂ atmosphere at −78° C. was added LDA (2.0 M in THF, 0.701 L, 1402 mmol). The solution was stirred for 1 h at −78° C. To the solution was added slowly over 30 minutes a solution of ethyldifluoroacetate (174 g, 1402 mmol) in THF (300 mL) maintaining a temperature of −78° C. The reaction mixture was allowed to warm to 27° C. and was then stirred for 1 h. Progress of the reaction was monitored by TLC (SiO₂, 20% Acetone/Hexane, Rf=0.3, UV-active). The reaction mixture was quenched via the addition of aq. HCl (1N, 2000 mL). The mixture was stirred for 30 min. and then was extracted with EtOAc (3×1000 mL). The combined organic layers were washed with brine (1000 mL), dried over anhydrous Na₂SO₄ and filtered. The filtrate was concentrated under reduced pressure to afford 2-(2,2-difluoroacetyl)bicyclo[3.1.0]hexan-3-one as a pale-yellow viscous liquid, 180 g (71%). ¹H NMR (400 MHz, CDCl₃) δ=6.18 (t, J=54.8 Hz, 1H), 2.70-2.62 (m, 1H), 2.35 (d, J=19.4 Hz, 1H), 2.14 (br s, 1H), 1.26-1.21 (m, 1H), 1.04-1.03 (m, 1H), 0.22-0.21 (m, 1H), LCMS: M/Z=173.17).

Preparation of ethyl 2-(3-(difluoromethyl)-3b,4,4a, 5-tetrahydro-1H-cyclopropa[3,4]cyclopenta[1,2-c]pyrazol-1-yl)acetate

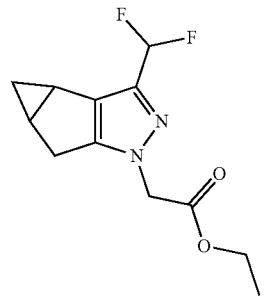 [SMILES: CCOC(=O)Cn1nc(C(F)F)c2c1CC1CC21]

To a stirred solution of 2-(2,2-difluoroacetyl)bicyclo[3.1.0]hexan-3-one (180 g, 910 mmol) in ethanol (2 L) under N₂ atmosphere at 27° C. was added ethyl 2-hydrazinylacetate hydrochloride (422 g, 2729 mmol) followed by sulfuric acid (20 mL, 375 mmol). The mixture was stirred for 30 min. and then was heated to 100° C. and stirred for 16 h. Progress of the reaction was monitored by TLC (SiO₂, 20% Acetone/Hexane, Rf=0.3, UV-active). The reaction mixture was concentrated under reduced pressure. The residue was dissolved in EtOAc (2000 mL) and was washed with water (2×1 L), brine (1.0 L), dried over anhydrous Na₂SO₄, filtered, and then was concentrated under reduced pressure. The resulting residue was subjected to silica gel column chromatography (pet.:acetone 100:0→98:2) to afford ethyl 2-(3-(difluoromethyl)-3b,4,4a,5-tetrahydro-1H-cyclopropa[3,4]cyclopenta[1,2-c]pyrazol-1-yl)acetate as an off-white solid, 110 g (46%). ¹H NMR (400 MHz, DMSO-d₆) δ=6.86 (t, J=54.8 Hz, 1H), 4.93 (s, 2H), 4.14 (q, J=7.2 Hz, 2H), 2.88-2.79 (m, 1H), 2.76-2.68 (m, 1H), 2.14-2.04 (m, 2H), 1.19 (t, J=7.2 Hz, 3H), 1.10-1.03 (m, 1H), 0.14 (q, J=4.3 Hz, 1H).

Preparation of ethyl 2-(3-(difluoromethy)-5-oxo-3b, 4,4a,5-tetrahydro-1H-cyclopropa[3,4]cyclopenta[,2-c]pyrazol-1-yl)acetate

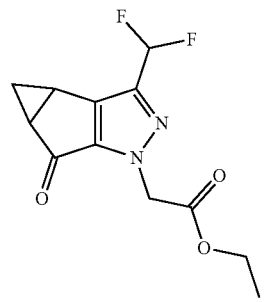 [SMILES: CCOC(=O)Cn1nc(C(F)F)c2c1C(=O)C1CC21]

To a stirred solution of ethyl 2-(3-(difluoromethyl)-3b,4,4a,5-tetrahydro-1H-cyclopropa[3,4]cyclopenta[1,2-c]pyrazol-1-yl)acetate (110 g, 422 mmol) and Celite (395 g) in cyclohexane (3.5 L) at 0° C. was added portionwise pyridinium dichromate (794 g, 2110 mmol). To the mixture under nitrogen atmosphere was added dropwise tert-butyl hydroperoxide (355 mL, 2130 mmol) over a period of 10 min. The reaction mixture was warmed to 27° C. and was then stirred at that temperature for 48 h. Progress of the reaction was monitored by TLC (SiO$_2$, 30% Acetone/pet, Rf=0.4, UV-active). The reaction mixture was filtered and the filter cake was extracted with EtOAc (1000 mL). The filtrate was washed with saturated aq. Na$_2$S$_2$O$_3$ (2×500 mL); saturated aq. FeSO$_4$ (300 mL); and then brine (500 mL). The organic layer was dried over anhydrous Na$_2$SO$_4$, filtered and concentrated under reduced pressure to obtain the crude title compound (150 g).

Preparation of ethyl 2-(3-(difluoromethyl)-4,4a-dihydrospiro[cyclopropa[3,4]cyclopenta[,2-c]pyrazole-5,2'-[1,3]dithiolane]-1(3bH)-yl)acetate

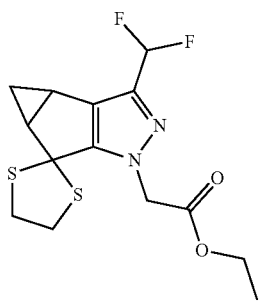 [SMILES: CCOC(=O)Cn1nc(C(F)F)c2c1C1(SCCS1)C1CC21]

To a stirred solution of ethyl 2-(3-(difluoromethyl)-5-oxo-3b,4,4a,5-tetrahydro-1H-cyclopropa[3,4]cyclopenta[1,2-c]pyrazol-1-yl)acetate (75 g, 269 mmol) in DCM (1500 mL) at 27° C. under nitrogen atmosphere was added ethane-1,2-dithiol (43.0 mL, 511 mmol) followed by the addition of boron trifluoride acetic acid (72.6 mL, 511 mmol). The solution was stirred for 16 h. Progress of the reaction was monitored by TLC (SiO$_2$, 20% Acetone/Pet, Rf=0.35, UV-Active). After completion, the reaction mixture was cooled to 0° C. and quenched via the addition of aq. saturated NaHCO$_3$ (500 mL). The mixture was extracted with DCM (2×1000 mL). The combined organics were washed with brine (1000 mL), dried over anhydrous Na$_2$SO$_4$, filtered and concentrated under reduced pressure to obtain a brown liquid. This material was subjected to silica gel column chromatography (Pet.:EtOAc 95:5→90:10) to afford ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate as an off-white solid, 80 g (74%). $^1$H-NMR (400 MHz, CDCl$_3$) δ=6.61 (t, J=55.2 Hz, 1H), 5.00-4.85 (m, 2H), 4.29-4.19 (m, 2H), 3.55-3.46 (m, 4H), 2.63-2.53 (m, 1H), 2.49-2.38 (m, 1H), 1.30-1.24 (m, 4H), 0.65-0.60 (m, 1H). LCMS M+H=346.9.

Preparation of ethyl 2-(3-(difluoromethyl)-5,5-difluoro-3b,4,4a,5-tetrahydro-1H-cyclopropa[3,4]cyclopenta[,2-c]pyrazol-1-yl)acetate

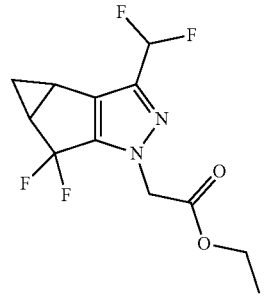 [SMILES: CCOC(=O)Cn1nc(C(F)F)c2c1C(F)(F)C1CC21]

To a stirred solution of 1,3-dibromo-5,5-dimethylimidazolidine-2,4-dione (26.3 g, 92 mmol) in DCM (20 mL) at −70° C. under N$_2$ atmosphere was added HF-pyridine (2.460 g, 24.83 mmol). The solution was for 30 min. To the solution was added a solution of ethyl 2-(3-(difluoromethyl)-4,4a-dihydrospiro[cyclopropa[3,4]cyclopenta[1,2-c]pyrazole-5,2'-1,3]dithiolane]-1(3bH)-yl)acetate (10 g, 25 mmol) in DCM (20 mL). The reaction mixture was allowed to warm to −40° C. and then was stirred at that temperature for 1 h. Progress of the reaction was monitored by TLC (SiO2, 30% EtOAc/Pet, Rf=0.3, UV in-active). The reaction mixture was quenched via the addition of aq. sat. NaHCO$_3$ (200 mL). The mixture was warmed to room temperature and was then extracted with EtOAc (2×100 mL). The combined organics were washed with brine (50 mL); dried over anhydrous Na$_2$SO$_4$; filtered; and were concentrated under reduced pressure to afford a brown solid. This material was subjected to silica gel column chromatography (Pet.:EtOAc 100:0475-25) to afford ethyl 2-(3-(difluoromethyl)-5,5-difluoro-3b,4,4a,5-tetrahydro-1H-cyclopropa[3,4]cyclopenta[1,2-c]pyrazol-1-yl)acetate as a pale-yellow solid, 8.5 g (91%). H NMR (400 MHz, CDCl$_3$) δ=6.62 (t, J=55.2 Hz, 1H), 4.82 (s, 2H), 4.30-4.18 (m, 2H), 2.51-2.37 (m, 2H), 1.42-1.35 (m, 1H), 1.31-1.23 (m, 3H), 1.14-1.08 (m, 1H). LCMS M+H=293.07.

Preparation of 2-(3-(difluoromethyl)-5,5-difluoro-3b,4,4a,5-tetrahydro-1H-cyclopropa[3,4]cyclopenta[1,2-c]pyrazol-1-yl)acetic acid

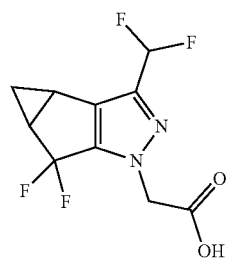 [SMILES: O=C(O)Cn1nc(C(F)F)c2c1C(F)(F)C1CC21]

To a stirred solution of ethyl 2-(3-(difluoromethyl)-5,5-difluoro-3b,4,4a,5-tetrahydro-1H-cyclopropa[3,4]cyclopenta[1,2-c]pyrazol-1-yl)acetate (15 g, 50 mmol) in THF (17 mL) and MeOH (66 mL) at 0° C. under N$_2$ atmosphere was added a solution of LiOH (1.788 g, 74.7 mmol) in water (66 mL). The reaction mixture was allowed to warm to 27°

C. and was then stirred for 3 h at that temperature. Progress of the reaction was monitored by TLC (SiO$_2$, 5% MeOH/DCM, Rf=0.2, UV Active). After completion, the reaction mixture was concentrated under reduced pressure; diluted with water (50 mL); and washed with EtOAc (2×250 mL) to remove impurities. The aqueous layer was adjusted to pH 2-3 using aq. HCl (1M), then was extracted with EtOAc (3×1000 mL). The combined organics were dried over anhydrous Na$_2$SO$_4$; filtered; and concentrated under reduced pressure to afford 2-(3-(difluoromethyl)-5,5-difluoro-3b,4,4a,5-tetrahydro-1H-cyclopropa[3,4]cyclopenta[1,2-c]pyrazol-1-yl)acetic acid as an off white solid, 14 g (98%). LCMS M+H=265.15.

Separation Affording 2-((3bS,4aR)-3-(difluoromethyl)-5,5-difluoro-3b,4,4a,5-tetrahydro-1H-cyclopropa[3,4]cyclopenta[,2-c]pyrazol-1-yl)acetic acid and 2-((3bR,4aS)-3-(difluoromethyl)-5,5-difluoro-3b,4,4a,5-tetrahydro-H-cyclopropa[3,4]cyclopenta[1,2-c]pyrazol-1-yl)acetic acid

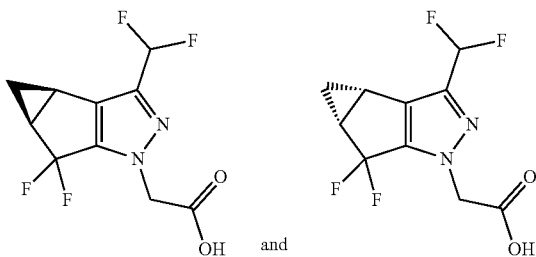 [SMILES: O=C(O)Cn1nc(C(F)F)c2c1C(F)(F)[C@H]1C[C@@H]21 ; O=C(O)Cn1nc(C(F)F)c2c1C(F)(F)[C@@H]1C[C@H]21]

2-(3-(difluoromethyl)-5,5-difluoro-3b,4,4a,5-tetrahydro-1H-cyclopropa[3,4]cyclopenta[1,2-c]pyrazol-1-yl)acetic acid (5.5 g) was dissolved in isopropanol (20 mL). The solution was subjected portion-wise to SFC chiral separation as follows: Instrument=Thar 80; column=Chiralpak IC 30×250 mm, 5 micron; solvent A=super critical CO$_2$; solvent B=isopropanol with 0.5% isopropylamine (v/v); eluent composition=70% A:30% B; flow-rate=65 g/min; back-pressure=100 bar; temperature=30° C.; injection volume=2.5 mL; detection=220 nm. 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid was collected as peak eluting from 7.5 min. to 14 min; 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid was collected as a peak eluting from 2.7 min. to 5.8 min. For each enantiomer, the resulting solution was concentrated under reduced pressure and the resulting solids were dissolved in EtOAc, then twice washed with aq. citric acid (1M) followed by water followed by brine. The organic solution was dried over Na$_2$SO$_4$; filtered; then concentrated in vacuo to afford the separated enantiomer in 80-90% recovery.

Preparation of ethyl 2-(3,5-bis(difluoromethyl)-H-pyrazol-1-yl)acetate

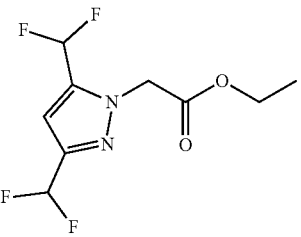 [SMILES: CCOC(=O)Cn1nc(C(F)F)cc1C(F)F]

To a stirred solution of 1,1,5,5-tetrafluoropentane-2,4-dione (15 g, 87 mmol) in ethanol (150 mL) under N$_2$ atmosphere at 26° C. was added sulfuric acid (1.394 mL, 26.2 mmol) followed by ethyl aminoglycinate hydrochloride (16.17 g, 105 mmol). The reaction mixture was heated to 100° C. and then stirred for 3 h at that temperature. Progress of the reaction was monitored by TLC (SiO$_2$, 30% EtOAc/pet, Rf=0.4, UV-active). After completion, the reaction mixture was cooled to room temperature and then was concentrated under reduced pressure. The resulting residue was dissolved in water (100 mL) and then extracted with EtOAc (2×100 mL). The combined organic layers were washed with brine (50 mL), dried over anhydrous Na$_2$SO$_4$, filtered and then concentrated under reduced pressure to afford ethyl 2-(3,5-bis(difluoromethyl)-1H-pyrazol-1-yl)acetate as pale-yellow solid, 22.0 g (86%). $^1$H NMR (400 MHz, CDCl$_3$) δ=6.91-6.52 (m, 3H), 5.03 (s, 2H), 4.30-4.20 (m, 2H), 1.32-1.25 (m, 3H). LCMS: (M+H)=255.21, LCMS Purity=86.6%.

Preparation of 2-(3,5-bis(difluoromethyl)-1H-pyrazol-1-yl)acetic acid

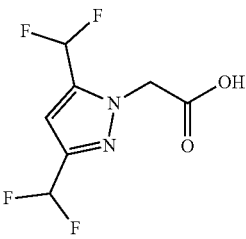 [SMILES: O=C(O)Cn1nc(C(F)F)cc1C(F)F]

To a stirred solution of ethyl 2-(3,5-bis(difluoromethyl)-1H-pyrazol-1-yl)acetate (22 g, 75 mmol) in THF (50 mL) and methanol (25 mL) under N$_2$ atmosphere at 0° C. was added dropwise a solution of lithium hydroxide (5.41 g, 226 mmol) in water (25 mL). The reaction mixture was allowed to warm to 27° C. and was then stirred for 16 h at that temperature. Progress of the reaction was monitored by TLC (SiO$_2$, 50% EtOAc/pet, Rf=0.2, UV-active). After completion, the reaction mixture was concentrated under reduced pressure. The resulting residue was dissolved in water (100 mL) and the solution was adjusted to pH 3 using aq. HCl (2 N). The solution was extracted with EtOAc (4×50 mL). The combined organic layers were washed with brine (50 mL), dried over anhydrous Na$_2$SO$_4$, filtered, and then concentrated under reduced pressure to afford 2-(3,5-bis(difluoromethyl)-1H-pyrazol-1-yl)acetic as pale-yellow solid acid, 15 g (87%). $^1$H NMR (400 MHz, DMSO-$d_6$) δ=13.53-13.24 (m, 1H), 7.46-7.07 (m, 3H), 5.14 (s, 2H). LCMS: (M−H)=225.15; LCMS Purity=98.7%.

Preparation of
1-cyclopropyl-4,4-difluorobutane-1,3-dione

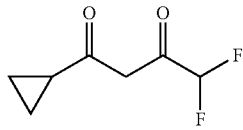 [SMILES: O=C(CC(=O)C1CC1)C(F)F]

To a stirred solution of 1-cyclopropylethan-1-one (20 g, 238 mmol) in diethyl ether (2000 mL) under $N_2$ atmosphere at −78° C. was slowly added NaHMDS (119 mL, 238 mmol) over a period of 20 min. The solution was then stirred for 45 min at −78° C. To the solution was added ethyl 2,2-difluoroacetate (75 mL, 713 mmol). The reaction mixture was slowly warmed to 27° C. and then stirred for 16 h. After completion, the reaction mixture was quenched with water (80 mL) and washed with diethyl ether (100 mL). The aqueous layer was acidified with aq. HCl (1N, 20 mL) and extracted with diethyl ether (2×100 mL). The combined organic layers were washed with brine (50 mL), dried over $Na_2SO_4$, filtered and concentrated under reduced pressure to afford 1-cyclopropyl-4,4-difluorobutane-1,3-dione as pale-yellow oil 25 g (65%). $^1$H NMR (400 MHz, CDCl$_3$) δ=6.07-5.87 (m, 2H), 1.84-1.75 (m, 1H), 1.28-1.19 (m, 2H), 1.10-1.05 (m, 2H).

Preparation of
5-cyclopropyl-3-(difluoromethyl)-1H-pyrazole

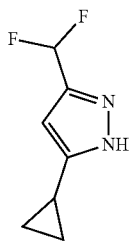 [SMILES: FC(F)c1cc(C2CC2)[nH]n1]

To a stirred solution of 1-cyclopropyl-4,4-difluorobutane-1,3-dione (25 g, 154 mmol) in ethanol (250 mL) at 27° C. was added hydrazine.$H_2O$ (16.13 mL, 385 mmol) followed by dropwise addition of hydrochloric acid (0.18 mL, 5.92 mmol). The reaction mixture was heated to 80° C. and stirred at that temperature for 6 h. The reaction was monitored by TLC (50% EtOAc in pet ether; RF: 0.2; Detection: KMnO$_4$ active). After completion, the reaction mixture was concentrated under reduced pressure. The resulting residue was dissolved in water (250 mL) and extracted with ethyl acetate (3×200 mL). The combined organic layers were washed with brine (50 mL), dried over $Na_2SO_4$, filtered and concentrated under reduced pressure to afford 5-cyclopropyl-3-(difluoromethyl)-1H-pyrazole as a yellow liquid 20 g (79%). $^1$H NMR (400 MHz, CDCl$_3$) δ=6.79-6.49 (m, 1H), 6.24-6.08 (m, 1H), 1.96-1.82 (m, 1H), 1.09-0.91 (m, 2H), 0.79-0.56 (m, 2H) LCMS: M+H=159.11, purity=96.91%.

Preparation of ethyl 2-(5-cyclopropyl-3-(difluoromethyl)-1H-pyrazol-1-yl) acetate

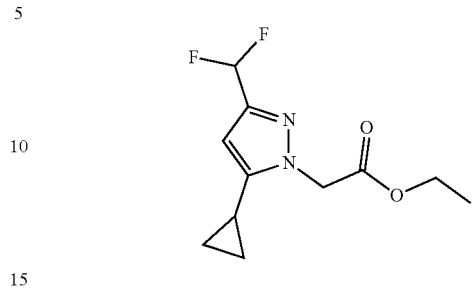

To a stirred solution of 5-cyclopropyl-3-(difluoromethyl)-1H-pyrazole (20 g, 123 mmol) in acetonitrile (200 mL) at 27° C. under $N_2$ atmosphere was added DIPEA (53.5 mL, 306 mmol) followed by ethyl bromoacetate (27.3 mL, 245 mmol). The reaction mixture was stirred at 65° C. for 48 hr. The progress of the reaction was monitored by TLC (SiO$_2$, Mobile phase: 30% ethyl acetate in pet ether; RE: 0.5 and KMnO$_4$ active). After completion, the reaction mixture was diluted with water (20 mL) and extracted with ethyl acetate (2×500 mL). The combined organic layers were washed with brine solution (500 mL) and dried over anhydrous $Na_2SO_4$, filtered and concentrated under vacuum to afford the crude compound as brown oil (30 g). This material was subjected to silica gel chromatography (pet.:EtOAc 80:20→70:30) to afford ethyl 2-(5-cyclopropyl-3-(difluoromethyl)-1H-pyrazol-1-yl)acetate as a mixture of regioisomers, 25 g. The material was further purified by HPLC using the following conditions: Column=KROMOSIL PHENYL, 25×150 mm, 10 μm; Mobile phase A: 10 mM ammonium bicarbonate in water; Mobile phase B: acetonitrile; flow rate=25 mL/min; temperature=ambient; Gradient (minute/% B)=0/10, 2/10, 10/30, 15/30, 15.2/100, 18/100, 18.2/10. Fractions containing the desired product were pooled and then concentrated under reduced pressure to afford an aqueous mixture. This mixture was extracted with ethyl acetate (3×100 mL). The combined organics were dried over anhydrous $Na_2SO_4$, filtered, and concentrated under reduced pressure to afford ethyl 2-(5-cyclopropyl-3-(difluoromethyl)-1H-pyrazol-1-yl) acetate as a pale yellow oil, 2.1 g (24%). $^1$H NMR (400 MHz, DMSO-$d_6$) δ=7.05-6.69 (m, 1H), 6.24-6.14 (m, 1H), 5.21-5.10 (m, 2H), 4.21-4.09 (m, 2H), 1.92-1.76 (m, 1H), 1.27-1.13 (m, 3H), 0.98-0.86 (m, 2H), 0.70-0.56 (m, 2H). LCMS: M+H=245.31, purity=98.89%.

Preparation of 2-(5-cyclopropyl-3-(difluoromethyl)-1H-pyrazol-1-yl) acetic acid

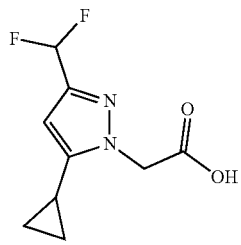 [SMILES: O=C(O)Cn1nc(C(F)F)cc1C1CC1]

To a stirred solution of ethyl 2-(5-cyclopropyl-3-(difluoromethyl)-1H-pyrazol-1-yl)acetate (2.1 g, 8.60 mmol) in THF:methanol (5 mL:2 mL) at 27° C. was added a solution of LiOH (1.647 g, 68.8 mmol) in water (2 mL). The reaction mixture was stirred at 27° C. for 16 hr. The progress of the reaction was monitored by TLC (SiO$_2$, ethyl acetate; Rf: 0.1, UV inactive and KMnO$_4$ active). After completion, the reaction mixture was concentrated under reduced pressure. The resulting aqueous mixture was diluted with water (50 mL) and then washed with ethyl acetate (3×50 mL). The aqueous layer was cooled to 0° C. and then adjusted to pH 2 via addition of aq. HCl (2N). The precipitated solid was collected via filtration and then dried under vacuum to afford 2-(5-cyclopropyl-3-(difluoromethyl)-1H-pyrazol-1-yl) acetic acid as an off white solid, 1.3 g (70%). $^1$H NMR (400 MHz, DMSO-d$_6$) δ=13.27-13.10 (m, 1H), 7.02-6.72 (m, 1H), 6.21-6.10 (m, 1H), 5.08-4.93 (m, 2H), 1.86-1.77 (m, 1H), 0.97-0.87 (m, 2H), 0.71-0.58 (m, 2H). LCMS: M+H=217.20, purity=99.52%.

Preparation of tert-butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate

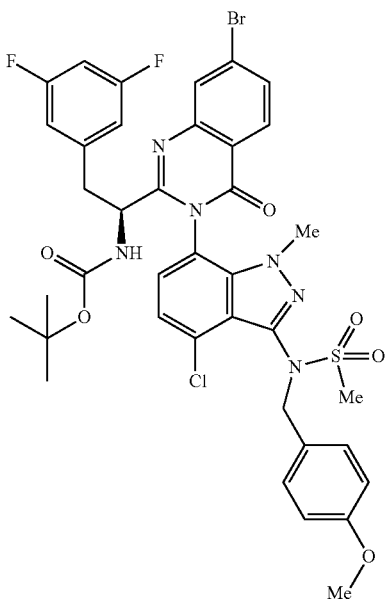 [SMILES: COc1ccc(CN(c2nn(C)c3c(-n4c([C@H](Cc5cc(F)cc(F)c5)NC(=O)OC(C)(C)C)nc5cc(Br)ccc5c4=O)ccc(Cl)c23)S(C)(=O)=O)cc1]

To a solution of (S)-2-((tert-butoxycarbonyl)amino)-3-(3,5-difluorophenyl)propanoic acid (3.82 g, 12.66 mmol), 2-amino-4-bromobenzoic acid (3.01 g, 13.93 mmol) and N-(7-amino-4-chloro-1-methyl-1H-indazol-3-yl)-N-(4-methoxybenzyl)methanesulfonamide (5 g, 12.66 mmol) in pyridine (50 mL) was added diphenyl phosphite (9.80 mL, 50.6 mmol). The resulting mixture was placed on a pre-heated oil bath (70° C.) and heated at 70° C. for 16 h. The mixture was cooled to room temperature and then concentrated under reduced pressure. The mixture was then diluted with EtOAc (approximately 500 mL) and washed with aqueous citric acid (0.5M, 2×50 mL), then aqueous NaOH (1M, 3×50 mL), dried over Na$_2$SO$_4$, filtered, and concentrated. The residue was then purified via silica gel chromatography (330 g silica gel column, gradient of hexanes:EtOAc 0:100→50:50) to afford tert-butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (6.2 g, 7.22 mmol, 57.1% yield) as pale yellow solid foam (inseparable mixture of atropisomers). LC/MS: m/z=801.10 [M–tBu].

Preparation of (S)—N-((6P)-7-(2-(1-amino-2-(3,5-difluorophenyl)ethyl)-7-bromo-4-oxoquinazolin-3 (4H)-yl)-4-chloro-1-methyl-1H-indazol-3-yl)methanesulfonamide

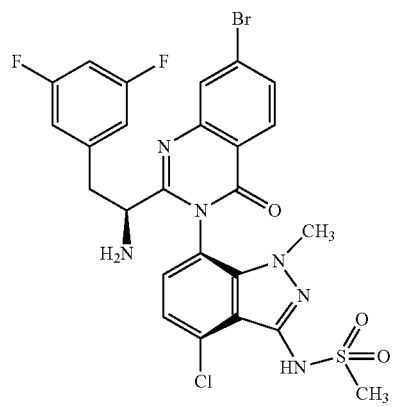

To a stirred solution of tert-butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (6.2 g, 7.22 mmol) in dichloromethane (DCM) (50 mL) was added trifluoroacetic acid (20 mL, 260 mmol) followed by trifluoromethanesulfonic acid (0.770 mL, 8.67 mmol). The resulting dark red solution was stirred at room temperature for 1 h. LCMS at this point indicates two peaks containing the desired product mass, consistent with the presence of two diastereomeric atropisomers (ratio of approximately 30:70). The mixture was concentrated in vacuo and the resulting residue was partitioned between EtOAc (300 mL) and aq. NaOH (1M, 30 mL). The aq. phase was tested and determined to be pH>=8.0. The organic phase was isolated and dried over Na$_2$SO$_4$, filtered, and then concentrated in vacuo. The residue was purified in three approximately equal portions via C18 chromatography (275 g RediSep Gold Column, Mobile Phase A: 5:95 acetonitrile:water with 0.1% TFA; Mobile Phase B: 95:5 acetonitrile:water with 0.1% TFA; gradient of 10-60% B over 30 min). Fractions containing the major atropisomer (second eluting) were combined, adjusted to pH 8 via addition of aq. 1M NaOH; extracted with ethyl acetate; washed with brine (sat. aq. NaCl); dried over Na$_2$SO$_4$; filtered; and then concentrated to afford the desired major atropisomer (S)—N-((6P)-7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (2.4 g, 3.76 mmol, 52% yield). $^1$H NMR (500 MHz, DMSO-d$_6$) δ ppm 8.11 (d, J=8.55 Hz, 1H), 8.06 (d, J=1.53 Hz, 1H), 7.81 (dd, J=8.55, 1.83 Hz, 1H), 7.33 (s, 2H), 6.96-7.05 (m, 1H), 6.75 (br d, J=7.02 Hz, 2H), 3.67 (s, 3H), 3.56 (dd, J=7.63, 5.19 Hz, 1H), 3.25-3.29 (m, 1H), 3.21 (s, 3H), 2.81 (dd, J=13.43, 8.24 Hz, 1H). LCMS: m/z=637.05 [M+H]$^+$.

Preparation of N—((S)-1-((3P)-7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[,2-c]pyrazol-1-yl)acetamide

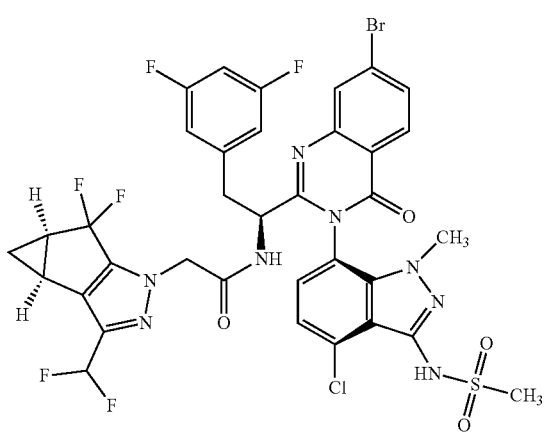

To a solution of (S)—N-((6P)-7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (2.08 g, 3.26 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.861 g, 3.26 mmol) and diisopropylethylamine ("DIPEA") (1.709 mL, 9.78 mmol) in tetrahydrofuran (THF) (30 mL) was added HATU (1.364 g, 3.59 mmol). The resulting mixture was stirred at room temp for 3 h. To the mixture was added ammonia in methanol (2M, 3 mL). The mixture was stirred at room temp for 30 min. Water was then added and the mixture was extracted with ethyl acetate; washed with brine; dried over Na$_2$SO$_4$, filtered; and concentrated in vacuo. The resulting residue was subjected to silica gel chromatography (hexanes:EtOAc 100:0→30:70) to afford N—((S)-1-((3P)-7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (2.5 g, 2.83 mmol, 87% yield). $^1$H NMR (500 MHz, CDCl$_3$) δ ppm 8.18 (d, J=8.24 Hz, 1H), 7.88 (d, J=1.53 Hz, 1H), 7.72 (dd, J=8.55, 1.83 Hz, 1H), 7.33 (s, 1H), 7.16 (d, J=7.63 Hz, 1H), 6.57-6.83 (m, 4H), 6.38 (br d, J=5.80 Hz, 2H), 4.71-4.80 (m, 1H), 4.63 (d, J=6.71 Hz, 2H), 3.56 (s, 3H), 3.40 (s, 3H), 3.18 (dd, J=13.73, 6.10 Hz, 1H), 2.86 (dd, J=13.58, 7.48 Hz, 1H), 2.52-2.61 (m, 1H), 2.41-2.50 (m, 1H), 1.42-1.50 (m, 1H), 1.09-1.16 (m, 1H). LCMS: m/z=883.05 [M+H]$^+$.

Preparation of tert-Butyl (S)-(1-(7-bromo-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate

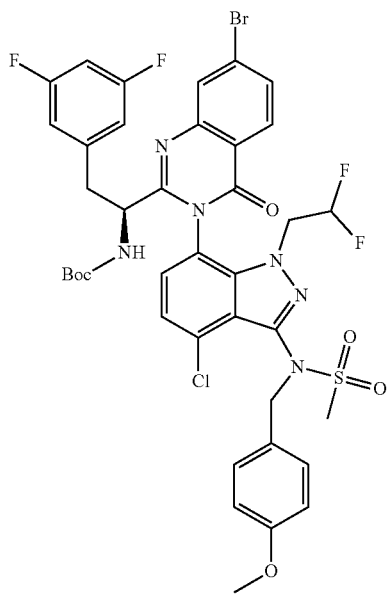 [SMILES: COc1ccc(CN(c2nn(CC(F)F)c3c(-n4c([C@H](Cc5cc(F)cc(F)c5)NC(=O)OC(C)(C)C)nc5cc(Br)ccc5c4=O)ccc(Cl)c23)S(C)(=O)=O)cc1]

To a stirred solution of (S)-2-((tert-butoxycarbonyl)amino)-3-(3,5-difluorophenyl)propanoic acid (15 g, 49.8 mmol) and 2-amino-4-bromobenzoic acid (10.76 g, 49.8 mmol) in pyridine (150 mL) was added diphenyl phosphite (9.64 mL, 49.8 mmol) at 27° C. The mixture was flushed with argon and the flask was then sealed. The reaction mixture was heated to 80° C. and stirred at that temperature for 2 hr. The reaction mixture was cooled to 27° C. and to the mixture was added N-(7-amino-4-chloro-1-(2,2-difluoroethyl)-1H-indazol-3-yl)-N-(4-methoxybenzyl)methanesulfonamide. The flask was sealed and the mixture was heated at 80° C. for 16 hr. The progress of the reaction was monitored by TLC (SiO$_2$, 30% EtOAc/Pet., Rf=0.4, UV-active). The reaction mixture was allowed to cool to 27° C. and then was concentrated under reduced pressure. The resulting residue was subjected to silica gel column chromatography (Pet.:EtOAc 80:20→70:30) to afford tert-butyl (S)-(1-(7-bromo-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate as an off-white solid, 18 g (35%). The isolated material is a mixture of stereoisomers. LCMS: M+H=907.18 and 909.12; purity=89%.

Preparation of (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide

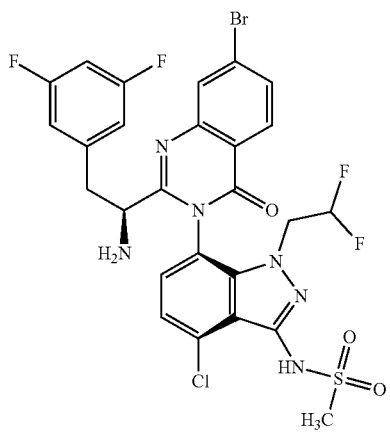

To a stirred solution of tert-butyl (S)-(1-(7-bromo-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate (N68085-33-A2, 15 g, 14.70 mmol) in DCM (150 mL) at 27° C. under $N_2$ atmosphere was added TFA (150 mL, 1947 mmol). The solution was stirred for 10 min. To the reaction mixture was added triflic acid (15 mL, 169 mmol). The solution was stirred for 1 h at 27° C. The progress of the reaction was monitored by TLC ($SiO_2$, 5% MeOH/DCM, Rf=0.4, UV-active). On completion, the solvent was removed under a gentle stream of nitrogen. The residue was dissolved in EtOAc (500 mL), washed with aq saturated $NaHCO_3$ (2×250 mL), brine (150 mL), dried over $Na_2SO_4$ and filtered. The filtrate was concentrated under reduced pressure to afford an off-white solid. LCMS analysis of the solid found a 75.42%:21.47% ratio of diastereomers. The crude solid subjected to C18 reverse-phase column chromatography (Mobile Phase: A: 0.1% TFA in water and B: 0.1% TFA in MeCN). Pure fractions containing the major diastereomer (atropisomer) were combined concentrated under reduced pressure. The resulting aqueous solution was made basic via the addition of aq. sat. $NaHCO_3$; then was extracted with EtOAc (2×500 mL). The combined organic layers were washed with brine (200 mL), dried over $Na_2SO_4$, filtered and concentrated to afford (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide as an off-white solid, 8.0 g (76%). LCMS: M+H=687.34, Purity=96%. This material was further purified to isolate the major enantiomer as follows: (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide (4.5 g, 6.28 mmol) was dissolved in MeOH:MeCN (1:1, 170 mL). The solution was subjected portion-wise to SFC chiral separation as follows: column=(R, R) WHELK-01, 30×250 mm, 5 micron; solvent A=super critical $CO_2$; solvent B=methanol); eluent composition=50% A:50% B; flow-rate=100 g/min; back-pressure=90 bar; injection volume=1.1 mL; detection=214 nm; Stack time=6.8 min. For each isolated enantiomer, the resulting solution was concentrated under reduced pressure to afford an off-white solid. (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide as was isolated as the peak eluting from 6 min to 8 min and afforded 2.1 g (48%). $^1$H NMR (400 MHz, DMSO-$d_6$) δ=8.11-8.05 (m, 2H), 7.83-7.78 (m, 1H), 7.47-7.41 (m, 2H), 7.03-6.97 (m, 1H), 6.76-6.69 (m, 2H), 6.41-6.14 (m, 1H), 4.47-4.22 (m, 2H), 3.54-3.49 (m, 1H), 3.25-3.21 (m, 4H), 2.83-2.76 (m, 1H). LCMS: M+H=687.04, Purity=99%, Chiral HPLC Purity=96%.

Preparation of N—((S)-1-((3P)-7-Bromo-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

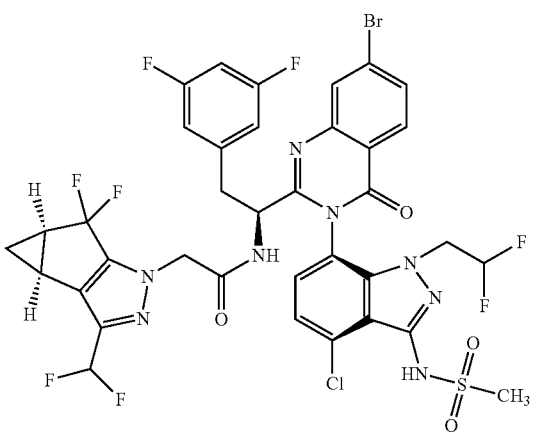

To a solution of (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide (1.75 g, 2.52 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.739 g, 2.77 mmol), HOBt hydrate (0.424 g, 2.77 mmol) and EDC.HCl (0.579 g, 3.02 mmol) in DMF (15 mL) at 27° C. under nitrogen atmosphere was added N-methylmorpholine (2.215 mL, 20.15 mmol). The solution was stirred at 27° C. for 36 h. The progress of the reaction was monitored by TLC ($SiO_2$, 50% EtOAc/Pet. Rf=0.5, UV-active). The reaction mixture was diluted with ice cold water (50 mL), and stirred for 15 min. The precipitated solid was isolated via filtration, washed with water (50 mL), and dried under vacuum to obtain the crude product. This material was treated with EtOAc (20 mL), stirred for 15 min, and then the solids were isolated via filtration and dried under vacuum to afford N—((S)-1-((3P)-7-bromo-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid, 1.6 g (64%). $^1$H NMR (400 MHz, DMSO-$d_6$) δ=10.00 (brs, 1H), 9.23 (d, J=8.1 Hz, 1H), 8.13 (d, J=8.6 Hz, 1H), 7.98 (d, J=2.0 Hz, 1H), 7.85 (dd, J=2.0, 2.1 Hz, 1H), 7.78 (d, J=7.9 Hz, 1H), 7.54 (d, J=7.9 Hz, 1H), 7.07-6.99 (m, 1H), 6.92 (t, J=51.7 Hz, 1H), 6.61 (d, J=6.3 Hz, 2H), 6.11 (t, J=54.6 Hz, 1H), 4.72-4.57 (m, 2H), 4.38 (tt, J=107, 2.9 Hz, 1H), 4.31-4.19 (m, 1H), 3.96-3.83 (m, 1H), 3.44-3.37 (m, 1H), 3.19 (s, 3H), 3.00-2.92 (m, 1H), 2.49-2.45 (m, 2H), 1.39-1.31 (m, 1H), 0.87-0.82 (m, 1H). LCMS: M+H=933.13, LCMS Purity=95%, HPLC Purity=96%, Chiral HPLC Purity=97%.

Preparation of tert-butyl (S)-(1-(7-bromo-3-(4-chloro-1-(2,2-difluoroethyl)-3-(N-(4-methoxybenzyl) cyclopropanesulfonamido)-1H-indazol-7-yl)-4-oxo-3,4-dihydroquinazolin-2-yl)-2-(3,5-difluorophenyl)ethyl)carbamate

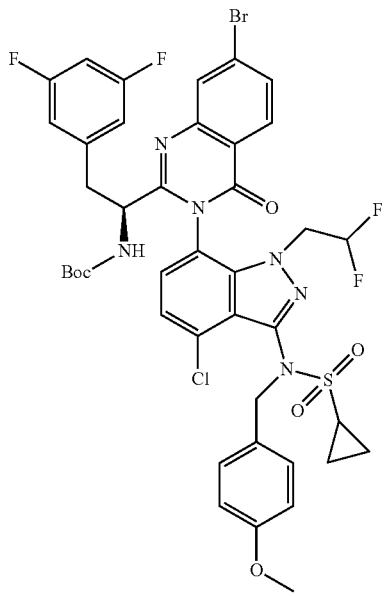 [SMILES: COc1ccc(CN(c2nn(CC(F)F)c3c(-n4c([C@H](Cc5cc(F)cc(F)c5)NC(=O)OC(C)(C)C)nc5cc(Br)ccc5c4=O)ccc(Cl)c23)S(=O)(=O)C2CC2)cc1]

To a stirred solution of (S)-2-((tert-butoxycarbonyl) amino)-3-(3,5-difluorophenyl)propanoic acid (15 g, 49.8 mmol) and 2-amino-4-bromobenzoic acid (12.91 g, 59.7 mmol) in pyridine (150 mL) in a sealed tube at 26° C. was added diphenyl phosphite (35.7 mL, 184 mmol). The reaction mixture was degassed with $N_2$ bubbling for each addition of reagents. The reaction mixture was heated to 80° C. and stirred for 2 hr. The reaction mixture was cooled to 26° C., then N-(7-amino-4-chloro-1-(2,2-difluoroethyl)-1H-indazol-3-yl)-N-(4-methoxybenzyl)cyclopropanesulfonamide (N66734-90-A2, 20.49 g, 34.9 mmol) was added. The mixture was heated at 80° C. for 16 h. The progress of the reaction was monitored by TLC ($SiO_2$, 30% EtOAc/Pet. Rf=0.3). The reaction mixture was cooled to 26° C. and then was concentrated under reduced pressure. The residue was diluted with water (150 mL) and extracted with ethyl acetate (2×500 mL). The combined organic layers were washed with aq. citric acid (5% w/v, 2×150 mL), then brine (250 mL); dried over anhydrous $Na_2SO_4$; filtered; and concentrated under reduced pressure to afford a brown gummy liquid (40 g). The above procedure was repeated, and the crude product of both iterations was combined. This material was then subjected to silica gel column chromatography (pet.:EtOAc, 60:40→55:45) to afforded tert-butyl (S)-(1-(7-bromo-3-(4-chloro-1-(2,2-difluoroethyl)-3-(N-(4-methoxybenzyl)cyclopropanesulfonamido)-1H-indazol-7-yl)-4-oxo-3,4-dihydroquinazolin-2-yl)-2-(3,5-difluorophenyl)ethyl) carbamate (mixture of diastereomers) as a yellow solid (42 g, 98%). LCMS: M+H=933.88 & 935.88; purity=76.91%.

Preparation of (S)—N-((6P)-7-(2-(1-amino-2-(3,5-difluorophenyl)ethyl)-7-bromo-4-oxoquinazolin-3 (4H)-yl)-4-chloro-1-(2,2-difluoroethyl)-1H-indazol-3-yl)cyclopropanesulfonamide

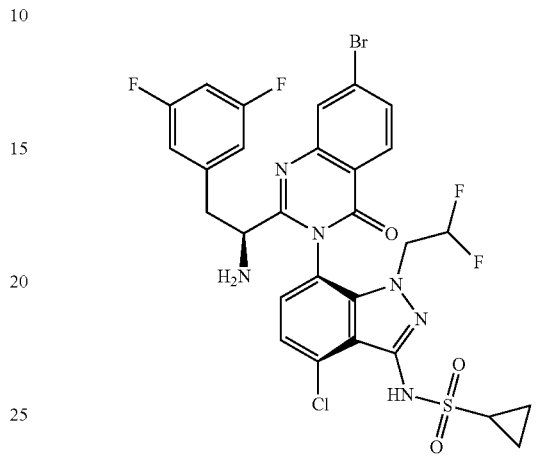

To a stirred solution of tert-butyl (S)-(1-(7-bromo-3-(4-chloro-1-(2,2-difluoroethyl)-3-(N-(4-methoxybenzyl)cyclopropanesulfonamido)-1H-indazol-7-yl)-4-oxo-3,4-dihydroquinazolin-2-yl)-2-(3,5-difluorophenyl)ethyl)carbamate (14 g, 11.53 mmol) in DCM (140 mL) at 27° C. under N2 atmosphere was added TFA (140 mL). The solution was stirred for 10 min. To the solution was added trifluoromethanesulfonic acid (7.16 mL, 81 mmol). The reaction mixture was stirred for 1 h at 27° C. The progress of the reaction was monitored by TLC ($SiO_2$, 50% EtOAc/pet, Rf=0.2). The solvent was removed under a gentle stream of nitrogen. The residue was dissolved in EtOAc (500 mL) and the organic layer was washed with aq. saturated $NaHCO_3$ (2×150 mL), brine (50 mL), dried over $Na_2SO_4$, filtered and concentrated to dryness to the crude compound as an off white solid (12 g). The above procedure was repeated twice more and the additional crude solids (2×14 g) were combined with the above. The combined material was dissolved in dichloromethane (500 mL) and concentrated to afford a homogeneous crude solid. This material was washed with pet. ether:EtOAc (80:20) and then dried under vacuum to afford a brown solid (30 g). This material was then subjected to C18 reverse phase chromatography under the following conditions: Column=RediSep Gold HP C18 275 g; Mobile Phase A=Water:MeCN:TFA (950:50:1); Mobile Phase B=Water:MeCN:TFA (50:950:1); flow rate=80 mL/min; gradient profile (time/% B)=5/5, 5/10, 5/15, 10/20, 15/30, 20/40, 15/45, 10/50; temperature=ambient. Fractions of the major peak were pooled and concentrated under reduced pressure to remove the non-aqueous solvent. The resulting aq. solution was neutralized via the addition of sat. aq. $NaHCO_3$(1000 mL), then was extracted with EtOAc (4×500 mL). The combined organics were washed with brine (500 mL), dried over anhydrous $Na_2SO_4$, filtered and concentrated to afford (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl) cyclopropanesulfonamide (single diastereomer) as an off white solid. The material was then subjected to SFC purification under the following conditions: Column/dimensions=Chiralpak OX—H (30×250 mm), 5µ; Solvent A=liquid CO₂; Solvent B=Methanol with 0.5% diethyl amine; Eluent=A:B (70:30); Flow-rate=100.0 g/min; Back Pressure=100.0 bar; Detection=UV (214 nm); injection volume=1.3 mL (93 mg/injection); 160 injections. Two peaks were collected separately and the major peak was concentrated under reduced pressure to afford (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (single stereoisomer) as a pale yellow solid, 7.5 g (20%). ¹H NMR (400 MHz, DMSO-d₆) δ=8.11-8.04 (m, 2H), 7.82-7.78 (m, 1H), 7.47-7.39 (m, 2H), 7.02-6.95 (m, 1H), 6.76-6.69 (m, 2H), 6.38-6.19 (m, 1H), 4.48-4.37 (m, 1H), 4.32-4.24 (m, 1H), 3.54-3.48 (m, 1H), 3.3-3.20 (m, 1H), 2.97-2.90 (m, 1H), 2.83-2.76 (m, 1H), 1.05-0.99 (m, 4H). LCMS: M+H=712.94 and 714.94; purity=98.37%, chiral HPLC purity=96%.

Preparation of N—((S)-1-((3P)-7-bromo-3-(4-chloro-3-(cyclopropanesulfonamido)-1-(2,2-difluoroethyl)-H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[,2-c]pyrazol-1-yl)acetamide

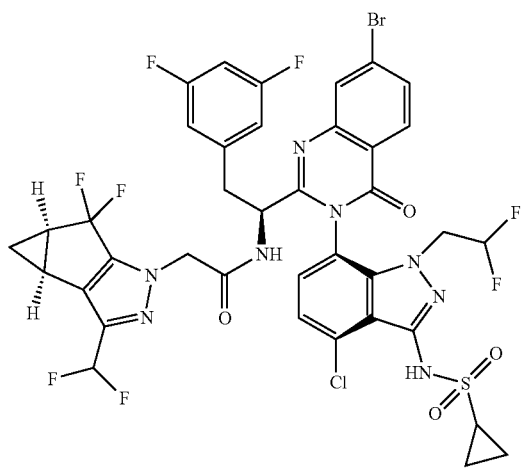

To a stirred solution of (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (500 mg, 0.700 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (N68084-15-A1, 185 mg, 0.700 mmol), and HOBt (42.9 mg, 0.280 mmol) in DMF (5 mL) at 27° C. was added N-methylmorpholine (0.308 mL, 2.80 mmol) and N-(3-dimethylaminopropyl)-N'-ethylcarbodiimide hydrochloride (242 mg, 1.261 mmol). The reaction mixture was stirred at 27° C. for 16 h. The progress of the reaction was monitored by TLC (SiO₂, 50% EtOAc/Pet., Rf=0.3, UV-active). On completion, the reaction mixture was diluted with ice cold water (70 mL) and then stirred for 15 min at 27° C. The precipitated solids were collected by filtration and then dried under vacuum to obtain the crude compound as an off-white solid. The crude compound was subjected to silica gel chromatography (pet.:EtOAc (98:2450:50) to afford N—((S)-1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid, 550 mg (80%).H NMR (400 MHz, DMSO-d₆) δ=9.99 (s, 1H), 9.24 (d, J=8.1 Hz, 1H), 8.13 (d, J=8.8 Hz, 1H), 7.97 (d, J=1.8 Hz, 1H), 7.87-7.83 (m, 1H), 7.77 (d, J=7.9 Hz, 1H), 7.54 (d, J=7.9 Hz, 1H), 7.06-6.79 (m, 2H), 6.64-6.58 (m, 2H), 6.23-5.98 (m, 1H), 4.74-4.57 (m, 2H), 4.41-4.35 (m, 1H), 4.29-4.16 (m, 1H), 3.94-3.84 (m, 1H), 3.38-3.34 (m, 1H), 3.02-2.93 (m, 1H), 2.90-2.83 (m, 1H), 2.48-2.35 (m, 2H), 1.37-1.30 (m, 1H), 1.02-0.90 (m, 4H), 0.87-0.82 (m, 1H). LCMS analysis method F: RT=6.74 mins, (M+H)=959.0 and 961.0; LCMS Purity=98%; Chiral HPLC Purity=98%.

Preparation of (S)-2-(3,5-bis(difluoromethyl)-H-pyrazol-1-yl)-N-(1-((3P)-7-bromo-3-(4-chloro-3-(cyclopropanesulfonamido)-1-(2,2-difluoroethyl)-H-indazol-7-yl)-4-oxo-3,4-dihydroquinazolin-2-yl)-2-(3,5-difluorophenyl)ethyl)acetamide

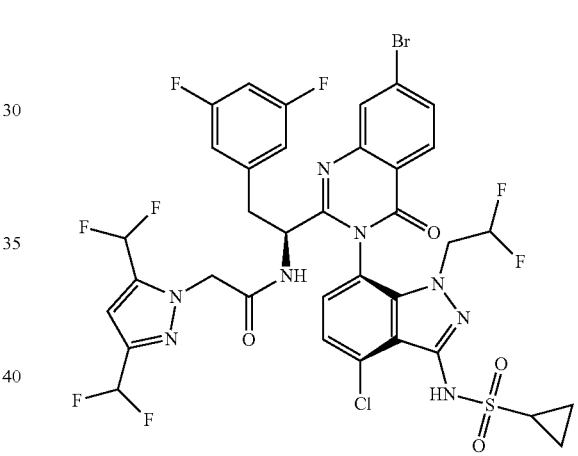

To a solution of (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (500 mg, 0.690 mmol), 2-(3,5-bis(difluoromethyl)-1H-pyrazol-1-yl)acetic acid (236 mg, 1.035 mmol) and HOBt (190 mg, 1.242 mmol) in DMF (10 mL) at 27° C. was added N-methylmorpholine (0.152 mL, 1.380 mmol) and N-(3-dimethylaminopropyl)-N'-ethylcarbodiimide hydrochloride (238 mg, 1.242 mmol). Then the reaction mixture was degassed for 10 min with nitrogen gas. The reaction mixture was stirred at 27° C. for 16 h; progress of the reaction was monitored by TLC (SiO₂, 50% EtOAc/Pet. Rf=0.2). After completion of reaction, the reaction mixture was diluted with ethyl acetate (50 mL) and washed with ice cold water (2×30 mL), and then brine (20 mL). The organic layer was separated, dried over anhydrous Na₂SO₄, filtered and concentrated to dryness to afford the crude compound as an off white solid (700 mg). This material was subjected to silica gel column chromatography using silica gel (pet:EtOAc, 100:0→50:50) to afford (S)-2-(3,5-bis(difluoromethyl)-1H-pyrazol-1-yl)-N-(1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3, 5-difluorophenyl)ethyl)acetamide as an off white solid, 500 mg (76%). ¹H NMR (400 MHz, DMSO-d₆) δ=9.99-9.94 (m, 1H), 9.31-9.25 (m, 1H), 8.14 (d, J=8.6 Hz, 1H), 7.99 (d, J=1.8 Hz, 1H), 7.88-7.83 (m, 1H), 7.75 (d, J=8.1 Hz, 1H), 7.52 (d, J=7.9 Hz, 1H), 7.07-6.82 (m, 4H), 6.65-6.57 (m, 2H), 6.19-5.99 (m, 1H), 4.94-4.81 (m, 2H), 4.45-4.38 (m, 1H), 4.31-4.19 (m, 1H), 3.97-3.87 (m, 1H), 3.39-3.34 (m, 1H), 3.01-2.94 (m, 1H), 2.89-2.82 (m, 1H), 1.00-0.92 (m, 4H). LCMS: M+H=921.24 and 923.12; purity=98.3%, chiral HPLC purity=99.46%.

Preparation of (S)—N-(1-((3P)-7-bromo-3-(4-chloro-3-(cyclopropanesufonamido)-1-(2,2-difluoro-ethyl)-H-indazol-7-yl)-4-oxo-3,4-dihydroquinazolin-2-yl)-2-(3,5-difluorophenyl)ethyl)-2-(5-cyclopropyl-3-(difluoromethyl)-1H-pyrazol-1-yl)acetamide

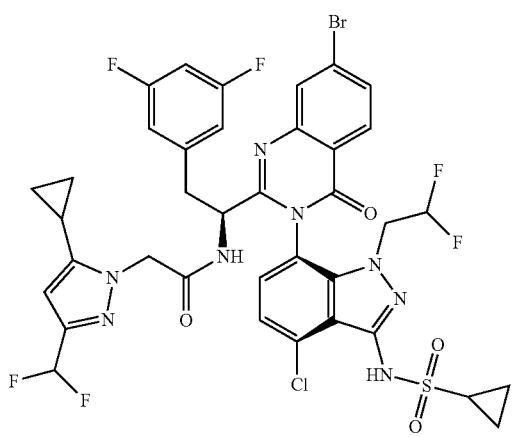

To a solution of (S)—N-((6P)-7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (600 mg, 0.826 mmol), 2-(3-cyclopropyl-5-(difluoromethyl)-1H-pyrazol-1-yl)acetic acid (179 mg, 0.826 mmol) and HOBt (50.6 mg, 0.330 mmol) in DMF (5 mL) at 27° C. was added N-methylmorpholine (0.363 mL, 3.30 mmol) and N-(3-dimethylaminopropyl)-N'-ethylcarbodiimide hydrochloride (285 mg, 1.487 mmol). Then the reaction mixture was degassed for 10 min with nitrogen gas and then stirred at 27° C. for 16 h. The progress of the reaction was monitored by TLC (SiO₂, 50% EtOAc/Pet. Rf=0.3). The reaction mixture was diluted with ice cold water (70 mL) and then was stirred for 30 min at 27° C. The precipitated solid was isolated via filtration and then dried under vacuum to afford (S)—N-(1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-(5-cyclopropyl-3-(difluoromethyl)-1H-pyrazol-1-yl)acetamide as a pale yellow solid, 550 mg (68%). ¹H NMR (400 MHz, DMSO-d₆) δ=10.02-9.85 (m, 1H), 9.17-9.10 (m, 1H), 8.14 (d, J=8.3 Hz, 1H), 7.99-7.95 (m, 1H), 7.87-7.84 (m, 1H), 7.77 (d, J=7.9 Hz, 1H), 7.52 (d, J=7.9 Hz, 1H), 7.07-7.00 (m, 1H), 6.86-6.59 (m, 3H), 6.20-5.98 (m, 2H), 4.77-4.67 (m, 2H), 4.50-4.43 (m, 1H), 4.33-4.22 (m, 1H), 4.00-3.87 (m, 1H), 3.39-3.32 (m, 1H), 3.06-2.94 (m, 2H), 2.60-2.55 (m, 1H), 1.46-1.38 (m, 1H), 1.00-0.91 (m, 4H), 0.75-0.64 (m, 2H), 0.57-0.46 (m, 2H). LCMS: M+H=910.89 and 912.91; purity=93.59%.

Preparation of N—((S)-1-((3P)-3-(4-chloro-1-methyl-3-(methylsufonamido)-H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl) ethyl)-2-((3bS,4aR)-3-(difluoromethyl)-5,5-difluoro-3b,4,4a,5-tetrahydro-1H-cyclopropa[3,4]cyclopenta [1,2-c]pyrazol-1-yl)acetamide

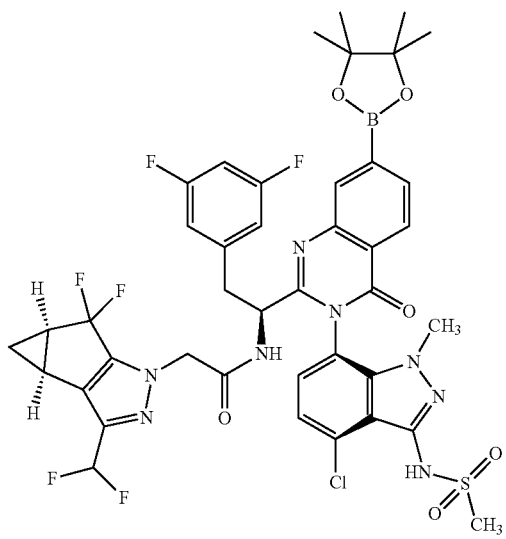

To a round bottom flask equipped with a stir bar was added N—((S)-1-((3P)-7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide (1.00 g, 1.13 mmol), 4,4,4',4',5,5,5',5'-octamethyl-2,2'-bi(1,3,2-dioxaborolane) (431 mg, 1.70 mmol), potassium acetate (333 mg, 3.39 mmol), and [1,1'-bis(diphenylphosphino)ferrocene]dichloropalladium(II) ("Pd(dppf)Cl₂") (83 mg, 0.113 mmol). The flask was sealed with a rubber septum, and then was placed under an argon atmosphere. To the flask was added dioxane (23 mL). The reaction mixture was degassed with argon, then the reaction mixture was stirred at 60° C. for 16 h. The reaction mixture was concentrated in vacuo and adsorbed onto Celite. The resulting powder was subjected to silica gel chromatography (hexanes:EtOAc 100:0-0:100 over 10 column volumes) to afford N—((S)-1-((3P)-3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.2 g, quantitative yield). LCMS: During LCMS analysis both the boronic acid and boronate were observed. Conditions: Wavelength1: 220 nm, Wavelength2: 254 nm, Injection Vol.: 5.00 μl, Stop Time: 4.00, Grad. Time: 3.0, Start % B: 0, End % B: 100, Total Flow: 0.80 ml/min, Solvent A: 95:5 Water:MeCN 0.1% TFA, Solvent B: 5:95 Water:MeCN 0.1% TFA, Column: Acquity UPLC BEH C18 1.7 um; Result: retention time (boronic acid): 2.112 min., mass found: 849.15 (M+H); retention time (boronic ester): 2.733 min., mass found: 931.25 (M+H). ¹H NMR (CDCl₃, 500 MHz) δ 8.26 (d, 1H, J=7.6 Hz), 8.11 (s, 1H), 7.95 (d, 1H, J=7.6 Hz), 7.3-7.3 (m, 1H), 7.14 (d, 1H, J=7.9 Hz), 6.7-6.7 (m, 3H), 6.35 (d, 2H, J=6.8 Hz), 4.7-4.8 (m, 1H), 4.1-4.2 (m, 1H), 3.70 (s, 1H), 3.47 (s, 3H), 3.37 (s, 3H), 3.1-3.2 (m, 1H), 2.8-2.9 (m, 1H), 2.6-2.7 (m, 1H), 2.3-2.5 (m, 1H), 1.8-1.9 (m, 2H), 1.24 (s, 12H), 1.1-1.2 (m, 1H)

Preparation of N—((S)-1-((3P)-3-(4-chloro-1-(2,2-difluoroethyl)-3-(methylsulfonamido)-H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

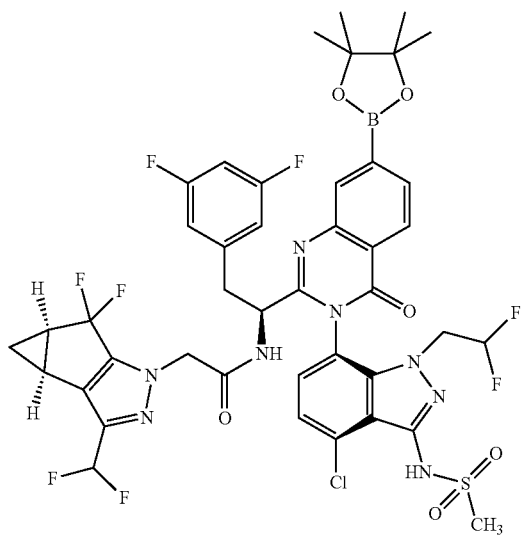

To a dry round-bottom flask equipped with a stir bar was added N—((S)-1-((3P)-7-bromo-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (500 mg, 0.535 mmol), 4,4,4',4',5,5,5',5'-octamethyl-2,2'-bi(1,3,2-dioxaborolane) (204 mg, 0.803 mmol), potassium acetate (158 mg, 1.606 mmol), and PdCl$_2$(dppf) (39.2 mg, 0.054 mmol). The flask was sealed with a septum and then placed under argon atmosphere (vac/fill×3). To the flask was added 1,4-dioxane (14 mL). The mixture was degassed (vac/fill with argon×3). The mixture was then stirred at 60° C. for overnight (16 h). The reaction mixture was concentrated under reduced pressure. The resulting residue was adsorbed onto Celite. The resulting powder was subjected to silica gel column chromatography (40 g silica gel column, hexanes:EtOAc 100:0→50:50 over 10 column volumes). The fractions containing the product were collected and concentrated in vacuo to afford N—((S)-1-((3P)-3-(4-chloro-1-(2,2-difluoroethyl)-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, 520 mg (99%). $^1$H NMR (METHANOL-d$_4$, 500 MHz) δ 8.2-8.3 (m, 2H), 7.97 (d, 1H, J=7.7 Hz), 7.40 (d, 1H, J=8.0 Hz), 7.28 (d, 1H, J=8.0 Hz), 6.5-6.9 (m, 4H), 6.00 (tt, 1H, J=4.1, 55.2 Hz), 4.75 (dd, 1H, J=4.8, 9.2 Hz), 4.6-4.7 (m, 2H), 4.38 (dtd, 1H, J=4.2, 13.3, 15.2 Hz), 4.12 (q, 1H, J=7.2 Hz), 3.9-4.0 (m, 1H), 3.3-3.5 (m, 1H), 3.3-3.3 (m, 3H), 3.06 (dd, 1H, J=9.2, 14.0 Hz), 2.4-2.5 (m, 2H), 2.0-2.0 (m, 2H), 1.3-1.4 (m, 2H), 1.22 (s, 12H), 1.0-1.1 (m, 1H)

Preparation of N—((S)-1-((3P)-3-(4-chloro-3-(cyclopropanesulfonamido)-1-(2,2-difluoroethyl)-H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

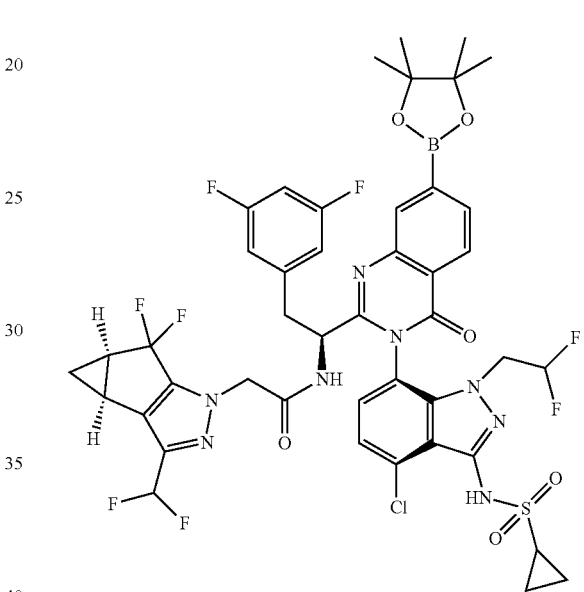

To a dry r.b. flask equipped with a stir bar was added N—((S)-1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (300 mg, 0.312 mmol), 4,4,4',4',5,5,5',5'-octamethyl-2,2'-bi(1,3,2-dioxaborolane) (119 mg, 0.469 mmol), potassium acetate (92 mg, 0.937 mmol) and PdCl$_2$(dppf) (22.86 mg, 0.031 mmol). The flask was sealed with a septum and then placed under argon atmosphere (vac/fill×3). To the flask was added dioxane (6.3 mL). The flask was again placed under argon atmosphere (vac/fill×3). The resulting mixture was stirred at 60° C. for 16 h overnight. Upon cooling to ambient temperature the reaction was concentrated in vacuo and the resulting residue was adsorbed onto Celite. The resulting powder was subjected to silica gel column chromatography (hexanes:EtOAc 100:0-0:100 over 10 CV) to afford N—((S)-1-((3P)-3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, 220 mg (70%). $^1$H NMR (METHANOL-d$_4$, 500 MHz) δ 8.27 (d, 2H, J=6.2

Hz), 8.26 (s, 1H), 7.97 (dd, 1H, J=1.0, 7.9 Hz), 7.41 (d, 1H, J=7.7 Hz), 7.29 (d, 1H, J=7.7 Hz), 6.8-6.8 (m, 1H), 6.70 (br t, 1H, J=54.8 Hz), 6.55 (dd, 2H, J=2.1, 8.0 Hz), 6.01 (t, 1H, J=55.3 Hz), 4.74 (dd, 1H, J=4.8, 9.5 Hz), 4.68 (d, 1H, J=16.4 Hz), 4.59 (d, 1H, J=16.4 Hz), 4.38 (dd, 1H, J=4.2, 15.2 Hz), 4.12 (q, 1H, J=7.2 Hz), 3.91 (dd, 1H, J=3.9, 15.2 Hz), 3.68 (s, 1H), 3.06 (dd, 1H, J=9.4, 14.2 Hz), 2.9-2.9 (m, 1H), 2.4-2.5 (m, 2H), 2.03 (s, 2H), 1.45 (s, 12H), 1.1-1.1 (m, 2H), 1.0-1.0 (m, 3H).

Preparation of N—((S)-1-((3P)-7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of N—((S)-1-((3P)-3-(4-chloro-3-(N-(4-methoxybenzyl)methylsulfonamido)-1-methyl-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

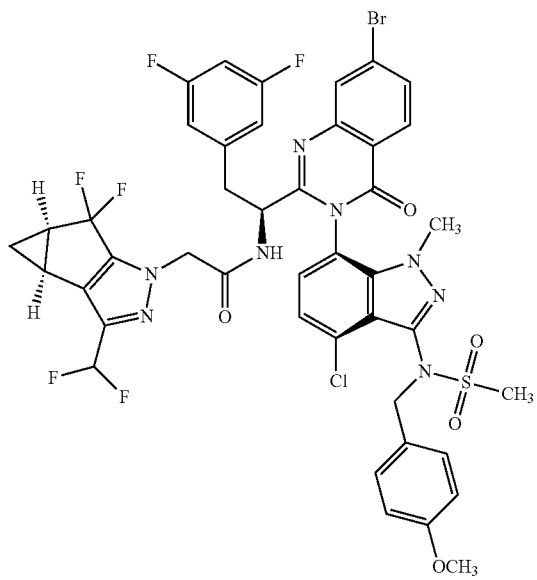

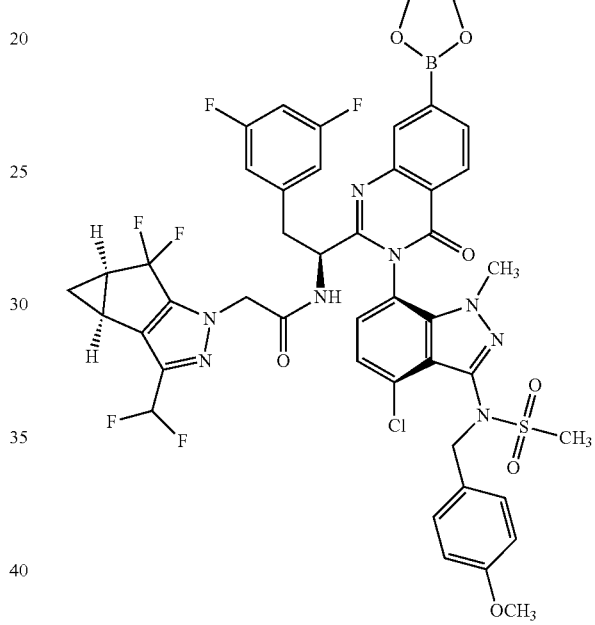

1-(chloromethyl)-4-methoxybenzene (0.276 mL, 2.036 mmol) was added to a stirred solution of N—((S)-1-((3P)-7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.5 g, 1.697 mmol) and cesium carbonate (0.553 g, 1.697 mmol) in N,N-Dimethylformamide (DMF) (10 mL), and the resulting mixture was stirred at room temp for 16 h. Water was then added and the mixture was extracted with ethyl acetate, washed with brine, dried (Na₂SO₄), filtered and concentrated. The residue was then subjected to silica gel column chromatography (hexanes:EtOAc 95:5→70:30) to afford N—((S)-1-((3P)-7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, 1.4 g (82%). LCMS analysis conditions: Wavelength1: 220 nm; Wavelength2: 254 nm; Injection Vol.: 5.00 μl; Stop Time: 4.50 min; Grad. Time: 3.50 min; Start % B: 0; End % B: 100; Total Flow: 0.80 ml/min; Solvent A: 95:5 Water:MeCN with 0.1% TFA; Solvent B: 5:95 Water:MeCN with 0.1% TFA; Column=Acquity UPLC BEH C18, 2.1×100 mm, 1.7 μm. LCMS analysis result: retention time: 3.536 min, M+H: 1003.05.

N—((S)-1-((3P)-7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (954 mg, 0.950 mmol), 4,4,4',4',5,5,5',5'-octamethyl-2,2'-bi(1,3,2-dioxaborolane) (362 mg, 1.425 mmol), potassium acetate (280 mg, 2.85 mmol) and PdCl₂(dppf) (69.5 mg, 0.095 mmol) were combined dry and degassed with Ar. Then they were taken up in dioxane (19 mL) and degassed again with argon and the resulting mixture was stirred at 60° C. overnight (16 h). The reaction mixture was concentrated, adsorbed onto Celite and, the resulting powder was subjected to silica gel column chromatography (hexanes:EtOAc 100:0→0:100 over 10 CVs) to afford N—((S)-1-((3P)-3-(4-chloro-3-(N-(4-methoxybenzyl)methylsulfonamido)-1-methyl-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide, 709 mg (71%). Under LCMS analysis both the boronic ester and the boronic acid are observed. However, 1H-NMR indicates that the product is entirely the boronic ester. LCMS analysis conditions: Wavelength1: 220 nm; Wavelength2: 254 nm; Injection Vol.: 5.00 μl; Stop Time: 2.50 min; Grad. Time: 1.50 min; Start %B: 0; End %B: 100; Total Flow: 0.80 ml/min; Solvent A: 95:5 Water:MeCN with 0.1% TFA; Solvent B: 5:95 Water:MeCN with 0.1% TFA; Column=Acquity UPLC BEH C18, 2.1×50 mm, 1.7 um. LCMS analysis result: retention time: 1.495 min, M+H: 969.15; retention time: 1.760 min, M+H: 1051.25.

Preparation of Example 1: N—((S)-1-((3P)-3-(4-chloro-1-methyl-3-(methylsulfonamido)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

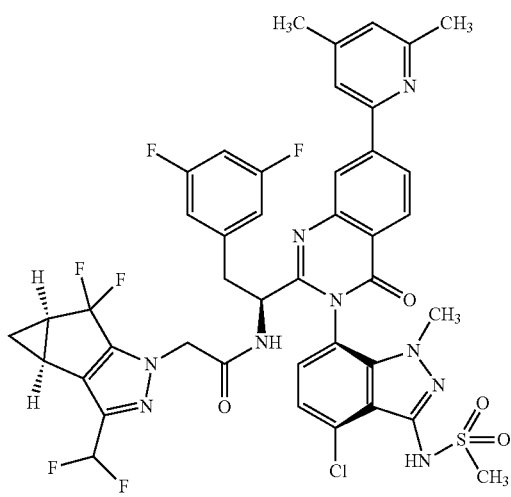

The title compound was prepared according to General Procedure D using 2-bromo-4,6-dimethylpyridine as the coupling partner. The experiment afforded the title compound, N—((S)-1-((3P)-3-(4-chloro-1-methyl-3-(methylsulfonamido)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.36 min.; observed ion=910.8 (M+H). 1H NMR (METHANOL-d4, 500 MHz) δ 8.46 (d, 1H, J=1.2 Hz), 8.38 (d, 1H, J=8.3 Hz), 8.24 (dd, 1H, J=1.8, 8.3 Hz), 7.71 (s, 1H), 7.31 (d, 1H, J=7.7 Hz), 7.23 (s, 1H), 7.20 (d, 1H, J=7.7 Hz), 6.8-6.8 (m, 1H), 6.64 (dd, 2H, J=2.2, 8.2 Hz), 6.71 (t, 1H, J=54.8 Hz), 4.9-4.9 (m, 1H), 4.55 (d, 2H, J=2.1 Hz), 3.64 (s, 3H), 3.5-3.5 (m, 1H), 3.2-3.3 (m, 4H), 3.1-3.2 (m, 2H), 2.64 (s, 3H), 2.4-2.5 (m, 5H)

Preparation of Example 2: N—((S)-1-((3P)-3-(4-chloro-1-methyl-3-(methylsulfonamido)-1H-indazol-7-yl)-7-(4-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

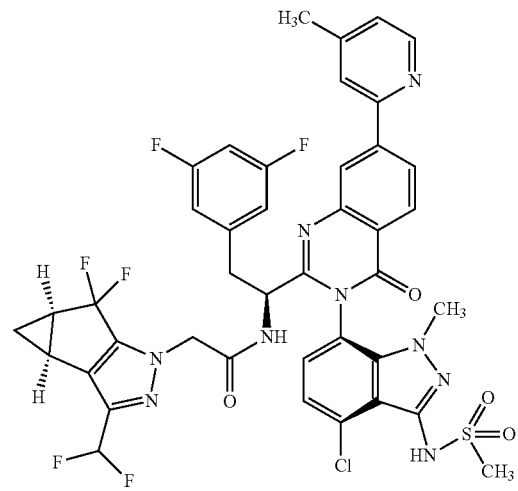

The title compound was prepared according to General Procedure D using 2-bromo-4-methylpyridine as the coupling partner. The experiment afforded the title compound, N—((S)-1-((3P)-3-(4-chloro-1-methyl-3-(methylsulfonamido)-1H-indazol-7-yl)-7-(4-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.37 min.; observed ion=896.7 (M+H). 1H NMR (METHANOL-d4, 500 MHz) δ 8.62 (d, 1H, J=5.7 Hz), 8.48 (d, 1H, J=1.5 Hz), 8.40 (d, 1H, J=8.3 Hz), 8.25 (dd, 1H, J=1.8, 8.3 Hz), 7.95 (d, 1H, J=1.5 Hz), 7.37 (d, 1H, J=5.1 Hz), 7.31 (d, 1H, J=7.7 Hz), 7.20 (d, 1H, J=7.7 Hz), 6.8-6.8 (m, 1H), 6.6-6.7 (m, 2H), 6.70 (t, 1H, J=54.8 Hz), 4.88 (d, 1H, J=5.1 Hz), 4.54 (s, 2H), 3.64 (s, 3H), 3.5-3.5 (m, 1H), 3.2-3.3 (m, 3H), 3.1-3.2 (m, 1H), 2.55 (s, 3H), 2.4-2.5 (m, 2H), 1.3-1.4 (m, 1H), 1.0-1.0 (m, 1H)

Preparation of Example 3: N—((S)-1-((3P)-3-(4-chloro-1-methyl-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 4: N—((S)-1-((3P)-3-(4-chloro-1-methyl-3-(methylsulfonamido)-1H-indazol-7-yl)-7-(4-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

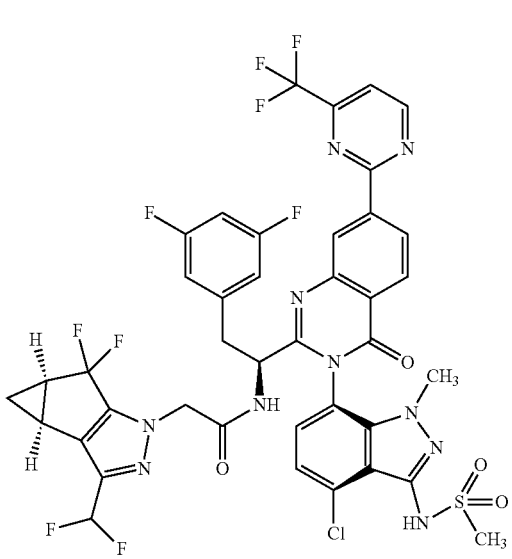

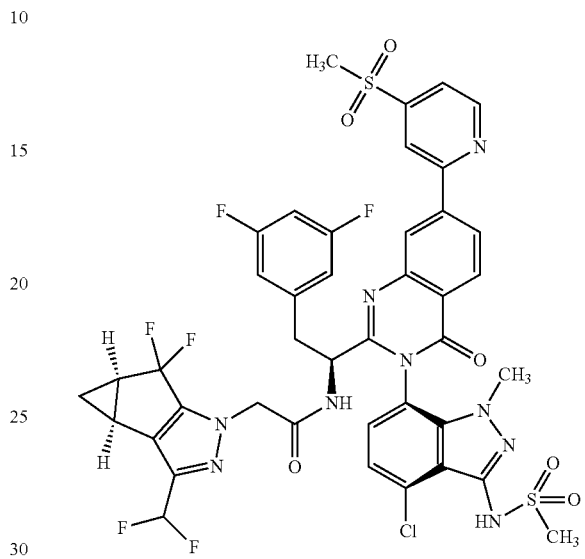

The title compound was prepared according to General Procedure D using 2-chloro-4-(trifluoromethyl)pyrimidine as the coupling partner. The experiment afforded the title compound, N—((S)-1-((3P)-3-(4-chloro-1-methyl-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.48 min.; observed ion=951.7 (M+H). 1H NMR (METHANOL-d4, 500 MHz) δ 9.31 (d, 1H, J=5.1 Hz), 9.02 (d, 1H, J=1.2 Hz), 8.76 (dd, 1H, J=1.8, 8.3 Hz), 8.46 (d, 1H, J=8.3 Hz), 7.92 (d, 1H, J=4.8 Hz), 7.33 (d, 1H, J=7.7 Hz), 7.25 (d, 1H, J=8.0 Hz), 6.8-6.8 (m, 1H), 6.70 (s, 1H), 6.63 (dd, 2H, J=2.2, 8.2 Hz), 6.69 (t, 1H, J=54.7 Hz), 4.89 (t, 1H, J=4.6 Hz), 4.5-4.6 (m, 2H), 3.6-3.7 (m, 3H), 3.5-3.5 (m, 1H), 3.26 (s, 3H), 3.14 (dd, 1H, J=9.2, 14.0 Hz), 2.4-2.5 (m, 1H), 1.3-1.4 (m, 1H), 1.01 (dt, 1H, J=1.9, 3.7 Hz)

The title compound was prepared according to General Procedure D using 2-chloro-4-(methylsulfonyl)pyridine as the coupling partner. The experiment afforded the title compound, N—((S)-1-((3P)-3-(4-chloro-1-methyl-3-(methylsulfonamido)-1H-indazol-7-yl)-7-(4-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.3 min.; observed ion=960.8 (M+H). 1H NMR (METHANOL-d4, 500 MHz) δ 9.11 (dd, 1H, J=0.9, 5.1 Hz), 8.65 (s, 1H), 8.59 (s, 1H), 8.4-8.5 (m, 2H), 8.00 (dd, 1H, J=1.6, 4.9 Hz), 7.32 (d, 1H, J=7.7 Hz), 7.23 (d, 1H, J=7.7 Hz), 6.7-6.8 (m, 1H), 6.64 (dd, 2H, J=2.1, 8.0 Hz), 6.70 (t, 1H, J=54.7 Hz), 4.9-4.9 (m, 2H), 4.5-4.6 (m, 2H), 3.65 (s, 3H), 3.5-3.5 (m, 1H), 3.4-3.4 (m, 1H), 3.2-3.3 (m, 4H), 3.1-3.2 (m, 1H), 2.4-2.5 (m, 2H), 1.3-1.4 (m, 1H), 1.0-1.0 (m, 1H)

Preparation of Example 5: N—((S)-1-((3P)-3-(4-chloro-1-methyl-3-(methylsulfonamido)-1H-indazol-7-yl)-7-(6-methoxy-2-methylpyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 6: N—((S)-1-((3P)-3-(4-chloro-1-methyl-3-(methylsulfonamido)-1H-indazol-7-yl)-7-(2,4-dimethylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

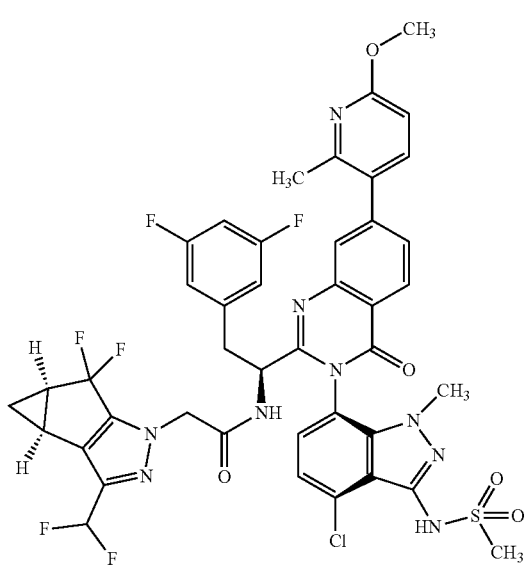

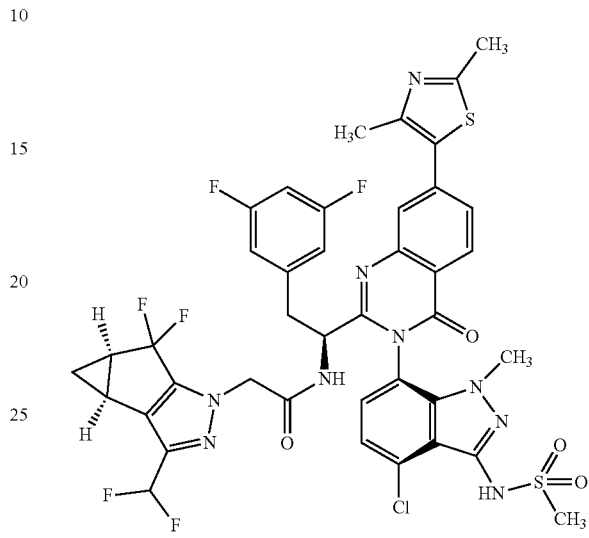

The title compound was prepared according to General Procedure D using 3-bromo-6-methoxy-2-methylpyridine as the coupling partner. The experiment afforded the title compound, N—((S)-1-((3P)-3-(4-chloro-1-methyl-3-(methylsulfonamido)-1H-indazol-7-yl)-7-(6-methoxy-2-methylpyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.46 min.; observed ion=926.8 (M+H). 1H NMR (METHANOL-d4, 500 MHz) δ 8.36 (d, 1H, J=8.0 Hz), 7.85 (d, 1H, J=1.8 Hz), 7.69 (d, 1H, J=8.6 Hz), 7.6-7.7 (m, 1H), 7.32 (d, 1H, J=7.7 Hz), 7.22 (d, 1H, J=8.0 Hz), 6.6-6.8 (m, 5H), 4.9-4.9 (m, 1H), 4.5-4.6 (m, 2H), 4.00 (s, 3H), 3.65 (s, 3H), 3.5-3.5 (m, 1H), 3.2-3.3 (m, 3H), 3.11 (dd, 1H, J=9.2, 14.0 Hz), 2.51 (s, 3H), 2.43 (ddd, 2H, J=4.0, 7.6, 11.3 Hz), 1.3-1.4 (m, 1H), 1.0-1.0 (m, 1H)

The title compound was prepared according to General Procedure D using 5-bromo-2,4-dimethylthiazole as the coupling partner. The experiment afforded the title compound, N—((S)-1-((3P)-3-(4-chloro-1-methyl-3-(methylsulfonamido)-1H-indazol-7-yl)-7-(2,4-dimethylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.37 min.; observed ion=916.8 (M+H). 1H NMR (METHANOL-d4, 500 MHz) δ 8.35 (d, 1H, J=8.1 Hz), 7.95 (d, 1H, J=1.5 Hz), 7.76 (dd, 1H, J=1.8, 8.3 Hz), 7.32 (d, 1H, J=8.0 Hz), 7.23 (d, 1H, J=7.7 Hz), 6.8-6.8 (m, 1H), 6.63 (dd, 2H, J=2.2, 8.2 Hz), 6.69 (t, 1H, J=54.7 Hz), 4.9-4.9 (m, 1H), 4.5-4.6 (m, 2H), 3.63 (s, 3H), 3.5-3.5 (m, 1H), 3.2-3.3 (m, 3H), 3.11 (dd, 1H, J=9.2, 14.0 Hz), 2.76 (s, 3H), 2.59 (s, 3H), 2.43 (ddd, 2H, J=3.9, 7.6, 11.2 Hz), 1.3-1.4 (m, 1H), 1.00 (td, 1H, J=2.1, 3.6 Hz)

Preparation of Example 7: N—((S)-1-((3P)-3-(4-chloro-1-methyl-3-(methylsulfonamido)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

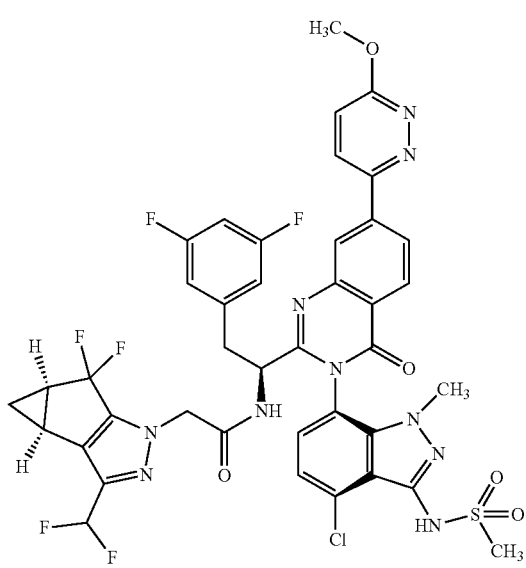

The title compound was prepared according to General Procedure D using 3-bromo-6-methoxypyridazine as the coupling partner. The experiment afforded the title compound, N—((S)-1-((3P)-3-(4-chloro-1-methyl-3-(methylsulfonamido)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.33 min.; observed ion=913.7 (M+H). 1H NMR (METHANOL-d4, 500 MHz) δ 8.54 (d, 1H, J=1.2 Hz), 8.44 (d, 1H, J=8.3 Hz), 8.29 (t, 2H, J=8.9 Hz), 7.39 (d, 1H, J=9.2 Hz), 7.32 (d, 1H, J=7.7 Hz), 7.21 (d, 1H, J=8.0 Hz), 6.8-6.8 (m, 1H), 6.64 (dd, 2H, J=2.2, 8.2 Hz), 6.69 (br t, 2H, J=54.7 Hz), 4.54 (s, 2H), 4.23 (s, 3H), 3.64 (s, 3H), 3.51 (dd, 1H, J=5.2, 13.9 Hz), 3.26 (s, 3H), 3.13 (dd, 1H, J=9.1, 14.2 Hz), 2.43 (br dd, 2H, J=3.7, 6.1 Hz), 1.3-1.4 (m, 1H), 1.0-1.0 (m, 1H)

Preparation of Example 8: N—((S)-1-((3P)-3-(4-chloro-1-methyl-3-(methylsulfonamido)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

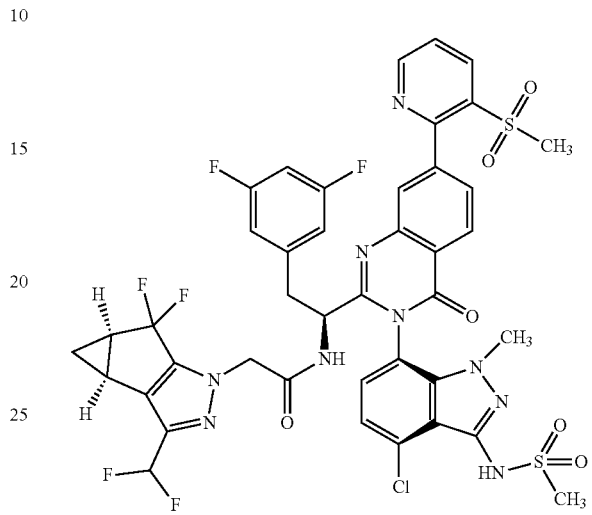

The title compound was prepared according to General Procedure D using 2-chloro-3-(methylsulfonyl)pyridine as the coupling partner. The experiment afforded the title compound, N—((S)-1-((3P)-3-(4-chloro-1-methyl-3-(methylsulfonamido)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.27 min.; observed ion=960.8 (M+H). 1H NMR (METHANOL-d4, 500 MHz) δ 8.98 (dd, 1H, J=1.8, 4.8 Hz), 8.7-8.7 (m, 1H), 8.41 (d, 1H, J=8.6 Hz), 8.11 (d, 1H, J=2.1 Hz), 7.83 (s, 1H), 7.8-7.8 (m, 1H), 7.33 (d, 1H, J=7.7 Hz), 7.23 (d, 1H, J=8.0 Hz), 6.8-6.8 (m, 1H), 6.63 (dd, 2H, J=2.2, 8.2 Hz), 6.69 (t, 1H, J=54.8 Hz), 4.8-4.9 (m, 1H), 4.52 (d, 2H, J=1.5 Hz), 3.67 (s, 3H), 3.5-3.5 (m, 1H), 3.26 (s, 3H), 3.11 (dd, 1H, J=9.2, 14.0 Hz), 3.01 (s, 3H), 2.43 (ddd, 2H, J=4.2, 7.7, 11.4 Hz), 1.3-1.4 (m, 1H), 1.0-1.0 (m, 1H)

121

Preparation of Example 9: N—((S)-1-((3P)-3-(4-chloro-1-methyl-3-(methylsulfonamido)-1H-indazol-7-yl)-7-(5-methoxy-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

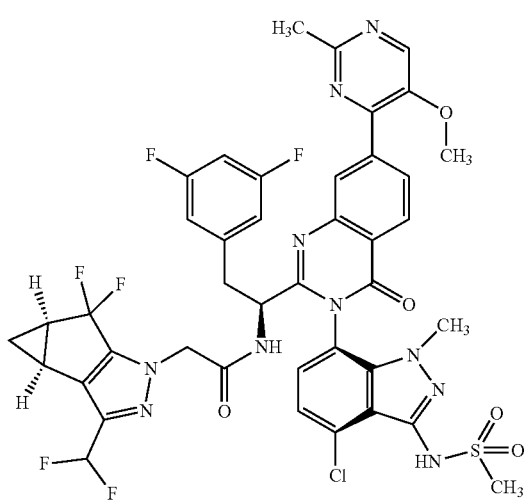

The title compound was prepared according to General Procedure D using 4-chloro-5-methoxy-2-methylpyrimidine as the coupling partner. The experiment afforded the title compound, N—((S)-1-((3P)-3-(4-chloro-1-methyl-3-(methylsulfonamido)-1H-indazol-7-yl)-7-(5-methoxy-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.32 min.; observed ion=927.9 (M+H). 1H NMR (METHANOL-d4, 500 MHz) δ 8.65 (s, 1H), 8.60 (s, 1H), 8.4-8.4 (m, 1H), 8.3-8.3 (m, 1H), 7.32 (d, 1H, J=8.0 Hz), 7.24 (d, 1H, J=8.0 Hz), 6.7-6.8 (m, 1H), 6.64 (dd, 2H, J=2.1, 8.0 Hz), 6.69 (br t, 2H, J=54.8 Hz), 4.5-4.6 (m, 2H), 4.10 (s, 3H), 3.64 (s, 3H), 3.5-3.5 (m, 1H), 3.26 (s, 3H), 3.12 (dd, 1H, J=9.2, 14.0 Hz), 2.76 (s, 3H), 2.4-2.5 (m, 2H), 1.3-1.4 (m, 1H), 1.0-1.0 (m, 1H)

122

Preparation of Example 10: N—((S)-1-((3P)-3-(4-chloro-1-methyl-3-(methylsulfonamido)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

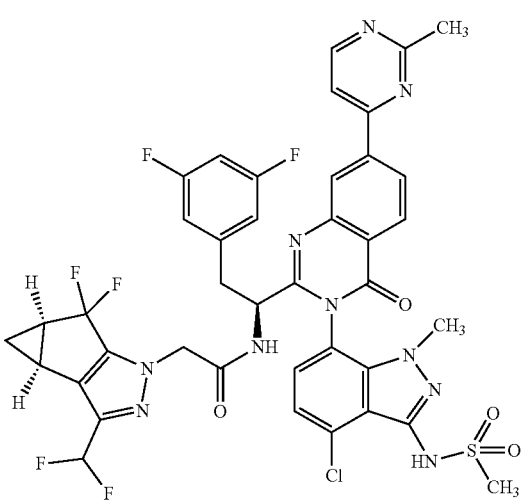 [SMILES: Cc1nccc(-c2ccc3c(=O)n(-c4ccc(Cl)c5c(NS(C)(=O)=O)nn(C)c45)c([C@H](Cc4cc(F)cc(F)c4)NC(=O)Cn4nc(C(F)F)c5c4C(F)(F)[C@@H]4C[C@H]54)nc3c2)n1]

The title compound was prepared according to General Procedure D using 4-chloro-2-methylpyrimidine as the coupling partner. The experiment afforded the title compound, N—((S)-1-((3P)-3-(4-chloro-1-methyl-3-(methylsulfonamido)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.32 min.; observed ion=897.8 (M+H). 1H NMR (METHANOL-d4, 500 MHz) δ 8.86 (d, 1H, J=5.4 Hz), 8.70 (d, 1H, J=1.5 Hz), 8.4-8.5 (m, 2H), 8.01 (d, 1H, J=5.1 Hz), 7.32 (d, 1H, J=8.0 Hz), 7.24 (d, 1H, J=7.7 Hz), 6.8-6.8 (m, 1H), 6.6-6.7 (m, 2H), 6.70 (t, 1H, J=54.8 Hz), 4.9-4.9 (m, 1H), 4.5-4.6 (m, 2H), 3.64 (s, 3H), 3.5-3.5 (m, 1H), 3.26 (s, 3H), 3.13 (dd, 1H, J=9.2, 14.0 Hz), 2.85 (s, 3H), 2.4-2.5 (m, 2H), 1.3-1.4 (m, 1H), 1.01 (td, 1H, J=2.1, 3.6 Hz)

123

Preparation of Example 11: N—((S)-1-((3P)-3-(4-chloro-1-methyl-3-(methylsulfonamido)-1H-indazol-7-yl)-7-(3-methoxypyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

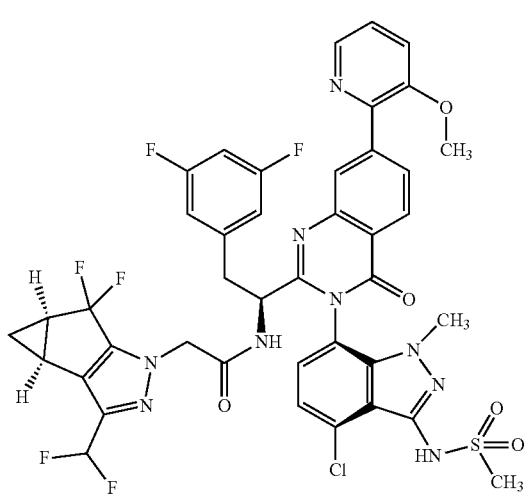

The title compound was prepared according to General Procedure D using 2-chloro-3-methoxypyridine as the coupling partner. The experiment afforded the title compound, N—((S)-1-((3P)-3-(4-chloro-1-methyl-3-(methylsulfonamido)-1H-indazol-7-yl)-7-(3-methoxypyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.35 min.; observed ion=912.8 (M+H). 1H NMR (METHANOL-d4, 500 MHz) δ 8.3-8.4 (m, 3H), 8.12 (dd, 1H, J=1.6, 8.2 Hz), 7.71 (dd, 1H, J=1.2, 8.3 Hz), 7.53 (dd, 1H, J=4.8, 8.3 Hz), 7.32 (d, 1H, J=7.7 Hz), 7.21 (d, 1H, J=8.0 Hz), 6.79 (tt, 1H, J=2.3, 9.1 Hz), 6.6-6.7 (m, 2H), 6.69 (br t, 2H, J=54.7 Hz), 4.54 (d, 2H, J=1.8 Hz), 4.00 (s, 3H), 3.64 (s, 3H), 3.5-3.5 (m, 1H), 3.26 (s, 3H), 3.12 (dd, 1H, J=9.1, 13.9 Hz), 2.43 (ddd, 2H, J=4.0, 7.6, 11.3 Hz), 1.3-1.4 (m, 1H), 1.0-1.0 (m, 1H)

124

Preparation of Example 12: N—((S)-1-((3P)-3-(4-chloro-1-methyl-3-(methylsulfonamido)-1H-indazol-7-yl)-7-(2-(difluoromethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

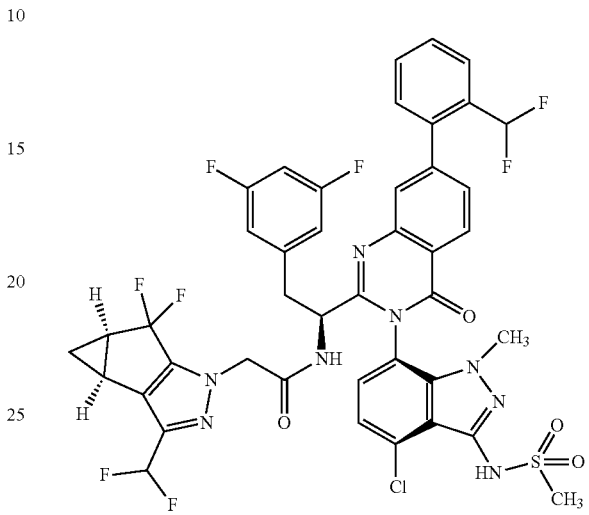

The title compound was prepared according to General Procedure D using 1-bromo-2-(difluoromethyl)benzene as the coupling partner. The experiment afforded the title compound, N—((S)-1-((3P)-3-(4-chloro-1-methyl-3-(methylsulfonamido)-1H-indazol-7-yl)-7-(2-(difluoromethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.49 min.; observed ion=931.8 (M+H). 1H NMR (METHANOL-d4, 500 MHz) δ 8.39 (d, 1H, J=8.0 Hz), 7.88 (d, 1H, J=1.2 Hz), 7.86 (d, 1H, J=7.5 Hz), 7.6-7.7 (m, 3H), 7.53 (d, 1H, J=7.5 Hz), 7.33 (d, 1H, J=8.0 Hz), 7.25 (d, 1H, J=8.0 Hz), 6.6-6.9 (m, 5H), 4.8-4.8 (m, 1H), 4.5-4.6 (m, 2H), 3.6-3.7 (m, 3H), 3.5-3.5 (m, 1H), 3.26 (s, 3H), 3.12 (dd, 1H, J=9.2, 14.0 Hz), 2.42 (ddd, 2H, J=4.0, 7.7, 11.5 Hz), 1.3-1.4 (m, 1H), 1.00 (dt, 1H, J=1.9, 3.8 Hz)

125

Preparation of Example 13: N—((S)-1-((3P)-3-(4-chloro-1-methyl-3-(methylsulfonamido)-1H-indazol-7-yl)-7-(2-(2-hydroxypropan-2-yl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

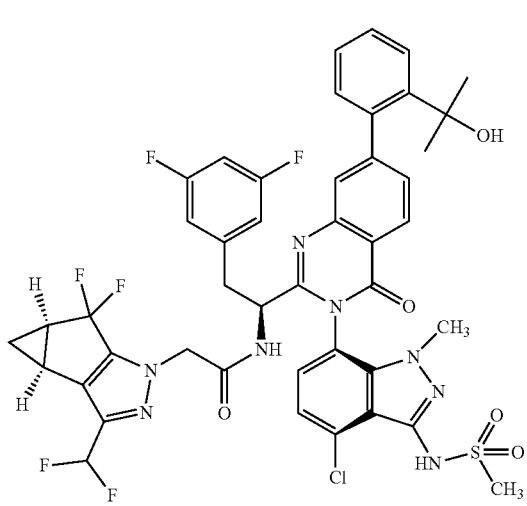

The title compound was prepared according to General Procedure D using 2-(2-bromophenyl)propan-2-ol as the coupling partner. The experiment afforded the title compound, N—((S)-1-((3P)-3-(4-chloro-1-methyl-3-(methylsulfonamido)-1H-indazol-7-yl)-7-(2-(2-hydroxypropan-2-yl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.42 min.; observed ion=939.9 (M+H). 1H NMR (METHANOL-d4, 500 MHz) δ 8.26 (d, 1H, J=8.6 Hz), 7.79 (d, 1H, J=8.2 Hz), 7.77 (d, 1H, J=1.5 Hz), 7.59 (dd, 1H, J=1.6, 8.2 Hz), 7.45 (t, 1H, J=7.6 Hz), 7.33 (dt, 1H, J=1.2, 7.5 Hz), 7.25 (br d, 1H, J=8.0 Hz), 7.1-7.2 (m, 1H), 7.11 (dd, 1H, J=1.3, 7.6 Hz), 6.8-6.8 (m, 1H), 6.69 (s, 1H), 6.6-6.6 (m, 1H), 6.69 (br t, 1H, J=54.7 Hz), 4.9-5.0 (m, 1H), 4.5-4.6 (m, 2H), 3.62 (s, 3H), 3.4-3.5 (m, 1H), 3.2-3.2 (m, 3H), 3.09 (dd, 1H, J=9.1, 13.9 Hz), 2.4-2.5 (m, 2H), 1.4-1.5 (m, 6H), 1.3-1.4 (m, 1H), 1.0-1.0 (m, 1H)

126

Preparation of Example 14: N—((S)-1-((3P)-3-(4-chloro-1-methyl-3-(methylsulfonamido)-1H-indazol-7-yl)-4-oxo-7-(2-(trifluoromethoxy)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

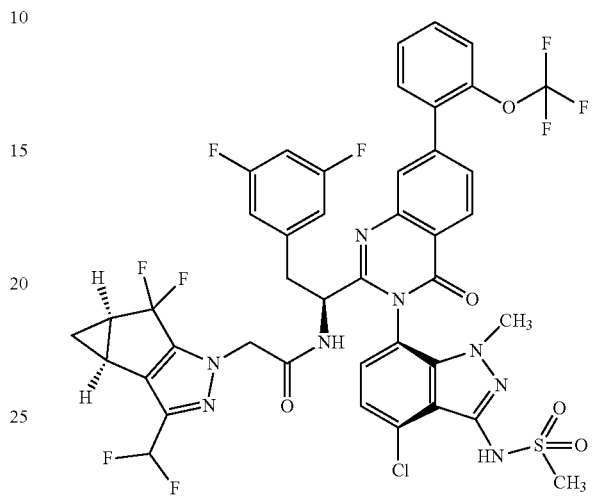

The title compound was prepared according to General Procedure D using 1-bromo-2-(trifluoromethoxy)benzene as the coupling partner. The experiment afforded the title compound, N—((S)-1-((3P)-3-(4-chloro-1-methyl-3-(methylsulfonamido)-1H-indazol-7-yl)-4-oxo-7-(2-(trifluoromethoxy)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.54 min.; observed ion=965.8 (M+H). 1H NMR (METHANOL-d4, 500 MHz) Shift 8.38 (br d, 1H, J=8.3 Hz), 7.99 (s, 1H), 7.77 (br d, 1H, J=8.0 Hz), 7.67 (br d, 1H, J=7.2 Hz), 7.5-7.6 (m, 3H), 7.31 (br d, 1H, J=7.7 Hz), 7.2-7.3 (m, 1H), 6.6-6.8 (m, 4H), 4.89 (br d, 1H, J=6.0 Hz), 4.54 (br s, 2H), 3.65 (s, 3H), 3.4-3.5 (m, 1H), 3.2-3.3 (m, 3H), 3.11 (br d, 1H, J=0.9 Hz), 2.4-2.5 (m, 2H), 1.3-1.4 (m, 1H), 1.01 (br d, 1H, J=3.6 Hz)

Preparation of Example 15: N—((S)-1-((3P)-3-(4-chloro-1-methyl-3-(methylsulfonamido)-1H-indazol-7-yl)-7-(3-methoxypyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

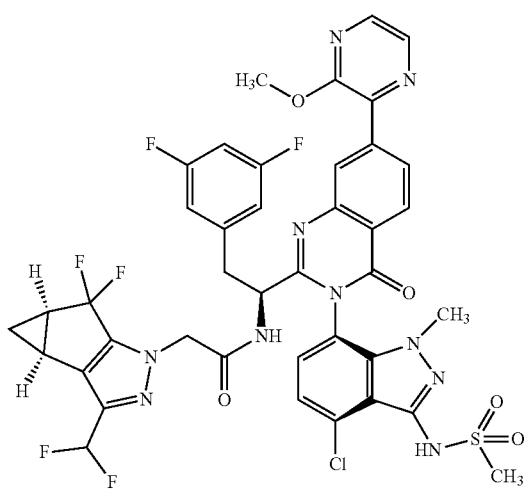

The title compound was prepared according to General Procedure D using 2-chloro-3-methoxypyrazine as the coupling partner. The experiment afforded the title compound, N—((S)-1-((3P)-3-(4-chloro-1-methyl-3-(methylsulfonamido)-1H-indazol-7-yl)-7-(3-methoxypyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.4 min.; observed ion=913.6 (M+H). 1H NMR (METHANOL-d4, 500 MHz) δ 8.61 (s, 1H), 8.3-8.4 (m, 3H), 8.30 (d, 1H, J=2.4 Hz), 7.32 (d, 1H, J=7.7 Hz), 7.22 (d, 1H, J=7.7 Hz), 6.8-6.8 (m, 1H), 6.64 (dd, 2H, J=2.2, 8.2 Hz), 6.69 (br t, 2H, J=54.8 Hz), 4.90 (br d, 1H, J=5.1 Hz), 4.5-4.6 (m, 2H), 4.16 (s, 3H), 3.6-3.7 (m, 3H), 3.5-3.5 (m, 1H), 3.26 (s, 3H), 2.4-2.5 (m, 2H), 1.3-1.4 (m, 1H), 1.0-1.0 (m, 1H)

Preparation of Example 16: N—((S)-1-((3P)-3-(4-chloro-1-methyl-3-(methylsulfonamido)-1H-indazol-7-yl)-7-(3-isopropylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

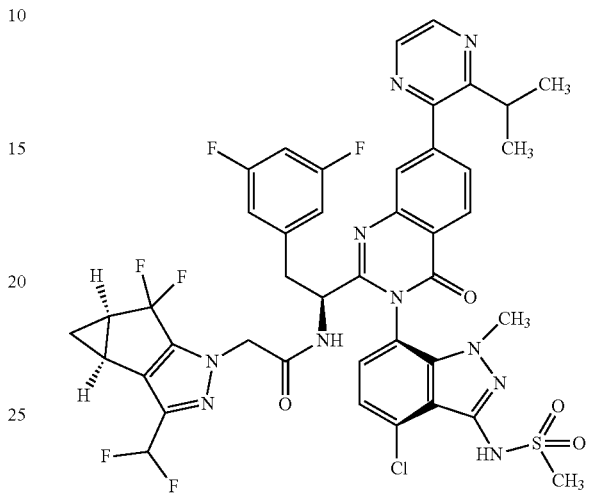

The title compound was prepared according to General Procedure D using 2-chloro-3-isopropylpyrazine as the coupling partner. The experiment afforded the title compound, N—((S)-1-((3P)-3-(4-chloro-1-methyl-3-(methylsulfonamido)-1H-indazol-7-yl)-7-(3-isopropylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.41 min.; observed ion=925.8 (M+H). 1H NMR (METHANOL-d4, 500 MHz) δ 8.71 (d, 1H, J=2.4 Hz), 8.60 (d, 1H, J=2.4 Hz), 8.44 (d, 1H, J=8.0 Hz), 8.01 (d, 1H, J=1.8 Hz), 7.80 (dd, 1H, J=1.6, 8.2 Hz), 7.33 (d, 1H, J=7.7 Hz), 7.26 (d, 1H, J=7.7 Hz), 6.8-6.8 (m, 1H), 6.63 (dd, 2H, J=2.2, 8.2 Hz), 6.68 (t, 2H, J=54.8 Hz), 4.8-4.8 (m, 1H), 4.5-4.6 (m, 2H), 3.66 (s, 3H), 3.3-3.4 (m, 2H), 3.2-3.3 (m, 3H), 3.11 (dd, 1H, J=9.2, 14.0 Hz), 2.4-2.5 (m, 2H), 1.33 (d, 6H, J=6.9 Hz), 1.0-1.0 (m, 1H)

Preparation of Example 17: N—((S)-1-((3P)-3-(4-chloro-1-methyl-3-(methylsulfonamido)-1H-indazol-7-yl)-7-(3-ethylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

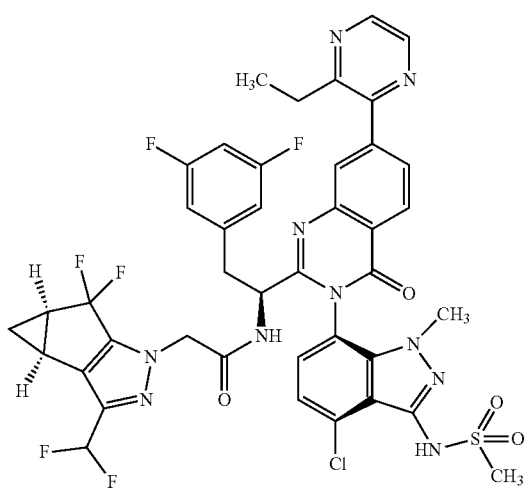

The title compound was prepared according to General Procedure D using 2-chloro-3-ethylpyrazine as the coupling partner. The experiment afforded the title compound, N—((S)-1-((3P)-3-(4-chloro-1-methyl-3-(methylsulfonamido)-1H-indazol-7-yl)-7-(3-ethylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.35 min.; observed ion=911.8 (M+H). 1H NMR (METHANOL-d4, 500 MHz) δ 8.68 (d, 1H, J=2.7 Hz), 8.63 (d, 1H, J=2.7 Hz), 8.44 (d, 1H, J=8.0 Hz), 8.06 (d, 1H, J=1.8 Hz), 7.84 (dd, 1H, J=1.6, 8.2 Hz), 7.33 (d, 1H, J=7.7 Hz), 7.25 (d, 1H, J=7.7 Hz), 6.6-6.8 (m, 4H), 4.8-4.8 (m, 1H), 4.5-4.6 (m, 3H), 3.70 (s, 1H), 3.66 (s, 3H), 3.5-3.5 (m, 1H), 3.2-3.3 (m, 3H), 3.00 (q, 2H, J=7.5 Hz), 2.4-2.5 (m, 2H), 1.3-1.3 (m, 3H), 1.00 (dt, 1H, J=1.8, 3.7 Hz)

Preparation of Example 18: N—((S)-1-((3P)-3-(4-chloro-1-methyl-3-(methylsulfonamido)-1H-indazol-7-yl)-7-(3-(hydroxymethyl)pyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide The title compound was prepared according to General Procedure D using (3-chloropyrazin-2-yl)methanol as the coupling partner. The experiment afforded the title compound, N—((S)-1-((3P)-3-(4-chloro-1-methyl-3-(methylsulfonamido)-1H-indazol-7-yl)-7-(3-(hydroxymethyl)pyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.21 min.; observed ion=913.8 (M+H). 1H NMR (METHANOL-d4, 500 MHz) δ 8.75 (s, 2H), 8.43 (br d, 1H, J=8.3 Hz), 8.26 (s, 1H), 7.99 (br d, 1H, J=8.0 Hz), 7.32 (br d, 1H, J=8.0 Hz), 7.23 (br d, 1H, J=8.3 Hz), 6.5-6.8 (m, 4H), 4.90 (br d, 1H, J=1.5 Hz), 4.5-4.6 (m, 3H), 3.65 (s, 3H), 3.4-3.5 (m, 1H), 3.4-3.4 (m, 1H), 3.2-3.3 (m, 4H), 3.1-3.2 (m, 1H), 2.4-2.5 (m, 2H), 1.3-1.4 (m, 1H), 1.00 (br d, 1H, J=3.3 Hz)

Preparation of Example 19: N—((S)-1-((3P)-3-(4-chloro-1-methyl-3-(methylsulfonamido)-1H-indazol-7-yl)-7-(3-methoxyquinoxalin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

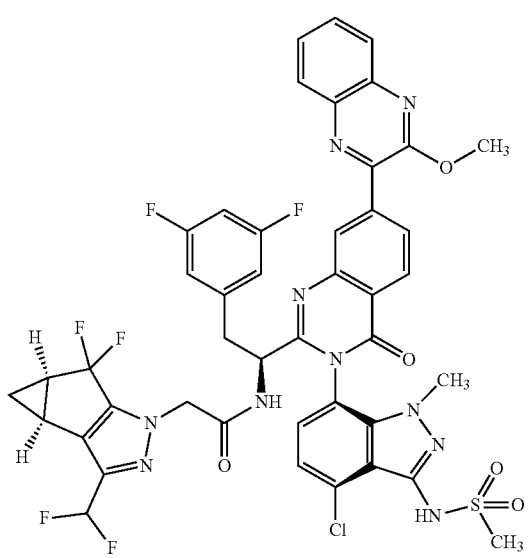

The title compound was prepared according to General Procedure D using 2-chloro-3-methoxyquinoxaline as the coupling partner. The experiment afforded the title compound, N—((S)-1-((3P)-3-(4-chloro-1-methyl-3-(methylsulfonamido)-1H-indazol-7-yl)-7-(3-methoxyquinoxalin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.54 min.; observed ion=963.8 (M+H). 1H NMR (METHANOL-d4, 500 MHz) δ 8.67 (s, 1H), 8.41 (s, 2H), 8.15 (dd, 1H, J=1.5, 8.3 Hz), 7.97 (dd, 1H, J=1.5, 8.3 Hz), 7.81 (t, 1H, J=7.6 Hz), 7.71 (ddd, 1H, J=1.3, 7.0, 8.3 Hz), 7.33 (d, 1H, J=7.7 Hz), 7.24 (d, 1H, J=7.7 Hz), 6.8-6.8 (m, 1H), 6.65 (dd, 2H, J=2.2, 8.2 Hz), 6.70 (br t, 2H, J=54.7 Hz), 4.9-4.9 (m, 1H), 4.5-4.6 (m, 3H), 4.27 (s, 3H), 3.66 (s, 3H), 3.52 (dd, 1H, J=5.2, 14.2 Hz), 3.1-3.2 (m, 2H), 2.4-2.5 (m, 2H), 1.3-1.4 (m, 1H), 1.0-1.0 (m, 1H)

Preparation of Example 20: N—((S)-1-((3P)-3-(4-chloro-1-methyl-3-(methylsulfonamido)-1H-indazol-7-yl)-7-(3-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

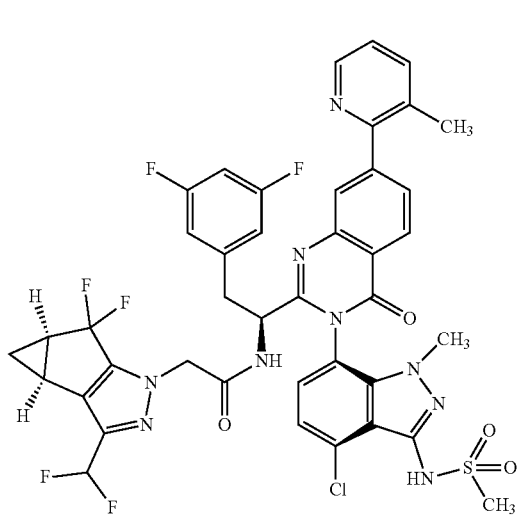

The title compound was prepared according to General Procedure D using 2-bromo-3-methylpyridine as the coupling partner. The experiment afforded the title compound, N—((S)-1-((3P)-3-(4-chloro-1-methyl-3-(methylsulfonamido)-1H-indazol-7-yl)-7-(3-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.29 min.; observed ion=896.7 (M+H). 1H NMR (METHANOL-d4, 500 MHz) δ 8.5-8.6 (m, 1H), 8.42 (d, 1H, J=8.6 Hz), 8.00 (d, 1H, J=1.2 Hz), 7.90 (d, 1H, J=7.9 Hz), 7.79 (dd, 1H, J=1.6, 8.2 Hz), 7.47 (dd, 1H, J=5.1, 7.7 Hz), 7.33 (d, 1H, J=7.7 Hz), 7.23 (d, 1H, J=8.0 Hz), 6.6-6.8 (m, 4H), 4.54 (d, 2H, J=2.1 Hz), 3.71 (s, 1H), 3.66 (s, 3H), 3.5-3.5 (m, 1H), 3.2-3.3 (m, 4H), 3.11 (dd, 1H, J=9.1, 14.2 Hz), 2.4-2.5 (m, 5H), 1.0-1.0 (m, 1H)

Preparation of Example 21: N—((S)-1-((3P)-3-(4-chloro-1-methyl-3-(methylsulfonamido)-1H-indazol-7-yl)-7-(3-fluoropyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

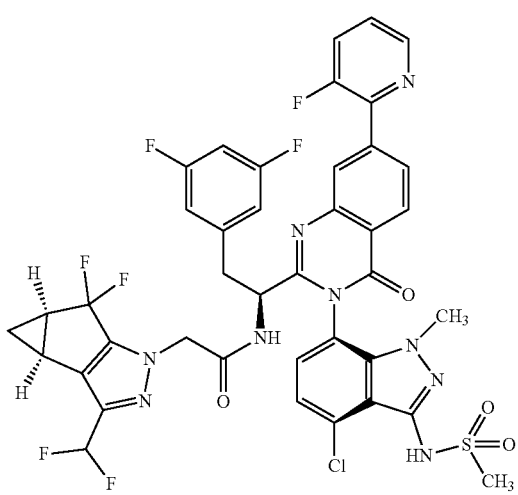

The title compound was prepared according to General Procedure D using 2-chloro-3-fluoropyridine as the coupling partner. The experiment afforded the title compound, N—((S)-1-((3P)-3-(4-chloro-1-methyl-3-(methylsulfonamido)-1H-indazol-7-yl)-7-(3-fluoropyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.38 min.; observed ion=900.7 (M+H). 1H NMR (METHANOL-d4, 500 MHz) δ 8.64 (td, 1H, J=1.5, 4.7 Hz), 8.46 (t, 1H, J=1.5 Hz), 8.42 (d, 1H, J=8.3 Hz), 8.24 (td, 1H, J=1.5, 8.3 Hz), 7.84 (ddd, 1H, J=1.5, 8.4, 11.3 Hz), 7.6-7.6 (m, 1H), 7.32 (d, 1H, J=7.7 Hz), 7.23 (d, 1H, J=8.0 Hz), 6.8-6.8 (m, 1H), 6.63 (dd, 2H, J=2.2, 8.2 Hz), 6.69 (br t, 2H, J=54.7 Hz), 4.9-4.9 (m, 2H), 4.5-4.6 (m, 2H), 3.6-3.7 (m, 3H), 3.5-3.5 (m, 1H), 3.3-3.3 (m, 3H), 2.4-2.5 (m, 2H), 1.0-1.0 (m, 1H)

Preparation of Example 22: N—((S)-1-((3P)-3-(4-chloro-1-methyl-3-(methylsulfonamido)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

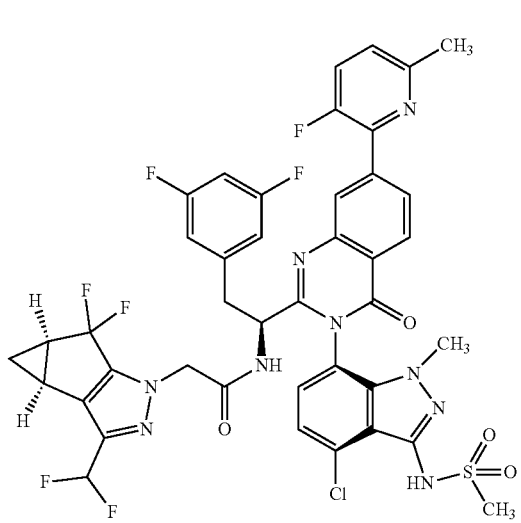

The title compound was prepared according to General Procedure D using 2-chloro-3-fluoro-6-methylpyridine as the coupling partner. The experiment afforded the title compound, N—((S)-1-((3P)-3-(4-chloro-1-methyl-3-(methylsulfonamido)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.44 min.; observed ion=914.8 (M+H). 1H NMR (METHANOL-d4, 500 MHz) δ 8.44 (t, 1H, J=1.3 Hz), 8.40 (d, 1H, J=8.3 Hz), 8.23 (td, 1H, J=1.5, 8.3 Hz), 7.69 (dd, 1H, J=8.5, 10.9 Hz), 7.42 (dd, 1H, J=3.3, 8.6 Hz), 7.32 (d, 1H, J=8.0 Hz), 7.22 (d, 1H, J=7.7 Hz), 6.8-6.8 (m, 1H), 6.63 (dd, 2H, J=2.2, 8.2 Hz), 6.69 (t, 2H, J=54.8 Hz), 4.55 (d, 2H, J=5.1 Hz), 3.6-3.7 (m, 3H), 3.5-3.5 (m, 1H), 3.26 (s, 3H), 3.12 (dd, 1H, J=9.1, 14.2 Hz), 2.67 (s, 3H), 2.43 (td, 2H, J=3.6, 7.4 Hz), 1.3-1.4 (m, 1H), 1.0-1.0 (m, 1H)

135

Preparation of Example 23: N—((S)-1-((3P)-3-(4-chloro-1-methyl-3-(methylsulfonamido)-1H-indazol-7-yl)-7-(2-isopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

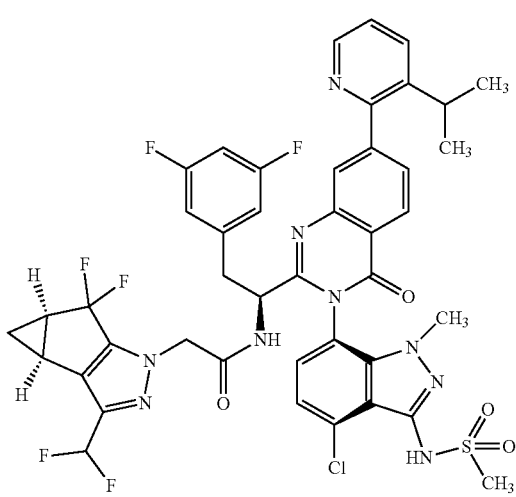

The title compound was prepared according to General Procedure D using 1-bromo-2-isopropylbenzene as the coupling partner. The experiment afforded the title compound, N—((S)-1-((3P)-3-(4-chloro-1-methyl-3-(methylsulfonamido)-1H-indazol-7-yl)-7-(2-isopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.59 min.; observed ion=923.8 (M+H). 1H NMR (METHANOL-d4, 500 MHz) δ 8.35 (d, 1H, J=8.6 Hz), 7.79 (d, 1H, J=1.8 Hz), 7.6-7.6 (m, 1H), 7.5-7.5 (m, 1H), 7.46 (dt, 1H, J=1.3, 7.5 Hz), 7.2-7.3 (m, 4H), 6.6-6.8 (m, 4H), 4.9-4.9 (m, 1H), 4.5-4.6 (m, 2H), 3.66 (s, 3H), 3.5-3.5 (m, 1H), 3.26 (s, 3H), 3.1-3.1 (m, 2H), 2.42 (ddd, 2H, J=4.0, 7.7, 11.3 Hz), 1.3-1.4 (m, 1H), 1.24 (d, 6H, J=6.9 Hz), 1.0-1.0 (m, 1H)

136

Preparation of Example 24: N—((S)-1-((3P)-3-(4-chloro-1-methyl-3-(methylsulfonamido)-1H-indazol-7-yl)-4-oxo-7-(2-(trifluoromethyl)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

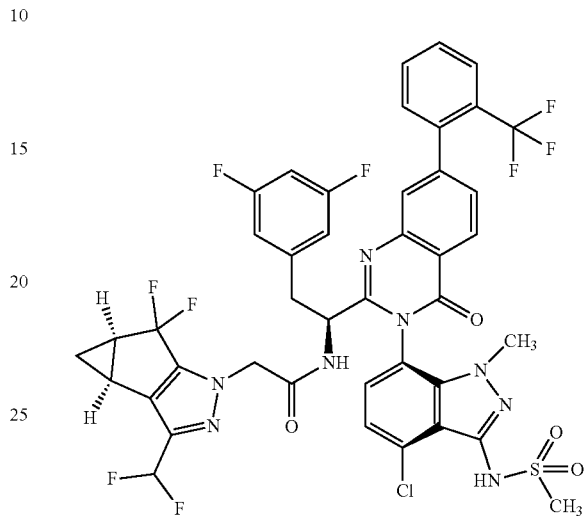

The title compound was prepared according to General Procedure D using 1-bromo-2-(trifluoromethyl)benzene as the coupling partner. The experiment afforded the title compound, N—((S)-1-((3P)-3-(4-chloro-1-methyl-3-(methylsulfonamido)-1H-indazol-7-yl)-4-oxo-7-(2-(trifluoromethyl)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.51 min.; observed ion=949.9 (M+H). 1H NMR (METHANOL-d4, 500 MHz) δ 8.35 (d, 1H, J=8.0 Hz), 7.91 (d, 1H, J=7.5 Hz), 7.85 (d, 1H, J=1.5 Hz), 7.78 (t, 1H, J=7.5 Hz), 7.70 (t, 1H, J=7.6 Hz), 7.62 (dd, 1H, J=1.5, 8.3 Hz), 7.53 (d, 1H, J=7.7 Hz), 7.32 (d, 1H, J=7.7 Hz), 7.25 (d, 1H, J=8.0 Hz), 6.6-6.8 (m, 4H), 4.9-4.9 (m, 1H), 4.5-4.6 (m, 2H), 3.66 (s, 3H), 3.4-3.5 (m, 1H), 3.2-3.3 (m, 3H), 3.11 (dd, 1H, J=9.4, 14.2 Hz), 2.4-2.5 (m, 2H), 1.3-1.4 (m, 1H), 1.00 (td, 1H, J=2.1, 3.6 Hz)

Preparation of Example 25: N—((S)-1-((3P)-3-(4-chloro-1-methyl-3-(methylsulfonamido)-1H-indazol-7-yl)-7-(2-(difluoromethoxy)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 26:N—((S)-1-((3P)-3-(4-chloro-1-methyl-3-(methylsulfonamido)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

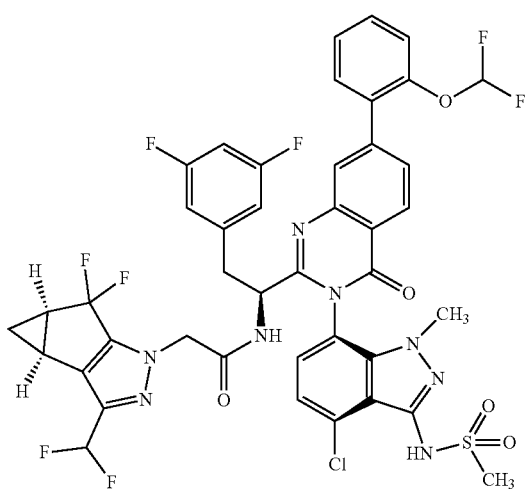

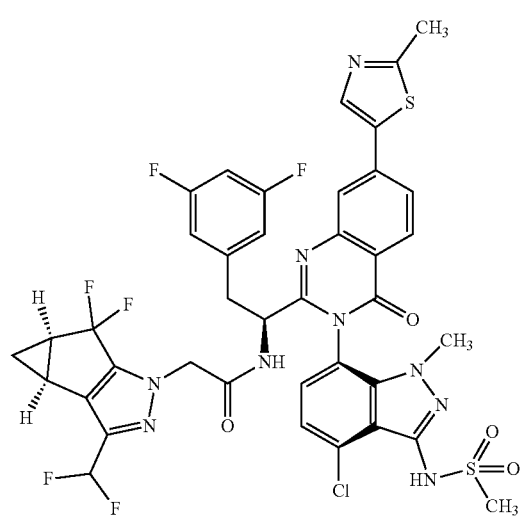

The title compound was prepared according to General Procedure D using 1-bromo-2-(difluoromethoxy)benzene as the coupling partner. The experiment afforded the title compound, N—((S)-1-((3P)-3-(4-chloro-1-methyl-3-(methylsulfonamido)-1H-indazol-7-yl)-7-(2-(difluoromethoxy)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.46 min.; observed ion=947.8 (M+H). 1H NMR (METHANOL-d4, 500 MHz) δ 8.35 (d, 1H, J=8.6 Hz), 8.02 (d, 1H, J=1.8 Hz), 7.79 (dd, 1H, J=1.6, 8.2 Hz), 7.62 (dd, 1H, J=1.6, 7.6 Hz), 7.5-7.6 (m, 1H), 7.45 (dt, 1H, J=1.2, 7.6 Hz), 7.40 (d, 1H, J=7.9 Hz), 7.32 (d, 1H, J=7.7 Hz), 7.22 (d, 1H, J=7.7 Hz), 6.6-7.0 (m, 5H), 4.87 (s, 1H), 4.53 (d, 2H, J=2.4 Hz), 3.6-3.7 (m, 3H), 3.5-3.5 (m, 1H), 3.26 (s, 3H), 3.12 (dd, 1H, J=9.2, 14.0 Hz), 2.42 (ddd, 2H, J=4.0, 7.7, 11.5 Hz), 1.3-1.4 (m, 1H), 1.0-1.0 (m, 1H)

The title compound was prepared according to General Procedure D using 5-bromo-2-methylthiazole as the coupling partner. The experiment afforded the title compound, N—((S)-1-((3P)-3-(4-chloro-1-methyl-3-(methylsulfonamido)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.34 min.; observed ion=902.7 (M+H). 1H NMR (METHANOL-d4, 500 MHz) δ 8.32 (br d, 1H, J=8.0 Hz), 8.22 (s, 1H), 8.06 (s, 1H), 7.94 (br d, 1H, J=8.0 Hz), 7.30 (br d, 1H, J=7.2 Hz), 7.20 (br d, 1H, J=8.0 Hz), 6.6-6.8 (m, 4H), 4.5-4.6 (m, 3H), 3.62 (s, 3H), 3.5-3.5 (m, 1H), 3.2-3.3 (m, 3H), 3.1-3.1 (m, 1H), 2.82 (s, 3H), 2.44 (br dd, 2H, J=3.0, 6.0 Hz), 1.37 (br d, 1H, J=6.3 Hz), 1.0-1.0 (m, 1H)

Preparation of Example 27: N—((S)-1-((3P)-3-(4-chloro-1-methyl-3-(methylsulfonamido)-1H-indazol-7-yl)-7-(2-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Preparation of Example 28: N—((S)-1-((3P)-3-(4-chloro-1-methyl-3-(methylsulfonamido)-1H-indazol-7-yl)-7-(3-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

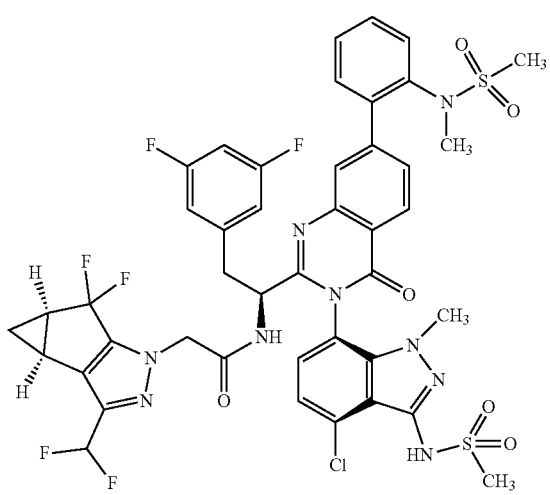

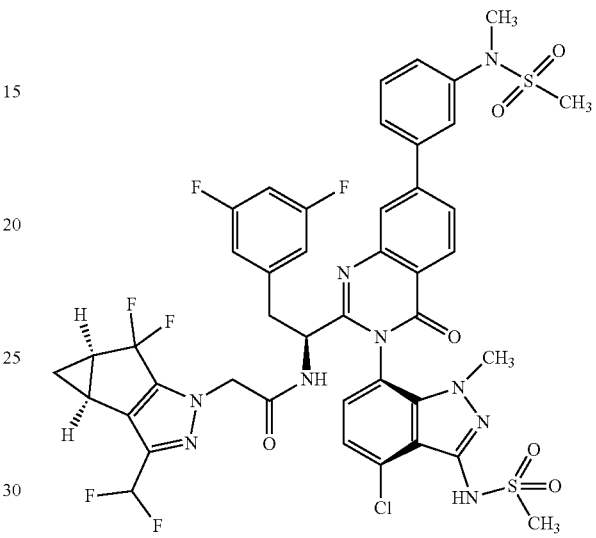

The title compound was prepared according to General Procedure D using N-(2-bromophenyl)-N-methylmethanesulfonamide as the coupling partner. The experiment afforded the title compound, N—((S)-1-((3P)-3-(4-chloro-1-methyl-3-(methylsulfonamido)-1H-indazol-7-yl)-7-(2-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.35 min.; observed ion=988.9 (M+H). 1H NMR (METHANOL-d4, 500 MHz) δ 8.34 (d, 1H, J=8.1 Hz), 7.99 (d, 1H, J=1.2 Hz), 7.74 (dd, 1H, J=1.6, 8.2 Hz), 7.6-7.7 (m, 1H), 7.6-7.6 (m, 3H), 7.31 (d, 1H, J=7.7 Hz), 7.20 (d, 1H, J=8.0 Hz), 6.8-6.8 (m, 1H), 6.63 (dd, 2H, J=2.2, 8.2 Hz), 6.69 (br t, 1H, J=54.8 Hz), 4.8-4.8 (m, 1H), 4.54 (d, 2H, J=3.0 Hz), 3.6-3.7 (m, 3H), 3.5-3.5 (m, 1H), 3.2-3.3 (m, 6H), 3.11 (dd, 1H, J=9.1, 13.9 Hz), 2.9-3.0 (m, 3H), 2.4-2.5 (m, 2H), 1.36 (br d, 1H, J=7.5 Hz), 1.0-1.0 (m, 1H)

The title compound was prepared according to General Procedure D using N-(3-bromophenyl)-N-methylmethanesulfonamide as the coupling partner. The experiment afforded the title compound, N—((S)-1-((3P)-3-(4-chloro-1-methyl-3-(methylsulfonamido)-1H-indazol-7-yl)-7-(3-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.36 min.; observed ion=988.8 (M+H). 1H NMR (METHANOL-d4, 500 MHz) δ 8.39 (d, 1H, J=8.3 Hz), 8.14 (d, 1H, J=1.5 Hz), 7.97 (dd, 1H, J=1.8, 8.3 Hz), 7.90 (t, 1H, J=1.8 Hz), 7.80 (d, 1H, J=7.4 Hz), 7.64 (t, 1H, J=7.7 Hz), 7.6-7.6 (m, 1H), 7.32 (d, 1H, J=7.7 Hz), 7.22 (d, 1H, J=7.7 Hz), 6.8-6.8 (m, 1H), 6.63 (dd, 2H, J=2.2, 8.2 Hz), 6.70 (br t, 1H, J=54.7 Hz), 4.8-4.8 (m, 1H), 4.55 (d, 2H, J=6.0 Hz), 3.6-3.6 (m, 3H), 3.4-3.5 (m, 4H), 3.26 (s, 3H), 3.1-3.2 (m, 1H), 2.99 (s, 3H), 2.4-2.5 (m, 2H), 1.36 (br d, 1H, J=7.5 Hz), 1.0-1.0 (m, 1H)

141

Preparation of Example 29: N—((S)-1-((3P)-3-(4-chloro-1-methyl-3-(methylsulfonamido)-1H-indazol-7-yl)-7-(4-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

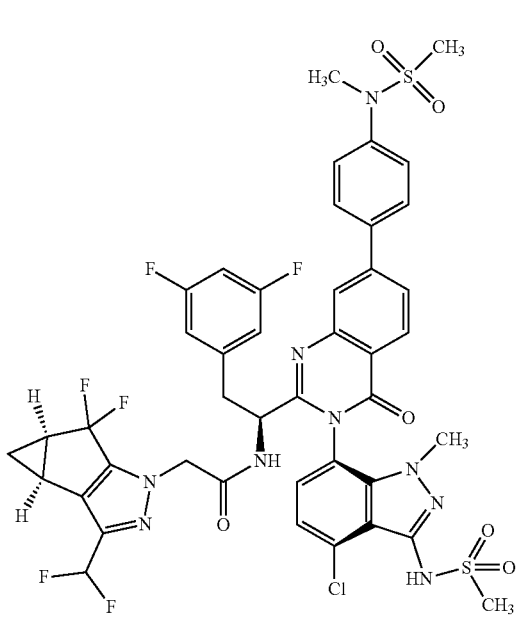

The title compound was prepared according to General Procedure D using N-(4-bromophenyl)-N-methylmethanesulfonamide as the coupling partner. The experiment afforded the title compound, N—((S)-1-((3P)-3-(4-chloro-1-methyl-3-(methylsulfonamido)-1H-indazol-7-yl)-7-(4-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.35 min.; observed ion=988.8 (M+H). 1H NMR (METHANOL-d4, 500 MHz) δ 8.37 (d, 1H, J=8.3 Hz), 8.14 (d, 1H, J=1.8 Hz), 7.97 (dd, 1H, J=1.8, 8.3 Hz), 7.9-7.9 (m, 2H), 7.6-7.7 (m, 2H), 7.31 (d, 1H, J=7.7 Hz), 7.20 (d, 1H, J=7.7 Hz), 6.8-6.8 (m, 1H), 6.64 (dd, 2H, J=2.2, 8.2 Hz), 6.69 (br t, 1H, J=54.7 Hz), 4.8-4.8 (m, 1H), 4.54 (d, 2H, J=3.6 Hz), 3.63 (s, 3H), 3.5-3.5 (m, 1H), 3.42 (s, 3H), 3.2-3.3 (m, 3H), 3.12 (dd, 1H, J=9.1, 14.2 Hz), 2.99 (s, 3H), 2.43 (ddd, 2H, J=4.0, 7.7, 11.5 Hz), 1.36 (br d, 1H, J=7.5 Hz), 1.01 (td, 1H, J=2.1, 3.6 Hz)

142

Preparation of Example 30: N—((S)-1-((3P)-3-(4-chloro-1-methyl-3-(methylsulfonamido)-1H-indazol-7-yl)-4-oxo-7-(3-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

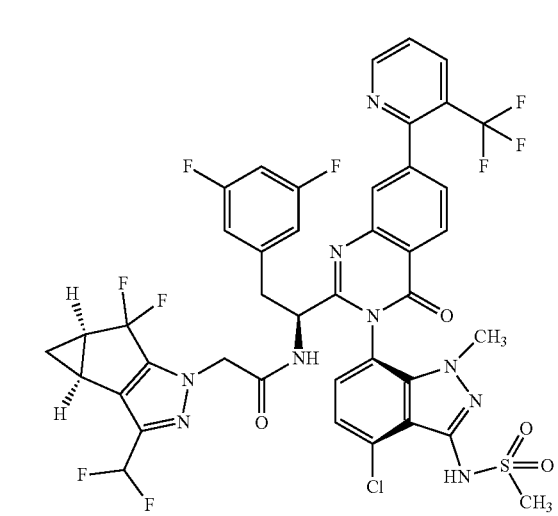

The title compound was prepared according to General Procedure D using 2-chloro-3-(trifluoromethyl)pyridine as the coupling partner. The experiment afforded the title compound, N—((S)-1-((3P)-3-(4-chloro-1-methyl-3-(methylsulfonamido)-1H-indazol-7-yl)-4-oxo-7-(3-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.4 min.; observed ion=950.8 (M+H). 1H NMR (METHANOL-d4, 500 MHz) δ 8.95 (br d, 1H, J=4.5 Hz), 8.40 (br t, 2H, J=7.6 Hz), 7.99 (s, 1H), 7.7-7.8 (m, 2H), 7.32 (d, 1H, J=7.6 Hz), 7.2-7.3 (m, 1H), 6.5-6.8 (m, 4H), 4.5-4.6 (m, 2H), 3.66 (s, 3H), 3.4-3.5 (m, 1H), 3.2-3.3 (m, 3H), 3.19 (s, 1H), 3.1-3.1 (m, 1H), 2.4-2.5 (m, 2H), 1.3-1.4 (m, 1H), 1.0-1.0 (m, 1H)

143

Preparation of Example 31: N—((S)-1-((3P)-3-(4-chloro-1-methyl-3-(methylsulfonamido)-1H-indazol-7-yl)-4-oxo-7-(pyridazin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

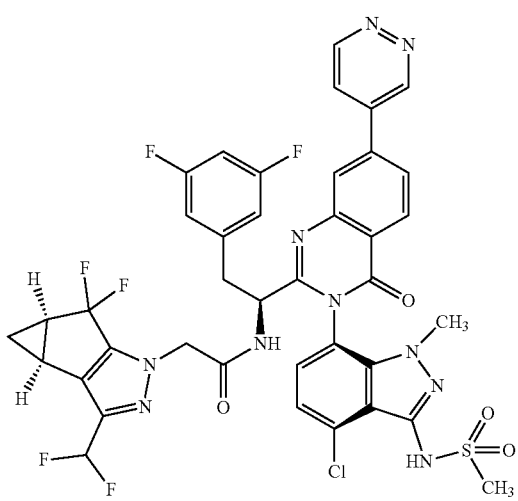

The title compound was prepared according to General Procedure D using 4-bromopyridazine as the coupling partner. The experiment afforded the title compound, N—((S)-1-((3P)-3-(4-chloro-1-methyl-3-(methylsulfonamido)-1H-indazol-7-yl)-4-oxo-7-(pyridazin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.2 min.; observed ion=883.5 (M+H). 1H NMR (METHANOL-d4, 500 MHz) δ 9.74 (dd, 1H, J=1.2, 2.4 Hz), 9.39 (dd, 1H, J=1.3, 5.5 Hz), 8.49 (d, 1H, J=8.6 Hz), 8.37 (d, 1H, J=1.8 Hz), 8.21 (dd, 1H, J=2.5, 5.5 Hz), 8.13 (dd, 1H, J=1.8, 8.3 Hz), 7.32 (d, 1H, J=7.7 Hz), 7.22 (d, 1H, J=7.7 Hz), 6.8-6.8 (m, 1H), 6.64 (dd, 2H, J=2.2, 8.2 Hz), 6.69 (t, 1H, J=54.7 Hz), 4.9-4.9 (m, 1H), 4.53 (s, 2H), 3.63 (s, 3H), 3.51 (dd, 1H, J=5.2, 14.2 Hz), 3.25 (s, 3H), 3.1-3.2 (m, 1H), 2.43 (ddd, 2H, J=3.9, 7.7, 11.3 Hz), 1.37 (br d, 1H, J=7.5 Hz), 1.0-1.0 (m, 1H)

144

Preparation of Example 32: N—((S)-1-(7-(2-(tert-butylsulfonyl)phenyl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

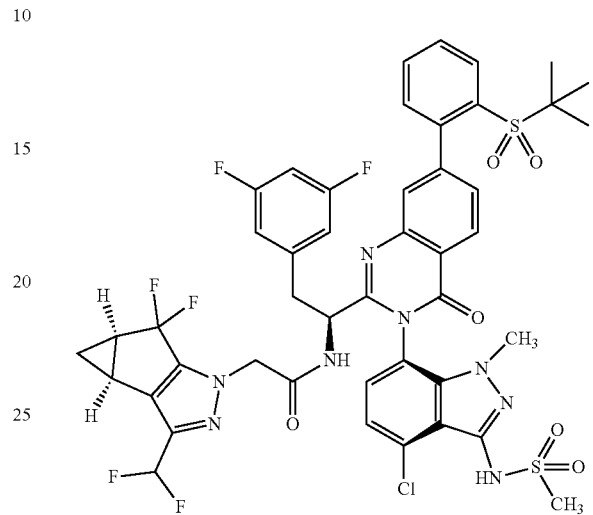

The title compound was prepared according to General Procedure D using 1-bromo-2-(tert-butylsulfonyl)benzene as the coupling partner. The experiment afforded the title compound, N—((S)-1-(7-(2-(tert-butylsulfonyl)phenyl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.44 min.; observed ion=999.5 (M+H). 1H NMR (METHANOL-d4, 500 MHz) δ 8.43 (d, 1H, J=8.3 Hz), 8.28 (t, 1H, J=1.6 Hz), 8.24 (td, 1H, J=1.1, 8.5 Hz), 8.17 (d, 1H, J=1.5 Hz), 8.03 (td, 1H, J=1.5, 7.8 Hz), 8.00 (dd, 1H, J=1.8, 8.3 Hz), 7.89 (t, 1H, J=7.9 Hz), 7.3-7.3 (m, 1H), 7.25 (d, 1H, J=8.0 Hz), 6.6-6.8 (m, 4H), 4.8-4.9 (m, 1H), 4.57 (d, 2H, J=7.2 Hz), 3.63 (s, 3H), 3.47 (s, 1H), 3.2-3.3 (m, 3H), 3.19 (s, 1H), 2.45 (br s, 2H), 1.42 (s, 9H), 1.3-1.4 (m, 1H), 1.0-1.0 (m, 1H)

Preparation of Example 33: N—((S)-1-(7-(3-(tert-butylsulfonyl)phenyl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Preparation of Example 34: N—((S)-1-((3P)-3-(4-chloro-1-methyl-3-(methylsulfonamido)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

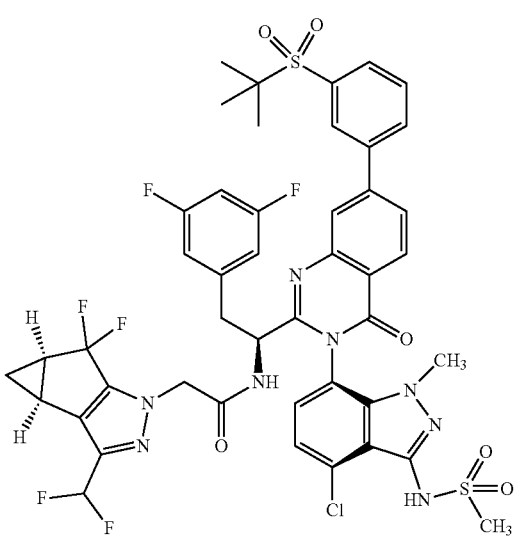

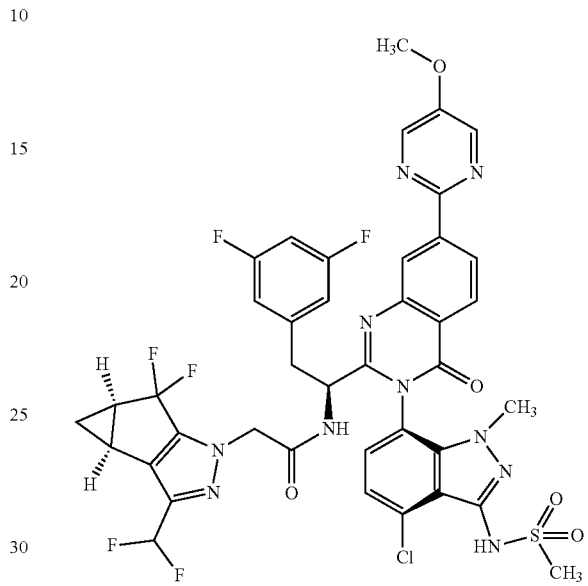

The title compound was prepared according to General Procedure D using 1-bromo-3-(tert-butylsulfonyl)benzene as the coupling partner. The experiment afforded the title compound, N—((S)-1-(7-(3-(tert-butylsulfonyl)phenyl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.44 min.; observed ion=1001.3 (M+H). 1H NMR (METHANOL-d4, 500 MHz) δ 8.27 (d, 1H, J=8.3 Hz), 8.18 (dd, 1H, J=1.2, 8.0 Hz), 7.9-7.9 (m, 2H), 7.78 (dt, 1H, J=1.5, 7.7 Hz), 7.6-7.7 (m, 1H), 7.52 (dd, 1H, J=1.2, 7.7 Hz), 7.31 (br d, 1H, J=7.7 Hz), 6.8-6.8 (m, 1H), 6.63 (br d, 1H, J=6.0 Hz), 6.69 (br t, 2H, J=54.8 Hz), 4.9-5.0 (m, 1H), 4.8-4.9 (m, 1H), 4.53 (s, 2H), 3.66 (s, 3H), 3.5-3.5 (m, 1H), 3.2-3.3 (m, 3H), 3.09 (dd, 1H, J=8.9, 14.0 Hz), 2.4-2.5 (m, 2H), 1.37 (br d, 1H, J=7.5 Hz), 1.21 (s, 9H), 1.0-1.0 (m, 1H)

The title compound was prepared according to General Procedure D using 2-chloro-5-methoxypyrimidine as the coupling partner. The experiment afforded the title compound, N—((S)-1-((3P)-3-(4-chloro-1-methyl-3-(methylsulfonamido)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.4 min.; observed ion=913.4 (M+H). 1H NMR (METHANOL-d4, 500 MHz) δ 8.86 (s, 1H), 8.70 (s, 2H), 8.63 (dd, 1H, J=1.8, 8.3 Hz), 8.37 (d, 1H, J=8.0 Hz), 7.31 (d, 1H, J=7.7 Hz), 7.22 (d, 1H, J=8.0 Hz), 6.6-6.8 (m, 4H), 4.9-4.9 (m, 1H), 4.55 (d, 2H, J=2.7 Hz), 4.08 (s, 3H), 3.64 (s, 3H), 3.5-3.5 (m, 1H), 3.2-3.3 (m, 3H), 3.1-3.2 (m, 1H), 2.4-2.5 (m, 2H), 1.3-1.4 (m, 1H), 1.02 (tdd, 1H, J=2.0, 3.8, 5.6 Hz)

Preparation of Example 35: N—((S)-1-(7-(6-(tert-butyl)pyridin-2-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

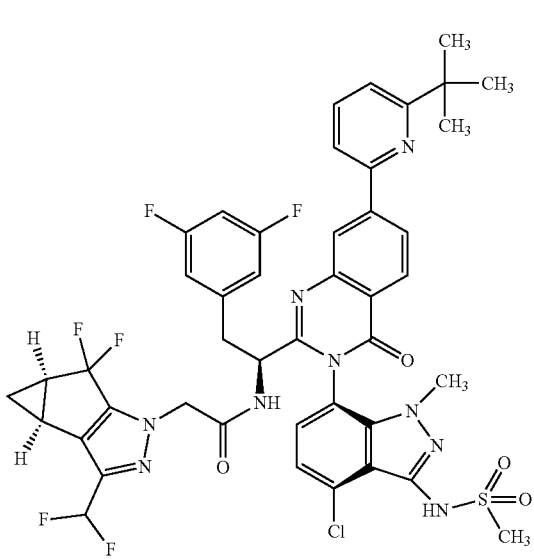

The title compound was prepared according to General Procedure D using 2-(tert-butyl)-6-chloropyridine as the coupling partner. The experiment afforded the title compound, N—((S)-1-(7-(6-(tert-butyl)pyridin-2-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.65 min.; observed ion=938.4 (M+H). 1H NMR (METHANOL-d4, 500 MHz) δ 8.69 (d, 1H, J=1.5 Hz), 8.4-8.4 (m, 2H), 7.9-7.9 (m, 2H), 7.54 (dd, 1H, J=1.2, 7.5 Hz), 7.32 (d, 1H, J=7.7 Hz), 7.23 (d, 1H, J=7.7 Hz), 6.8-6.8 (m, 1H), 6.6-6.7 (m, 2H), 6.69 (t, 1H, J=54.7 Hz), 4.8-4.9 (m, 1H), 4.5-4.6 (m, 2H), 3.63 (s, 3H), 3.5-3.5 (m, 1H), 3.2-3.3 (m, 3H), 3.1-3.2 (m, 1H), 2.4-2.5 (m, 2H), 1.51 (s, 9H), 1.3-1.4 (m, 1H), 1.01 (td, 1H, J=2.0, 3.7 Hz)

Preparation of Example 36: N—((S)-1-((3P)-3-(4-chloro-1-methyl-3-(methylsulfonamido)-1H-indazol-7-yl)-7-(4-ethyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

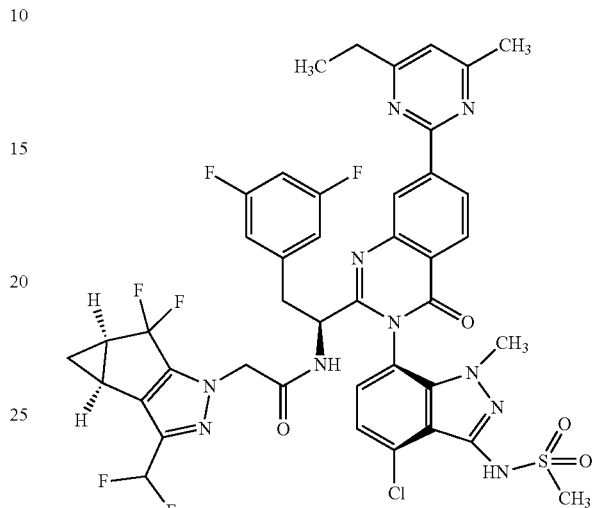

The title compound was prepared according to General Procedure D using 2-chloro-4-ethyl-6-methylpyrimidine as the coupling partner. The experiment afforded the title compound, N—((S)-1-((3P)-3-(4-chloro-1-methyl-3-(methylsulfonamido)-1H-indazol-7-yl)-7-(4-ethyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.55 min.; observed ion=925.4 (M+H). 1H NMR (METHANOL-d4, 500 MHz) δ 8.95 (d, 1H, J=1.5 Hz), 8.70 (dd, 1H, J=1.5, 8.3 Hz), 8.39 (d, 1H, J=8.3 Hz), 7.32 (d, 1H, J=8.0 Hz), 7.29 (s, 1H), 7.23 (d, 1H, J=7.7 Hz), 6.8-6.8 (m, 1H), 6.64 (dd, 2H, J=2.2, 8.2 Hz), 6.71 (br t, 1H, J=54.8 Hz), 4.9-4.9 (m, 1H), 4.56 (d, 2H, J=6.0 Hz), 3.64 (s, 3H), 3.5-3.5 (m, 1H), 3.2-3.3 (m, 3H), 3.13 (dd, 1H, J=9.2, 14.0 Hz), 2.92 (q, 2H, J=7.7 Hz), 2.65 (s, 3H), 2.4-2.5 (m, 2H), 1.4-1.5 (m, 3H), 1.3-1.4 (m, 1H), 1.02 (td, 1H, J=2.0, 3.7 Hz)

149

Preparation of Example 37: N—((S)-1-((3P)-3-(4-chloro-1-methyl-3-(methylsulfonamido)-1H-indazol-7-yl)-7-(4-isopropyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

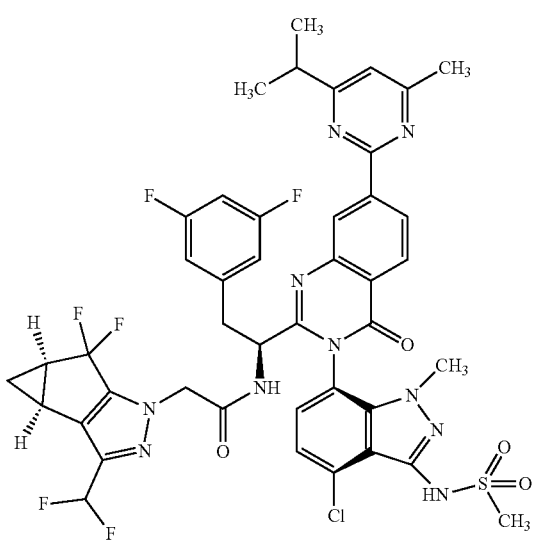

The title compound was prepared according to General Procedure D using 2-chloro-4-isopropyl-6-methylpyrimidine as the coupling partner. The experiment afforded the title compound, N—((S)-1-((3P)-3-(4-chloro-1-methyl-3-(methylsulfonamido)-1H-indazol-7-yl)-7-(4-isopropyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.61 min.; observed ion=939.4 (M+H). 1H NMR (METHANOL-d4, 500 MHz) δ 8.97 (s, 1H), 8.72 (dd, 1H, J=1.5, 8.3 Hz), 8.40 (d, 1H, J=8.0 Hz), 7.2-7.3 (m, 3H), 6.8-6.8 (m, 1H), 6.6-6.7 (m, 2H), 6.70 (br t, 1H, J=54.7 Hz), 4.8-4.9 (m, 1H), 4.6-4.6 (m, 2H), 3.64 (s, 3H), 3.5-3.5 (m, 1H), 3.2-3.3 (m, 3H), 3.1-3.2 (m, 1H), 2.65 (s, 3H), 2.44 (br s, 2H), 1.43 (d, 6H, J=7.2 Hz), 1.3-1.4 (m, 2H), 1.02 (td, 1H, J=2.0, 3.5 Hz)

150

Preparation of Example 38: N—((S)-1-((3P)-3-(4-chloro-1-methyl-3-(methylsulfonamido)-1H-indazol-7-yl)-7-(4,6-diethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

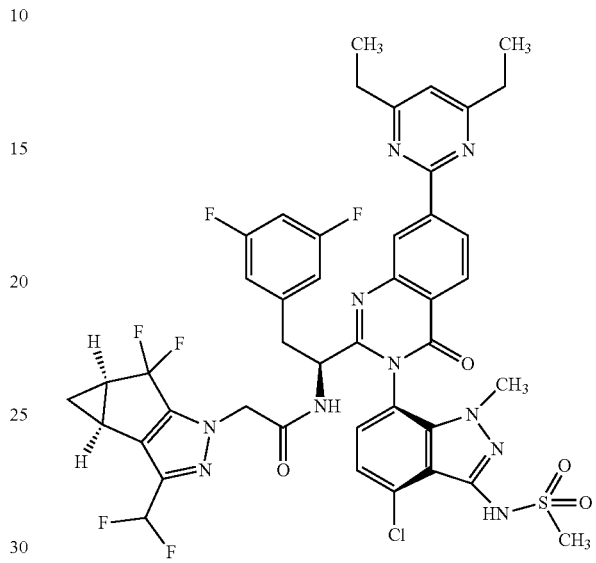

The title compound was prepared according to General Procedure D using 2-chloro-4,6-diethylpyrimidine as the coupling partner. The experiment afforded the title compound, N—((S)-1-((3P)-3-(4-chloro-1-methyl-3-(methylsulfonamido)-1H-indazol-7-yl)-7-(4,6-diethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.62 min.; observed ion=939.5 (M+H). 1H NMR (METHANOL-d4, 500 MHz) δ 8.97 (d, 1H, J=1.2 Hz), 8.73 (dd, 1H, J=1.5, 8.3 Hz), 8.40 (d, 1H, J=8.3 Hz), 7.2-7.3 (m, 3H), 6.8-6.8 (m, 1H), 6.64 (dd, 2H, J=2.2, 8.2 Hz), 6.71 (br t, 1H, J=54.8 Hz), 4.8-4.9 (m, 1H), 4.5-4.6 (m, 2H), 3.64 (s, 3H), 3.5-3.5 (m, 1H), 3.2-3.3 (m, 3H), 3.1-3.2 (m, 1H), 2.93 (q, 4H, J=7.5 Hz), 2.4-2.5 (m, 2H), 1.44 (t, 6H, J=7.6 Hz), 1.3-1.4 (m, 1H), 1.0-1.0 (m, 1H)

151

Preparation of Example 39: N—((S)-1-((3P)-3-(4-chloro-1-methyl-3-(methylsulfonamido)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

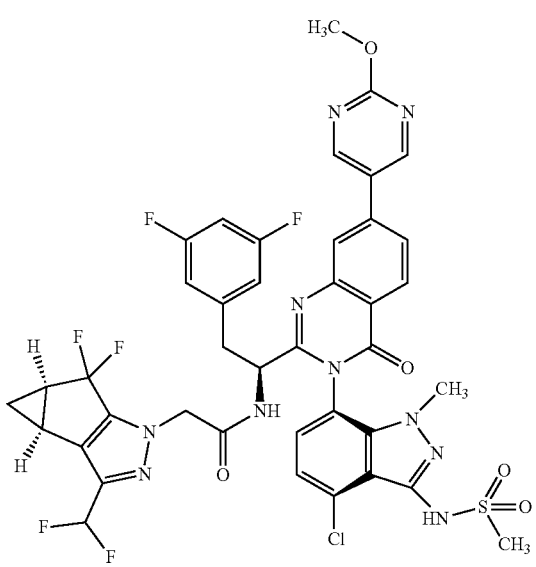

The title compound was prepared according to General Procedure D using 5-bromo-2-methoxypyrimidine as the coupling partner. The experiment afforded the title compound, N—((S)-1-((3P)-3-(4-chloro-1-methyl-3-(methylsulfonamido)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.33 min.; observed ion=913.4 (M+H). 1H NMR (METHANOL-d4, 500 MHz) δ 9.07 (s, 2H), 8.41 (d, 1H, J=8.1 Hz), 8.18 (d, 1H, J=1.5 Hz), 7.98 (dd, 1H, J=1.8, 8.3 Hz), 7.31 (d, 1H, J=8.0 Hz), 7.21 (d, 1H, J=7.7 Hz), 6.6-6.8 (m, 4H), 4.9-5.0 (m, 1H), 4.5-4.5 (m, 2H), 4.14 (s, 3H), 3.63 (s, 3H), 3.5-3.5 (m, 1H), 3.2-3.3 (m, 3H), 3.1-3.2 (m, 1H), 2.44 (ddd, 2H, J=4.0, 7.7, 11.5 Hz), 1.3-1.4 (m, 1H), 1.0-1.0 (m, 1H)

152

Preparation of Example 40: N—((S)-1-((3P)-3-(4-chloro-1-methyl-3-(methylsulfonamido)-1H-indazol-7-yl)-7-(4,6-dimethylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

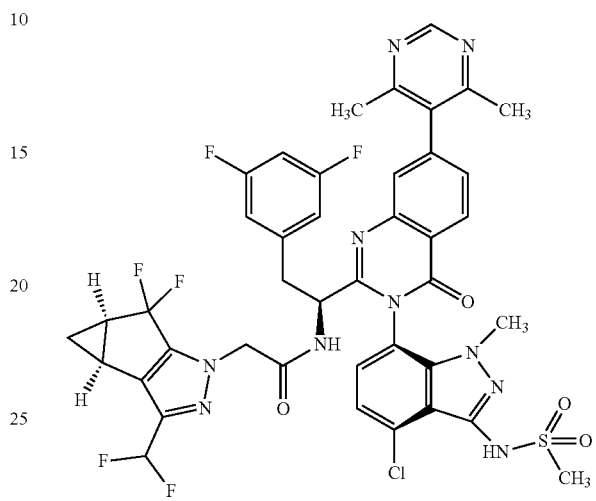

The title compound was prepared according to General Procedure D using 5-bromo-4,6-dimethylpyrimidine as the coupling partner. The experiment afforded the title compound, N—((S)-1-((3P)-3-(4-chloro-1-methyl-3-(methylsulfonamido)-1H-indazol-7-yl)-7-(4,6-dimethylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.264 min.; observed ion=911.4 (M+H). 1H NMR (METHANOL-d4, 500 MHz) δ 8.98 (s, 1H), 8.45 (d, 1H, J=8.0 Hz), 7.83 (d, 1H, J=1.2 Hz), 7.59 (dd, 1H, J=1.6, 8.2 Hz), 7.3-7.3 (m, 2H), 6.8-6.8 (m, 1H), 6.63 (dd, 2H, J=2.2, 8.2 Hz), 6.69 (br t, 1H, J=54.7 Hz), 4.9-4.9 (m, 1H), 4.54 (d, 2H, J=4.2 Hz), 3.67 (s, 3H), 3.4-3.5 (m, 1H), 3.2-3.3 (m, 3H), 3.11 (dd, 1H, J=9.4, 14.2 Hz), 2.4-2.4 (m, 8H), 1.3-1.4 (m, 1H), 1.0-1.0 (m, 1H)

153

Preparation of Example 41:N—((S)-1-((3P)-3-(4-chloro-1-methyl-3-(methylsulfonamido)-1H-indazol-7-yl)-7-(6-cyclopropylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

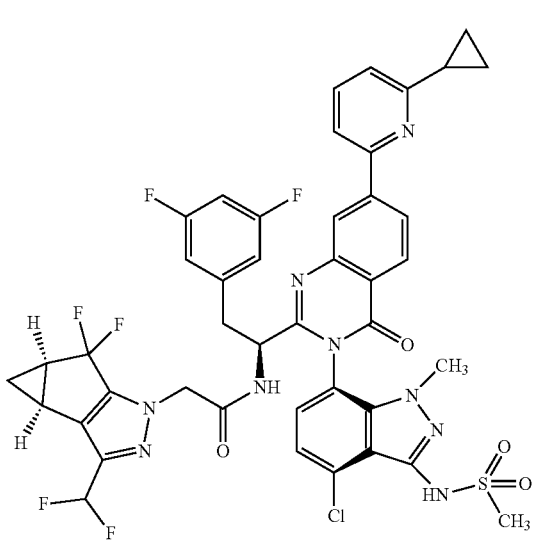

The title compound was prepared according to General Procedure D using 2-chloro-6-cyclopropylpyridine as the coupling partner. The experiment afforded the title compound, N—((S)-1-((3P)-3-(4-chloro-1-methyl-3-(methylsulfonamido)-1H-indazol-7-yl)-7-(6-cyclopropylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.55 min.; observed ion=922.4 (M+H). 1H NMR (METHANOL-d4, 500 MHz) δ 8.58 (d, 1H, J=1.8 Hz), 8.4-8.4 (m, 1H), 8.3-8.3 (m, 1H), 7.8-7.9 (m, 2H), 7.3-7.4 (m, 2H), 7.22 (d, 1H, J=8.0 Hz), 6.5-6.8 (m, 4H), 4.5-4.6 (m, 3H), 3.63 (s, 3H), 3.5-3.5 (m, 1H), 3.2-3.3 (m, 3H), 3.13 (dd, 1H, J=9.4, 14.2 Hz), 2.43 (dt, 2H, J=2.1, 4.9 Hz), 2.2-2.2 (m, 1H), 1.3-1.4 (m, 1H), 1.1-1.2 (m, 2H), 1.1-1.1 (m, 2H), 1.0-1.0 (m, 1H)

154

Preparation of Example 42: N—((S)-1-((3P)-3-(4-chloro-1-methyl-3-(methylsulfonamido)-1H-indazol-7-yl)-7-(4-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

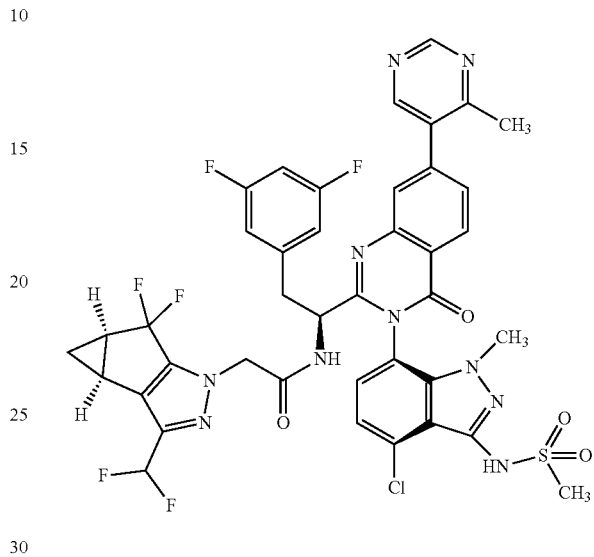

The title compound was prepared according to General Procedure D using 5-bromo-4-methylpyrimidine as the coupling partner. The experiment afforded the title compound, N—((S)-1-((3P)-3-(4-chloro-1-methyl-3-(methylsulfonamido)-1H-indazol-7-yl)-7-(4-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.27 min.; observed ion=897.4 (M+H). 1H NMR (METHANOL-d4, 500 MHz) δ 9.13 (s, 1H), 8.76 (s, 1H), 8.44 (d, 1H, J=8.0 Hz), 7.97 (d, 1H, J=1.8 Hz), 7.74 (dd, 1H, J=1.6, 8.2 Hz), 7.33 (d, 1H, J=7.7 Hz), 7.25 (d, 1H, J=7.7 Hz), 6.8-6.8 (m, 1H), 6.63 (dd, 2H, J=2.2, 8.2 Hz), 6.69 (t, 1H, J=54.7 Hz), 4.8-4.9 (m, 1H), 4.53 (d, 2H, J=2.7 Hz), 3.65 (s, 3H), 3.5-3.5 (m, 1H), 3.2-3.3 (m, 3H), 3.12 (dd, 1H, J=9.2, 14.3 Hz), 2.63 (s, 3H), 2.43 (ddd, 2H, J=4.0, 7.7, 11.5 Hz), 1.3-1.4 (m, 1H), 1.0-1.0 (m, 1H)

Preparation of Example 43: N—((S)-1-((3P)-3-(4-chloro-1-methyl-3-(methylsulfonamido)-1H-indazol-7-yl)-7-(4-ethylpyrimidin-2-yl)-4-oxo-3,4-dihydro-quinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Preparation of Example 44: N—((S)-1-((3P)-3-(4-chloro-1-methyl-3-(methylsulfonamido)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

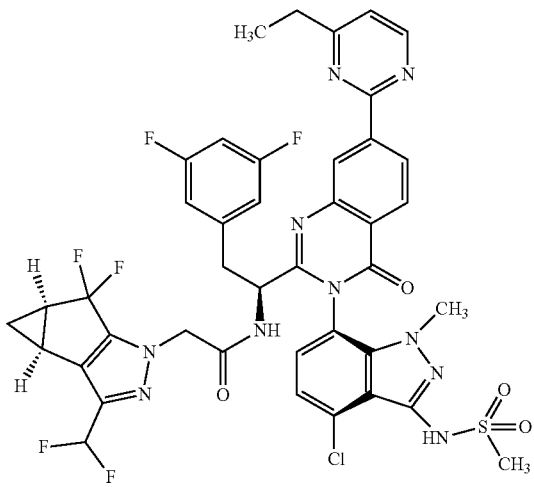

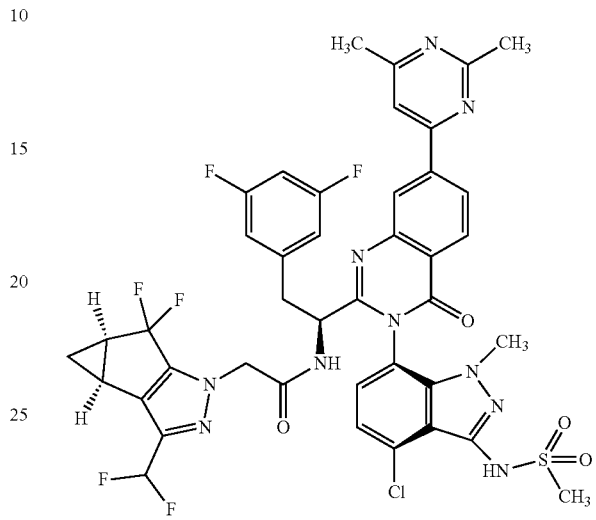

The title compound was prepared according to General Procedure D using 2-chloro-4-ethylpyrimidine as the coupling partner. The experiment afforded the title compound, N—((S)-1-((3P)-3-(4-chloro-1-methyl-3-(methylsulfonamido)-1H-indazol-7-yl)-7-(4-ethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.48 min.; observed ion=911.4 (M+H). 1H NMR (METHANOL-d4, 500 MHz) Shift 8.96 (s, 1H), 8.84 (d, 1H, J=5.1 Hz), 8.71 (dd, 1H, J=1.8, 8.3 Hz), 8.41 (d, 1H, J=8.0 Hz), 7.41 (d, 1H, J=5.1 Hz), 7.32 (br d, 1H, J=7.4 Hz), 7.24 (d, 1H, J=7.7 Hz), 6.6-6.8 (m, 4H), 4.56 (d, 3H, J=5.4 Hz), 3.6-3.7 (m, 3H), 3.5-3.5 (m, 1H), 3.25 (s, 3H), 3.13 (dd, 1H, J=9.2, 14.0 Hz), 2.98 (q, 2H, J=7.6 Hz), 2.43 (br d, 2H, J=4.5 Hz), 1.46 (t, 3H, J=7.6 Hz), 1.35 (s, 1H), 1.0-1.0 (m, 1H)

The title compound was prepared according to General Procedure D using 4-chloro-2,6-dimethylpyrimidine as the coupling partner. The experiment afforded the title compound, N—((S)-1-((3P)-3-(4-chloro-1-methyl-3-(methylsulfonamido)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.35 min.; observed ion=911.4 (M+H). 1H NMR (METHANOL-d4, 500 MHz) Shift 8.67 (s, 1H), 8.4-8.4 (m, 2H), 7.91 (s, 1H), 7.32 (d, 1H, J=7.7 Hz), 7.23 (d, 1H, J=8.0 Hz), 6.7-6.8 (m, 1H), 6.71 (br t, 1H, J=54.8 Hz), 6.64 (br dd, 2H, J=2.2, 8.2 Hz), 4.54 (d, 2H, J=2.7 Hz), 3.64 (s, 3H), 3.4-3.5 (m, 1H), 3.2-3.3 (m, 3H), 3.1-3.2 (m, 1H), 2.81 (s, 2H), 2.67 (d, 3H, J=11.0 Hz), 2.44 (br dd, 2H, J=4.3, 8.2 Hz), 1.7-1.8 (m, 1H), 1.3-1.5 (m, 1H), 1.1-1.2 (m, 1H), 1.01 (br dd, 1H, J=1.9, 3.7 Hz)

Preparation of Example 45: N—((S)-1-((3P)-3-(4-chloro-1-methyl-3-(methylsulfonamido)-1H-indazol-7-yl)-7-(5-methoxypyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 46: N—((S)-1-((3P)-3-(4-chloro-1-methyl-3-(methylsulfonamido)-1H-indazol-7-yl)-7-(6-isopropylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

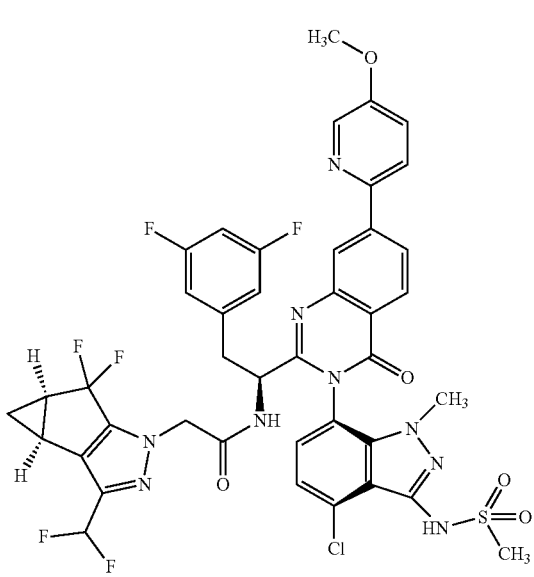

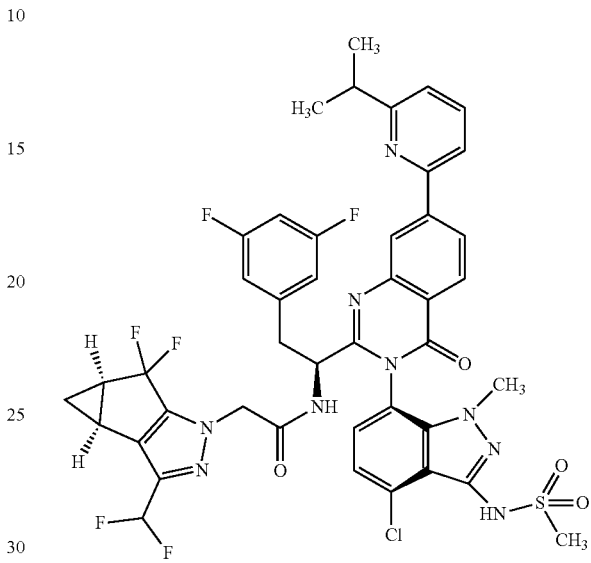

The title compound was prepared according to General Procedure D using 2-chloro-5-methoxypyridine as the coupling partner. The experiment afforded the title compound, N—((S)-1-((3P)-3-(4-chloro-1-methyl-3-(methylsulfonamido)-1H-indazol-7-yl)-7-(5-methoxypyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.4 min.; observed ion=912.4 (M+H). 1H NMR (METHANOL-d4, 500 MHz) Shift 8.46 (s, 1H), 8.47 (d, 2H, J=4.4 Hz), 8.36 (d, 1H, J=8.3 Hz), 8.25 (dd, 1H, J=1.8, 8.3 Hz), 8.07 (d, 1H, J=8.3 Hz), 7.59 (dd, 1H, J=3.0, 8.6 Hz), 7.31 (d, 1H, J=7.7 Hz), 7.20 (d, 1H, J=7.7 Hz), 6.79 (br t, 1H, J=2.4 Hz), 6.64 (dd, 2H, J=2.1, 8.0 Hz), 6.70 (t, 1H, J=54.8 Hz), 4.54 (s, 2H), 4.00 (s, 3H), 3.64 (s, 3H), 3.5-3.5 (m, 1H), 3.2-3.3 (m, 3H), 3.12 (dd, 1H, J=9.1, 14.2 Hz), 2.43 (br dd, 2H, J=4.8, 6.9 Hz), 1.3-1.4 (m, 1H), 1.0-1.0 (m, 1H)

The title compound was prepared according to General Procedure D using 2-chloro-6-isopropylpyridine as the coupling partner. The experiment afforded the title compound, N—((S)-1-((3P)-3-(4-chloro-1-methyl-3-(methylsulfonamido)-1H-indazol-7-yl)-7-(6-isopropylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.58 min.; observed ion=924.5 (M+H). 1H NMR (METHANOL-d4, 500 MHz) Shift 8.62 (d, 1H, J=1.5 Hz), 8.3-8.4 (m, 2H), 7.91 (s, 1H), 7.90 (d, 1H, J=2.4 Hz), 7.4-7.4 (m, 1H), 7.31 (d, 1H, J=7.7 Hz), 7.22 (d, 1H, J=7.7 Hz), 6.80 (br t, 1H, J=2.4 Hz), 6.64 (dd, 2H, J=2.1, 8.0 Hz), 6.69 (br t, 1H, J=54.7 Hz), 4.8-4.9 (m, 1H), 4.56 (d, 2H, J=5.7 Hz), 3.63 (s, 3H), 3.51 (dd, 1H, J=4.9, 14.2 Hz), 3.1-3.3 (m, 5H), 2.4-2.5 (m, 2H), 1.43 (d, 6H, J=7.2 Hz), 1.36 (br d, 1H, J=5.7 Hz), 1.0-1.0 (m, 1H)

Preparation of Example 47: N—((S)-1-(7-(4-(tert-butyl)pyrimidin-2-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 48: N—((S)-1-((3P)-3-(4-chloro-1-methyl-3-(methylsulfonamido)-1H-indazol-7-yl)-7-(6-methyl-4-(trifluoromethyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

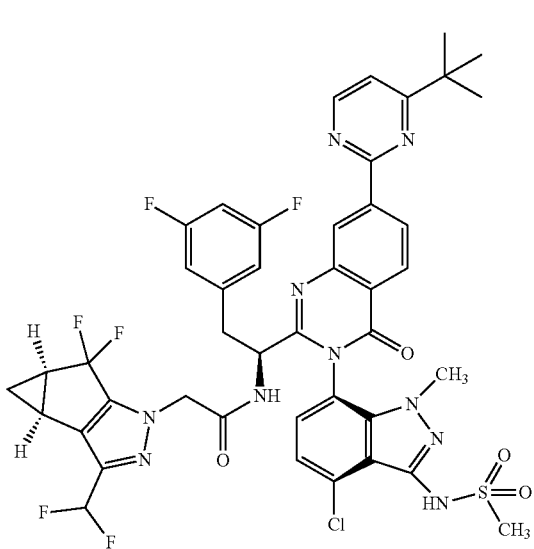

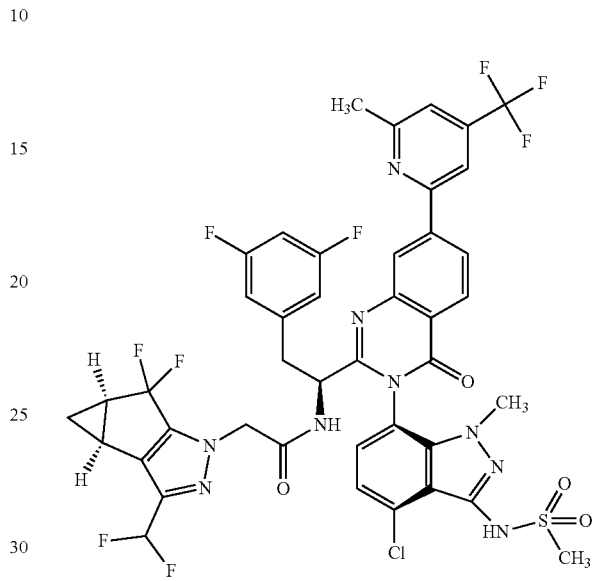

The title compound was prepared according to General Procedure D using 4-(tert-butyl)-2-chloropyrimidine as the coupling partner. The experiment afforded the title compound, N—((S)-1-(7-(4-(tert-butyl)pyrimidin-2-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.59 min.; observed ion=939.4 (M+H). 1H NMR (METHANOL-d4, 500 MHz) Shift 8.62 (d, 1H, J=1.2 Hz), 8.4-8.4 (m, 2H), 8.17 (s, 1H), 7.67 (s, 1H), 7.31 (d, 1H, J=7.7 Hz), 7.23 (d, 1H, J=7.7 Hz), 6.8-6.8 (m, 1H), 6.64 (dd, 2H, J=2.1, 8.0 Hz), 6.71 (br t, 1H, J=54.8 Hz), 4.56 (d, 2H, J=4.8 Hz), 3.64 (s, 3H), 3.5-3.5 (m, 1H), 3.2-3.3 (m, 3H), 3.1-3.2 (m, 1H), 2.80 (s, 3H), 2.68 (s, 1H), 2.4-2.5 (m, 2H), 1.3-1.4 (m, 1H), 1.0-1.0 (m, 1H)

The title compound was prepared according to General Procedure D using 2-chloro-6-methyl-4-(trifluoromethyl)pyridine as the coupling partner. The experiment afforded the title compound, N—((S)-1-((3P)-3-(4-chloro-1-methyl-3-(methylsulfonamido)-1H-indazol-7-yl)-7-(6-methyl-4-(trifluoromethyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.57 min.; observed ion=964.4 (M+H). 1H NMR (METHANOL-d4, 500 MHz) Shift 8.62 (d, 1H, J=1.2 Hz), 8.4-8.4 (m, 2H), 8.17 (s, 1H), 7.67 (s, 1H), 7.31 (d, 1H, J=7.7 Hz), 7.23 (d, 1H, J=7.7 Hz), 6.8-6.8 (m, 1H), 6.64 (dd, 2H, J=2.1, 8.0 Hz), 6.71 (br t, 1H, J=54.8 Hz), 4.56 (d, 2H, J=4.8 Hz), 3.64 (s, 3H), 3.5-3.5 (m, 1H), 3.2-3.3 (m, 3H), 3.1-3.2 (m, 1H), 2.80 (s, 3H), 2.68 (s, 1H), 2.4-2.5 (m, 2H), 1.3-1.4 (m, 1H), 1.0-1.0 (m, 1H)

Preparation of Example 49: N—((S)-1-((3P)-3-(4-chloro-1-methyl-3-(methylsulfonamido)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 50: N—((S)-1-((3P)-3-(4-chloro-1-methyl-3-(methylsulfonamido)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

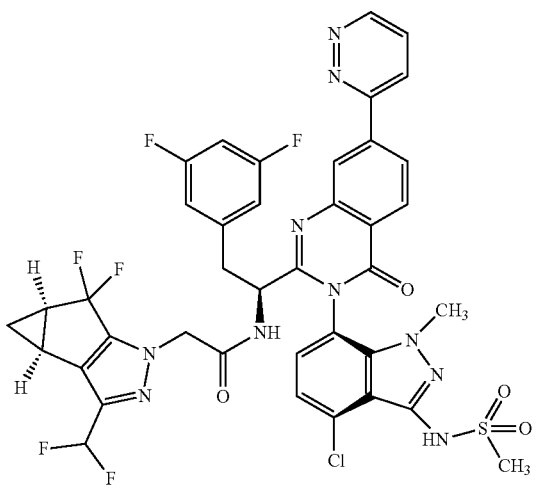

The title compound was prepared according to General Procedure D using 3-chloropyridazine as the coupling partner. The experiment afforded the title compound, N—((S)-1-((3P)-3-(4-chloro-1-methyl-3-(methylsulfonamido)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.25 min.; observed ion=883.4 (M+H). 1H NMR (METHANOL-d4, 500 MHz) Shift 9.28 (dd, 1H, J=1.5, 4.8 Hz), 8.63 (d, 1H, J=1.8 Hz), 8.45 (d, 1H, J=8.3 Hz), 8.37 (dd, 1H, J=6.9, 18.8 Hz), 8.38 (dd, 1H, J=10.3, 18.9 Hz), 7.92 (dd, 1H, J=5.1, 8.6 Hz), 7.29 (d, 1H, J=7.7 Hz), 7.20 (d, 1H, J=8.0 Hz), 6.77 (br t, 1H, J=2.4 Hz), 6.62 (dd, 2H, J=2.2, 8.2 Hz), 6.67 (br t, 1H, J=54.8 Hz), 4.9-4.9 (m, 1H), 4.52 (d, 2H, J=2.4 Hz), 3.62 (s, 3H), 3.4-3.6 (m, 1H), 3.23 (s, 3H), 3.12 (dd, 1H, J=9.2, 14.0 Hz), 2.4-2.4 (m, 2H), 1.33 (s, 1H), 1.0-1.0 (m, 1H)

The title compound was prepared according to General Procedure D using 3-chloro-6-methylpyridazine as the coupling partner. The experiment afforded the title compound, N—((S)-1-((3P)-3-(4-chloro-1-methyl-3-(methylsulfonamido)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.27 min.; observed ion=897.4 (M+H). 1H NMR (METHANOL-d4, 500 MHz) Shift 8.63 (d, 1H, J=1.5 Hz), 8.46 (d, 1H, J=8.3 Hz), 8.36 (dd, 1H, J=1.8, 8.3 Hz), 8.31 (d, 1H, J=8.6 Hz), 7.82 (d, 1H, J=8.6 Hz), 7.31 (d, 1H, J=7.7 Hz), 7.23 (d, 1H, J=7.7 Hz), 6.8-6.8 (m, 1H), 6.64 (dd, 2H, J=2.1, 8.0 Hz), 6.70 (br t, 1H, J=54.7 Hz), 4.9-5.0 (m, 1H), 4.8-4.9 (m, 1H), 4.54 (d, 2H, J=1.5 Hz), 3.64 (s, 3H), 3.5-3.5 (m, 1H), 3.14 (dd, 1H, J=9.4, 13.9 Hz), 2.82 (s, 3H), 2.68 (s, 2H), 2.4-2.5 (m, 2H), 1.3-1.4 (m, 1H), 1.0-1.0 (m, 1H)

163

Preparation of Example 51: N—((S)-1-((3P)-3-(4-chloro-1-methyl-3-(methylsulfonamido)-1H-indazol-7-yl)-7-(4-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

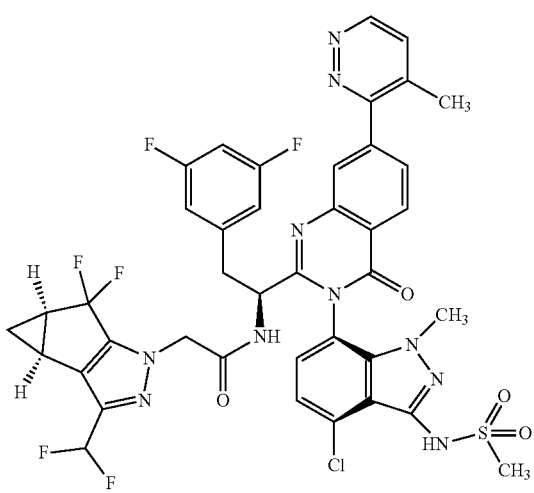

The title compound was prepared according to General Procedure D using 3-chloro-4-methylpyridazine as the coupling partner. The experiment afforded the title compound, N—((S)-1-((3P)-3-(4-chloro-1-methyl-3-(methylsulfonamido)-1H-indazol-7-yl)-7-(4-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.25 min.; observed ion=897.4 (M+H). 1H NMR (METHANOL-d4, 500 MHz) δ 9.15 (d, 1H, J=5.4 Hz), 8.47 (d, 1H, J=8.1 Hz), 8.1-8.1 (m, 1H), 7.88 (d, 1H, J=8.1 Hz), 7.80 (d, 1H, J=5.6 Hz), 7.33 (d, 1H, J=7.7 Hz), 7.25 (d, 1H, J=7.7 Hz), 6.6-6.8 (m, 4H), 4.8-4.8 (m, 1H), 4.53 (d, 2H, J=2.7 Hz), 3.6-3.7 (m, 3H), 3.4-3.5 (m, 1H), 3.2-3.3 (m, 3H), 3.12 (dd, 1H, J=9.2, 14.0 Hz), 2.51 (s, 3H), 2.4-2.5 (m, 2H), 1.36 (s, 1H), 1.0-1.0 (m, 1H)

164

Preparation of Example 52: N—((S)-1-((3P)-3-(4-chloro-1-methyl-3-(methylsulfonamido)-1H-indazol-7-yl)-7-(4,6-dimethyl-3-(trifluoromethyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

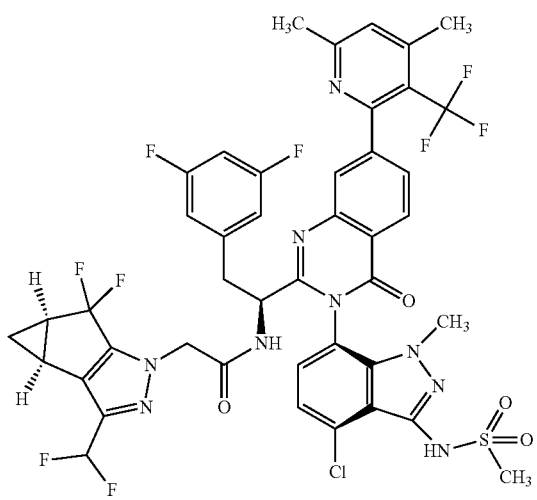

The title compound was prepared according to General Procedure D using 2-chloro-4,6-dimethyl-3-(trifluoromethyl)pyridine as the coupling partner. The experiment afforded the title compound, N—((S)-1-((3P)-3-(4-chloro-1-methyl-3-(methylsulfonamido)-1H-indazol-7-yl)-7-(4,6-dimethyl-3-(trifluoromethyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=978.4 (M+H). 1H NMR (METHANOL-d4,500 MHz) Shift 8.37 (d, 1H, J=8.0 Hz), 7.87 (d, 1H, J=1.8 Hz), 7.67 (dd, 1H, J=1.8, 8.0 Hz), 7.46 (s, 1H), 7.31 (d, 1H, J=7.7 Hz), 7.23 (d, 1H, J=8.0 Hz), 6.7-6.8 (m, 1H), 6.69 (br t, 1H, J=54.7 Hz), 6.62 (br dd, 2H, J=2.2, 8.2 Hz), 4.54 (d, 2H, J=4.5 Hz), 3.64 (s, 3H), 3.4-3.5 (m, 1H), 3.25 (s, 3H), 3.10 (dd, 1H, J=9.2, 14.0 Hz), 2.6-2.7 (m, 7H), 2.42 (td, 2H, J=3.7, 7.5 Hz), 1.3-1.4 (m, 1H), 1.01 (br dd, 1H, J=1.6, 3.7 Hz)

Preparation of Example 53: N—((S)-1-((3P)-3-(4-chloro-1-methyl-3-(methylsulfonamido)-1H-indazol-7-yl)-7-(4-methyl-6-(trifluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

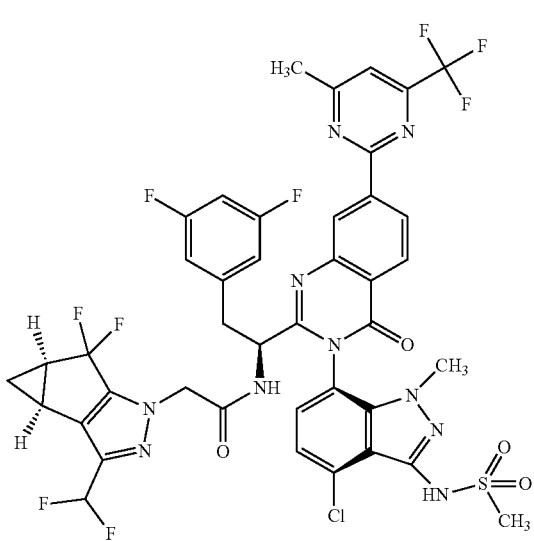

The title compound was prepared according to General Procedure D using 2-chloro-4-methyl-6-(trifluoromethyl)pyrimidine as the coupling partner. The experiment afforded the title compound, N—((S)-1-((3P)-3-(4-chloro-1-methyl-3-(methylsulfonamido)-1H-indazol-7-yl)-7-(4-methyl-6-(trifluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.54 min.; observed ion=963.4 (M+H). 1H NMR (METHANOL-d4,500 MHz) Shift 9.01 (d, 1H, J=1.8 Hz), 8.75 (dd, 1H, J=1.8, 8.3 Hz), 8.44 (d, 1H, J=8.3 Hz), 7.83 (s, 1H), 7.32 (d, 1H, J=8.0 Hz), 7.25 (d, 1H, J=7.7 Hz), 6.8-6.8 (m, 1H), 6.70 (br t, 1H, J=54.7 Hz), 6.64 (dd, 2H, J=2.2, 8.2 Hz), 4.5-4.6 (m, 2H), 3.64 (s, 3H), 3.5-3.5 (m, 1H), 3.2-3.3 (m, 3H), 3.1-3.2 (m, 1H), 2.82 (s, 3H), 2.68 (s, 1H), 2.4-2.5 (m, 2H), 1.36 (br dd, 1H, J=1.3, 7.0 Hz), 1.02 (td, 1H, J=2.0, 3.5 Hz)

Preparation of Example 54: N—((S)-1-((3P)-3-(4-chloro-1-methyl-3-(methylsulfonamido)-1H-indazol-7-yl)-7-(4-methoxy-6-(trifluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

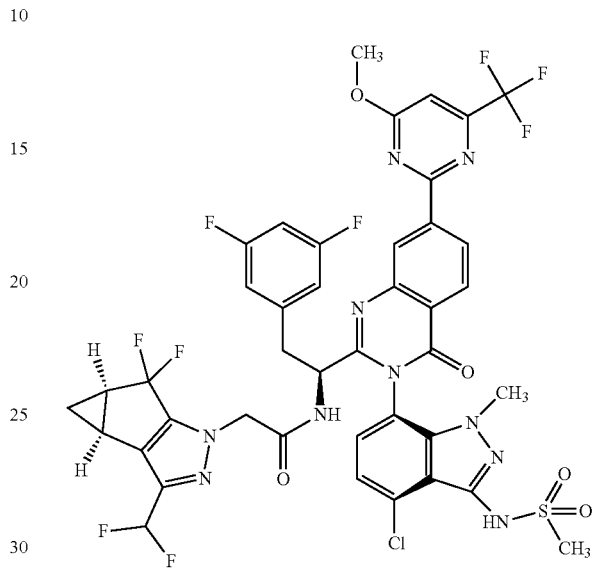

The title compound was prepared according to General Procedure D using 2-chloro-4-methoxy-6-(trifluoromethyl)pyrimidine as the coupling partner. The experiment afforded the title compound, N—((S)-1-((3P)-3-(4-chloro-1-methyl-3-(methylsulfonamido)-1H-indazol-7-yl)-7-(4-methoxy-6-(trifluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.58 min.; observed ion=979.4 (M−H). 1H NMR (METHANOL-d4, 500 MHz) Shift 9.0-9.0 (m, 1H), 8.71 (dd, 1H, J=1.8, 8.3 Hz), 8.42 (d, 1H, J=8.0 Hz), 7.3-7.3 (m, 1H), 7.2-7.2 (m, 1H), 6.7-6.8 (m, 1H), 6.67 (br t, 1H, J=54.7 Hz), 6.60 (br dd, 2H, J=2.1, 8.0 Hz), 4.5-4.6 (m, 2H), 4.27 (s, 2H), 3.61 (s, 4H), 3.4-3.5 (m, 2H), 3.3-3.4 (m, 1H), 3.22 (s, 2H), 3.1-3.1 (m, 1H), 2.4-2.5 (m, 2H), 1.34 (br dd, 1H, J=1.3, 6.7 Hz), 0.99 (br dd, 1H, J=1.8, 3.3 Hz), 0.0-0.0 (m, 1H)

Preparation of Example 55: N—((S)-1-((3P)-3-(4-chloro-1-methyl-3-(methylsulfonamido)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

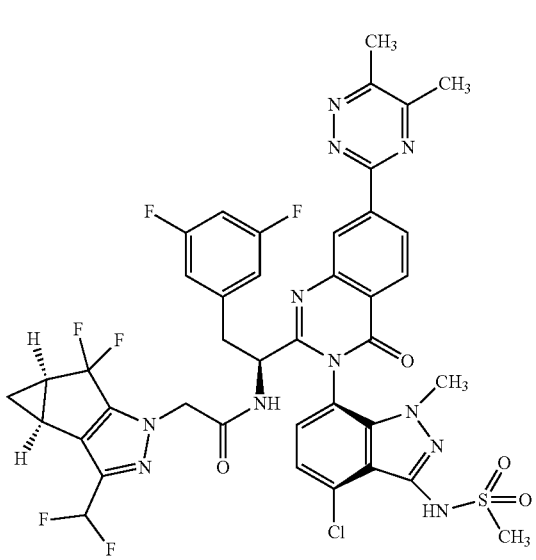

The title compound was prepared according to General Procedure D using 3-chloro-5,6-dimethyl-1,2,4-triazine as the coupling partner. The experiment afforded the title compound, N—((S)-1-((3P)-3-(4-chloro-1-methyl-3-(methylsulfonamido)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.36 min.; observed ion=910.3 (M−H). 1H NMR (METHANOL-d4, 500 MHz) Shift 8.95 (d, 1H, J=1.8 Hz), 8.69 (dd, 1H, J=1.8, 8.3 Hz), 8.42 (d, 1H, J=8.0 Hz), 7.28 (d, 1H, J=8.0 Hz), 7.21 (d, 1H, J=8.0 Hz), 6.7-6.8 (m, 1H), 6.68 (br t, 2H, J=54.8 Hz), 6.61 (dd, 2H, J=2.2, 8.2 Hz), 4.5-4.6 (m, 2H), 3.61 (s, 3H), 3.4-3.5 (m, 1H), 3.22 (s, 3H), 3.10 (dd, 1H, J=9.1, 14.2 Hz), 2.78 (s, 3H), 2.73 (s, 3H), 2.42 (br d, 1H, J=4.5 Hz), 1.34 (br dd, 2H, J=1.2, 6.9 Hz), 0.99 (td, 1H, J=2.1, 3.6 Hz)

Preparation of Example 56: N—((S)-1-((3P)-3-(4-chloro-1-methyl-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

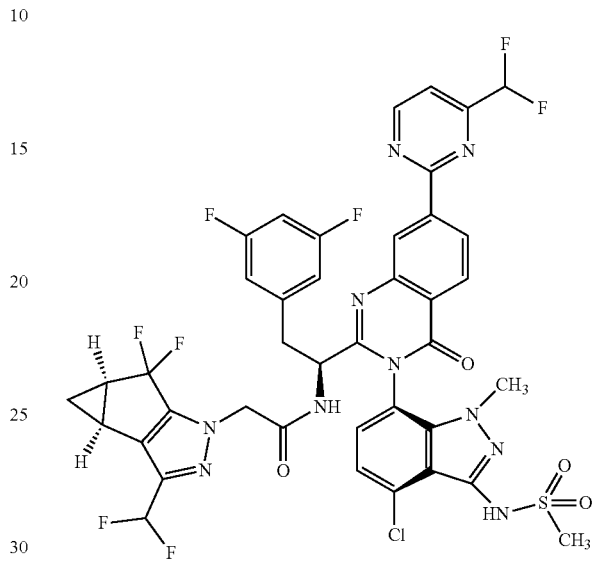

The title compound was prepared according to General Procedure D using 2-chloro-4-(difluoromethyl)pyrimidine as the coupling partner. The experiment afforded the title compound, N—((S)-1-((3P)-3-(4-chloro-1-methyl-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.43 min.; observed ion=933.4 (M+H). 1H NMR (METHANOL-d4, 500 MHz) Shift 9.19 (d, 1H, J=5.1 Hz), 8.98 (s, 1H), 8.73 (dd, 1H, J=1.8, 8.3 Hz), 8.41 (d, 1H, J=8.0 Hz), 7.76 (d, 1H, J=5.1 Hz), 7.29 (d, 1H, J=7.7 Hz), 7.21 (d, 1H, J=7.7 Hz), 6.6-7.0 (m, 5H), 4.9-4.9 (m, 1H), 4.54 (d, 2H, J=6.3 Hz), 3.61 (s, 3H), 3.4-3.5 (m, 1H), 3.23 (s, 3H), 3.11 (dd, 1H, J=9.4, 14.2 Hz), 2.4-2.5 (m, 2H), 1.34 (br dd, 1H, J=1.2, 6.9 Hz), 1.0-1.0 (m, 1H)

Preparation of Example 57: N—((S)-1-((3P)-3-(4-chloro-1-methyl-3-(methylsulfonamido)-1H-indazol-7-yl)-7-(4-methoxy-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 58: N—((S)-1-(7-(4,6-bis(trifluoromethyl)pyridin-2-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

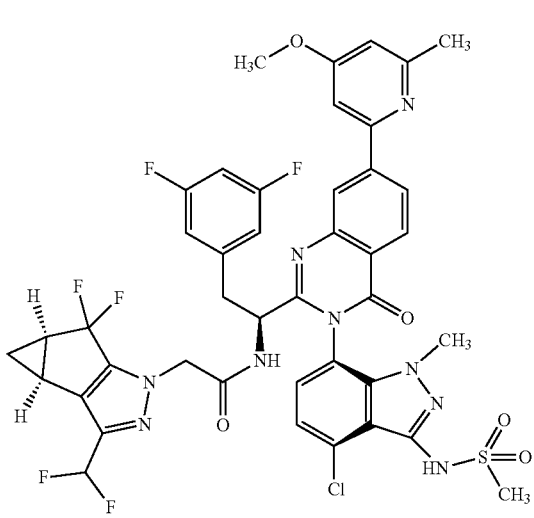

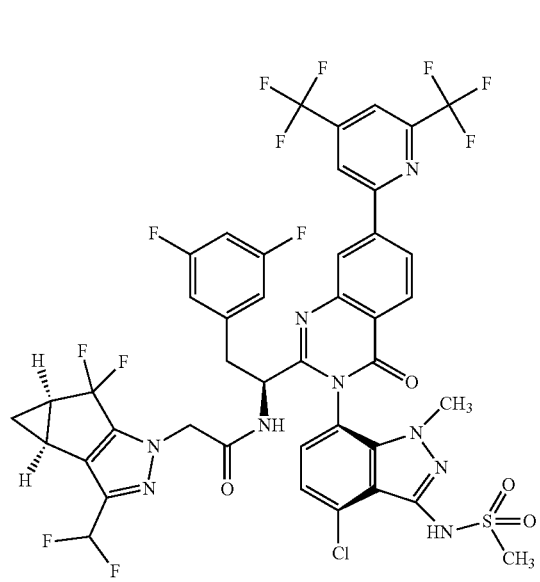

The title compound was prepared according to General Procedure D using 2-chloro-4-methoxy-6-methylpyridine as the coupling partner. The experiment afforded the title compound, N—((S)-1-((3P)-3-(4-chloro-1-methyl-3-(methylsulfonamido)-1H-indazol-7-yl)-7-(4-methoxy-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.2 min.; observed ion=926.4 (M+H). 1H NMR (METHANOL-d4, 500 MHz) Shift 8.41 (d, 1H, J=1.8 Hz), 8.36 (d, 1H, J=8.1 Hz), 8.19 (dd, 1H, J=1.5, 8.3 Hz), 7.37 (d, 1H, J=2.4 Hz), 7.28 (d, 1H, J=8.0 Hz), 7.1-7.2 (m, 1H), 6.94 (d, 1H, J=1.8 Hz), 6.77 (br d, 1H, J=2.4 Hz), 6.68 (br t, 1H, J=54.7 Hz), 6.61 (br dd, 2H, J=2.4, 8.3 Hz), 4.8-4.9 (m, 1H), 4.7-4.8 (m, 1H), 4.5-4.6 (m, 2H), 3.98 (s, 2H), 3.6-3.6 (m, 3H), 3.4-3.5 (m, 1H), 3.2-3.2 (m, 3H), 3.09 (dd, 1H, J=9.1, 14.2 Hz), 2.63 (d, 3H, J=17.6 Hz), 2.41 (br dd, 2H, J=4.0, 7.6 Hz), 1.34 (br d, 1H, J=5.7 Hz), 0.99 (br dd, 1H, J=1.8, 3.3 Hz)

The title compound was prepared according to General Procedure D using 2-chloro-4,6-bis(trifluoromethyl)pyridine as the coupling partner. The experiment afforded the title compound, N—((S)-1-(7-(4,6-bis(trifluoromethyl)pyridin-2-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.6 min.; observed ion=1016.5 (M−H). 1H NMR (METHANOL-d4, 500 MHz) Shift 8.72 (t, 1H, J=1.2 Hz), 8.70 (s, 1H), 8.45 (d, 2H, J=1.2 Hz), 8.19 (s, 1H), 7.27 (d, 1H, J=7.9 Hz), 7.20 (d, 1H, J=7.7 Hz), 6.7-6.8 (m, 1H), 6.67 (br t, 1H, J=54.7 Hz), 6.61 (dd, 2H, J=2.1, 8.0 Hz), 4.9-4.9 (m, 1H), 4.54 (d, 2H, J=7.2 Hz), 3.61 (s, 3H), 3.4-3.5 (m, 1H), 3.22 (s, 3H), 3.11 (dd, 1H, J=9.2, 14.3 Hz), 2.41 (br dd, 2H, J=3.6, 7.2 Hz), 1.3-1.4 (m, 1H), 0.99 (br dd, 1H, J=1.8, 3.9 Hz)

Preparation of Example 59: N—((S)-1-((3P)-3-(4-chloro-1-methyl-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 60: N—((S)-1-((3P)-3-(4-chloro-1-methyl-3-(methylsulfonamido)-1H-indazol-7-yl)-7-(4-ethylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

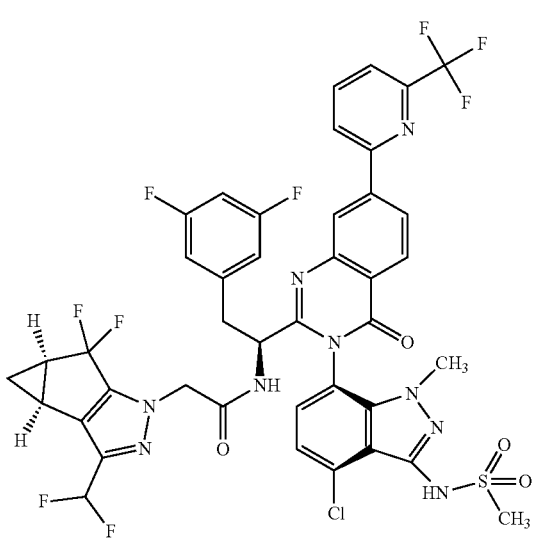

The title compound was prepared according to General Procedure D using 2-chloro-6-(trifluoromethyl)pyridine as the coupling partner. The experiment afforded the title compound, N—((S)-1-((3P)-3-(4-chloro-1-methyl-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=948.4 (M−H). 1H NMR (METHANOL-d4, 500 MHz) Shift 8.66 (s, 1H), 8.4-8.4 (m, 3H), 8.22 (t, 1H, J=7.9 Hz), 7.88 (d, 1H, J=7.7 Hz), 7.28 (br d, 1H, J=8.0 Hz), 7.20 (d, 1H, J=7.7 Hz), 6.7-6.8 (m, 1H), 6.61 (dd, 2H, J=2.2, 8.2 Hz), 6.67 (br t, 2H, J=54.7 Hz), 4.5-4.6 (m, 2H), 3.61 (s, 3H), 3.4-3.5 (m, 1H), 3.2-3.2 (m, 3H), 3.1-3.2 (m, 1H), 2.41 (br dd, 2H, J=3.7, 7.3 Hz), 1.34 (br d, 1H, J=5.4 Hz), 0.99 (br dd, 1H, J=1.9, 3.7 Hz)

The title compound was prepared according to General Procedure D using 5-bromo-4-ethylpyrimidine as the coupling partner. The experiment afforded the title compound, N—((S)-1-((3P)-3-(4-chloro-1-methyl-3-(methylsulfonamido)-1H-indazol-7-yl)-7-(4-ethylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.32 min.; observed ion=911.4 (M+H). 1H NMR (METHANOL-d4, 500 MHz) Shift 9.16 (s, 1H), 8.70 (s, 1H), 8.41 (br d, 1H, J=8.3 Hz), 7.90 (s, 1H), 7.69 (br d, 1H, J=7.7 Hz), 7.29 (br s, 1H), 7.2-7.3 (m, 1H), 6.6-6.8 (m, 4H), 4.52 (br s, 2H), 3.62 (s, 3H), 3.4-3.5 (m, 1H), 3.23 (br s, 3H), 3.1-3.1 (m, 1H), 2.89 (br d, 2H, J=7.7 Hz), 2.4-2.4 (m, 2H), 1.34 (br d, 1H, J=6.0 Hz), 1.28 (br t, 4H, J=7.5 Hz), 1.0-1.0 (m, 1H)

173

Preparation of Example 61: N—((S)-1-((3P)-3-(4-chloro-1-methyl-3-(methylsulfonamido)-1H-indazol-7-yl)-7-(3-cyclopropylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

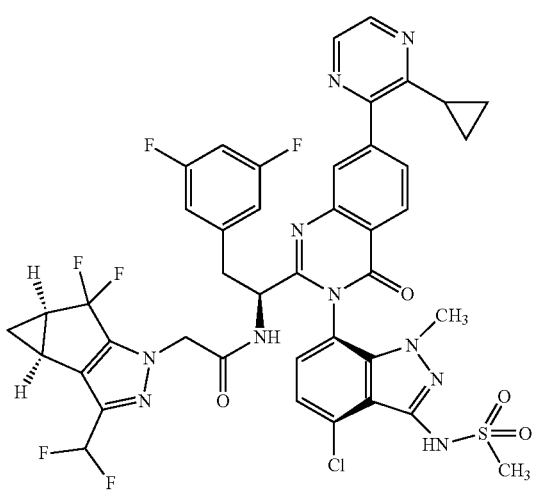

174

Preparation of Example 62: N—((S)-1-((3P)-3-(4-chloro-1-methyl-3-(methylsulfonamido)-1H-indazol-7-yl)-7-(6-ethyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

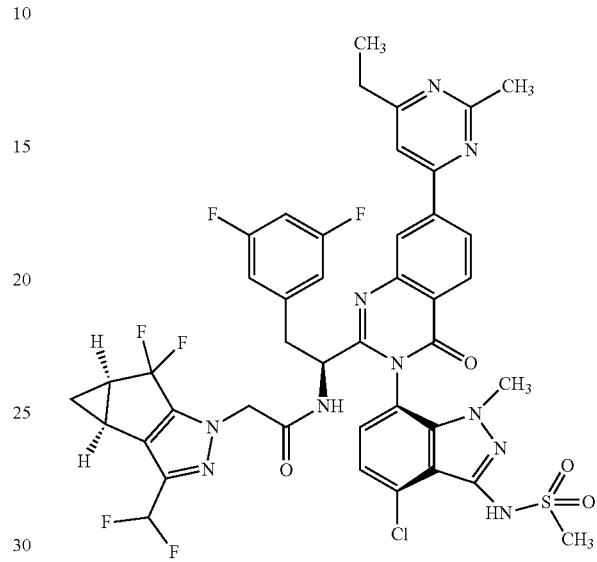

The title compound was prepared according to General Procedure D using 2-chloro-3-cyclopropylpyrazine as the coupling partner. The experiment afforded the title compound, N—((S)-1-((3P)-3-(4-chloro-1-methyl-3-(methylsulfonamido)-1H-indazol-7-yl)-7-(3-cyclopropylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.44 min.; observed ion=923.3 (M+H). 1H NMR (METHANOL-d4, 500 MHz) Shift 8.5-8.6 (m, 1H), 8.47 (d, 1H, J=2.4 Hz), 8.42 (d, 1H, J=8.1 Hz), 8.18 (d, 1H, J=1.8 Hz), 7.9-8.0 (m, 1H), 7.28 (d, 1H, J=7.7 Hz), 7.21 (d, 1H, J=7.7 Hz), 6.7-6.8 (m, 1H), 6.61 (dd, 2H, J=2.4, 8.0 Hz), 6.66 (t, 1H, J=54.8 Hz), 4.8-4.9 (m, 1H), 4.53 (d, 2H, J=4.2 Hz), 3.62 (s, 3H), 3.4-3.5 (m, 1H), 3.22 (s, 3H), 3.09 (dd, 1H, J=9.2, 14.0 Hz), 2.40 (br dd, 2H, J=4.3, 7.3 Hz), 2.24 (s, 1H), 1.34 (br d, 1H, J=5.7 Hz), 1.25 (qd, 2H, J=3.2, 4.7 Hz), 1.0-1.1 (m, 2H), 0.9-1.0 (m, 1H)

The title compound was prepared according to General Procedure D using 4-chloro-6-ethyl-2-methylpyrimidine as the coupling partner. The experiment afforded the title compound, N—((S)-1-((3P)-3-(4-chloro-1-methyl-3-(methylsulfonamido)-1H-indazol-7-yl)-7-(6-ethyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.43 min.; observed ion=925.4 (M+H). 1H NMR (METHANOL-d4, 500 MHz) δ 8.65 (s, 1H), 8.4-8.4 (m, 2H), 7.87 (s, 1H), 7.28 (d, 1H, J=7.5 Hz), 7.21 (d, 1H, J=7.7 Hz), 6.6-6.8 (m, 4H), 4.52 (d, 2H, J=3.3 Hz), 3.61 (s, 3H), 3.48 (br dd, 3H, J=4.9, 14.2 Hz), 3.23 (s, 2H), 3.0-3.1 (m, 1H), 2.9-2.9 (m, 2H), 2.79 (s, 3H), 2.4-2.5 (m, 2H), 1.40 (t, 4H, J=7.6 Hz), 0.9-1.0 (m, 1H)

175

Preparation of Example 63: N—((S)-1-((3P)-3-(4-chloro-1-methyl-3-(methylsulfonamido)-1H-indazol-7-yl)-7-(2-methyl-6-(trifluoromethyl)pyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

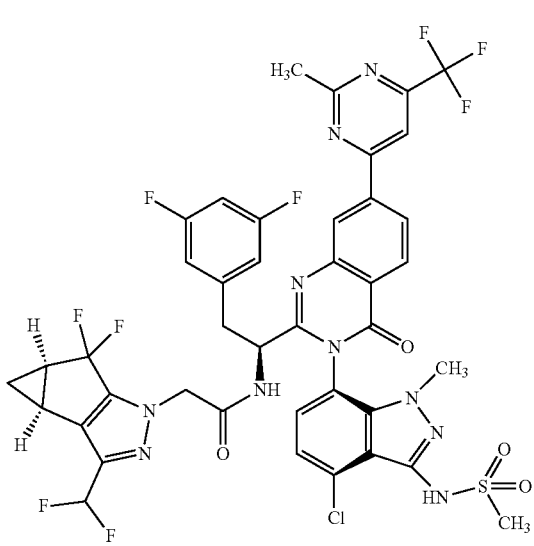

The title compound was prepared according to General Procedure D using 4-chloro-2-methyl-6-(trifluoromethyl)pyrimidine as the coupling partner. The experiment afforded the title compound, N—((S)-1-((3P)-3-(4-chloro-1-methyl-3-(methylsulfonamido)-1H-indazol-7-yl)-7-(2-methyl-6-(trifluoromethyl)pyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=963.3 (M−H). 1H NMR (METHANOL-d4, 500 MHz) Shift 8.75 (s, 1H), 8.4-8.5 (m, 2H), 8.36 (s, 1H), 7.28 (br d, 1H, J=8.0 Hz), 7.21 (d, 1H, J=8.0 Hz), 6.6-6.8 (m, 4H), 4.52 (d, 2H, J=4.2 Hz), 3.60 (s, 3H), 3.48 (dd, 1H, J=4.9, 14.2 Hz), 3.26 (br s, 1H), 3.22 (s, 3H), 3.11 (dd, 1H, J=9.2, 14.3 Hz), 2.92 (s, 3H), 2.42 (br dd, 2H, J=4.0, 8.2 Hz), 1.3-1.4 (m, 1H), 1.0-1.0 (m, 1H)

176

Preparation of Example 64: N—((S)-1-((3P)-3-(4-chloro-1-methyl-3-(methylsulfonamido)-1H-indazol-7-yl)-7-(5-fluoro-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

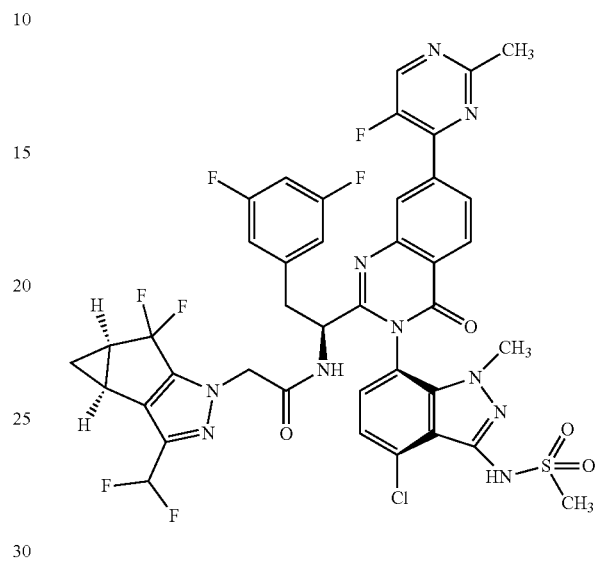

The title compound was prepared according to General Procedure D using 4-chloro-5-fluoro-2-methylpyrimidine as the coupling partner. The experiment afforded the title compound, N—((S)-1-((3P)-3-(4-chloro-1-methyl-3-(methylsulfonamido)-1H-indazol-7-yl)-7-(5-fluoro-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.39 min.; observed ion=913.4 (M−H). 1H NMR (METHANOL-d4, 500 MHz) Shift 8.78 (d, 1H, J=3.3 Hz), 8.59 (s, 1H), 8.4-8.4 (m, 1H), 8.35 (d, 1H, J=8.3 Hz), 7.30 (d, 1H, J=7.7 Hz), 7.23 (d, 1H, J=7.7 Hz), 6.7-6.8 (m, 1H), 6.67 (br t, 1H, J=54.7 Hz), 6.61 (dd, 2H, J=2.2, 8.2 Hz), 4.8-4.8 (m, 1H), 4.52 (d, 2H, J=5.7 Hz), 3.6-3.6 (m, 3H), 3.48 (dd, 1H, J=4.8, 14.0 Hz), 3.2-3.3 (m, 3H), 3.11 (dd, 1H, J=9.4, 14.2 Hz), 2.81 (d, 3H, J=0.9 Hz), 2.41 (br dd, 2H, J=3.9, 7.5 Hz), 1.34 (br d, 1H, J=5.7 Hz), 1.0-1.0 (m, 1H)

Preparation of Example 65: N—((S)-1-((3P)-3-(4-chloro-1-methyl-3-(methylsulfonamido)-1H-indazol-7-yl)-4-oxo-7-(2,5,6-trimethylpyrimidin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 66: N—((S)-1-((3P)-3-(4-chloro-1-methyl-3-(methylsulfonamido)-1H-indazol-7-yl)-7-(6-isopropyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

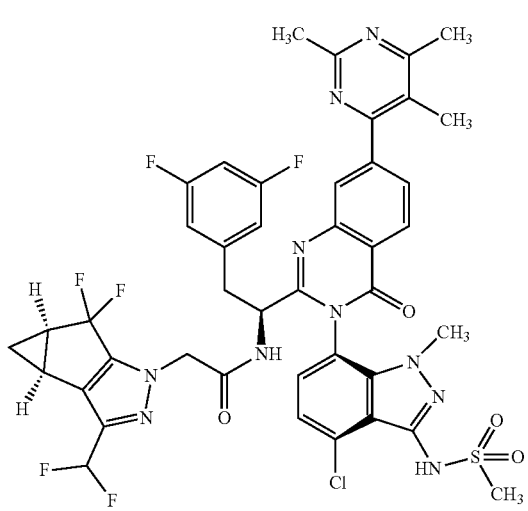

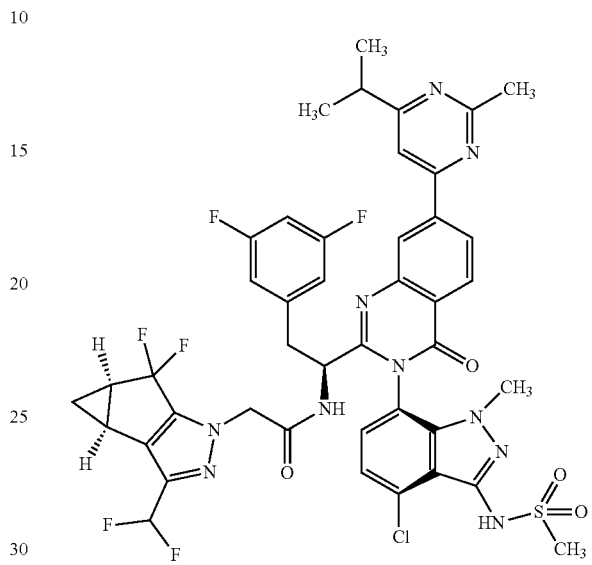

The title compound was prepared according to General Procedure D using 4-chloro-2,5,6-trimethylpyrimidine as the coupling partner. The experiment afforded the title compound, N—((S)-1-((3P)-3-(4-chloro-1-methyl-3-(methylsulfonamido)-1H-indazol-7-yl)-4-oxo-7-(2,5,6-trimethylpyrimidin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.32 min.; observed ion=925.4 (M+H). 1H NMR (METHANOL-d4, 500 MHz) Shift 8.40 (d, 1H, J=7.9 Hz), 8.00 (s, 1H), 7.77 (dd, 1H, J=1.5, 8.0 Hz), 7.30 (d, 1H, J=7.7 Hz), 7.21 (d, 1H, J=7.7 Hz), 6.77 (br d, 1H, J=2.4 Hz), 6.67 (br t, 1H, J=54.7 Hz), 6.6-6.6 (m, 2H), 4.51 (d, 2H, J=2.7 Hz), 3.62 (s, 3H), 3.4-3.5 (m, 2H), 3.2-3.2 (m, 3H), 3.1-3.1 (m, 1H), 2.69 (s, 3H), 2.6-2.6 (m, 3H), 2.40 (br d, 2H, J=3.9 Hz), 2.33 (s, 3H), 1.33 (s, 1H), 0.98 (br d, 1H, J=3.3 Hz)

The title compound was prepared according to General Procedure D using 4-chloro-6-isopropyl-2-methylpyrimidine as the coupling partner. The experiment afforded the title compound, N—((S)-1-((3P)-3-(4-chloro-1-methyl-3-(methylsulfonamido)-1H-indazol-7-yl)-7-(6-isopropyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=939.4 (M+H). 1H NMR (METHANOL-d4, 500 MHz) Shift 8.63 (s, 1H), 8.4-8.4 (m, 2H), 7.84 (s, 1H), 7.29 (d, 1H, J=7.7 Hz), 7.21 (d, 1H, J=7.8 Hz), 6.6-6.8 (m, 4H), 4.8-4.8 (m, 1H), 4.52 (d, 2H, J=3.6 Hz), 3.61 (s, 3H), 3.48 (dd, 2H, J=4.9, 14.2 Hz), 3.2-3.2 (m, 3H), 3.1-3.1 (m, 1H), 2.80 (s, 3H), 2.42 (br dd, 2H, J=4.3, 8.2 Hz), 1.40 (d, 6H, J=6.9 Hz), 1.3-1.4 (m, 1H), 0.99 (br dd, 1H, J=1.9, 3.4 Hz)

Preparation of Example 67: N—((S)-1-((3P)-3-(4-chloro-1-methyl-3-(methylsulfonamido)-1H-indazol-7-yl)-7-(2-isopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Preparation of Example 68: N—((S)-1-((3P)-3-(4-chloro-1-methyl-3-(methylsulfonamido)-1H-indazol-7-yl)-7-(2,6-diethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

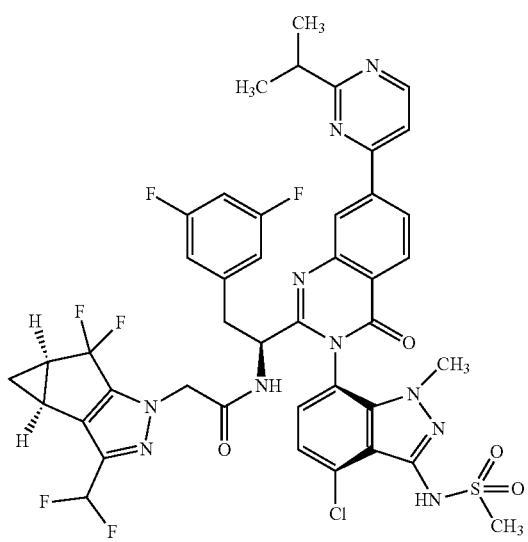

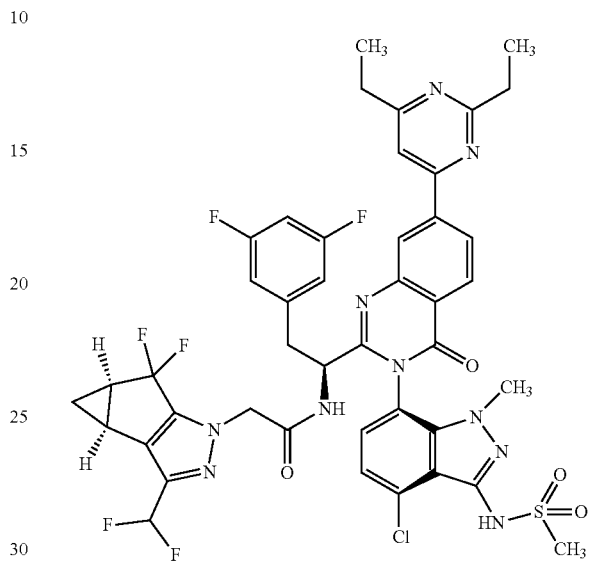

The title compound was prepared according to General Procedure D using 4-chloro-2-isopropylpyrimidine as the coupling partner. The experiment afforded the title compound, N—((S)-1-((3P)-3-(4-chloro-1-methyl-3-(methylsulfonamido)-1H-indazol-7-yl)-7-(2-isopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.47 min.; observed ion=925.4 (M+H). 1H NMR (METHANOL-d4, 500 MHz) Shift 8.86 (d, 1H, J=5.4 Hz), 8.74 (t, 1H, J=1.2 Hz), 8.42 (d, 2H, J=1.2 Hz), 7.99 (d, 1H, J=5.4 Hz), 7.3-7.3 (m, 1H), 7.22 (d, 1H, J=7.7 Hz), 6.6-6.8 (m, 4H), 4.8-4.8 (m, 1H), 4.53 (d, 2H, J=6.0 Hz), 3.61 (s, 3H), 3.4-3.5 (m, 2H), 3.2-3.2 (m, 3H), 3.12 (dd, 1H, J=9.4, 14.2 Hz), 2.4-2.4 (m, 2H), 1.46 (d, 6H, J=6.9 Hz), 1.33 (s, 1H), 1.0-1.0 (m, 1H)

The title compound was prepared according to General Procedure D using 4-chloro-2,6-diethylpyrimidine as the coupling partner. The experiment afforded the title compound, N—((S)-1-((3P)-3-(4-chloro-1-methyl-3-(methylsulfonamido)-1H-indazol-7-yl)-7-(2,6-diethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=939.5 (M+H). 1H NMR (METHANOL-d4, 500 MHz) Shift 8.7-8.7 (m, 1H), 8.4-8.4 (m, 2H), 7.87 (s, 1H), 7.29 (d, 1H, J=7.7 Hz), 7.21 (d, 1H, J=8.0 Hz), 6.6-6.8 (m, 4H), 4.53 (d, 2H, J=5.1 Hz), 3.61 (s, 3H), 3.48 (br dd, 2H, J=4.9, 14.2 Hz), 3.2-3.2 (m, 3H), 3.0-3.1 (m, 3H), 2.91 (q, 2H, J=7.5 Hz), 2.41 (br dd, 2H, J=4.0, 7.9 Hz), 1.3-1.5 (m, 7H), 0.99 (br dd, 1H, J=2.1, 3.6 Hz)

Preparation of Example 69: N—((S)-1-((3P)-3-(4-chloro-1-methyl-3-(methylsulfonamido)-1H-indazol-7-yl)-7-(6-ethoxy-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

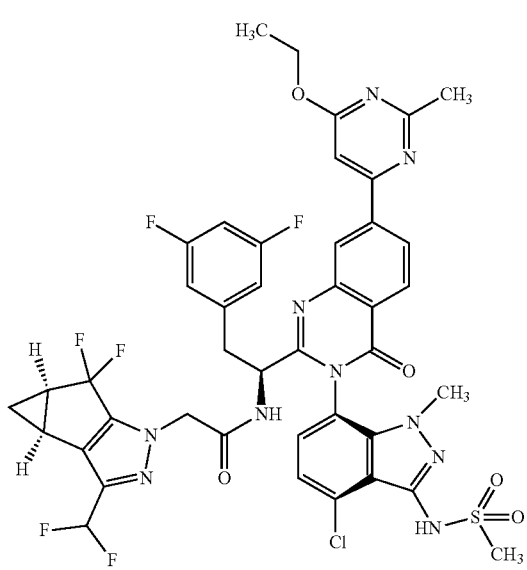

The title compound was prepared according to General Procedure D using 4-chloro-6-ethoxy-2-methylpyrimidine as the coupling partner. The experiment afforded the title compound, N—((S)-1-((3P)-3-(4-chloro-1-methyl-3-(methylsulfonamido)-1H-indazol-7-yl)-7-(6-ethoxy-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.53 min.; observed ion=941.4 (M+H). 1H NMR (METHANOL-d4, 500 MHz) Shift 8.55 (d, 1H, J=1.2 Hz), 8.4-8.4 (m, 1H), 8.2-8.3 (m, 1H), 7.28 (br d, 1H, J=7.7 Hz), 7.26 (s, 1H), 7.19 (d, 1H, J=8.0 Hz), 6.6-6.8 (m, 4H), 4.9-4.9 (m, 1H), 4.7-4.8 (m, 2H), 4.5-4.5 (m, 3H), 3.6-3.7 (m, 3H), 3.48 (br d, 1H, J=19.4 Hz), 3.3-3.4 (m, 1H), 3.2-3.2 (m, 3H), 3.10 (s, 1H), 2.70 (s, 2H), 2.42 (ddd, 2H, J=2.2, 3.9, 5.8 Hz), 1.45 (t, 2H, J=7.2 Hz), 1.34 (s, 1H), 0.9-1.0 (m, 1H)

Preparation of Example 70: N-((1S)-1-(7-(2-(sec-butyl)pyrimidin-4-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

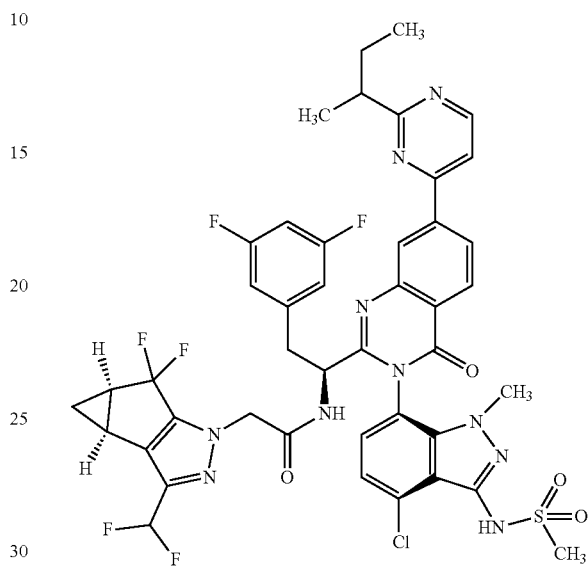

The title compound was prepared according to General Procedure D using 2-(sec-butyl)-4-chloropyrimidine as the coupling partner. The experiment afforded the title compound, N-((1S)-1-(7-(2-(sec-butyl)pyrimidin-4-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.52 min.; observed ion=939.4 (M+H). 1H NMR (METHANOL-d4, 500 MHz) Shift 8.86 (d, 1H, J=5.4 Hz), 8.7-8.7 (m, 1H), 8.42 (t, 2H, J=1.3 Hz), 7.99 (d, 1H, J=5.4 Hz), 7.29 (d, 1H, J=7.7 Hz), 7.22 (d, 1H, J=7.5 Hz), 6.7-6.8 (m, 1H), 6.61 (dd, 2H, J=2.1, 8.0 Hz), 6.67 (br t, 1H, J=54.8 Hz), 4.9-4.9 (m, 1H), 4.54 (d, 2H, J=6.9 Hz), 3.6-3.6 (m, 3H), 3.46 (d, 1H, J=4.8 Hz), 3.2-3.2 (m, 3H), 3.1-3.2 (m, 2H), 2.41 (br dd, 2H, J=3.9, 7.5 Hz), 2.01 (s, 1H), 1.79 (s, 1H), 1.43 (d, 3H, J=7.2 Hz), 1.3-1.4 (m, 1H), 0.9-1.0 (m, 4H)

183

Preparation of Example 71: N—((S)-1-((3P)-3-(4-chloro-1-methyl-3-(methylsulfonamido)-1H-indazol-7-yl)-7-(2-ethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

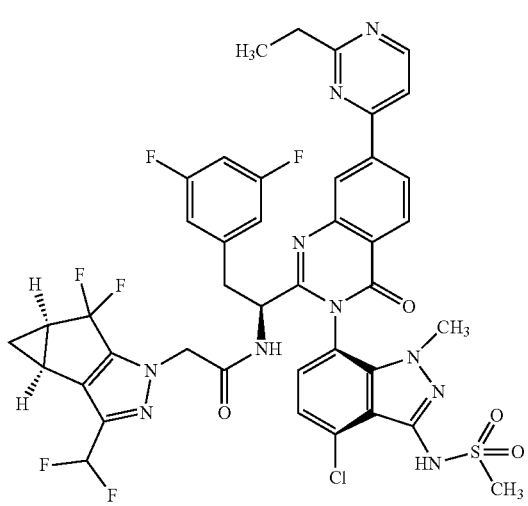

The title compound was prepared according to General Procedure D using 4-chloro-2-ethylpyrimidine as the coupling partner. The experiment afforded the title compound, N—((S)-1-((3P)-3-(4-chloro-1-methyl-3-(methylsulfonamido)-1H-indazol-7-yl)-7-(2-ethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.4 min.; observed ion=911.4 (M+H). 1H NMR (METHANOL-d4, 500 MHz) Shift 8.85 (d, 1H, J=5.1 Hz), 8.71 (s, 1H), 8.42 (s, 2H), 8.00 (d, 1H, J=5.1 Hz), 7.29 (br d, 1H, J=7.7 Hz), 7.21 (br d, 1H, J=7.7 Hz), 6.6-6.8 (m, 4H), 4.53 (br d, 2H, J=4.2 Hz), 3.61 (s, 3H), 3.46 (br s, 1H), 3.2-3.2 (m, 3H), 3.1-3.2 (m, 4H), 2.4-2.4 (m, 2H), 1.47 (t, 3H, J=7.7 Hz), 1.34 (br d, 1H, J=6.0 Hz), 0.99 (br s, 1H)

184

Preparation of Example 72: N—((S)-1-(7-(2-(tert-butyl)pyrimidin-4-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

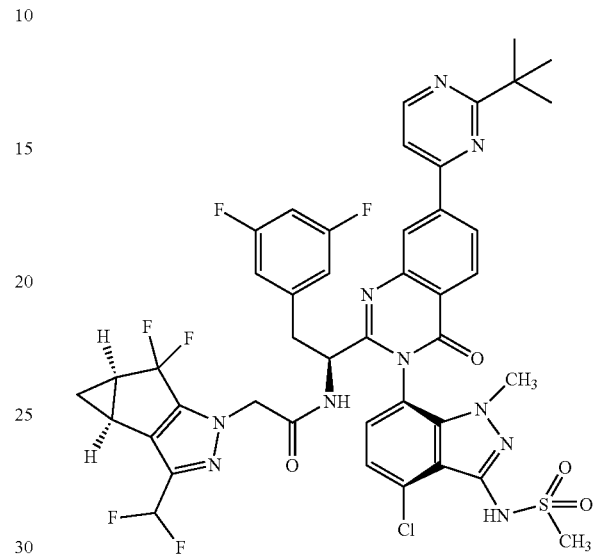

The title compound was prepared according to General Procedure D using 2-(tert-butyl)-4-chloropyrimidine as the coupling partner. The experiment afforded the title compound, N—((S)-1-(7-(2-(tert-butyl)pyrimidin-4-yl)-(3P)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.56 min.; observed ion=939.4 (M+H). 1H NMR (METHANOL-d4, 500 MHz) Shift 8.87 (d, 1H, J=5.4 Hz), 8.8-8.8 (m, 1H), 8.4-8.4 (m, 2H), 7.96 (d, 1H, J=5.4 Hz), 7.2-7.3 (m, 1H), 7.21 (d, 1H, J=8.0 Hz), 6.6-6.8 (m, 4H), 4.5-4.6 (m, 2H), 3.60 (s, 3H), 3.48 (dd, 1H, J=4.8, 14.0 Hz), 3.3-3.4 (m, 1H), 3.22 (s, 3H), 3.12 (dd, 1H, J=9.4, 14.2 Hz), 2.4-2.4 (m, 2H), 1.5-1.5 (m, 9H), 1.3-1.4 (m, 1H), 1.0-1.0 (m, 1H)

Preparation of Example 73: N—((S)-1-((3P)-3-(4-chloro-1-methyl-3-(methylsulfonamido)-1H-indazol-7-yl)-7-(2-cyclopentylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 74: N—((S)-1-((3P)-3-(4-chloro-1-methyl-3-(methylsulfonamido)-1H-indazol-7-yl)-7-(2-(methoxymethyl)pyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

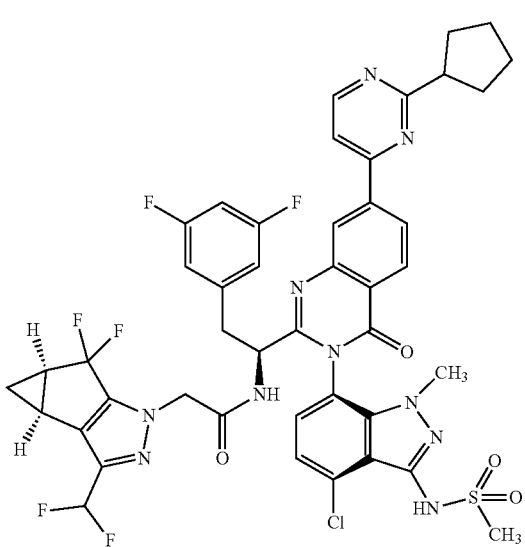

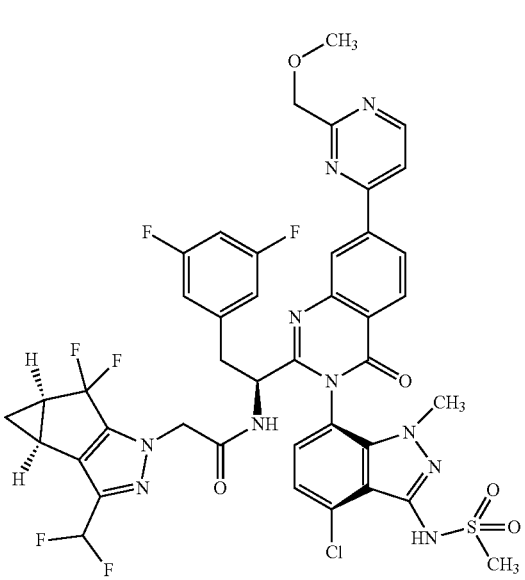

The title compound was prepared according to General Procedure D using 4-chloro-2-cyclopentylpyrimidine as the coupling partner. The experiment afforded the title compound, N—((S)-1-((3P)-3-(4-chloro-1-methyl-3-(methylsulfonamido)-1H-indazol-7-yl)-7-(2-cyclopentylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.55 min.; observed ion=951.5 (M+H). 1H NMR (METHANOL-d4, 500 MHz) Shift 8.84 (d, 1H, J=5.1 Hz), 8.72 (s, 1H), 8.41 (s, 2H), 7.97 (d, 1H, J=5.4 Hz), 7.29 (d, 1H, J=7.7 Hz), 7.22 (d, 1H, J=7.7 Hz), 6.6-6.8 (m, 4H), 4.54 (d, 2H, J=6.6 Hz), 3.61 (s, 3H), 3.4-3.6 (m, 3H), 3.2-3.2 (m, 3H), 3.12 (dd, 1H, J=9.5, 14.0 Hz), 2.41 (br dd, 2H, J=4.0, 7.3 Hz), 2.2-2.2 (m, 2H), 2.0-2.1 (m, 2H), 1.95 (br dd, 2H, J=3.3, 5.1 Hz), 1.8-1.8 (m, 2H), 1.33 (br d, 1H, J=5.7 Hz), 0.98 (br dd, 1H, J=1.8, 3.6 Hz)

The title compound was prepared according to General Procedure D using 4-chloro-2-(methoxymethyl)pyrimidine as the coupling partner. The experiment afforded the title compound, N—((S)-1-((3P)-3-(4-chloro-1-methyl-3-(methylsulfonamido)-1H-indazol-7-yl)-7-(2-(methoxymethyl)pyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.3 min.; observed ion=927.4 (M+H). 1H NMR (METHANOL-d4, 500 MHz) Shift 8.94 (d, 1H, J=5.4 Hz), 8.72 (s, 1H), 8.43 (d, 2H, J=1.2 Hz), 8.10 (d, 1H, J=5.4 Hz), 7.29 (d, 1H, J=8.0 Hz), 7.20 (d, 1H, J=7.9 Hz), 6.6-6.8 (m, 4H), 4.9-4.9 (m, 1H), 4.52 (d, 2H, J=3.3 Hz), 3.6-3.6 (m, 7H), 3.4-3.5 (m, 2H), 3.2-3.2 (m, 3H), 3.11 (dd, 1H, J=9.2, 14.3 Hz), 2.41 (br dd, 2H, J=4.0, 8.2 Hz), 1.33 (s, 1H), 0.98 (br dd, 1H, J=2.1, 3.6 Hz)

Preparation of Example 75: N—((S)-1-((3P)-3-(4-chloro-1-methyl-3-(methylsulfonamido)-1H-indazol-7-yl)-7-(2-(methoxymethyl)-6-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

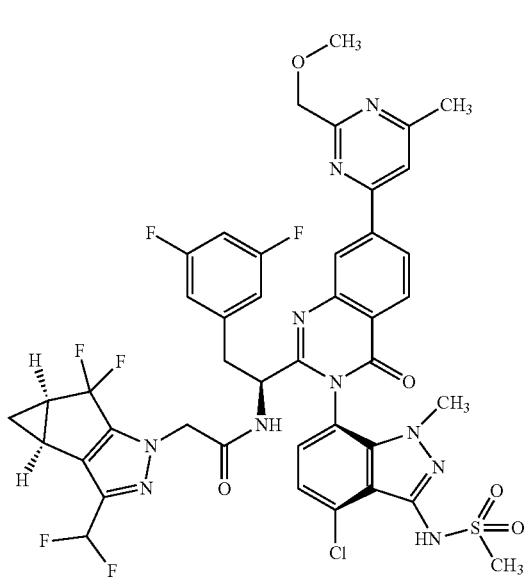

The title compound was prepared according to General Procedure D using 4-chloro-2-(methoxymethyl)-6-methylpyrimidine as the coupling partner. The experiment afforded the title compound, N—((S)-1-((3P)-3-(4-chloro-1-methyl-3-(methylsulfonamido)-1H-indazol-7-yl)-7-(2-(methoxymethyl)-6-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.34 min.; observed ion=941.4 (M+H). 1H NMR (METHANOL-d4,500 MHz) Shift 8.70 (t, 1H, J=1.0 Hz), 8.41 (s, 2H), 7.99 (s, 1H), 7.29 (d, 1H, J=7.7 Hz), 7.20 (d, 1H, J=8.0 Hz), 6.6-6.8 (m, 4H), 4.9-4.9 (m, 1H), 4.75 (s, 2H), 4.52 (d, 2H, J=3.3 Hz), 3.6-3.6 (m, 6H), 3.48 (dd, 1H, J=5.1, 14.0 Hz), 3.2-3.2 (m, 3H), 3.11 (dd, 1H, J=9.1, 13.9 Hz), 2.7-2.7 (m, 3H), 2.41 (br dd, 2H, J=4.2, 8.0 Hz), 1.3-1.4 (m, 1H), 0.99 (br dd, 1H, J=1.9, 3.4 Hz)

Preparation of Example 76: N—((S)-1-((3P)-3-(4-chloro-1-methyl-3-(methylsulfonamido)-1H-indazol-7-yl)-7-(2-cyclobutylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

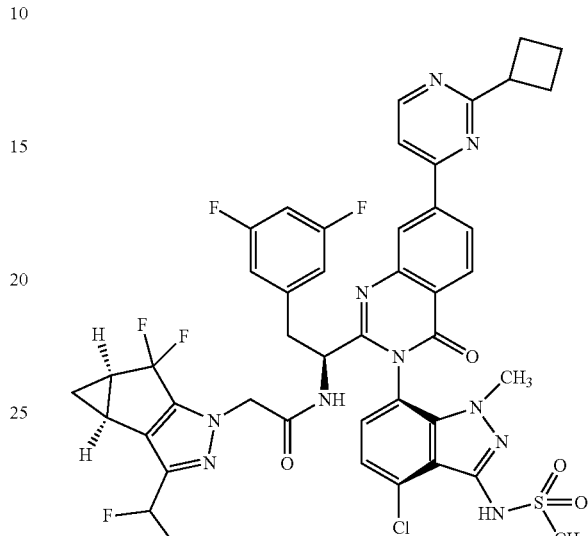

The title compound was prepared according to General Procedure D using 4-chloro-2-cyclobutylpyrimidine as the coupling partner. The experiment afforded the title compound, N—((S)-1-((3P)-3-(4-chloro-1-methyl-3-(methylsulfonamido)-1H-indazol-7-yl)-7-(2-cyclobutylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=937.4 (M+H). 1H NMR (METHANOL-d4, 500 MHz) Shift 8.85 (d, 1H, J=5.4 Hz), 8.76 (s, 1H), 8.43 (d, 2H, J=1.5 Hz), 7.98 (d, 1H, J=5.1 Hz), 7.29 (d, 1H, J=8.0 Hz), 7.22 (d, 1H, J=8.0 Hz), 6.6-6.8 (m, 4H), 4.54 (d, 2H, J=6.6 Hz), 3.9-4.0 (m, 1H), 3.6-3.7 (m, 4H), 3.48 (br dd, 2H, J=4.8, 14.0 Hz), 3.3-3.4 (m, 2H), 3.2-3.2 (m, 3H), 2.4-2.5 (m, 2H), 2.4-2.4 (m, 2H), 2.2-2.2 (m, 1H), 2.06 (br d, 1H, J=1.2 Hz), 1.33 (br d, 1H, J=5.4 Hz), 1.0-1.0 (m, 1H)

189

Preparation of Example 77: N—((S)-1-((3P)-3-(4-chloro-1-methyl-3-(methylsulfonamido)-1H-indazol-7-yl)-7-(2,5-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

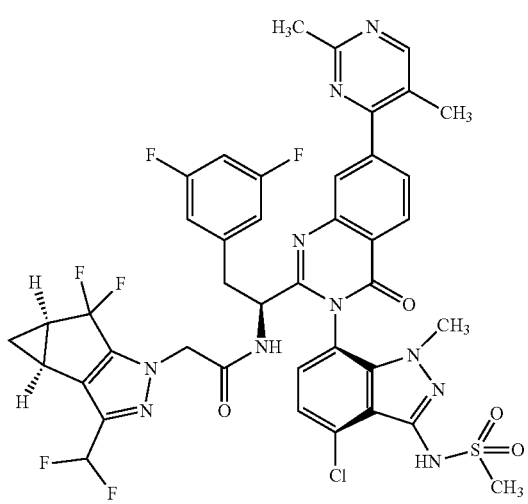

The title compound was prepared according to General Procedure D using 4-chloro-2,5-dimethylpyrimidine as the coupling partner. The experiment afforded the title compound, N—((S)-1-((3P)-3-(4-chloro-1-methyl-3-(methylsulfonamido)-1H-indazol-7-yl)-7-(2,5-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.32 min.; observed ion=911.4 (M+H). 1H NMR (METHANOL-d4, 500 MHz) Shift 8.70 (s, 1H), 8.42 (d, 1H, J=8.1 Hz), 8.08 (d, 1H, J=1.5 Hz), 7.87 (dd, 1H, J=1.6, 8.2 Hz), 7.29 (d, 1H, J=7.7 Hz), 7.21 (d, 1H, J=7.7 Hz), 6.7-6.8 (m, 1H), 6.67 (br t, 1H, J=54.7 Hz), 6.61 (dd, 2H, J=2.1, 8.0 Hz), 4.9-4.9 (m, 1H), 4.52 (d, 2H, J=3.6 Hz), 3.62 (s, 3H), 3.47 (dd, 1H, J=5.1, 14.0 Hz), 3.2-3.2 (m, 3H), 3.09 (dd, 1H, J=9.2, 14.0 Hz), 2.75 (s, 3H), 2.4-2.4 (m, 5H), 1.3-1.4 (m, 1H), 1.0-1.0 (m, 1H)

190

Preparation of Example 78: N—((S)-1-((3P)-3-(4-chloro-1-methyl-3-(methylsulfonamido)-1H-indazol-7-yl)-7-(2-cyclopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

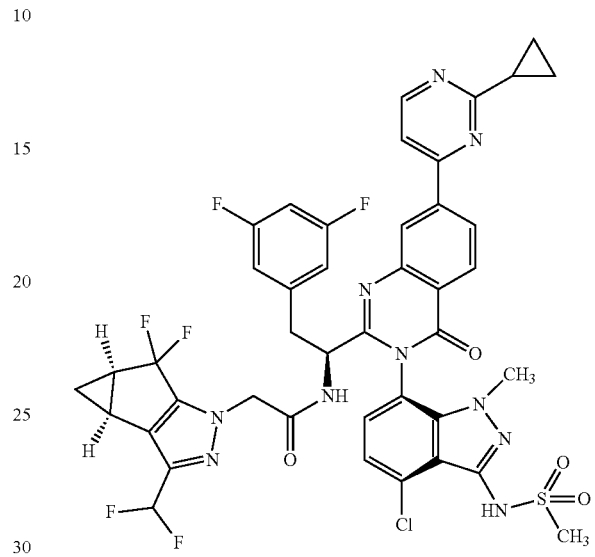

The title compound was prepared according to General Procedure D using 4-chloro-2-cyclopropylpyrimidine as the coupling partner. The experiment afforded the title compound, N—((S)-1-((3P)-3-(4-chloro-1-methyl-3-(methylsulfonamido)-1H-indazol-7-yl)-7-(2-cyclopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.43 min.; observed ion=923.6 (M+H). 1H NMR (METHANOL-d4, 500 MHz) Shift 8.75 (d, 1H, J=5.4 Hz), 8.66 (s, 1H), 8.3-8.4 (m, 2H), 7.90 (d, 1H, J=5.4 Hz), 7.3-7.3 (m, 1H), 7.21 (d, 1H, J=7.7 Hz), 6.6-6.8 (m, 4H), 4.8-4.9 (m, 1H), 4.53 (d, 2H, J=6.0 Hz), 3.6-3.6 (m, 3H), 3.5-3.5 (m, 1H), 3.3-3.4 (m, 1H), 3.2-3.2 (m, 3H), 2.37 (s, 3H), 1.2-1.4 (m, 3H), 1.1-1.2 (m, 2H), 1.0-1.0 (m, 1H)

Preparation of Example 79: N—((S)-1-((3P)-3-(4-chloro-1-methyl-3-(methylsulfonamido)-1H-indazol-7-yl)-7-(6-ethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

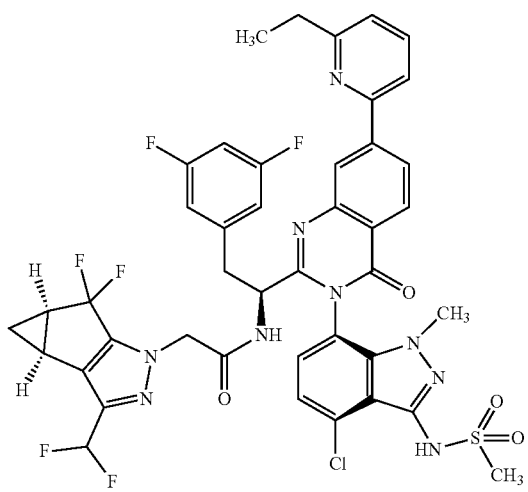

Alternate Preparation of N-(7-amino-4-chloro-1-methyl-H-indazol-3-yl)-N-(4-methoxybenzyl)methanesulfonamide

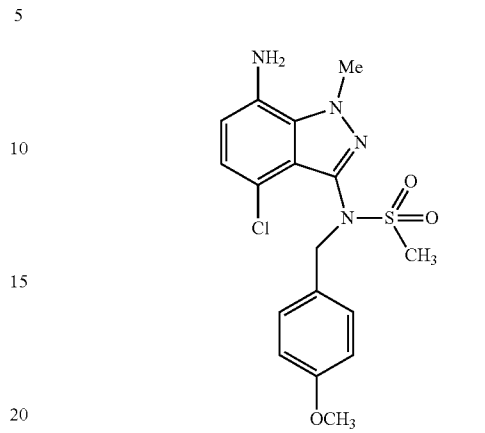

Synthesis Scheme:

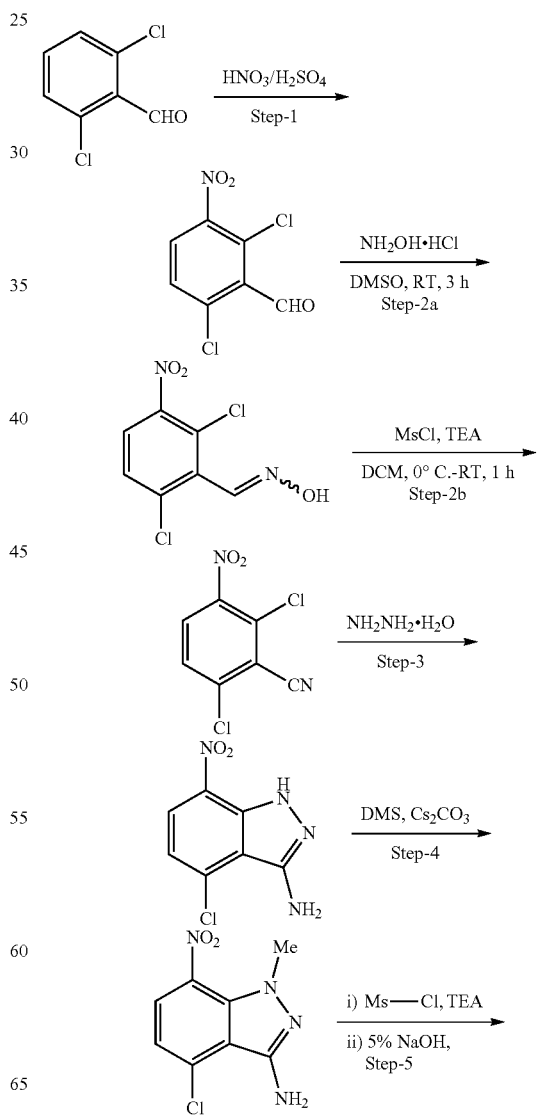

The title compound was prepared according to General Procedure D using 2-bromo-6-ethylpyridine as the coupling partner. The experiment afforded the title compound, N—((S)-1-((3P)-3-(4-chloro-1-methyl-3-(methylsulfonamido)-1H-indazol-7-yl)-7-(6-ethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=910.4 (M+H). 1H NMR (METHANOL-d4, 500 MHz) Shift 8.53 (d, 1H, J=1.5 Hz), 8.37 (d, 1H, J=8.2 Hz), 8.29 (dd, 1H, J=1.8, 8.3 Hz), 7.9-7.9 (m, 2H), 7.36 (dd, 1H, J=2.2, 6.4 Hz), 7.28 (d, 1H, J=7.7 Hz), 7.18 (d, 1H, J=8.0 Hz), 6.7-6.8 (m, 1H), 6.68 (br t, 1H, J=54.7 Hz), 6.61 (dd, 2H, J=2.2, 8.2 Hz), 4.9-4.9 (m, 1H), 4.53 (d, 2H, J=4.2 Hz), 3.61 (s, 3H), 3.4-3.5 (m, 1H), 3.2-3.2 (m, 3H), 3.10 (dd, 1H, J=9.2, 14.0 Hz), 2.95 (q, 2H, J=7.5 Hz), 2.41 (br dd, 2H, J=4.0, 7.6 Hz), 1.41 (t, 3H, J=7.6 Hz), 1.34 (br d, 1H, J=5.7 Hz), 1.0-1.0 (m, 1H)

-continued

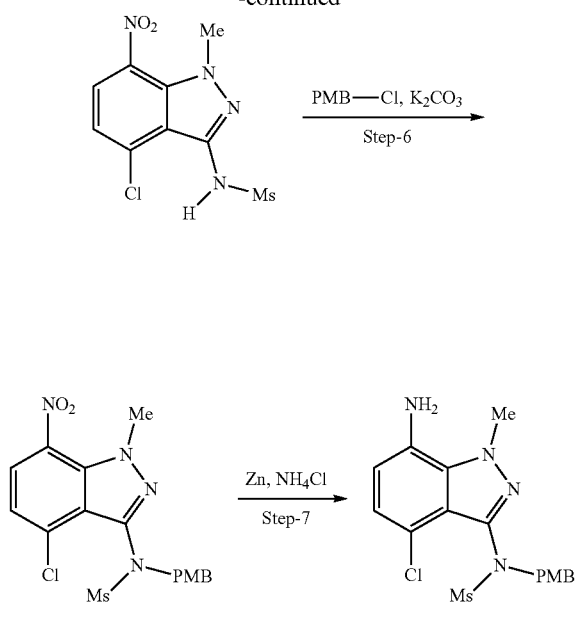

Step 1: Preparation of 2,6-dichloro-3-nitrobenzaldehyde

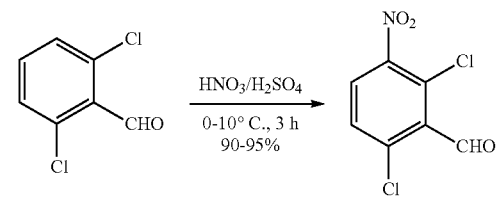 [SMILES: O=Cc1c(Cl)cccc1Cl ; "HNO3/H2SO4" ; O=Cc1c(Cl)ccc([N+](=O)[O-])c1Cl]

To a solution of sulfuric acid (H₂SO₄) (5.63 L, 4.5 V) in a round-bottom flask at 0-5° C. was added 2,6-dichlorobenzaldehyde (1.25 kg, 7.10 mol, 1.0 equiv.) in portions at below 15° C. The reaction mass was stirred at 0-5° C. for 30 min. A solution of freshly prepared nitration mixture [Prepared from Conc. H₂SO₄ (0.425 L, 0.34 V) and 70% HNO₃ (0.85 kg, 13.49 mol, 1.30 equiv.) at 0° C.] was added to the above reaction mixture at below 10° C. [Note: Reaction is slightly exothermic (3-6° C.); so that addition is preferred at lower temperature]. The reaction mixture was stirred at 5-10° C. for 2-3 h. After completion of the reaction (monitored by TLC), it was quenched with ice cold water (18.75 L, 15 V) at below 25° C. Then the reaction mass was allowed warm to room temperature and stirred for 2 h. The solids were isolated by filtration and then were washed with water (2.5 L, 2.0 V). Bulk residual water was removed from the solids by maintaining vacuum filtration for 60-90 min. The crude wet solid was initially dried under air atmosphere; then in a hot air oven at 50-55° C. for 10-12 h (until moisture content is not more than 5.0%) to get the dried title product, 2,6-dichloro-3-nitrobenzaldehyde (1.44 kg, 92% yield) as a yellow solid. ¹H NMR (400 MHz, CDCl₃): δ 10.44 (s, 1H), 7.88 (d, J=8.4 Hz, 1H), 7.56 (d, J=8.8 Hz, 1H).

Step 2: Preparation of 2,6-dichloro-3-nitrobenzonitrile

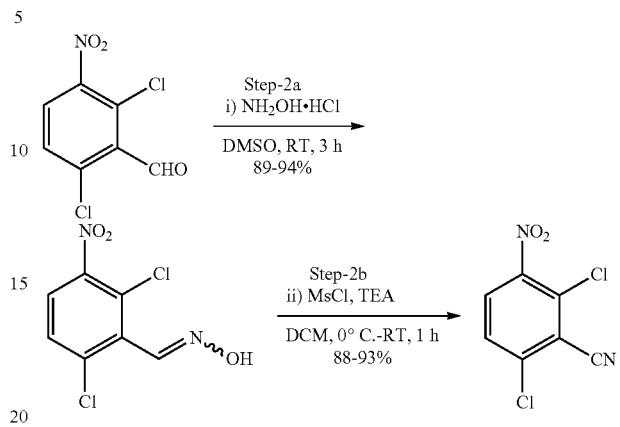

(Step-2a) To a solution of DMSO (5.9 L, 5.0 V)) in a round-bottom flask was added 2,6-dichloro-3-nitrobenzaldehyde (1.17 kg, 5.31 mol, 1.0 equiv.) at room temperature. After being stirred for 30 min at room temperature, hydroxylamine hydrochloride (0.63 kg, 9.04 mol, 1.70 equiv.) was added and the reaction mass was stirred at room temperature for 3 h. After completion of the reaction (monitored by TLC), the reaction mass was quenched by the addition of ice-cold water (18.0 L, 15.0 V) added at a rate sufficient to maintain the temperature below 30° C. (Observation: Solids formed upon water addition). The reaction mass was stirred at room temperature for 60-90 min. The solids were isolated by filtration; washed with water (2.5 L, 2.0 V); followed by washing with a mixture of acetone and hexanes (6.0 L, 1:1 ratio). Bulk residual water was removed from the solids by maintaining vacuum filtration for 60-90 min. The wet solid was initially air dried and then finally dried in a hot air oven at 50-55° C. for 10-12 h (until moisture content was not more than 1.0%) to get the dried target product, 2,6-dichloro-3-nitrobenzaldehyde oxime (1.22 kg, 92% yield) as an off-white solid. The crude product (which contains 10-20% of 2,6-dichloro-3-nitrobenzonitrile) was used directly in the next step without further purification.

(Step-2b) To a stirred solution of the crude oxime (preparation described above, 1.13 kg, 4.80 mol, 1.0 equiv.) in DCM (9.04 L, 8.0 V) at 0-5° C. was added triethylamine ("TEA", 1.02 kg, 10.09 mol, 2.1 equiv.). After being stirred for 5 min, methanesulfonyl chloride (0.60 kg, 5.29 mol, 1.1 equiv.) was added (Observation: An exotherm is noted during the addition) slowly at 15° C. Then the reaction mass was stirred at room temperature for 30-45 min. After completion of the reaction (progress of reaction was monitored by TLC; mobile phase: 20% ethyl acetate in hexanes), the reaction mass was diluted with water (6.78 L, 6.0 V); the organic layer was separated; and the aqueous layer was extracted with DCM (3.4 L, 3.0 V). The combined organic layers were washed with brine (5.65 L, 5.0 V); dried over Na₂SO₄; and concentrated under vacuum. The resulting crude solids were triturated with hexanes (4.50 L, 4.0 V) at room temperature. The wet material was dried in a hot air oven at 50-55° C. for 5-6 h to get the dried product, 2,6-dichloro-3-nitrobenzonitrile (0.95 kg, 91% yield) as a yellow solid. ¹H NMR (400 MHz, CDCl₃): δ 8.07 (d, J=8.8 Hz, 1H), 7.63 (d, J=8.8 Hz, 1H).

Step 3: Preparation of 4-chloro-7-nitro-1H-indazol-3-amine

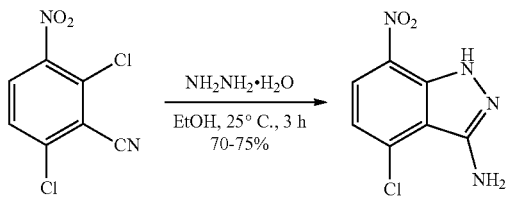 [SMILES: N#Cc1c(Cl)ccc([N+](=O)[O-])c1Cl ; "NH2NH2·H2O" ; Nc1n[nH]c2c([N+](=O)[O-])ccc(Cl)c12]

To a stirred solution of 2,6-dichloro-3-nitrobenzonitrile (750.0 g, 3.45 mol, 1.0 equiv.) in ethanol (7.5 L, 10.0 V) at 15-20° C. was slowly added hydrazine hydrate (519.0 g, 10.36 mol, 3.0 equiv.) while maintaining the reaction mass below 25° C. (Observation: Addition is slightly exothermic and solid formation will begin upon addition). The reaction mixture temperature was slowly raised to room temperature and then the mixture was stirred for 3 h (Observation: the quantity of solids will increase during this time). After completion of the reaction (monitored by TLC), the mixture was diluted with water (7.5 L, 10.0 V) and further stirred for 1 h at room temperature. The solids were isolated via filtration and then were washed with water (2.25 L, 3.0 V). The wet solid was washed with a 1:1 ratio mixture of acetone (1.875 L, 2.5 V) and hexanes (1.875 L, 2.5 V). Bulk residual water was removed from the solids by maintaining vacuum filtration for 60-90 min. The wet solid was finally dried in a hot air oven for 7-8 h at 50° C. (until moisture content reaches below 1.5%) to get the dried product, 4-chloro-7-nitro-1H-indazol-3-amine (549.0 g, 75% yield) as a brick red-colored solid. $^1$H NMR (400 MHz, CDCl$_3$): δ 10.36 (bs, 1H), 8.20 (d, J=8.4 Hz, 1H), 7.07 (d, J=8.40 Hz, 1H), 4.73 (bs, 2H).

Step 4: Preparation of 4-chloro-1-methyl-7-nitro-1H-indazol-3-amine

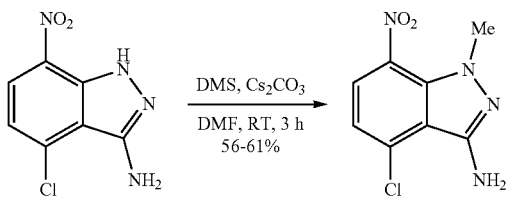

To a stirred solution of 4-chloro-7-nitro-1H-indazol-3-amine (500 g, 0.42 mol, 1.0 equiv.) in DMF (5.0 L, 10.0 V) at 5-10° C. was slowly added cesium carbonate (Cs$_2$CO$_3$) (1.91 kg, 5.88 mol, 2.5 equiv.) while maintaining the reaction mass below 10° C. After being stirred for 5-10 min, dimethyl sulphate (326.3 g, 2.59 mol, 1.1 equiv.) was added while maintaining the reaction mass below 10° C. (Note: Slow addition is preferred for obtaining more favorable regio-selectivity). Then, the reaction temperature was slowly raised to room temperature and stirring was continued an additional 2 h at the same temperature. After completion of the reaction (monitored by TLC), the reaction mass was quenched by the addition of ice-cold water (15.0 L, 30.0 V) and the resulting mixture was then stirred for 6-8 h at room temperature. The solids were isolated via filtration and were then washed with water (1.5 L, 3.0 V). The wet solid was washed with IPA (1.5 L, 3.0 V) followed by hexanes (1.0 L, 2.0 V). Bulk residual water was removed from the solids by maintaining vacuum filtration for 60-90 min. The wet solid was dried in a hot air oven for 7-8 h at 50° C. (until moisture content is below 1.0%). The isolated material, 4-chloro-1-methyl-7-nitro-1H-indazol-3-amine (319.0 g, 60% yield), was used in the next step without further purification. $^1$H NMR (400 MHz, CDCl$_3$): δ 7.97 (d, J=8.32 Hz, 1H), 6.97 (d, J=8.24 Hz, 1H), 4.63 (bs, 2H), 3.96 (s, 3H).

Step 5: Preparation of N-(4-chloro-1-methyl-7-nitro-1H-indazol-3-yl)methanesulfonamide

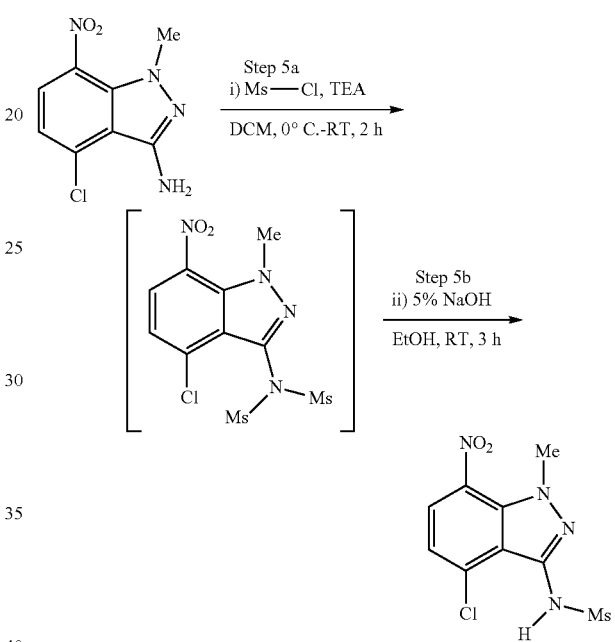

(Step 5a) To a solution of 4-chloro-1-methyl-7-nitro-1H-indazol-3-amine (625.0 g, 2.76 mol, 1.0 equiv.) in DCM (6.25 L, 10.0 V) at 0-5° C. was added triethylamine (TEA) (837.0 g, 8.27 mol, 3.0 equiv.); followed by the addition of 4-dimethylaminopyridine (DMAP) (20.60 g, 0.165 mol, 0.06 equiv.). The reaction mass was stirred for 5-10 min., then methanesulfonyl chloride (MsCl) (790.0 g, 6.89 mol, 2.5 equiv.) added slowly while maintaining the reaction mass below 10° C. The reaction mixture was allowed to warm to room temperature and was then stirred for 1.5-2.0 h. After completion of the reaction (monitored by TLC), the mixture was diluted with water (6.25 L, 10.0 V) and then stirred at room temperature for 15 min. The organic layer was separated, and the aqueous layer was extracted with DCM (6.25 L, 10.0 V). The combined organic layers were washed with brine (1.25 L, 2.0 V), dried over Na$_2$SO$_4$ and concentrated to get the crude solids. The solids were triturated with hexanes (1.25 L, 2.0 V) at room temperature to obtain the intermediate, N-(4-chloro-1-methyl-7-nitro-1H-indazol-3-yl)-N-(methylsulfonyl)methanesulfonamide, which was used directly in the next step.

(ii) To a stirred solution of N-(4-chloro-1-methyl-7-nitro-1H-indazol-3-yl)-N-(methylsulfonyl)methanesulfonamide (prepared above) in ethanol (10.5 L, 20.0 V) at room temperature was added slowly an aq. 5% NaOH solution (4.38 L, 7.0 V) [Note: Slow addition is preferred via dropping funnel]. The reaction mass was stirred at the same temperature for 3 h. After completion of the reaction (monitored by TLC) [Sample preparation for TLC analysis: ~1.0 ml of sample acidified with aq. 2.0 N HCl to reach the pH: 2-3, extract it with ethyl acetate and analyze the organic layer by TLC], the reaction mass was cooled to 0-5° C. and the pH was adjusted to 2-3 by the addition of aq. 2.0 N HCl (3.13 L, 5.0 V) while maintain the reaction temperature below 10° C. [Note: Precipitation occurred upon addition of HCl and increased with stirring]. The reaction mixture was warmed to room temperature and then stirred for 1.5-2.0 h. Solids obtained were isolated via filtration and were then washed with water (1.25 L, 2.0 V); followed by washing with hexanes (1.25 L, 2.0 V). Bulk residual water was removed from the solids by maintaining vacuum filtration for 60-90 min. The wet material was dried in a hot air oven at 50° C. for 6-7 h (Until the moisture content is below 1.0%) to get the dried product, N-(4-chloro-1-methyl-7-nitro-1H-indazol-3-yl)methanesulfonamide (640.0 g, 76%) as a yellow solid. $^1$H NMR (400 MHz, CDCl$_3$): δ 8.05 (d, J=8.32 Hz, 1H), 7.32 (bs, 1H), 7.17 (d, J=8.28 Hz, 1H), 4.15 (s, 3H), 3.45 (s, 3H).

Step 6: Preparation of N-(4-chloro-1-methyl-7-nitro-1H-indazol-3-yl)-N-(4-methoxybenzyl)methanesulfonamide

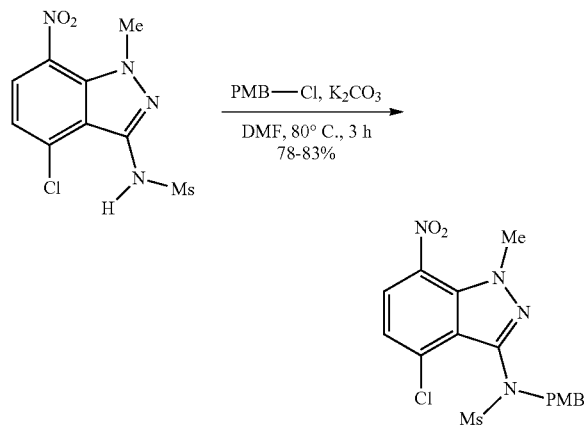

To a mixture of N-(4-chloro-1-methyl-7-nitro-1H-indazol-3-yl)methanesulfonamide (635.0 g, 2.08 mol, 1.0 equiv.) and 1-(chloromethyl)-4-methoxybenzene (359.0 g, 2.30 mol, 1.1 equiv.) in DMF (6.35 L, 10.0 V) at room temperature was added potassium carbonate (374.7 g, 2.70 mol, 1.3 equiv.). The reaction mixture was heated to 80-90° C. and maintained at that temperature for 3 h. After completion of the reaction (monitored by TLC), the mixture was poured into ice cold water (19.05 L, 30.0 V) [Note: Slow quenching with vigorous stirring is preferred to avoid clumping as the product precipitates]. The resulting solids were isolated via filtration and washed with water (1.90 L, 3.0 V); then the solids were washed with hexanes (1.27 L, 2.0 V). Bulk residual water was removed from the solids by maintaining vacuum filtration for 60-90 min. The isolated solid was dissolved in Ethyl acetate (12.7 L, 20.0 V) and charcoal was added (63.5 g). The mixture was heated to 60-70° C. and then stirred for 30-45 min. at that temperature. The mixture was filtered while still hot (40-50° C.) through a pad of Celite and the Celite pad was then extracted with ethyl acetate (3.17 L, 5.0 V). The combined filtrates were concentrated to dryness under reduced pressure at below 50° C. Ethyl acetate (0.635 L, 1.0 V) was added to the solids at room temperature. The resultant solid suspension was stirred for 30 min. The solids were isolated via filtration and then were washed with hexanes (1.27 L, 2.0 V). Residual water was removed from the solids by maintaining vacuum filtration for 45-60 min. to afford the product N-(4-chloro-1-methyl-7-nitro-1H-indazol-3-yl)-N-(4-methoxybenzyl) methane sulfonamide (705.0 g, 80% yield) as a yellow solid. $^1$H NMR (400 MHz, CDCl$_3$): δ 7.99 (d, J=8.24 Hz, 1H), 7.27 (d, J=8.68 Hz, 2H), 7.19 (d, J=8.24 Hz, 1H), 6.80 (d, J=8.44 Hz, 2H), 4.95-4.76 (m, 2H), 4.17 (s, 3H), 3.76 (s, 3H), 3.01 (s, 3H).

Step 7: Preparation of N-(7-Amino-4-chloro-1-methyl-1H-indazol-3-yl)-N-(4-methoxybenzyl)methanesulfonamide

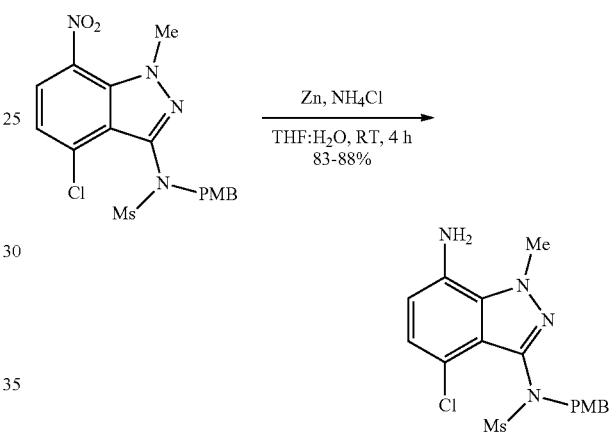

To a stirred suspension of zinc powder (540.0 g, 8.23 mol, 10.0 equiv.) in a mixture of THF (3.50 L, 10.0 V) and water (7.0 L, 20.0 V) at room temperature was added ammonium chloride (NH$_4$Cl) (449.0 g, 8.23 mol, 10.0 equiv.). To the mixture was added N-(4-chloro-1-methyl-7-nitro-1H-indazol-3-yl)-N-(4-methoxybenzyl)methanesulfonamide (350 g, 0.823 mol, 1.0 equiv.) in THF (7.0 L, 20.0 V). The reaction mixture was stirred at room temperature for 3-4 h. After completion of the reaction (monitored by in-process TLC/HPLC), the mixture was diluted with ethyl acetate (3.5 L, 10.0 V) and water (1.12 L, 2.5 V). The mixture was stirred for 15 min. The reaction mass was filtered through a pad of Celite bed washing with ethyl acetate (1.75 L, 5.0 V). The bi-phasic filtrate was collected, and the phases were separated. The aqueous layer was extracted with ethyl acetate (3.50 L, 10.0 V). The combined organic layers were washed with brine (3.50 L, 10 V), dried over Na$_2$SO$_4$, and then concentrated in vacuo to afford a crude solid. To the crude product was added MTBE (3.25 L, 10 V) and the suspension was stirred for 30 min at room temperature. The solids were isolated by filtration. Bulk residual water was removed from the solids by maintaining vacuum filtration for 30-45 min. The wet product was dried in a hot air oven (50° C.) for 2 h to afford the title product, N-(7-amino-4-chloro-1-methyl-1H-indazol-3-yl)-N-(4-methoxybenzyl)methanesulfonamide (276.0 g, 85% yield) as off-white solid. $^1$H NMR (400 MHz, CDCl$_3$): δ 7.29-7.26 (m, 2H), 6.86-6.79 (m, 2H), 6.42 (d, J=7.80 Hz, 1H), 4.99-4.70 (m, 2H), 4.25 (s, 3H), 3.77 (s, 5H), 2.98 (s, 3H).

Alternate Preparation of N-(7-amino-4-chloro-1-(2,2-difluoroethyl)-1H-indazol-3-yl)-N-(4-methoxybenzyl)methanesulfonamide

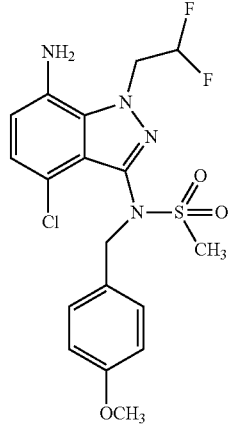 [SMILES: COc1ccc(CN(c2nn(CC(F)F)c3c(N)ccc(Cl)c23)S(C)(=O)=O)cc1]

Synthesis Scheme:

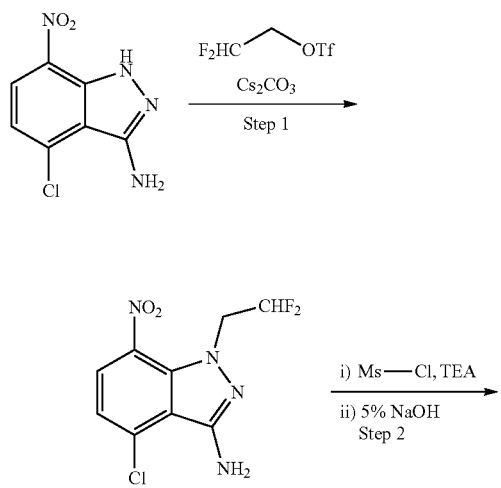

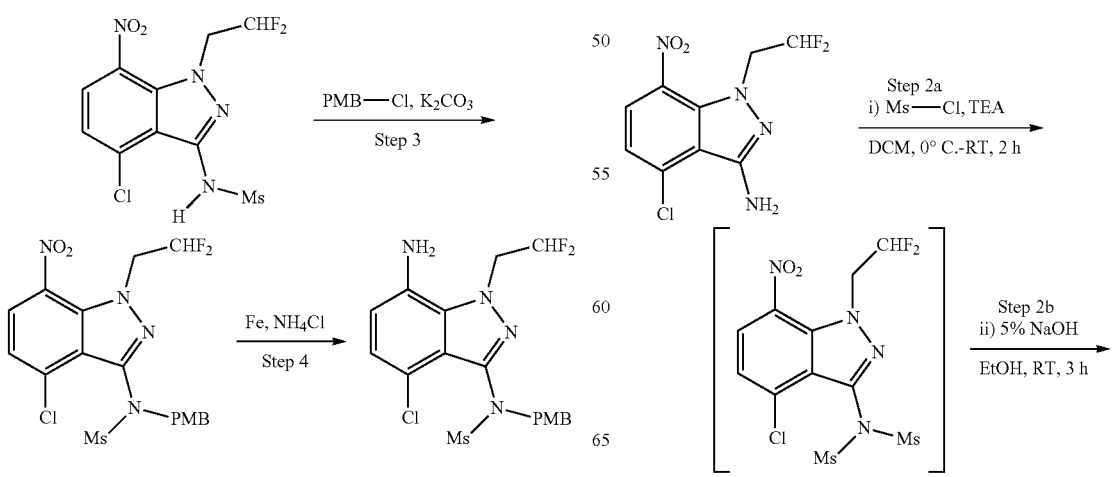

Step 1: Preparation of 4-chloro-1-(2,2-difluoroethyl)-7-nitro-1H-indazol-3-amine

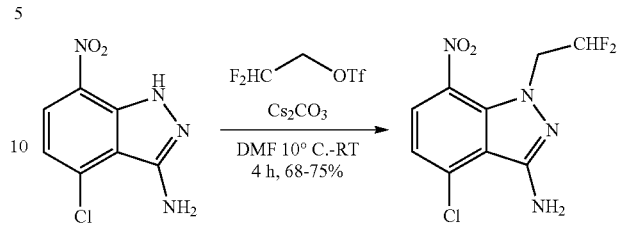

To a stirred solution of 4-chloro-7-nitro-1H-indazol-3-amine (180 g, 0.85 mol, 1.0 equiv.) in DMF (1.8 L, 10.0 V) at 10-15° C. was added cesium carbonate ($Cs_2CO_3$) (551 g, 1.70 mol, 2.0 equiv.) at a rate necessary to maintaining the reaction mass below 20° C. The mixture was stirred for 5-10 min, then to the stirred mixture at 10-15° C. was added 2,2-difluoroethyl trifluoromethanesulfonate (133 mL, 0.93 mol, 1.1 equiv.) at a rate necessary to maintain the reaction mass below 20° C. (Note: Slow addition is preferred to obtain more favorable regio-selectivity). The reaction mass was allowed to slowly warm to room temperature and was then stirred at the same temperature for 3 h. After completion of the reaction (monitored by TLC), the reaction mass was quenched by the addition of ice-cold water (5.4 L, 30.0 V) and the resulting mixture was allowed to warm to room temperature with stirring for 6-8 h. The solids were isolated via filtration and were then washed with water (540 mL, 3.0 V). The wet solid was washed with hexanes (0.9 L, 5.0 V). Bulk residual water was removed from the solids by maintaining vacuum filtration for 60-90 min. The wet solid was dried in a hot air oven for 7-8 h at 50° C. (until the moisture content was below 1.0%). The isolated material, 4-chloro-1-(2,2-difluoroethyl)-7-nitro-1H-indazol-3-amine (160 g, 71% yield), was used in the next step without further purification. $^1$H NMR (400 MHz, $CDCl_3$): δ 8.05 (d, J=8.4 Hz, 1H), 7.07 (d, J=8.4 Hz, 1H), 6.00 (tt, $J_1$=3.9 Hz, $J_2$=7.7 Hz, 1H), 4.76-4.84 (m, 4H).

Step 2: Preparation of N-(4-chloro-1-(2,2-difluoroethyl)-7-nitro-1H-indazol-3-yl)methane sulfonamide -continued

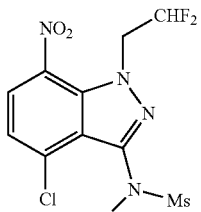

Step 2a: To a solution of 4-chloro-1-(2,2-difluoroethyl)-7-nitro-1H-indazol-3-amine (170.0 g, 0.96 mol, 1.0 equiv.) in DCM (1.7 L, 10.0 V) at 0-5° C. was added triethyl amine (264 mL, 2.88 mol, 3.0 equiv.), followed by 4-dimethylaminopyridine (3.4 g, 0.048 mol, 0.05 equiv.). The reaction mass was stirred for 5-10 min., then methanesulfonyl chloride (120 mL, 2.4 mol, 2.5 equiv.) was added slowly while maintaining the reaction mass below 10° C. The reaction mixture was allowed to warm to room temperature and then was stirred for 1.5-2.0 h. After completion of the reaction (monitored by TLC), the mixture was diluted with water (1.7 L, 10.0 V) and then stirred at room temperature for 15 min. The organic layer was separated, and the aqueous layer was extracted with DCM (1.7 L, 10.0 V). The combined organic layers were washed with 10% brine solution (340 mL, 2.0 V), dried over $Na_2SO_4$ and concentrated to afford the product as a crude solid. The solids were triturated with hexanes (340 mL, 2.0 V) at room temperature to obtain N-(4-chloro-1-(2,2-difluoroethyl)-7-nitro-1H-indazol-3-yl)-N-(methylsulfonyl) methanesulfonamide which was used directly in the next step.

Step 2b: To a stirred solution of N-(4-chloro-1-(2,2-difluoroethyl)-7-nitro-1H-indazol-3-yl)-N-(methylsulfonyl) methanesulfonamide (entirety of material prepared above) in ethanol (1.7 L, 10.0 V) at room temperature was added slowly aq. 5% NaOH solution (1.19 L, 7.0 V) [Note: Slow addition is preferred via dropping funnel]. The reaction mass was stirred at the same temperature for 3 h. After completion of the reaction [Sample preparation for TLC analysis: an aliquot of reaction solution (~1 mL) was acidified with aq. 2.0 N HCl to reach the pH 2-3; then the mixture was extracted with ethyl acetate and organic layer was analyzed by TLC], the reaction mass was cooled to 0-5° C. and the pH was adjusted to 2-3 by the addition of aq. 2.0 N HCl (~850 mL, 5.0 V) at below 10° C. [Note: Precipitation occurred upon addition of HCl and the solids increased gradually with stirring]. The reaction mixture was warmed to room temperature and then stirred for 1.5-2.0 h. Solids obtained were isolated via filtration and were then washed with water (340 mL, 2.0 V); followed by washing with hexanes (340 mL, 2.0 V). Bulk residual water was removed from the solids by maintaining vacuum filtration for 60-90 min. The wet material was dried in a hot air oven at 50° C. for 6-7 h (until the moisture content was below 1.0%) to afford the dried product, N-(4-chloro-1-(2,2-difluoroethyl)-7-nitro-1H-indazol-3-yl)methanesulfonamide (170.0 g, 75%) as a yellow solid. $^1$H NMR (400 MHz, $CDCl_3$): δ 8.15 (d, J=8.3 Hz, 1H), 7.52 (bs, 1H), 7.24 (d, J=8.3 Hz, 1H), 6.04 (tt, $J_1$=3.7 Hz, $J_2$=7.9 Hz, 1H), 5.02 (td, J=3.9 Hz, $J_2$=14.3 Hz, 2H), 3.42 (s, 4H).

Step 3: Preparation of N-(4-chloro-1-(2,2-difluoroethyl)-7-nitro-1H-indazol-3-yl)-N-(4-methoxy benzyl)methanesulfonamide

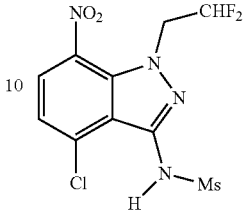

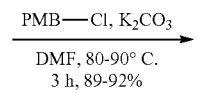

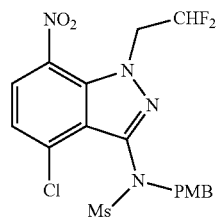

To a mixture of N-(4-chloro-1-(2,2-difluoroethyl)-7-nitro-1H-indazol-3-yl)methane sulfonamide (160.0 g, 0.45 mol, 1.0 equiv.) and 1-(chloromethyl)-4-methoxybenzene (67.6 mL, 0.5 mol, 1.1 equiv.) in DMF (1.6 L, 10.0 V) at room temperature was added potassium carbonate (93.8 g, 0.59 mol, 1.3 equiv.). The reaction mixture was heated to 80-90° C. and maintained at the same temperature for 3 h. After completion of the reaction (monitored by TLC), the mixture was poured into ice cold water (4.8 L, 60.0 V) [Note: Slow quenching with vigorous stirring is preferred to avoid clumping as the product precipitates]. The resulting solids were isolated via filtration and washed with water (480 mL, 3.0 V); then the solids were washed with hexanes (320 mL, 2.0 V). Bulk residual water was removed from the solids by maintaining vacuum filtration for 1-2 h. The isolated solid was dissolved in ethyl acetate (1.6 L, 10.0 V) and charcoal was added (16.0 g). The mixture was heated to 60-70° C. and then stirred for 30-45 min. at that temperature. The mixture was filtered while hot (40-50° C.) through a pad of Celite and the Celite pad was then extracted with ethyl acetate (800 mL, 5.0 V). The combined filtrates were concentrated to dryness under reduced pressure at below 50° C. To the resulting solids at room temperature was added ethyl acetate (160 mL, 1.0 V). The suspension was stirred for 30 min. The solids were isolated via filtration and then were washed with hexanes (320 mL, 2.0 V). Residual water was removed from the solids by maintaining vacuum filtration for 45-60 min. to afford the product N-(4-chloro-1-(2,2-difluoroethyl)-7-nitro-1H-indazol-3-yl)-N-(4-methoxybenzyl)methanesulfonamide (180.0 g, 92% yield) as a yellow solid. $^1$H NMR (400 MHz, $CDCl_3$): δ 8.06 (d, J=8.4 Hz, 1H), 7.52 (bs, 1H), 7.27-7.21 (m, 4H), 6.77 (d, J=8.3 Hz, 2H), 6.01 (tt, $J_1$=3.8 Hz, $J_2$=7.9 Hz, 1H), 5.12-4.78 (m, 4H), 3.74 (s, 3H), 3.02 (s, 3H).

Step 4: Preparation of N-(7-amino-4-chloro-1-(2,2-difluoroethyl)-1H-indazol-3-yl)-N-(4-methoxybenzyl)methanesulfonamide

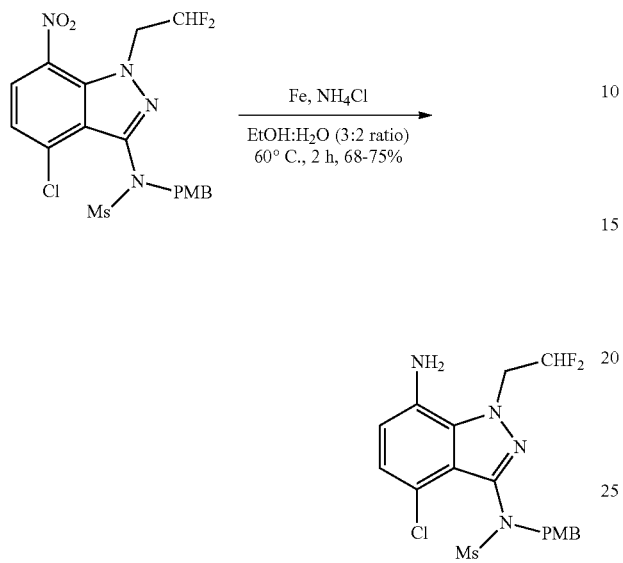

To a stirred suspension of iron powder (76.5 g, 1.37 mol, 5.0 equiv.) in a mixture of EtOH (650 mL, 5.0 V) and water (780 mL, 6.0 V) at room temperature was added ammonium chloride (118.0 g, 2.18 mol, 8.0 equiv.). To the mixture was added N-(4-chloro-1-(2,2-difluoroethyl)-7-nitro-1H-indazol-3-yl)-N-(4-methoxybenzyl)methanesulfonamide (130 g, 0.27 mol, 1.0 equiv.) in EtOH (520 mL, 4.0 V). The reaction mixture was heated to 60° C. and then stirred for 2 h. After completion of the reaction (monitored by in-process TLC/HPLC), the mixture was cooled to room temperature and diluted with ethyl acetate (1.3 L, 10.0 V) and water (390 mL, 3.0 V). The mixture was stirred for 15 min. The mixture was filtered through a pad of Celite and the Celite pad was then extracted with ethyl acetate (650 mL, 5.0 V). The bi-phasic filtrate was partitioned, and the organic phase was reserved while the aqueous layer was extracted with ethyl acetate (650 mL, 5.0 V). The combined organic layers were washed with brine (1.3 L, 10 V), dried over $Na_2SO_4$, and then concentrated in vacuo to afford a crude solid. To the crude product was added MTBE (650 mL, 5.0 V) and the suspension was stirred for 30 min. at room temperature. The solids were isolated via filtration. Bulk residual water was removed from the solids by maintaining vacuum filtration for 30-45 min. The wet product was dried in a hot air oven (50° C.) for 2 h to afford the title compound N-(7-amino-4-chloro-1-(2,2-difluoroethyl)-1H-indazol-3-yl)-N-(4-methoxy benzyl)methanesulfonamide (100.0 g, 70% yield) as off-white solid. $^1$H NMR (400 MHz, $CDCl_3$): δ 7.21 (d, J=8.5 Hz, 2H), 6.87 (d, J=8.4 Hz, 1H), 6.78 (d, J=8.5 Hz, 2H), 6.52 (d, J=8.3 Hz, 1H), 6.01 (tt, J=3.8 Hz, $J_2$=7.7 Hz, 1H), 4.98-4.69 (m, 4H), 3.75 (s, 3H), 2.98 (s, 3H).

Alternate Preparation of N-(7-amino-4-chloro-1-(2,2-difluoroethyl)-1H-indazol-3-yl)-N-(4-methoxybenzyl)cyclopropanesulfonamide

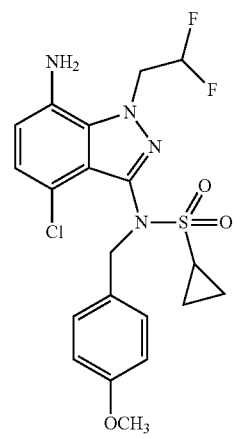 [SMILES: COc1ccc(CN(c2nn(CC(F)F)c3c(N)ccc(Cl)c23)S(=O)(=O)C2CC2)cc1]

Synthesis Scheme:

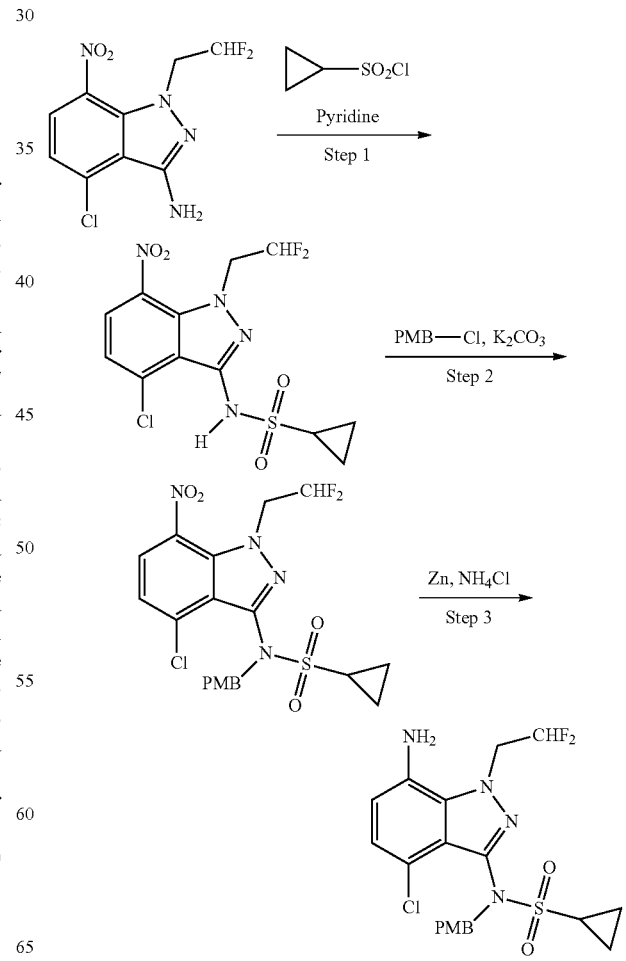

Step 1: Preparation of N-(4-chloro-1-(2,2-difluoro-ethyl)-7-nitro-1H-indazol-3-yl)cyclopropanesulfonamide

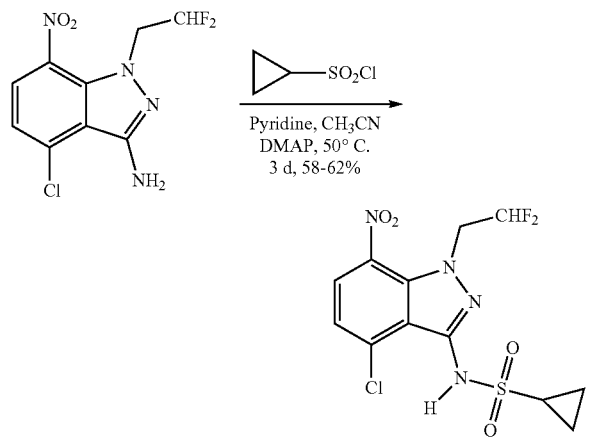

To a stirred solution of 4-chloro-1-(2,2-difluoroethyl)-7-nitro-1H-indazol-3-amine (150.0 g, 0.54 mol, 1.0 equiv.) in acetonitrile (600 mL, 4.0 V) at room temperature was added pyridine (600 mL, 4.0 V), followed by the addition of 4-dimethylaminopyridine (30.0 g, 0.27 mol, 0.5 equiv.). The reaction mass was stirred for 5-10 min., then cyclopropylsulfonyl chloride (114 mL, 1.08 mol, 2.0 equiv.) was added at room temperature. The reaction mixture was heated to 50° C. and then stirred at that temperature for 3 days. After completion of the reaction (monitored by TLC), the mixture was cooled to room temperature and diluted with water (1.5 L, 10.0 V) and ethyl acetate (1.5 L, 10.0 V), then stirred at room temperature for 15 min. The organic layer was separated, and the aqueous layer was extracted with EtOAc (300 mL, 2.0 V). The combined organic layers were washed with aq. 1.0 N HCl (600 mL, 4.0 V), followed by 10% brine solution (1.5 L, 10.0 V). The organic layer was dried over Na$_2$SO$_4$, filtered, and then concentrated under reduced pressure to afford N-(4-chloro-1-(2,2-difluoroethyl)-7-nitro-1H-indazol-3-yl)cyclopropanesulfonamide (124.0 g, 61%) as a viscous liquid. $^1$H NMR (400 MHz, CDCl$_3$): δ 8.11 (d, J=8.5 Hz, 1H), 7.25 (d, J=8.5 Hz, 1H), 6.04 (tt, J$_1$=3.8 Hz, J$_2$=7.7 Hz, 1H), 5.05 (td, J=3.8 Hz, J$_2$=14.4 Hz, 2H), 3.06-3.00 (m, 1H), 1.65-1.42 (m, 2H), 1.19-1.13 (m, 2H).

Step 2: Preparation of N-(4-chloro-1-(2,2-difluoro-ethyl)-7-nitro-1H-indazol-3-yl)-N-(4-methoxyben-zyl)cyclopropanesulfonamide

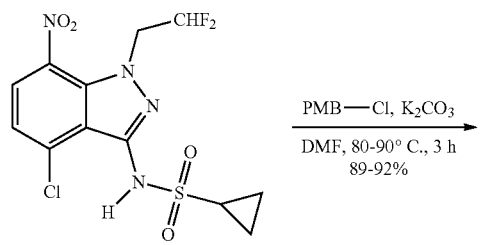

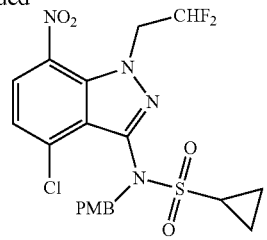

To a mixture of N-(4-chloro-1-(2,2-difluoroethyl)-7-nitro-1H-indazol-3-yl)cyclopropanesulfonamide (100.0 g, 0.20 mol, 1.0 equiv.) and 1-(chloromethyl)-4-methoxybenzene (39.2 mL, 0.22 mol, 1.1 equiv.) in DMF (1.0 L, 10.0 V) at room temperature was added potassium carbonate (128 g, 0.33 mol, 1.3 equiv.). The reaction mixture was heated to 80-90° C. and maintained at that temperature for 3 h. After completion of the reaction (monitored by TLC), the mixture was poured into ice cold water (3.0 L, 30.0 V) [Note: Slow quenching with vigorous stirring is preferred to avoid clumping as the product precipitates]. The resulting solids were isolated via filtration and washed with water (300 mL, 3.0 V); then the solids were washed with hexanes (300 mL, 3.0 V). Bulk residual water was removed from the solids by maintaining vacuum filtration for 1-2 h. The wet solid was dissolved in ethyl acetate (500 mL, 5.0 V) and charcoal was added (10.0 g). The mixture was heated to 60-70° C. and then stirred for 30-45 minutes at that temperature. The mixture was filtered while hot (40-50° C.) through a pad of Celite and the Celite pad was extracted with ethyl acetate (500 mL, 5.0 V). The combined filtrates were concentrated to dryness under reduced pressure at below 50° C. to afford N-(4-chloro-1-(2,2-difluoroethyl)-7-nitro-1H-indazol-3-yl)-N-(4-methoxy-benzyl)cyclopropanesulfonamide (122.0 g, 92% yield) as a yellow solid. $^1$H NMR (400 MHz, CDCl$_3$): δ 8.05 (d, J=8.6 Hz, 1H), 7.26-7.22 (m, 3H), 6.73 (d, J=8.5 Hz, 2H), 5.98 (tt, J$_1$=3.7 Hz, J$_2$=7.8 Hz, 1H), 5.09-4.88 (m, 4H), 3.72 (s, 3H), 2.65-2.60 (m, 1H), 1.15-1.06 (m, 2H), 0.89-0.86 (m, 2H).

Step 3: Preparation of N-(7-amino-4-chloro-1-(2,2-difluoroethyl)-1H-indazol-3-yl)-N-(4-methoxyben-zyl)cyclopropanesulfonamide

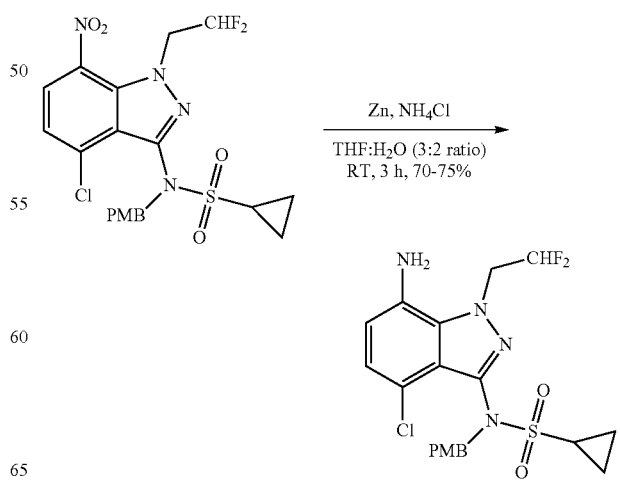

To a stirred suspension of zinc powder (156.0 g, 2.4 mol, 10.0 equiv.) in a mixture of THF (1.2 L, 10.0 V) and water (2.4 L, 20.0 V) at room temperature was added ammonium chloride (129.0 g, 2.40 mol, 10.0 equiv.). To the mixture was added N-(4-chloro-1-(2,2-difluoroethyl)-7-nitro-1H-indazol-3-yl)-N-(4-methoxybenzyl)cyclopropanesulfonamide (120 g, 0.2 mol, 1.0 equiv.) in THF (2.4 L, 20.0 V). The reaction mixture was stirred at room temperature for 2 h. After completion of the reaction (monitored by in-process TLC/HPLC), the mixture was diluted with ethyl acetate (1.2 L, 10.0 V) and water (360 mL, 3.0 V). The mixture was stirred for 15 min. The mixture was filtered through Celite and the Celite pad was extracted with ethyl acetate (600 mL, 5.0 V). The bi-phasic filtrate was partitioned, and the organic phase was reserved while the aqueous layer was extracted with ethyl acetate (600 mL, 5.0 V). The combined organic layers were washed with 10% brine solution (1.2 L, 10 V), dried over Na$_2$SO$_4$, filtered, and then concentrated in vacuo to afford a crude solid. To the crude product was added MTBE (600 mL, 5.0 V) and the suspension was stirred for 30-45 min. at room temperature. The solids were isolated by filtration and then bulk residual water was removed from the solids by maintaining vacuum filtration for 30-45 min. The wet product was dried in a hot air oven (50° C.) for 2 h to afford the product, N-(7-amino-4-chloro-1-(2,2-difluoroethyl)-1H-indazol-3-yl)-N-(4-methoxybenzyl)cyclopropanesulfonamide (81.0 g, 73% yield) as off-white solid. $^1$H NMR (400 MHz, CDCl$_3$): δ 7.25 (d, J=8.5 Hz, 2H), 6.93 (d, J=8.4 Hz, 1H), 6.75 (d, J=8.3 Hz, 2H), 6.57 (d, J=8.4 Hz, 1H), 6.03 (tt, J$_1$=3.7 Hz, J$_2$=7.9 Hz, 1H), 4.80-4.95 (m, 4H), 3.74 (s, 3H), 2.67-2.61 (m, 1H), 1.14 (d, J=2.4 Hz, 2H), 0.96 (d, J=2.3 Hz, 2H).

Alternate Preparation of N-(7-amino-4-chloro-1-(2,2,2-trifluoroethyl)-1H-indazol-3-yl)-N-(4-methoxybenzyl)methanesulfonamide

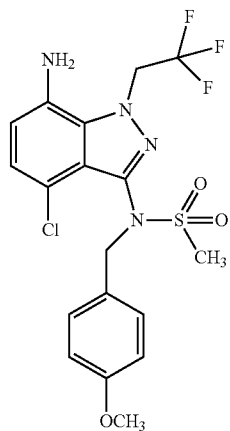 [SMILES: COc1ccc(CN(c2nn(CC(F)(F)F)c3c(N)ccc(Cl)c23)S(C)(=O)=O)cc1]

Synthesis Scheme:

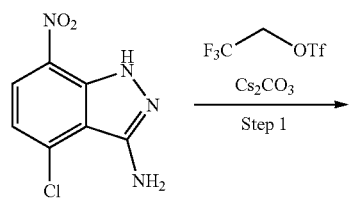

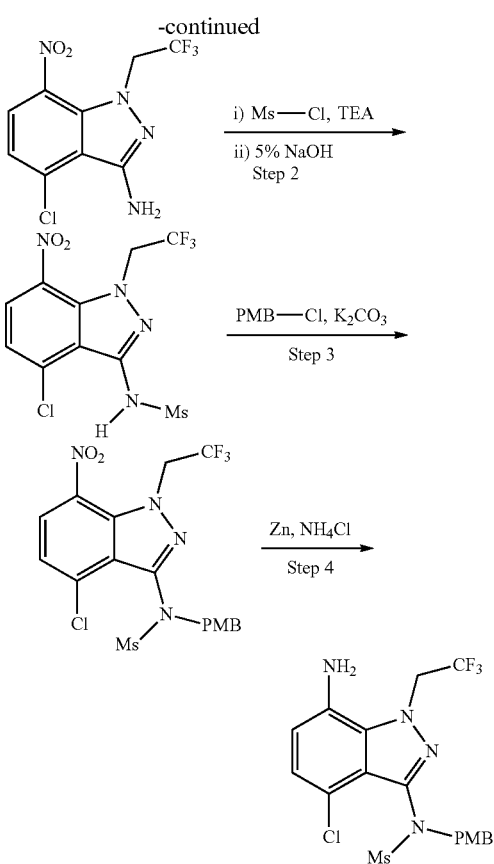

Step 1: Preparation of 4-chloro-7-nitro-1-(2,2,2-trifluoroethyl)-1H-indazol-3-amine

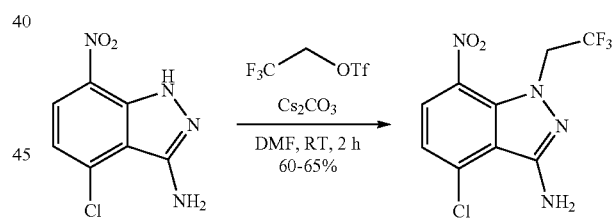

To a stirred solution of 4-chloro-7-nitro-1H-indazol-3-amine (50 g, 0.23 mol, 1.0 equiv.) in DMF (500 mL, 10.0 V) at 10-15° C. was added cesium carbonate (Cs$_2$CO$_3$) (153.3 g, 0.47 mol, 2.0 equiv.) at a rate sufficient to maintain the reaction mass below 20° C. The mixture was stirred for 5-10 min, then to the stirred mixture at 10-15° C. was added 2,2,2-trifluoroethyl trifluoromethanesulfonate (60.18 g, 0.26 mol, 1.1 equiv.) at a rate sufficient to maintain the reaction mass below 20° C. (Note: slow addition is preferred for obtaining more favorable regio-selectivity). The reaction mass was allowed to slowly warm to room temperature and was then stirred at the same temperature for 2 h. After completion of the reaction (monitored by TLC), the reaction mass was quenched via the addition of ice-cold water (1.5 L, 30.0 V) and the resulting mixture was allowed to warm to room temperature with stirring for 6-8 h. The solids were isolated via filtration and were then washed with water (150 mL, 3.0 V). The wet solid was washed with hexanes (250 mL, 5.0 V) and then bulk residual water was removed from the solids by maintaining vacuum filtration for 60-90 min. The wet solid was dried in a hot air oven for 7-8 h at 50° C. (until the moisture content was below 1.0%). The isolated material, 4-chloro-7-nitro-1-(2,2,2-trifluoroethyl)-1H-indazol-3-amine (45.0 g, 60% yield), was used directly in the next step without further purification. ¹H-NMR (400 MHz, CDCl₃): δ 8.09 (d, J=8.40 Hz, 1H), 7.12 (d, J=8.40 Hz, 1H), 5.14 (q, J=8.52 Hz, 2H), 4.77 (bs, H).

Step 2: Preparation of N-(4-chloro-7-nitro-1-(2,2,2-trifluoroethyl)-1H-indazol-3-yl)methanesulfonamide

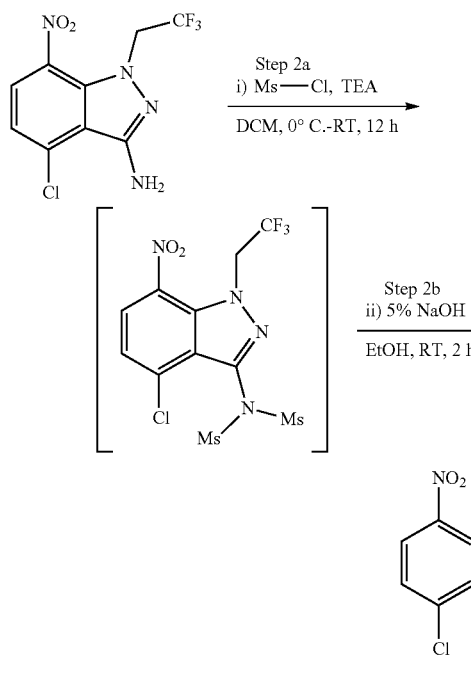

(Step 2a): To a solution of 4-chloro-7-nitro-1-(2,2,2-trifluoroethyl)-1H-indazol-3-amine (20.0 g, 0.068 mol, 1.0 equiv.) in DCM (200 mL, 10.0 V) at 0-5° C. was added triethylamine (29.0 mL, 0.204 mol, 3.0 equiv.), followed by the addition of 4-dimethylaminopyridine (415 mg, 0.03 mol, 0.05 equiv.). The reaction mass was stirred for 5-10 min., then to the mixture was added methanesulfonyl chloride (13.25 mL, 0.17 mol, 2.5 equiv) at a rate sufficient to maintain the reaction mass below 10° C. The reaction mixture was allowed to warm to room temperature with stirring for 12 h. After completion of the reaction (monitored by TLC), the mixture was diluted with water (200 mL, 10.0 V) and then stirred at room temperature for 15 min. The organic layer was separated, and the aqueous layer was extracted with DCM (200 mL, 10.0 V). The combined organic layers were washed with 10% brine solution (60 mL, 3.0 V), dried over Na₂SO₄, filtered, and concentrated to afford the crude solids. The solids were triturated with hexanes (60 mL, 3.0 V) at room temperature to obtain the intermediate, N-(4-chloro-7-nitro-1-(2,2,2-trifluoroethyl)-1H-indazol-3-yl)-N-(methylsulfonyl)methanesulfonamide, which was used directly in the next step.
(Step 2b): To a stirred solution of N-(4-chloro-7-nitro-1-(2,2,2-trifluoroethyl)-1H-indazol-3-yl)-N-(methylsulfonyl)methanesulfonamide (entirety of the material prepared above) in ethanol (200 mL, 10.0 V) at room temperature was added slowly aq. 5% NaOH solution (140 mL, 7.0 V) [Note: Slow addition is preferred via dropping funnel]. The reaction mass was stirred at the same temperature for 2 h. After completion of the reaction [Sample preparation for TLC analysis: An aliquot of the reaction solution (~1.0 ml) was acidified by the addition of aq. 2.0 N HCl to reach pH 2-3; then the mixture was extracted with ethyl acetate and the organic phase was analyzed by TLC], the reaction mass was cooled to 0-5° C. and the pH was adjusted to 2-3 by the addition of aq. 2.0 N HCl (100 mL, 5.0 V) while maintain the temperature below 10° C. [Note: Precipitation occurred upon addition of HCl and increased with stirring]. The reaction mixture was warmed to room temperature and then stirred for 1.5-2.0 h. The solids were isolated via filtration and were then washed with water (60 mL, 3.0 V), followed by washing with hexanes (60 mL, 3.0 V). Bulk residual water was removed from the solids by maintaining vacuum filtration for 60-90 min. The wet material was dried in a hot air oven at 50° C. for 6-7 h (until the moisture content was below 1.0%) to afford N-(4-chloro-7-nitro-1-(2,2,2-trifluoroethyl)-1H-indazol-3-yl)methanesulfonamide (22.1 g, 87%) as a yellow solid. ¹H NMR (400 MHz, CDCl₃): δ 8.19 (d, J=8.40 Hz, 1H), 7.56 (bs, 1H), 7.30 (d, J=8.40 Hz, 1H), 5.34 (q, J=8.30 Hz, 2H), 3.46 (s, 3H).

Step 3: Preparation of N-(4-chloro-7-nitro-1-(2,2,2-trifluoroethyl)-1H-indazol-3-yl)-N-(4-methoxybenzyl)methanesulfonamide

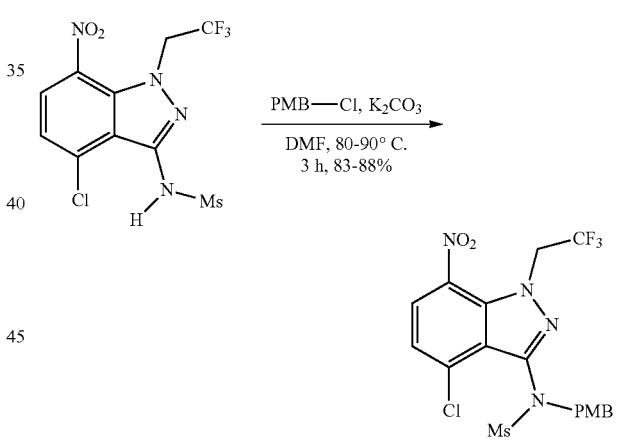

To a mixture of N-(4-chloro-7-nitro-1-(2,2,2-trifluoroethyl)-1H-indazol-3-yl)methanesulfonamide (50.0 g, 0.134 mol, 1.0 equiv.) and 1-(chloromethyl)-4-methoxybenzene (23.0 g, 0.147 mol, 1.1 equiv.) in DMF (500 mL, 10.0 V) at room temperature was added potassium carbonate (27.8 g, 0.201 mol, 1.5 equiv.). The reaction mixture was heated to 80-90° C. and maintained at that temperature for 3 h. After completion of the reaction (monitored by TLC), the mixture was poured into ice cold water (2.0 L, 40.0 V) [Note: Slow quenching with vigorous stirring is preferred to avoid clumping as the product precipitates]. The resulting solids were isolated via filtration and washed with water (150 mL, 3.0 V); then the solids were washed with hexanes (150 mL, 3.0 V). Bulk residual water was removed from the solids by maintaining vacuum filtration for 1-2 h. The solids were dissolved in ethyl acetate (500 mL, 10.0 V) and to the solution was added charcoal (5.0 g). The mixture was heated to 60-70° C. and then stirred at that temperature for 30-45 min. The mixture was filtered while hot (40-50° C.) through a pad of Celite and the Celite pad was extracted with ethyl acetate (250 mL, 5.0 V). The combined filtrate was concentrated to dryness under reduced pressure at below 50° C. The solids were combined with ethyl acetate (50 mL, 1.0 V) at room temperature. The resulting suspension was stirred for 30 min. The solids were isolated via filtration and then were washed with hexanes (100 mL, 2.0 V). Residual water was removed from the solids by maintaining vacuum filtration for 45-60 min. to afford N-(4-chloro-7-nitro-1-(2,2,2-trifluoroethyl)-1H-indazol-3-yl)-N-(4-methoxybenzyl)methanesulfonamide (56.0 g, 85% yield) as a yellow solid. $^1$H NMR (400 MHz, CDCl$_3$): δ 8.12 (d, J=8.36 Hz, 1H), 7.31 (d, J=8.36 Hz, 1H), 7.22 (d, J=8.44 Hz, 2H), 6.77 (d, J=8.44 Hz, 2H), 5.50-5.25 (m, 2H), 4.94-4.79 (m, 2H), 3.75 (s, 3H), 3.02 (s, 3H).

Step 4: Preparation of N-(7-amino-4-chloro-1-(2,2,2-trifluoroethyl)-1H-indazol-3-yl)-N-(4-methoxybenzyl)methanesulfonamide

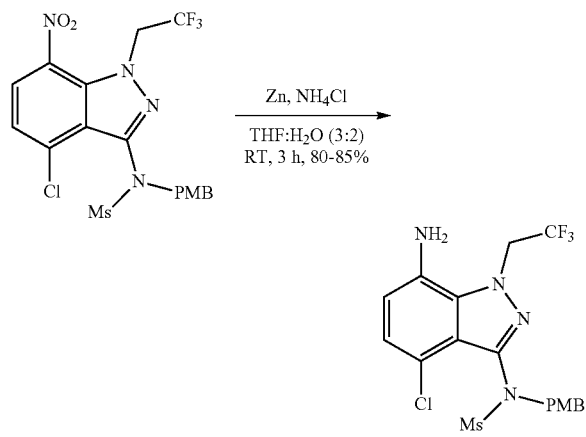

To a stirred suspension of zinc powder (66.31 g, 1.01 mol, 10.0 equiv.) in THF (500 mL, 10.0 V) and water (1.0 L, 20.0 V) at room temperature was added ammonium chloride (54.78 g, 1.01 mol, 10.0 equiv.). To the mixture was added a solution of N-(4-chloro-7-nitro-1-(2,2,2-trifluoroethyl)-1H-indazol-3-yl)-N-(4-methoxybenzyl)methanesulfonamide (50.0 g, 0.101 mol, 1.0 equiv.) in THF (1.0 L, 20.0 V). The reaction mixture was stirred at room temperature for 3 h. After completion of the reaction (monitored by in-process TLC/HPLC), the mixture was diluted with ethyl acetate (1.0 L, 20.0 V) and water (250 mL, 5.0 V). The mixture was stirred for 15 min. The mixture was filtered through a pad of Celite and the Celite pad was extracted with ethyl acetate (250 mL, 5.0 V). The bi-phasic filtrate was partition and the organic layer was reserved while the aqueous layer was extracted with ethyl acetate (500 mL, 10.0 V). The combined organic layers were washed with 10% brine solution (500 mL, 10.0 V), dried over Na$_2$SO$_4$, filtered, and then concentrated in vacuo to afford a crude solid. To the crude product was added MTBE (250 mL, 5.0 V) and the resulting suspension was stirred for 30 min. at room temperature. The solids were isolated by filtration and then bulk residual water was removed from the solids by maintaining vacuum filtration for 30-45 min. The wet product was dried in a hot air oven (50° C.) for 2 h to afford the title product N-(7-amino-4-chloro-1-(2,2,2-trifluoroethyl)-1H-indazol-3-yl)-N-(4-methoxybenzyl)methanesulfonamide (39.0 g, 83% yield) as off-white solid. $^1$H NMR (400 MHz, CDCl$_3$): δ 7.25 (d, J=8.48 Hz, 2H), 6.98 (d, J=7.80 Hz, 1H), 6.79 (d, J=8.48 Hz, 2H), 6.66 (d, J=7.84 Hz, 1H), 5.35-4.75 (m, 4H), 3.77 (s, 3H), 3.56 (bs, 2H), 2.98 (s, 3H).

The general procedures, general analytical methods, and general purification methods used to prepare examples 80-151 are described above or detailed below. The experimental procedure supplied for each specific example identifies the general method used to prepare and purify that compound.

General Procedure I:

To a vial equipped with a stir bar was added Pd(OAc)$_2$ (0.1 equiv), dicyclohexyl(2',6'-dimethoxy-[1,1'-biphenyl]-2-yl)phosphane (0.2 equiv), K$_3$PO$_4$ (3 equiv), and N—((S)-1-(3-(4-chloro-1-(2,2-difluoroethyl)-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 50-100 mg). To the vial was added the appropriate aryl halide or heteroaryl halide (3 equiv). The vial was capped with a septum cap and then placed under argon atmosphere (vac/fillx3). To the vial was added THF:water (4:1) to afford a reaction volume 0.05M in boronic ester. The reaction mixture was degassed via vac/fill (×3) with argon. The reaction mixture was stirred at either ambient temperature, 45° C., or 60° C. for overnight (~18 h). Upon cooling to ambient temperature, the reaction mixture was concentrated and the residue was subjected to HPLC purification to afford the indicated product.

General Procedure J:

To a vial equipped with a stir bar was added Pd(OAc)$_2$ (0.1 equiv), dicyclohexyl(2',6'-dimethoxy-[1,1'-biphenyl]-2-yl)phosphane (0.2 equiv), K$_3$PO$_4$ (3 equiv), and N—((S)-1-(3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 50-100 mg). To the vial was added the appropriate aryl halide or heteroaryl halide (3 equiv). The vial was capped with a septum cap and then placed under argon atmosphere (vac/fillx3). To the vial was added THF:water (4:1) to afford a reaction volume 0.05M in boronic ester. The reaction mixture was degassed via vac/fill (×3) with argon. The reaction mixture was stirred at either ambient temperature, 45° C., or 60° C. overnight (18 h). Upon cooling to ambient temperature, the reaction mixture was concentrated and the residue was subjected to HPLC purification to afford the indicated product.

General Procedure Q:

Pd(OAc)$_2$ (0.1 equiv), dicyclohexyl(2',6'-dimethoxy-[1,1'-biphenyl]-2-yl)phosphane (0.2 equiv) tripotassium phosphate (3 equiv), and N—((S)-1-(3-(4-chloro-3-(methylsulfonamido)-1-(2,2,2-trifluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv) were combined in a dry reaction vessel equipped with a stir bar under argon. To the vessel was added the appropriate aryl or heteroaryl halide (3 equiv). The vessel was degassed with argon and THF/water (4:1, 0.05M) was added. The mixture was degassed with argon and the mixture was then stirred at either ambient temperature, 45° C., or 60° C. for overnight (approximately 18 h). Upon cooling to ambient temperature, the mixture subjected to HPLC purification to afford the desired product.

LCMS Method A:
Column: Acquity BEH C18, 2.1×100 mm, 1.7 m particles; Solvent A=0.05% TFA in Water; Solvent B=Acetonitrile; Flow Rate=0.45 mL/min.; Gradient {time-point (min.)/% B at time-point (%)}=0/3, 0.4/3, 7.5/98, 9.5/98, 9.6/3, 10/3; Column Temperature=35° C.

LCMS Method B:
Column: Acquity BEH C18, 2.1×50 mm, 1.7 m particles; Solvent A=0.1% Formic acid in Water; Solvent B=0.1% Formic Acid in Acetonitrile; Flow Rate=0.6 mL/min.; Gradient {time-point (min.)/% B at time-point (%)}=0/3, 0.4/3, 3.2/98, 3.8/98, 4.2/3, 4.5/3; Column Temperature=35° C.

LCMS Method D:
Column: Acquity BEH C18, 2.1×50 mm, 1.7 m particles; Solvent A=0.1% Formic acid in Water; Solvent B=0.1% Formic Acid in Acetonitrile; Flow Rate=0.6 mL/min.; Gradient {time-point (min.)/% B at time-point (%)}=0/3, 0.4/3, 7.5/98, 9.5/98, 9.6/3, 10/3; Column Temperature=35° C.

LCMS Method G:
Column: Acquity UPLC BEH C18, 2.1×100 mm, 1.7 m particles; Solvent A=95:5 Water:MeCN w/0.1% Formic Acid; Solvent B=5:95 Water:MeCN w/0.1% Formic Acid; Flow Rate=0.8 mL/min.; Gradient {time-point (min.)/% B at time-point (%)}=0/0, 3.5/100, 4.5/100; UV Detection=220 nm and 254 nm.

Preparation of Example 80: N—((S)-1-((3P)-3-(4-chloro-1-methyl-3-(methylsulfonamido)-1H-indazol-7-yl)-4-oxo-7-(4-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

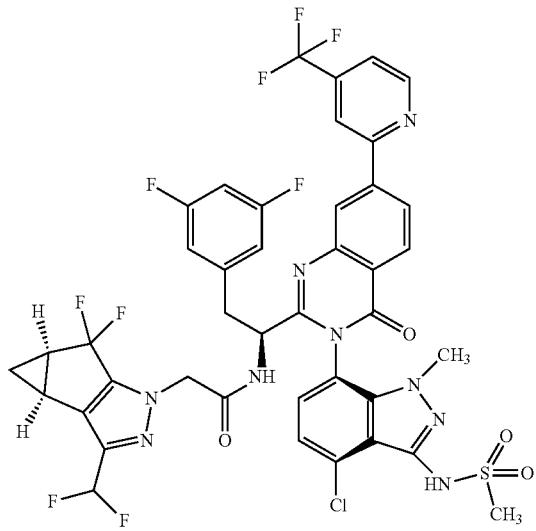

The title compound was prepared according to General Procedure Q using 2-chloro-4-(trifluoromethyl)pyridine as the coupling partner. The experiment afforded the title compound, N—((S)-1-((3P)-3-(4-chloro-1-methyl-3-(methylsulfonamido)-1H-indazol-7-yl)-4-oxo-7-(4-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.59 min.; observed ion=950.2 (M+H). $^1$H NMR (500 MHz, METHANOL-$d_4$) δ ppm 9.02 (d, J=5.07 Hz, 1H), 8.61 (d, J=1.19 Hz, 1H), 8.35-8.47 (m, 3H), 7.77 (dd, J=5.07, 0.89 Hz, 1H), 7.17-7.32 (m, 2H), 6.57-6.81 (m, 4H), 4.46-4.57 (m, 2H), 3.61 (s, 3H), 3.49 (dd, J=14.01, 5.07 Hz, 1H), 3.23 (s, 3H), 3.11 (dd, J=14.16, 9.39 Hz, 1H), 2.37-2.46 (m, 2H), 1.31-1.37 (m, 1H), 0.96-1.03 (m, 1H).

Preparation of Example 81: N—((S)-1-((3P)-3-(4-chloro-3-(cyclopropanesulfonamido)-1-(2,2-difluoroethyl)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

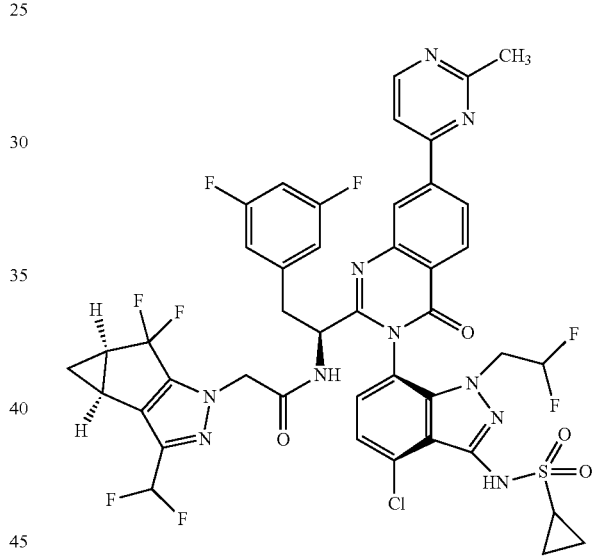

The title compound was prepared according to General Procedure J using 4-chloro-2-methylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.38 min.; observed ion=973.3 (M+H). 1H NMR (METHANOL-d4, 500 MHz) Shift 8.86 (d, 1H, J=5.4 Hz), 8.69 (s, 1H), 8.4-8.4 (m, 2H), 8.02 (d, 1H, J=5.4 Hz), 7.40 (br d, 1H, J=7.7 Hz), 7.31 (d, 1H, J=8.0 Hz), 6.80 (tt, 1H, J=2.2, 9.1 Hz), 6.70 (br t, 1H, J=54.8 Hz), 6.57 (br dd, 2H, J=2.1, 7.7 Hz), 6.04 (t, 1H, J=55.3 Hz), 4.77 (dd, 1H, J=4.8, 9.2 Hz), 4.6-4.7 (m, 2H), 4.4-4.5 (m, 1H), 3.9-4.0 (m, 1H), 3.4-3.5 (m, 1H), 3.09 (dd, 1H, J=9.5, 14.0 Hz), 2.9-2.9 (m, 1H), 2.86 (s, 3H), 2.4-2.5 (m, 2H), 1.3-1.4 (m, 1H), 1.1-1.2 (m, 2H), 0.9-1.0 (m, 3H)

215

Preparation of Example 82: N—((S)-1-((3P)-3-(4-chloro-3-(cyclopropanesulfonamido)-1-(2,2-difluoroethyl)-1H-indazol-7-yl)-7-(4-ethyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

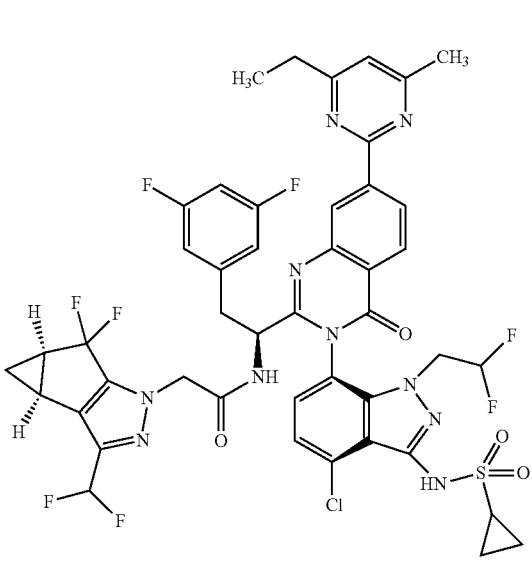

The title compound was prepared according to General Procedure J using 2-chloro-4-ethyl-6-methylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(4-ethyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.5 min.; observed ion=1001.3 (M+H). 1H NMR (METHANOL-d4, 500 MHz) Shift 8.94 (s, 1H), 8.70 (d, 1H, J=8.2 Hz), 8.39 (d, 1H, J=8.2 Hz), 7.2-7.3 (m, 2H), 6.6-6.8 (m, 4H), 6.04 (br t, 1H, J=55.3 Hz), 4.8-4.9 (m, 1H), 4.77 (dd, 1H, J=4.8, 9.5 Hz), 4.6-4.7 (m, 2H), 4.3-4.5 (m, 1H), 3.9-4.0 (m, 1H), 3.4-3.5 (m, 1H), 3.09 (dd, 1H, J=9.2, 14.3 Hz), 2.9-3.0 (m, 3H), 2.65 (s, 2H), 2.4-2.5 (m, 2H), 1.4-1.5 (m, 2H), 1.3-1.4 (m, 2H), 1.1-1.2 (m, 2H), 0.9-1.1 (m, 4H)

216

Preparation of Example 83: N—((S)-1-((3P)-3-(4-chloro-3-(cyclopropanesulfonamido)-1-(2,2-difluoroethyl)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

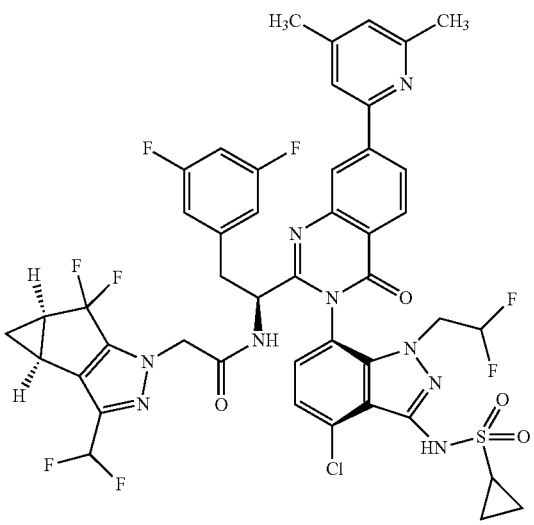

The title compound was prepared according to General Procedure J using 2-bromo-4,6-dimethylpyridine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.46 min.; observed ion=986.2 (M+H). 1H NMR (METHANOL-d4, 500 MHz) Shift 8.45 (d, 1H, J=1.5 Hz), 8.38 (d, 1H, J=8.3 Hz), 8.23 (dd, 1H, J=1.5, 8.3 Hz), 7.72 (s, 1H), 7.39 (br d, 1H, J=7.7 Hz), 7.27 (d, 1H, J=8.0 Hz), 7.24 (s, 1H), 6.8-6.8 (m, 1H), 6.71 (br t, 1H, J=54.8 Hz), 6.5-6.6 (m, 2H), 6.04 (t, 1H, J=55.4 Hz), 4.77 (dd, 1H, J=5.1, 9.2 Hz), 4.6-4.7 (m, 2H), 4.39 (br dd, 1H, J=4.0, 14.5 Hz), 3.9-4.0 (m, 1H), 3.4-3.5 (m, 1H), 3.08 (dd, 1H, J=9.2, 14.0 Hz), 2.92 (tt, 1H, J=4.9, 7.9 Hz), 2.64 (s, 3H), 2.4-2.5 (m, 5H), 1.36 (dt, 1H, J=5.5, 7.5 Hz), 1.1-1.1 (m, 2H), 0.9-1.1 (m, 3H)

Preparation of Example 84: N—((S)-1-((3P)-3-(4-chloro-3-(cyclopropanesulfonamido)-1-(2,2-difluoroethyl)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

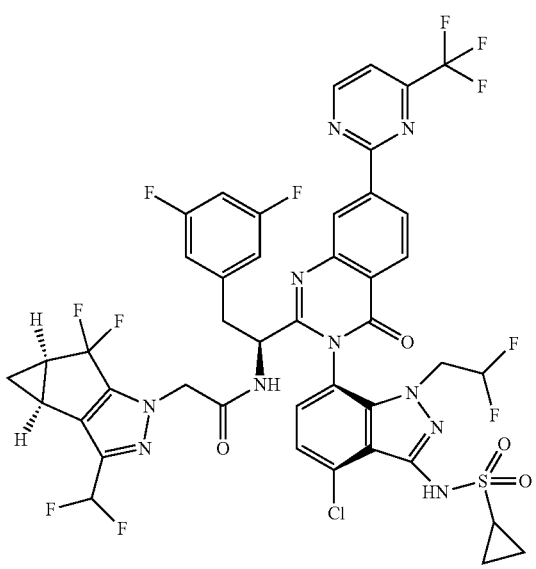

The title compound was prepared according to General Procedure J using 2-chloro-4-(trifluoromethyl)pyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.33 min.; observed ion=1027.2 (M+H). 1H NMR (METHANOL-d4, 500 MHz) Shift 9.32 (d, 1H, J=5.1 Hz), 9.03 (s, 1H), 8.77 (dd, 1H, J=1.8, 8.3 Hz), 8.45 (d, 1H, J=8.3 Hz), 7.92 (d, 1H, J=5.1 Hz), 7.41 (br d, 1H, J=7.7 Hz), 7.33 (d, 1H, J=8.0 Hz), 6.8-6.8 (m, 1H), 6.69 (t, 1H, J=54.8 Hz), 6.57 (br dd, 2H, J=2.1, 8.0 Hz), 6.04 (t, 1H, J=55.3 Hz), 4.7-4.8 (m, 2H), 4.6-4.7 (m, 1H), 4.3-4.5 (m, 1H), 3.96 (br dd, 1H, J=2.8, 13.9 Hz), 3.4-3.5 (m, 1H), 3.09 (dd, 1H, J=9.5, 14.0 Hz), 2.92 (tt, 1H, J=4.8, 8.0 Hz), 2.4-2.5 (m, 2H), 1.36 (dt, 1H, J=6.6, 7.3 Hz), 1.1-1.1 (m, 2H), 1.0-1.0 (m, 3H)

Preparation of Example 85: N—((S)-1-((3P)-3-(4-chloro-3-(cyclopropanesulfonamido)-1-(2,2-difluoroethyl)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

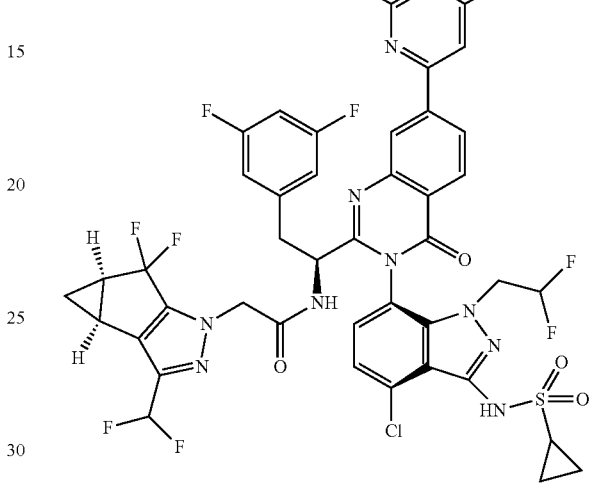

The title compound was prepared according to General Procedure J using 4-chloro-2,6-dimethylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.61 min.; observed ion=987.3 (M+H). 1H NMR (METHANOL-d4, 500 MHz) Shift 8.67 (d, 1H, J=1.2 Hz), 8.4-8.4 (m, 2H), 7.91 (s, 1H), 7.40 (br d, 1H, J=8.0 Hz), 7.30 (d, 1H, J=7.7 Hz), 6.8-6.8 (m, 1H), 6.71 (br t, 1H, J=54.8 Hz), 6.5-6.6 (m, 2H), 6.04 (br t, 1H, J=55.3 Hz), 4.77 (dd, 1H, J=4.8, 9.2 Hz), 4.6-4.7 (m, 2H), 4.3-4.4 (m, 1H), 3.9-4.0 (m, 1H), 3.4-3.5 (m, 1H), 3.09 (dd, 1H, J=9.4, 13.9 Hz), 2.92 (tt, 1H, J=4.8, 8.0 Hz), 2.81 (s, 3H), 2.66 (s, 3H), 2.4-2.5 (m, 2H), 1.3-1.4 (m, 1H), 1.1-1.1 (m, 2H), 1.0-1.0 (m, 3H)

Preparation of Example 86: N—((S)-1-((3P)-3-(4-chloro-3-(cyclopropanesulfonamido)-1-(2,2-difluoroethyl)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

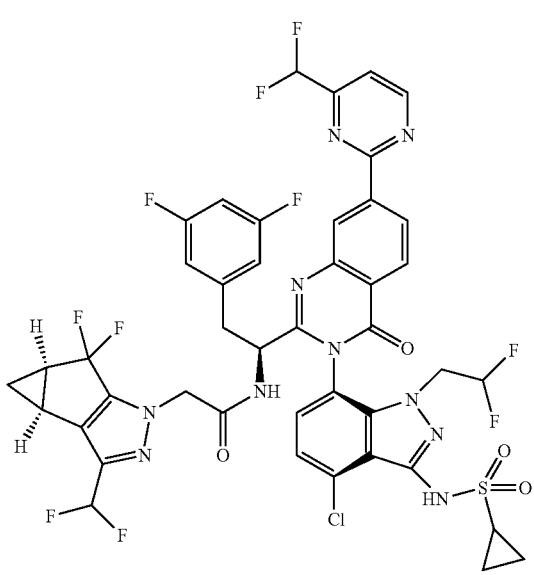

The title compound was prepared according to General Procedure J using 2-chloro-4-(difluoromethyl)pyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.49 min.; observed ion=1009.2 (M+H). 1H NMR (METHANOL-d4, 500 MHz) Shift 9.21 (d, 1H, J=5.1 Hz), 9.01 (d, 1H, J=1.8 Hz), 8.76 (dd, 1H, J=1.5, 8.3 Hz), 8.43 (d, 1H, J=8.3 Hz), 7.78 (d, 1H, J=5.1 Hz), 7.41 (br d, 1H, J=7.7 Hz), 7.32 (d, 1H, J=8.0 Hz), 6.5-7.0 (m, 5H), 6.05 (br t, 1H, J=55.3 Hz), 4.77 (dd, 1H, J=4.8, 9.5 Hz), 4.6-4.7 (m, 2H), 4.4-4.5 (m, 1H), 3.96 (br dd, 1H, J=3.4, 14.8 Hz), 3.4-3.5 (m, 1H), 3.09 (dd, 1H, J=9.5, 14.3 Hz), 2.92 (tt, 1H, J=4.8, 8.0 Hz), 2.4-2.5 (m, 2H), 1.3-1.4 (m, 1H), 1.1-1.1 (m, 2H), 0.9-1.0 (m, 3H)

Preparation of Example 87: N—((S)-1-((3P)-3-(4-chloro-3-(cyclopropanesulfonamido)-1-(2,2-difluoroethyl)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

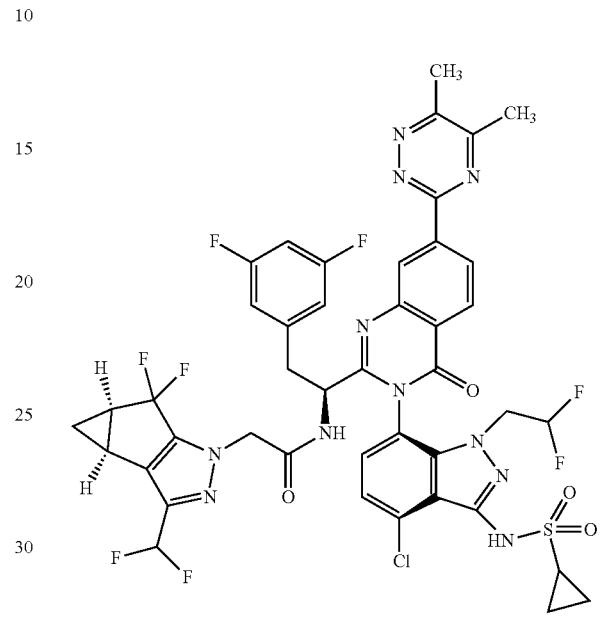

The title compound was prepared according to General Procedure J using 3-chloro-5,6-dimethyl-1,2,4-triazine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.54 min.; observed ion=988.3 (M+H). 1H NMR (METHANOL-d4, 500 MHz) Shift 8.98 (d, 1H, J=1.5 Hz), 8.73 (dd, 1H, J=1.8, 8.3 Hz), 8.44 (d, 1H, J=8.4 Hz), 7.41 (br d, 1H, J=8.0 Hz), 7.32 (d, 1H, J=8.0 Hz), 6.6-6.8 (m, 4H), 6.04 (br t, 1H, J=55.3 Hz), 4.77 (dd, 1H, J=4.8, 9.5 Hz), 4.6-4.7 (m, 2H), 4.3-4.5 (m, 1H), 3.9-4.0 (m, 1H), 3.43 (dd, 1H, J=4.6, 14.2 Hz), 3.09 (dd, 1H, J=9.5, 14.3 Hz), 2.9-2.9 (m, 1H), 2.81 (s, 3H), 2.75 (s, 3H), 2.4-2.5 (m, 2H), 1.3-1.4 (m, 1H), 1.1-1.2 (m, 2H), 0.9-1.1 (m, 3H)

Preparation of Example 88: N—((S)-1-((3P)-3-(4-chloro-3-(cyclopropanesulfonamido)-1-(2,2-difluoroethyl)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 89: N—((S)-1-((3P)-3-(4-chloro-3-(cyclopropanesulfonamido)-1-(2,2-difluoroethyl)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

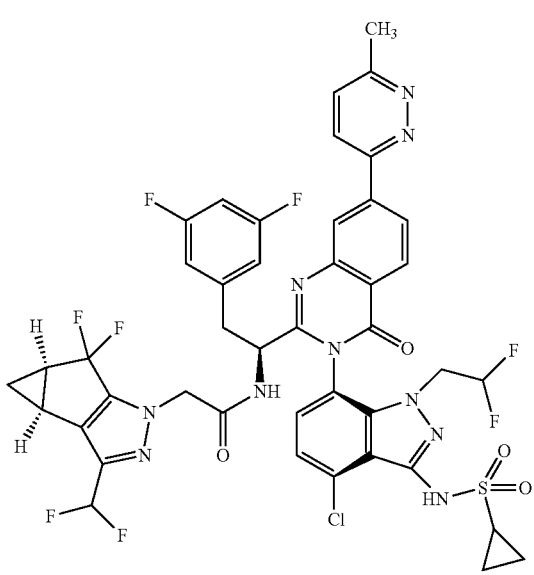

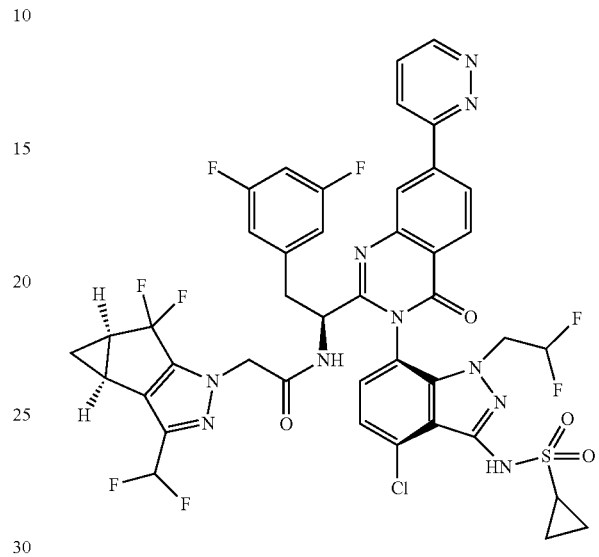

The title compound was prepared according to General Procedure J using 3-chloro-6-methylpyridazine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=973.4 (M+H). 1H NMR (METHANOL-d4, 500 MHz) Shift 8.63 (d, 1H, J=1.8 Hz), 8.45 (d, 1H, J=8.3 Hz), 8.36 (dd, 1H, J=1.5, 8.3 Hz), 8.31 (d, 1H, J=8.9 Hz), 7.83 (d, 1H, J=8.9 Hz), 7.40 (d, 1H, J=7.7 Hz), 7.31 (d, 1H, J=8.0 Hz), 6.5-6.8 (m, 4H), 6.05 (t, 1H, J=55.4 Hz), 4.77 (dd, 1H, J=4.8, 9.2 Hz), 4.6-4.7 (m, 2H), 4.4-4.4 (m, 1H), 3.96 (br d, 1H, J=11.3 Hz), 3.4-3.5 (m, 1H), 3.10 (dd, 1H, J=9.5, 14.0 Hz), 2.9-3.0 (m, 1H), 2.82 (s, 3H), 2.4-2.5 (m, 2H), 1.3-1.4 (m, 1H), 1.1-1.2 (m, 2H), 0.9-1.1 (m, 3H)

The title compound was prepared according to General Procedure J using 3-chloropyridazine as the coupling partner. The experiment afforded the title compound, N—((S)-1-((3P)-3-(4-chloro-3-(cyclopropanesulfonamido)-1-(2,2-difluoroethyl)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.41 min.; observed ion=959.2 (M+H). 1H NMR (METHANOL-d4, 500 MHz) Shift 9.31 (dd, 1H, J=1.5, 4.8 Hz), 8.66 (d, 1H, J=1.2 Hz), 8.4-8.5 (m, 3H), 7.9-8.0 (m, 1H), 7.4-7.4 (m, 1H), 7.31 (d, 1H, J=8.0 Hz), 6.5-6.8 (m, 4H), 6.05 (br t, 1H, J=55.4 Hz), 4.78 (dd, 1H, J=4.8, 9.5 Hz), 4.6-4.7 (m, 2H), 4.4-4.4 (m, 1H), 3.9-4.0 (m, 1H), 3.4-3.5 (m, 1H), 3.10 (dd, 1H, J=9.5, 14.0 Hz), 2.9-2.9 (m, 1H), 2.4-2.5 (m, 2H), 1.2-1.4 (m, 1H), 1.1-1.1 (m, 2H), 0.9-1.1 (m, 3H)

223

Preparation of Example 90: N—((S)-1-((3P)-3-(4-chloro-3-(cyclopropanesulfonamido)-1-(2,2-difluoroethyl)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

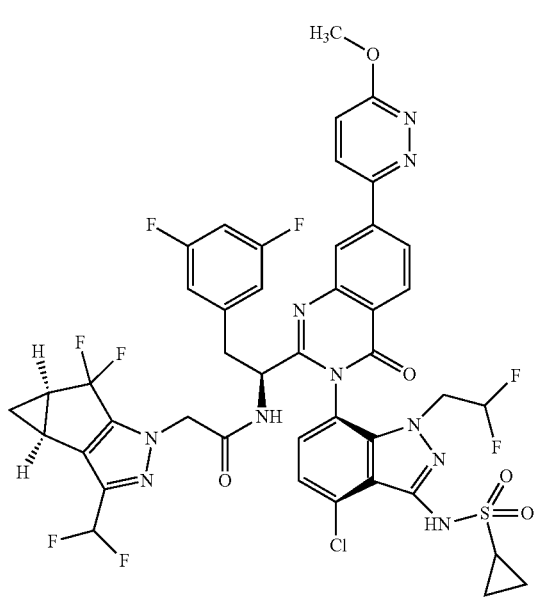

The title compound was prepared according to General Procedure J using 3-chloro-6-methoxypyridazine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.4 min.; observed ion=989.2 (M+H). 1H NMR (METHANOL-d4, 500 MHz) Shift 8.5-8.6 (m, 1H), 8.43 (d, 1H, J=8.2 Hz), 8.30 (s, 1H), 8.3-8.3 (m, 1H), 7.39 (d, 2H, J=9.2 Hz), 7.29 (d, 1H, J=8.0 Hz), 6.5-6.9 (m, 4H), 6.05 (t, 1H, J=55.3 Hz), 4.77 (dd, 1H, J=4.9, 9.4 Hz), 4.6-4.7 (m, 2H), 4.3-4.4 (m, 1H), 4.23 (s, 3H), 3.95 (br dd, 1H, J=3.6, 14.9 Hz), 3.4-3.5 (m, 1H), 3.09 (dd, 1H, J=9.2, 14.0 Hz), 2.9-2.9 (m, 1H), 2.4-2.5 (m, 2H), 1.3-1.4 (m, 1H), 1.1-1.1 (m, 2H), 1.0-1.1 (m, 3H)

224

Preparation of Example 91: N—((S)-1-((3P)-3-(4-chloro-3-(cyclopropanesulfonamido)-1-(2,2-difluoroethyl)-1H-indazol-7-yl)-7-(2-isopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

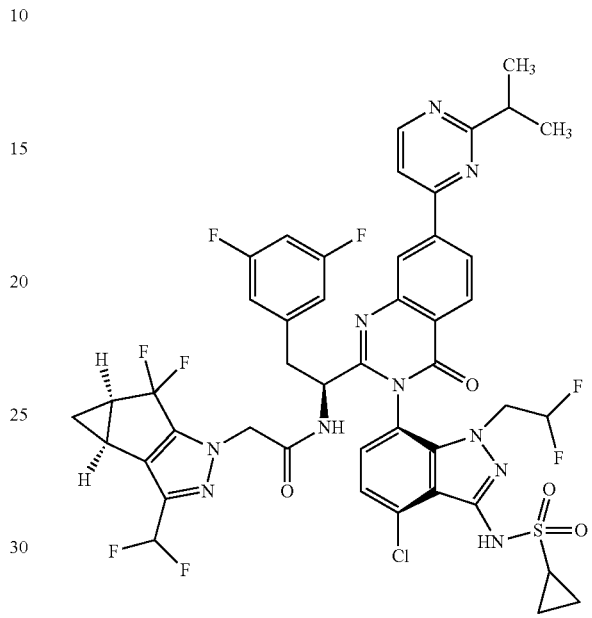

The title compound was prepared according to General Procedure J using 4-chloro-2-isopropylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(2-isopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=1001.3 (M+H). 1H NMR (METHANOL-d4, 500 MHz) Shift 8.88 (d, 1H, J=5.4 Hz), 8.8-8.8 (m, 1H), 8.44 (s, 2H), 8.02 (d, 1H, J=5.4 Hz), 7.41 (br d, 1H, J=7.5 Hz), 7.32 (d, 1H, J=7.7 Hz), 6.5-6.8 (m, 4H), 6.04 (t, 1H, J=55.4 Hz), 4.77 (dd, 1H, J=4.8, 9.5 Hz), 4.6-4.7 (m, 2H), 4.40 (br dd, 1H, J=3.6, 14.6 Hz), 3.9-4.0 (m, 1H), 3.4-3.5 (m, 1H), 3.3-3.4 (m, 1H), 3.10 (dd, 1H, J=9.5, 14.0 Hz), 2.9-2.9 (m, 1H), 2.4-2.5 (m, 2H), 1.49 (d, 6H, J=6.9 Hz), 1.3-1.4 (m, 1H), 1.1-1.1 (m, 2H), 0.9-1.0 (m, 3H)

Preparation of Example 92: N—((S)-1-((3P)-3-(4-chloro-3-(cyclopropanesulfonamido)-1-(2,2-difluoroethyl)-1H-indazol-7-yl)-4-oxo-7-(2,5,6-trimethylpyrimidin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

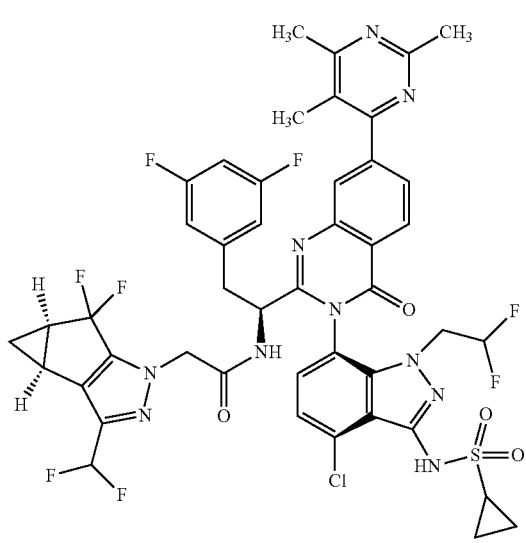

The title compound was prepared according to General Procedure J using 4-chloro-2,5,6-trimethylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-4-oxo-7-(2,5,6-trimethylpyrimidin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.42 min.; observed ion=1001.2 (M+H). 1H NMR (METHANOL-d4, 500 MHz) Shift 8.42 (d, 1H, J=7.7 Hz), 8.02 (d, 1H, J=1.2 Hz), 7.8-7.8 (m, 1H), 7.41 (br d, 1H, J=7.7 Hz), 7.32 (d, 1H, J=8.0 Hz), 6.5-6.8 (m, 4H), 6.05 (t, 1H, J=55.4 Hz), 4.76 (dd, 1H, J=4.8, 9.2 Hz), 4.6-4.7 (m, 2H), 4.40 (br dd, 1H, J=4.0, 14.5 Hz), 3.9-4.0 (m, 1H), 3.4-3.5 (m, 1H), 3.07 (dd, 1H, J=9.5, 14.0 Hz), 2.92 (tt, 1H, J=4.8, 8.0 Hz), 2.72 (s, 3H), 2.65 (s, 3H), 2.4-2.5 (m, 2H), 2.36 (s, 3H), 1.2-1.4 (m, 1H), 1.1-1.2 (m, 2H), 0.9-1.0 (m, 3H)

Preparation of Example 93: N—((S)-1-((3P)-3-(4-chloro-3-(cyclopropanesulfonamido)-1-(2,2-difluoroethyl)-1H-indazol-7-yl)-7-(4-ethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

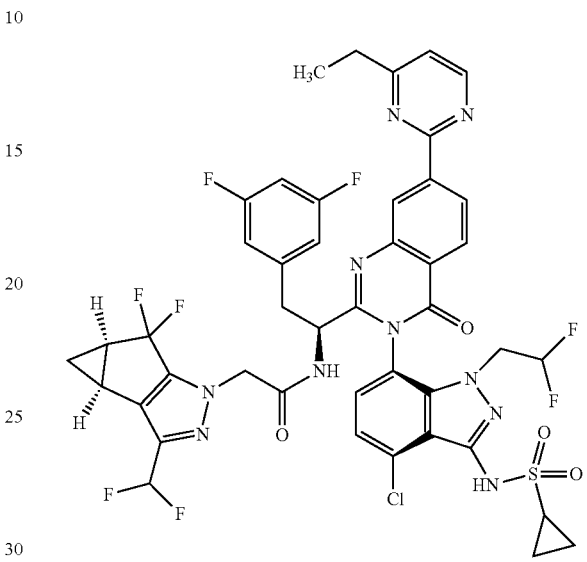

The title compound was prepared according to General Procedure J using 2-chloro-4-ethylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(4-ethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.33 min.; observed ion=987.2 (M+H). 1H NMR (METHANOL-d4, 500 MHz) Shift 8.96 (s, 1H), 8.85 (d, 1H, J=5.1 Hz), 8.71 (dd, 1H, J=1.5, 8.3 Hz), 8.40 (d, 1H, J=8.3 Hz), 7.4-7.4 (m, 2H), 7.31 (d, 1H, J=7.7 Hz), 6.8-6.8 (m, 1H), 6.70 (br t, 1H, J=54.8 Hz), 6.5-6.6 (m, 2H), 6.04 (br t, 1H, J=55.3 Hz), 4.77 (dd, 1H, J=4.8, 9.5 Hz), 4.6-4.7 (m, 2H), 4.3-4.4 (m, 1H), 3.9-4.0 (m, 1H), 3.43 (dd, 1H, J=4.8, 14.0 Hz), 3.09 (dd, 1H, J=9.5, 14.3 Hz), 2.9-3.0 (m, 3H), 2.4-2.5 (m, 2H), 1.46 (t, 3H, J=7.6 Hz), 1.3-1.4 (m, 1H), 1.1-1.1 (m, 2H), 0.9-1.1 (m, 3H)

Preparation of Example 94: N—((S)-1-((3P)-3-(4-chloro-3-(cyclopropanesulfonamido)-1-(2,2-difluoroethyl)-1H-indazol-7-yl)-7-(6-ethyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

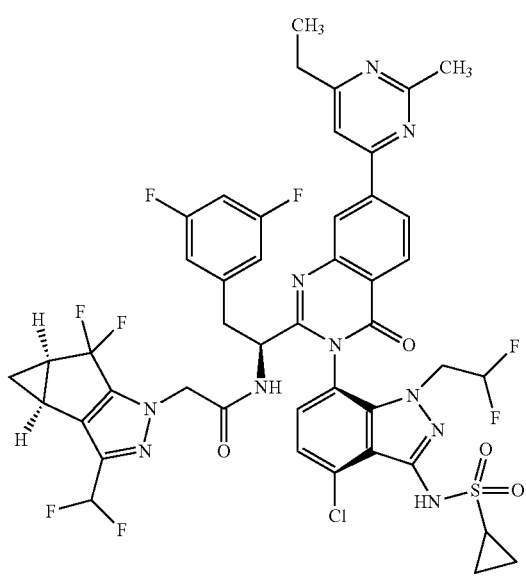

The title compound was prepared according to General Procedure J using 4-chloro-6-ethyl-2-methylpyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(6-ethyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.49 min.; observed ion=1001.2 (M+H). 1H NMR (METHANOL-d4, 500 MHz) Shift 8.66 (d, 1H, J=1.8 Hz), 8.4-8.4 (m, 2H), 7.90 (s, 1H), 7.4-7.4 (m, 1H), 7.31 (d, 1H, J=7.7 Hz), 6.8-6.8 (m, 1H), 6.71 (br t, 1H, J=54.8 Hz), 6.5-6.6 (m, 2H), 6.04 (t, 1H, J=55.3 Hz), 4.77 (dd, 1H, J=4.8, 9.5 Hz), 4.6-4.7 (m, 2H), 4.40 (br dd, 1H, J=3.3, 14.6 Hz), 3.95 (br dd, 1H, J=3.6, 14.9 Hz), 3.4-3.5 (m, 1H), 3.09 (dd, 1H, J=9.5, 14.0 Hz), 2.9-3.0 (m, 3H), 2.82 (s, 3H), 2.4-2.5 (m, 2H), 1.3-1.4 (m, 4H), 1.1-1.1 (m, 2H), 0.9-1.0 (m, 3H)

Preparation of Example 95: N—((S)-1-((3P)-3-(4-chloro-3-(cyclopropanesulfonamido)-1-(2,2-difluoroethyl)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

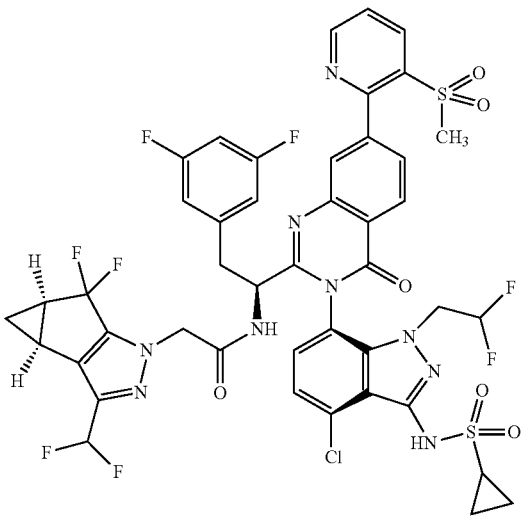

The title compound was prepared according to General Procedure J using 2-chloro-3-(methylsulfonyl)pyridine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.34 min.; observed ion=1036.3 (M+H). 1H NMR (METHANOL-d4, 500 MHz) Shift 8.98 (dd, 1H, J=1.5, 4.8 Hz), 8.69 (dd, 1H, J=1.6, 8.2 Hz), 8.41 (d, 1H, J=8.3 Hz), 8.13 (d, 1H, J=2.1 Hz), 7.8-7.9 (m, 2H), 7.41 (d, 1H, J=7.8 Hz), 7.34 (d, 1H, J=7.7 Hz), 6.7-6.8 (m, 1H), 6.69 (br t, 1H, J=54.8 Hz), 6.5-6.6 (m, 2H), 6.06 (t, 1H, J=55.3 Hz), 4.79 (dd, 1H, J=4.8, 9.5 Hz), 4.6-4.6 (m, 2H), 4.4-4.5 (m, 1H), 3.9-4.0 (m, 1H), 3.4-3.5 (m, 1H), 3.08 (dd, 1H, J=9.4, 14.2 Hz), 2.9-3.0 (m, 4H), 2.43 (ddd, 2H, J=4.0, 7.6, 11.3 Hz), 1.7-1.8 (m, 1H), 1.1-1.2 (m, 2H), 0.9-1.1 (m, 3H)

Preparation of Example 96: N—((S)-1-((3P)-3-(4-chloro-3-(cyclopropanesulfonamido)-1-(2,2-difluoroethyl)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

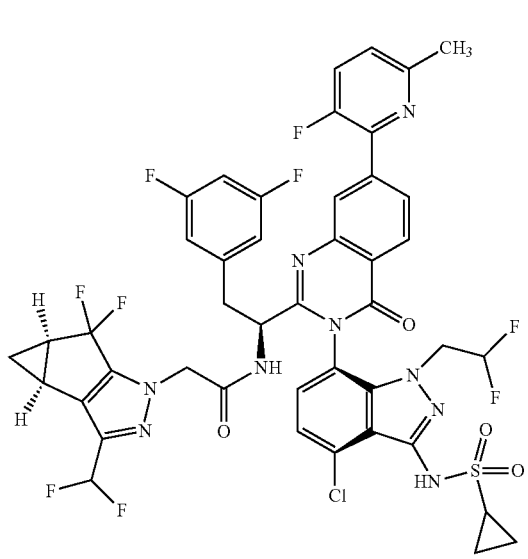

The title compound was prepared according to General Procedure J using 2-chloro-3-fluoro-6-methylpyridine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.46 min.; observed ion=990.3 (M+H). 1H NMR (METHANOL-d4, 500 MHz) Shift 8.44 (t, 1H, J=1.3 Hz), 8.40 (d, 1H, J=8.3 Hz), 8.23 (d, 1H, J=8.1 Hz), 7.70 (dd, 1H, J=8.5, 10.9 Hz), 7.4-7.5 (m, 2H), 7.30 (d, 1H, J=8.0 Hz), 6.8-6.8 (m, 1H), 6.69 (t, 1H, J=54.8 Hz), 6.5-6.6 (m, 2H), 6.05 (t, 1H, J=55.4 Hz), 4.77 (dd, 1H, J=4.8, 9.5 Hz), 4.6-4.7 (m, 2H), 4.40 (br dd, 1H, J=3.9, 15.2 Hz), 3.9-4.0 (m, 1H), 3.4-3.5 (m, 1H), 3.08 (dd, 1H, J=9.5, 14.0 Hz), 2.92 (tt, 1H, J=4.8, 8.0 Hz), 2.67 (s, 3H), 2.4-2.5 (m, 2H), 1.36 (dt, 1H, J=5.4, 7.5 Hz), 1.1-1.1 (m, 2H), 0.9-1.0 (m, 3H)

Preparation of Example 97: N—((S)-1-((3P)-3-(4-chloro-3-(cyclopropanesulfonamido)-1-(2,2-difluoroethyl)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

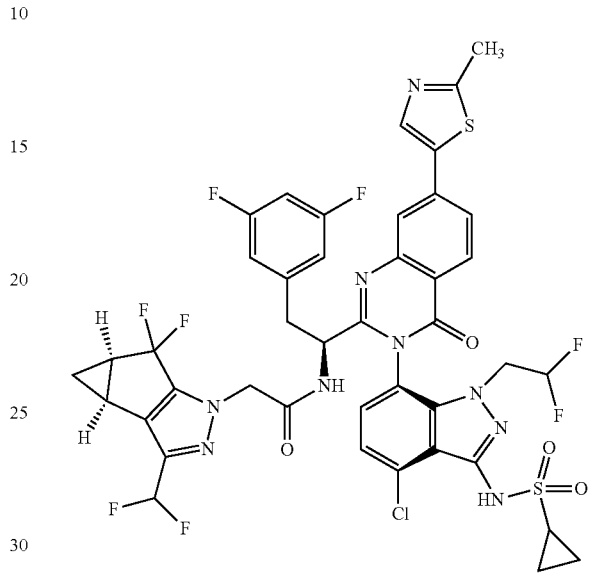

The title compound was prepared according to General Procedure J using 5-bromo-2-methylthiazole as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.44 min.; observed ion=978.3 (M+H). 1H NMR (METHANOL-d4, 500 MHz) Shift 8.37 (d, 1H, J=1.8 Hz), 8.35 (d, 1H, J=8.3 Hz), 8.17 (dd, 1H, J=1.8, 8.3 Hz), 7.73 (s, 1H), 7.40 (br d, 1H, J=7.7 Hz), 7.30 (d, 1H, J=7.7 Hz), 6.80 (tt, 1H, J=2.4, 9.2 Hz), 6.69 (t, 1H, J=54.8 Hz), 6.5-6.6 (m, 2H), 6.04 (t, 1H, J=55.3 Hz), 4.7-4.8 (m, 2H), 4.6-4.6 (m, 1H), 4.3-4.4 (m, 1H), 3.95 (br dd, 1H, J=3.0, 14.0 Hz), 3.4-3.5 (m, 1H), 3.08 (dd, 1H, J=9.5, 14.0 Hz), 2.92 (tt, 1H, J=4.8, 8.0 Hz), 2.64 (d, 3H, J=1.2 Hz), 2.4-2.5 (m, 2H), 1.3-1.4 (m, 1H), 1.1-1.1 (m, 2H), 0.9-1.1 (m, 3H)

Preparation of Example 98: N—((S)-1-((3P)-3-(4-chloro-3-(cyclopropanesulfonamido)-1-(2,2-difluoroethyl)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

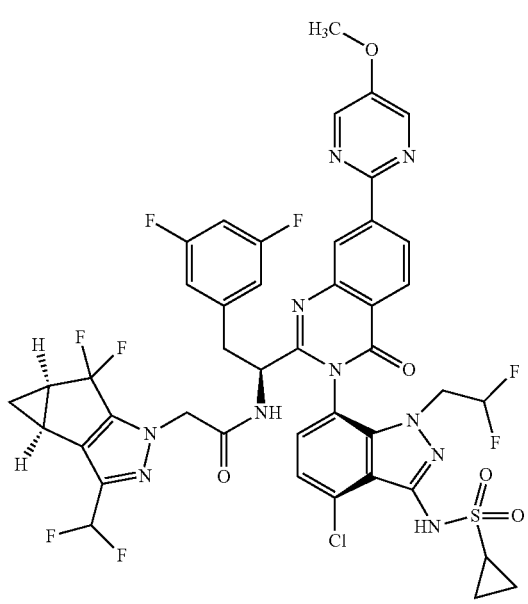

The title compound was prepared according to General Procedure J using 2-chloro-5-methoxypyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.47 min.; observed ion=989.2 (M+H). 1H NMR (METHANOL-d4, 500 MHz) Shift 8.86 (s, 1H), 8.70 (s, 2H), 8.64 (dd, 1H, J=1.8, 8.3 Hz), 8.36 (d, 1H, J=8.1 Hz), 7.40 (d, 1H, J=7.5 Hz), 7.29 (d, 1H, J=7.7 Hz), 6.8-6.8 (m, 1H), 6.70 (br t, 1H, J=54.8 Hz), 6.5-6.6 (m, 2H), 6.04 (t, 1H, J=55.3 Hz), 4.77 (dd, 1H, J=4.8, 9.5 Hz), 4.69 (d, 1H, J=16.7 Hz), 4.61 (d, 1H, J=16.7 Hz), 4.3-4.4 (m, 1H), 4.08 (s, 3H), 3.9-4.0 (m, 1H), 3.4-3.5 (m, 1H), 3.09 (dd, 1H, J=9.4, 14.2 Hz), 2.92 (tt, 1H, J=4.8, 8.0 Hz), 2.4-2.5 (m, 2H), 1.3-1.4 (m, 1H), 1.1-1.1 (m, 2H), 0.9-1.0 (m, 3H)

Preparation of Example 99: N—((S)-1-((3P)-3-(4-chloro-3-(cyclopropanesulfonamido)-1-(2,2-difluoroethyl)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

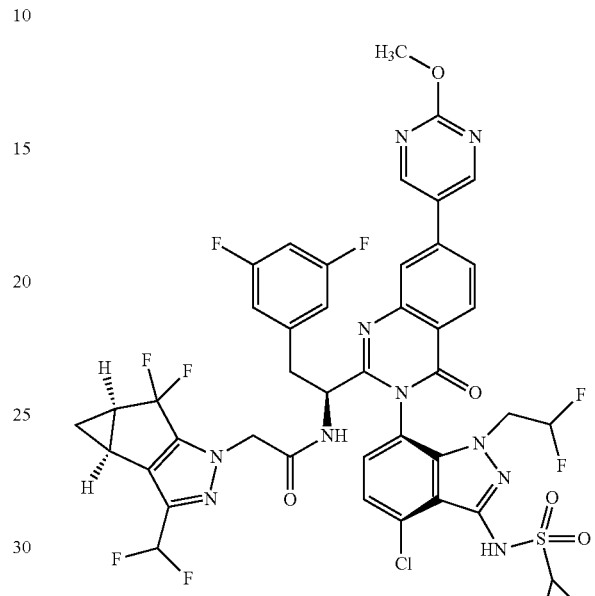

The title compound was prepared according to General Procedure J using 5-bromo-2-methoxypyrimidine as the coupling partner. The experiment afforded the title compound, N—((S)-1-((3P)-3-(4-chloro-3-(cyclopropanesulfonamido)-1-(2,2-difluoroethyl)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.56 min.; observed ion=989.2 (M+H). 1H NMR (METHANOL-d4, 500 MHz) Shift 9.08 (s, 2H), 8.41 (d, 1H, J=8.1 Hz), 8.18 (d, 1H, J=1.8 Hz), 7.99 (dd, 1H, J=1.8, 8.3 Hz), 7.39 (br d, 1H, J=7.5 Hz), 7.27 (d, 1H, J=8.0 Hz), 6.8-6.8 (m, 1H), 6.69 (t, 1H, J=54.8 Hz), 6.5-6.6 (m, 2H), 6.04 (t, 1H, J=55.4 Hz), 4.8-4.9 (m, 1H), 4.76 (dd, 1H, J=4.8, 9.2 Hz), 4.6-4.7 (m, 2H), 4.3-4.4 (m, 1H), 4.14 (s, 2H), 3.9-4.0 (m, 1H), 3.4-3.5 (m, 1H), 3.08 (dd, 1H, J=9.4, 14.2 Hz), 2.92 (tt, 1H, J=4.8, 8.0 Hz), 2.44 (ddd, 2H, J=4.0, 7.7, 11.2 Hz), 1.2-1.4 (m, 1H), 1.1-1.2 (m, 2H), 0.9-1.1 (m, 3H)

233
Preparation of Example 100: N—((S)-1-((3P)-3-(4-chloro-3-(methylsulfonamido)-1-(2,2,2-trifluoroethyl)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

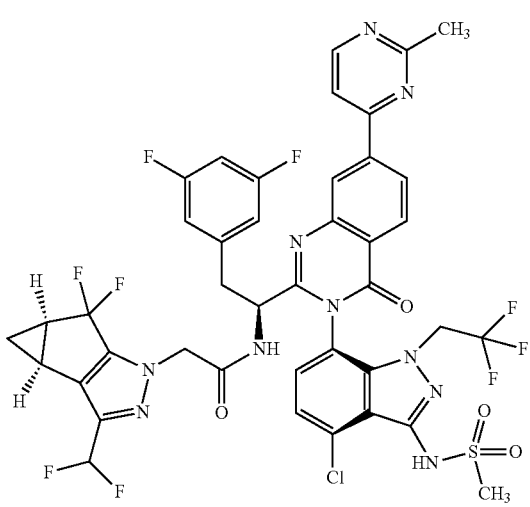

The title compound was prepared according to General Procedure Q using 4-chloro-2-methylpyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.4 min.; observed ion=963 (M−H). 1H NMR (METHANOL-d4, 500 MHz) Shift 8.86 (d, 1H, J=5.4 Hz), 8.68 (t, 1H, J=1.0 Hz), 8.42 (d, 2H, J=1.2 Hz), 8.01 (d, 1H, J=4.8 Hz), 7.4-7.5 (m, 2H), 6.7-6.8 (m, 1H), 6.71 (br t, 1H, J=54.8 Hz), 6.5-6.5 (m, 2H), 4.7-4.8 (m, 3H), 4.66 (s, 1H), 4.21 (br d, 1H, J=7.7 Hz), 3.3-3.4 (m, 1H), 3.25 (s, 3H), 3.04 (dd, 1H, J=9.4, 14.2 Hz), 2.86 (s, 3H), 2.45 (br dd, 2H, J=4.2, 8.3 Hz), 1.37 (br dd, 1H, J=1.0, 6.7 Hz), 1.0-1.0 (m, 1H)

234
Preparation of Example 101: N—((S)-1-((3P)-3-(4-chloro-3-(methylsulfonamido)-1-(2,2,2-trifluoroethyl)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

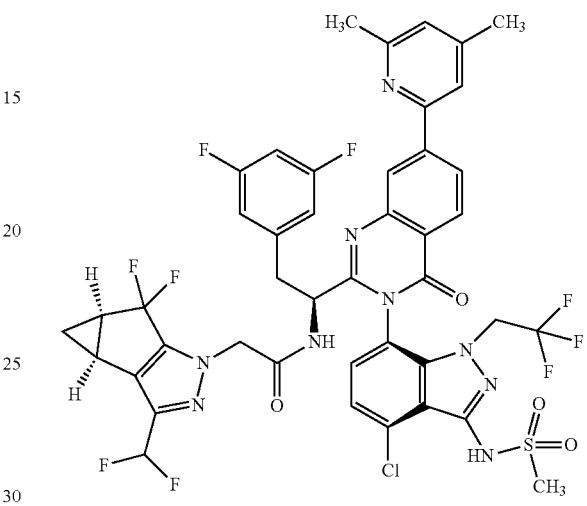

The title compound was prepared according to General Procedure Q using 2-bromo-4,6-dimethylpyridine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.48 min.; observed ion=978.2 (M+H). 1H NMR (METHANOL-d4, 500 MHz) Shift 8.42 (d, 1H, J=1.2 Hz), 8.33 (d, 1H, J=8.3 Hz), 8.20 (dd, 1H, J=1.8, 8.3 Hz), 7.69 (s, 1H), 7.41 (br d, 1H, J=7.7 Hz), 7.32 (d, 1H, J=8.0 Hz), 7.22 (s, 1H), 6.4-6.8 (m, 4H), 4.6-4.8 (m, 4H), 4.18 (dd, 1H, J=8.3, 16.1 Hz), 3.3-3.4 (m, 1H), 3.2-3.2 (m, 3H), 3.01 (dd, 1H, J=9.2, 14.0 Hz), 2.62 (s, 3H), 2.47 (s, 3H), 2.4-2.4 (m, 2H), 1.35 (br dd, 1H, J=1.8, 8.0 Hz), 0.99 (dt, 1H, J=1.8, 3.7 Hz)

235

Preparation of Example 102: N—((S)-1-((3P)-3-(4-chloro-3-(methylsulfonamido)-1-(2,2,2-trifluoroethyl)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

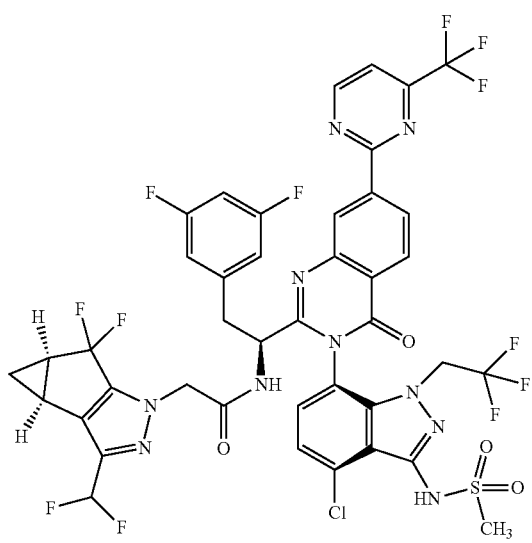

The title compound was prepared according to General Procedure Q using 2-chloro-4-(trifluoromethyl)pyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.56 min.; observed ion=1019.2 (M+H). 1H NMR (METHANOL-d4, 500 MHz) Shift 9.29 (d, 1H, J=5.1 Hz), 8.99 (d, 1H, J=1.8 Hz), 8.74 (dd, 1H, J=1.8, 8.3 Hz), 8.40 (d, 1H, J=8.0 Hz), 7.90 (d, 1H, J=5.1 Hz), 7.4-7.4 (m, 2H), 6.7-6.8 (m, 1H), 6.67 (br t, 1H, J=54.8 Hz), 6.4-6.5 (m, 2H), 4.6-4.8 (m, 4H), 4.20 (dd, 1H, J=8.5, 16.2 Hz), 3.3-3.4 (m, 1H), 3.22 (s, 3H), 3.02 (dd, 1H, J=9.5, 14.3 Hz), 2.4-2.5 (m, 2H), 1.3-1.4 (m, 1H), 0.99 (dt, 1H, J=2.2, 3.7 Hz)

236

Preparation of Example 103: N—((S)-1-((3P)-3-(4-chloro-3-(methylsulfonamido)-1-(2,2,2-trifluoroethyl)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

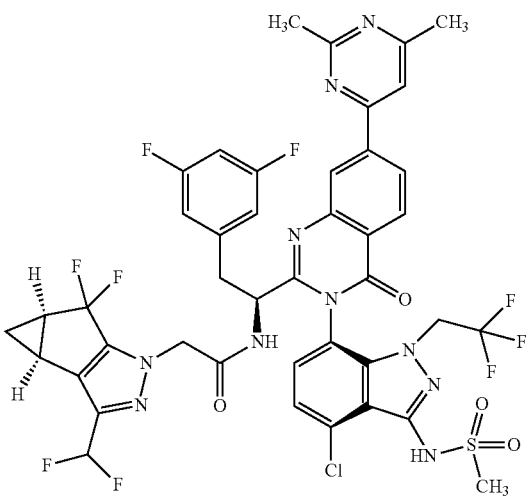

The title compound was prepared according to General Procedure Q using 4-chloro-2,6-dimethylpyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.42 min.; observed ion=979.2 (M+H). 1H NMR (METHANOL-d4, 500 MHz) Shift 8.63 (d, 1H, J=1.5 Hz), 8.37 (s, 1H), 8.3-8.4 (m, 1H), 7.88 (s, 1H), 7.4-7.5 (m, 1H), 7.35 (d, 1H, J=8.0 Hz), 6.7-6.8 (m, 1H), 6.69 (br t, 1H, J=54.8 Hz), 6.5-6.5 (m, 2H), 4.6-4.8 (m, 4H), 4.1-4.2 (m, 1H), 3.3-3.4 (m, 1H), 3.22 (s, 3H), 3.01 (dd, 1H, J=9.5, 14.0 Hz), 2.79 (s, 3H), 2.63 (s, 3H), 2.4-2.5 (m, 2H), 1.3-1.4 (m, 1H), 0.99 (td, 1H, J=2.1, 3.6 Hz)

237

Preparation of Example 104: N—((S)-1-((3P)-3-(4-chloro-3-(methylsulfonamido)-1-(2,2,2-trifluoroethyl)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

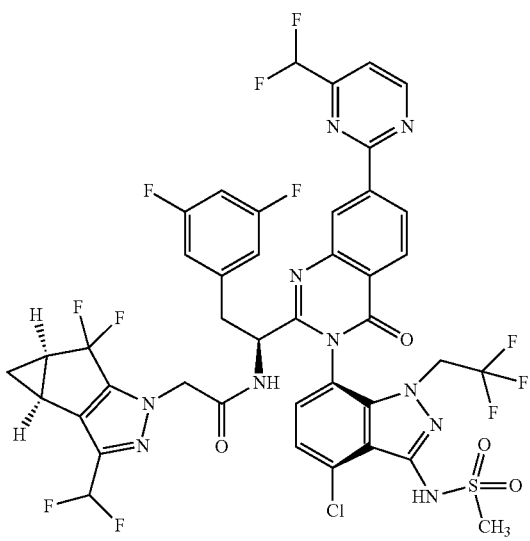

The title compound was prepared according to General Procedure Q using 2-chloro-4-(difluoromethyl)pyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.5 min.; observed ion=999.2 (M−H). 1H NMR (METHANOL-d4, 500 MHz) Shift 9.19 (d, 1H, J=5.1 Hz), 8.98 (d, 1H, J=1.2 Hz), 8.73 (dd, 1H, J=1.8, 8.3 Hz), 8.38 (d, 1H, J=8.3 Hz), 7.76 (d, 1H, J=5.1 Hz), 7.43 (d, 1H, J=8.0 Hz), 7.37 (d, 1H, J=8.0 Hz), 6.5-7.0 (m, 5H), 4.6-4.8 (m, 4H), 4.20 (d, 1H, J=8.0 Hz), 3.3-3.4 (m, 1H), 3.2-3.3 (m, 3H), 3.02 (dd, 1H, J=9.7, 14.2 Hz), 2.4-2.5 (m, 2H), 1.34 (br d, 1H, J=6.6 Hz), 0.99 (td, 1H, J=2.1, 3.6 Hz)

238

Preparation of Example 105: N—((S)-1-((3P)-3-(4-chloro-3-(methylsulfonamido)-1-(2,2,2-trifluoroethyl)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

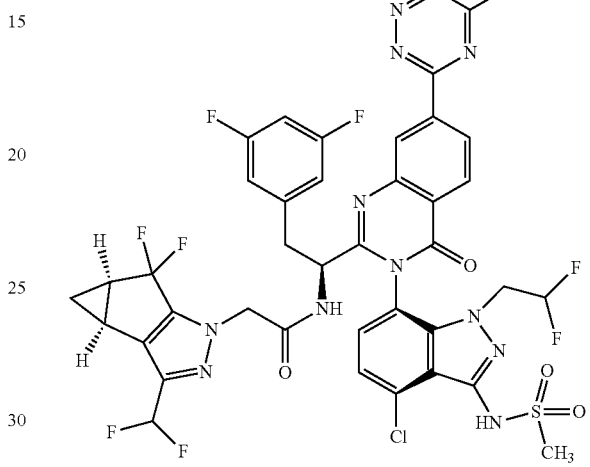

The title compound was prepared according to General Procedure Q using 3-chloro-5,6-dimethyl-1,2,4-triazine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.43 min.; observed ion=980.1 (M+H). 1H NMR (METHANOL-d4, 500 MHz) Shift 8.97 (d, 1H, J=1.5 Hz), 8.72 (dd, 1H, J=1.5, 8.3 Hz), 8.42 (d, 1H, J=8.6 Hz), 7.4-7.5 (m, 2H), 6.8-6.8 (m, 1H), 6.71 (br t, 1H, J=54.8 Hz), 6.51 (dd, 2H, J=1.9, 7.9 Hz), 4.7-4.8 (m, 4H), 4.22 (dd, 1H, J=8.3, 16.1 Hz), 3.3-3.4 (m, 1H), 3.25 (s, 3H), 3.04 (dd, 1H, J=9.5, 14.0 Hz), 2.81 (s, 3H), 2.75 (s, 3H), 2.4-2.5 (m, 2H), 1.3-1.4 (m, 1H), 1.01 (dt, 1H, J=1.8, 3.7 Hz)

Preparation of Example 106: N—((S)-1-((3P)-3-(4-chloro-3-(methylsulfonamido)-1-(2,2,2-trifluoroethyl)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

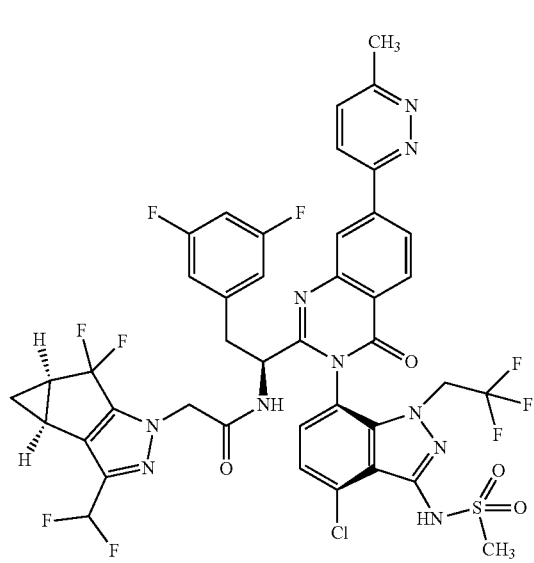

The title compound was prepared according to General Procedure Q using 3-chloro-6-methylpyridazine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.34 min.; observed ion=965.2 (M+H). 1H NMR (METHANOL-d4,500 MHz) Shift 8.62 (d, 1H, J=1.5 Hz), 8.43 (d, 1H, J=8.3 Hz), 8.35 (dd, 1H, J=1.5, 8.3 Hz), 8.30 (d, 1H, J=8.6 Hz), 7.83 (d, 1H, J=8.6 Hz), 7.44 (br d, 1H, J=7.7 Hz), 7.37 (d, 1H, J=8.0 Hz), 6.8-6.8 (m, 1H), 6.70 (t, 1H, J=54.7 Hz), 6.5-6.5 (m, 2H), 4.7-4.8 (m, 4H), 4.22 (dd, 1H, J=8.3, 16.1 Hz), 3.3-3.4 (m, 1H), 3.2-3.3 (m, 3H), 3.04 (dd, 1H, J=9.5, 14.0 Hz), 2.82 (s, 3H), 2.4-2.5 (m, 2H), 1.3-1.4 (m, 1H), 1.0-1.0 (m, 1H)

Preparation of Example 107: N—((S)-1-((3P)-3-(4-chloro-3-(methylsulfonamido)-1-(2,2,2-trifluoroethyl)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

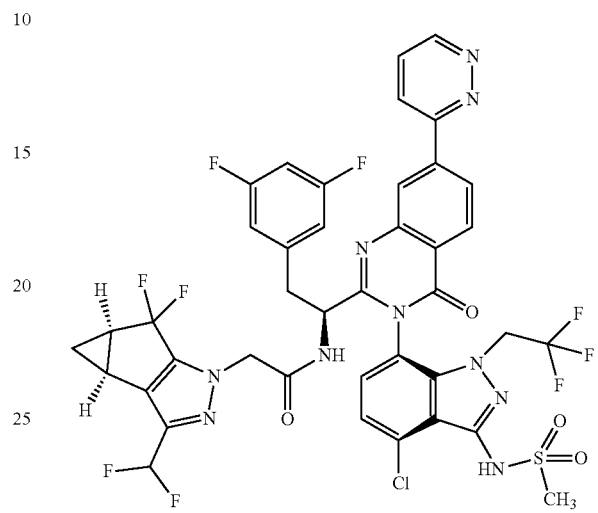

The title compound was prepared according to General Procedure Q using 3-chloropyridazine as the coupling partner. The experiment afforded the title compound, N—((S)-1-((3P)-3-(4-chloro-3-(methylsulfonamido)-1-(2,2,2-trifluoroethyl)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.31 min.; observed ion=951.2 (M+H). 1H NMR (METHANOL-d4, 500 MHz) Shift 9.31 (dd, 1H, J=1.5, 5.1 Hz), 8.65 (d, 1H, J=1.2 Hz), 8.4-8.5 (m, 3H), 7.95 (dd, 1H, J=5.1, 8.6 Hz), 7.45 (d, 1H, J=7.7 Hz), 7.38 (d, 1H, J=8.0 Hz), 6.5-6.8 (m, 4H), 4.7-4.8 (m, 4H), 4.23 (dd, 1H, J=8.2, 16.2 Hz), 3.3-3.4 (m, 1H), 3.2-3.3 (m, 3H), 3.05 (dd, 1H, J=9.5, 14.3 Hz), 2.4-2.5 (m, 2H), 1.3-1.4 (m, 1H), 1.01 (dt, 1H, J=1.9, 3.7 Hz)

241

Preparation of Example 108: N—((S)-1-((3P)-3-(4-chloro-3-(methylsulfonamido)-1-(2,2,2-trifluoroethyl)-1H-indazol-7-yl)-7-(2-isopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

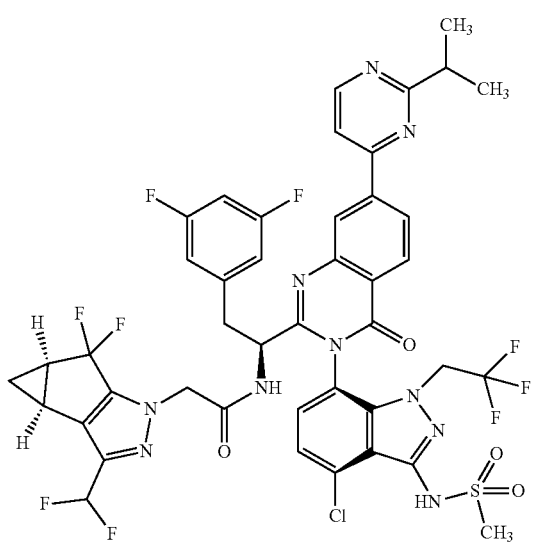

The title compound was prepared according to General Procedure Q using 4-chloro-2-isopropylpyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(2-isopropylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.54 min.; observed ion=993.3 (M+H). 1H NMR (METHANOL-d4, 500 MHz) Shift 8.88 (d, 1H, J=5.4 Hz), 8.76 (d, 1H, J=0.9 Hz), 8.4-8.5 (m, 2H), 8.01 (d, 1H, J=5.4 Hz), 7.45 (br d, 1H, J=7.5 Hz), 7.39 (d, 1H, J=8.0 Hz), 6.5-6.8 (m, 4H), 4.7-4.8 (m, 4H), 4.22 (dd, 1H, J=8.5, 16.2 Hz), 3.4-3.4 (m, 1H), 3.2-3.3 (m, 3H), 3.05 (dd, 1H, J=9.7, 13.9 Hz), 2.4-2.5 (m, 2H), 1.49 (d, 6H, J=6.9 Hz), 1.36 (br dd, 2H, J=1.8, 7.7 Hz), 0.9-1.0 (m, 1H)

242

Preparation of Example 109: N—((S)-1-((3P)-3-(4-chloro-3-(methylsulfonamido)-1-(2,2,2-trifluoroethyl)-1H-indazol-7-yl)-4-oxo-7-(2,5,6-trimethylpyrimidin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

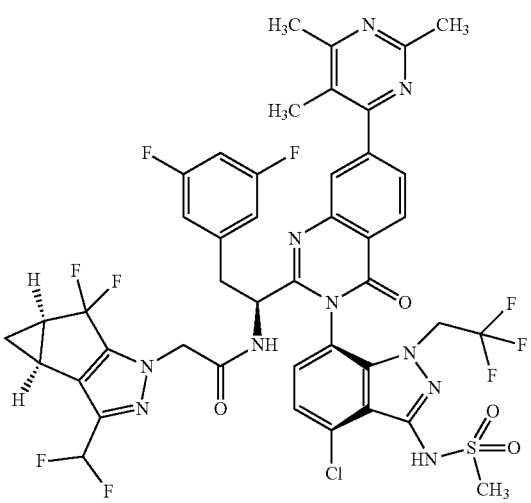

The title compound was prepared according to General Procedure Q using 4-chloro-2,5,6-trimethylpyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-4-oxo-7-(2,5,6-trimethylpyrimidin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.39 min.; observed ion=993.2 (M+H). 1H NMR (METHANOL-d4, 500 MHz) Shift 8.40 (d, 1H, J=8.0 Hz), 8.00 (d, 1H, J=1.2 Hz), 7.8-7.8 (m, 1H), 7.4-7.5 (m, 1H), 7.4-7.4 (m, 1H), 6.7-6.8 (m, 1H), 6.69 (t, 1H, J=54.8 Hz), 6.5-6.5 (m, 2H), 4.6-4.8 (m, 4H), 4.21 (dd, 1H, J=8.0, 16.4 Hz), 3.3-3.4 (m, 1H), 3.2-3.3 (m, 3H), 3.03 (dd, 1H, J=9.4, 14.2 Hz), 2.72 (s, 3H), 2.65 (s, 3H), 2.4-2.5 (m, 2H), 2.35 (s, 3H), 1.3-1.4 (m, 1H), 1.0-1.0 (m, 1H)

243

Preparation of Example 110: N—((S)-1-((3P)-3-(4-chloro-3-(methylsulfonamido)-1-(2,2,2-trifluoroethyl)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

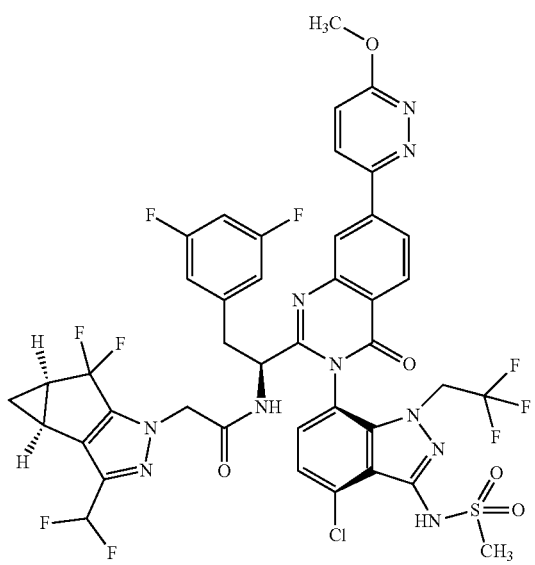

The title compound was prepared according to General Procedure Q using 3-chloro-6-methoxypyridazine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.41 min.; observed ion=981.2 (M+H). 1H NMR (METHANOL-d4, 500 MHz) Shift 8.53 (d, 1H, J=1.8 Hz), 8.41 (d, 1H, J=8.3 Hz), 8.3-8.3 (m, 2H), 7.3-7.5 (m, 3H), 6.8-6.8 (m, 1H), 6.70 (t, 1H, J=54.8 Hz), 6.5-6.5 (m, 2H), 4.7-4.8 (m, 4H), 4.1-4.2 (m, 4H), 3.4-3.4 (m, 1H), 3.24 (s, 3H), 3.04 (dd, 1H, J=9.5, 14.3 Hz), 2.4-2.5 (m, 2H), 1.3-1.4 (m, 1H), 1.01 (td, 1H, J=2.1, 3.6 Hz)

244

Preparation of Example 111: N—((S)-1-((3P)-3-(4-chloro-3-(methylsulfonamido)-1-(2,2,2-trifluoroethyl)-1H-indazol-7-yl)-7-(4-ethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

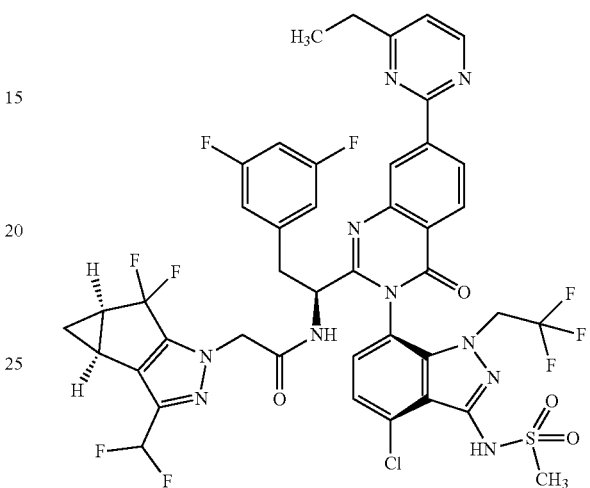

The title compound was prepared according to General Procedure Q using 2-chloro-4-ethylpyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(4-ethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.55 min.; observed ion=979.2 (M+H). 1H NMR (METHANOL-d4, 500 MHz) Shift 8.95 (d, 1H, J=1.2 Hz), 8.85 (d, 1H, J=5.1 Hz), 8.71 (dd, 1H, J=1.5, 8.3 Hz), 8.38 (d, 1H, J=8.3 Hz), 7.4-7.5 (m, 3H), 6.8-6.8 (m, 1H), 6.71 (t, 1H, J=54.7 Hz), 6.5-6.5 (m, 2H), 4.7-4.8 (m, 4H), 4.22 (dd, 1H, J=8.5, 16.2 Hz), 3.3-3.4 (m, 1H), 3.25 (s, 3H), 3.0-3.1 (m, 3H), 2.4-2.5 (m, 2H), 1.4-1.5 (m, 3H), 1.3-1.4 (m, 1H), 1.0-1.0 (m, 1H)

245

Preparation of Example 112: N—((S)-1-((3P)-3-(4-chloro-3-(methylsulfonamido)-1-(2,2,2-trifluoroethyl)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

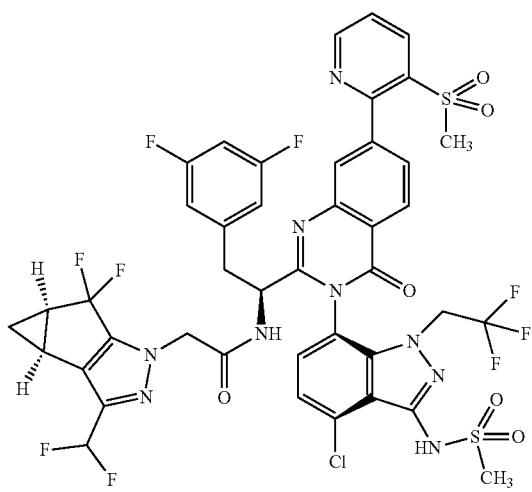

The title compound was prepared according to General Procedure Q using 2-chloro-3-(methylsulfonyl)pyridine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.35 min.; observed ion=1028.2 (M+H). 1H NMR (METHANOL-d4,500 MHz) Shift 8.98 (dd, 1H, J=1.6, 4.9 Hz), 8.69 (d, 1H, J=7.9 Hz), 8.39 (d, 1H, J=8.2 Hz), 8.11 (d, 1H, J=1.2 Hz), 7.8-7.9 (m, 2H), 7.4-7.5 (m, 2H), 6.79 (br t, 1H, J=2.4 Hz), 6.69 (br t, 1H, J=54.8 Hz), 6.50 (br d, 2H, J=6.3 Hz), 4.7-4.8 (m, 3H), 4.6-4.7 (m, 1H), 4.24 (s, 1H), 3.3-3.4 (m, 1H), 3.25 (s, 3H), 3.03 (dd, 1H, J=9.5, 14.0 Hz), 2.96 (s, 3H), 2.44 (ddd, 2H, J=3.9, 7.5, 11.3 Hz), 1.37 (br d, 1H, J=7.5 Hz), 1.01 (br dd, 1H, J=1.8, 3.6 Hz)

246

Preparation of Example 113: N—((S)-1-((3P)-3-(4-chloro-3-(methylsulfonamido)-1-(2,2,2-trifluoroethyl)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

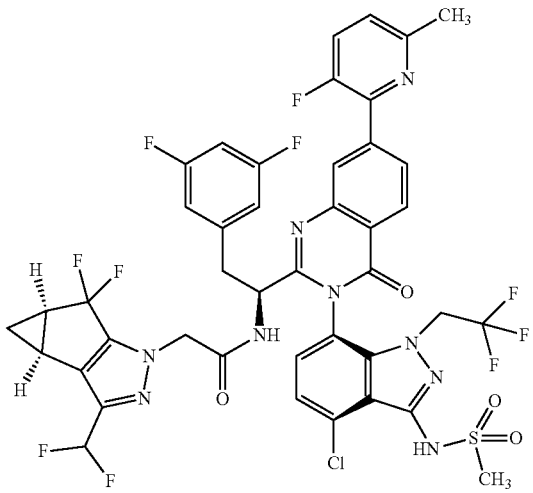

The title compound was prepared according to General Procedure Q using 2-chloro-3-fluoro-6-methylpyridine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.53 min.; observed ion=982.2 (M+H). 1H NMR (METHANOL-d4, 500 MHz) Shift 8.43 (s, 1H), 8.38 (d, 1H, J=8.3 Hz), 8.23 (td, 1H, J=1.3, 8.5 Hz), 7.70 (dd, 1H, J=8.5, 10.9 Hz), 7.4-7.5 (m, 3H), 6.8-6.8 (m, 1H), 6.70 (br t, 1H, J=54.7 Hz), 6.50 (d, 2H, J=6.7 Hz), 4.6-4.8 (m, 4H), 4.22 (dd, 1H, J=8.3, 16.4 Hz), 3.3-3.4 (m, 1H), 3.2-3.3 (m, 3H), 3.04 (dd, 1H, J=9.5, 14.3 Hz), 2.67 (s, 3H), 2.45 (td, 2H, J=3.6, 7.4 Hz), 1.3-1.4 (m, 1H), 1.0-1.0 (m, 1H)

247

Preparation of Example 114: N—((S)-1-((3P)-3-(4-chloro-3-(methylsulfonamido)-1-(2,2,2-trifluoro-ethyl)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

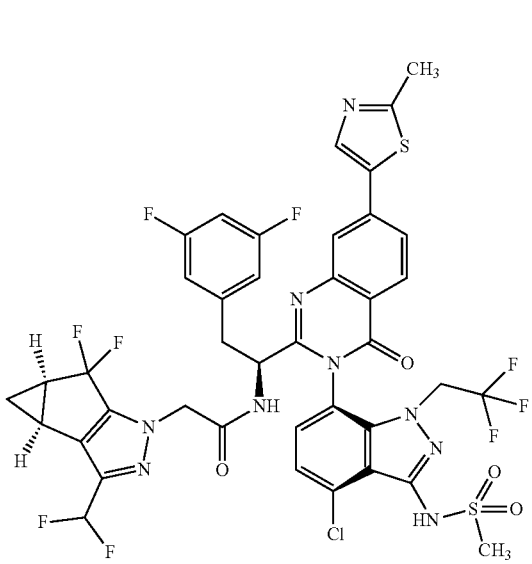

The title compound was prepared according to General Procedure Q using 5-bromo-2-methylthiazole as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=970.4 (M+H). 1H NMR (METHANOL-d4, 500 MHz) Shift 8.37 (d, 1H, J=1.8 Hz), 8.33 (d, 1H, J=8.3 Hz), 8.17 (dd, 1H, J=1.8, 8.3 Hz), 7.73 (d, 1H, J=1.2 Hz), 7.44 (br d, 1H, J=7.5 Hz), 7.38 (d, 1H, J=8.0 Hz), 6.8-6.8 (m, 1H), 6.70 (br t, 1H, J=54.7 Hz), 6.50 (d, 2H, J=6.6 Hz), 4.7-4.8 (m, 4H), 4.2-4.3 (m, 1H), 3.3-3.4 (m, 1H), 3.2-3.3 (m, 3H), 3.03 (dd, 1H, J=9.7, 14.2 Hz), 2.64 (d, 3H, J=1.2 Hz), 2.4-2.5 (m, 2H), 1.3-1.4 (m, 1H), 1.01 (td, 1H, J=2.1, 3.6 Hz)

248

Preparation of Example 115: N—((S)-1-((3P)-3-(4-chloro-3-(methylsulfonamido)-1-(2,2,2-trifluoro-ethyl)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

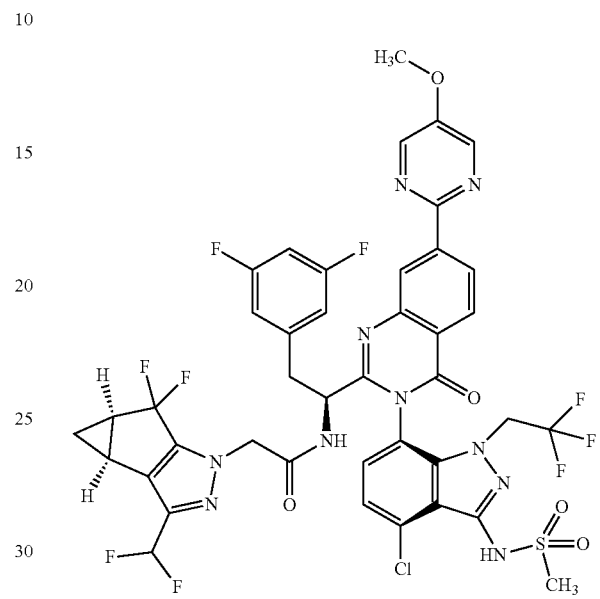

The title compound was prepared according to General Procedure Q using 2-chloro-5-methoxypyrimidine as the coupling partner. The experiment afforded the title compound, N—((S)-1-((3P)-3-(4-chloro-3-(methylsulfona-mido)-1-(2,2,2-trifluoroethyl)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.47 min.; observed ion=981.2 (M+H). 1H NMR (METHANOL-d4, 500 MHz) Shift 8.83 (d, 1H, J=2.1 Hz), 8.68 (s, 2H), 8.61 (dd, 1H, J=1.8, 8.3 Hz), 8.32 (d, 1H, J=8.9 Hz), 7.42 (br d, 1H, J=7.7 Hz), 7.34 (d, 1H, J=8.0 Hz), 6.7-6.8 (m, 1H), 6.68 (br t, 1H, J=54.8 Hz), 6.49 (d, 2H, J=6.6 Hz), 4.6-4.8 (m, 4H), 4.1-4.2 (m, 1H), 4.05 (s, 3H), 3.3-3.4 (m, 1H), 3.2-3.2 (m, 3H), 3.02 (dd, 1H, J=9.5, 14.3 Hz), 2.43 (td, 2H, J=4.0, 8.0 Hz), 1.35 (br dd, 1H, J=1.5, 6.9 Hz), 0.99 (td, 1H, J=2.1, 3.6 Hz)

249

Preparation of Example 116: N—((S)-1-((3P)-3-(4-chloro-3-(methylsulfonamido)-1-(2,2,2-trifluoroethyl)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

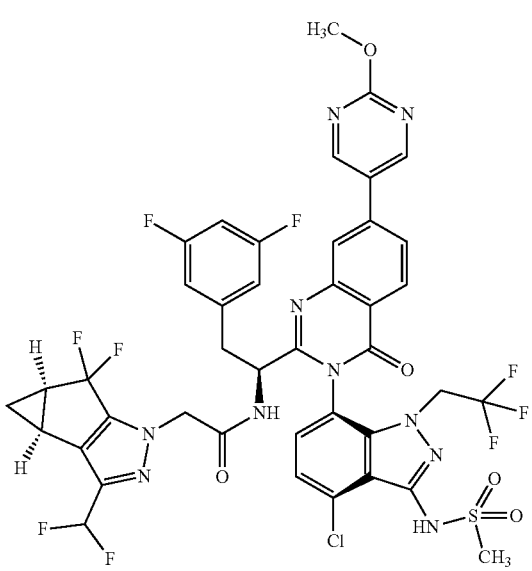

The title compound was prepared according to General Procedure Q using 5-bromo-2-methoxypyrimidine as the coupling partner. The experiment afforded the title compound, N—((S)-1-((3P)-3-(4-chloro-3-(methylsulfonamido)-1-(2,2,2-trifluoroethyl)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.39 min.; observed ion=981.3 (M+H). 1H NMR (METHANOL-d4, 500 MHz) Shift 9.05 (s, 2H), 8.36 (d, 1H, J=8.3 Hz), 8.14 (d, 1H, J=1.8 Hz), 7.97 (dd, 1H, J=1.8, 8.3 Hz), 7.42 (d, 1H, J=8.0 Hz), 7.32 (d, 1H, J=8.0 Hz), 6.5-6.8 (m, 2H), 6.48 (dd, 2H, J=1.9, 7.9 Hz), 4.7-4.8 (m, 4H), 4.19 (s, 1H), 4.12 (s, 3H), 3.3-3.4 (m, 1H), 3.23 (s, 3H), 3.01 (dd, 1H, J=9.5, 14.0 Hz), 2.42 (dt, 2H, J=4.0, 7.4 Hz), 1.35 (br d, 1H, J=7.2 Hz), 0.99 (br dd, 1H, J=2.1, 3.6 Hz)

250

Preparation of Example 117: N—((S)-1-((3P)-3-(4-chloro-1-methyl-3-(methylsulfonamido)-1H-indazol-7-yl)-7-(6-(difluoromethyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

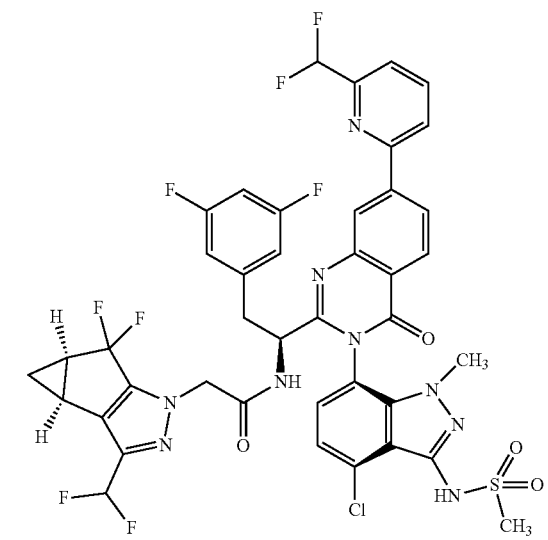

The title compound was prepared according to General Procedure D using 2-bromo-6-(difluoromethyl)pyridine as the coupling partner. The experiment afforded the title compound, N—((S)-1-((3P)-3-(4-chloro-1-methyl-3-(methylsulfonamido)-1H-indazol-7-yl)-7-(6-(difluoromethyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.42 min.; observed ion=930.1 (M−H). 1H NMR (METHANOL-d4, 500 MHz) Shift 9.2-9.2 (m, 1H), 8.88 (d, 1H, J=1.5 Hz), 8.47 (s, 1H), 8.45 (d, 1H, J=8.0 Hz), 8.24 (d, 1H, J=1.5 Hz), 8.04 (dd, 1H, J=1.8, 8.0 Hz), 7.33 (d, 1H, J=8.0 Hz), 7.23 (d, 1H, J=7.7 Hz), 7.09 (t, 1H, J=55.3 Hz), 6.6-6.8 (m, 4H), 4.8-4.9 (m, 1H), 4.54 (d, 2H, J=3.0 Hz), 3.64 (s, 3H), 3.51 (dd, 1H, J=5.1, 14.0 Hz), 3.26 (s, 3H), 3.13 (dd, 1H, J=9.4, 14.2 Hz), 2.43 (dt, 2H, J=3.7, 7.5 Hz), 1.3-1.4 (m, 1H), 1.01 (br dd, 1H, J=1.8, 3.6 Hz)

251

Preparation of Example 118: N—((S)-1-((3P)-3-(4-chloro-1-methyl-3-(methylsulfonamido)-1H-indazol-7-yl)-7-(2-(hydroxymethyl)-6-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

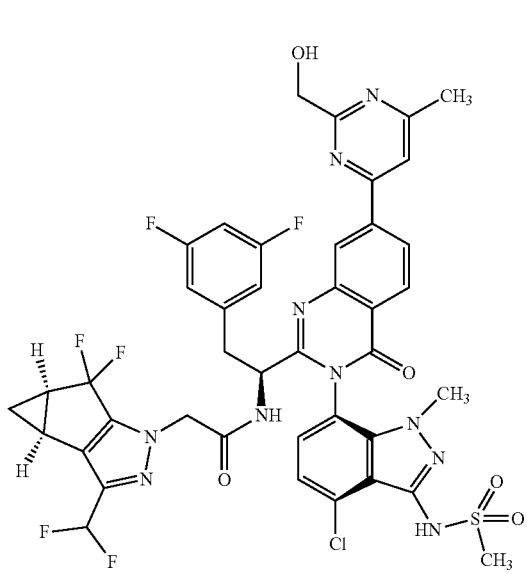

The title compound was prepared according to General Procedure D using (4-chloro-6-methylpyrimidin-2-yl)methanol as the coupling partner. The experiment afforded the title compound, N—((S)-1-((3P)-3-(4-chloro-1-methyl-3-(methylsulfonamido)-1H-indazol-7-yl)-7-(2-(hydroxymethyl)-6-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.31 min.; observed ion=927.3 (M+H). 1H NMR (METHANOL-d4, 500 MHz) Shift 8.75 (d, 1H, J=0.9 Hz), 8.4-8.5 (m, 2H), 7.99 (s, 1H), 7.31 (d, 1H, J=7.7 Hz), 7.22 (d, 1H, J=7.7 Hz), 6.8-6.8 (m, 1H), 6.71 (br t, 1H, J=54.7 Hz), 6.65 (dd, 2H, J=2.2, 8.2 Hz), 4.9-4.9 (m, 1H), 4.8-4.9 (m, 2H), 4.53 (s, 2H), 3.64 (s, 3H), 3.4-3.5 (m, 1H), 3.25 (s, 3H), 3.13 (dd, 1H, J=8.9, 14.0 Hz), 2.70 (s, 3H), 2.4-2.5 (m, 2H), 1.36 (br d, 1H, J=5.7 Hz), 1.01 (br dd, 1H, J=1.9, 3.4 Hz)

252

Preparation of Example 119: N—((S)-1-((3P)-3-(4-chloro-1-methyl-3-(methylsulfonamido)-1H-indazol-7-yl)-7-(5-fluoro-2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

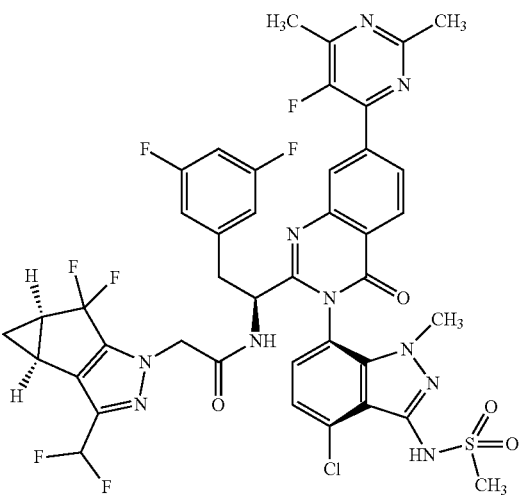

The title compound was prepared according to General Procedure D using 4-chloro-5-fluoro-2,6-dimethylpyrimidine as the coupling partner. The experiment afforded the title compound, N—((S)-1-((3P)-3-(4-chloro-1-methyl-3-(methylsulfonamido)-1H-indazol-7-yl)-7-(5-fluoro-2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.49 min.; observed ion=929.2 (M+H). 1H NMR (METHANOL-d4, 500 MHz) Shift 8.57 (s, 1H), 8.44 (d, 1H, J=8.3 Hz), 8.32 (td, 1H, J=1.3, 8.5 Hz), 7.32 (d, 1H, J=7.7 Hz), 7.25 (d, 1H, J=7.7 Hz), 6.79 (br t, 1H, J=2.4 Hz), 6.70 (br t, 1H, J=54.7 Hz), 6.63 (dd, 2H, J=2.1, 8.0 Hz), 4.8-4.9 (m, 1H), 4.54 (d, 2H, J=5.1 Hz), 3.64 (s, 3H), 3.50 (dd, 1H, J=5.1, 14.0 Hz), 3.26 (s, 3H), 3.13 (dd, 1H, J=9.2, 14.0 Hz), 2.77 (d, 3H, J=0.9 Hz), 2.64 (d, 3H, J=2.7 Hz), 2.44 (br dd, 2H, J=3.9, 7.5 Hz), 1.3-1.4 (m, 1H), 1.01 (br dd, 1H, J=2.1, 3.6 Hz).

Preparation of Example 120: N—((S)-1-((3P)-3-(4-chloro-1-methyl-3-(methylsulfonamido)-1H-indazol-7-yl)-7-(3-(difluoromethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 121: N—((S)-1-((3P)-3-(4-chloro-1-(2,2-difluoroethyl)-3-(methylsulfonamido)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[1,2-c]pyrazol-1-yl)acetamide

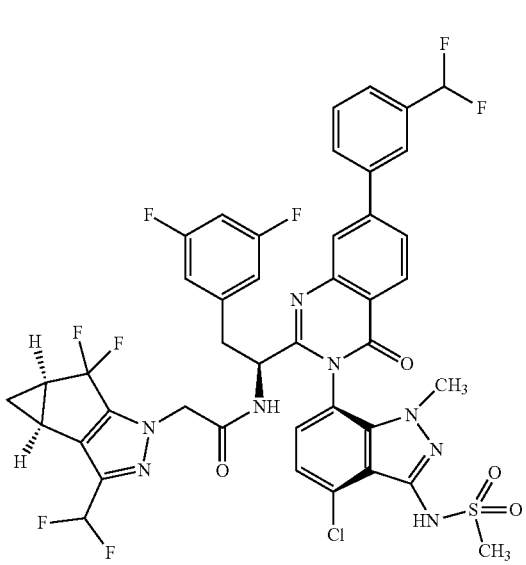

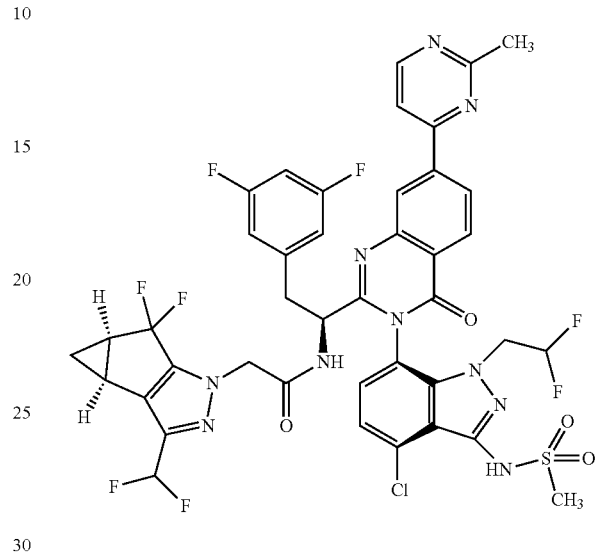

The title compound was prepared according to General Procedure D using 1-bromo-3-(difluoromethyl)benzene as the coupling partner. The experiment afforded the title compound, N—((S)-1-((3P)-3-(4-chloro-1-methyl-3-(methylsulfonamido)-1H-indazol-7-yl)-7-(3-(difluoromethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.55 min.; observed ion=929 (M–H). 1H NMR (METHANOL-d4, 500 MHz) Shift 8.40 (d, 1H, J=8.1 Hz), 8.17 (d, 1H, J=1.5 Hz), 8.0-8.0 (m, 3H), 7.7-7.7 (m, 2H), 7.32 (d, 1H, J=7.7 Hz), 7.23 (d, 1H, J=8.0 Hz), 6.94 (t, 1H, J=56.0 Hz), 6.80 (br t, 1H, J=2.4 Hz), 6.70 (br t, 1H, J=54.8 Hz), 6.64 (dd, 2H, J=2.4, 8.0 Hz), 4.8-4.9 (m, 1H), 4.55 (d, 2H, J=4.5 Hz), 3.64 (s, 3H), 3.50 (dd, 1H, J=4.9, 14.2 Hz), 3.26 (s, 3H), 3.13 (dd, 1H, J=9.2, 14.3 Hz), 2.43 (dt, 2H, J=4.2, 7.6 Hz), 1.36 (br d, 1H, J=7.5 Hz), 1.01 (br dd, 1H, J=1.9, 3.4 Hz)

The title compound was prepared according to General Procedure I using 4-chloro-2-methylpyrimidine as the coupling partner. The experiment afforded the title compound, N—((S)-1-((3P)-3-(4-chloro-1-(2,2-difluoroethyl)-3-(methylsulfonamido)-1H-indazol-7-yl)-7-(2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.38 min.; observed ion=947.2 (M+H). 1H NMR (METHANOL-d4, 500 MHz) δ 8.83 (d, 1H, J=5.4 Hz), 8.67 (s, 1H), 8.4-8.4 (m, 2H), 7.99 (d, 1H, J=5.4 Hz), 7.3-7.4 (m, 1H), 7.28 (d, 1H, J=7.7 Hz), 6.5-6.8 (m, 4H), 6.02 (br d, 1H, J=8.3 Hz), 6.02 (br t, 1H, J=55.3 Hz), 4.75 (dd, 1H, J=4.8, 9.2 Hz), 4.6-4.6 (m, 2H), 3.2-3.3 (m, 3H), 3.07 (dd, 1H, J=9.4, 14.2 Hz), 2.83 (s, 3H), 2.4-2.5 (m, 2H), 1.1-1.2 (m, 3H), 0.99 (td, 1H, J=2.1, 3.6 Hz)

255

Preparation of Example 122: N—((S)-1-((3P)-3-(4-chloro-1-(2,2-difluoroethyl)-3-(methylsulfonamido)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

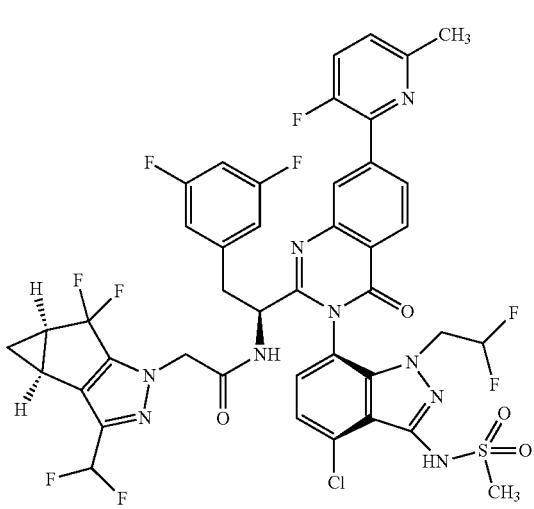

The title compound was prepared according to General Procedure I using 2-chloro-3-fluoro-6-methylpyridine as the coupling partner. The experiment afforded the title compound, N—((S)-1-((3P)-3-(4-chloro-1-(2,2-difluoroethyl)-3-(methylsulfonamido)-1H-indazol-7-yl)-7-(3-fluoro-6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.52 min.; observed ion=964.2 (M+H). 1H NMR (METHANOL-d4, 500 MHz) Shift 8.42 (t, 1H, J=1.3 Hz), 8.37 (d, 1H, J=8.3 Hz), 8.20 (td, 1H, J=1.3, 8.5 Hz), 7.68 (dd, 1H, J=8.5, 10.9 Hz), 7.41 (dd, 1H, J=3.6, 8.6 Hz), 7.37 (d, 1H, J=7.7 Hz), 7.27 (d, 1H, J=7.7 Hz), 6.5-6.8 (m, 4H), 6.02 (br d, 1H, J=8.3 Hz), 6.02 (br t, 1H, J=55.3 Hz), 4.7-4.8 (m, 1H), 4.5-4.7 (m, 2H), 4.35 (br d, 1H, J=4.2 Hz), 3.8-4.0 (m, 1H), 3.4-3.4 (m, 1H), 3.24 (s, 3H), 3.07 (dd, 1H, J=9.4, 14.2 Hz), 2.64 (s, 3H), 2.4-2.5 (m, 2H), 1.3-1.4 (m, 1H), 1.0-1.0 (m, 1H)

256

Preparation of Example 123: N—((S)-1-((3P)-3-(4-chloro-1-(2,2-difluoroethyl)-3-(methylsulfonamido)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

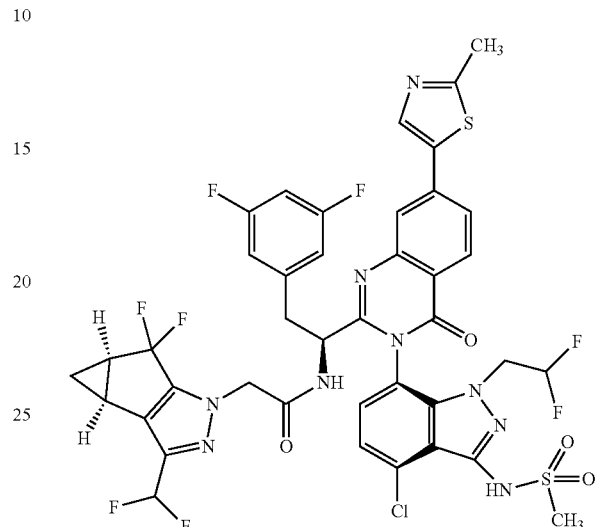

The title compound was prepared according to General Procedure I using 5-bromo-2-methylthiazole as the coupling partner. The experiment afforded the title compound, N—((S)-1-((3P)-3-(4-chloro-1-(2,2-difluoroethyl)-3-(methylsulfonamido)-1H-indazol-7-yl)-7-(2-methylthiazol-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.5 min.; observed ion=952.1 (M+H). 1H NMR (METHANOL-d4, 500 MHz) Shift 8.35 (d, 1H, J=1.8 Hz), 8.33 (d, 1H, J=8.6 Hz), 8.15 (dd, 1H, J=1.8, 8.3 Hz), 7.71 (s, 1H), 7.36 (d, 1H, J=8.0 Hz), 7.27 (d, 1H, J=8.0 Hz), 6.5-6.8 (m, 4H), 6.01 (br d, 1H, J=8.0 Hz), 6.01 (t, 1H, J=55.3 Hz), 4.73 (dd, 1H, J=4.8, 9.2 Hz), 4.5-4.7 (m, 2H), 4.3-4.4 (m, 1H), 3.93 (br dd, 1H, J=4.0, 15.3 Hz), 3.4-3.4 (m, 1H), 3.24 (s, 3H), 3.06 (dd, 1H, J=9.4, 14.2 Hz), 2.61 (d, 3H, J=1.2 Hz), 2.4-2.5 (m, 2H), 1.3-1.4 (m, 1H), 1.0-1.0 (m, 1H)

257

Preparation of Example 124: N—((S)-1-((3P)-3-(4-chloro-1-(2,2-difluoroethyl)-3-(methylsulfonamido)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

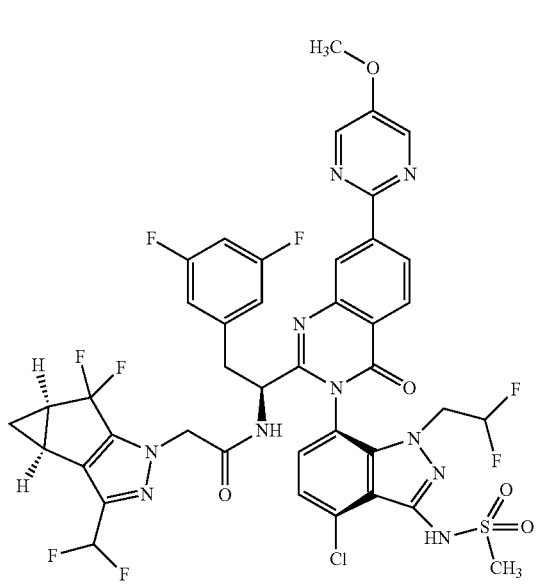

The title compound was prepared according to General Procedure I using 2-chloro-5-methoxypyrimidine as the coupling partner. The experiment afforded the title compound, N—((S)-1-((3P)-3-(4-chloro-1-(2,2-difluoroethyl)-3-(methylsulfonamido)-1H-indazol-7-yl)-7-(5-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.46 min.; observed ion=963.2 (M+H). 1H NMR (METHANOL-d4, 500 MHz) Shift 8.83 (s, 1H), 8.68 (s, 2H), 8.61 (dd, 1H, J=1.8, 8.3 Hz), 8.34 (d, 1H, J=8.2 Hz), 7.36 (d, 1H, J=8.0 Hz), 7.26 (d, 1H, J=7.7 Hz), 6.7-6.8 (m, 1H), 6.67 (br t, 1H, J=51.1 Hz), 6.5-6.6 (m, 2H), 6.02 (br d, 1H, J=8.3 Hz), 6.02 (t, 1H, J=55.4 Hz), 4.9-4.9 (m, 1H), 4.8-4.8 (m, 1H), 4.75 (dd, 1H, J=4.8, 9.2 Hz), 4.61 (q, 2H, J=16.4 Hz), 4.35 (br d, 1H, J=4.5 Hz), 4.05 (s, 3H), 3.94 (br d, 1H, J=11.3 Hz), 3.42 (dd, 1H, J=4.9, 14.5 Hz), 3.07 (dd, 1H, J=9.4, 14.2 Hz), 2.4-2.5 (m, 2H), 1.3-1.4 (m, 1H), 1.0-1.0 (m, 1H)

258

Preparation of Example 125: N—((S)-1-((3P)-3-(4-chloro-1-(2,2-difluoroethyl)-3-(methylsulfonamido)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

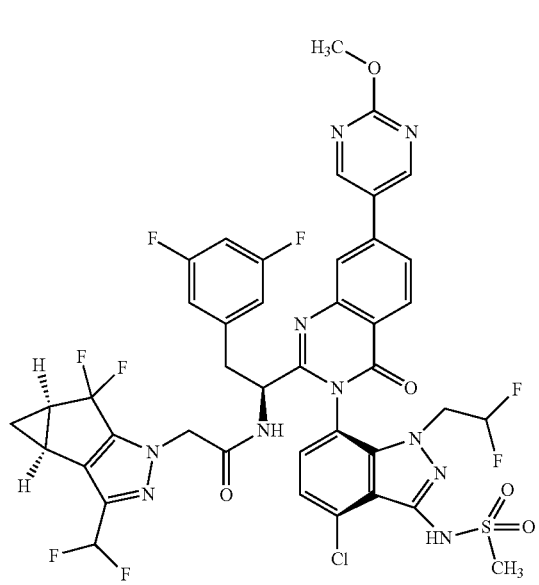

The title compound was prepared according to General Procedure I using 5-bromo-2-methoxypyrimidine as the coupling partner. The experiment afforded the title compound, N—((S)-1-((3P)-3-(4-chloro-1-(2,2-difluoroethyl)-3-(methylsulfonamido)-1H-indazol-7-yl)-7-(2-methoxypyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.38 min.; observed ion=963.3 (M+H). 1H NMR (METHANOL-d4, 500 MHz) Shift 9.05 (s, 2H), 8.38 (d, 1H, J=7.7 Hz), 8.16 (d, 1H, J=1.8 Hz), 7.97 (dd, 1H, J=1.8, 8.3 Hz), 7.3-7.4 (m, 1H), 7.24 (d, 1H, J=8.0 Hz), 6.5-6.8 (m, 4H), 6.02 (br d, 1H, J=8.3 Hz), 6.02 (t, 1H, J=55.3 Hz), 4.74 (dd, 1H, J=4.8, 9.2 Hz), 4.6-4.6 (m, 2H), 4.35 (br d, 1H, J=4.2 Hz), 4.12 (s, 3H), 3.92 (br d, 1H, J=11.3 Hz), 3.4-3.4 (m, 1H), 3.24 (s, 3H), 3.06 (dd, 1H, J=9.4, 14.2 Hz), 2.4-2.5 (m, 2H), 1.3-1.4 (m, 1H), 0.9-1.0 (m, 1H)

259

Preparation of Example 126: N—((S)-1-((3P)-3-(4-chloro-1-(2,2-difluoroethyl)-3-(methylsulfonamido)-1H-indazol-7-yl)-7-(4-ethyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

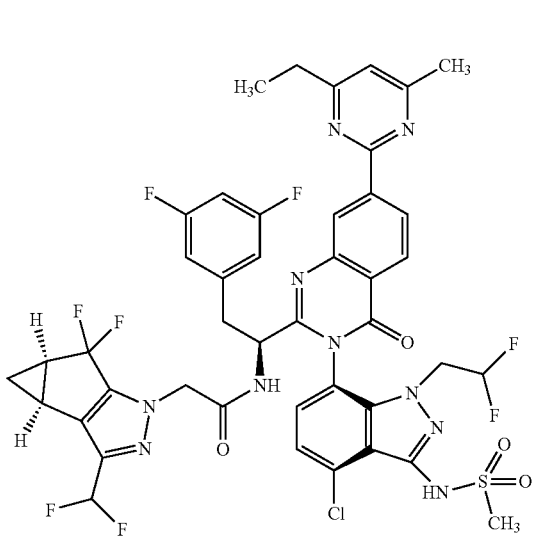

The title compound was prepared according to General Procedure I using 2-chloro-4-ethyl-6-methylpyrimidine as the coupling partner. The experiment afforded the title compound, N—((S)-1-((3P)-3-(4-chloro-1-(2,2-difluoroethyl)-3-(methylsulfonamido)-1H-indazol-7-yl)-7-(4-ethyl-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.61 min.; observed ion=975.2 (M+H). 1H NMR (METHANOL-d4, 500 MHz) Shift 8.92 (d, 1H, J=1.5 Hz), 8.67 (dd, 1H, J=1.5, 8.3 Hz), 8.36 (d, 1H, J=8.3 Hz), 7.36 (d, 1H, J=7.7 Hz), 7.27 (s, 1H), 7.27 (d, 2H, J=6.4 Hz), 6.7-6.8 (m, 1H), 6.68 (br t, 1H, J=54.7 Hz), 6.56 (dd, 2H, J=2.2, 8.2 Hz), 6.02 (br d, 1H, J=8.3 Hz), 6.02 (t, 1H, J=55.4 Hz), 4.76 (dd, 1H, J=4.9, 9.4 Hz), 4.6-4.7 (m, 2H), 4.3-4.4 (m, 1H), 3.95 (br s, 1H), 3.4-3.5 (m, 1H), 3.24 (s, 3H), 3.07 (dd, 1H, J=9.2, 14.0 Hz), 2.90 (q, 2H, J=7.7 Hz), 2.63 (s, 3H), 2.41 (td, 1H, J=4.5, 8.6 Hz), 1.41 (t, 3H, J=7.6 Hz), 1.34 (br dd, 1H, J=1.5, 6.9 Hz), 1.0-1.0 (m, 1H)

260

Preparation of Example 127: N—((S)-1-(7-(3-(tert-butylsulfonyl)phenyl)-(3P)-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

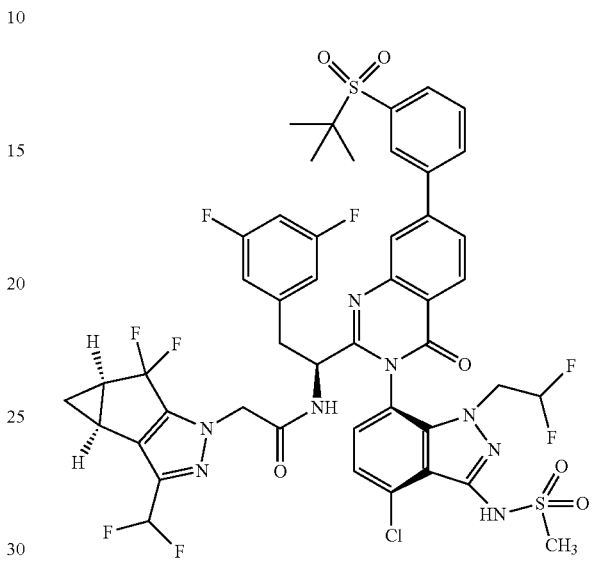

The title compound was prepared according to General Procedure I using 1-bromo-3-(tert-butylsulfonyl)benzene as the coupling partner. The experiment afforded the title compound, N—((S)-1-(7-(3-(tert-butylsulfonyl)phenyl)-(3P)-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=1051.3 (M+H). 1H NMR (METHANOL-d4, 500 MHz) Shift 8.40 (d, 1H, J=8.3 Hz), 8.27 (t, 1H, J=1.6 Hz), 8.22 (d, 1H, J=7.6 Hz), 8.14 (d, 1H, J=1.8 Hz), 8.0-8.0 (m, 2H), 7.86 (t, 1H, J=7.5 Hz), 7.37 (d, 1H, J=7.8 Hz), 7.29 (d, 1H, J=8.0 Hz), 6.5-6.8 (m, 4H), 6.02 (br d, 1H, J=8.3 Hz), 6.02 (br t, 1H, J=55.4 Hz), 4.6-4.7 (m, 2H), 4.3-4.4 (m, 1H), 3.9-4.0 (m, 1H), 4.6-4.6 (m, 1H), 3.4-3.4 (m, 1H), 3.2-3.3 (m, 3H), 3.06 (dd, 1H, J=9.5, 14.0 Hz), 2.4-2.5 (m, 2H), 1.40 (s, 9H), 1.3-1.4 (m, 1H), 0.9-1.0 (m, 1H)

261

Preparation of Example 128: N—((S)-1-((3P)-3-(4-chloro-1-(2,2-difluoroethyl)-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

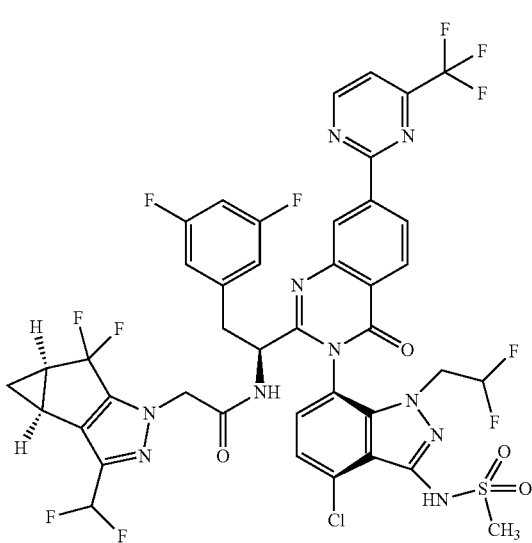

The title compound was prepared according to General Procedure I using 2-chloro-4-(trifluoromethyl)pyrimidine as the coupling partner. The experiment afforded the title compound, N—((S)-1-((3P)-3-(4-chloro-1-(2,2-difluoroethyl)-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.54 min.; observed ion=999.3 (M–H). 1H NMR (METHANOL-d4, 500 MHz) Shift 9.29 (d, 1H, J=5.1 Hz), 9.00 (s, 1H), 8.74 (dd, 1H, J=1.5, 8.3 Hz), 8.42 (d, 1H, J=8.2 Hz), 7.90 (d, 1H, J=5.1 Hz), 7.38 (d, 1H, J=8.0 Hz), 7.30 (d, 1H, J=8.0 Hz), 6.5-6.8 (m, 4H), 6.02 (br d, 1H, J=8.3 Hz), 6.02 (t, 1H, J=55.4 Hz), 4.75 (dd, 1H, J=4.8, 9.5 Hz), 4.6-4.7 (m, 2H), 4.3-4.4 (m, 1H), 3.95 (br dd, 1H, J=4.2, 15.2 Hz), 3.4-3.4 (m, 1H), 3.24 (s, 3H), 3.08 (dd, 1H, J=9.5, 14.0 Hz), 2.4-2.5 (m, 2H), 1.3-1.4 (m, 1H), 0.99 (tdd, 1H, J=2.2, 3.8, 5.6 Hz)

262

Preparation of Example 129: N—((S)-1-((3P)-3-(4-chloro-1-(2,2-difluoroethyl)-3-(methylsulfonamido)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

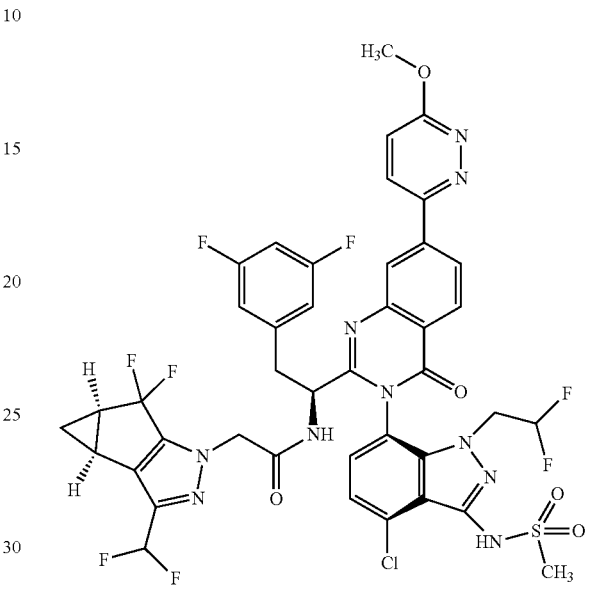

The title compound was prepared according to General Procedure I using 3-chloro-6-methoxypyridazine as the coupling partner. The experiment afforded the title compound, N—((S)-1-((3P)-3-(4-chloro-1l-(2,2-difluoroethyl)-3-(methylsulfonamido)-1H-indazol-7-yl)-7-(6-methoxypyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.4 min.; observed ion=963.4 (M+H). 1H NMR (METHANOL-d4, 500 MHz) Shift 8.52 (d, 1H, J=1.2 Hz), 8.40 (d, 1H, J=8.3 Hz), 8.28 (s, 1H), 8.3-8.3 (m, 1H), 7.3-7.4 (m, 2H), 7.26 (d, 1H, J=7.7 Hz), 6.7-6.8 (m, 1H), 6.66 (s, 1H), 6.5-6.6 (m, 2H), 6.02 (br d, 1H, J=8.3 Hz), 6.02 (t, 1H, J=55.3 Hz), 4.76 (dd, 1H, J=4.9, 9.4 Hz), 4.6-4.7 (m, 2H), 4.3-4.4 (m, 1H), 4.21 (s, 3H), 3.94 (br s, 1H), 3.4-3.4 (m, 1H), 3.2-3.3 (m, 3H), 3.07 (dd, 1H, J=9.2, 14.0 Hz), 2.4-2.4 (m, 2H), 1.3-1.4 (m, 1H), 0.98 (dt, 1H, J=1.9, 3.7 Hz)

Preparation of Example 130: N—((S)-1-(7-(2-(tert-butylsulfonyl)phenyl)-(3P)-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

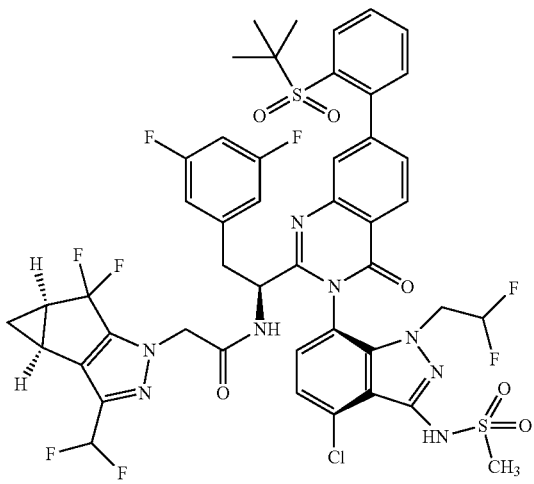

The title compound was prepared according to General Procedure I using 1-bromo-2-(tert-butylsulfonyl)benzene as the coupling partner. The experiment afforded the title compound, N—((S)-1-(7-(2-(tert-butylsulfonyl)phenyl)-(3P)-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=1051.2 (M+H). 1H NMR (METHANOL-d4, 500 MHz) Shift 8.23 (d, 1H, J=8.6 Hz), 8.16 (dd, 1H, J=1.3, 8.2 Hz), 7.8-7.9 (m, 2H), 7.76 (t, 1H, J=7.7 Hz), 7.64 (dd, 1H, J=1.6, 8.2 Hz), 7.53 (dd, 1H, J=1.2, 7.5 Hz), 7.36 (d, 1H, J=7.6 Hz), 7.2-7.3 (m, 1H), 6.5-6.8 (m, 4H), 6.04 (t, 1H, J=55.3 Hz), 4.75 (br s, 1H), 4.5-4.6 (m, 2H), 4.3-4.4 (m, 1H), 3.9-4.0 (m, 1H), 3.4-3.4 (m, 1H), 3.24 (s, 3H), 3.04 (dd, 1H, J=8.9, 14.0 Hz), 2.4-2.5 (m, 2H), 1.3-1.4 (m, 1H), 1.17 (s, 9H), 1.0-1.0 (m, 1H)

Preparation of Example 131: N—((S)-1-((3P)-3-(4-chloro-1-(2,2-difluoroethyl)-3-(methylsulfonamido)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

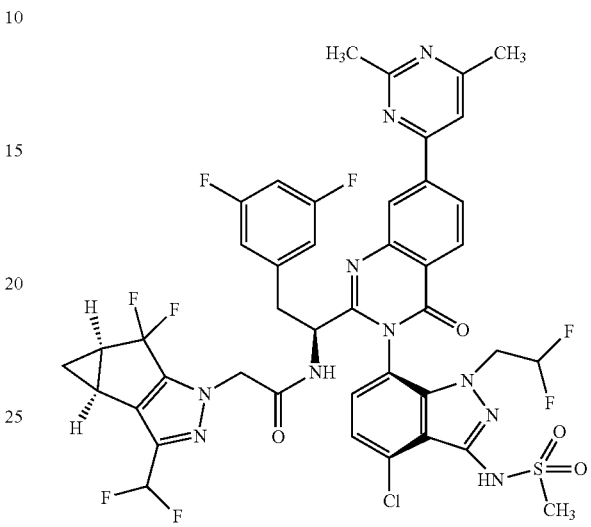

The title compound was prepared according to General Procedure I using 4-chloro-2,6-dimethylpyrimidine as the coupling partner. The experiment afforded the title compound, N—((S)-1-((3P)-3-(4-chloro-1-(2,2-difluoroethyl)-3-(methylsulfonamido)-1H-indazol-7-yl)-7-(2,6-dimethylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.41 min.; observed ion=961.4 (M+H). 1H NMR (METHANOL-d4, 500 MHz) Shift 8.64 (s, 1H), 8.3-8.4 (m, 2H), 7.89 (s, 1H), 7.3-7.4 (m, 1H), 7.27 (d, 1H, J=8.0 Hz), 6.5-6.8 (m, 4H), 6.01 (br t, 1H, J=55.3 Hz), 4.75 (dd, 1H, J=5.1, 9.2 Hz), 4.5-4.7 (m, 2H), 4.3-4.4 (m, 1H), 3.9-4.0 (m, 1H), 3.4-3.4 (m, 1H), 3.2-3.3 (m, 3H), 3.07 (dd, 1H, J=9.5, 14.0 Hz), 2.79 (s, 3H), 2.63 (s, 3H), 2.4-2.5 (m, 2H), 1.2-1.4 (m, 1H), 0.9-1.0 (m, 1H)

265

Preparation of Example 132: N—((S)-1-((3P)-3-(4-chloro-1-(2,2-difluoroethyl)-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

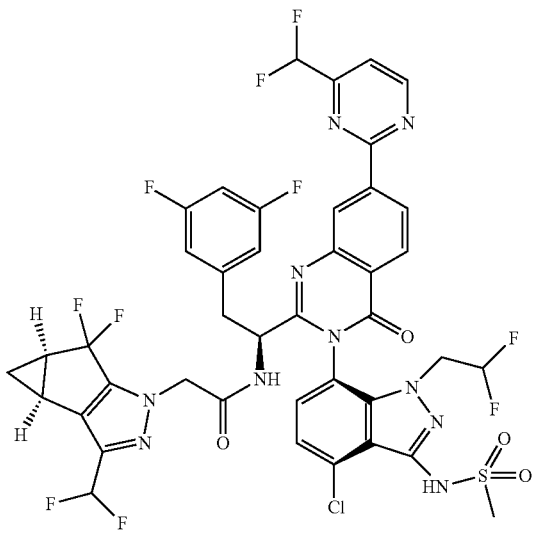

The title compound was prepared according to General Procedure I using 2-chloro-4-(difluoromethyl)pyrimidine as the coupling partner. The experiment afforded the title compound, N—((S)-1-((3P)-3-(4-chloro-1-(2,2-difluoroethyl)-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=983.2 (M+H). 1H NMR (METHANOL-d4, 500 MHz) Shift 9.19 (d, 1H, J=5.1 Hz), 8.99 (s, 1H), 8.7-8.7 (m, 1H), 8.40 (d, 1H, J=8.3 Hz), 7.76 (d, 1H, J=5.1 Hz), 7.37 (d, 1H, J=8.0 Hz), 7.29 (d, 1H, J=8.0 Hz), 6.5-7.0 (m, 5H), 6.02 (t, 1H, J=55.4 Hz), 4.76 (dd, 1H, J=4.8, 9.2 Hz), 4.6-4.7 (m, 2H), 4.3-4.4 (m, 1H), 3.95 (br dd, 1H, J=4.0, 15.1 Hz), 3.4-3.5 (m, 1H), 3.24 (s, 3H), 3.08 (dd, 1H, J=9.2, 14.0 Hz), 2.4-2.5 (m, 2H), 1.3-1.4 (m, 1H), 1.0-1.0 (m, 1H)

266

Preparation of Example 133: N—((S)-1-((3P)-3-(4-chloro-1-(2,2-difluoroethyl)-3-(methylsulfonamido)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

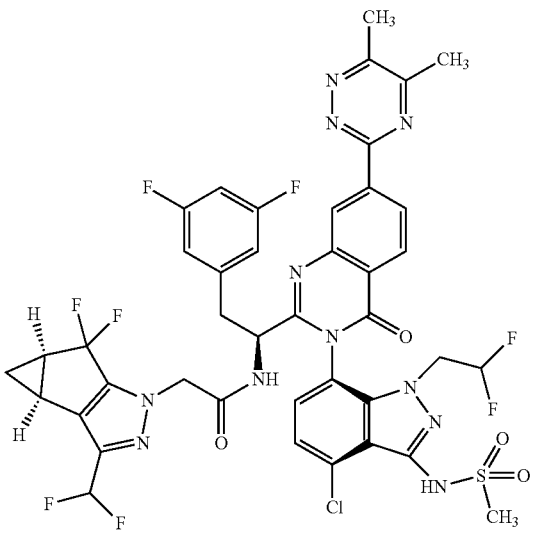

The title compound was prepared according to General Procedure I using 3-chloro-5,6-dimethyl-1,2,4-triazine as the coupling partner. The experiment afforded the title compound, N—((S)-1-((3P)-3-(4-chloro-1-(2,2-difluoroethyl)-3-(methylsulfonamido)-1H-indazol-7-yl)-7-(5,6-dimethyl-1,2,4-triazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.42 min.; observed ion=960.2 (M−H). 1H NMR (METHANOL-d4, 500 MHz) Shift 8.95 (d, 1H, J=1.2 Hz), 8.70 (dd, 1H, J=1.5, 8.3 Hz), 8.41 (d, 1H, J=8.3 Hz), 7.37 (d, 1H, J=8.0 Hz), 7.29 (d, 1H, J=8.0 Hz), 6.6-6.8 (m, 4H), 6.02 (br t, 1H, J=55.4 Hz), 4.76 (dd, 1H, J=4.8, 9.5 Hz), 4.6-4.6 (m, 2H), 4.3-4.4 (m, 1H), 3.9-4.0 (m, 1H), 3.4-3.4 (m, 1H), 3.2-3.2 (m, 3H), 3.07 (dd, 1H, J=9.4, 14.2 Hz), 2.78 (s, 3H), 2.73 (s, 3H), 2.4-2.5 (m, 2H), 1.3-1.4 (m, 1H), 1.0-1.0 (m, 1H)

Preparation of Example 134: N—((S)-1-((3P)-3-(4-chloro-1-(2,2-difluoroethyl)-3-(methylsulfonamido)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 135: N—((S)-1-((3P)-3-(4-chloro-1-(2,2-difluoroethyl)-3-(methylsulfonamido)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

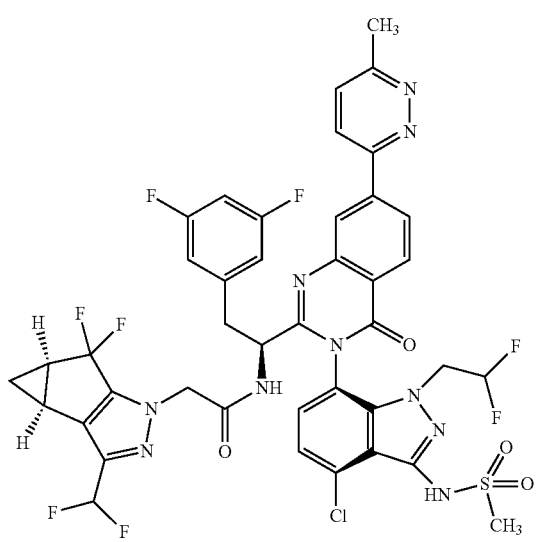

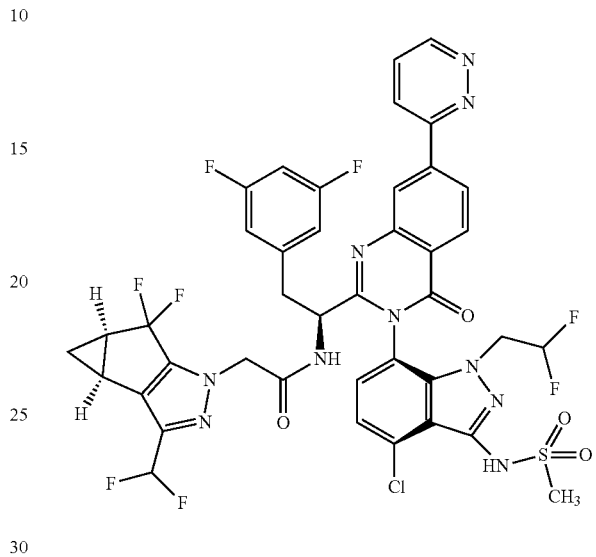

The title compound was prepared according to General Procedure I using 3-chloro-6-methylpyridazine as the coupling partner. The experiment afforded the title compound, N—((S)-1-((3P)-3-(4-chloro-1-(2,2-difluoroethyl)-3-(methylsulfonamido)-1H-indazol-7-yl)-7-(6-methylpyridazin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.33 min.; observed ion=947.2 (M+H). 1H NMR (METHANOL-d4, 500 MHz) Shift 8.60 (d, 1H, J=1.5 Hz), 8.42 (d, 1H, J=8.2 Hz), 8.33 (dd, 1H, J=1.8, 8.3 Hz), 8.28 (d, 1H, J=8.9 Hz), 7.80 (d, 1H, J=8.9 Hz), 7.36 (d, 1H, J=8.0 Hz), 7.27 (d, 1H, J=8.0 Hz), 6.55 (s, 4H), 6.02 (br t, 1H, J=55.4 Hz), 4.76 (dd, 1H, J=4.8, 9.2 Hz), 4.6-4.6 (m, 2H), 4.3-4.4 (m, 1H), 3.9-4.0 (m, 1H), 3.4-3.4 (m, 1H), 3.23 (s, 3H), 3.07 (dd, 1H, J=9.5, 14.0 Hz), 2.80 (s, 3H), 2.4-2.4 (m, 2H), 1.3-1.4 (m, 1H), 0.98 (tdd, 1H, J=2.1, 3.9, 5.6 Hz)

The title compound was prepared according to General Procedure I using 3-chloropyridazine as the coupling partner. The experiment afforded the title compound, N—((S)-1-((3P)-3-(4-chloro-1-(2,2-difluoroethyl)-3-(methylsulfonamido)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.3 min.; observed ion=933.2 (M+H). 1H NMR (METHANOL-d4, 500 MHz) Shift 9.28 (dd, 1H, J=1.6, 4.9 Hz), 8.63 (d, 1H, J=1.8 Hz), 8.3-8.5 (m, 3H), 7.92 (dd, 1H, J=5.1, 8.6 Hz), 7.37 (d, 1H, J=8.0 Hz), 7.28 (d, 1H, J=7.7 Hz), 6.5-6.8 (m, 4H), 6.03 (br t, 1H, J=55.4 Hz), 4.76 (dd, 1H, J=4.9, 9.4 Hz), 4.6-4.7 (m, 2H), 4.38 (br dd, 1H, J=4.3, 15.1 Hz), 3.9-4.0 (m, 1H), 3.4-3.5 (m, 1H), 3.2-3.3 (m, 3H), 3.08 (dd, 1H, J=9.4, 14.2 Hz), 2.4-2.4 (m, 2H), 1.3-1.4 (m, 1H), 0.98 (dt, 1H, J=1.9, 3.7 Hz)

269

Preparation of Example 136: N—((S)-1-((3P)-3-(4-chloro-1-(2,2-difluoroethyl)-3-(methylsulfonamido)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

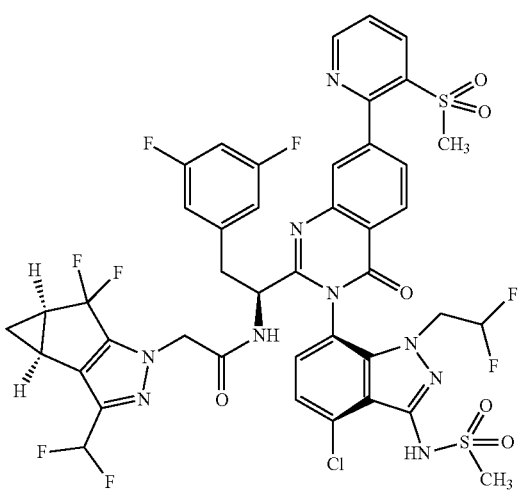

The title compound was prepared according to General Procedure I using 2-chloro-3-(methylsulfonyl)pyridine as the coupling partner. The experiment afforded the title compound, N—((S)-1-((3P)-3-(4-chloro-1-(2,2-difluoroethyl)-3-(methylsulfonamido)-1H-indazol-7-yl)-7-(3-(methylsulfonyl)pyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.34 min.; observed ion=1010.1 (M+H). 1H NMR (METHANOL-d4, 500 MHz) δ 8.95 (dd, 1H, J=1.6, 4.9 Hz), 8.66 (dd, 1H, J=1.5, 8.0 Hz), 8.38 (d, 1H, J=7.9 Hz), 8.1-8.1 (m, 1H), 7.8-7.8 (m, 2H), 7.3-7.4 (m, 1H), 7.30 (d, 1H, J=7.7 Hz), 6.7-6.8 (m, 1H), 6.66 (br t, 1H, J=53.9 Hz), 6.5-6.6 (m, 2H), 6.03 (s, 1H), 6.04 (br t, 1H, J=55.3 Hz), 4.5-4.6 (m, 2H), 4.3-4.5 (m, 1H), 3.9-4.0 (m, 1H), 3.4-3.4 (m, 1H), 3.24 (s, 3H), 3.06 (dd, 1H, J=9.2, 14.0 Hz), 2.94 (s, 3H), 2.41 (ddd, 2H, J=4.0, 7.6, 11.3 Hz), 1.3-1.4 (m, 1H), 1.0-1.0 (m, 1H)

270

Preparation of Example 137: N—((S)-1-((3P)-3-(4-chloro-1-(2,2-difluoroethyl)-3-(methylsulfonamido)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

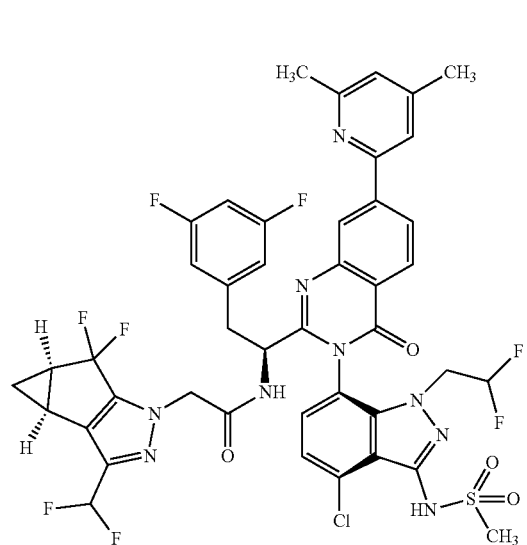

The title compound was prepared according to General Procedure I using 2-bromo-4,6-dimethylpyridine as the coupling partner. The experiment afforded the title compound, N—((S)-1-((3P)-3-(4-chloro-1-(2,2-difluoroethyl)-3-(methylsulfonamido)-1H-indazol-7-yl)-7-(4,6-dimethylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.46 min.; observed ion=960.2 (M+H). 1H NMR (METHANOL-d4, 500 MHz) Shift 8.43 (d, 1H, J=1.2 Hz), 8.35 (d, 1H, J=7.7 Hz), 8.20 (dd, 1H, J=1.5, 8.3 Hz), 7.69 (s, 1H), 7.35 (d, 1H, J=7.7 Hz), 7.24 (d, 1H, J=8.0 Hz), 7.22 (s, 1H), 6.5-6.8 (m, 4H), 6.02 (t, 1H, J=55.4 Hz), 4.75 (dd, 1H, J=4.8, 9.2 Hz), 4.6-4.7 (m, 2H), 4.3-4.4 (m, 1H), 3.9-4.0 (m, 1H), 3.4-3.4 (m, 1H), 3.24 (s, 3H), 3.06 (dd, 1H, J=9.2, 14.0 Hz), 2.62 (s, 3H), 2.4-2.5 (m, 5H), 1.3-1.4 (m, 1H), 0.9-1.0 (m, 1H)

Preparation of Example 138: N—((S)-1-((3P)-3-(4-chloro-1-(2,2-difluoroethyl)-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 139: 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1,4-dimethyl-3-(methylsulfonamido)-1H-indazol-7-yl)-(3P)-7-(6-ethyl-2-methylpyrimidin-4-yl)-4-oxo-3,4-dihydroquinazolin-2-yl)ethyl)acetamide

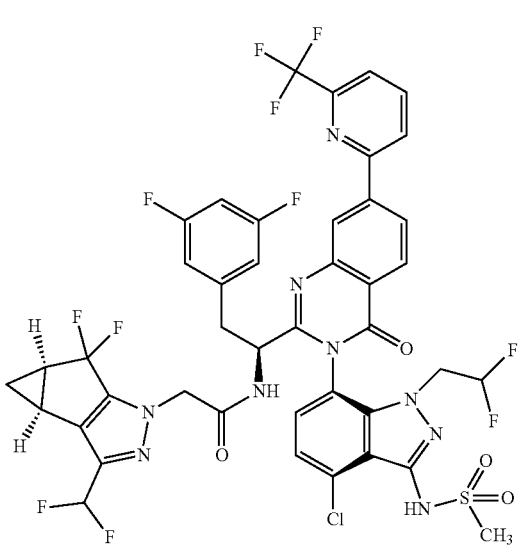

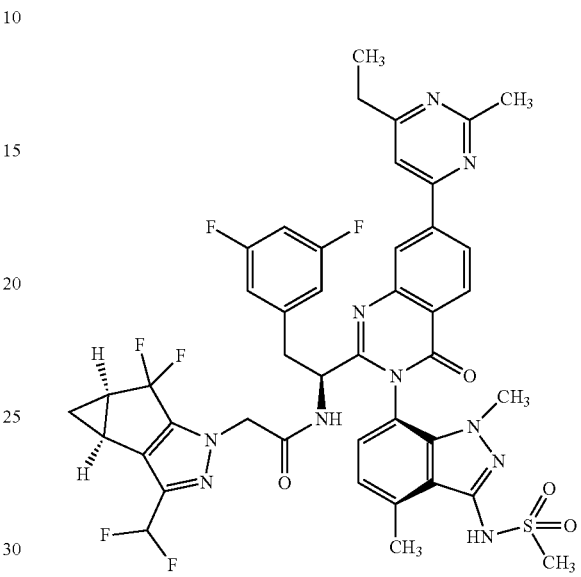

The title compound was prepared according to General Procedure I using 2-chloro-6-(trifluoromethyl)pyridine as the coupling partner. The experiment afforded the title compound, N—((S)-1-((3P)-3-(4-chloro-1-(2,2-difluoroethyl)-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.56 min.; observed ion=100.3 (M+H). 1H NMR (METHANOL-d4, 500 MHz) Shift 8.7-8.7 (m, 1H), 8.3-8.4 (m, 3H), 8.22 (t, 1H, J=7.9 Hz), 7.88 (d, 1H, J=7.7 Hz), 7.37 (d, 1H, J=7.7 Hz), 7.28 (d, 1H, J=7.7 Hz), 6.5-6.8 (m, 4H), 6.02 (br d, 1H, J=8.3 Hz), 6.02 (br t, 1H, J=55.3 Hz), 4.75 (dd, 1H, J=4.8, 9.2 Hz), 4.6-4.6 (m, 2H), 4.3-4.4 (m, 1H), 3.9-4.0 (m, 1H), 3.4-3.4 (m, 1H), 3.2-3.3 (m, 3H), 3.08 (dd, 1H, J=9.4, 14.2 Hz), 2.3-2.5 (m, 2H), 1.2-1.4 (m, 1H), 0.9-1.0 (m, 1H)

Synthesis Scheme:

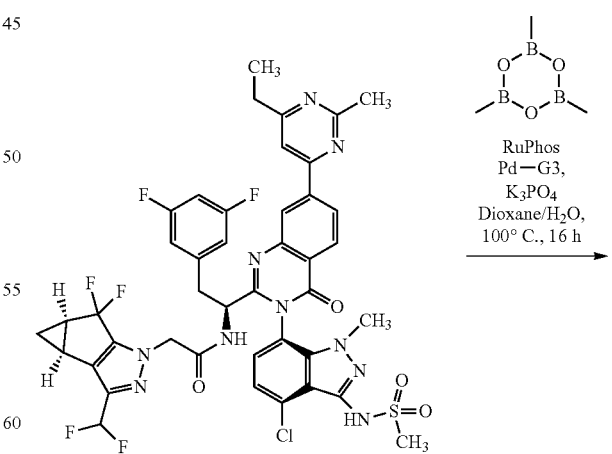

Example 62

-continued

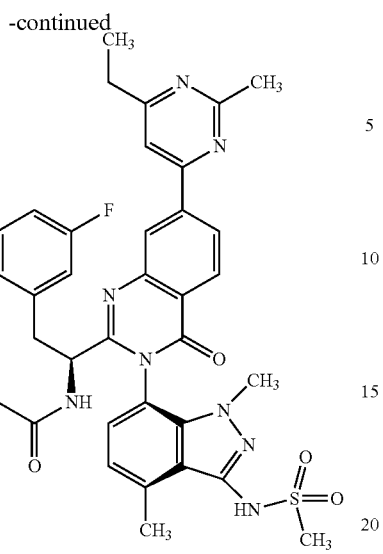

Example 139

To a stirred solution of N—((S)-1-((3P)-3-(4-chloro-1-methyl-3-(methylsulfonamido)-1H-indazol-7-yl)-7-(6-ethyl-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Example 62", 50 mg, 0.054 mmol) in 1,4-dioxane (2 mL) and water (0.400 mL) was added tri-basic potassium phosphate (34.4 mg, 0.162 mmol) and the resulting reaction mixture was degassed under argon gas for 10 min. Then, to the reaction mixture was added 2,4,6-trimethyl-1,3,5,2,4,6-trioxatriborinane (271 mg, 1.081 mmol) followed by RuPhos Pd G3 (4.52 mg, 5.40 μmol) at 27° C. The reaction mixture was heated to 100° C. and stirred for 16 hr. The progress of the reaction was monitored by TLC (SiO$_2$, 50% EtOAc/Pet., Rf=0.4, UV-active). On completion, the reaction mixture was diluted with EtOAc (50 mL) and filtered through a small pad of Celite. The Celite pad was extracted with EtOAc (5×20 mL). The combined filtrate was washed with water (2×10 mL), dried over Na$_2$SO$_4$, filtered and concentrated under reduced pressure to afford the crude residue as a pale yellow semi-solid (90 mg) which was purified by Prep-HPLC using the following conditions: Mobile Phase A=10 mM ammonium bicarbonate (aq); Mobile Phase B=acetonitrile; Column=X-Select-C18 (150× 25 mm, 10μ); Flow-rate=25 mL/min.; Gradient (Time (minutes)/% of B)=0/57, 15/57, 15.1/98, 20/98, 20.1/57, 23/57; Sample solution (dissolved in)=acetonitrile:Water:THF; Temperature=ambient. The fractions containing product were collected, frozen, and then lyophilized to afford 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1,4-dimethyl-3-(methylsulfonamido)-1H-indazol-7-yl)-(3P)-7-(6-ethyl-2-methylpyrimidin-4-yl)-4-oxo-3,4-dihydroquinazolin-2-yl) ethyl)acetamide as a white solid. 1H-NMR (400 MHz, CD$_3$OD) δ=8.62 (d, J=1.3 Hz, 1H), 8.42-8.34 (m, 2H), 7.86 (s, 1H), 7.11 (d, J=7.4 Hz, 1H), 7.02 (d, J=7.0 Hz, 1H), 6.82-6.51 (m, 4H), 4.81 (dd, J=9.3, 4.4 Hz, 1H), 4.65-4.54 (m, 2H), 3.56 (s, 3H), 3.49-3.42 (m, 1H), 3.16 (s, 3H), 3.06-2.99 (m, 1H), 2.90 (q, J=7.6 Hz, 2H), 2.86 (s, 3H), 2.79 (s, 3H), 2.46-2.37 (m, 2H), 1.39 (t, J=7.6 Hz, 2H), 1.36-1.31 (m, 1H), 1.02-0.98 (m, 1H). LCMS Method B: retention time=2.73 mins.; observed ion=905.55 (M+H).

Preparation of Example 140: 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1,4-dimethyl-3-(methylsulfonamido)-1H-indazol-7-yl)-(3P)-7-(5-fluoro-2-methylpyrimidin-4-yl)-4-oxo-3,4-dihydroquinazolin-2-yl)ethyl)acetamide

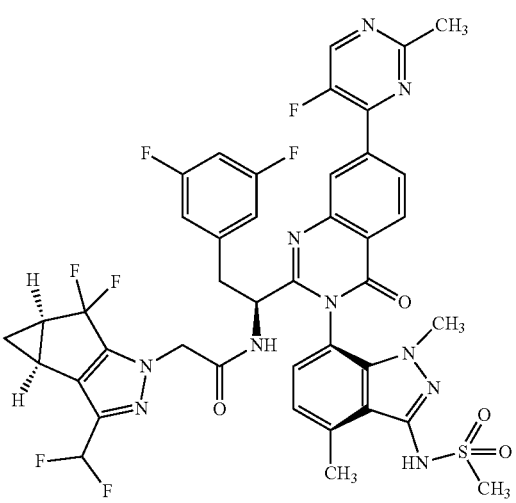

Synthesis Scheme:

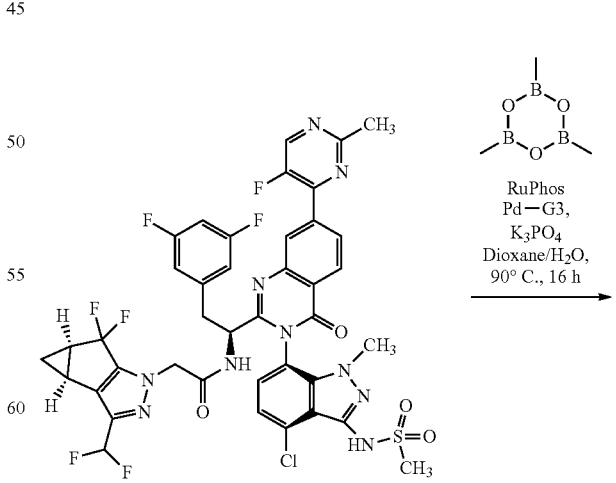

Example 64

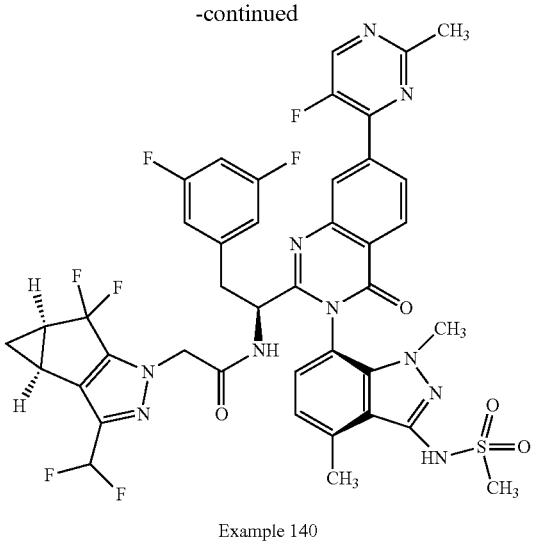

Example 140

To a stirred solution of N—((S)-1-((3P)-3-(4-chloro-1-methyl-3-(methylsulfonamido)-1H-indazol-7-yl)-7-(5-fluoro-2-methylpyrimidin-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Example 64", 20 mg, 0.022 mmol) in 1,4-dioxane (1 mL) and water (0.200 mL) was added tri-basic potassium phosphate (13.92 mg, 0.066 mmol) and the resulting reaction mixture was degassed under argon gas for 5 min. Then, to the reaction mixture was added 2,4,6-trimethyl-1,3,5,2,4,6-trioxatriborinane (54.9 mg, 0.437 mmol) followed by RuPhos-Pd-G3 (1.828 mg, 2.185 µmol) at 27° C. The reaction mixture was heated to 90° C. and stirred for 16 hr. Progress of the reaction was monitored by TLC (SiO$_2$, 80% EtOAc/Pet., Rf=0.4, UV-active). On completion, the reaction mixture was diluted with EtOAc (50 mL) and filtered through a small pad of Celite. The Celite pad was extracted with EtOAc (5×20 mL). The combined filtrate was washed with water (2×20 mL), dried over Na$_2$SO$_4$, filtered, and concentrated under reduced pressure to obtain the crude residue as a pale-yellow semi-solid (45 mg). This material was purified by silica gel chromatography (4 g column) eluting with 0-60% EtOAc/Pet. The fractions containing product were collected and concentrated under reduced pressure to afford 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1,4-dimethyl-3-(methylsulfonamido)-1H-indazol-7-yl)-(3P)-7-(5-fluoro-2-methylpyrimidin-4-yl)-4-oxo-3,4-dihydroquinazolin-2-yl)ethyl)acetamide as an off-white solid. 1H-NMR (400 MHz, CD$_3$OD) δ=8.78 (d, J=3.5 Hz, 1H), 8.59 (s, 1H), 8.43 (d, J=8.3 Hz, 1H), 8.34 (d, J=7.4 Hz, 1H), 7.16 (d, J=7.5 Hz, 1H), 7.08 (d, J=7.4 Hz, 1H), 6.79-6.50 (m, 4H), 4.83-4.79 (m, 1H), 4.64-4.53 (m, 2H), 3.61 (s, 3H), 3.58-3.42 (m, 1H), 3.20 (s, 3H), 3.06-3.00 (m, 1H), 3.86 (s, 3H), 3.81 (s, 3H), 2.43-2.37 (m, 2H), 1.36-1.33 (m, 1H), 1.00-0.96 (m, 1H). LCMS Method D: retention time=5.09 mins.; observed ion=895.46 (M+H).

Preparation of Example 141: 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-((3P)-3-(1,4-dimethyl-3-(methylsulfonamido)-1H-indazol-7-yl)-4-oxo-7-(pyridazin-3-yl)-3,4-dihydroquinazolin-2-yl)ethyl)acetamide

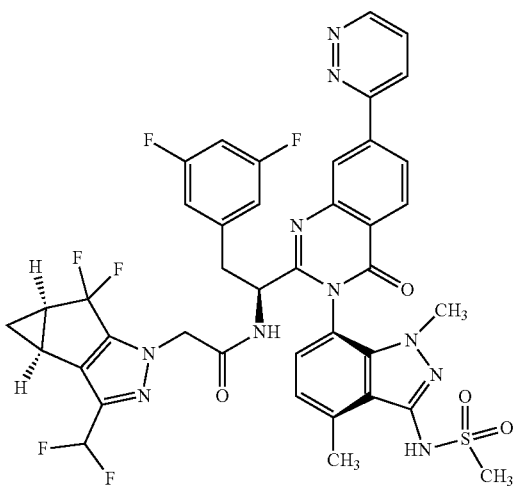

Synthesis Scheme:

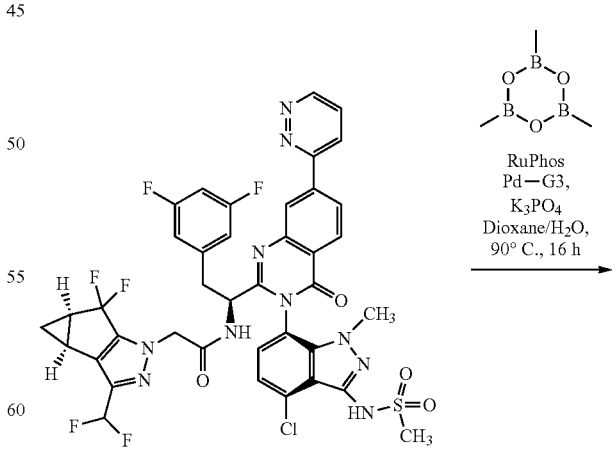

Example 49

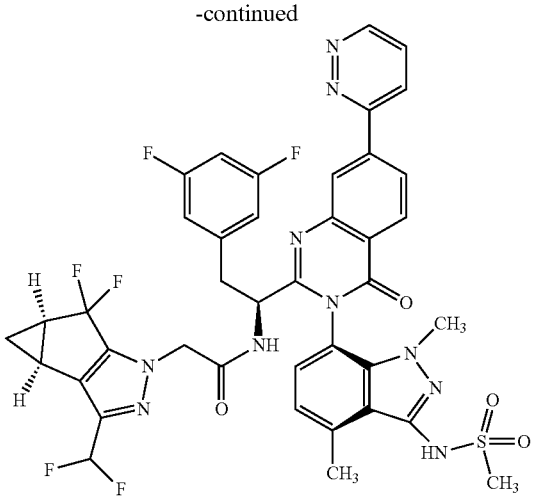

Example 141

To a stirred solution of N—((S)-1-((3P)-3-(4-chloro-1-methyl-3-(methylsulfonamido)-1H-indazol-7-yl)-4-oxo-7-(pyridazin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Example 49", 45 mg, 0.051 mmol) in 1,4-dioxane (2 mL) and water (0.400 mL) was added tri-basic potassium phosphate (32.4 mg, 0.153 mmol) and the resulting reaction mixture was degassed under argon gas for 5 min. Then, to the reaction mixture was added 2,4,6-trimethyl-1,3,5,2,4,6-trioxatriborinane (256 mg, 1.019 mmol) followed by RuPhos-Pd-G3 (8.52 mg, 10.19 μmol) at 27° C. The reaction mixture was heated to 90° C. and stirred for 16 hr. The progress of the reaction was monitored by TLC (SiO₂, 50% EtOAc/Pet., Rf=0.3, UV-active). On completion, the reaction mixture was diluted with EtOAc (50 mL) and filtered through a small pad of Celite. The Celite pad was extracted with EtOAc (5×20 mL). The combined filterate was washed with water (2×20 mL), dried over Na₂SO₄, filtered, and concentrated under reduced pressure to afford the crude residue as a pale-yellow semi-solid (95 mg). This material was purified by Prep-HPLC using the following conditions: Mobile Phase A=10 mM ammonium bicarbonate (aq); Mobile Phase B=acetonitrile; Column=X-Select-C18 (250×19 mm, 5μ); Flow-rate=25 mL/min.; Gradient (Time (minutes)/% of B)=0/50, 14/50, 14.1/98, 22/98, 22.1/50, 25/50; Sample solution (dissolved in)=acetonitrile:Water:THF; Temperature=ambient. The fractions containing product were collected and frozen, and then lyophilized to afford 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-((3P)-3-(1,4-dimethyl-3-(methylsulfonamido)-1H-indazol-7-yl)-4-oxo-7-(pyridazin-3-yl)-3,4-dihydroquinazolin-2-yl)ethyl)acetamide as an off-white solid. 1H-NMR (400 MHz, CD₃OD) δ=9.27 (dd, J=4.8, 1.3 Hz, 1H), 8.60 (d, J=1.8 Hz, 1H), 8.45 (d, J=8.3 Hz, 1H), 8.40 (d, J=1.3 Hz, 1H), 8.38-8.33 (m, 1H), 7.92 (dd, J=8.6, 5.1 Hz, 1H), 7.11 (d, J=7.5 Hz, 1H), 7.03 (d, J=7.0 Hz, 1H), 6.79-6.52 (m, 4H), 4.83-4.81 (m, 1H), 4.64-4.53 (m, 2H), 3.58 (s, 3H), 3.45 (dd, J=13.8, 4.6 Hz, 1H), 3.17 (s, 3H), 3.07-3.01 (m, 1H), 2.86 (s, 3H), 2.44-2.38 (m, 2H), 1.37-1.31 (m, 1H), 1.00-0.97 (m, 1H). LCMS Method B: retention time=2.42 mins.; observed ion=863.42 (M+H).

Preparation of Example 142: N—((S)-1-(7-(2-(tert-butylsulfonyl)phenyl)-(3P)-3-(3-(cyclopropanesulfonamido)-1-(2,2-difluoroethyl)-4-methyl-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

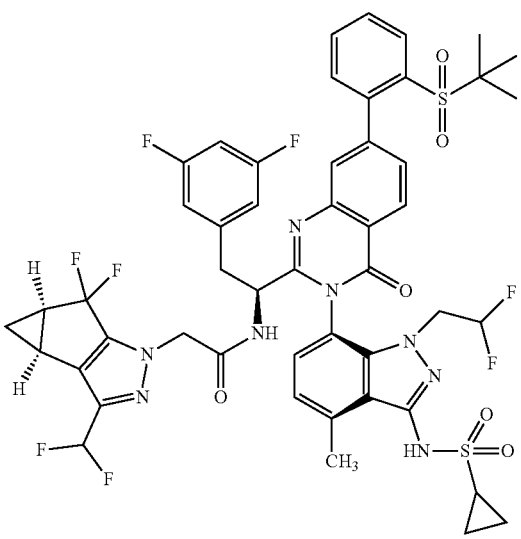

Synthesis Scheme:

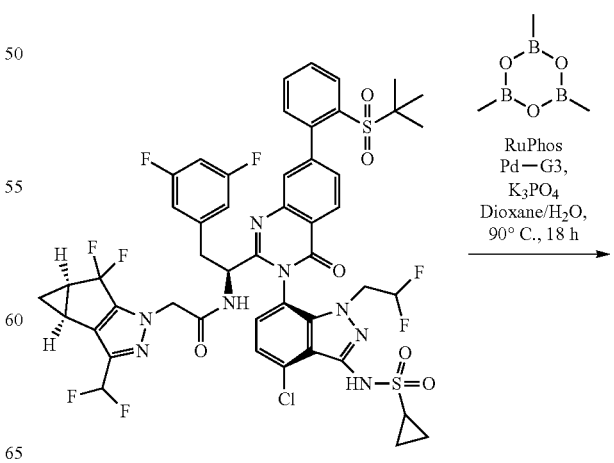

Example 143

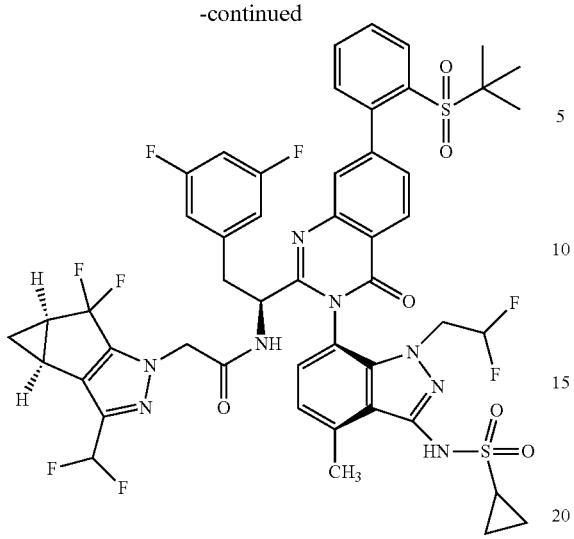

Example 142

To a stirred solution of N—((S)-1-(7-(2-(tert-butylsulfonyl)phenyl)-(3P)-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Example 143", 40 mg, 0.037 mmol) in 1,4-dioxane (2 mL) and water (0.4 mL) was added tri-basic potassium phosphate (23.64 mg, 0.111 mmol) and the resulting reaction mixture was degassed under argon gas for 5 min. Then, to the reaction mixture was added 2,4,6-trimethyl-1,3,5,2,4,6-trioxatriborinane (186 mg, 0.742 mmol) followed by RuPhos-Pd-G3 (6.21 mg, 7.42 μmol) at 27° C. The reaction mixture was heated to 90° C. and stirred for 18 hr. The progress of the reaction was monitored by TLC (SiO$_2$, 50% EtOAc/Pet., Rf=0.4, UV-active). On completion, the reaction mixture was diluted with EtOAc (50 mL) and filtered through a small pad of Celite. The Celite pad was extracted with EtOAc (5×20 mL). The combined filtrate was washed with water (2×10 mL), dried over Na$_2$SO$_4$, filtered, and concentrated under reduced pressure to afford the crude residue as a pale-yellow semi-solid (110 mg). This material was purified by Prep-HPLC using the following conditions: Mobile Phase A=10 mM ammonium bicarbonate (aq); Mobile Phase B=acetonitrile; Column=X-Select CSH C18 (250×19 mm, 5μ); Flow-rate=25 mL/min.; Gradient (Time (minutes)/% of B)=0/65, 2/65, 10/35, 20/35; Sample solution (dissolved in)=acetonitrile:THF; Temperature=ambient. The fractions containing product were pooled, frozen, and then lyophilized to afford N—((S)-1-(7-(2-(tert-butylsulfonyl)phenyl)-(3P)-3-(3-(cyclopropanesulfonamido)-1-(2,2-difluoroethyl)-4-methyl-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid. 1H-NMR (400 MHz, CD$_3$OD) δ=8.23 (d, J=8.3 Hz, 1H), 8.16 (dd, J=7.9, 1.4 Hz, 1H), 7.87-7.83 (m, 2H), 7.77-7.73 (m, 1H), 7.63 (dd, J=8.1, 1.6 Hz, 1H), 7.53 (dd, J=7.7, 1.1 Hz, 1H), 7.21-7.18 (m, 1H), 7.12-7.09 (m, 1H), 6.78-6.51 (m, 2H), 6.43 (d, J=6.6 Hz, 2H), 6.15-5.85 (m, 1H), 4.74-4.58 (m, 3H), 4.35-4.31 (m, 1H), 3.94-3.91 (m, 1H), 3.37-3.32 (m, 1H), 2.99-2.93 (m, 1H), 2.90 (s, 3H), 2.89-2.83 (m, 1H), 2.44-2.38 (m, 2H), 1.36-1.31 (m, 1H), 1.18 (s, 9H), 1.08-1.02 (m, 2H), 1.01-0.96 (m, 3H). LCMS Method A: retention time=6.50 mins.; observed ion=1057.2 (M+H).

Preparation of Example 143: N—((S)-1-((7-(2-(tert-butylsulfonyl)phenyl)-(3P)-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

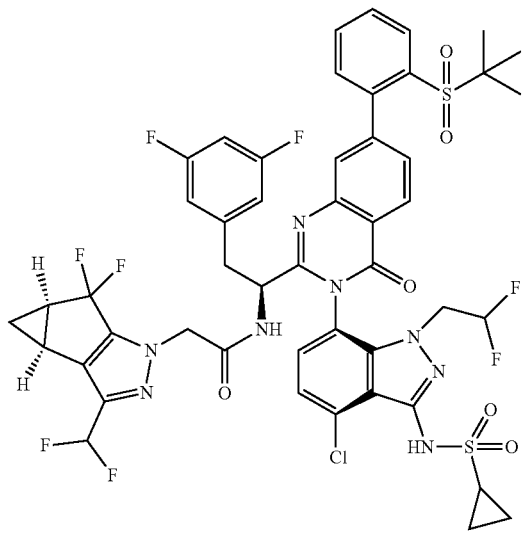

To a stirred solution of N—((S)-1-((3P)-3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoro methyl)-5,5-difluoro-3b,4,4a,5-tetrahydro-1H-cyclopropa[3,4]cyclopenta[1,2-c]pyrazol-1-yl)acetamide (250 mg, 0.129 mmol), 1-bromo-2-(tert-butylsulfonyl)benzene (54.2 mg, 0.194 mmol) in THF (4 mL) and water (4 mL) at 26° C. under N$_2$ atmosphere was added dibasic potassium phosphate (67.4 mg, 0.387 mmol). The mixture was degassed with N$_2$ bubbling for 10 min. and then to the reaction mixture was added dichloro[9,9-dimethyl-4,5-bis(diphenylphosphino)xanthene]palladium(II) (4.88 mg, 6.45 μmol). The mixture was stirred for 5 h at 60° C. The progress of the reaction was monitored by TLC (SiO$_2$, 80% EtOAc/Pet, Rf=0.3). After completion of the reaction, the reaction mixture was diluted with water (20 mL) and extracted with ethyl acetate (2×35 mL). The combined organics were dried over anhydrous Na$_2$SO$_4$, filtered, and concentrated under reduced pressure to afford the crude product. This material was purified by Prep-HPLC using the following conditions: Mobile Phase A=0.1% formic acid in water; Mobile Phase B=acetonitrile; Column=Synergy Polar (250×21 mm, 4.7μ); Flow-rate=18 mL/min.; Gradient (Time (minutes)/% of B)=0/15, 2/15, 10/50; Sample solution (dissolved in)=acetonitrile:Water: THF; Temperature=ambient. Fractions containing the pure product were pooled, frozen, and then lyophilized to afford N—((S)-1-((7-(2-(tert-butylsulfonyl)phenyl)-(3P)-3-(4- chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid. $^1$H-NMR (400 MHz, DMSO-$d_6$) δ=9.98 (br s, 1H), 9.24 (br s, 1H), 8.15 (d, J=8.1 Hz, 1H), 8.08 (dd, J=8.1, 1.2 Hz, 1H), 7.89-7.73 (m, 4H), 7.61-7.46 (m, 3H), 7.04-6.75 (m, 2H), 6.61-6.56 (m, 2H), 6.23-5.96 (m, 1H), 4.71-4.55 (m, 2H), 4.46-4.40 (m, 1H), 4.28-4.19 (m, 1H), 3.92-3.86 (m, 1H), 3.41-3.34 (m, 1H), 2.98-2.92 (m, 1H), 2.88-2.82 (m, 1H), 2.46-2.40 (m, 2H), 1.35-1.29 (m, 1H), 1.12 (s, 9H), 0.97-0.82 (m, 5H). LCMS Method A: retention time=6.77 mins.; observed ion=1077.00 (M+H).

Preparation of Example 144: N—((S)-1-((3P)-3-(4-chloro-3-(cyclopropanesulfonamido)-1-(2,2-difluoroethyl)-1H-indazol-7-yl)-7-(2-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

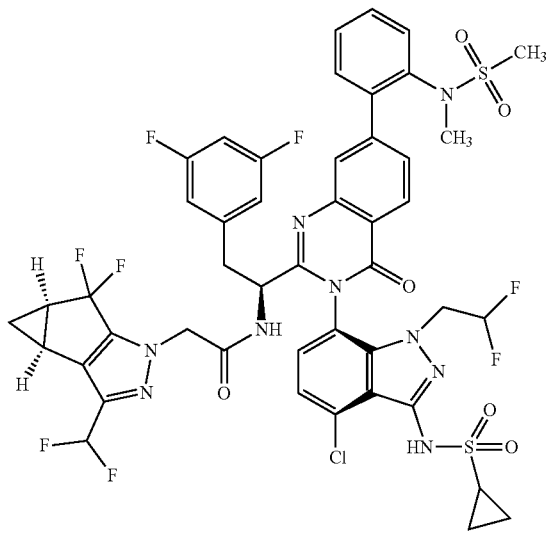

To a stirred solution of N—((S)-1-((3P)-3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoro methyl)-5,5-difluoro-3b,4,4a,5-tetrahydro-1H-cyclopropa[3,4]cyclopenta[1,2-c]pyrazol-1-yl)acetamide (250 mg, 0.213 mmol) and N-(2-bromophenyl)-N-methylmethanesulfonamide (89 mg, 0.320 mmol) in THF (4 mL) and Water (4 mL)) at 26° C. under $N_2$ atmosphere was added dibasic potassium phosphate (112 mg, 0.640 mmol. The mixture was degassed via $N_2$ bubbling for 10 min. Then, to the reaction mixture was added dichloro[9,9-dimethyl-4,5-bis(diphenylphosphino)xanthene]palladium(II) (8.07 mg, 10.67 μmol) and the mixture was stirred for 5 h at 60° C. The progress of the reaction was monitored by TLC ($SiO_2$, 80% EtOAc/Pet, Rf=0.3). After completion of reaction, the reaction mixture was diluted with water (20 mL) and extracted with ethyl acetate (2×35 mL). The combined organics were dried over anhydrous $Na_2SO_4$, filtered, and concentrated under reduced pressure to afford the crude product. This material was purified by Prep-HPLC using the following conditions: Mobile Phase A=10 mM ammonium bicarbonate (aq); Mobile Phase B=acetonitrile; Column=X-Select Cis (250×19 mm, 5μ); Flow-rate=16 mL/min.; Gradient (Time (minutes)/% of B)=0/40, 2/40, 10/50; Sample solution (dissolved in)=acetonitrile:THF:MeOH; Temperature=ambient. Fractions containing the pure product were pooled, frozen, and then lyophilized to afford N—((S)-1-((3P)-3-(4-chloro-3-(cyclopropanesulfonamido)-1-(2,2-difluoroethyl)-1H-indazol-7-yl)-7-(2-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid. 1H-NMR (400 MHz, DMSO-$d_6$) δ=9.98 (br s, 1H), 9.19 (d, J=8.8 Hz, 1H), 8.22 (d, J=8.3 Hz, 1H), 7.85-7.81 (m, 2H), 7.72-7.61 (m, 2H), 7.61-7.54 (m, 4H), 7.06-7.76 (m, 2H), 6.58 (d, J=6.4 Hz, 2H), 6.07 (t, J=55.4 Hz, 1H), 4.72 (d, J=16.7 Hz, 1H), 4.60 (d, J=16.6 Hz, 1H), 4.48-4.43 (m, 1H), 4.17-4.13 (m, 1H), 3.86-3.82 (m, 1H), 3.41-3.35 (m, 1H), 3.16 (s, 3H), 3.01-2.81 (m, 5H), 2.46-2.39 (m, 2H), 1.36-1.31 (m, 1H), 0.92-0.94 (m, 4H), 0.86-0.82 (m, 1H). LCMS Method B: retention time=2.69 mins.; observed ion=1064.30 (M+H).

Preparation of Example 145: N—((S)-1-((3P)-3-(3-(cyclopropanesulfonamido)-1-(2,2-difluoroethyl)-4-methyl-1H-indazol-7-yl)-7-(2-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

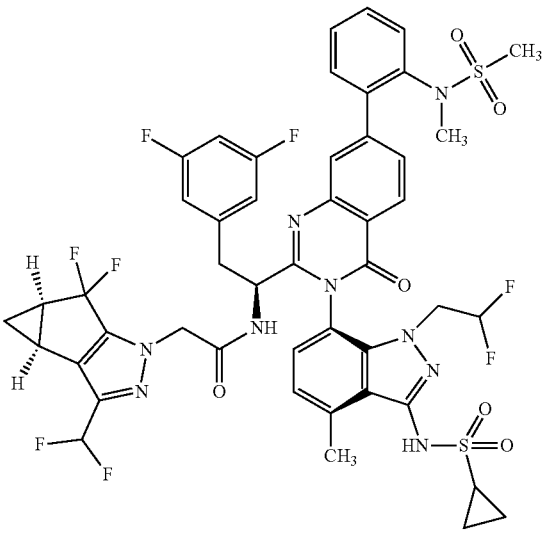

Synthesis Scheme:

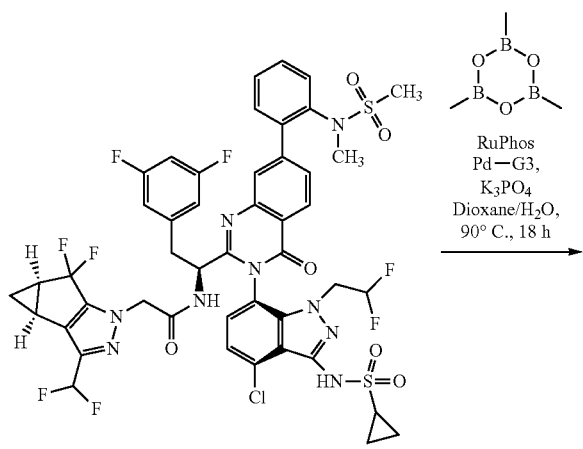

Example 144

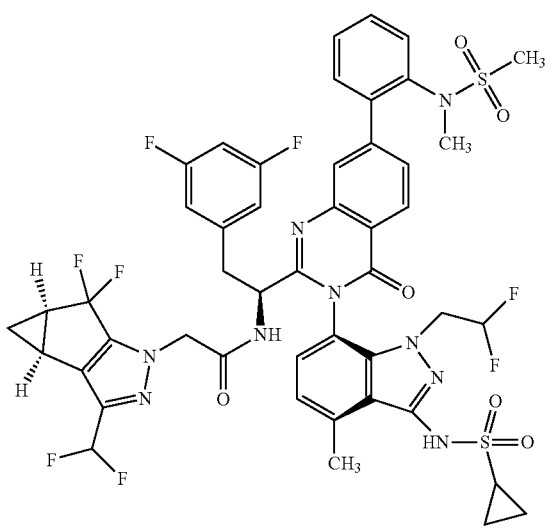

Example 145

To a stirred solution of N—((S)-1-((3P)-3-(4-chloro-3-(cyclopropanesulfonamido)-1-(2,2-difluoroethyl)-1H-indazol-7-yl)-7-(2-(N-methylmethylsulfonamido)phenyl)-4-oxo-3,4-dihydroquinazolin-2-yl)-2-(3,5-difluorophenyl) ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide ("Example 144", 40 mg, 0.038 mmol) in 1,4-Dioxane (2 mL) and Water (0.400 mL) at 26° C. under N₂ atmosphere was added tri-basic potassium phosphate (23.93 mg, 0.113 mmol). The mixture was degassed via N₂ bubbling for 10 min., then to the mixture was added 2,4,6-trimethyl-1,3,5,2,4,6-trioxatriborinane (189 mg, 0.752 mmol) followed by RuPhos-Pd-G3 (3.14 mg, 3.76 µmol). The mixture was stirred for 16 h at 75° C. The progress of the reaction was monitored by TLC (SiO₂, 50% EtOAc/Pet, Rf=0.4). After completion of reaction, the reaction mixture was diluted with ethyl acetate (40 mL) and was filtered through a pad of Celite. The Celite pad was extracted with ethyl acetate (5×20 mL). The combined filtrate was dried over anhydrous Na₂SO₄, filtered, and concentrated under reduced pressure to afford the crude product. This material was purified by Prep-HPLC using the following conditions: Mobile Phase A=10 mM ammonium bicarbonate (aq); Mobile Phase B=acetonitrile; Column=X-Select CSH Cis (150×19 mm, 5µ); Flow-rate=19 mL/min.; Gradient (Time (minutes)/% of B)=0/50, 2/50, 10/60; Sample solution (dissolved in)=water:acetonitrile: THF; Temperature=ambient. Fractions containing the pure product were pooled, frozen, and then lyophilized to afford N—((S)-1-((3P)-3-(3-(cyclopropanesulfonamido)-1-(2,2-difluoroethyl)-4-methyl-1H-indazol-7-yl)-7-(2-(N-methyl-methylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid. ¹H-NMR (400 MHz, DMSO-d₆) δ=9.96-9.86 (m, 1H), 9.30-9.24 (m, 1H), 8.29-8.21 (m, 1H), 7.83-7.77 (m, 1H), 7.76-7.62 (m, 3H), 7.59-7.44 (m, 3H), 7.23-7.14 (m, 1H), 7.06-6.88 (m, 2H), 6.55-6.45 (m, 2H), 6.27-5.92 (m, 1H), 4.77-4.60 (m, 2H), 4.44-4.38 (m, 1H), 4.30-4.19 (m, 1H), 3.98-3.88 (m, 1H), 3.45-3.37 (m, 1H), 3.21-3.08 (m, 3H), 3.04-2.82 (m, 5H), 2.80-2.58 (m, 3H), 2.45-2.29 (m, 2H), 1.40-1.32 (m, 1H), 1.08-0.89 (m, 4H), 0.84-0.76 (m, 1H). LCMS Method A: retention time=6.24 mins.; observed ion=1044.10 (M+H).

Preparation of
1-bromo-3-(tert-butylsulfonyl)benzene

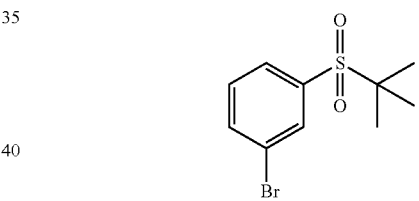

To a stirred solution of (3-bromophenyl)(tert-butyl)sulfane (10 g, 24.47 mmol) in DCM (100 mL) at 0° C. under nitrogen atmosphere was added portion-wise mCPBA (20 g, 116 mmol). The reaction mixture was allowed to warm to 28° C. and then was stirred for 24 h. The progress of the reaction was monitored by TLC (SiO₂, 20% EtOAc/Pet., Rf=0.3, UV-active). On completion, the reaction mixture was diluted with water (100 mL) and extracted with DCM (3×300 mL). The combined organic layers were washed with saturated sodium thiosulfate (2×200 mL), saturated NaHCO₃ (2×200 mL), followed by brine (500 mL) and then were dried over anhydrous Na₂SO₄, filtered and concentrated under reduced pressure to give the crude compound as off-white solid. This material was purified by silica gel chromatography eluted with 0-5% EtOAc/Pet. The fractions containing product were collected and concentrated under reduced pressure to afford 1-bromo-3-(tert-butylsulfonyl) benzene (5 g, 15%) as an off-white solid. ¹H-NMR (400 MHz, DMSO-d₆) δ=8.02-7.99 (m, 1H), 7.93-7.91 (m, 1H), 7.86-7.83 (m, 1H), 7.64 (t, J=8.1 Hz, 1H), 1.25 (s, 9H).

Preparation of 2-(3-(tert-butylsulfonyl)phenyl)-4,4,5,5-tetramethyl-1,3,2-dioxaborolane

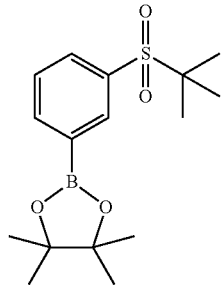 [SMILES: CC1(C)OB(c2cccc(S(=O)(=O)C(C)(C)C)c2)OC1(C)C]

To a stirred solution of 1-bromo-3-(tert-butylsulfonyl)benzene (500 mg, 1.752 mmol) and bis(pinacol)diborane (667 mg, 2.63 mmol) in DMF (5 mL) was added potassium acetate (860 mg, 8.76 mmol). The reaction mixture was degassed under via nitrogen bubbling for 10 min., then to the reaction mixture was added PdCl$_2$(dppf)-CH$_2$Cl$_2$ adduct (229 mg, 0.280 mmol). The mixture was stirred at 80° C. for 16 h. The progress of the reaction was monitored by TLC (SiO$_2$, 30% EtOAc/Pet., Rf=0.5, UV-active). On completion, the reaction mixture was filtered through small pad of Celite. The Celite pad was extracted with EtOAc (2×10 mL). The combined filtrate was washed with water (20 mL), brine (10 mL), dried over anhydrous Na$_2$SO$_4$, filtered and concentrated under reduced pressure to afford 2-(3-(tert-butylsulfonyl)phenyl)-4,4,5,5-tetramethyl-1,3,2-dioxaborolane (250 mg, 16%) as a brown liquid. This material was used directly in the next step without further purification.

Preparation of Example 146: N—((S)-1-(7-(3-(tert-butylsulfonyl)phenyl)-(3P)-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

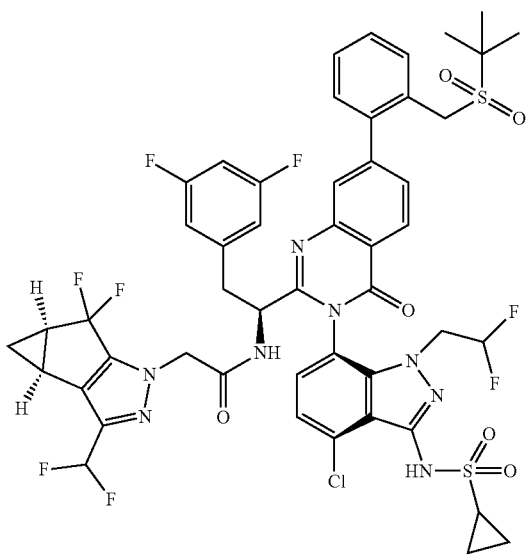

To a solution of N—((S)-1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50 mg, 0.051 mmol) in THF (5 mL) and water (0.5 mL) at 27° C. degassed via nitrogen gas bubbling for 10 min. was added 2-(3-(tert-butylsulfonyl)phenyl)-4,4,5,5-tetramethyl-1,3,2-dioxaborolane (65.7 mg, 0.077 mmol) and dibasic potassium phosphate (44.4 mg, 0.255 mmol). To the reaction mixture was added dichloro[9,9-dimethyl-4,5-bis(diphenylphosphino)xanthene]palladium(II) (2.93 mg, 3.06 μmol) and the mixture was then stirred at 70° C. for 3 h. The progress of the reaction was monitored by TLC (SiO$_2$, 50% EtOAc/Pet., Rf=0.3, UV-active). On completion, the reaction mixture was filtered through a pad of Celite. The Celite pad was extracted with EtOAc (30 mL). The combined filtrate was dried over anhydrous Na$_2$SO$_4$, filtered and concentrated under reduced pressure to afford the crude product as brown solid which was purified by Prep-HPLC using the following conditions: Mobile Phase A=10 mM ammonium bicarbonate (aq); Mobile Phase B=acetonitrile; Column=Kromosil-phenyl Cis (150×25 mm, 10); Flow-rate=25 mL/min.; Gradient (Time (minutes)/% of B)=0/60, 15/60, 15.1/98, 18/98, 18.1/60, 20/60; Sample solution (dissolved in)=water:acetonitrile: THF; Temperature=ambient. The fractions containing product were collected, frozen, and lyophilized to afford N—((S)-1-(7-(3-(tert-butylsulfonyl)phenyl)-(3P)-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid. $^1$H-NMR (400 MHz, DMSO-d$_6$) δ=9.97 (br s, 1H), 1.19 (d, J=7.2 Hz, 1H), 8.34-8.29 (m, 2H), 8.18 (br s, 1H), 8.07-8.02 (m, 2H), 7.99-7.95 (m, 1H), 7.92-7.88 (m, 1H), 7.74 (br s, 1H), 7.49 (br s, 1H), 7.06-6.76 (m, 2H), 6.61 (d, J=6.6 Hz, 2H), 6.11 (t, J=54.8 Hz, 1H), 4.74 (d, J=16.6 Hz, 1H), 4.62 (d, J=16.5 Hz, 1H), 4.46-4.40 (m, 1H), 4.26-4.19 (m, 1H), 3.94-3.88 (m, 1H), 3.41-3.35 (m, 1H), 3.03-2.97 (m, 1H), 2.99-2.83 (m, 1H), 2.46-2.41 (m, 2H), 1.34 (s, 10H), 1.24 (br s, 1H), 0.97-0.82 (m, 4H). LCMS Method B: retention time=2.83 mins.; observed ion=1077.3 (M+H).

Preparation of N-methyl-N-(4-(4,4,5,5-tetramethyl-1,3,2-dioxaborolan-2-yl)phenyl)methanesulfonamide

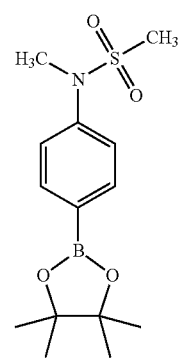

To a stirred solution of N-(4-bromophenyl)-N-methyl-methanesulfonamide (1.5 g, 5.45 mmol), in 1,4-Dioxane (5 mL) was added bis(pinacol)diborane (2.077 g, 8.18 mmol), and potassium acetate (0.535 g, 5.45 mmol). The reaction mixture was degassed via nitrogen bubbling for 10 min. To the reaction mixture was added PdCl$_2$(dppf)-CH$_2$Cl$_2$ adduct (0.712 g, 0.872 mmol) and the mixture was then stirred at 90° C. for 16 h. The progress of the reaction was monitored by TLC (SiO$_2$, 30% EtOAc/Pet., Rf=0.5, UV-active). On completion, the reaction mixture was filtered through small pad of Celite. The Celite pad was extracted with EtOAc (2×10 mL). The combined filtrate was washed with water (20 mL), brine (10 mL), dried over anhydrous Na$_2$SO$_4$, filtered and concentrated under reduced pressure to afford the crude compound as brown liquid. This material was purified by silica gel chromatography eluting with 0-10% EtOAc/Pet. The fractions containing product were pooled and concentrated under reduced pressure to afford N-methyl-N-(4-(4,4,5,5-tetramethyl-1,3,2-dioxaborolan-2-yl)phenyl)methanesulfonamide (200 mg, 9% yield) as an off-white solid. $^1$H-NMR (400 MHz, DMSO-d$_6$) δ=7.69 (d, J=8.8 Hz, 2H), 7.42 (d, J=8.9 Hz, 2H), 3.23 (s, 3H), 2.92 (s, 3H), 1.31 (s, 12H).

Preparation of N-methyl-N-(3-(4,4,5,5-tetramethyl-1,3,2-dioxaborolan-2-yl)phenyl)methanesulfonamide

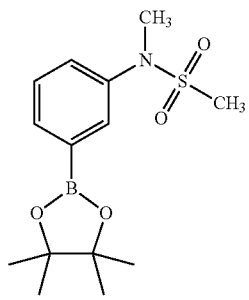

To a stirred solution of N-(3-bromophenyl)-N-methyl-methanesulfonamide (1 g, 3.45 mmol) in 1,4-Dioxane (10 mL) was added bis(pinacol)diborane (1.315 g, 5.18 mmol) and potassium acetate (0.678 g, 6.91 mmol). The reaction mixture was degassed via nitrogen gas bubbling for 10 min. To the reaction mixture was added PdCl$_2$(dppf)-CH$_2$Cl$_2$ adduct (0.423 g, 0.518 mmol) and the mixture was then stirred at 90° C. for 16 h. The progress of the reaction was monitored by TLC (SiO$_2$, 30% EtOAc/Pet., Rf=0.5, UV-active). On completion, the reaction mixture was filtered through a small pad of Celite. The Celite pad was extracted with EtOAc (2×100 mL). The combined filtrate was washed with water (20 mL), brine (30 mL), dried over anhydrous Na$_2$SO$_4$, filtered and concentrated under reduced pressure to afford the crude compound as a brown liquid. This material was purified by silica gel chromatography eluting with 0-10% EtOAc/Pet. The fractions containing product were collected and concentrated under reduced pressure to afford N-methyl-N-(3-(4,4,5,5-tetramethyl-1,3,2-dioxaborolan-2-yl)phenyl)methanesulfonamide (250 mg, 13% yield) as a brown solid. $^1$H-NMR (400 MHz, CDCl$_3$) δ=7.76-7.69 (m, 2H), 7.54-7.48 (m, 1H), 7.40-7.37 (m, 1H), 3.35 (s, 3H), 2.83 (s, 3H), 1.35 (s, 12H).

Preparation of Example 147: N—((S)-1-((3P)-3-(4-chloro-3-(cyclopropanesulfonamido)-1-(2,2-difluoroethyl)-1H-indazol-7-yl)-7-(4-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

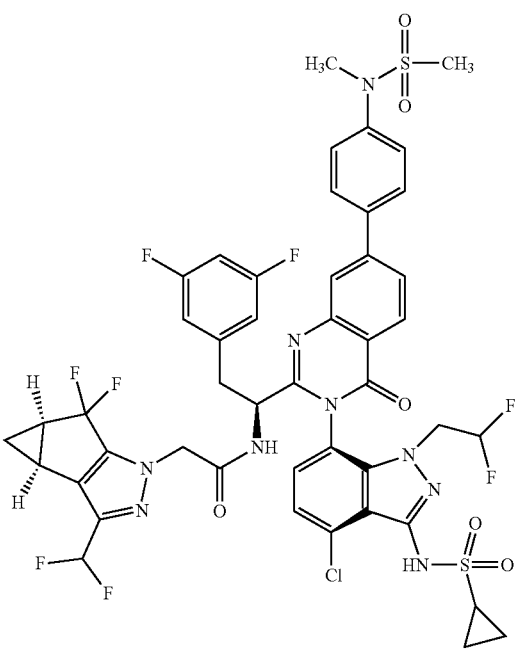

To a stirred solution of N—((S)-1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50 mg, 0.051 mmol) in THF (4 mL) and water (0.5 mL) at 27° C. and degassed via nitrogen gas bubbling for 10 min. was added N-methyl-N-(4-(4,4,5,5-tetramethyl-1,3,2-dioxaborolan-2-yl)phenyl)methanesulfonamide (28.3 mg, 0.077 mmol) and tribasic potassium phosphate (108 mg, 0.510 mmol). To the reaction mixture was added dichloro[9,9-dimethyl-4,5-bis(diphenylphosphino)xanthene]palladium(II) (2.93 mg, 3.06 µmol) and the mixture was then stirred at 70° C. for 3 h. The progress of the reaction was monitored by TLC (SiO$_2$, 50% EtOAc/Pet., Rf=0.3, UV-active). On completion, the reaction mixture was filtered through a small Celite pad. The Celite pad was extracted with EtOAc (30 mL). The combined filtrate was dried over anhydrous Na$_2$SO$_4$, filtered, and concentrated under reduced pressure to give the crude compound as a brown solid which was purified by prep-HPLC using the following conditions: Mobile Phase A=10 mM ammonium bicarbonate (aq); Mobile Phase B=acetonitrile; Column=YMC Triart Cis (150×25 mm, 10µ); Flow-rate=25 mL/min.; Gradient (Time (minutes)/% of B)=0/50, 2/50, 10/70; Sample solution (dissolved in)=water:acetonitrile:THF; Temperature=ambient. The fractions containing product were pooled and concentrated under reduced pressure. The remaining solution (aq) was frozen and then lyophilized to afford N—((S)-1-((3P)-3-(4-chloro- 3-(cyclopropanesulfonamido)-1-(2,2-difluoroethyl)-1H-indazol-7-yl)-7-(4-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid. $^1$H-NMR (400 MHz, DMSO-d$_6$) δ=10.1-9.95 (br s, 1H), 9.18 (d, J=7.2 Hz, 1H), 8.28 (d, J=8.3 Hz, 1H), 8.04-7.99 (m, 2H), 7.92 (d, J=8.8 Hz, 2H), 7.70 (br s, 1H), 7.61 (d, J=8.6 Hz, 1H), 7.46-7.36 (m, 2H), 7.06-6.76 (m, 2H), 6.61 (d, J=7.1 Hz, 2H), 6.10 (t, J=55.7 Hz, 1H), 4.72 (d, J=16.6 Hz, 1H), 4.60 (d, J=16.6 Hz, 1H), 4.48-4.42 (m, 1H), 4.20 (br s, 1H), 3.91 (br s, 1H), 3.38 (d, J=12.1 Hz, 1H), 3.33 (s, 3H), 3.03 (s, 3H), 3.01-2.96 (m, 1H), 2.87-2.81 (m, 1H), 2.47-2.40 (m, 2H), 1.36-1.30 (m, 1H), 0.93 (br s, 5H). LCMS Method A: retention time=6.51 mins.; observed ion=1064.1 (M+H).

Preparation of Example 148: N—((S)-1-((3P)-3-(4-chloro-3-(cyclopropanesulfonamido)-1-(2,2-difluoroethyl)-1H-indazol-7-yl)-7-(3-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

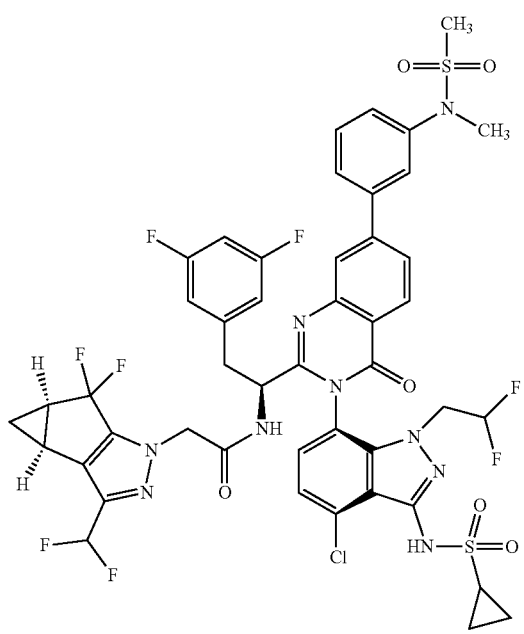

To a stirred solution of N—((S)-1-((3P)-7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50 mg, 0.051 mmol) in THF (4 mL) and water (0.5 mL) at 27° C. and degassed with nitrogen gas bubbling for 10 min. was added N-methyl-N-(3-(4,4,5,5-tetramethyl-1,3,2-dioxaborolan-2-yl)phenyl)methanesulfonamide (42.6 mg, 0.077 mmol) and tribasic potassium phosphate (108 mg, 0.510 mmol). To the reaction mixture was added dichloro[9,9-dimethyl-4,5-bis(diphenylphosphino)xanthene]palladium(II) (2.93 mg, 3.06 µmol) and the reaction mixture was then stirred at 70° C. for 3 h. The progress of the reaction was monitored by TLC (SiO$_2$, 50% EtOAc/Pet., Rf=0.3, UV-active). On completion, the reaction mixture was filtered through a small pad of Celite. The Celite pad was extracted with EtOAc (30 mL). The combined filtrate was dried over anhydrous Na$_2$SO$_4$, filtered, and concentrated under reduced pressure to afford the crude compound as a brown solid which was purified by prep-HPLC using the following conditions: Mobile Phase A=10 mM ammonium bicarbonate (aq); Mobile Phase B=acetonitrile; Column=YMC Triart C$_8$ (150×25 mm, 10µ); Flow-rate=25 mL/min.; Gradient (Time (minutes)/% of B)=0/60, 15/60, 15.1/98, 18/98, 18.1/60, 20/60; Sample solution (dissolved in)=water:acetonitrile:THF; Temperature=ambient. The fractions containing product were pooled, frozen, and then lyophilized to afford N—((S)-1-((3P)-3-(4-chloro-3-(cyclopropanesulfonamido)-1-(2,2-difluoroethyl)-1H-indazol-7-yl)-7-(3-(N-methylmethylsulfonamido)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide and an off white solid. $^1$HNMR (400 MHz, MeOH-d$_4$) δ=8.35 (d, J=8.3 Hz, 1H), 8.11 (d, J=1.8 Hz, 1H), 7.95 (dd, J=8.3, 1.8 Hz, 1H), 7.89 (t, J=1.6 Hz, 1H), 7.79-7.76 (m, 1H), 7.64-7.56 (m, 2H), 7.38-7.35 (m, 1H), 7.24 (d, J=7.9 Hz, 1H), 6.81-6.52 (m, 4H), 6.18-5.86 (m, 1H), 4.76-4.71 (m, 1H), 4.69-4.56 (m, 2H), 4.42-4.31 (m, 1H), 3.97-3.87 (m, 1H), 3.42 (s, 3H), 3.41-3.37 (m, 1H), 3.05 (dd, J=14.0, 9.2 Hz, 1H), 2.95 (s, 3H), 2.89 (tt, J=8.1, 4.9 Hz, 1H), 2.45-2.37 (m, 2H), 1.37-1.28 (m, 1H), 1.13-1.03 (m, 2H), 1.01-0.89 (m, 3H). LCMS Method D: retention time=5.28 mins.; observed ion=1064.09 (M+H).

Preparation of 2-amino-4-(4-(trifluoromethyl)pyrimidin-2-yl)benzoic acid

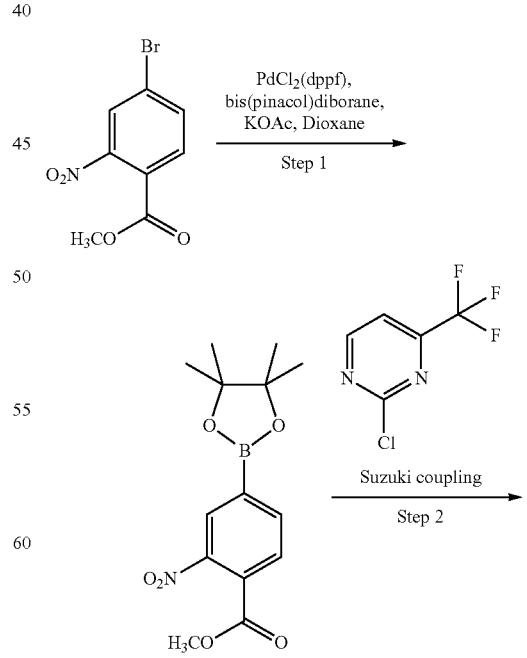

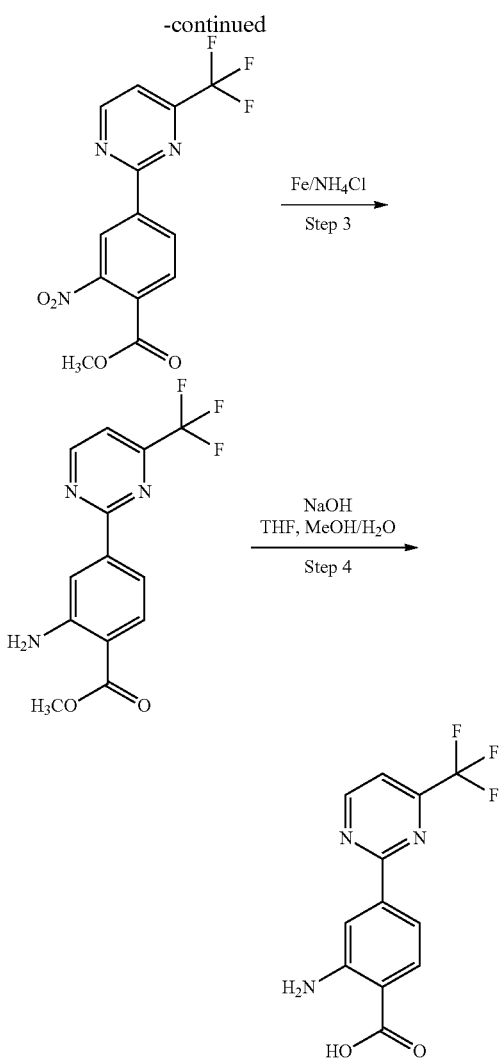

Step 1: Preparation of methyl 2-nitro-4-(4,4,5,5-tetramethyl-1,3,2-dioxaborolan-2-yl)benzoate To a stirred solution of methyl 4-bromo-2-nitrobenzoate (600 g, 2307 mmol) in 1,4-dioxane (6000 mL) at 26° C. under $N_2$ atmosphere was added bis(pinacol)diborane (615 g, 2423 mmol) and potassium acetate (679 g, 6922 mmol). The reaction mixture was degassed by bubbling $N_2$ gas through the mixture for 10 min. To the reaction mixture was added $PdCl_2$(dppf) (84 g, 115 mmol) and the mixture was then stirred at 80° C. for 3 hr. The progress of the reaction was monitored by TLC ($SiO_2$, 20% EtOAc/Pet, Rf=0.4). On completion, the reaction mixture was concentrated under reduced pressure. The resulting residue was dissolved in EtOAc (6000 mL) and then diluted with water (2400 mL). The mixture was mixed and then filtered through a pad of Celite to remove solids. The Celite pad was extracted with EtOAc (2400 mL). The combined filtrate was partitioned, and the organic layer was isolated, dried over anhydrous $Na_2SO_4$, filtered, and concentrated under reduced pressure to afford the crude product. This material was triturated with diethyl ether as follows: First, the material was triturated with $Et_2O$ (2400 mL) and the resulting off-white solid was collected via filtration, washed with $Et_2O$ (2×900 mL), and reserved (480 g isolated). The combined filtrate was concentrated under a stream of $N_2$ gas to half of the original volume, upon which the solution cooled to below ambient temperature and an off-white solid precipitated. The precipitate was collected via filtration, washed with $Et_2O$ (2×600 mL), and reserved (90 g isolated). The combined filtrate was concentrated under a stream of $N_2$ gas to half the original volume, upon which the solution cooled to below ambient temperature and an off-white solid precipitated. The precipitate was collected via filtration, washed with $Et_2O$ (2×600 mL), and this material (30 g isolated) was combined with the previously isolated solids to afford the product methyl 2-nitro-4-(4,4,5,5-tetramethyl-1,3,2-dioxaborolan-2-yl)benzoate as an off-white solid, 600 g (83% yield). $^1$H NMR (400 MHz, DMSO-$d_6$) δ=8.20-8.14 (m, 1H), 8.10-8.05 (m, 1H), 7.87 (d, J=7.5 Hz, 1H), 3.86 (s, 3H), 1.33 (s, 12H). GCMS Purity=97.5%.

Step 2: Preparation of methyl 2-nitro-4-(4-(trifluoromethyl)pyrimidin-2-yl)benzoate To a solution of methyl 2-nitro-4-(4,4,5,5-tetramethyl-1,3,2-dioxaborolan-2-yl)benzoate (600 g, 1954 mmol) and 2-chloro-4-(trifluoromethyl)pyrimidine (357 mL, 2931 mmol) in tetrahydrofuran (THF) (5214 mL) at 26° C. under $N_2$ atmosphere was added slowly a solution of tribasic potassium phosphate (1244 g, 5861 mmol) in water (1307 mL). The reaction mixture was degassed by bubbling $N_2$ gas through the mixture for 10 min. To the mixture was added dichloro[9,9-dimethyl-4,5-bis(diphenylphosphino)xanthene]palladium(II) (73.8 g, 98 mmol), then the mixture was stirred under nitrogen atmosphere at 60° C. for 16 hr. The progress of the reaction was monitored by TLC ($SiO_2$, 20% EtOAc/Pet, Rf=0.3). On completion, the reaction mixture was concentrated under reduced pressure and the resulting residue was diluted with ethyl acetate (5000 mL) and then washed with water (2×2000 mL). The organic layer was dried over anhydrous $Na_2SO_4$, filtered, and concentrated to dryness. The residue was mixed with diethyl ether (634 mL) and the solids were collected via filtration, washed with $Et_2O$ (634 mL), and then dried under vacuum to afford an off-white solid (420 g isolated) which was reserved. The combined filtrate (red in color) was concentrated under a stream of $N_2$ gas to half of the original volume upon which an off-white solid precipitated. The solids were collected via filtration, were washed with diethyl ether (2×634 mL), and the isolated material (80 g) was combined with the previously isolated solids. The blended material was dried under vacuum to afford methyl 2-nitro-4-(4-(trifluoromethyl)pyrimidin-2-yl)benzoate as an off-white solid, 500 g (75% yield). $^1$H NMR (400 MHz, DMSO-$d_6$)=9.39 (d, J=5.0 Hz, 1H), 8.91 (d, J=1.4 Hz, 1H), 8.82-8.78 (m, 1H), 8.14 (d, J=5.1 Hz, 1H), 8.08 (d, J=8.1 Hz, 1H), 3.91 (s, 3H). LCMS purity=95.71%.

Step 3: Preparation of methyl 2-amino-4-(4-(trifluoromethyl)pyrimidin-2-yl)benzoate To a solution methyl 2-nitro-4-(4-(trifluoromethyl)pyrimidin-2-yl) benzoate (500 g, 1528 mmol) in ethanol (6945 mL) and water (695 mL) at 26° C. was added Fe powder (853 g, 15.3 mol) and $NH_4Cl$ (817 g, 15.3 mol). The reaction mixture was stirred at 70° C. for 16 hr. The progress of the reaction was monitored by TLC ($SiO_2$, 20% EtOAc/Pet Rf: 0.4). On completion, the reaction mixture was filtered while hot through a Celite pad and the filtrate was concentrated under reduced pressure. The resulting residue was diluted with water (2500 mL) and then extracted with EtOAc (2×5000 mL). The combined organics were washed with brine solution (3000 mL) and then dried over anhydrous Na$_2$SO$_4$, filtered, and concentrated under reduced pressure to afford methyl 2-amino-4-(4-(trifluoromethyl) pyrimidin-2-yl)benzoate as a yellow solid, 330 g (69% yield). $^1$H-NMR (400 MHz, DMSO-d$_6$) δ=9.30-9.28 (m, 1H), 8.00 (d, J=5.0 Hz, 1H), 7.93 (d, J=1.5 Hz, 1H), 7.88 (d, J=8.5 Hz, 1H), 7.55 (dd, J=1.7, 8.5 Hz, 1H), 6.93 (s, 2H), 3.84 (s, 3H). LCMS purity=95.51%.

Step 4: Preparation of 2-amino-4-(4-(trifluoromethyl)pyrimidin-2-yl)benzoic acid To a solution of methyl 2-amino-4-(4-(trifluoromethyl) pyrimidin-2-yl)benzoate (320 g, 1077 mmol) in methanol (1600 mL) and THF (1600 mL) at 20° C. was added dropwise aq. 5M sodium hydroxide (646 mL, 3230 mmol). The reaction mixture was stirred 60° C. for 16 hr. The progress of the reaction was monitored by TLC (SiO$_2$, 80% EtOAc/Pet. Rf: 0.3). On completion, reaction mixture was concentrated under reduced pressure to remove the volatile organics and the resulting residue was then acidified to pH4 by the addition of aq. 1N HCl. The solids were collected via filtration and were washed with water (5000 mL). The solids were dried under vacuum and then further dried in a 50° C. oven for 24 hr to afford 2-amino-4-(4-(trifluoromethyl) pyrimidin-2-yl)benzoic acid as a yellow solid, 288 g (91% yield). $^1$H-NMR (400 MHz, DMSO-d$_6$) δ=9.31-9.26 (m, 1H), 7.99 (d, J=5.0 Hz, 1H), 7.90-7.85 (m, 2H), 7.53 (dd, J=1.7, 8.4 Hz, 1H). LCMS Purity=96.71%.

Alternate Preparation of Example 3: N—((S)-1-((3P)-3-(4-chloro-1-methyl-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Synthesis Scheme:

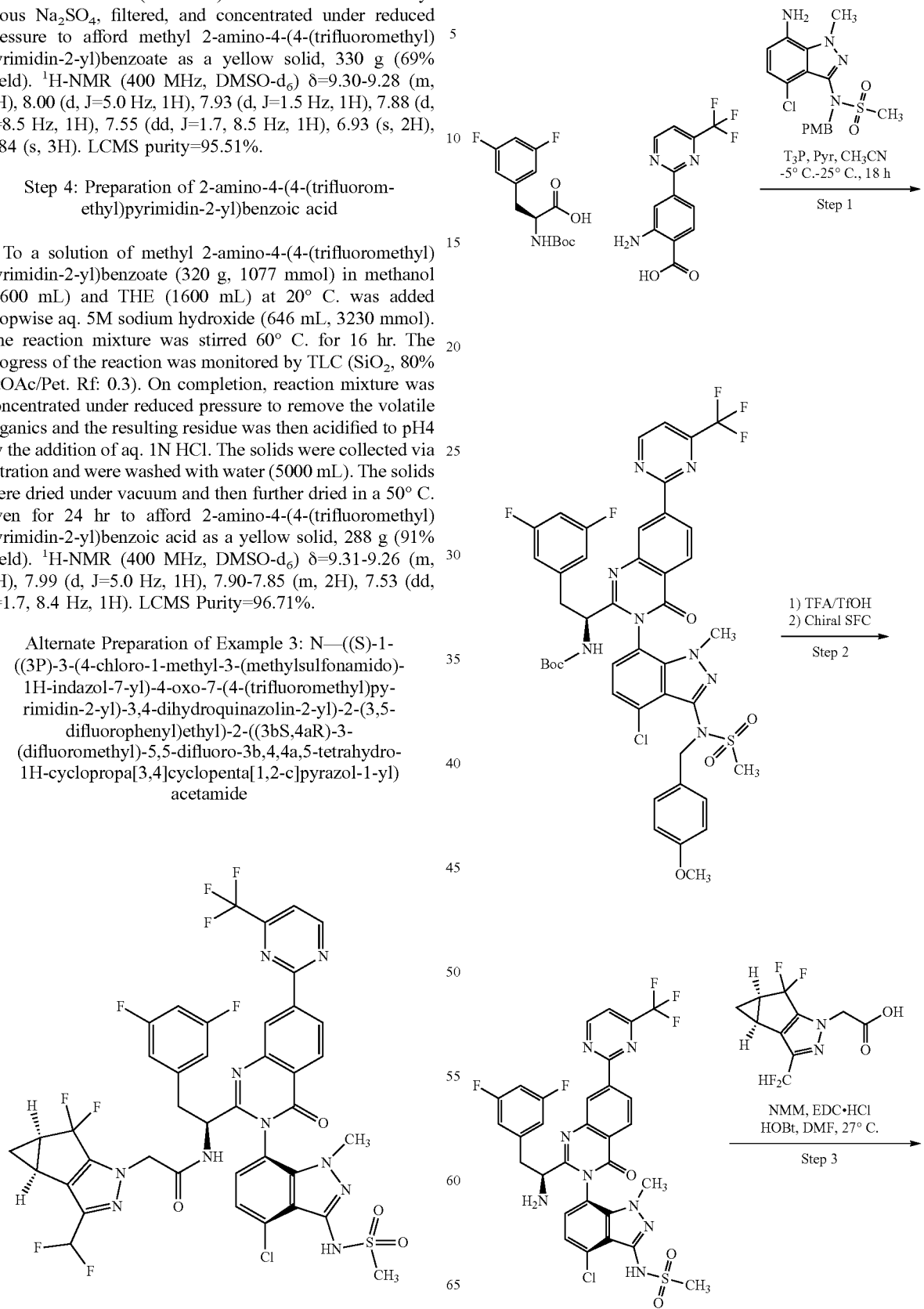

-continued

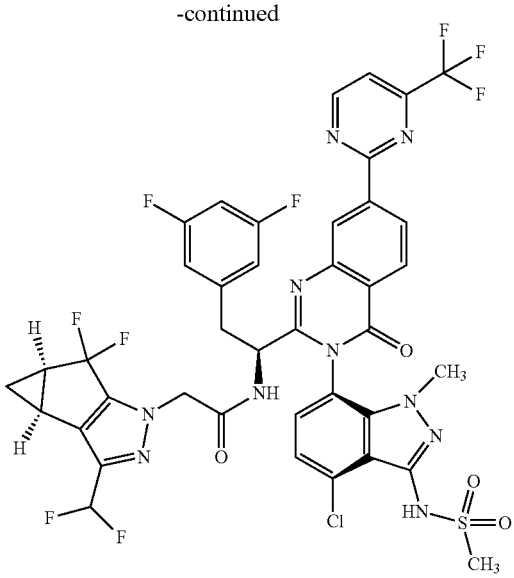

Step 1: Preparation of tert-butyl (S)-(1-(3-(4-chloro-3-(N-(4-methoxybenzyl)methylsulfonamido)-1-methyl-1H-indazol-7-yl)-4-oxo-7-(4-(trifluoromethyl)pyrimidin-2-yl)-3,4-dihydroquinazolin-2-yl)-2-(3,5-difluorophenyl)ethyl)carbamate To a stirred solution of (S)-2-((tert-butoxycarbonyl)amino)-3-(3,5-difluorophenyl) propanoic acid (76 g, 253 mmol) and 2-amino-4-(4-(trifluoromethyl)pyrimidin-2-yl) benzoic acid (79 g, 279 mmol) in acetonitrile (2560 mL) was added pyridine (49.2 mL, 608 mmol) and the mixture was then cooled to −5° C. and stirred at this temperature for 10 min. To the mixture at −5° C. was slowly added T3P (50% in EtOAc, 754 mL, 1266 mmol). The reaction mixture was stirred at −5° C. for 2 hr, then to the mixture was added N-(7-amino-4-chloro-1-methyl-1H-indazol-3-yl)-N-(4-methoxybenzyl)methanesulfonamide (100 g, 253 mmol) in one portion. The mixture was slowly warmed to 25° C. and was stirred for 18 hr. The progress of the reaction was monitored by TLC (SiO$_2$, 40% EtOAc/Pet. Rf=0.2). On completion, the reaction mixture was concentrated under reduced pressure to remove acetonitrile and pyridine. The resulting residue was diluted in EtOAc (2500 mL) and was washed with aq. 2M sodium hydroxide (4000 mL) followed by brine (4000 mL). The organic layer was dried over Na$_2$SO$_4$, filtered, and concentrated under reduced pressure to afford the crude product. This material was purified by silica gel chromatography eluting with 30-40% EtOAc/Pet. ether. The fractions containing the desired product were collected and concentrated under reduced pressure to afford tert-butyl (S)-(1-(3-(4-chloro-3-(N-(4-methoxybenzyl)methylsulfonamido)-1-methyl-1H-indazol-7-yl)-4-oxo-7-(4-(trifluoromethyl)pyrimidin-2-yl)-3,4-dihydroquinazolin-2-yl)-2-(3,5-difluorophenyl)ethyl)carbamate (215 g, 87% yield, a yellow solid) as a mixture of homochiral atropisomers (diastereomers). LCMS Purity=94.91%.

Step 2: Preparation of (S)—N-((6P)-7-(2-(1-amino-2-(3,5-difluorophenyl)ethyl)-4-oxo-7-(4-(trifluoromethyl)pyrimidin-2-yl)quinazolin-3(4H)-yl)-4-chloro-1-methyl-1H-indazol-3-yl)methanesulfonamide To a stirred solution of tert-butyl (S)-(1-(3-(4-chloro-3-(N-(4-methoxybenzyl) methylsulfonamido)-1-methyl-1H-indazol-7-yl)-4-oxo-7-(4-(trifluoromethyl)pyrimidin-2-yl)-3,4-dihydroquinazolin-2-yl)-2-(3,5-difluorophenyl)ethyl) carbamate (425 g, 459 mmol) in TFA (1415 ml, 18.4 mol) at 27° C. was added slowly triflic acid (122 ml, 1378 mmol). The solution was and stirred under nitrogen atmosphere for 2 hr. The progress of the reaction was monitored by TLC (SiO$_2$, 50% EtOAc/Pet. Rf=0.2). On completion, the volatiles were removed under a gentle stream of nitrogen gas. The resulting residue was dissolved in EtOAc (3000 mL). The organic solution was washed with and 2M sodium hydroxide (4000 mL, sufficient to achieve aq. phase pH>7), followed by brine (4000 mL). The organic layer was dried over Na$_2$SO$_4$, filtered and concentrated under reduced pressure to afford crude (S)—N-(7-(2-(1-amino-2-(3,5-difluorophenyl)ethyl)-4-oxo-7-(4-(trifluoromethyl)pyrimidin-2-yl) quinazolin-3(4H)-yl)-4-chloro-1-methyl-1H-indazol-3-yl) methanesulfonamide (425 g, 97% yield, a yellow solid) as a mixture of homochiral atropisomers (diastereomers). The above procedure was repeated and the product from both instances was combined (825 g total), blended, and then purified by silica gel chromatography eluting with 5-10% MeOH in DCM. Fractions containing the desired product were pooled and then concentrated under reduced pressure to afford a yellow solid, 580 g, a mixture of atropisomers (diastereomers). A portion of this material (490 g) was mixed with methanol (5000 mL, 10V) and then filtered to remove the solids which were reserved. The filtrate was concentrated under reduced pressure to afford 255 g of the product, a ~85:15 ratio of atropisomers favoring the desired atropisomer. This material was dissolved in methanol:acetonitrile (10:90, app. 1.5 L). The resulting solution was subjected to prep-SFC chromatography using the following method: Column=(R,R) Welk-01, 30×250 mm, 5; Eluent=CO$_2$:methanol (1:1); Flow-rate=100.0 g/min.; Back-pressure=100.0 bar; Detection=254 nm (UV); Stack time=14.0 min.; Load per injection=1000 mg. The two peaks were collected separately and the major peak (second to elute) was concentrated under reduced pressure to afford (S)—N-((6P)-7-(2-(1-amino-2-(3,5-difluorophenyl)ethyl)-4-oxo-7-(4-(trifluoromethyl)pyrimidin-2-yl)quinazolin-3 (4H)-yl)-4-chloro-1-methyl-1H-indazol-3-yl)methanesulfonamide as a yellow solid, 199 g. This material was contaminated with 0.5% of the other atropisomer (first peak to elute); therefore, a portion of the material (173 g) was subjected to a second round of prep-SFC purification following the method described above. Fractions corresponding to the major peak were pooled and concentrated under reduced pressure to obtain (S)—N-((6P)-7-(2-(1-amino-2-(3,5-difluorophenyl)ethyl)-4-oxo-7-(4-(trifluoromethyl)pyrimidin-2-yl)quinazolin-3(4H)-yl)-4-chloro-1-methyl-1H-indazol-3-yl)methanesulfonamide as a yellow solid, 160 g. The material is a single stereoisomer. $^1$H-NMR (300 MHz, DMSO-d$_6$) δ=9.42 (d, J=5.1 Hz, 1H), 8.81 (d, J=1.5 Hz, 1H), 8.59 (dd, J=8.9, 2.9 Hz, 1H), 8.39 (d, J=8.4 Hz, 1H), 8.13 (d, J=5.1 Hz, 1H), 7.40-7.34 (m, 2H), 7.01 (tt, J=9.5, 2.2 Hz, 1H), 6.81-6.72 (m, 2H), 3.71 (s, 3H), 3.62-3.57 (m, 1H), 3.38-3.34 (m, 1H), 3.23 (s, 3H), 2.92-2.85 (m, 1H). LCMS Purity=95.86%.

Step 3: Preparation of N—((S)-1-((3P)-3-(4-chloro-1-methyl-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide To a stirred solution of (S)—N-((6P)-7-(2-(1-amino-2-(3,5-difluorophenyl)ethyl)-4-oxo-7-(4-(trifluoromethyl)pyrimidin-2-yl)quinazolin-3(4H)-yl)-4-chloro-1-methyl-1H-indazol-3-yl)methanesulfonamide (40 g, 56.7 mmol) in DMF (280 mL) at 27° C. under N₂ atmosphere was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (17.99 g, 68.1 mmol), followed by the addition of EDC.HCl (13.05 g, 68.1 mmol), HOBt hydrate (10.43 g, 68.1 mmol) and N-methylmorpholine (24.95 mL, 227 mmol). The reaction was stirred for 16 hr at 27° C. The progress of the reaction was monitored by TLC (SiO₂, 50% EtOAc/Pet. Rf=0.5). On completion, the reaction mixture was diluted with ice water (2000 mL) and the precipitated solid was isolated via filtration, washed with ice water (2000 mL), and dried under reduced pressure to afford crude N—((S)-1-((3P)-3-(4-chloro-1-methyl-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl) ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid, 60 g (98% yield.). LCMS Purity=88.31%. The above procedure was repeated an additional three times to produce in total 233 g of crude product. This crude material was purified in two equal portions via silica gel chromatography eluting with 40% EtOAC in Pet. ether. The purified product thus obtained was combined and heated in isopropanol (1650 mL) at 95° C. for 2 hr and then slowly cooled to 27° C. over 16 h to promote crystallization. The resulting solids were collected via filtration, washed with isopropanol (1200 mL), and then dried under vacuum. Trace isopropanol residue was removed by grinding the compound using a mortar and pestle and then maintaining the fine solids in a 52° C. oven for 1-2 h; this process of grinding and heating was repeated an additional 4 times until the residual isopropanol was completely removed to afford N—((S)-1-((3P)-3-(4-chloro-1-methyl-3-(methylsulfonamido)-1H-indazol-7-yl)-4-oxo-7-(4-(trifluoromethyl)pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid, 132.2 g (80% yield). ¹H NMR (acetone-d6) δ: 9.40 (d, J=4.8 Hz, 1H), 8.88 (d, J=1.5 Hz, 1H), 8.69 (dd, J=8.3, 1.5 Hz, 1H), 8.58 (br s, 1H), 8.41 (d, J=8.3 Hz, 1H), 8.14 (br d, J=8.6 Hz, 1H), 8.02 (d, J=5.1 Hz, 1H), 7.52 (d, J=7.7 Hz, 1H), 7.38 (d, J=7.7 Hz, 1H), 6.86 (tt, J=9.3, 2.2 Hz, 1H), 6.73 (br d, J=6.3 Hz, 2H), 6.77 (br t, J=54.7 Hz, 1H), 4.93 (td, J=8.9, 4.8 Hz, 1H), 4.65-4.77 (m, 2H), 3.69 (s, 3H), 3.56 (dd, J=14.3, 4.5 Hz, 1H), 3.27 (s, 3H), 3.15 (dd, J=14.0, 9.2 Hz, 1H), 2.41-2.53 (m, 2H), 1.37-1.43 (m, 1H), 0.95-1.00 (m, 1H). LCMS Method A: retention time=6.59 mins.; observed ion=951.0 (M+H), purity=99.78%.

Preparation of 2-amino-4-(4-(difluoromethyl)pyrimidin-2-yl)benzoic acid

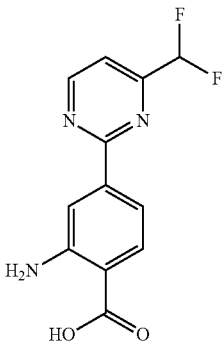 [SMILES: Nc1cc(-c2nccc(C(F)F)n2)ccc1C(=O)O]

Synthesis Scheme:

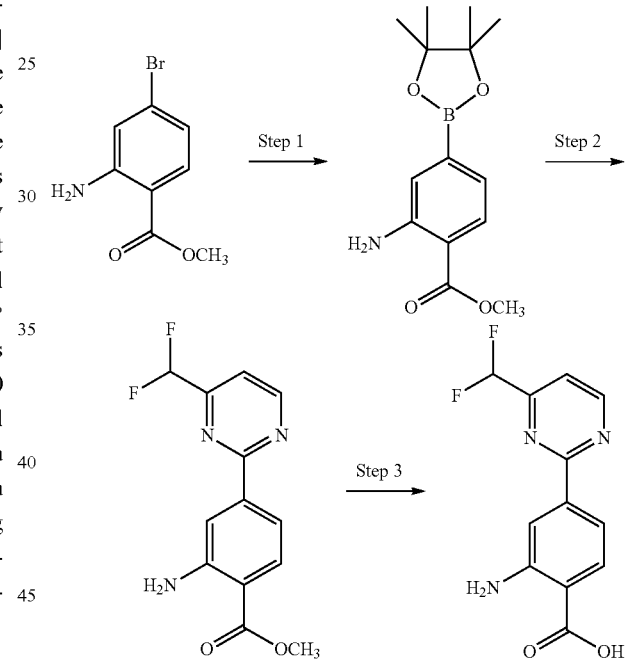

Step 1: Preparation of methyl 2-amino-4-(4,4,5,5-tetramethyl-1,3,2-dioxaborolan-2-yl)benzoate A mixture of methyl 2-amino-4-bromobenzoate (10 g, 43.5 mmol), 4,4,4',4',5,5,5',5'-octamethyl-2,2'-bi(1,3,2-dioxaborolane) (11.04 g, 43.5 mmol), PdCl₂(dppf) (1.590 g, 2.173 mmol), and potassium acetate (12.80 g, 130 mmol) in 1,4-dioxane (100 mL) under argon was heated at 97° C. for 2 h. The mixture was cooled to room temperature and then was diluted with DCM. The organic layer was washed with water, followed by brine, dried over MgSO₄, filtered, and concentrated under reduced pressure to afford the crude product. The crude product was purified via silica gel chromatography (330 g column, 5-30% EtOAc:Hex) to afford the product methyl 2-amino-4-(4,4,5,5-tetramethyl-1,3,2-dioxaborolan-2-yl)benzoate (9.2 g, 76%) as a yellow solid. ¹H NMR (500 MHz, CDCl₃) δ ppm 7.86 (d, J=8.05

Hz, 1H), 7.14 (s, 1H), 7.06 (dd, J=7.90, 1.04 Hz, 1H), 5.67 (br s, 2H), 3.89 (s, 3H), 1.37 (s, 12H).

Step 2: Preparation of methyl 2-amino-4-(4-(difluoromethyl)pyrimidin-2-yl)benzoate In a round-bottom flask was combined methyl 2-amino-4-(4,4,5,5-tetramethyl-1,3,2-dioxaborolan-2-yl)benzoate (14.8 g, 53.4 mmol), 2-chloro-4-(difluoromethyl)pyrimidine (8.79 g, 53.4 mmol), PdCl$_2$(xantphos) (2.019 g, 2.67 mmol) and potassium carbonate (22.14 g, 160 mmol). The flask was sealed with a rubber septum and to the flask was added 1,4-dioxane (200 mL) and water (50.0 mL). The flask was then backfilled with argon (vac then backfill with argon 3 times). The mixture was stirred at 60° C. for 3.5 h. The mixture was cooled to room temperature and the volatile organics were removed under reduced pressure to afford an aqueous mixture. The slurry was taken up in EtOAc (300 mL) and then was further diluted with water (400 mL). The mixture was mixed and then filtered through a Celite pad to removed insoluble material. The organic layer was then separated and washed with brine, dried over MgSO$_4$, filtered and concentrated under reduced pressure. The residue was taken up in a minimum amount of EtOAc (100 mL) and was then mixed with Celite and concentrated under reduced pressure to afford a free-flowing powder. This powder was separated into three equal portions and each portion was subjected to reverse phase chromatography (415 g RediSep Gold C18 column) eluting with (95:5 water:MeCN+0.1% formic acid):(95:5 MeCN:water+0.1% Formic acid) 25:75-0:100. Fractions containing the desired product were pooled and partially concentrated under reduced pressure to afford an aqueous mixture. The slurry was combined with EtOAc and the aqueous layer was made slightly basic (pH 8) by the addition of aq. 5 N NaOH. The mixture was mixed and then the organic layer was isolated and washed with brine, dried over MgSO$_4$, and concentrated under reduced pressure to afford the product methyl 2-amino-4-(4-(difluoromethyl)pyrimidin-2-yl)benzoate (10.2 g, 68%) as a dark yellow solid. $^1$H NMR (500 MHz, CDCl$_3$) δ ppm 9.02 (br d, J=4.77 Hz, 1H), 8.01 (d, J=8.34 Hz, 1H), 7.86 (s, 1H), 7.76 (br d, J=8.35 Hz, 1H), 7.55 (br d, J=4.77 Hz, 1H), 6.52-6.78 (m, 1H), 5.88 (br s, 2H), 3.94 (s, 3H). LCMS Method G: retention time=2.66 mins.; observed ion=321.1 (M+MeCN).

Step 3: Preparation of 2-amino-4-(4-(difluoromethyl)pyrimidin-2-yl)benzoic acid

To a solution of methyl 2-amino-4-(4-(difluoromethyl)pyrimidin-2-yl)benzoate (12 g, 43.0 mmol) in methanol (50 mL) and THF (50.0 mL) was added aqueous 5 N sodium hydroxide (25.8 mL, 129 mmol) and the mixture was then stirred at 60° C. for 1 h upon which LCMS analysis indicated the reaction was complete. The mixture was cooled to room temperature and then to the mixture was added aqueous 1 M HCl (129 mL, 129 mmol). To the thick yellow slurry was added EtOAc (250 mL) and water (150 mL) upon which the yellow slurry partially dissolved; the organic layer was cloudy while the aqueous layer appeared homogeneous. The organic layer was washed with brine and remained cloudy. The organic layer was isolated and heated until the cloudy mixture became a clear yellow solution. The solution was dried over MgSO$_4$, filtered and concentrated under reduced pressure to afford the product 2-amino-4-(4-(difluoromethyl)pyrimidin-2-yl)benzoic acid (11.3 g, 99%) as a yellow solid. $^1$H NMR (500 MHz, CD$_3$OD) δ ppm 9.06 (d, J=5.07 Hz, 1H), 7.96 (d, J=8.35 Hz, 1H), 7.93 (d, J=1.19 Hz, 1H), 7.67 (dd, J=8.49, 1.64 Hz, 1H), 7.64 (d, J=5.07 Hz, 1H), 6.66-6.91 (m, 1H). LCMS Method G: retention time=2.14 mins.; observed ion=307.0 (M+MeCN).

Alternate Preparation of 2-amino-4-(4-(difluoromethyl)pyrimidin-2-yl)benzoic acid

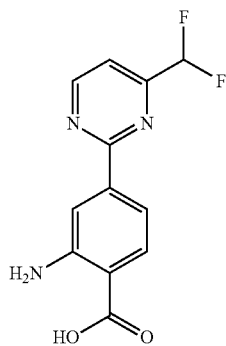 [SMILES: Nc1cc(-c2nccc(C(F)F)n2)ccc1C(=O)O]

Synthesis Scheme:

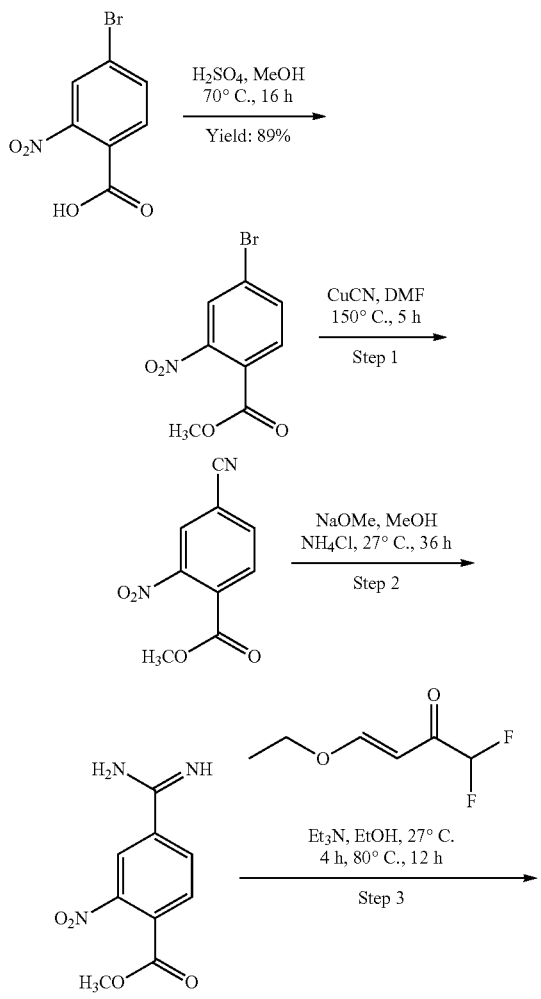

-continued

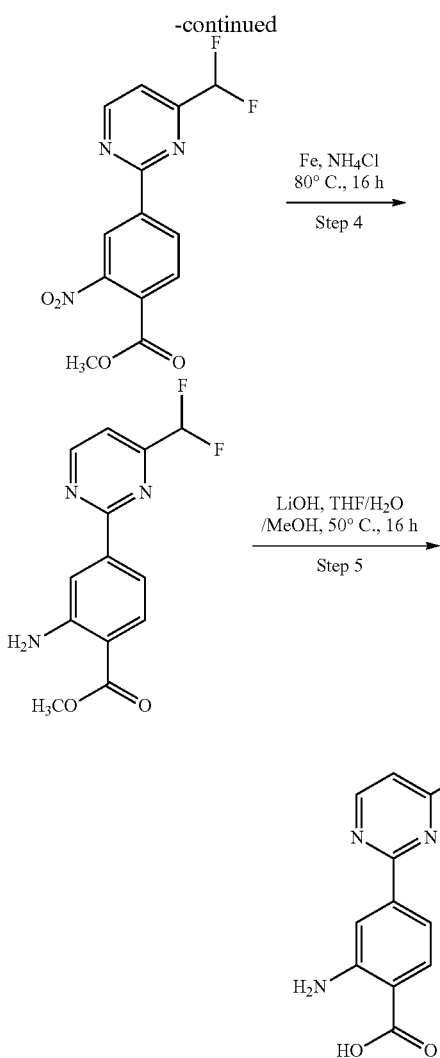

Preparation of methyl 4-bromo-2-nitrobenzoate

This compound was prepared on 200 g scale by following the reported procedure of WO 2005037796 and *J. Am. Chem. Soc.*, 2018, 140 (33), 10553-10561.

Step 1: Preparation of methyl 4-cyano-2-nitrobenzoate

To a stirred solution of methyl 4-bromo-2-nitrobenzoate (340 g, 1307 mmol) in DMF (3000 mL) under nitrogen at 27° C. was added copper (I) cyanide (234 g, 2615 mmol). The reaction mixture was then stirred at 150° C. for 5 h. Progress of the reaction was monitored by TLC (SiO$_2$, 20% EtOAc/Pet., Rf=0.6, UV-active). On completion, the reaction mixture was allowed to cool to 27° C.
The reaction mixture was poured into EtOAc (5000 mL) and the resulting mixture was washed with aq. 5% ethylenediamine (5000 mL) to remove copper salts. The organic solution was then washed with ice cold water (3×3000 mL) followed by ice cold brine (3000 mL). The organic layer was dried over Na$_2$SO$_4$, filtered, and concentrated under reduced pressure to afford methyl 4-cyano-2-nitrobenzoate as a brown solid, 280 g (83%). The product was used directly in the next step without further purification. $^1$HNMR (400 MHz, CDCl$_3$) δ=8.37 (d, J=1.6 Hz, 1H), 7.97 (dd, J=7.9, 1.6 Hz, 1H), 7.87 (d, J=7.9 Hz, 1H), 3.97 (s, 3H). Note: The work-up process was further optimized to avoid the need for filtration: The reaction mixture was poured into EtOAc (5000 mL) and the resulting mixture was washed with aq. 5% ethylenediamine (5000 mL) to remove copper salts. The organic solution was then washed with ice cold water (3×3000 mL) followed by ice cold brine (3000 mL). The remaining process is the same as described above.

Step 2: Preparation of methyl 4-carbamimidoyl-2-nitrobenzoate hydrochloride

To a stirred solution of methyl 4-cyano-2-nitrobenzoate (280 g, 1358 mmol) in MeOH (4000 mL) under nitrogen was added sodium methoxide (44.0 g, 815 mmol) and the reaction mixture was then stirred at 27° C. for 16 h. To the reaction mixture was added ammonium chloride (72.6 g, 1358 mmol) and the reaction mixture was then stirred at 27° C. for 18 h. Progress of the reaction was monitored by TLC (SiO$_2$, 80% EtOAc/Pet., Rf=0.1, UV-active). On completion the reaction mixture was filtered, and the filter cake was extracted with 10% MeOH in DCM (3×1000 mL). The combined filtrate was concentrated under reduced pressure to obtain the crude product as a gummy solid. This material was triturated with EtOAc (1000 mL) to afford methyl 4-carbamimidoyl-2-nitrobenzoate hydrochloride as a yellow solid, 250 g (56%). The product was used directly in the next step without further purification. $^1$H-NMR (400 MHz, DMSO-d$_6$) δ=9.01 (br s, 3H), 8.50 (d, J=1.6 Hz, 1H), 8.23 (dd, J=7.9, 1.6 Hz, 1H), 8.08 (d, J=7.9 Hz, 1H), 3.91 (s, 3H). LCMS purity=79%.

Preparation of (E)-4-ethoxy-1,1-difluorobut-3-en-2-one

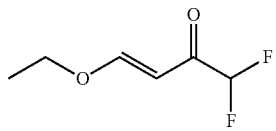

To a stirred solution of 2,2-difluoroacetic anhydride (179 mL, 1436 mmol) in DCM (1250 mL) at 0° C. was added dropwise over 1 h a mixture of pyridine (128 mL, 1580 mmol) and ethoxyethene (165 mL, 1724 mmol). The reaction mixture was allowed to warm to 27° C. and was then stirred for 12 h. The reaction mixture was quenched by the addition of ice-cold water (1000 mL). The organic layer was separated and washed with aq. sat. NaHCO$_3$ (1000 mL), then brine (1000 mL), dried over Na$_2$SO$_4$, and filtered. The filtrate was carefully concentrated under reduced pressure (pressure ≥100 mbar; bath temperature ≤25° C.) to afford (E)-4-ethoxy-1,1-difluorobut-3-en-2-one as a brown liquid, 180 g (80%). The crude compound was used directly in the next step without further purification. $^1$HNMR (400 MHz, CDCl$_3$) δ=7.84 (d, J=12.4 Hz, 1H), 5.89-5.63 (m, 2H), 4.06 (q, J=7.0 Hz, 2H), 1.39 (t, J=7.0 Hz, 3H). GC-MS purity=95%.

Step 3: Preparation of methyl 4-(4-(difluoromethyl) pyrimidin-2-yl)-2-nitrobenzoate To a stirred solution of methyl 4-carbamimidoyl-2-nitrobenzoate (200 g, 708 mmol) in EtOH (2000 mL) in a 5 L autoclave flask under nitrogen atmosphere at 27° C. was added (E)-4-ethoxy-1,1-difluorobut-3-en-2-one (159 g, 1062 mmol) followed by triethylamine (296 mL, 2124 mmol). The reaction mixture was stirred at 80° C. for 16 h. Progress of the reaction was monitored by TLC (SiO$_2$, 20% EtOAc/Pet., Rf=0.5, UV-active). The reaction mixture was filtered and the filtrate was concentrated under reduced pressure to afford methyl 4-(4-(difluoromethyl)pyrimidin-2-yl)-2-nitrobenzoate as a brown liquid, 220 g (58%). The product was used directly the next step without further purification. $^1$H-NMR (400 MHz, CDCl$_3$) δ=9.07-9.00 (m, 1H), 8.80 (dd, J=7.9, 1.6 Hz, 1H), 7.88 (d, J=7.9 Hz, 1H), 7.78-7.56 (m, 1H), 7.62 (d, J=4.8 Hz, 1H), 6.65 (t, J=54.8 Hz, 1H), 3.96 (s, 3H). HPLC Purity: 58%.

Step 4: Preparation of methyl 2-amino-4-(4-(difluoromethyl)pyrimidin-2-yl)benzoate To a stirred solution of methyl 4-(4-(difluoromethyl)pyrimidin-2-yl)-2-nitrobenzoate (220 g, 711 mmol) in EtOH (2150 mL) and water (215 mL) at 27° C. was added ammonium chloride (190 g, 3557 mmol) followed by iron (199 g, 3557 mmol). The reaction mixture was stirred at 80° C. for 16 h. Progress of the reaction was monitored by TLC (SiO$_2$, 20% EtOAc/Pet., Rf=0.4, UV-active). On completion, the reaction mixture was filtered while hot through a Celite pad and the Celite pad was then extracted with EtOAc (4×500 mL). The combined filtrate was concentrated under reduced pressure to afford methyl 2-amino-4-(4-(difluoromethyl)pyrimidin-2-yl)benzoate as a yellow solid, 230 g (64%). The product was used directly in the next step without any further purification. $^1$H-NMR (400 MHz, CDCl$_3$) δ=8.99 (d, J=4.8 Hz, 1H), 7.98 (d, J=8.3 Hz, 1H), 7.83 (s, 1H), 7.73 (d, J=8.4 Hz, 1H), 7.52 (d, J=4.8 Hz, 1H), 6.61 (t, J=54.8 Hz, 1H), 3.91 (s, 3H). LCMS purity=56%.

Step 5: Preparation of 2-amino-4-(4-(difluoromethyl)pyrimidin-2-yl)benzoic acid

To a stirred solution of methyl 2-amino-4-(4-(difluoromethyl)pyrimidin-2-yl)benzoate (230 g, 461 mmol) in THF (2300 mL), MeOH (575 mL) and water (192 mL) at 27° C. was added LiOH (66.3 g, 2767 mmol). The reaction mixture was stirred at 50° C. for 16 h. Progress of the reaction was monitored by TLC (SiO$_2$, 40% EtOAc/Pet., Rf=0.1, UV-active). On completion the reaction mixture was allowed to cool to 27° C. and was then concentrated under reduced pressure. The crude residue was dissolved in water (1000 mL) and washed with EtOAc (2×250 mL). The aqueous layer was acidified with aq. 1N HCl to pH ~6. The precipitated solid was collected via filtration and wash with water (500 mL), then n-pentane (500 mL) and then dried to afford 2-amino-4-(4-(difluoromethyl)pyrimidin-2-yl)benzoic acid as a yellow solid, 80 g (63%). $^1$H-NMR (400 MHz, DMSO-d$_6$) δ=9.15 (d, J=4.8 Hz, 1H), 7.87-7.84 (m, 2H), 7.74 (d, J=4.8 Hz, 1H), 7.53 (d, J=8.4 Hz, 1H), 7.06 (t, J=54.2 Hz, 1H). LCMS purity=96%.

Alternate Preparation of Example 56: N—((S)-1-((3P)-3-(4-chloro-1-methyl-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

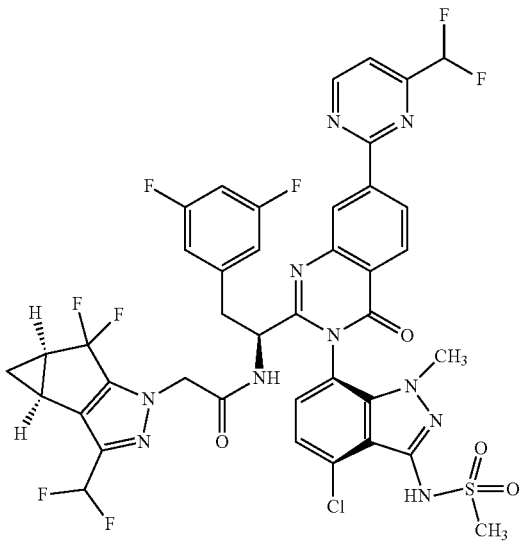

Synthesis Scheme:

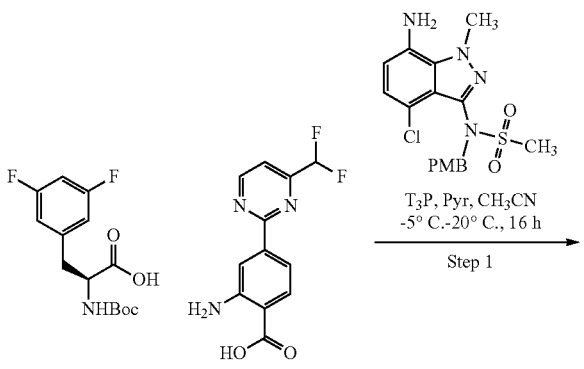

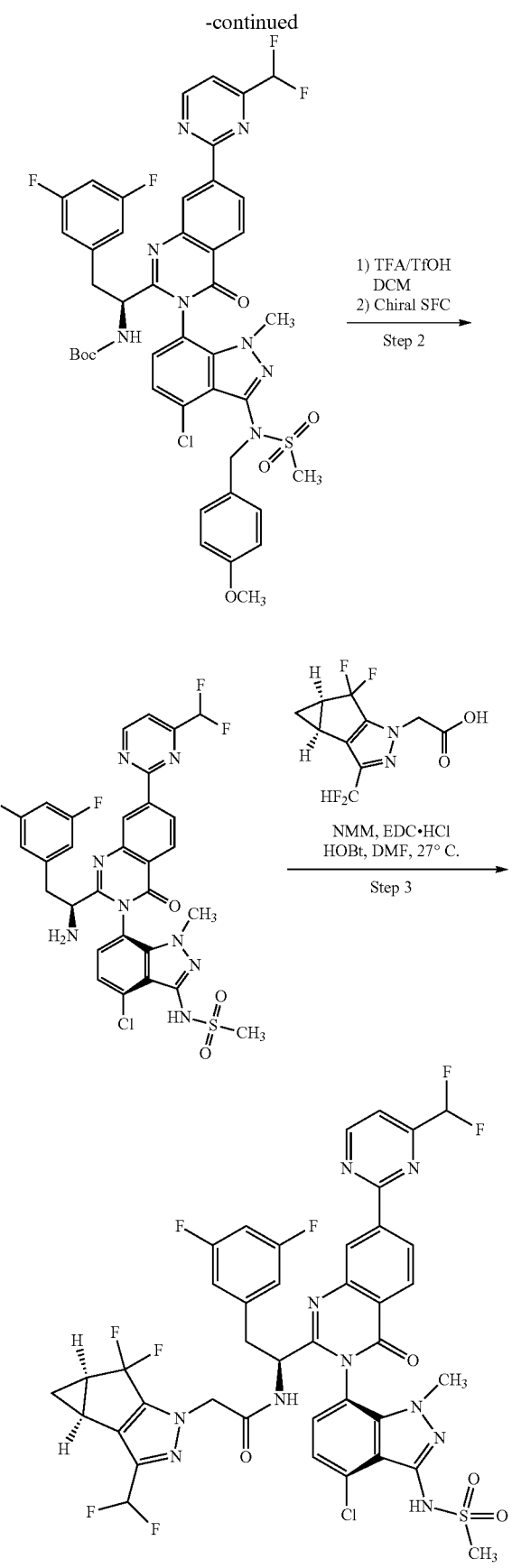

Step 1: Preparation of tert-butyl (S)-(1-(3-(4-chloro-3-(N-(4-methoxybenzyl)methylsulfonamido)-1-methyl-1H-indazol-7-yl)-7-(4-(difluoromethyl)pyrimidin-2-yl)-4-oxo-3,4-dihydroquinazolin-2-yl)-2-(3,5-difluorophenyl)ethyl)carbamate To a stirred solution of (S)-2-((tert-butoxycarbonyl)amino)-3-(3,5-difluorophenyl)propanoic acid (76 g, 253 mmol) and 2-amino-4-(4-(difluoromethyl)pyrimidin-2-yl)benzoic acid (73.9 g, 279 mmol) in acetonitrile (2.1 L) was added pyridine (0.049 L, 608 mmol) and the reaction mixture was cooled to −5° C. and stirred at same temperature for 10 min. Then to the reaction mixture at −5° C. was slowly added T3P (50% in EtOAc) (0.754 L, 1266 mmol). The mixture was stirred at −5° C. for 20 min., then was allowed to warm to 27° C., and then was stirred for 2 h. To the reaction mixture was added N-(7-amino-4-chloro-1-methyl-1H-indazol-3-yl)-N-(4-methoxybenzyl) methanesulfonamide (100 g, 253 mmol) in one portion at 27° C. and the mixture was then stirred for 18 h. The progress of the reaction was monitored by TLC (SiO$_2$, 40% EtOAc/Pet., Rf=0.4, UV-active). The reaction mixture was concentrated under reduced pressure to remove acetonitrile and then was diluted with EtOAc (1000 mL) and washed with water (2000 mL). The organic layer was separated and washed with sat. aq. Na$_2$CO$_3$ (3×500 mL) and then brine (500 mL), dried over anhydrous Na$_2$SO$_4$, filtered and concentrated under reduced pressure to afford the crude product as a brown gummy liquid which was purified by column chromatography on silica gel eluting with 30-40% EtOAc/Pet. The fractions containing the desired product were collected and concentrated under reduced pressure to afford tert-butyl (S)-(1-(3-(4-chloro-3-(N-(4-methoxybenzyl)methylsulfonamido)-1-methyl-1H-indazol-7-yl)-7-(4-(difluoromethyl)pyrimidin-2-yl)-4-oxo-3,4-dihydroquinazolin-2-yl)-2-(3,5-difluorophenyl)ethyl)carbamate (180 g, 78%, a yellow solid) as a mixture of homochiral atropisomers (diastereomers).

Step 2: Preparation of (S)—N-((6P)-7-(2-(1-amino-2-(3,5-difluorophenyl)ethyl)-7-(4-(difluoromethyl)pyrimidin-2-yl)-4-oxoquinazolin-3(4H)-yl)-4-chloro-1-methyl-1H-indazol-3-yl)methanesulfonamide To a stirred solution of tert-butyl (S)-(1-(3-(4-chloro-3-(N-(4-methoxybenzyl)methylsulfonamido)-1-methyl-1H-indazol-7-yl)-7-(4-(difluoromethyl)pyrimidin-2-yl)-4-oxo-3,4-dihydroquinazolin-2-yl)-2-(3,5-difluorophenyl)ethyl)carbamate (110 g, 121 mmol) in DCM (500 mL) at 27° C. under N$_2$ atmosphere was added TFA (374 mL, 4849 mmol) and the solution was stirred for 10 min. To the solution was added trifluoromethanesulfonic acid (32.3 mL, 364 mmol) and the solution was stirred for 1 h at 27° C. The progress of the reaction was monitored by TLC (SiO$_2$, 50% EtOAc/Pet., Rf=0.2). The volatiles were removed under a gentle stream of nitrogen gas. The resulting residue was dissolved in EtOAc (1500 mL) and then washed with 1M aq. NaOH (2×750 mL), followed by brine (750 mL), dried over Na$_2$SO$_4$, filtered and concentrated under reduced pressure to afford the crude product as an off-white solid. This material was purified by silica gel chromatography eluting with 80-98% EtOAc/Pet. The fractions containing the desired product were collected and concentrated under reduced pressure to afford (S)—N-(7-(2-(1-amino-2-(3,5-difluorophenyl)ethyl)-7-(4-(difluoromethyl)pyrimidin-2-yl)-4-oxoquinazolin-3(4H)-yl)-4-chloro-1-methyl-1H-indazol-3-yl)methanesulfonamide as a yellow solid, 65 g (74%). The product is a mixture of homochiral atropisomers (diastereomers). The above procedure was repeated an addition four times to produce in total 310 g of (S)—N-(7-(2-(1-amino-2-(3,5-difluorophenyl)ethyl)-7-(4-(difluoromethyl)pyrimidin-2-yl)-4-oxoquinazolin-3(4H)-yl)-4-chloro-1-methyl-1H-indazol-3-yl)methanesulfonamide which was dissolved in DCM:MeCN (30:70, 3055 mL) and then subjected to prep-SFC using the following method: Column=(R,R) Welk-01, 30×250 mm, 5p; Eluent=CO₂:methanol (1:1); Flow-rate=90.0 g/min.; Back-pressure=120.0 bar; Detection=254 nm (UV); Stack time=16.0 min.; Load per injection=800 mg. The separation produced two peaks. The major peak (second to elute) was collected and concentrated under reduced pressure to afford (S)—N-((6P)-7-(2-(1-amino-2-(3,5-difluorophenyl)ethyl)-7-(4-(difluoromethyl)pyrimidin-2-yl)-4-oxoquinazolin-3(4H)-yl)-4-chloro-1-methyl-1H-indazol-3-yl)methanesulfonamide as a yellow solid, 170 g (51%). The product is a single stereoisomer. $^1$H NMR (400 MHz, CDCl₃) δ=9.16-9.07 (m, 1H), 9.01-8.95 (m, 1H), 8.71-8.62 (m, 1H), 8.46-8.37 (m, 1H), 7.68-7.61 (m, 1H), 7.11 (d, J=7.8 Hz, 1H), 6.86-6.55 (m, 2H), 6.54-6.45 (m, 3H), 3.79-3.74 (m, 3H), 3.71-3.63 (m, 1H), 3.44-3.33 (m, 4H), 2.94-2.83 (m, 1H). LCMS Purity=94%.

Step 3: Preparation of N—((S)-1-((3P)-3-(4-chloro-1-methyl-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide To a solution of (S)—N-((6P)-7-(2-(1-amino-2-(3,5-difluorophenyl)ethyl)-7-(4-(difluoromethyl)pyrimidin-2-yl)-4-oxoquinazolin-3(4H)-yl)-4-chloro-1-methyl-1H-indazol-3-yl)methanesulfonamide (50 g, 61.9 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (16.34 g, 61.9 mmol) and 1-hydroxybenzotriazole hydrate ("HOBt hydrate", 3.79 g, 24.74 mmol) in DMF (500 mL) at 27° C. was added N-methylmorpholine (13.60 mL, 124 mmol) and N-(3-dimethylaminopropyl)-N'-ethylcarbodiimide hydrochloride (21.34 g, 111 mmol). The reaction mixture was stirred at 27° C. for 16 h. The progress of the reaction was monitored by TLC (SiO₂, 50% EtOAc/Pet., Rf=0.5, UV-active). The reaction mixture was diluted with ice cold water (7 L) and then stirred for 30 min. The precipitated solid was collected via filtration and was then dried under vacuum to afford the crude compound as an off-white solid, 75 g. LCMS purity=60%. The above procedure was repeated an additional three times to produce in total 185 g of crude N—((S)-1-((3P)-3-(4-chloro-1-methyl-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide which was blended and then purified silica gel chromatography eluting with 30-40% EtOAc/Pet. The fractions containing the desired product were collected and concentrated under reduced pressure to afford the desired product as an off-white solid (100 g, LCMS Purity: 97%). This material was suspended in isopropanol (1000 mL, 10V), heated at 70° C. for 30 min, then allowed to slowly cool to 27° C. over 16 h to produce the crystalline product. The obtained solid was collected via filtration and then dried under vacuum to afford N—((S)-1-((3P)-3-(4-chloro-1-methyl-3-(methylsulfonamido)-1H-indazol-7-yl)-7-(4-(difluoromethyl)pyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid, 80 g (79%). 1H NMR (acetone-d6) δ: 9.27 (d, J=5.1 Hz, 1H), 8.89 (d, J=1.8 Hz, 1H), 8.69 (dd, J=8.3, 1.8 Hz, 1H), 8.57 (br s, 1H), 8.39 (d, J=8.3 Hz, 1H), 8.12 (d, J=8.9 Hz, 1H), 7.84 (d, J=5.1 Hz, 1H), 7.51 (d, J=7.7 Hz, 1H), 7.37 (d, J=8.0 Hz, 1H), 7.03 (t, J=54.4 Hz, 1H), 6.86 (tt, J=9.2, 2.4 Hz, 1H), 6.70-6.76 (m, 2H), 6.78 (t, J=54.7 Hz, 1H), 4.93 (td, J=9.0, 4.6 Hz, 1H), 4.65-4.76 (m, 2H), 3.69 (s, 3H), 3.56 (dd, J=14.2, 4.6 Hz, 1H), 3.27 (s, 3H), 3.15 (dd, J=14.3, 9.2 Hz, 1H), 2.42-2.53 (m, 2H), 1.37-1.44 (m, 1H), 0.95-1.00 (m, 1H). LCMS Method B: retention time=2.73 mins.; observed ion=933.09 (M+H); purity=99%.

Preparation of 2-amino-4-(6-(trifluoromethyl)pyridin-2-yl)benzoic acid

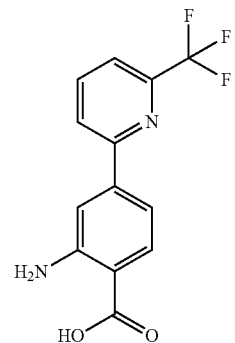 [SMILES: Nc1cc(-c2cccc(C(F)(F)F)n2)ccc1C(=O)O]

Synthesis Scheme:

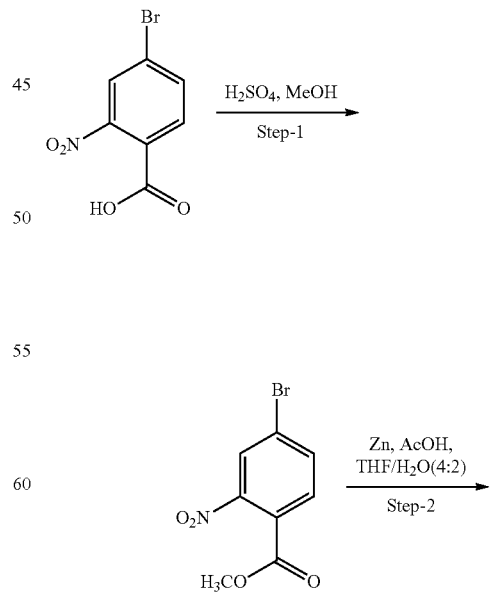

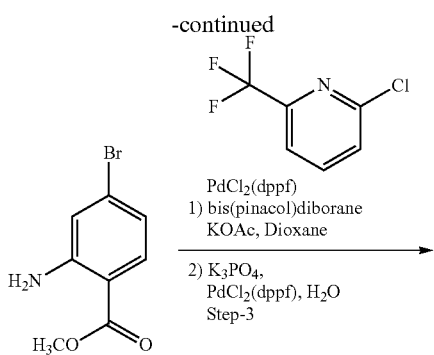

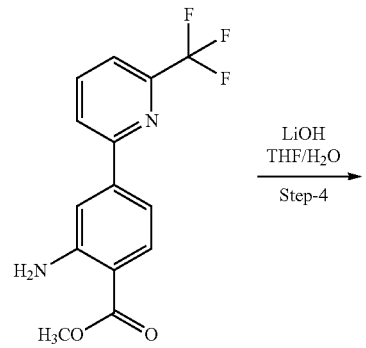

Step 1: Preparation of methyl 4-bromo-2-nitrobenzoate

To a stirred solution of 4-bromo-2-nitrobenzoic acid (500 g, 2032 mmol) in methanol (2000 mL) was added sulfuric acid (500 mL, 9381 mmol) at 0° C. The solution was stirred for 4 hr at 70° C. The progress of the reaction was monitored by TLC ($SiO_2$, 30% EtOAc/Pet. Rf=0.3). After completion of the reaction, the reaction mass was cooled to room temperature and then concentrated under reduced pressure to remove the methanol. The resulting residue was poured into water (1000 mL) and the pH was adjusted to pH 9 via the addition of anhydrous sodium carbonate. The mixture was extracted with ethyl acetate (2×1000 mL). The combined organics were washed with water (500 mL) and then brine solution (500 mL). The organic layer was dried over anhydrous $Na_2SO_4$, filtered, and then concentrated under reduced pressure to afford methyl 4-bromo-2-nitrobenzoate (520 g, 94%) as an off-white solid. 1H-NMR (400 MHz, $CDCl_3$) δ=8.04-7.99 (m, 1H), 7.85-7.78 (m, 1H), 7.66 (d, J=8.2 Hz, 1H), 3.92 (s, 3H). LCMS Purity=95.2%. The product was used directly in the next step without further purification.

Step 2: Preparation of methyl 2-amino-4-bromobenzoate

To a stirred solution of zinc powder (704 g, 10.8 mol) in water (2000 mL) at 0° C. under nitrogen atmosphere was slowly added a solution of methyl 4-bromo-2-nitrobenzoate (400 g, 1538 mmol) in tetrahydrofuran (THF) (4000 mL) followed by acetic acid (1057 mL, 18.5 mol). The reaction mixture was stirred at 27° C. for 4 hr. The progress of the reaction was monitored by TLC ($SiO_2$, 20% EtOAc/Pet. Rf=0.4). On completion, the reaction mixture was filtered through a Celite pad and the Celite pad was extracted with EtOAc (2000 mL). The combined filtrate was concentrated under reduced pressure. The resulting residue was diluted with water (3000 mL) and extracted with EtOAc (2×4000 mL). The combined organics were washed with saturated $Na_2CO_3$ solution (2×3000 mL) and then brine (2×2000 mL). The organic layer was dried over anhydrous $Na_2SO_4$, filtered, and then concentrated under reduced pressure to afford methyl 2-amino-4-bromobenzoate (350 g, 94%) as an off white solid. 1H-NMR (400 MHz, $CDCl_3$) δ=7.76-7.65 (m, 1H), 6.84 (d, J=1.9 Hz, 1H), 6.78-6.72 (m, 1H), 5.91-5.63 (m, 2H), 3.86 (s, 3H). LCMS Purity=95.0%. The product was used directly in the next step without further purification.

Step 3: Preparation of methyl 2-amino-4-(6-(trifluoromethyl)pyridin-2-yl)benzoate

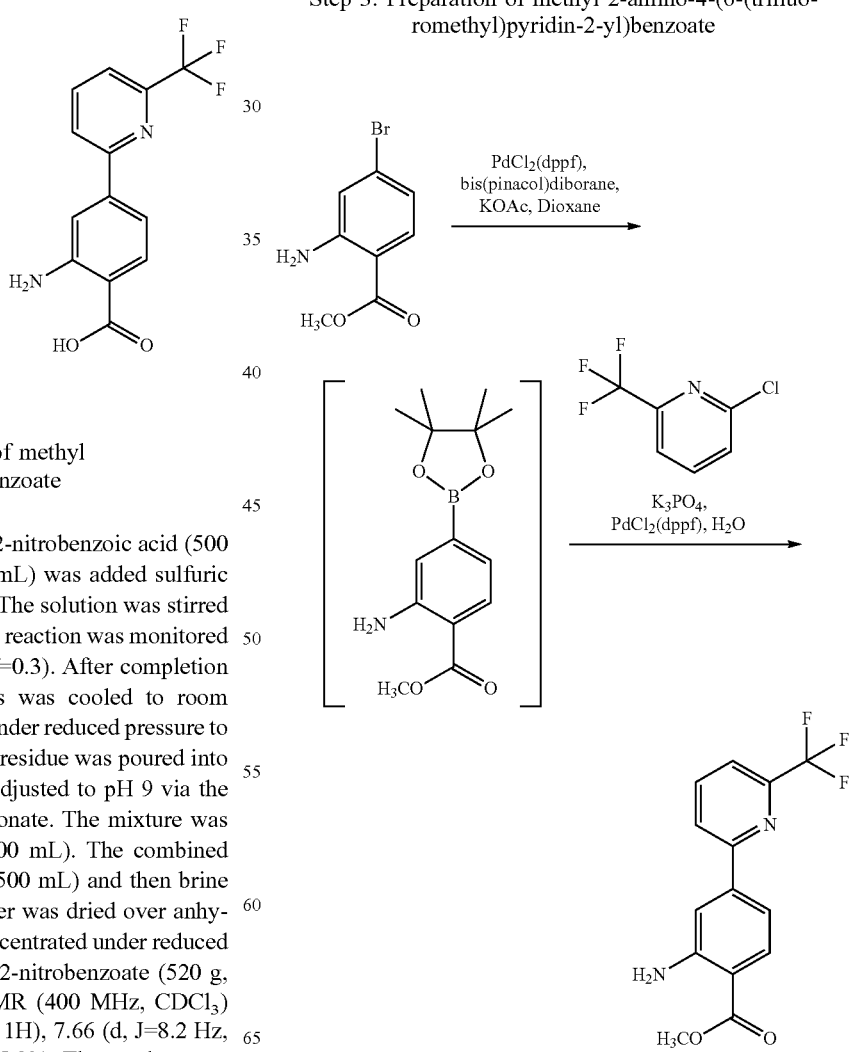

To a stirred solution of methyl 2-amino-4-bromobenzoate (350 g, 1521 mmol) in 1,4-dioxane (7000 mL) was added bis(pinacol)diborane (522 g, 2054 mmol) and potassium acetate (597 g, 6085 mmol). The reaction mixture was degassed by bubbling N₂ gas through the mixture for 10 min. To the reaction mixture was added PdCl₂(dppf) (78 g, 106 mmol). The mixture was stirred at 90° C. for 4 hr. The progress of the reaction was monitored by TLC. On completion of the reaction the mixture was cooled to room temperature. To the mixture was added 2-chloro-6-(trifluoromethyl)pyridine (359 g, 1978 mmol), tribasic potassium phosphate (1130 g, 5325 mmol) and water (1190 mL). The mixture was degassed via nitrogen gas bubbling for 10 mins. To the mixture was added PdCl₂(dppf) (78 g, 106 mmol). The reaction mixture was stirred at 60° C. for 16 hr. The progress of the reaction was monitored by TLC (SiO₂, 20% EtOAc/Pet. Rf=0.4). On completion, the reaction mixture was filtered through Celite and the Celite pad was then extracted with ethyl acetate (2000 mL). The combined filtrate was concentrated under reduced pressure to afford crude the crude product (550 g) as a brown liquid. This material was purified via silica gel chromatography eluting with 5-30% EtOAc/Pet. The fractions containing the desired product were pooled and concentrated under reduced pressure. The isolated material was washed with n-pentane (2200 mL) and the solids were collected via filtration and then dried under vacuum to afford methyl 2-amino-4-(6-(trifluoromethyl)pyridin-2-yl)benzoate (380 g, 83%) as an off white solid. $^1$H NMR (CHLOROFORM-d) δ: 7.99 (d, J=8.3 Hz, 1H), 7.92-7.98 (m, 2H), 7.67 (dd, J=6.9, 1.5 Hz, 1H), 7.49 (d, J=1.5 Hz, 1H), 7.27 (dd, J=8.3, 1.8 Hz, 1H), 5.90 (br s, 2H), 3.93 (s, 3H). LCMS Purity=98.25%.

Step 4: Preparation of 2-amino-4-(6-(trifluoromethyl)pyridin-2-yl)benzoic acid

To a stirred solution of methyl 2-amino-4-(6-(trifluoromethyl)pyridin-2-yl)benzoate (650 g, 2194 mmol) in tetrahydrofuran (THF) (5000 mL) and water (2167 mL) at 0° C. under nitrogen atmosphere was added lithium hydroxide monohydrate (369 g, 8776 mmol). The reaction mixture was stirred at 70° C. for 16 hr. The progress of the reaction was monitored by TLC (SiO₂, 50% EtOAc/Pet. Rf=0.4). On completion, the reaction mixture was concentrated under reduced pressure and the resulting residue was then dissolved in water (5000 mL) and acidified to pH 4 via the addition of 3N HCl (3000 mL). The resulting precipitate was collected via filtration and was washed with water (4000 mL), then n-hexane (5000 mL), and then dried to afford 2-amino-4-(6-(trifluoromethyl)pyridin-2-yl)benzoic acid (581 g, 93%) as an off-white solid. 1H-NMR (400 MHz, DMSO-d₆)=8.18 (d, J=4.0 Hz, 2H), 7.92-7.88 (m, 1H), 7.84 (d, J=8.3 Hz, 1H), 7.54 (d, J=1.7 Hz, 1H), 7.22 (d, J=8.4, 1.8 Hz, 1H). LCMS Purity=99.62%.

Alternate Preparation of Example 59: N—((S)-1-((3P)-3-(4-chloro-1-methyl-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

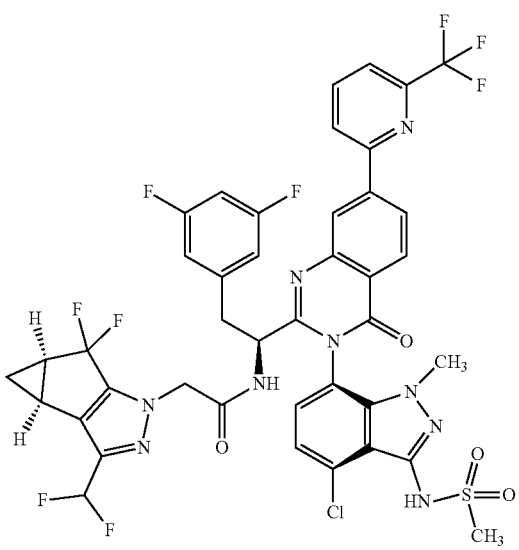

Synthesis Scheme:

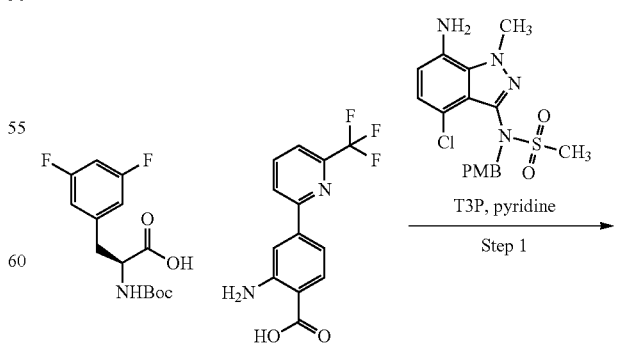

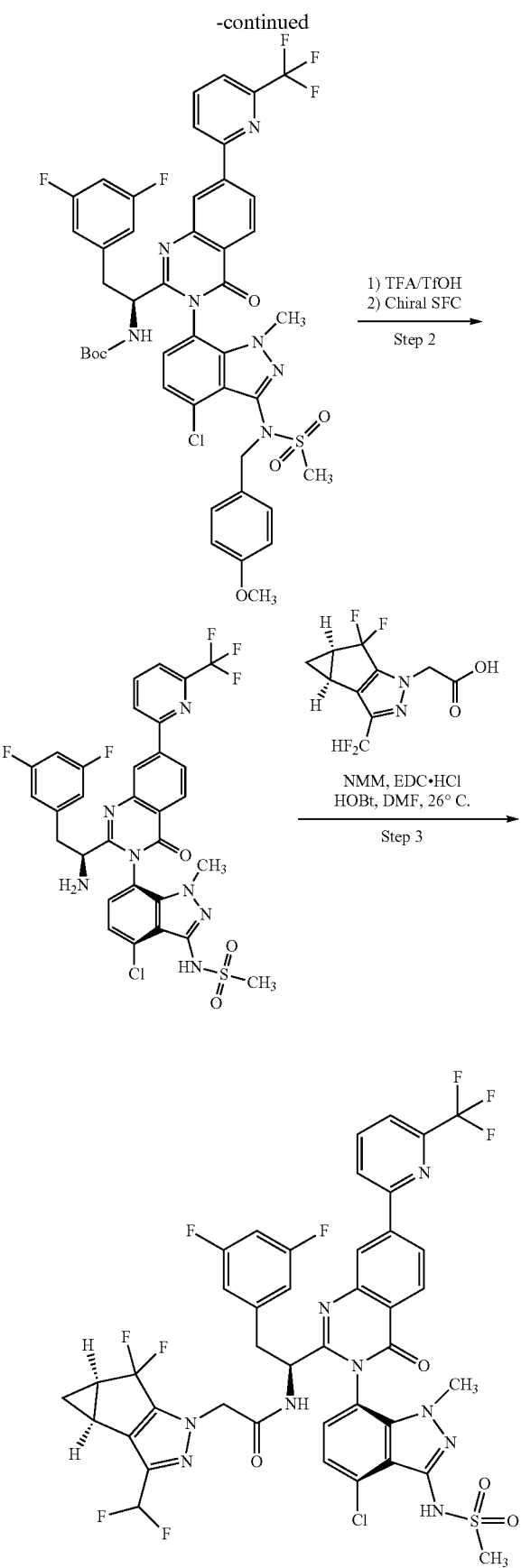

Step 1: Preparation of tert-butyl (S)-(1-(3-(4-chloro-3-(N-(4-methoxybenzyl)methylsulfonamido)-1-methyl-1H-indazol-7-yl)-4-oxo-7-(6-(trifluoromethyl)pyridin-2-yl)-3,4-dihydroquinazolin-2-yl)-2-(3,5-difluorophenyl)ethyl)carbamate To a stirred solution of (S)-2-((tert-butoxycarbonyl)amino)-3-(3,5-difluorophenyl) propanoic acid (91 g, 301 mmol) and 2-amino-4-(6-(trifluoromethyl)pyridin-2-yl)benzoic acid (94 g, 332 mmol) in acetonitrile (3.8 L)) under nitrogen atmosphere at 27° C. was added pyridine (0.059 L, 724 mmol). The resulting mixture was cooled to −9° C. for 10 min., then 2,4,6-tripropyl-1,3,5,2,4,6-trioxatriphosphinane 2,4,6-trioxide ("T3P", 5000 wt in EtOAc, 0.888 L, 1507 mmol) was added drop-wise over 10 min. The solution was stirred for 2.1 hr at −9° C. under $N_2$ atmosphere. To the solution at −9° C. was added N-(7-amino-4-chloro-1l-methyl-1H-indazol-3-yl)-N-(4-methoxybenzyl)methanesulfonamide (120 g, 301 mmol) upon which the solution warmed to −5° C. and was maintained at that temperature with stirring for 1 hr. The reaction mass was then allowed to slowly warm to 27° C. and was then stirred at that temperature for 16 hrs. The progress of the reaction was monitored by TLC ($SiO_2$, 50% EtOAc/Pet. Rf=0.5). On completion, the reaction mixture was concentrated under reduced pressure and the resulting residue was dissolved in EtOAc (5000 mL) and then washed with 1N NaOH solution (2000 mL) followed by brine (1000 mL). The organic layer was dried over $Na_2SO_4$, filtered, and then concentrated under reduced pressure to afford the crude product which was purified by silica gel chromatography eluting with 30-35% EtOAc/Pet. The fractions containing the desired product were pooled and concentrated under reduced pressure to afford tert-butyl (S)-(1-(3-(4-chloro-3-(N-(4-methoxybenzyl)methylsulfonamido)-1-methyl-1H-indazol-7-yl)-4-oxo-7-(6-(trifluoromethyl)pyridin-2-yl)-3,4-dihydroquinazolin-2-yl)-2-(3,5-difluorophenyl)ethyl)carbamate (252 g, 88%, an off-white solid) as a mixture of homochiral atropisomers (diastereomers).

Step 2: Preparation of (S)—N-((6P)-7-(2-(1-amino-2-(3,5-difluorophenyl)ethyl)-4-oxo-7-(6-(trifluoromethyl)pyridin-2-yl)quinazolin-3(4H)-yl)-4-chloro-1-methyl-1H-indazol-3-yl)methanesulfonamide To a stirred solution of tert-butyl (S)-(1-(3-(4-chloro-3-(N-(4-methoxybenzyl)methylsulfonamido)-1-methyl-1H-indazol-7-yl)-4-oxo-7-(6-(trifluoromethyl)pyridin-2-yl)-3,4-dihydroquinazolin-2-yl)-2-(3,5-difluorophenyl)ethyl)carbamate (97% purity, 252 g, 264 mmol) in TFA (815 ml, 10.6 mol) at 27° C. was added triflic acid (70.4 ml, 793 mmol). The solution was stirred for 2 h under nitrogen atmosphere. The progress of the reaction was monitored by TLC ($SiO_2$, 50% EtOAc/Pet. Rf=0.2). On completion, the volatiles were removed under a gentle stream of nitrogen gas. The residue was dissolved in EtOAc (5000 mL) and then washed with 1N NaOH solution (2000 mL) followed by brine (1500 mL). The organic layer was dried over $Na_2SO_4$, filtered, and then concentrated under reduced pressure to afford the crude product which was purified by silica gel chromatography eluting with 5-15% MeOH in DCM. The fractions containing the desired product were pooled and concentrated under reduced pressure to afford (S)—N-(7-(2-(1-amino-2-(3,5-difluorophenyl)ethyl)-4-oxo-7-(6-(trifluoromethyl)pyridin-2-yl)quinazolin-3(4H)-yl)-4-chloro-1-methyl-1H-indazol-3-yl) methane sulfonamide (180 g, 95%, an off-white solid) as a mixture of homochiral atropisomers (diastereomers). The material was dissolved in methanol: acetonitrile (40:60, 3000 mL) and was then purified by prep-SFC using the following method: Column=(R,R) Welk-01, 30×250 mm, 5p; eluent=$CO_2$:methanol (1:1); Flow-rate=90.0 g/min.; Back-pressure=120.0 bar; Detection=254 nm (UV); Stack time=8.8 min.; Load per injection=700 mg. The SFC separation produced two peaks which were collected separately. The major peak (second peak to elute) was concentrated under reduced pressure to afford (S)—N-((6P)-7-(2-(1-amino-2-(3,5-difluorophenyl) ethyl)-4-oxo-7-(6-(trifluoromethyl)pyridin-2-yl)quinazolin-3(4H)-yl)-4-chloro-1-methyl-1H-indazol-3-yl)methanesulfonamide (100 g, 54%) as an off-white solid. The product is a single stereoisomer. 1H-NMR (400 MHz, DMSO-$d_6$) δ=8.64-8.55 (m, 2H), 8.44-8.25 (m, 3H), 8.01 (d, J=7.7 Hz, 1H), 7.42-7.31 (m, 2H), 7.07-6.95 (m, 1H), 6.76 (dd, J=2.0, 8.5 Hz, 2H), 3.70 (s, 3H), 3.59 (dd, J=4.8, 8.2 Hz, 1H), 3.35 (br d, J=4.8 Hz, 1H), 3.17 (d, J=5.1 Hz, 3H), 2.92-2.83 (m, 1H). LCMS Purity=99%.

Step 3: Preparation of N—((S)-1-((3P)-3-(4-chloro-1-methyl-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide To a stirred solution of (S)—N-((6P)-7-(2-(1-amino-2-(3,5-difluorophenyl)ethyl)-4-oxo-7-(6-(trifluoromethyl)pyridin-2-yl)quinazolin-3(4H)-yl)-4-chloro-1-methyl-1H-indazol-3-yl)methanesulfonamide (45 g, 63.9 mmol) in DMF (450 mL) at 27° C. was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (20.26 g, 77 mmol) followed by N-(3-dimethylaminopropyl)-N'-ethylcarbodiimide hydrochloride ("EDC-HCl", 14.70 g, 77 mmol), 1-hydroxybenzotriazole hydrate ("HOBt hydrate", 11.75 g, 77 mmol) and N-methylmorpholine (28.1 mL, 256 mmol). The reaction mass was stirred for 24 hr at 27° C. The progress of the reaction was monitored by TLC ($SiO_2$, 50% EtOAc/Pet. Rf=0.5). On completion, the reaction mass was diluted with ice water (1.5 L) and the resulting precipitate was collected via filtration and then dried under vacuum to afford the crude product (59 g) as an off-white solid. This crude product was blended with another batch of crude product (61 g) generated by repeating the procedure on the same scale. Together, the 120 g of crude product was purified by silica gel chromatography eluting with 20-40% EtOAc/Pet. The fractions containing the desired product were pooled and concentrated under reduced pressure to afford the purified product. Trace EtOAc residue was removed by grinding the compound using a mortar and pestle and then maintaining the fine solids in a 50° C. oven for approximately 2 h; this process of grinding and heating was repeated an additional 4 times until the EtOAc content was reduced to below 4000 ppm to afford N—((S)-1-((3P)-3-(4-chloro-1-methyl-3-(methylsulfonamido)-1H-indazol-7-yl)-4-oxo-7-(6-(trifluoromethyl)pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (85.7 g, 79%) as an off-white solid. $^1$H NMR (acetone-d6) δ: 8.60 (t, J=1.0 Hz, 1H), 8.58 (s, 1H), 8.48 (d, J=8.0 Hz, 1H), 8.39 (d, J=0.9 Hz, 2H), 8.32 (t, J=7.9 Hz, 1H), 8.16 (d, J=8.6 Hz, 1H), 7.95-7.99 (m, 1H), 7.49 (d, J=7.7 Hz, 1H), 7.37 (d, J=8.0 Hz, 1H), 6.86 (tt, J=9.3, 2.3 Hz, 1H), 6.70-6.76 (m, 2H), 6.77 (t, J=54.7 Hz, 1H), 4.93 (td, J=9.0, 4.6 Hz, 1H), 4.63-4.74 (m, 2H), 3.69 (s, 3H), 3.55 (dd, J=14.2, 4.6 Hz, 1H), 3.28 (s, 3H), 3.15 (dd, J=14.2, 9.4 Hz, 1H), 2.42-2.51 (m, 2H), 1.37-1.43 (m, 1H), 0.95-1.00 (m, 1H). LCMS Method D: retention time=5.57 mins.; observed ion=949.98 (M+H); LCMS Purity=99.4%.

IUPAC Chemical Names:

The IUPAC chemical names for each example are listed below. At this time these names are not recognized by common software such tools such as ChemDraw or JChem. Therefore, the chemical names used throughout the Examples section above were generated with ChemDraw with P/M nomenclature manually inserted. The chemical names can be converted to chemical structures using ChemDraw after the P/M nomenclature e.g., "(3P)-"—is removed.

| Example | IUPAC Name |
|---|---|
| Example 1 | N-(1S)-1-[3(4-chloro-3-methanesulfonamido-1-methyl-1H-indazol-7-yl)-7-(4,6-dimethylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 2 | N-[(1S)-1-[3(4-chloro-3-methanesulfonamido-1-methyl-1H-indazol-7-yl)-7-(4-methylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 3 | N-[(1S)-1-[3(4-chloro-3-methanesulfonamido-1-methyl-1H-indazol-7-yl)-4-oxo-7[4-(trifluoromethyl)pyrimidin-2-yl)-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 4 | N-[(1S)-1-[3(4-chloro-3-methanesulfonamido-1-methyl-1H-indazol-7-yl)-7-(4-methanesulfonylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 5 | N-[(1S)-1-[3(4-chloro-3-methanesulfonamido-1-methyl-1H-indazol-7-yl)-7-(6-methoxy-2-methylpyridin-3-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 6 | N-[(1S)-1-[3(4-chloro-3-methanesulfonamido-1-methyl-1H-indazol-7-yl)-7-(2,4-dimethyl-1,3-thiazol-5-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 7 | N-[(1S)-1-[3(4-chloro-3-methanesulfonamido-1-methyl-1H-indazol-7-yl)-7-(6-methoxypyridazin-3-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 8 | N-[(1S)-1-[3(4-chloro-3-methanesulfonamido-1-methyl-1H-indazol-7-yl)-7-(3-methanesulfonylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 9 | N-[(1S)-1-[3(4-chloro-3-methanesulfonamido-1-methyl-1H-indazol-7-yl)-7-(5-methoxy-2-methylpyrimidin-4-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 10 | N-[(1S)-1-[3(4-chloro-3-methanesulfonamido-1-methyl-1H-indazol-7-yl)-7-(2-methylpyrimidin-4-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 11 | N-[(1S)-1-[3(4-chloro-3-methanesulfonamido-1-methyl-1H-indazol-7-yl)-7-(3-methoxypyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 12 | N-[(1S)-1-[3(4-chloro-3-methanesulfonamido-1-methyl-1H-indazol-7-yl)-7-[2-(difluoromethyl)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 13 | N-[(1S)-1-[3(4-chloro-3-methanesulfonamido-1-methyl-1H-indazol-7-yl)-7-[2-(2-hydroxypropan-2-yl)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 14 | N-[(1S)-1-[3(4-chloro-3-methanesulfonamido-1-methyl-1H-indazol-7-yl)-4-oxo-7-[2-(trifluoromethoxy)phenyl]-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 15 | N-[(1S)-1-[3(4-chloro-3-methanesulfonamido-1-methyl-1H-indazol-7-yl)-7-(3-methoxypyrazin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 16 | N-[(1S)-1-[3(4-chloro-3-methanesulfonamido-1-methyl-1H-indazol-7-yl)-4-oxo-7-[3-(propan-2-yl)pyrazin-2-yl]-3,4-dihydroquinazolin-2-yl]-2-(3,5-difluoropheny)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 17 | N-[(1S)-1-[3(4-chloro-3-methanesulfonamido-1-methyl-1H-indazol-7-yl)-7-(3-ethylpyrazin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 18 | N-[(1S)-1-[3(4-chloro-3-methanesulfonamido-1-methyl-1H-indazol-7-yl)-7-[3-(hydroxymethyl)pyrazin-2-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 19 | N-[(1S)-1-[3(4-chloro-3-methanesulfonamido-1-methyl-1H-indazol-7-yl)-7-(3-methoxyquinoxalin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 20 | N-[(1S)-1-[3(4-chloro-3-methanesulfonamido-1-methyl-1H-indazol-7-yl)-7-(3-methylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 21 | N-[(1S)-1-[3(4-chloro-3-methanesulfonamido-1-methyl-1H-indazol-7-yl)-7-(3-fluoropyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 22 | N-[(1S)-1-[3(4-chloro-3-methanesulfonamido-1-methyl-1H-indazol-7-yl)-7-(3-fluoro-6-methylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 23 | N-[(1S)-1-[3(4-chloro-3-methanesulfonamido-1-methyl-1H-indazol-7-yl)-4-oxo-7-[2-(propan-2-yl)phenyl]-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 24 | N-[(1S)-1-[3(4-chloro-3-methanesulfonamido-1-methyl-1H-indazol-7-yl)-4-oxo-7-[2-(trifluoromethyl)phenyl]-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 25 | N-[(1S)-1-[3(4-chloro-3-methanesulfonamido-1-methyl-1H-indazol-7-yl)-7-[2-(difluoromethoxy)phenyl]-4-oxo-3,4-dihydroquinazolin-2-yl]-2-(3,5-difluoropheny)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 26 | N-[(1S)-1-[3-(4-chloro-3-methanesulfonamido-1-methyl-1H-indazol-7-yl)-7-(2-methyl-1,3-thiazol-5-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 27 | N-[(1S)-1-[3-(4-chloro-3-methanesulfonamido-1-methyl-1H-indazol-7-yl)-7-[2-(N-methylmethanesulfonamido)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 28 | N-[(1S)-1-[3-(4-chloro-3-methanesulfonamido-1-methyl-1H-indazol-7-yl)-7-[3-(N-methylmethanesulfonamido)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 29 | N-[(1S)-1-[3-(4-chloro-3-methanesulfonamido-1-methyl-1H-indazol-7-yl)-7-[4-(N-methylmethanesulfonamido)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 30 | N-[(1S)-1-[3-(4-chloro-3-methanesulfonamido-1-methyl-1H-indazol-7-yl)-4-oxo-7-(trifluoromethyl)pyridin-2-yl]-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 31 | N-[(1S)-1-[3-(4-chloro-3-methanesulfonamido-1-methyl-1H-indazol-7-yl)-4-oxo-7-(pyridazin-4-yl)-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 32 | N-[(1S)-1-[3-(4-chloro-3-methanesulfonamido-1-methyl-1H-indazol-7-yl)-7-[2-(2-methylpropane-2-sulfonyl)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 33 | N-[(1S)-1-[3-(4-chloro-3-methanesulfonamido-1-methyl-1H-indazol-7-yl)-7-[3-(2-methylpropane-2-sulfonyl)phenyl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 34 | N-[(1S)-1-[3-(4-chloro-3-methanesulfonamido-1-methyl-1H-indazol-7-yl)-7-(5-methoxypyrimidin-2-y1)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 35 | N-[(1S)-1-[7-(6-tert-butylpyridin-2-y1)-3-(4-chloro-3-methanesulfonamido-1-methyl-1H-indazol-7-yl)-4-oxo-3,4-dihydroquinazolin-2-yl-243,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 36 | N-[(1S)-1-[3-(4-chloro-3-methanesulfonamido-1-methyl-1H-indazol-7-yl)-7-(4-ethyl-6-methylpyrimidin-2-y1)-4-oxo-3,4-dihydroquinazolin-2-yl]-2(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 37 | N-[(1S)-1-[3-(4-chloro-3-methanesulfonamido-1-methyl-1H-indazol-7-yl)-7-[4-methyl-6-(propan-2-yl)pyrimidin-2-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 38 | N-[(1S)-1-[3-(4-chloro-3-methanesulfonamido-1-methyl-1H-indazol-7-yl)-7-(4,6-diethylpyrimidin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 39 | N-[(1S)-1-[3-(4-chloro-3-methanesulfonamido-1-methyl-1H-indazol-7-yl)-7-(2-methoxypyrimidin-5-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 40 | N-[(1S)-1-[3-(4-chloro-3-methanesulfonamido-1-methyl-1H-indazol-7-yl)-7-(4,6-dimethylpyrimidin-5-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 41 | N-[(1S)-1-[3-(4-chloro-3-methanesulfonamido-1-methyl-1H-indazol-7-yl)-7-(6-cyclopropylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 42 | N-[(1S)-1-[3-(4-chloro-3-methanesulfonamido-1-methyl-1H-indazol-7-yl)-7-(4-methylpyrimidin-5-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 43 | N-[(1S)-1-[3-(4-chloro-3-methanesulfonamido-1-methyl-1H-indazol-7-yl)-7-(4-ethylpyrimidin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 44 | N-[(1S)-1-[3-(4-chloro-3-methanesulfonamido-1-methyl-1H-indazol-7-yl)-7-(2,6-dimethylpyrimidin-4-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 45 | N-[(1S)-1-[3-(4-chloro-3-methanesulfonamido-1-methyl-1H-indazol-7-yl)-7-(5-methoxypyridin-2-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 46 | N-[(1S)-1-[3-(4-chloro-3-methanesulfonamido-1-methyl-1H-indazol-7-yl)-4-oxo-7-[6-(propan-2-yl)pyridin-2-yl]-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 47 | N-[(1S)-147-(4-tert-butylpyrimidin-2-yl)-3-(4-chloro-3-methanesulfonamido-1-methyl-1H-indazol-7-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 48 | N-[(1S)-1-[3-(4-chloro-3-methanesulfonamido-1-methyl-1H-indazol-7-yl)-7-[6-methyl-4-(trifluoromethyl)pyridin-2-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 49 | N-[(1S)-1-[3-(4-chloro-3-methanesulfonamido-1-methyl-1H-indazol-7-yl)-4-oxo-7-(pyridazin-3-yl)-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 50 | N-[(1S)-1-[3-(4-chloro-3-methanesulfonamido-1-methyl-1H-indazol-7-yl)-7-(6-methylpyridazin-3-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 51 | N-[(1S)-1-[3-(4-chloro-3-methanesulfonamido-1-methyl-1H-indazol-7-yl)-7-(4-methylpyridazin-3-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 52 | N-[(1S)-1-[3-(4-chloro-3-methanesulfonamido-1-methyl-1H-indazol-7-yl)-7-[4,6-dimethyl-3-(trifluoromethyl)pyridin-2-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 53 | N-[(1S)-1-[3-(4-chloro-3-methanesulfonamido-1-methyl-1H-indazol-7-yl)-7-[4-methyl-6-(trifluoromethyl)pyrimidin-2-yl]-4-oxo-3,4-dihydroquinazolin-2-yl]-2-(3,5-difluorophenyl)ethyl]-2-[(2S,4R)-9-(difluoromethyl)-5,5-difluoro-[4.3.0.0$^{2,4}$]nona-1(6),8-dien-7-yl]acetamide |
| Example 54 | N-[(1S)-1-[3-(4-chloro-3-methanesulfonamido-1-methyl-1H-indazol-7-yl)-7-[4-methoxy-6-(trifluoromethyl)pyrimidin-2-yl]-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 55 | N-[(1S)-1-[3-(4-chloro-3-methanesulfonamido-1-methyl-1H-indazol-7-yl)-7-(5,6-dimethyl-1,2,4-triazin-3-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 56 | N-[(1S)-1-[3-(4-chloro-3-methanesulfonamido-1-methyl-1H-indazol-7-yl)-7-[4-(difluoromethyl)pyrimidin-2-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 57 | N-[(1S)-1-[3-(4-chloro-3-methanesulfonamido-1-methyl-1H-indazol-7-yl)-7-(4-methoxy-6-methylpyridin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 58 | N-[(1S)-1-{7[4,6-bis(trifluoromethyl)pyridin-2-yl]-3-(4-chloro-3-methanesulfonamido-1-methyl-1H-indazol-7-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 59 | N-[(1S)-1-[3-(4-chloro-3-methanesulfonamido-1-methyl-1H-indazol-7-yl)-4-oxo-7-[6-(trifluoromethyl)pyridin-2-yl]-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 60 | N-[(1S)-1-[3-(4-chloro-3-methanesulfonamido-1-methyl-1H-indazol-7-yl)-7-(4-ethylpyrimidin-5-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 61 | N-[(1S)-1-[3-(4-chloro-3-methanesulfonamido-1-methyl-1H-indazol-7-yl)-7-(3-cyclopropylpyrazin-2-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 62 | N-[(1S)-1-[3-(4-chloro-3-methanesulfonamido-1-methyl-1H-indazol-7-yl)-7-(6-ethyl-2-methylpyrimidin-4-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 63 | N-[(1S)-1-[3-(4-chloro-3-methanesulfonamido-1-methyl-1H-indazol-7-yl)-7-[2-methyl-6-(trifluoromethyl)pyrimidin-4-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 64 | N-[(1S)-1-[3-(4-chloro-3-methanesulfonamido-1-methyl-1H-indazol-7-yl)-7-(5-fluoro-2-methylpyrimidin-4-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 65 | N-[(1S)-1-[3-(4-chloro-3-methanesulfonamido-1-methyl-1H-indazol-7-yl)-4-oxo-7-(2,5,6-trimethylpyrimidin-4-yl)-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 66 | N-[(1S)-1-[3-(4-chloro-3-methanesulfonamido-1-methyl-1H-indazol-7-yl)-7-[2-methyl-6-(propan-2-yl)pyrimidin-4-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 67 | N-[(1S)-1-[3-(4-chloro-3-methanesulfonamido-1-methyl-1H-indazol-7-yl)-4-oxo-7-42-(propan-2-yl)pyrimidin-4-yl)-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 68 | N-[(1S)-1-[3-(4-chloro-3-methanesulfonamido-1-methyl-1H-indazol-7-yl)-7-(2,6-diethylpyrimidin-4-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 69 | N-[(1S)-1-[3-(4-chloro-3-methanesulfonamido-1-methyl-1H-indazol-7-yl)-7-(6-ethoxy-2-methylpyrimidin-4-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 70 | N-[(1S)-1-{7-[2-(butan-2-yl)pyrimidin-4-yl]-(4-chloro-3-methanesulfonamido-1-methyl-1H-indazol-7-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 71 | N-[(1S)-1-[3-(4-chloro-3-methanesulfonamido-1-methyl-1H-indazol-7-yl)-7-(2-ethylpyrimidin-4-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 72 | N-[(1S)-1-[7-(2-tert-butylpyrimidin-4-yl)-3-(4-chloro-3-methanesulfonamido-1-methyl-1H-indazol-7-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 73 | N-[(1S)-1-[3-(4-chloro-3-methanesulfonamido-1-methyl-1H-indazol-7-yl)-7-(2-cyclopentylpyrimidin-4-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 74 | N-[(1S)-1-[3-(4-chloro-3-methanesulfonamido-1-methyl-1H-indazol-7-yl)-7-[2-(methoxymethyl)pyrimidin-4-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 75 | N-[(1S)-1-[3-(4-chloro-3-methanesulfonamido-1-methyl-1H-indazol-7-yl)-7-[2-(methoxymethyl)-6-methylpyrimidin-4-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 76 | N-[(1S)-1-[3-(4-chloro-3-methanesulfonamido-1-methyl-1H-indazol-7-yl)-7-(2-cyclobutylpyrimidin-4-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 77 | N-[(1S)-1-[3-(4-chloro-3-methanesulfonamido-1-methyl-1H-indazol-7-yl)-7-(2,5-dimethylpyrimidin-4-yl)-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 78 | N-[(1S)-1-[3-(4-chloro-3-methanesulfonamido-1-methyl-1H-indazol-7-yl)-7-(2-cyclopropylpyrimidin-4-yl)-4-oxo-3,4-dihydroquinazolin-2-yl]-2-(3,5-difluorophenypethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 79 | N-[(1S)-1-[3-(4-chloro-3-methanesulfonamido-1-methyl-1H-indazol-7-yl)-7-(6-ethylpyridin-2-yl)-4-oxo-3,4-dihydroquinazolin-2-yl]-2(3,5-difluorophenypethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 80 | N-[(1S)-1-[3-(4-chloro-3-methanesulfonamido-1-methyl-1H-indazol-7-yl)-4-oxo-7-[4-(trifluoromethyl)pyridin-2-yl]-3,4-dihydroquinazolin-2-yl]-2(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 81 | N-[(1S)-1-{3-4-chloro-3-cyclopropanesulfonamido-1-(2,2-difluoroethyl)-1H-indazol-7-yl]-7-(2-methylpyrimidin-4-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 82 | N-[(1S)-1-{3-[4-chloro-3-cyclopropanesulfonamido-1-(2,2-difluoroethyl)-1H-indazol-7-yl]-7-(4-ethyl-6-methylpyrimidin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 83 | N-[(1S)-1-{3-[4-chloro-3-cyclopropanesulfonamido-1-(2,2-difluoroethyl)-1H-indazol-7-yl]-7-(4,6-dimethylpyridin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 84 | N-[(1S)-1-{3-[4-chloro-3-cyclopropanesulfonamido-1-(2,2-difluoroethyl)-1H-indazol-7-yl]-4-oxo-7-[4-(trifluoromethyl)pyrimidin-2-yl]-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 85 | N-[(1S)-1-{3-[4-chloro-3-cyclopropanesulfonamido-1-(2,2-difluoroethyl)-1H-indazol-7-yl]-7-(2,6-dimethylpyrimidin-4-yl)-4-oxo-3,4-dihydroquinazolin-2-yl}-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 86 | N-[(1S)-1-{3-[4-chloro-3-cyclopropanesulfonamido-1-(2,2-difluoroethyl)-1H-indazol-7-yl]-7-4-(difluoromethyl)pyrimidin-2-yl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 87 | N-[(1S)-1-{3-[4-chloro-3-cyclopropanesulfonamido-1-(2,2-difluoroethyl)-1H-indazol-7-yl]-7-(5,6-dimethyl-1,2,4-triazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 88 | N-[(1S)-1-{3-[4-chloro-3-cyclopropanesulfonamido-1-(2,2-difluoroethyl)-1H-indazol-7-yl]-7-(6-methylpyridazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 89 | N-[(1S)-1-{3-[4-chloro-3-cyclopropanesulfonamido-1-(2,2-difluoroethyl)-1H-indazol-7-yl]-4-oxo-7-(pyridazin-3-yl)-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 90 | N-[(1S)-1-{3-[4-chloro-3-cyclopropanesulfonamido-1-(2,2-difluoroethyl)-1H-indazol-7-yl]-7-(6-methoxypyridazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 91 | N-[(1S)-1-{3-[4-chloro-3-cyclopropanesulfonamido-1-(2,2-difluoroethyl)-1H-indazol-7-yl]-4-oxo-7-[2-(propan-2-yl)pyrimidin-4-yl]-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 92 | N-[(1S)-1-{3-[4-chloro-3-cyclopropanesulfonamido-1-(2,2-difluoroethyl)-1H-indazol-7-yl]-4-oxo-7-(2,5,6-trimethylpyrimidin-4-yl)-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 93 | N-[(1S)-1-{3-[4-chloro-3-cyclopropanesulfonamido-1-(2,2-difluoroethyl)-1H-indazol-7-yl]-7-(4-ethylpyrimidin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 94 | N-[(1S)-1-{3-[4-chloro-3-cyclopropanesulfonamido-1-(2,2-difluoroethyl)-1H-indazol-7-yl]-7-(6-ethyl-2-methylpyrimidin-4-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 95 | N-[(1S)-1-{3-[4-chloro-3-cyclopropanesulfonamido-1-(2,2-difluoroethyl)-1H-indazol-7-yl]-7-(3-methanesulfonylpyridin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 96 | N-[(1S)-1-{3-[4-chloro-3-cyclopropanesulfonamido-1-(2,2-difluoroethyl)-1H-indazol-7-yl]-7-(3-fluoro-6-methylpyridin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

| Example | IUPAC Name |
|---|---|
| Example 97 | N-[(1S)-1-{3-[4-chloro-3-cyclopropanesulfonamido-1-(2,2-difluoroethyl)-1H-indazol-7-yl]-7-(2-methyl-1,3-thiazol-5-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 98 | N-[(1S)-1-{3-[4-chloro-3-cyclopropanesulfonamido-1-(2,2-difluoroethyl)-1H-indazol-7-yl]-7-(5-methoxypyrimidin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 99 | N-[(1S)-1-{3-[4-chloro-3-cyclopropanesulfonamido-1-(2,2-difluoroethyl)-1H-indazol-7-yl]-7-(2-methoxypyrimidin-5-yl)-4-oxo-3,4-dihydroquinazolin-2-yl}-2-(3,5-difluorophenyl)ethyl]-2-+(2S,4R)-9-(difluoromethyl)-5,5-difluoro-7,8-diazatricyclo[4.3.0.0$^{2,4}$]nona-1(6),8-dien-7-yl]acetamide |
| Example 100 | N-[(1S)-1-{3-[4-chloro-3-methanesulfonamido-1-(2,2,2-trifluoroethyl)-1H-indazol-7-yl]-7-(2-methylpyrimidin-4-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 101 | N-[(1S)-1-{3-[4-chloro-3-methanesulfonamido-1-(2,2,2-trifluoroethyl)-1H-indazol-7-yl]-7-(4,6-dimethylpyridin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 102 | N-[(1S)-1-{3-[4-chloro-3-methanesulfonamido-1-(2,2,2-trifluoroethyl)-1H-indazol-7-yl]-4-oxo-7-[4-(trifluoromethyppyrimidin-2-yl]-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 103 | N-[(1S)-1-{3-[4-chloro-3-methanesulfonamido-1-(2,2,2-trifluoroethyl)-1H-indazol-7-yl]-7-(2,6-dimethylpyrimidin-4-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 104 | N-[(1S)-1-{3-[4-chloro-3-methanesulfonamido-1-(2,2,2-trifluoroethyl)-1H-indazol-7-yl]-7-[4-(difluoromethyl)pyrimidin-2-yl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 105 | N-[(1S)-1-{3-[4-chloro-3-methanesulfonamido-1-(2,2,2-trifluoroethyl)-1H-indazol-7-yl]-7-(5,6-dimethyl-1,2,4-triazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 106 | N-[(1S)-1-{3-[4-chloro-3-methanesulfonamido-1-(2,2,2-trifluoroethyl)-1H-indazol-7-yl]-7-(6-methylpyridazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 107 | N-[(1S)-1-{3-[4-chloro-3-methanesulfonamido-1-(2,2,2-trifluoroethyl)-1H-indazol-7-yl]-4-oxo-7-(pyridazin-3-yl)-3,4-dihydroquinazolin-2-yl}-2-(3,5-difluoropheny)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 108 | N-[(1S)-1-{3-[4-chloro-3-methanesulfonamido-1-(2,2,2-trifluoroethyl)-1H-indazol-7-yl]-4-oxo-742-(propan-2-yl)pyrimidin-4-yl]-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 109 | N-[(1S)-1-{3-[4-chloro-3-methanesulfonamido-1-(2,2,2-trifluoroethyl)-1H-indazol-7-yl]-4-oxo-7-(2,5,6-trimethylpyrimidin-4-yl)-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 110 | N-[(1S)-1-{3-[4-chloro-3-methanesulfonamido-1-(2,2,2-trifluoroethyl)-1H-indazol-7-yl]-7-(6-methoxypyridazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 111 | N-[(1S)-1-{3-[4-chloro-3-methanesulfonamido-1-(2,2,2-trifluoroethyl)-1H-indazol-7-yl]-7-(4-ethylpyrimidin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 112 | N-[(1S)-1-{3-[4-chloro-3-methanesulfonamido-1-(2,2,2-trifluoroethyl)-1H-indazol-7-yl]-7-(3-methanesulfonylpyridin-2-yl)-4-oxo-3,4-dihydroquinazolin-2-yl}-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
| --- | --- |
| Example 113 | N-[(1S)-1-{3-[4-chloro-3-methanesulfonamido-1-(2,2,2-trifluoroethyl)-1H-indazol-7-yl]-7-(3-fluoro-6-methylpyridin-2-yl)-4-oxo-3,4-dihydroquinazolin-2-yl}-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 114 | N-[(1S)-1-{3-[4-chloro-3-methanesulfonamido-1-(2,2,2-trifluoroethyl)-1H-indazol-7-yl]-7-(2-methyl-1,3-thiazol-5-yl)-4-oxo-3,4-dihydroquinazolin-2-ylI-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 115 | N-[(1S)-1-{3-[4-chloro-3-methanesulfonamido-1-(2,2,2-trifluoroethyl)-1H-indazol-7-yl]-7-(5-methoxypyrimidin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 116 | N-[(1S)-1-{3-[4-chloro-3-methanesulfonamido-1-(2,2,2-trifluoroethyl)-1H-indazol-7-yl]-7-(2-methoxypyrimidin-5-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 117 | N-[(1S)-1-[3-(4-chloro-3-methanesulfonamido-1-methyl-1H-indazol-7-yl)-7-[6-(difluoromethyl)pyridin-2-yl]-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 118 | N-[(1S)-1-[3-(4-chloro-3-methanesulfonamido-1-methyl-1H-indazol-7-yl)-7-[2-(hydroxymethyl)-6-methylpyrimidin-4-yl]-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-y]acetamide |
| Example 119 | N-[(1S)-1-[3-(4-chloro-3-methanesulfonamido-1-methyl-1H-indazol-7-yl)-7-(5-fluoro-2,6-dimethylpyrimidin-4-yl)-4-oxo-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 120 | N-[(1S)-1-[3-(4-chloro-3-methanesulfonamido-1-methyl-1H-indazol-7-yl)-7-[3-(difluoromethyl)phenyl]-4-oxo-3,4-dihydroquinazolin-2-yl]-2-(3,5-difluorophenyl)ethyl]-2-(2S,4R)-9-(difluoromethyl)-5,5-difluoro-7,8-diazatricyclo[4.3.0.0$^{2,4}$]nona-1(6),8-dien-7-yl]acetamide |
| Example 121 | N-[(1S)-1-{3-[4-chloro-1-(2,2-difluoroethyl)-3-methanesulfonamido-1H-indazol-7-yl]-7-(2-methylpyrimidin-4-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 122 | N-[(1S)-1-{3-[4-chloro-1-(2,2-difluoroethyl)-3-methanesulfonamido-1H-indazol-7-yl]-7-(3-fluoro-6-methylpyridin-2-yl)-4-oxo-3,4-dihydroquinazolin-2-yl}-2-(3,5-difluorophenyl)ethyl]-[2S,4R)-9-(difluoromethyl)-5,5-difluoro-7,8-diazatricyclo[4.3.0.0$^{2,4}$]nona-1(6),8-dien-7-yl]acetamide |
| Example 123 | N-[(1S)-1-{3-[4-chloro-1-(2,2-difluoroethyl)-3-methanesulfonamido-1H-indazol-7-yl]-7-(2-methyl-1,3-thiazol-5-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 124 | N-[(1S)-1-{3-[4-chloro-1-(2,2-difluoroethyl)-3-methanesulfonamido-1H-indazol-7-yl]-7-(5-methoxypyrimidin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 125 | N-[(1S)-1-{3-[4-chloro-1-(2,2-difluoroethyl)-3-methanesulfonamido-1H-indazol-7-yl]-7-(2-methoxypyrimidin-5-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 126 | N-[(1S)-1-{3-[4-chloro-1-(2,2-difluoroethyl)-3-methanesulfonamido-1H-indazol-7-yl]-7-(4-ethy1-6-methylpyrimidin-2-y1)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 127 | N-[(1S)-1-{3-[4-chloro-1-(2,2-difluoroethyl)-3-methanesulfonamido-1H-indazol-7-yl]-7-[3-(2-methylpropane-2-sulfonyl)phenyl-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 128 | N-[(1S)-1-{3-[4-chloro-1-(2,2-difluoroethyl)-3-methanesulfonamido-1H-indazol-7-yl]-4-oxo-7-[4-(trifluoromethyl)pyrimidin-2-yl]-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 129 | N-[(1S)-1-{3-[4-chloro-1-(2,2-difluoroethyl)-3-methanesulfonamido-1H-indazol-7-yl]-7-(6-methoxypyridazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

-continued

| Example | IUPAC Name |
|---|---|
| Example 130 | N-[(1S)-1-{3-[4-chloro-1-(2,2-difluoroethyl)-3-methanesulfonamido-1H-indazol-7-yl]-742-(2-methylpropane-2-sulfonyl)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 131 | N-[(1S)-1-{3-[4-chloro-1-(2,2-difluoroethyl)-3-methanesulfonamido-1H-indazol-7-yl]-7-(2,6-dimethylpyrimidin-4-y1)-4-oxo-3,4-dihydroquinazolin-2-y1}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 132 | N-[(1S)-1-{3-[4-chloro-1-(2,2-difluoroethyl)-3-methanesulfonamido-1H-indazol-7-yl]-7-[4-(difluoromethyl)pyrimidin-2-yl]-4-oxo-3,4-dihydroquinazolin-2-yl}-2-(3,5-difluorophenyl)ethyl]-2-+(2S,4R)-9-(difluoromethyl)-5,5-difluoro-7,8-diazatricyclo[4.3.0.0$^{2,4}$]nona-1(6),8-dien-7-yl]acetamide |
| Example 133 | N-[(1S)-1-{3-[4-chloro-1-(2,2-difluoroethyl)-3-methanesulfonamido-1H-indazol-7-yl]-7-(5,6-dimethyl-1,2,4-triazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 134 | N-[(1S)-1-{3-[4-chloro-1-(2,2-difluoroethyl)-3-methanesulfonamido-1H-indazol-7-yl]-7-(6-methylpyridazin-3-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 135 | N-[(1S)-1-{3-[4-chloro-1-(2,2-difluoroethyl)-3-methanesulfonamido-1H-indazol-7-yl]-4-oxo-7-(pyridazin-3-yl)-3,4-dihydroquinazolin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 136 | N-[(1S)-1-{3-[4-chloro-1-(2,2-difluoroethyl)-3-methanesulfonamido-1H-indazol-7-yl]-7-(3-methanesulfonylpyridin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 137 | N-[(1S)-1-{3-[4-chloro-1-(2,2-difluoroethyl)-3-methanesulfonamido-1H-indazol-7-yl]-7-(4,6-dimethylpyridin-2-yl)-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 138 | N-[(1S)-1-{3-[4-chloro-1-(2,2-difluoroethyl)-3-methanesulfonamido-1H-indazol-7-yl]-4-oxo-7-(trifluoromethyppyridin-2-yl)-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 139 | 2-[(2S,4R)-9-(difluoromethyl)-5,5-difluoro-7,8-diazatricyclo[4.3.0.0$^{2,4}$]nona-1(6),8-dien-7-yl]-N-[(1S)-2-(3,5-difluorophenyl)-1-[7-(6-ethy1-2-methylpyrimidin-4-yl)-3-(3-methanesulfonamido-1,4-dimethyl-1H-indazol-7-yl)-4-oxo-3,4-dihydroquinazolin-2-yl]ethyl]acetamide |
| Example 140 | 2-[(2S,4R)-9-(difluoromethyl)-5,5-difluoro-7,8-diazatricyclo[4.3.0.0$^{2,4}$]nona-1(6),8-dien-7-yl]-N-[(1S)-2-(3,5-difluorophenyl)-1-[7-(5-fluoro-2-methylpyrimidin-4-yl)-3-(3-methanesulfonamido-1,4-dimethyl-1H-indazol-7-yl)-4-oxo-3,4-dihydroquinazolin-2-yl]ethyl]acetamide |
| Example 141 | 2-[(2S,4R)-9-(difluoromethyl)-5,5-difluoro-7,8-diazatricyclo[4.3.0.0$^{2,4}$]nona-1(6),8-dien-7-yl]-N-[(1S)-2-(3,5-difluorophenyl)-1-[3-(3-methanesulfonamido-1,4-dimethyl-1H-indazol-7-yl)-4-oxo-7-(pyridazin-3-yl)-3,4-dihydroquinazolin-2-yl]ethyl]acetamide |
| Example 142 | N-[(1S)-1-{3-[3-cyclopropanesulfonamido-1-(2,2-difluoroethyl)-4-methyl-1H-indazol-7-yl]-7-[2-(2-methylpropane-2-sulfonyl)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 143 | N-[(1S)-1-{3-[4-chloro-3-cyclopropanesulfonamido-1-(2,2-difluoroethyl)-1H-indazol-7-yl]-742-(2-methylpropane-2-sulfonyl)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 144 | N-[(1S)-1-{3-[4-chloro-3-cyclopropanesulfonamido-1-(2,2-difluoroethyl)-1H-indazol-7-yl]-742-(N-methylmethanesulfonamido)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 145 | N-[(1S)-1-{3-[3-cyclopropanesulfonamido-1-(2,2-difluoroethyl)-4-methyl-1H-indazol-7-yl]-7-[2-(N-methylmethanesulfonamido)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

| Example | IUPAC Name |
|---|---|
| Example 146 | N-[(1S)-1-{3-[4-chloro-3-cyclopropanesulfonamido-1-(2,2-difluoroethyl)-1H-indazol-7-yl]-7-[3-(2-methylpropane-2-sulfonyl)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 147 | N-[(1S)-1-{3-[4-chloro-3-cyclopropanesulfonamido-1-(2,2-difluoroethyl)-1H-indazol-7-yl]-7-[4-(N-methylmethanesulfonamido)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |
| Example 148 | N-[(1S)-1-{3-[4-chloro-3-cyclopropanesulfonamido-1-(2,2-difluoroethyl)-1H-indazol-7-yl]-7-[3-(N-methylmethanesulfonamido)phenyl]-4-oxo-3,4-dihydroquinazolin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide |

Biological Methods:

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 mg/ml penicillin G and up to 100 units/mL streptomycin. The 293T cells were propagated in DMEM media supplemented with 10% heat inactivated FBS, 100 mg/mL penicillin G and 100 mg/mL streptomycin. A recombinant $NL_40.3$ proviral clone, in which a section of the nef gene was replaced with the *Renilla* luciferase gene, was used to make the reference virus used in these studies. The recombinant virus was prepared through transfection of the recombinant $NL_{4-3}$ proviral clone into 293T cells using Transit-293 Transfection Reagent from Minis Bio LLC (Madison, Wis.). Supernatent was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where $(Fa)=1/[1+(ED_{50}/\text{drug conc.})m]$ (Johnson V A, Byington R T. Infectivity Assay. In Techniques in HIV Research. ed. Aldovini A, Walker B D. 71-76. New York: Stockton Press. 1990). The 50% inhibitory concentration ($EC_{50}$) was calculated by using the exponential form of the median effect equation where percent inhibition=$1/[1+(EC_{50}/\text{drug concentration})m]$, where m is a parameter that reflects the slope of the concentration-response curve. Compound cytotoxicity and the corresponding $CC_{50}$ values were determined using the same protocol as described in the antiviral assay except that uninfected cells were used. Cytotoxicity was assessed on day 4 in uninfected MT2 cells by using a XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

| Example | $EC_{50}$ nM | $CC_{50}$ μM |
|---|---|---|
| Example 1 | 0.15 | >0.5 |
| Example 2 | 0.059 | >0.5 |
| Example 3 | 0.10 | >0.5 |
| Example 4 | 0.053 | >0.5 |
| Example 5 | 0.94 | >0.5 |
| Example 6 | 0.12 | >0.5 |
| Example 7 | 0.053 | >0.5 |
| Example 8 | 0.078 | >0.5 |
| Example 9 | 0.058 | >0.5 |
| Example 10 | 0.042 | >0.5 |
| Example 11 | 0.12 | >0.5 |
| Example 12 | 0.37 | >0.5 |
| Example 14 | 2.1 | >0.5 |
| Example 15 | 0.15 | >0.5 |
| Example 16 | 0.12 | >0.5 |
| Example 17 | 0.11 | >0.5 |
| Example 18 | 0.099 | >0.5 |
| Example 19 | 5.5 | >0.5 |
| Example 21 | 0.091 | >0.5 |
| Example 22 | 0.11 | >0.5 |
| Example 23 | 2.2 | >0.5 |
| Example 24 | 0.84 | >0.5 |
| Example 25 | 0.85 | >0.5 |
| Example 26 | 0.11 | >0.5 |
| Example 27 | 0.49 | >0.5 |
| Example 28 | 0.22 | >0.5 |
| Example 29 | 0.29 | >0.5 |
| Example 30 | 0.22 | >0.5 |
| Example 31 | 0.29 | >0.5 |
| Example 32 | 0.11 | >0.5 |
| Example 33 | 0.12 | >0.5 |
| Example 34 | 0.058 | >0.5 |
| Example 35 | 0.97 | >0.5 |
| Example 36 | 0.087 | >0.5 |
| Example 37 | 0.16 | >0.5 |
| Example 38 | 0.21 | >0.5 |
| Example 39 | 0.042 | >0.5 |
| Example 40 | 0.053 | >0.5 |
| Example 41 | 0.33 | >0.5 |
| Example 42 | 0.074 | >0.5 |
| Example 43 | 0.058 | >0.5 |
| Example 44 | 0.040 | >0.5 |
| Example 45 | 0.10 | >0.5 |
| Example 46 | 0.23 | >0.5 |
| Example 47 | 0.19 | >0.5 |
| Example 48 | 0.50 | >0.5 |
| Example 49 | 0.071 | >0.5 |
| Example 50 | 0.047 | >0.5 |
| Example 51 | 0.14 | >0.5 |
| Example 52 | 0.48 | >0.5 |
| Example 53 | 0.16 | >0.5 |
| Example 54 | 0.31 | >0.5 |
| Example 55 | 0.032 | >0.5 |
| Example 56 | 0.056 | >0.5 |
| Example 57 | 0.15 | >0.5 |
| Example 58 | 0.95 | >0.5 |
| Example 59 | 0.12 | >0.5 |
| Example 60 | 0.077 | >0.5 |

-continued

| Example | EC$_{50}$ nM | CC$_{50}$ µM |
|---|---|---|
| Example 61 | 0.16 | >0.5 |
| Example 62 | 0.11 | >0.5 |
| Example 63 | 0.33 | >0.5 |
| Example 64 | 0.093 | >0.5 |
| Example 66 | 0.15 | >0.5 |
| Example 67 | 0.15 | >0.5 |
| Example 68 | 0.18 | >0.5 |
| Example 69 | 0.43 | >0.5 |
| Example 70 | 0.26 | >0.5 |
| Example 72 | 0.43 | >0.5 |
| Example 73 | 0.96 | >0.5 |
| Example 74 | 0.079 | >0.5 |
| Example 75 | 0.077 | >0.5 |
| Example 76 | 0.18 | >0.5 |
| Example 77 | 0.071 | >0.5 |
| Example 78 | 0.16 | >0.5 |
| Example 80 | 0.20 | >0.1 |
| Example 81 | 0.092 | >0.5 |
| Example 82 | 0.25 | >0.5 |
| Example 83 | 0.44 | >0.5 |
| Example 84 | 0.22 | >0.5 |
| Example 85 | 0.088 | >0.5 |
| Example 86 | 0.078 | >0.5 |
| Example 87 | 0.058 | >0.5 |
| Example 88 | 0.058 | >0.5 |
| Example 89 | 0.075 | >0.5 |
| Example 90 | 0.085 | >0.5 |
| Example 91 | 0.19 | >0.5 |
| Example 92 | 0.10 | >0.5 |
| Example 93 | 0.18 | >0.5 |
| Example 94 | 0.13 | >0.5 |
| Example 95 | 0.053 | >0.5 |
| Example 96 | 0.24 | >0.5 |
| Example 97 | 0.22 | >0.5 |
| Example 98 | 0.16 | >0.5 |
| Example 99 | 0.089 | >0.5 |
| Example 100 | 0.042 | >0.5 |
| Example 101 | 0.21 | >0.5 |
| Example 102 | 0.13 | >0.5 |
| Example 103 | 0.059 | >0.5 |
| Example 104 | 0.063 | >0.5 |
| Example 105 | 0.040 | >0.5 |
| Example 106 | 0.043 | >0.5 |
| Example 107 | 0.048 | >0.5 |
| Example 108 | 0.12 | >0.5 |
| Example 109 | 0.11 | >0.5 |
| Example 110 | 0.071 | >0.5 |
| Example 111 | 0.11 | >0.5 |
| Example 112 | 0.075 | >0.5 |
| Example 113 | 0.10 | >0.5 |
| Example 114 | 0.15 | >0.5 |
| Example 115 | 0.098 | >0.5 |
| Example 116 | 0.072 | >0.5 |
| Example 117 | 0.069 | >0.5 |
| Example 118 | 0.048 | >0.5 |
| Example 119 | 0.087 | >0.5 |
| Example 120 | 0.38 | >0.5 |
| Example 121 | 0.067 | >0.5 |
| Example 122 | 0.080 | >0.5 |
| Example 123 | 0.087 | >0.5 |
| Example 124 | 0.092 | >0.5 |
| Example 125 | 0.060 | >0.5 |
| Example 126 | 0.12 | >0.5 |
| Example 127 | 0.14 | >0.5 |
| Example 128 | 0.079 | >0.5 |
| Example 129 | 0.054 | >0.5 |
| Example 130 | 0.13 | >0.5 |
| Example 131 | 0.038 | >0.5 |
| Example 132 | 0.060 | >0.5 |
| Example 133 | 0.040 | >0.5 |

-continued

| Example | EC$_{50}$ nM | CC$_{50}$ µM |
|---|---|---|
| Example 134 | 0.032 | >0.5 |
| Example 135 | 0.054 | >0.5 |
| Example 136 | 0.046 | >0.5 |
| Example 137 | 0.20 | >0.5 |
| Example 138 | 0.079 | >0.5 |
| Example 139 | 0.13 | >0.5 |
| Example 140 | 0.097 | >0.5 |
| Example 141 | 0.13 | >0.5 |
| Example 142 | 0.38 | >0.5 |
| Example 143 | 0.28 | >0.5 |
| Example 144 | 0.18 | >0.5 |
| Example 145 | 0.68 | >0.5 |
| Example 146 | 0.39 | >0.5 |
| Example 147 | 0.34 | >0.5 |
| Example 148 | 0.28 | >0.5 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:

1. A compound which is:

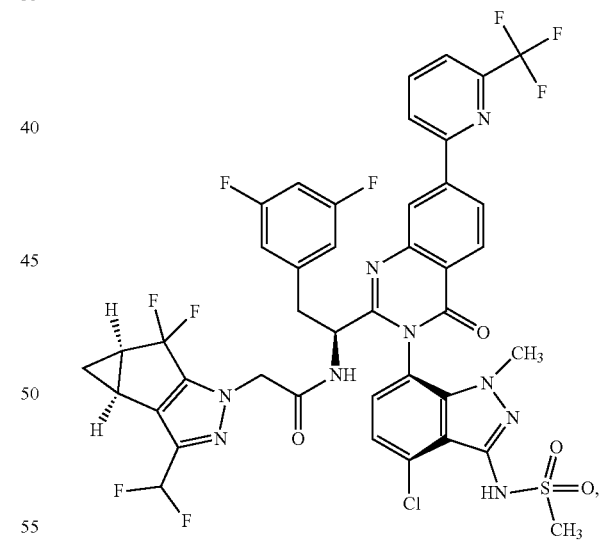

or a pharmaceutically acceptable salt thereof.

2. A pharmaceutical composition

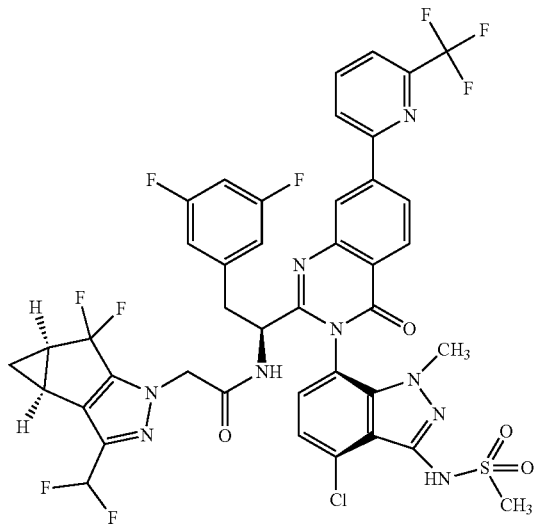

or a pharmaceutically acceptable salt thereof according to claim 1.

3. The pharmaceutical composition according to claim 2 further comprising a pharmaceutically acceptable carrier, excipient, or diluent.

4. A method of treating HIV infection comprising administering to a patient in need thereof a pharmaceutical composition according to claim 2.

5. The method of claim 4 wherein said administration is oral.

6. The method of claim 4 wherein said administration comprises administering by injection subcutaneously.

7. The method of claim 4 wherein said administration comprises administering by injection intramuscularly.

8. The method of claim 4 wherein said method further comprises administration of at least one other agent useful in the prevention or treatment of HIV.

9. The method of claim 8 wherein said other agent is selected from the group consisting of dolutegravir, lamivudine, fostemsavir, and cabotegravir.

10. A compound which is:

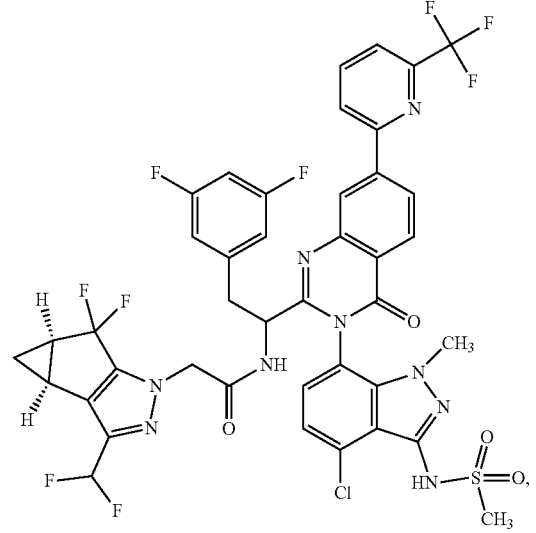 [SMILES: Cn1nc(NS(C)(=O)=O)c2c(Cl)ccc(-n3c(C(Cc4cc(F)cc(F)c4)NC(=O)Cn4nc(C(F)F)c5c4C(F)(F)[C@@H]4C[C@H]54)nc4cc(-c5cccc(C(F)(F)F)n5)ccc4c3=O)c21]

or a pharmaceutically acceptable salt thereof.

11. A pharmaceutical composition comprising

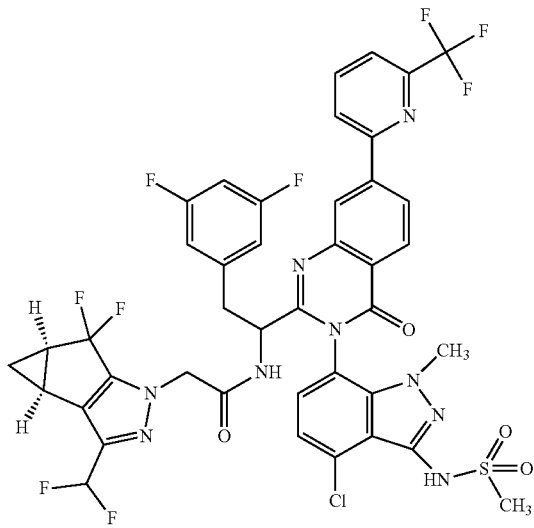 [SMILES: Cn1nc(NS(C)(=O)=O)c2c(Cl)ccc(-n3c(C(Cc4cc(F)cc(F)c4)NC(=O)Cn4nc(C(F)F)c5c4C(F)(F)[C@@H]4C[C@H]54)nc4cc(-c5cccc(C(F)(F)F)n5)ccc4c3=O)c21]

or a pharmaceutically acceptable salt thereof, according to claim 10.

12. A method of treating HIV infection comprising administering to a patient in need

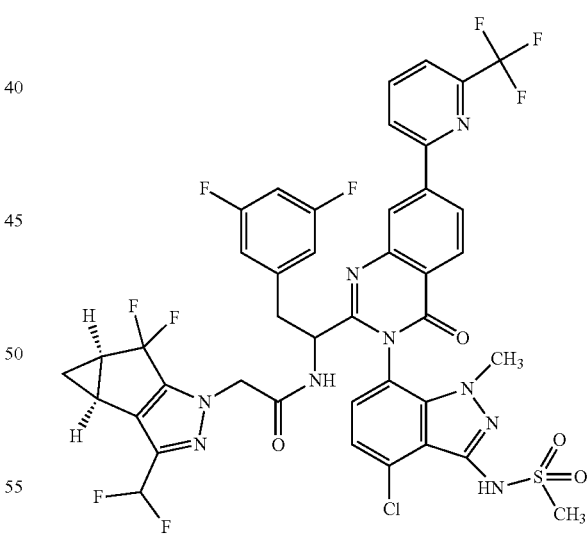

or a pharmaceutically acceptable salt thereof according to claim 10.

13. A method of treating HIV infection comprising administering to a patient in need

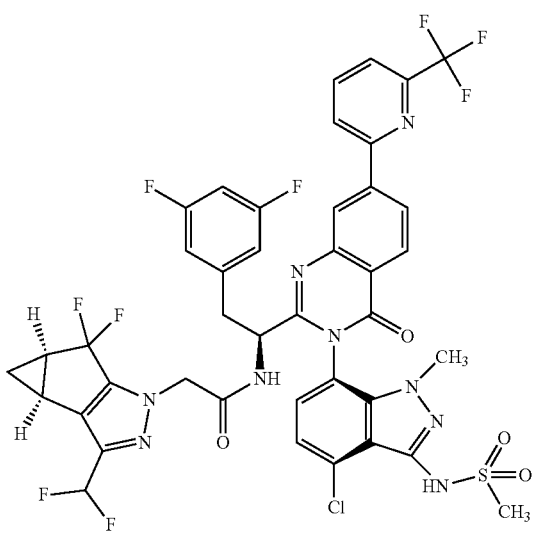

or a pharmaceutically acceptable salt thereof according to claim 1.

14. The pharmaceutical composition according to claim 11 further comprising a pharmaceutically acceptable carrier, excipient, or diluent.

15. The method of claim 13 wherein said administration is oral.

16. The method of claim 13 wherein said administration comprises administering by injection subcutaneously.

17. The method of claim 13 wherein said administration comprises administering by injection intramuscularly.

18. The method of claim 13 wherein said method further comprises administration of at least one other agent useful in the prevention or treatment of HIV.

19. The method of claim 18 wherein said other agent is selected from the group consisting of dolutegravir, lamivudine, fostemsavir, and cabotegravir.

20. A compound which is:

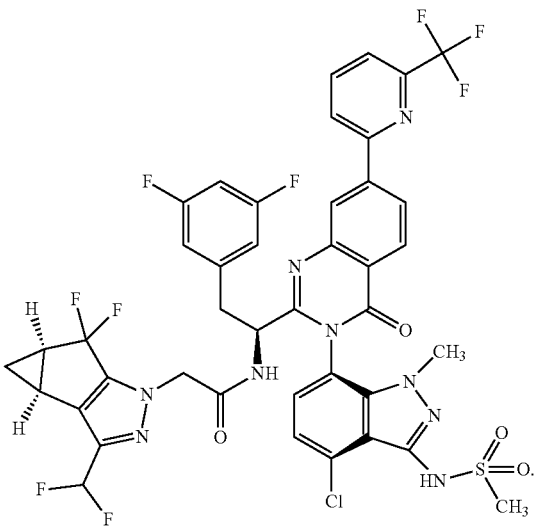

21. A pharmaceutical composition comprising

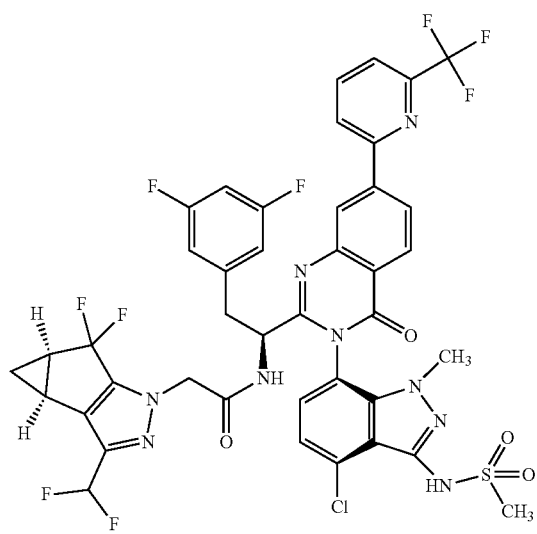

according to claim 20.

22. The pharmaceutical composition according to claim 21 further comprising a pharmaceutically acceptable carrier, excipient, or diluent.

23. A method of treating HIV infection comprising administering to a patient in need thereof

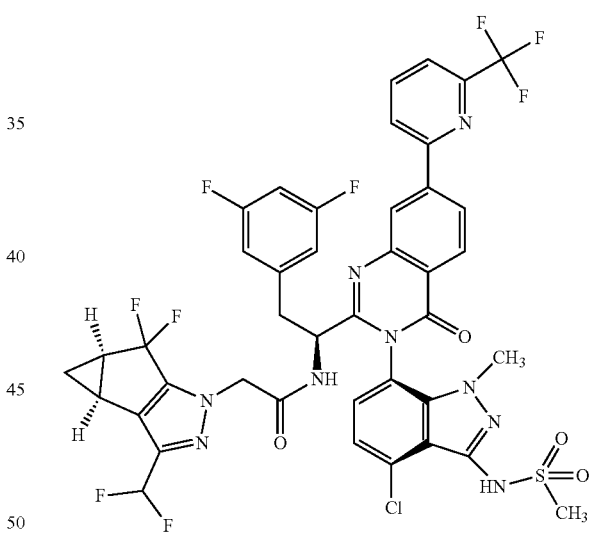

according to claim 20.

24. The method of claim 23 wherein said administration is oral.

25. The method of claim 23 wherein said administration comprises administering by injection subcutaneously.

26. The method of claim 23 wherein said administration comprises administering by injection intramuscularly.

27. The method of claim 23 wherein said method further comprises administration of at least one other agent useful in the prevention or treatment of HIV.

28. The method of claim 27 wherein said other agent is selected from the group consisting of dolutegravir, lamivudine, fostemsavir, and cabotegravir.

* * * * *